United States Patent
Zhang et al.

(10) Patent No.: US 11,633,482 B2
(45) Date of Patent: *Apr. 25, 2023

(54) CONJUGATES AND PREPARATION AND USE THEREOF

(71) Applicant: SUZHOU RIBO LIFE SCIENCE CO., LTD., Kunshan (CN)

(72) Inventors: Hongyan Zhang, Kunshan (CN); Zhiwei Yang, Kunshan (CN); Liqiang Cao, Kunshan (CN); Liangyi Wan, Kunshan (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 177 days.

This patent is subject to a terminal disclaimer.

(21) Appl. No.: 16/758,318

(22) PCT Filed: Nov. 29, 2018

(86) PCT No.: PCT/CN2018/118224
§ 371 (c)(1),
(2) Date: Apr. 22, 2020

(87) PCT Pub. No.: WO2019/128611
PCT Pub. Date: Jul. 4, 2019

(65) Prior Publication Data
US 2020/0338201 A1    Oct. 29, 2020

(30) Foreign Application Priority Data
Dec. 29, 2017 (CN) .......................... 201711479058.9
Sep. 30, 2018 (CN) .......................... 201811165363.5

(51) Int. Cl.
*C12N 15/11*    (2006.01)
*C12N 15/113*    (2010.01)
(Continued)

(52) U.S. Cl.
CPC .............. *A61K 47/549* (2017.08); *A61P 1/16* (2018.01); *A61P 31/20* (2018.01); *C07H 15/04* (2013.01);
(Continued)

(58) Field of Classification Search
CPC ........ C12N 2310/312; C12N 2310/321; C12N 2310/351; C12N 2320/32; C12N 15/113
See application file for complete search history.

(56) References Cited

U.S. PATENT DOCUMENTS

| 8,106,022 B2 | 1/2012 | Manoharan et al. |
| 8,344,125 B2 | 1/2013 | Manoharan et al. |

(Continued)

FOREIGN PATENT DOCUMENTS

| AU | 2014208251 A1 | 8/2014 |
| CA | 2930393 A1 | 6/2009 |

(Continued)

OTHER PUBLICATIONS

Berthold, et al., "Celluler Delivery and Antisense Effects of Peptide Nucleic Acid Conjugated to Polyethyleneimine via Disulfide Linkers" (2010) Bioconjugate Chemistry, vol. 21, No. 10, p. 1933-1938.

(Continued)

*Primary Examiner* — Terra C Gibbs
(74) *Attorney, Agent, or Firm* — Buchanan, Ingersoll & Rooney PC

(57) ABSTRACT

A compound for forming a conjugate with an active agent such as an oligonucleotide having a structure represented by Formula (321). The present disclosure also provides a corresponding conjugate. The conjugate of the present disclosure can specifically target hepatocytes, thereby effectively solve the problems associated with delivery of oligonucleotide drugs in vivo, and have low toxicity and excellent (Continued)

delivery efficiency while maintaining high stability for the delivered oligonucleotide.

Formula (321)

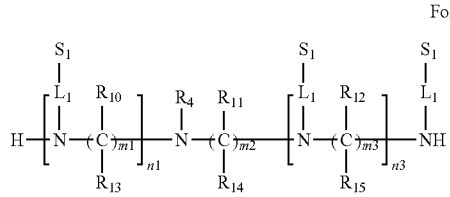

42 Claims, 33 Drawing Sheets

Specification includes a Sequence Listing.

(51) Int. Cl.
| | |
|---|---|
| A61P 31/20 | (2006.01) |
| A61P 3/06 | (2006.01) |
| A61K 47/54 | (2017.01) |
| A61P 1/16 | (2006.01) |
| C07H 15/04 | (2006.01) |

(52) U.S. Cl.
CPC ...... *C12N 15/1131* (2013.01); *C12N 15/1136* (2013.01); *C12N 2310/14* (2013.01); *C12N 2310/315* (2013.01); *C12N 2310/3519* (2013.01)

(56) References Cited

U.S. PATENT DOCUMENTS

| | | |
|---|---|---|
| 9,428,751 B2 | 8/2016 | MacDonald et al. |
| 10,130,651 B2 | 11/2018 | Wooddell et al. |
| 10,246,708 B2 | 4/2019 | Kasperkovitz et al. |
| 10,294,477 B2 | 5/2019 | Swayze |
| 2003/0206887 A1 | 11/2003 | Morrissey et al. |
| 2005/0245475 A1 | 11/2005 | Khvorova et al. |
| 2005/0246794 A1 | 11/2005 | Khvorova et al. |
| 2005/0255487 A1 | 11/2005 | Khvorova et al. |
| 2008/0113351 A1 | 5/2008 | Naito et al. |
| 2008/0146788 A1 | 6/2008 | Bhat et al. |
| 2010/0063132 A1 | 3/2010 | Kim et al. |
| 2010/0137414 A1 | 6/2010 | Freier et al. |
| 2011/0015252 A1 | 1/2011 | Fitzgerald et al. |
| 2011/0039914 A1 | 2/2011 | Pavco et al. |
| 2011/0054005 A1 | 3/2011 | Naito et al. |
| 2012/0052487 A9 | 3/2012 | Khvorova et al. |
| 2012/0108803 A1 | 5/2012 | Han et al. |
| 2012/0172412 A1 | 7/2012 | Rozema et al. |
| 2012/0184595 A1 | 7/2012 | MacDonald et al. |
| 2012/0201756 A1 | 8/2012 | Sexton |
| 2013/0005793 A1 | 1/2013 | Chin et al. |
| 2013/0023579 A1 | 1/2013 | Crooke et al. |
| 2013/0041133 A1* | 2/2013 | Aaronson ............ A61K 47/645 530/324 |
| 2013/0096288 A1 | 4/2013 | Han et al. |
| 2013/0123482 A1 | 5/2013 | Xi et al. |
| 2013/0158021 A1 | 6/2013 | Dong et al. |
| 2014/0099666 A1 | 4/2014 | Rossomando et al. |
| 2014/0128453 A1 | 5/2014 | Mullick et al. |
| 2014/0179768 A1 | 6/2014 | Bettencourt et al. |
| 2014/0194489 A1 | 7/2014 | Bumcrot et al. |
| 2014/0343123 A1 | 11/2014 | Prakash et al. |
| 2015/0093444 A1 | 4/2015 | Zhang et al. |
| 2015/0152436 A1 | 6/2015 | Musunuru et al. |
| 2015/0174260 A1 | 6/2015 | Yang et al. |
| 2015/0191726 A1 | 7/2015 | Manoharan et al. |
| 2015/0247143 A1 | 9/2015 | Fitzgerald et al. |
| 2015/0291958 A1 | 10/2015 | Albaek et al. |
| 2015/0315584 A1 | 11/2015 | MacDonald et al. |
| 2015/0315594 A1 | 11/2015 | Prakash et al. |
| 2016/0017335 A1 | 1/2016 | Borodovsky et al. |
| 2016/0186180 A1 | 6/2016 | Bettencourt et al. |
| 2016/0237438 A1 | 8/2016 | Brown et al. |
| 2016/0283653 A1 | 9/2016 | Staudt et al. |
| 2016/0354404 A1 | 12/2016 | Hinkle et al. |
| 2017/0000815 A1 | 1/2017 | Fitzgerald et al. |
| 2017/0002094 A1 | 1/2017 | Sexton et al. |
| 2017/0114341 A1 | 4/2017 | Bradshaw et al. |
| 2018/0087054 A1 | 3/2018 | Querbes et al. |
| 2018/0148722 A1 | 5/2018 | Fitzgerald et al. |
| 2018/0216114 A1 | 8/2018 | Fitzgerald et al. |
| 2018/0245077 A1 | 8/2018 | Chiu et al. |
| 2019/0062749 A1 | 2/2019 | Zhang |
| 2019/0202855 A1 | 7/2019 | Sakamuri et al. |
| 2019/0255091 A1 | 8/2019 | Li et al. |
| 2019/0292547 A1 | 9/2019 | Li et al. |
| 2020/0199591 A1 | 6/2020 | Fitzgerald et al. |
| 2020/0350346 A1 | 11/2020 | Ohura et al. |
| 2020/0360522 A1 | 11/2020 | Zhang et al. |
| 2021/0032623 A1 | 2/2021 | Zhang et al. |
| 2021/0275564 A1 | 9/2021 | Zhang et al. |
| 2021/0277400 A1 | 9/2021 | Zhang et al. |
| 2021/0401994 A1 | 12/2021 | Zhang et al. |
| 2022/0049249 A1 | 2/2022 | Zhang et al. |

FOREIGN PATENT DOCUMENTS

| | | |
|---|---|---|
| CN | 102006890 A | 4/2011 |
| CN | 102016036 A | 4/2011 |
| CN | 102124107 A | 7/2011 |
| CN | 102140459 A | 8/2011 |
| CN | 102140460 A | 8/2011 |
| CN | 102344477 A | 2/2012 |
| CN | 102439148 A | 5/2012 |
| CN | 102719434 A | 10/2012 |
| CN | 102753186 A | 10/2012 |
| CN | 102140461 B | 12/2012 |
| CN | 102869774 A | 1/2013 |
| CN | 101603042 B | 5/2013 |
| CN | 102140458 B | 5/2013 |
| CN | 103380113 A | 10/2013 |
| CN | 102083983 B | 4/2014 |
| CN | 103890000 A | 6/2014 |
| CN | 104107437 A | 10/2014 |
| CN | 104232644 A | 12/2014 |
| CN | 104328121 A | 2/2015 |
| CN | 102344477 B | 4/2015 |
| CN | 104717982 A | 6/2015 |
| CN | 104854242 A | 8/2015 |
| CN | 104922141 A | 9/2015 |
| CN | 105324485 A | 2/2016 |
| CN | 105378082 A | 3/2016 |
| CN | 105392488 A | 3/2016 |
| CN | 105452465 A | 3/2016 |
| CN | 105517556 A | 4/2016 |
| CN | 105713092 A | 6/2016 |
| CN | 105814204 A | 7/2016 |
| CN | 106132442 A | 11/2016 |
| CN | 106146591 A | 11/2016 |
| CN | 106232831 A | 12/2016 |
| CN | 106255755 A | 12/2016 |
| CN | 106460025 A | 2/2017 |
| CN | 107075516 A | 8/2017 |
| CN | 107109405 A | 8/2017 |
| CN | 107250362 A | 10/2017 |
| CN | 107854478 A | 3/2018 |
| CN | 108064294 A | 5/2018 |
| CN | 108064313 A | 5/2018 |
| CN | 108220293 A | 6/2018 |
| CN | 108239644 A | 7/2018 |
| CN | 108265052 A | 7/2018 |
| CN | 108271386 A | 7/2018 |
| CN | 108348541 A | 7/2018 |
| CN | 110945131 A | 3/2020 |
| CN | 110959011 A | 4/2020 |
| CN | 111050807 A | 4/2020 |

(56) References Cited

FOREIGN PATENT DOCUMENTS

| | | |
|---|---|---|
| CN | 111973617 A | 11/2020 |
| CN | 111973618 A | 11/2020 |
| CN | 111973619 A | 11/2020 |
| CN | 111979237 A | 11/2020 |
| CN | 112423795 A | 2/2021 |
| CN | 113330117 A | 8/2021 |
| EP | 2194128 A1 | 6/2010 |
| EP | 2213738 A2 | 8/2010 |
| EP | 2376641 A1 | 10/2011 |
| EP | 2213738 B1 | 10/2012 |
| EP | 2669377 A2 | 12/2013 |
| EP | 2990410 A1 | 3/2016 |
| EP | 3312281 A2 | 4/2018 |
| EP | 3315608 A1 | 5/2018 |
| EP | 3335715 A2 | 6/2018 |
| EP | 3719128 A1 | 10/2020 |
| EP | 3862024 A1 | 8/2021 |
| TW | 201925471 A | 7/2019 |
| TW | 201929905 A | 8/2019 |
| WO | WO-0027795 A1 | 5/2000 |
| WO | WO-2004078181 A1 | 9/2004 |
| WO | WO-2005116204 A1 | 12/2005 |
| WO | WO-2006006948 A2 | 1/2006 |
| WO | WO-2006096018 A1 | 9/2006 |
| WO | WO-2007134161 A2 | 11/2007 |
| WO | WO-2008011431 A2 | 1/2008 |
| WO | WO-2008109472 A2 | 9/2008 |
| WO | WO-2009073809 A2 | 6/2009 |
| WO | WO-2009082607 A2 | 7/2009 |
| WO | WO-2009134487 A2 | 11/2009 |
| WO | WO-2010012244 A1 | 2/2010 |
| WO | WO-2010045509 A2 | 4/2010 |
| WO | WO-2010068978 A1 | 6/2010 |
| WO | WO-2010083615 A1 | 7/2010 |
| WO | WO-2010101951 A1 | 9/2010 |
| WO | WO-2010121074 A1 | 10/2010 |
| WO | WO-2010131916 A2 | 11/2010 |
| WO | WO-2010147992 A1 | 12/2010 |
| WO | WO-2011085271 A2 | 7/2011 |
| WO | WO-2011104169 A1 | 9/2011 |
| WO | WO-2011139702 A2 | 11/2011 |
| WO | WO-2011154331 A1 | 12/2011 |
| WO | WO-2012013127 A1 | 2/2012 |
| WO | WO-2012024170 A2 | 2/2012 |
| WO | WO-2012037254 A1 | 3/2012 |
| WO | WO-2012068176 A1 | 5/2012 |
| WO | WO-2012083185 A2 | 6/2012 |
| WO | WO-2012089352 A1 | 7/2012 |
| WO | WO-2012130086 A1 | 10/2012 |
| WO | WO-2012139469 A1 | 10/2012 |
| WO | WO-2012177784 A2 | 12/2012 |
| WO | WO-2013060261 A1 | 5/2013 |
| WO | WO-2013070771 A1 | 5/2013 |
| WO | WO-2013166155 A1 | 11/2013 |
| WO | WO-2014025805 A1 | 2/2014 |
| WO | WO-2014089313 A1 | 6/2014 |
| WO | WO-2014118267 A1 | 8/2014 |
| WO | WO-2014179626 A2 | 11/2014 |
| WO | WO-2014179627 A1 | 11/2014 |
| WO | WO-2014179629 A2 | 11/2014 |
| WO | WO-2015006498 A2 | 1/2015 |
| WO | WO-2015006740 A2 | 1/2015 |
| WO | WO-2015015496 A1 | 2/2015 |
| WO | WO-2015031679 A2 | 3/2015 |
| WO | WO-2015100394 A1 | 7/2015 |
| WO | WO-2015113922 A1 | 8/2015 |
| WO | WO-2015148580 A2 | 10/2015 |
| WO | WO-2015168532 A2 | 11/2015 |
| WO | WO-2015188197 A2 | 12/2015 |
| WO | WO-2016011123 A1 * | 1/2016 ........... A61K 31/713 |
| WO | WO-2016028649 A1 | 2/2016 |
| WO | WO-2016077321 A1 | 5/2016 |
| WO | WO-2016081444 A1 | 5/2016 |
| WO | WO-2016099982 A2 | 6/2016 |
| WO | WO-2016149331 A2 | 9/2016 |
| WO | WO-2016154127 A2 | 9/2016 |
| WO | WO-2016168286 A1 | 10/2016 |
| WO | WO-2016179342 A2 | 11/2016 |
| WO | WO-2016188473 A1 | 12/2016 |
| WO | WO-2016206626 A1 | 12/2016 |
| WO | WO-2017015175 A1 | 1/2017 |
| WO | WO-2017019660 A1 | 2/2017 |
| WO | WO-2017019891 A2 | 2/2017 |
| WO | WO-2017035340 A1 | 3/2017 |
| WO | WO-2017055627 A1 | 4/2017 |
| WO | WO-2017100542 A1 | 6/2017 |
| WO | WO-2017120397 A1 | 7/2017 |
| WO | WO-2017184689 A1 | 10/2017 |
| WO | WO-2017189813 A1 | 11/2017 |
| WO | WO-2018027106 A2 | 2/2018 |
| WO | WO-2018044350 A1 | 3/2018 |
| WO | WO-2018075658 A1 | 4/2018 |
| WO | WO-2018140920 A1 | 8/2018 |
| WO | WO-2018191278 A2 | 10/2018 |
| WO | WO-2018209848 A1 | 11/2018 |
| WO | WO-2018223073 A1 | 12/2018 |
| WO | WO-2019105403 A1 | 6/2019 |
| WO | WO-2019105404 A1 | 6/2019 |
| WO | WO-2019105414 A1 | 6/2019 |
| WO | WO-2019105418 A1 | 6/2019 |
| WO | WO-2019105419 A1 | 6/2019 |
| WO | WO-2019105435 A1 | 6/2019 |
| WO | WO-2019105437 A1 | 6/2019 |
| WO | WO-2019128611 A1 | 7/2019 |
| WO | WO-2020038377 A1 | 2/2020 |
| WO | WO-2020093053 A1 | 5/2020 |
| WO | WO-2020135581 A1 | 7/2020 |
| WO | WO-2020147847 A1 | 7/2020 |

OTHER PUBLICATIONS

Paris, et al., "Conjugating Phosphospermines to siRNAs for Improved Stability in Serum, Intracelluler Delivery and RNAi-Mediated Gene Silencing" Molecular Pharmaceutics, vol. 9, No. 12, (2012) pp. 3464-3475.

Beaucage et al., "Tetrahedron Report No. 309: Advances in Synthesis of Oligonucleotides by the Phosphoramidite Approach", Tetrahedron, 1992, vol. 48, No. 12, pp. 2223-2311.

Dong et al., "A novel packaging system of recombinant AAV5/5 vector", Chinese Journal of Biotechnology, May 25, 2010, vol. 26, No. 5, pp. 679-686, Abstract only.

Dong et al., "Lipopeptide nanoparticles for potent and selective siRNA delivery in rodents and nonhuman primates", PNAS Early Edition, 2014, vol. 111, No. 11, pp. 1-6 doi: 10.1073/pnas. 1322937111.

International Search Report and Written Opinion for corresponding PCT Application PCT/CN2018/118224 dated Jul. 4, 2019.

International Search Report and Written Opinion for corresponding PCT Application PCT/CN2018/118303 dated Mar. 7, 2019.

Khvorova et al., "The chemical evolution of oligonucleotide therapies of clinical utility", Nature Biotechnology, 2017, vol. 35, pp. 1-11.

Love et al., "Lipid-like materials for low-dose in vivo gene silencing", PNAS, Feb. 2, 2010, vol. 107, No. 5, pp. 1864-1869. (Correction included May 25, 2010, vol. 107, No. 21, p. 9915).

Matsuda et al., "siRNA Conjugates Carrying Sequentially Assembled Trivalent N-Aceytlgalactosamine Linked Through Nucleosides Elicit Robust Gene Silencing In Vivo in Hepatocytes", ACS Chem Biol., 2015, vol. 10, No. 5, 7 pages.

Nair et al., "Multivalent N-Acetylgalactosamine-Conjugated siRNA Localizes in Hepatocytes and Elicits Robust RNAi-Mediated Gene Silencing", J. Am. Chem. Soc., 2014, vol. 136, pp. 16958-16961.

Protective Groups in Organic Synthesis, by Theodora W. Greene and Wuts Peter G M., Wiley, 1999, Chapter 2, pp. 17-245.

Rajeev et al., "Hepatocyte-Specific Delivery of siRNAs Conjugated to Novel Non-nucleosidic Trivalent N-Aceytlgalactosamine Elicits Robust Gene Slicing in Vivo", ChemBioChem, 2015, vol. 16, pp. 903-908.

(56) References Cited

OTHER PUBLICATIONS

Ren et al., "Gene Expression Profile of Transgenic Mouse Kidney Reveals Pathogenesis of Hepatitis B Virus Associated Nephropathy", Journal of Medical Virology, 2006, vol. 78, pp. 551-560.
Ui-Tei et al., "Functional dissection of siRNA sequence by systematic DNA substitution: modified siRNA with a DNA seed arm is a powerful took for mammalian gene silencing with significantly reduced off-target effect", Nucleic Acids Research, 2008, vol. 36, No. 7, pp. 2136-2151.
Unpublished U.S. Appl. No. 16/765,799, filed May 20, 2020.
Watts et al., "Chemically modified siRNA tools and applications", Drug Discovery Today, Oct. 2008, vol. 13, No. 19/20, pp. 842-855.
Woodell et al., "Hepatocyte-targeted RNAi Therapeutics for the Treatment of Chronic Hepatitis B Virus Infection", Molecular Therapy, 2013, vol. 21, No. 15, pp. 1-13, doi: 10.1038/mt.2013.31.
"European Search Report for EP Application No. EP18896766.5 dated Jul. 10, 2021".
"Kim, K S, et al., "Bifunctional compounds for targeted heptatic gene delivery", Gene Therapy, Nature Publishing Group (2007) vol. 14, No. 8, pp. 704-708".
"Prakash, T.P., et al., "Comprehensive Structure—Activity Relationship of Triantennary N-Acetylgalactosamine Conjugated Antisense Oligonucleotides for Targeted Delivery to Hepatocytes" Journal of Medicinal Chemistry, vol. 59, No. 6 (2016) pp. 2718-2733".
"Ren Tan, et al., "Synthesis of bifunctional cationic compound fro gene delivery" Thetrahedron Letters, vol. 42, No. 6, pp. 1007-1010".
Behlke, M. A. "Chemical Modification of siRNAs for In Vivo Use," Oligonucleotides, Nov. 29, 2008, vol. 18, No. 4, pp. 305-320, XP002546697.
Chen, Y. et al., "Research Progress on Factor XI as a Novel Target for Antithrombotic Therapy", Chinese Pharmacological Bulletin, Apr. 15, 2015, vol. 31, No. 5, pp. 619-622 (with English abstract).
Dai, R., et al., "A vital role for AngptlS in the PAN-induced podocyte loss by affecting detachment and apoptosis in vitro", BMC. Nephrology, 2015, pp. 1-10.
Ding, C. et al., "Limited role of kininogen in the host response during gram-negative pneumonia derived sepsis", Am J Physiol Lung Cell Mol Physiol., .Nov. 9, 2017, pp. 1-33, doi:10.1152/ajplung.00288.2017.
Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).
Foster, D.J. et al., "Advanced siRNA Designs Further Improve In Vivo Performance of GalNac-siRNA Conjugates", Molecular Therapy, vol. 26, No. 3, Mar. 2018, pp. 708-717.
Khaitmetova, S.B. et al., "Synthesis and Study of the Properties of Polymer Complexes of Ethacizin with Carboxymethylcellulose", Chemistry of Plant Raw Materials, 2017, vol. 4, pp. 23-30.
Khan, M.M. et al., "High-Molecular-Weight Kininogen Fragments Stimulate the Secretion of Cytokines and Chemokines Through uPAR, Mac-1, and gC1qR in Monocytes", Arterioscler Thromb Vasc Biol., 2006;26:2260-2266, DOI: 10.1161/01.ATV.0000240290.70852.C0.
Khvorova et al., "The chemical evolution of oligonucleotide therapies of clinical utility", Nature Biotechnology, 2017, vol. 35, No. 3, pp. 238-248; doi:10.1038/nbt.3765.
Liu, W., et al., "Coagulation factor XI induces Ca2+ response and accelerates cell migration in vascular smooth muscle cells via proteinase-activated receptor 1", Am J Physiol Cell Physiol, Dec. 19, 2018, vol. 316, No. 3, C377-C392 https://doi.org/10.1152/ajpcell.00426.2018.
Liu, Z. et al. "Determination of Human Plasma Pre-Kallikrein", Journal of China Medical University. 1988, vol. 17, No. 6, ISSN: 0238-4646, pp. 432-436, with English Abstract.
Love et al., "Lipid-like materials for low-dose, in vivo gene silencing", Proceedings of the National Academy of Sciences, Feb. 2, 2010, vol. 107, No. 5 with correction. (7 pages).
Montagne, A. et al., "Pericyte degeneration causes white matter dysfunction in the mouse CNS", Nat Med., Mar. 2018; 24(3): 326-337.
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961. (4 pages).
Nakagawa, A. et al., "The RNAi-Mediated Silencing of Xanthine Dehydrogenase Impairs Growth and Fertility and Accelerates Leaf Senescence in Transgenic Arabidopsis Plants", Plant Cell Physiol., Dec. 31, 2007, vol. 48, No. 10, , pp. 1484-1495.
No Author, "Experiment 21 RNA interference technology", retrieved from internet https://img.duxiu.com/n/jpgfs/book/base/12143891/af4f71d173f4fb48deb54aaf0ef2adcd/9ce955611111536dd3aefc5607ec2ae7.sthmil?uf=1&t=2&ti . . . retrieved online Oct. 15, 2021, pp. 5 pages. [English Translation included].
Norata, G.D. et al., "Gene silencing approaches for the management of dyslipidaemia", Trends in Pharmacological Sciences, 2013, vol. 34, No. 4, pp. 198-205.
Nordestgaard, B., et al., "Advances in lipid-lowering therapy through gene-silencing technologies," Nature Reviews Cardiology, May 2018, published online Feb. 8, 2018, vol. 15, pp. 261-272.
Papulov, Y.G., "Relationship of the Properties of Substances with the Structure of Molecules: Math Modeling", Advances in Modern Natural Sciences, 2006, vol. 2, pp. 75-76.[English Translation included].
Pena-Altamira, L.E. et al., "Release of soluble and vesicular purine nucleoside phosphorylase from rat astrocytes and microglia induced by pro-inflammatory stimulation with extracellular ATP via P2X7 receptors", Neurochemistry International, May 31, 2018, vol. 115, ISSN: 0197-0186, pp. 37-49.
Pessentheiner, A.R., et al., "ANGPTL3 targeting: The power of versatile lipid-lowering", Atherosclerosis, 2018, vol. 268, pp. 185-187.
Springer, A. D. et al., "GalNac-siRNA Conjugates: Leading the Way for Delivery of RNAi Therapeutics", Nucleic Acid Therapeutics, May 24, 2018, vol. 28, No. 3, , pp. 109-118.
Su, L., et al., "Progress on Inhibition of Hepatitis B Virus by siRNA Strategy", China Biotechnology, Sep. 15, 2014, vol. 34, No. 9, pp. 102-105 , English abstract.
Tangkijvanich, P. et al., "Low pretreatment serum HBsAg level and viral mutations as predictors of response to PEG-interferon alpha-2b therapy in chronic hepatitis B", Journal of Clinical Virology, Aug. 3, 2009, vol. 46, Issue 2, pp. 117-123.
Watts et al., "Chemically modified siRNA: tools and applications", Drug Discovery Today, Oct. 2008, vol. 13, Nos. 19/20, pp. 842-855. (14 pages).
Wu, Y., et al., "Cleaved high molecular weight kininogen inhibits tube formation of endothelial progenitor cells via suppression of matrix metalloproteinase 2", J Thromb Haemost. 2010, vol. 8, pp. 185-193, DOI: 10.1111/j.1538-7836.2009.03662.x.
Wu, Y. et al., "Contact pathway of coagulation and inflammation", Thrombosis Journal. 2015, vol. 13, No. 17, pp. 1-9, DOI 10.1186/s12959-015-0048-y.
Xu, Y.X., et al., "Role of angiopoietin-like 3 (ANGPTL3) in regulating plasma level of low-density lipoprotein cholesterol", Atherosclerosis, 2018, vol. 268, pp. 196-206.
Yang, A., et al., "A critical role for plasma kallikrein in the pathogenesis of autoantibody-induced arthritis", The FASEB Journal, 2017, vol. 31, No. 12, pp. 5419-5431, doi: 10.1096/fj.201700018R.
Yang, A., et al., "An essential role of high-molecular-weight kininogen in endotoxemia", J. Exp. Med., 2017, vol. 214, No. 9, pp. 2649-2670, https://doi.org/10.1084/jem.20161900.

* cited by examiner

CONJUGATES AND PREPARATION AND USE THEREOF

CROSS REFERENCE TO RELATED APPLICATIONS

This application is a national phase entry under 35 U.S.C. 371 of International Application No. PCT/CN2018/118224, filed on Nov. 29, 2018, which claims priority to Chinese patent application No. 201711479058.9, filed on Dec. 29, 2017, and Chinese patent application No. 201811165363.5, filed on Sep. 30, 2018, each of which is incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 29, 2018, is named Sequence listing_ESP1V192694ZX-CNSZRB-US.txt and is 52,048 bytes in size.

BACKGROUND OF THE INVENTION

Delivery system is one of key technologies in the development of small RNA drugs. One type of small RNA delivery system is a targeted conjugation delivery technology on liver cells.

SUMMARY OF THE INVENTION

According to one aspect of the invention, provided herein is a compound having a structure represented by Formula (321):

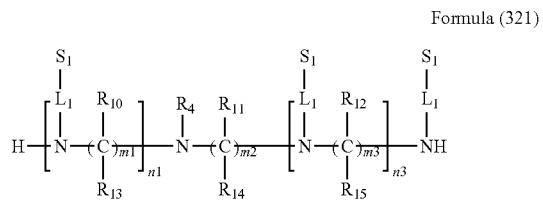

Formula (321)

wherein,
n1 is an integer of 1-3, and n3 is an integer of 0-4;
each of m1, m2, and m3 is independently an integer of 2-10;
each of $R_{10}$, $R_{11}$, $R_{12}$, $R_{13}$, $R_{14}$ and $R_{15}$ is independently selected from H, $C_1$-$C_{10}$ alkyl, $C_1$-$C_{10}$ haloalkyl, and $C_1$-$C_{10}$ alkoxy;
$R_4$ is a moiety capable of binding to an active drug or active agent via a covalent bond;
each $L_1$ is a linear alkylene of 1 to 70 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $S_1$ is independently an $M_1$, wherein any active hydroxyl, if any, is protected with a hydroxyl protecting group;

each $M_1$ is independently selected from a ligand capable of binding to a cell surface receptor.

In some embodiments, each $L_1$ is independently selected from the group consisting of groups A1-A26 and any combinations thereof:

(A1)

(A2)

(A3)

(A4)

(A5)

(A6)

(A7)

(A8)

(A9)

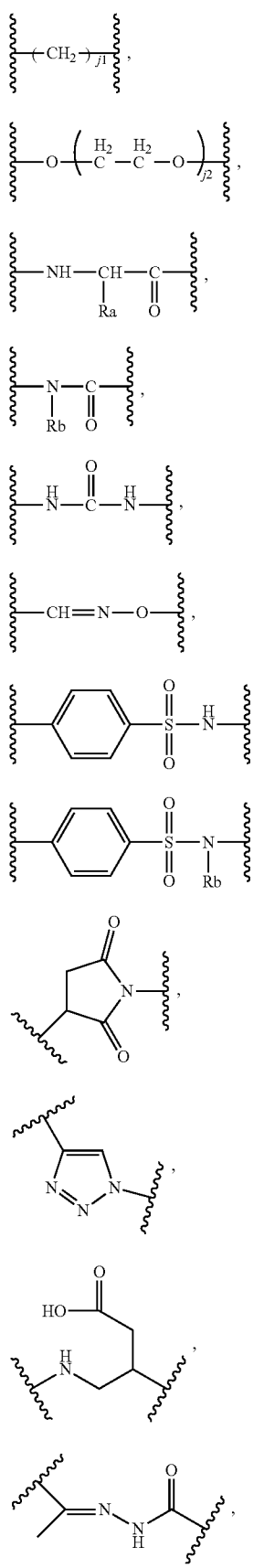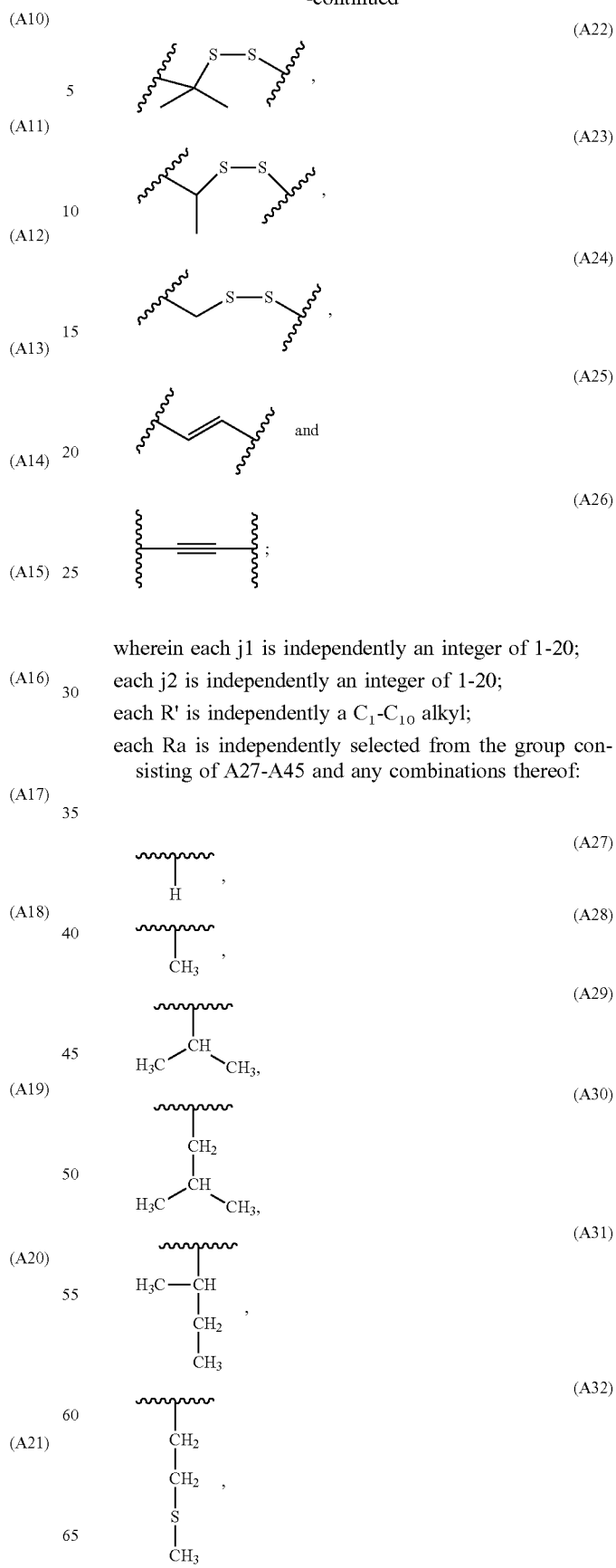
wherein each j1 is independently an integer of 1-20;
each j2 is independently an integer of 1-20;
each R' is independently a $C_1$-$C_{10}$ alkyl;
each Ra is independently selected from the group consisting of A27-A45 and any combinations thereof:

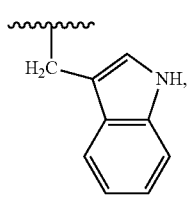 (A33)

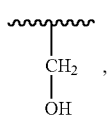 (A34)

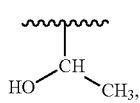 (A35)

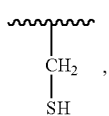 (A36)

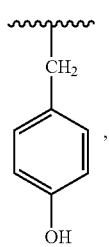 (A37)

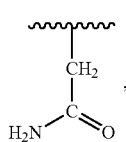 (A38)

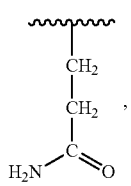 (A39)

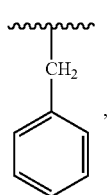 (A40)

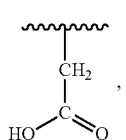 (A41)

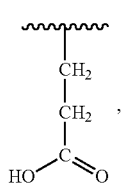 (A42)

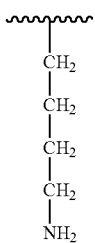 (A43)

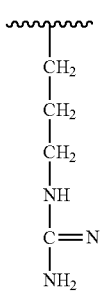 (A44)

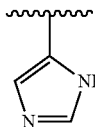 (A45)

each Rb is independently a $C_1$-$C_{10}$ alkyl; and

∿∿∿ represents a site where a group is attached to the rest of the molecule.

In one aspect of the invention, provided herein is a conjugate having a structure represented by Formula (1):

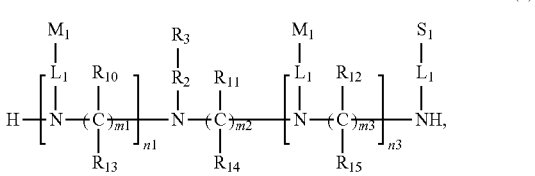

Formula (1)

wherein, n1 is an integer of 1-3, and n3 is an integer of 0-4;

each of m1, m2, and m3 is independently an integer of 2-10;

each of R10, R11, R12, R13, R14 and R15 is independently selected from H, $C_1$-$C_{10}$ alkyl, $C_1$-$C_{10}$ haloalkyl, and $C_1$-$C_{10}$ alkoxy;

R3 is an active drug;

R2 is a linear alkylene of 1 to 20 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein R2 is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)(C₁-C₁₀ alkylphenyl), —NH(C₁-C₁₀ alkylphenyl), cyano, nitro, —CO₂H, —C(O)OC₁-C₁₀ alkyl, —CON(C₁-C₁₀ alkyl)(C₁-C₁₀ alkyl), —CONH(C₁-C₁₀ alkyl), —CONH₂, —NHC(O)(C₁-C₁₀ alkyl), —NHC(O)(phenyl), —N(C₁-C₁₀ alkyl)C(O)(C₁-C₁₀ alkyl), —N(C₁-C₁₀ alkyl)C(O)(phenyl), —C(O)C₁-C₁₀ alkyl, —C(O)C₁-C₁₀ alkylphenyl, —C(O)C₁-C₁₀ haloalkyl, —OC(O)C₁-C₁₀ alkyl, —SO₂(C₁-C₁₀ alkyl), —SO₂(phenyl), —SO₂(C₁-C₁₀ haloalkyl), —SO₂NH₂, —SO₂NH(C₁-C₁₀ alkyl), —SO₂NH(phenyl), —NHSO₂(C₁-C₁₀ alkyl), —NHSO₂(phenyl), and —NHSO₂(C₁-C₁₀ haloalkyl);

each L₁ is independently a linear alkylene of 1 to 70 carbon atoms in length, wherein one or more carbon atoms are optionally replaced with any one or more of the group consisting of: C(O), NH, O, S, CH=N, S(O)₂, C₂-C₁₀ alkenylene, C₂-C₁₀ alkynylene, C₆-C₁₀ arylene, C₃-C₁₈ heterocyclylene, and C₅-C₁₀ heteroarylene, and wherein L₁ is optionally substituted by any one or more of the group consisting of: C₁-C₁₀ alkyl, C₆-C₁₀ aryl, C₅-C₁₀ heteroaryl, C₁-C₁₀ haloalkyl, —OC₁-C₁₀ alkyl, —OC₁-C₁₀ alkylphenyl, —C₁-C₁₀ alkyl-OH, —OC₁-C₁₀ haloalkyl, —SC₁-C₁₀ alkyl, —SC₁-C₁₀ alkylphenyl, —C₁-C₁₀ alkyl-SH, —SC₁-C₁₀ haloalkyl, halo, —OH, —SH, —NH₂, —C₁-C₁₀ alkyl-NH₂, —N(C₁-C₁₀ alkyl)(C₁-C₁₀ alkyl), —NH(C₁-C₁₀ alkyl), —N(C₁-C₁₀ alkyl)(C₁-C₁₀ alkylphenyl), —NH(C₁-C₁₀ alkylphenyl), cyano, nitro, —CO₂H, —C(O)OC₁-C₁₀ alkyl, —CON(C₁-C₁₀ alkyl)(C₁-C₁₀ alkyl), —CONH(C₁-C₁₀ alkyl), —CONH₂, —NHC(O)(C₁-C₁₀ alkyl), —NHC(O)(phenyl), —N(C₁-C₁₀ alkyl)C(O)(C₁-C₁₀ alkyl), —N(C₁-C₁₀ alkyl)C(O)(phenyl), —C(O)C₁-C₁₀ alkyl, —C(O)C₁-C₁₀ alkylphenyl, —C(O)C₁-C₁₀ haloalkyl, —OC(O)C₁-C₁₀ alkyl, —SO₂(C₁-C₁₀ alkyl), —SO₂(phenyl), —SO₂(C₁-C₁₀ haloalkyl), —SO₂NH₂, —SO₂NH(C₁-C₁₀ alkyl), —SO₂NH(phenyl), —NHSO₂(C₁-C₁₀ alkyl), —NHSO₂(phenyl), and —NHSO₂(C₁-C₁₀ haloalkyl);

each M₁ is selected from one of ligands capable of binding to a cell surface receptor.

In some embodiments, each L₁ is independently selected from the group consisting of groups A1-A26 and any combinations thereof:

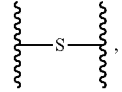  (A1)

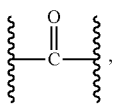  (A2)

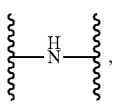  (A3)

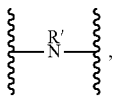  (A4)

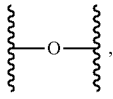  (A5)

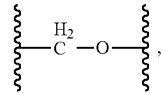  (A6)

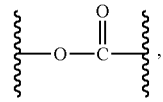  (A7)

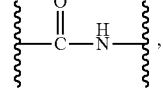  (A8)

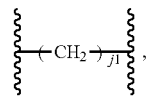  (A9)

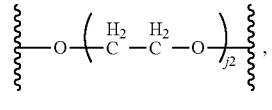  (A10)

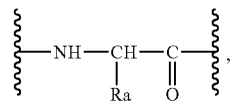  (A11)

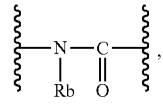  (A12)

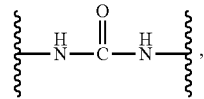  (A13)

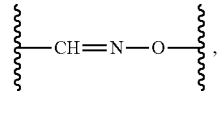  (A14)

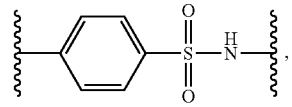  (A15)

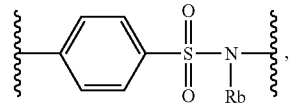  (A16)

(A17)

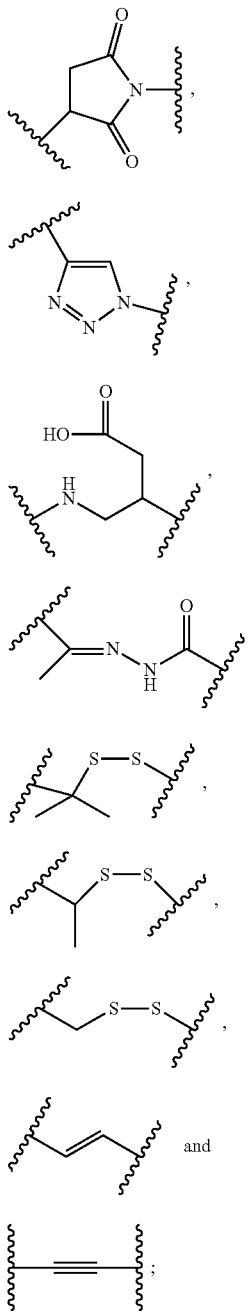
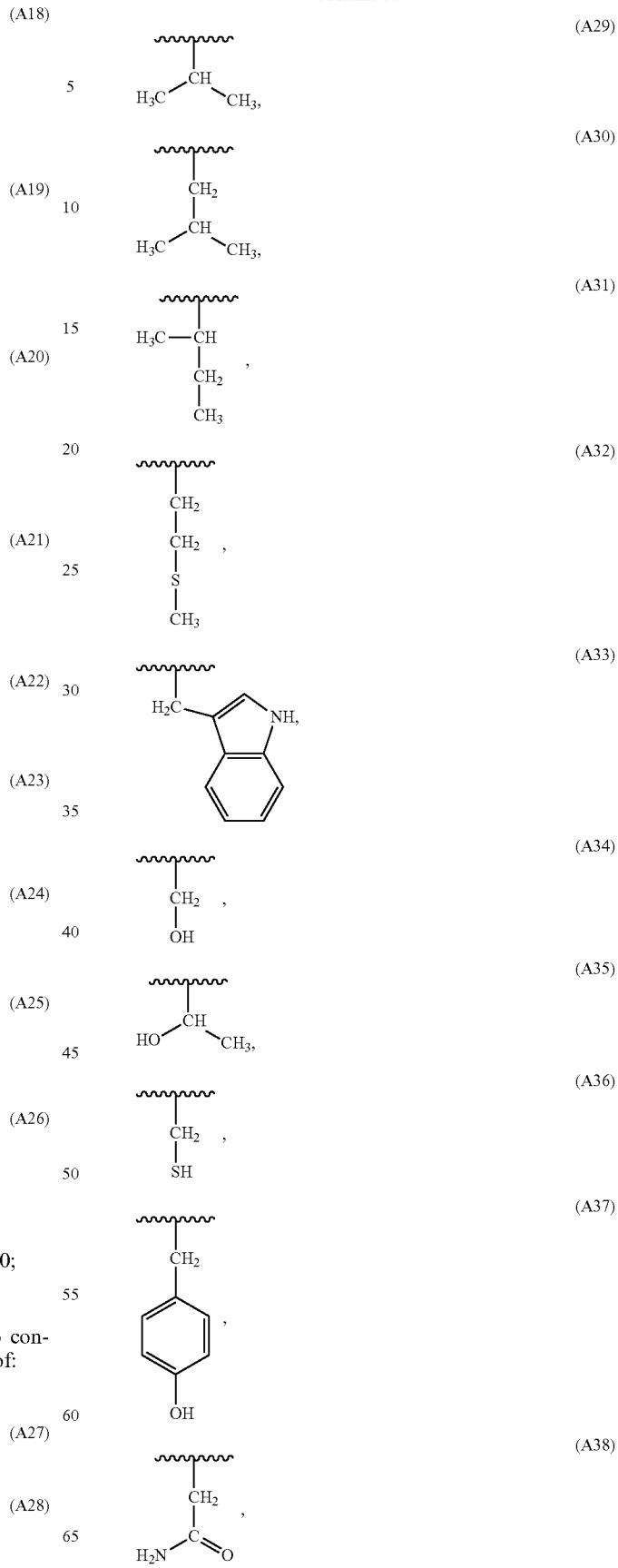
wherein each j1 is independently an integer of 1-20;
each j2 is independently an integer of 1-20;
each R' is independently a $C_1$-$C_{10}$ alkyl;
each Ra is independently selected from the group consisting of A27-A45 and any combinations thereof:

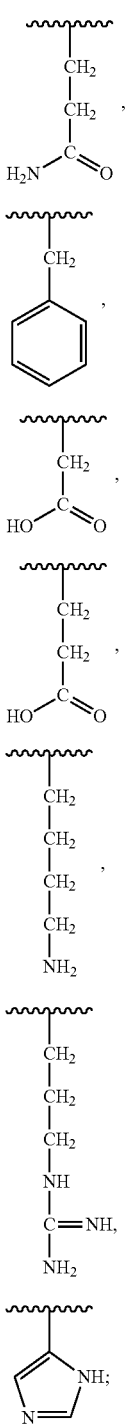

each Rb is independently a $C_1$-$C_{10}$ alkyl; and
 ⌇⌇⌇ represents a site where a group is attached to the rest of the molecule.

In one aspect of the invention, provided herein is use of the conjugate disclosed herein for preparing a medicament for treating and/or preventing a pathological condition or disease caused by expression of a specific gene in hepatocytes.

In one aspect of the invention, provided herein is a method for treating in a subject in need thereof a pathological condition or disease caused by expression of a specific gene in hepatocytes, comprising administering to the subject an effective amount of the conjugate disclosed herein.

In one aspect of the invention, provided herein is a method for inhibiting expression of a specific gene in hepatocytes, comprising contacting the conjugate disclosed herein.

In one aspect of the invention, provided herein is a kit comprising the conjugate disclosed herein.

Additional features and advantages of the present disclosure will be illustrated in detail hereinafter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
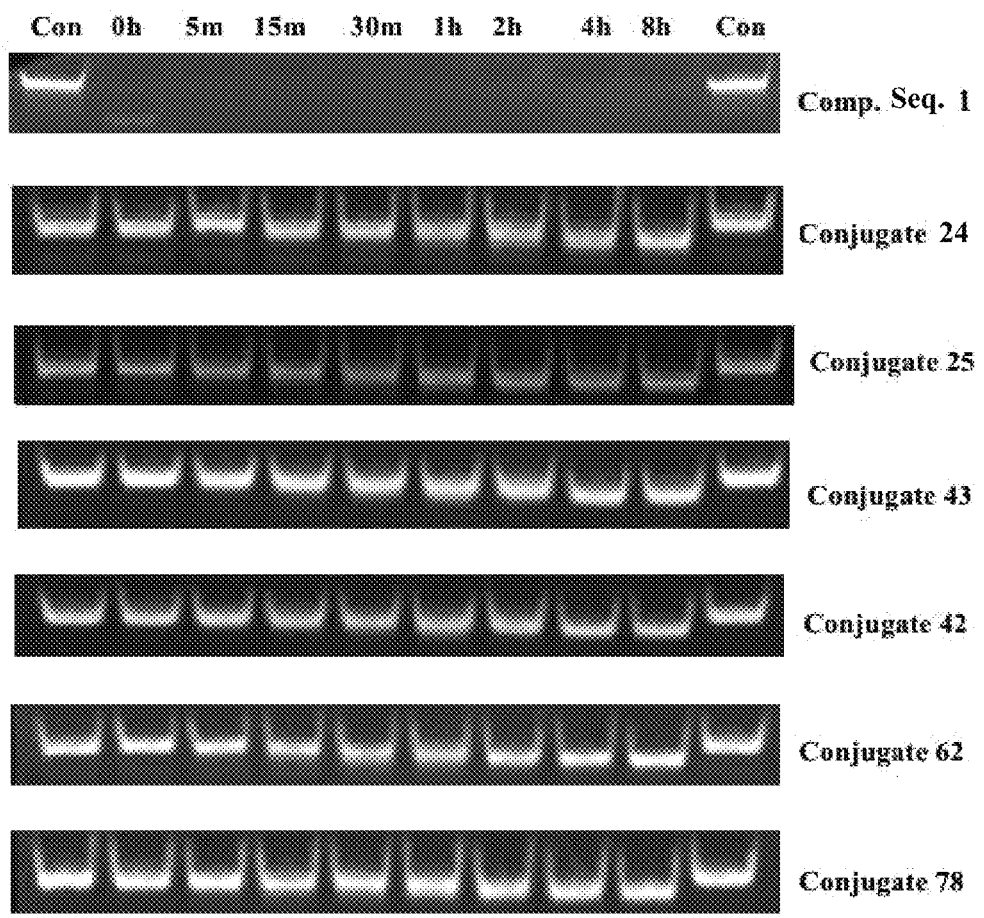
FIGS. 1A and 1B show the semiquantitative result of the stability test of the siRNA conjugates in the Tritosome in vitro.

The detailed embodiments of the present disclosure are described in detail as below. It should be understood that the detailed embodiments described herein are only used to illustrate and explain the present disclosure and are not intended to limit the present disclosure in any respect.

Definitions

In the context of the present disclosure, unless otherwise specified, capital letters C, G, U, and A indicate the base composition of the nucleotides; lowercase letter m indicates that the nucleotide adjacent to the left side of the letter m is a 2'-methoxy modified nucleotide; lowercase letter f indicates that the nucleotide adjacent to the left side of the letter f is a 2'-fluoro modified nucleotide; lowercase letter s indicates the phosphorothioate linkage between the two nucleotides adjacent to both sides of the letter s: P1 indicates that the nucleotide adjacent to the right side of P1 is a 5'-phosphate nucleotide or a nucleotide modified by a 5'-phosphate analog, especially a nucleotide modified by vinyl phosphate (represented as VP in the examples below), a 5'-phosphate nucleotide (represented as P in the examples below) or a nucleotide modified by 5'-thiophosphate (represented as Ps in the examples below).

In the context of the present disclosure, expressions "complementary" and "reverse complementary" are interchangeably used herein, and have the meaning well-known in the art, namely, bases in one strand are each paired in complementary with those in another strand in a double-stranded nucleic acid molecule. In DNAs, a purine base adenine (A) is always paired with a pyrimidine base thymine (T) (or a uracil (U) in RNAs); and a purine base guanine (G) is always paired with a pyrimidine base cytosine (C). Each base pair comprises a purine and a pyrimidine. While adenines in a strand are always paired with thymines (or uracils) in another strand, and guanines paired with cytosines, the strands are considered as complementary; and a base sequence of a strand may be deduced from the sequence of its complementary strand. Correspondingly, a "mispairing" refers to the bases at corresponding sites are not presented in a complementary pair in a double-stranded nucleic acid.

In the context of the present disclosure, unless otherwise specified, "basically reverse complementary" refers to no more than 3 mispairings in two nucleotide sequences. "Substantially reverse complementary" refers to no more than 1 mispairing in two nucleotide sequences. "Completely reverse complementary" refers to no mispairing in two nucleotide sequences.

In the context of the present disclosure, a "nucleotide difference" between a nucleotide sequence and another refers to a change in the base of the nucleotides at the same site therebetween. For example, in the case that a nucleotide base in the second sequence is A while the base at the same site in the first sequence is U, C, G or T, it is considered a nucleotide difference exists at the site between the 2 sequences. In some embodiments, while a nucleotide at a site is replaced with an abasic nucleotide or a nucleotide analogue, it is also considered that there is a nucleotide difference at the site.

In the context of the present disclosure, particularly in the description of the method for preparing the conjugating molecule or the siRNA conjugate described in the disclosure, unless otherwise specified, the "nucleoside monomer" or "nucleoside monomers" refers to, according to the RNA sequence to be prepared, "unmodified or modified RNA phosphoramidite", or "unmodified or modified RNA phosphoramidites" respectively used in a so called "solid phase phosphoramidite synthesis" which is well-known in the art for synthesis of RNA. The RNA phosphoramidites are also referred to as nucleoside phosphoramidites elsewhere. Nucleoside monomers used in the disclosure are all commercially available.

As used herein, a dash ("-") that is not between two letters or symbols is used to indicate a point of attachment for a substituent. For example, —$C_1$-$C_{10}$ alkyl-$NH_2$ is attached through the $C_1$-$C_{10}$ alkyl.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 10 carbon atoms, such as 1 to 8 or 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. Alkylene is a subset of alkyl, referring to the same residues as alkyl, but having two points of attachment.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 10, 2 to 8, or 2 to 6 carbon atoms. Alkenylene is a subset of alkenyl, referring to the same residues as alkenyl, but having two points of attachment.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 2 to 10, 2 to 8, or 2 to 6 carbon atoms. Alkynylene is a subset of alkynyl, referring to the same residues as alkynyl, but having two points of attachment.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 10, 1 to 8, 1 to 6, or 1 to 4 carbon atoms attached through the oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Huckel theory. Aryl groups include, but are not limited to, groups such as phenyl, fluorenyl, and naphthyl. Arylene is a subset of aryl, referring to the same residues as aryl, but having two points of attachment.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbomane.

As used herein, "halo" or "halogen" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Huckel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta [4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

Various hydroxyl protecting groups may be used in the present disclosure. In general, protecting groups render chemical functionalities inert to specific reaction conditions, and may be appended to and removed from such functionalities in a molecule without substantially damaging the remainder of the molecule. Representative hydroxylprotecting groups are disclosed by Beaucage, et al., *Tetrahedron* 1992, 48, 2223-2311, and also in Greene and Wuts, *Protective Groups in Organic Synthesis*, Chapter 2, 2d ed, John Wiley & Sons, New York, 1991, each of which are hereby incorporated by reference in their entirety. In some embodiments, the protecting group is stable under basic conditions but may be removed under acidic conditions. In some embodiments, non-exclusive examples of the hydroxyl protecting groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of the hydroxyl protecting groups that may be used herein comprises Tr (trityl), MMTr (4-methoxytrityl), DMTr (4,4'-dimethoxytrityl), and TMTr (4,4',4"-trimethoxytrityl).

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

As used herein, "treatment" or "treating," or "palliating" or "ameliorating" are used interchangeably herein. These terms refers to an approach for obtaining beneficial or desired results including but not limited to therapeutic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, "prevention" and "preventing" are used interchangeably. These terms refers to an approach for obtaining beneficial or desired results including but not limited to a prophylactic benefit. For "prophylactic benefit", the conjugates or compositions may be administered to a patient at risk of developing a particular disease, or to a patient reporting one or more of the physiological symptoms of a disease, even though a diagnosis of this disease may not have been made.

Conjugating Molecules

In one aspect, disclosed herein is a conjugating molecule for delivering an active agent or active drug. In some embodiments, the conjugating molecules disclosed herein are useful for tissue specific targeting. In some embodiments, the conjugating molecules disclosed here bind to a cell surface receptor. For this purpose, any cell surface receptor or biomarker or a fraction thereof is envisaged to be suitable. In some embodiments, the conjugating molecules disclosed herein specifically bind to a receptor unique to a certain tissue, and thereby achieving tissue specific targeting. In some embodiments, the conjugating molecules disclosed herein specifically targets hepatocyte surface receptors, and thus specifically target liver tissues. In some embodiments, the conjugating molecules disclosed herein specifically targets cell surface receptors that are unique to liver cells. In some embodiments, the conjugating molecules disclosed herein specifically targets hepatic surface asialoglycoprotein receptors (ASGPR).

As used herein, an "active agent" is used interchangeably with the term an "active drug", both referring to the molecule capable of being delivered by the conjugating molecule disclosed herein. In some embodiments, the active agents are agents delivery of which to hepatocyte is desired. Such agents are known to those skilled in the art and include but are not limited to functional nucleotides, such as functional oligonucleotides, especially those disclosed herein.

In some embodiments, the disclosure provides a conjugating molecule having a structure represented by Formula (321):

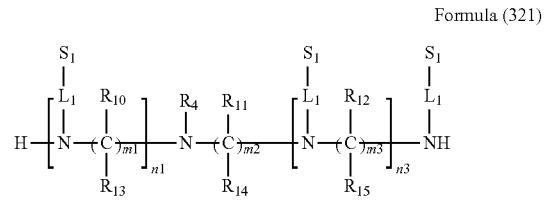

Formula (321)

wherein:
n1 is an integer of 1-3, and n3 is an integer of 0-4;
each of m1, m2, and m3 is independently an integer of 2-10;
each of $R_{10}$, $R_{11}$, $R_{12}$, $R_{13}$, $R_{14}$ and $R_{15}$ is independently selected from H, $C_1$-$C_{10}$ alkyl, $C_1$-$C_{10}$ haloalkyl, and $C_1$-$C_{10}$ alkoxy;
$R_4$ is a moiety capable of binding to an active drug or active agent via a covalent bond; each $L_1$ is a linear alkylene of 1 to 70 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

each $S_1$ is independently an $M_1$, wherein any active hydroxyl, if any, is protected with a hydroxyl protecting group;

each $M_1$ is independently selected from a ligand capable of binding to a cell surface receptor.

In some embodiments, n1 may be an integer of 1-3, and n3 may be an integer of 0-4 to ensure that there are at least 2 $S_1$ groups in the conjugating molecule. In some embodiments, n1+n3≥2, so that the number of $M_1$ ligand in the conjugate formed by the conjugating molecule may be at least 3, thereby allowing the $M_1$ ligand to bind to the asialoglycoprotein receptors on the surface of hepatocytes more conveniently, which may facilitates the endocytosis of the conjugate into cells. Experiments have shown that when the number of $M_1$ ligands is greater than 3, the feasibility of binding $M_1$ ligand to the asialoglycoprotein receptors on the surface of hepatocytes is not significantly increased. Therefore, in view of various aspects such as the synthesis convenience, structure/process costs and delivery efficiency, In some embodiments, n1 is an integer of 1-2, n3 is an integer of 0-1, and n1+n3=2-3.

In some embodiments, when m1, m2, and m3 are each independently selected from an integer of 2-10, it is believed that the steric position among a plurality of $M_1$ ligands in the conjugate formed by the conjugating molecule may be fit for binding $M_1$ ligands to the asialoglycoprotein receptors on the surface of hepatocytes. In order to make the conjugating molecule provided by the disclosure simpler, more convenient to synthesize and/or costs reduced, in some embodiments of the disclosure, m1, m2 and m3 are each independently an integer of 2-5, in some embodiments, m1=m2=m3.

It may be understood by those skilled in the art that with each of $R_{10}$, $R_{11}$, $R_{12}$, $R_{13}$, $R_{14}$, and $R_{15}$ being independently selected from H, $C_1$-$C_{10}$ alkyl, $C_1$-$C_{10}$ haloalkyl, and $C_1$-$C_{10}$ alkoxy, the purpose of the present disclosure may be achieved without changing the properties of the conjugating molecule disclosed herein. In some embodiments, $R_{10}$, $R_{11}$, $R_{12}$, $R_{13}$, $R_{14}$, and $R_{15}$ are each independently selected from H, methyl and ethyl. In some embodiments, $R_{10}$, $R_{11}$, $R_{12}$, $R_{13}$, $R_{14}$, and $R_{15}$ are all H.

$R_4$ is a moiety capable of binding to the active agent to be delivered by the conjugating molecules disclosed herein. In some embodiments, $R_4$ is a moiety capable of binding to an oligonucleotide to be delivered by the conjugating molecules disclosed herein. In some embodiments, $R_4$ is a moiety capable of binding to an oligonucleotide via a covalent bond. In some embodiments, $R_4$ is a moiety capable of binding to an oligonucleotide via a phosphodiester bond. In some embodiments, $R_4$ is selected to achieve the linkage to the N atom on a nitrogenous backbone and to provide suitable reaction sites for synthesizing the oligonucleotide conjugate. In the context of the present disclosure, a "nitrogenous backbone" refers to a chain structure in which the carbon atoms to which $R_{10}$, $R_{11}$, $R_{12}$, $R_{13}$, $R_{14}$, and $R_{15}$ are attached and the N atoms are linked to each other. In some embodiments, $R_4$ is a moiety that may be attached to the N atom on a nitrogenous backbone in an appropriate manner. In some embodiments, $R_4$ comprises a site linking to the N atom on the nitrogenous backbone and any functional group that may be conjugated to an oligonucleotide via a phosphodiester bond by reaction.

In some embodiments, $R_4$ comprises a first functional group that can react with a group on an oligonucleotide or a nucleotide to form a phosphate ester bond, and a second functional group that can form a covalent bond with a hydroxy group or an amino group, or a solid phase support linked via the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support attached to the rest of the molecule via a covalent bond formed with a hydroxy group or an amino group. In some embodiments, the solid phase support is linked via a phosphoester bond, a carboxyl ester bond, or an amido bond. In some embodiments, the solid phase support is a resin.

In some embodiments, the first functional group comprises hydroxy, —$OR_k$ or a group represented by Formula (C3); and/or the second functional group comprises a group represented by Formula (C1), (C2), (C3), (C1'), or (C3'):

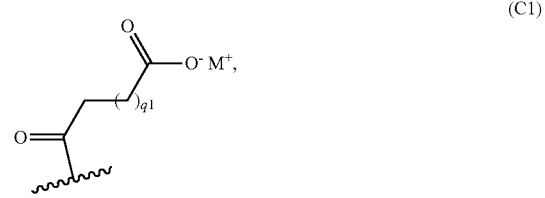

(C1)

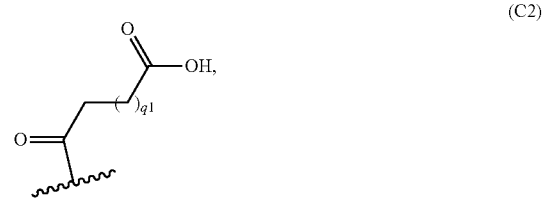

(C2)

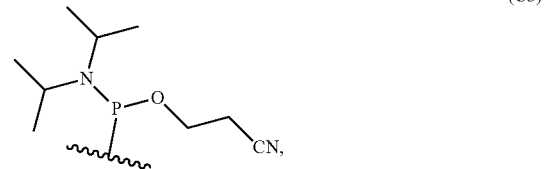

(C3)

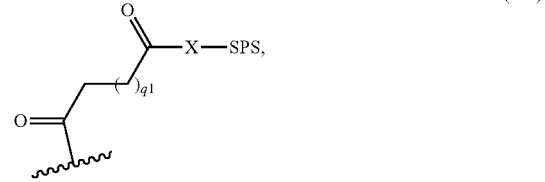

(C1')

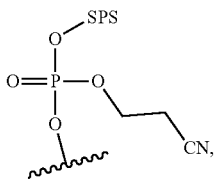

(C3')

wherein $q_1$ is an integer of 1-4, X is O or NH, $M^+$ is a cation, $R_k$ is a hydroxy protecting group, SPS represents a solid phase support, and ∼∼∼ represents the site where the group is covalently attached.

In some embodiments, the first functional group comprises a phosphoramidite group, such as the group represented by Formula (C3). The phosphoramidite group can couple with a hydroxy at any site on a nucleotide, such as a 2'- or 3'-hydroxy, and form a phosphodiester bond by oxidation, so as to conjugating the conjugating molecule to an oligonucleotide. Thus even if the second functional group does not exist, the conjugating molecule disclosed herein will be able to be conjugated with the nucleotide. In this case, the conjugating molecule is fit for reacting with a hydroxy on the last nucleotide of a nucleotide sequence, and forming a phosphodiester bond by a subsequent oxidation, thereby conjugating the conjugating molecule of the disclosure to an oligonucleotide.

In some embodiments, the first functional group comprises a protected hydroxy group. In some embodiments, the second functional group comprises a group reactive to a solid phase support to provide a conjugating molecule comprising a solid phase support. In some embodiments, the second functional group comprises a carboxyl, a carboxylate or a phosphoramidite, such as the functional group represented by Formula (C1), (C2) or (C3). The carboxyl or carboxylate can react via an esterification or an amidation with a hydroxy or an amino group on a solid phase support, such as a resin, to form a conjugating molecule comprising a solid phase support linked via a carboxylate ester bond or an amido bond. The phosphoramidite can couple with a hydroxy group on a universal solid phase support, such as a resin, and form a conjugating molecule comprising a solid phase support linked via a phosphodiester bond by subsequent oxidation. Accordingly, in one aspect of the invention, provided herein is a method for preparing a conjugate disclosed herein with such a conjugating molecule. In some embodiments, the method comprises firstly linking the conjugating molecule with a solid phase support by a condensation or a coupling reaction, and then adding nucleoside monomers in accordance with solid phase phosphoramidite synthesis method, thereby providing the conjugate disclosed herein comprising the conjugating molecule of the disclosure conjugated to an oligonucleotide. In some embodiments, during the solid phase phosphoramidite synthesis, the first functional group is deprotected, followed by a coupling with a phosphoramidite group on a nucleoside under a coupling condition.

In some embodiments, $R^4$ comprises a first functional group and a second functional group, wherein the first functional group comprises a hydroxy or a protected hydroxy group, and the second functional group comprises a carboxylate ester bond, an amido bond or a phosphodiester bond, or a solid phase support linked via the carboxylate ester bond, the amido bond or the phosphodiester bond. In some embodiments, the second functional group is a moiety represented by Formula (C1') or (C3'). In some embodiments, when the second function group comprises a solid phase support, the conjugating molecule comprising such a solid phase support is useful for preparing the conjugate disclosed herein. Accordingly, in one aspect of the invention, provided herein is a method for preparing the conjugate disclosed herein with the conjugating molecule. In some embodiments, the method comprises reacting the conjugating molecule comprising a solid phase support with nucleoside monomers in accordance with solid phase phosphoramidite synthesis method, thereby providing the conjugating molecule of the disclosure conjugated to an oligonucleotide. In some embodiments, the conjugating molecule comprising a solid phase support may be prepared inhouse from the conjugating molecule with a carboxyl, a carboxylate or a phosphoramidite by reacting the conjugating molecule with a solid phase support. In some embodiments, the conjugating molecule may be supplied by a supplier.

In some embodiments, the carboxylate may be represented by $—COO^-M^+$, wherein $M^+$ is a cation such as a metal cation, an ammonium cation $NH_4^+$ or an organic ammonium cation. In some embodiments, the metal cation may be an alkali metal cation, such as $K^+$ or $Na^+$. In order to increase solubility and facilitate the reaction, in some embodiments, the organic ammonium cation is an ammonium cation formed by a tertiary amine or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments of the disclosure, $R_4$ is a group represented by Formula (B9), (B10), (B9'), (B10'), (B11), (B12), (B11') or (B12'):

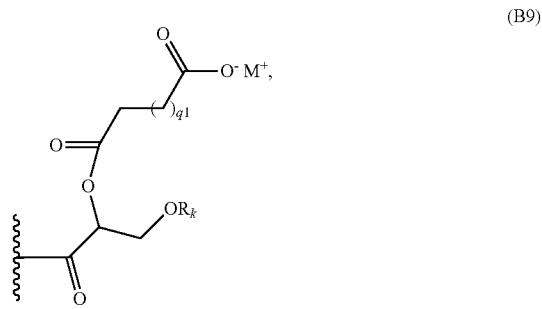

(B9)

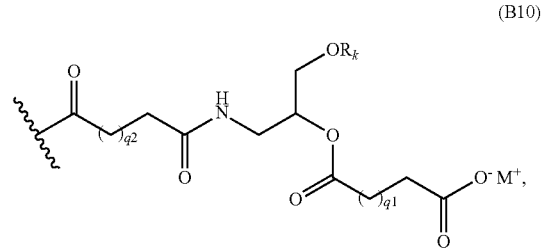

(B10)

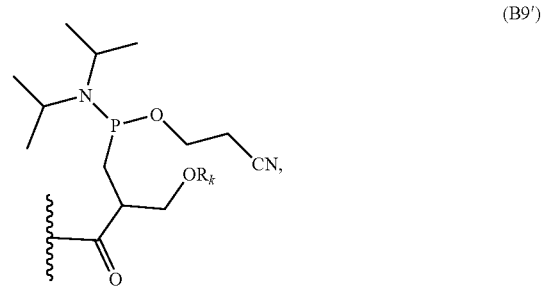

(B9')

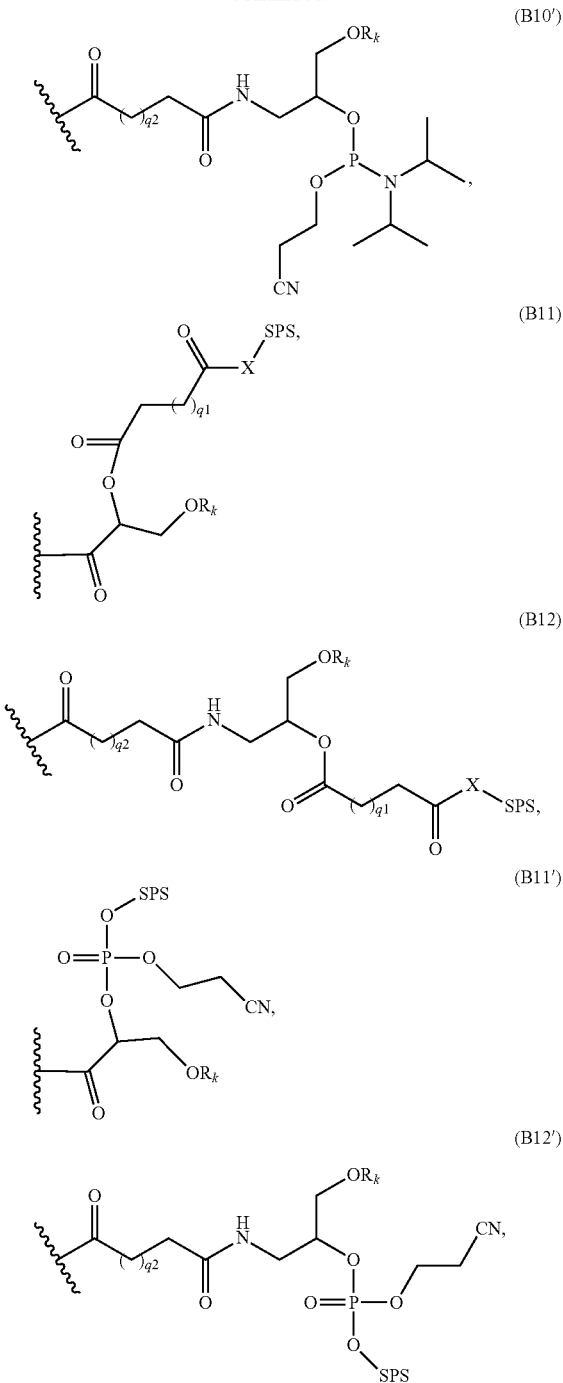

wherein $q_1$ is an integer of 1-4, $q_2$ is an integer of 1-10, X is O or NH, M⁺ is a cation, $R_k$ is a hydroxy protecting group, SPS represents a solid phase support, and ∿ represents the site there the group is covalently attached. In some embodiments, $q_1$ is 1 or 2. In some embodiments, $q_2$ is an integer of 1-5. In some embodiments, $R_4$ comprises a group represented by Formula (B9) or (B10). In some embodiments, $R_4$ comprises a group represented by Formula (B11) or (B12).

In some embodiments, $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ is DMTr.

$L_1$ a linear alkylene of 1 to 70 carbon atoms in length, wherein one or more carbon atoms are optionally replaced with any one or more of the group consisting of: C(O), NH, O, S, CH=N, S(O)₂, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH₂, —$C_1$-$C_{10}$ alkyl-NH₂, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO₂H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH₂, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO₂($C_1$-$C_{10}$ alkyl), —SO₂(phenyl), —SO₂($C_1$-$C_{10}$ haloalkyl), —SO₂NH₂, —SO₂NH($C_1$-$C_{10}$ alkyl), —SO₂NH(phenyl), —NHSO₂($C_1$-$C_{10}$ alkyl), —NHSO₂(phenyl), and —NHSO₂($C_1$-$C_{10}$ haloalkyl). A skilled one would understand that, though $L_1$ is defined as a linear alkylene for convenience, but it may not be a linear group or be named differently, such as an amine or alkenyl as a result of the above replacement and/or substitution. For the purpose of the disclosure herein, the length of $L_1$ is the atom number in the chain connecting the two attaching point. For this purpose, a ring resulted from replacement of a carbon atom of the linear alkylene, such as a heterocyclylene or heteroarylene, is counted as one atom.

In some embodiments, $L_1$ is used to link the $M_1$ ligand (or the corresponding $S_1$ group) to the N atom on the nitrogenous backbone, thereby providing liver targeting function for the conjugate of the disclosure. In some embodiments, $L_1$ comprises any one of Formulae A1-A26, and any combinations thereof. In some embodiments, L is any one of A1, A4, A5, A6, A8, A10, A11, A13, and combinations thereof. In some embodiments, $L_1$ is a combination of at least two of A1, A4, A8, A10, and A11; In some embodiments, $L_1$ is a combination of at least two groups of A1, A8, and A10.

In some embodiments, the length of L may be 3 to 25, 3 to 20, 4 to 15 or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

In some embodiments according to the present disclosure, therefore, j is an integer of 2-10, and in some embodiments is an integer of 3-5; j2 is an integer of 2-10, and in some embodiments is an integer of 3-5; R' is a $C_1$-$C_4$ alkyl, and in some embodiments is one of methyl, ethyl, and isopropyl. Ra is one of A27, A28, A29, A30, and A31, and in some embodiments is A27 or A28; Rb is a $C_1$-$C_5$ alkyl, and in some embodiments is one of methyl, ethyl, isopropyl, and butyl. In some embodiments, j1, j2, R', Ra, and Rb of A1-A26 are respectively selected to achieve the linkage between the $M_1$ ligands and the N atom on the nitrogenous backbone in the oligonucleotide conjugate formed by the conjugating molecule, and to make the steric position among $M_1$ ligands more suitable for binding $M_1$ ligands to the asialoglycoprotein receptors on the surface of hepatocytes.

Each $M_1$ is independently selected from a ligand capable of binding to a cell surface receptor. In some embodiments, at least one $M_1$ is a ligand capable of binding to a hepatocyte surface receptor. In some embodiments, at least one $M_1$ is a ligand capable of binding to a mammalian cell surface receptor. In some embodiments, at least one $M_1$ is a ligand capable of binding to a human hepatocyte surface receptor. In some embodiments, at least one $M_1$ is a ligand capable of binding to hepatic surface asialoglycoprotein receptors (ASGPR).

In some embodiments, $M_1$ may be any one of the ligands that have affinity to the asialoglycoprotein receptors (ASGP-R) on the surface of mammalian hepatocytes. The types of these ligands are well known to those skilled in the art. In some embodiments, at least one of M is a saccharide. In some embodiments, each $M_1$ is a saccharide. In some embodiments, at least one of $M_1$ is a monosaccharide, disaccharide, trisaccharide or polysaccharide. In some embodiments, each $M_1$ is a monosaccharide, disaccharide, trisaccharide or polysaccharide. In some embodiments, at least one of $M_1$ is a modified saccharide. In some embodiments, each M is a modified saccharide. In some embodiments, each $M_1$ is independently selected from polysaccharides, modified polysaccharides, monosaccharides or monosaccharide derivatives. In some embodiments, each or at least one $M_1$ may be independently selected from a group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each or at least one $M_1$ may be independently selected from a group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose. In some embodiments, at least one $M_1$ is N-acetylgalactosamine (GalNAc). In some embodiments, each $M_1$ is N-acetylgalactosamine (GalNAc). Ligand selection may be found, for example, in the disclosure of CN105378082A, which is incorporated herein by reference in its entirety.

CN105378082A discloses a compound comprising a modified oligonucleotide and a conjugating group, wherein the conjugating group comprises at least one phosphorus linking group or neutral linking group, as well as one or more ligand(s). Each ligand is selected from the group consisting of polysaccharides, modified polysaccharides, mannose, galactose, mannose derivatives, galactose derivatives, D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, α-D-galactosamine, N-acetylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose and L-4-thioribose. It is alleged that the compound can reduce the amount or activity of nucleic acid transcription in cells.

WO2016077321A1 discloses a number of siRNAs specifically targeting HBV gene and delivery methods thereof, and the serum stability of the siRNAs is enhanced by modifying the nucleotides thereof. This document also discloses siRNA conjugates, and further specifically discloses several siRNA conjugates.

WO2016168286A1 discloses a number of siRNAs specifically targeting ANGPTL3 gene and delivery methods thereof, and the serum stability of the siRNAs is enhanced by modifying the nucleotides thereof. This document also discloses siRNA conjugates.

N-acetylgalactosamine (GalNAc) is a ligand that binds to a hepatic surface asialoglycoprotein receptors (ASGPR). ASGPR is an endocytic receptor that is specifically expressed by hepatocytes. Recently, N-acetylgalactosamine (GalNAc) has been used as a targeting molecule to deliver small RNA drugs to liver. For example, Alnylam Pharmaceuticals, Inc. firstly reported that siRNAs based on GalNAc conjugation technology exert interference activity in mice (Nair et al., J. Am. Chem. Soc., 2014, 136, 16958-16961). The article reported that a siRNA conjugated to three clusters of GalNAc exhibits good delivery activity both in vitro and in vivo. Via in vivo experiments of mice administered subcutaneously, $ED_{50}$ of a single dose was determined to be 1 mg/kg when a single injection dose was less than 1 ml. In long-term administration experiments, a stable interfering activity for up to 9 months allegedly may be obtained by subcutaneously injection once a week.

In some embodiments, $S_1$ is independently an $M_1$. In some embodiments, $S_1$ is independently an $M_1$ having at least one active hydroxyl protected with a hydroxyl protecting group. In some embodiments, $S_1$ is independently an $M_1$ where all active hydroxyl, if any, has been protected with a hydroxyl protecting group. In some embodiments, any hydroxyl protecting group known to a skilled one may be used to protect the active hydroxyl on $M_1$. In some embodiments, the protected hydroxy is presented by the formula YCOO— wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

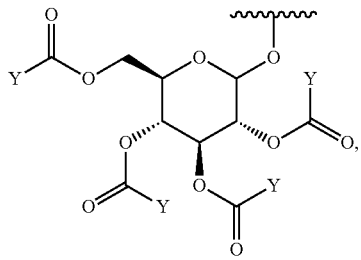
(A46)

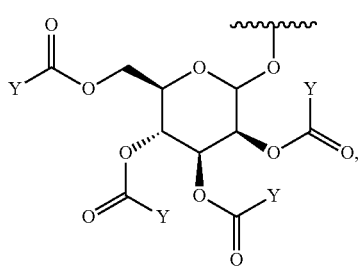
(A47)

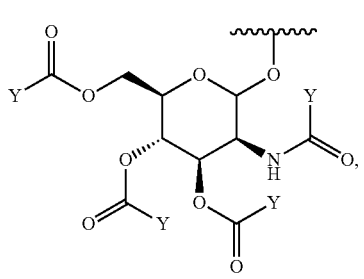
(A48)

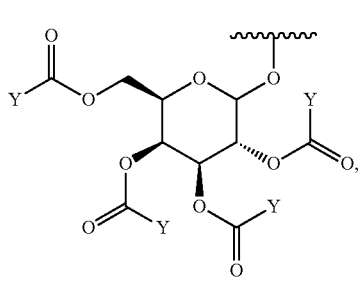
(A49)

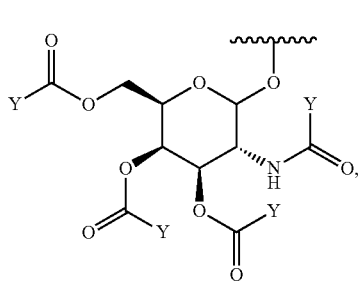
(A50)

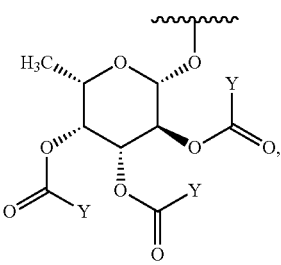
(A51)

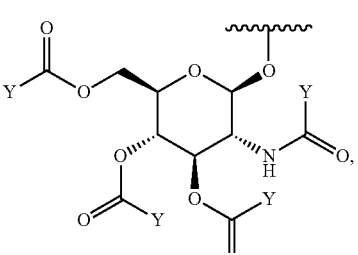
(A52)

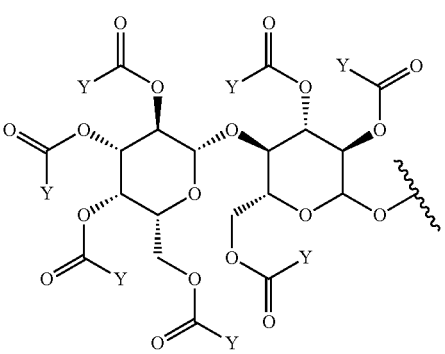
(A53)

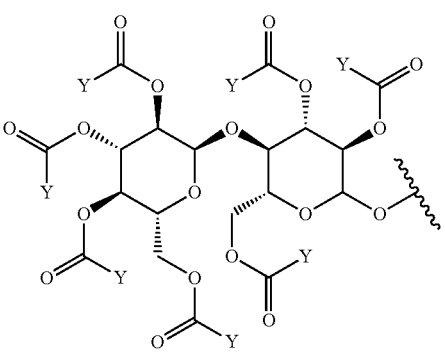
(A54)

In some embodiments, $S_1$ is A49 or A50. In some embodiments, Y is independently for each occurrence one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In order to simplify the conjugating molecule of the disclosure, In some embodiments, Y is methyl.

In some embodiments, the conjugating molecule of the present disclosure has a structure represented by Formula (403), (404), (405), (406), (407), (408), (409), (410), (411), (412), (413), (414), (415), (416), (417), (418), (419), (420), (421), or (422):

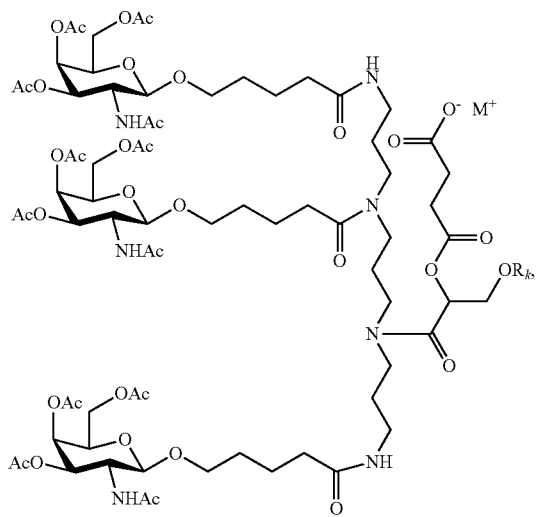
(403)
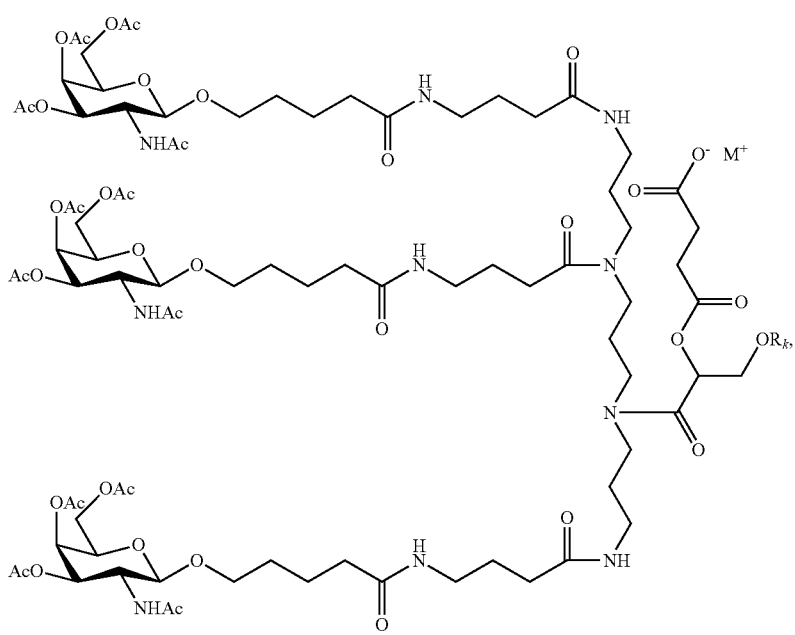
(404)

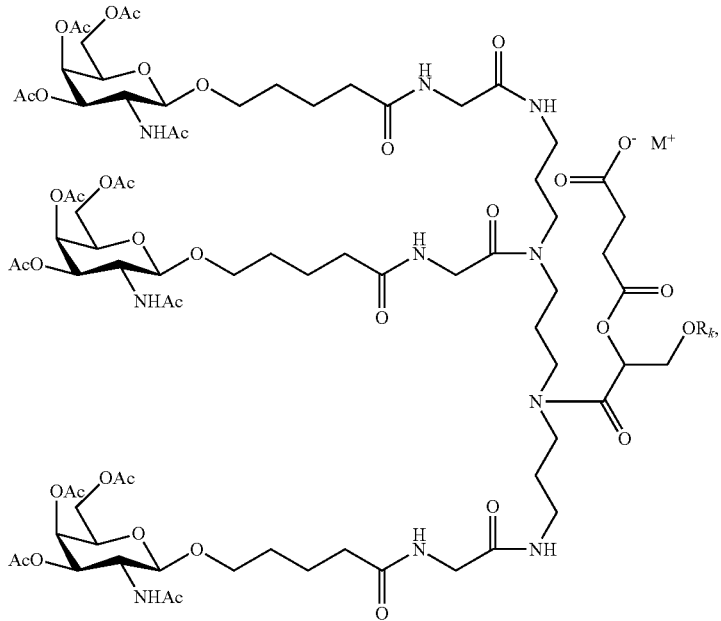
(405)
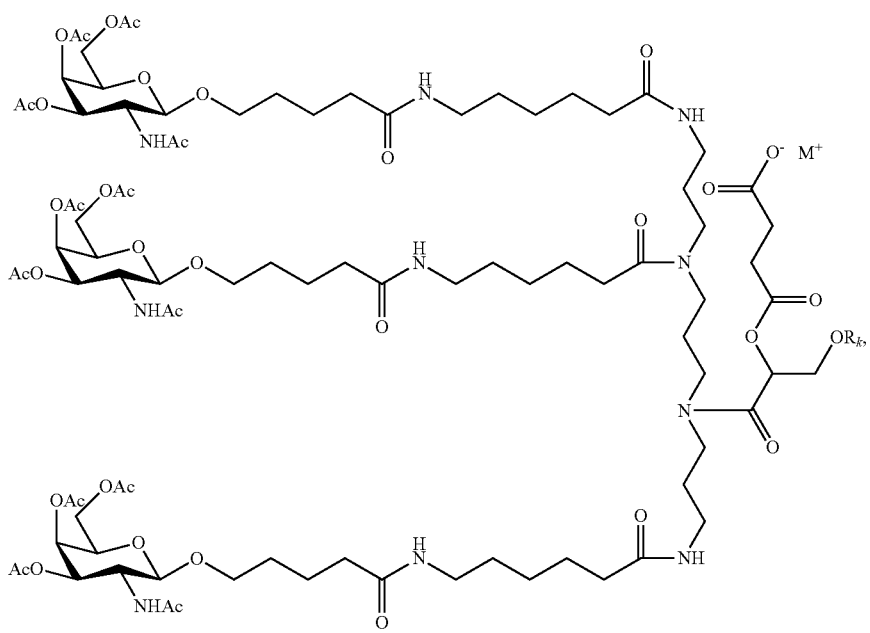
(406)

-continued
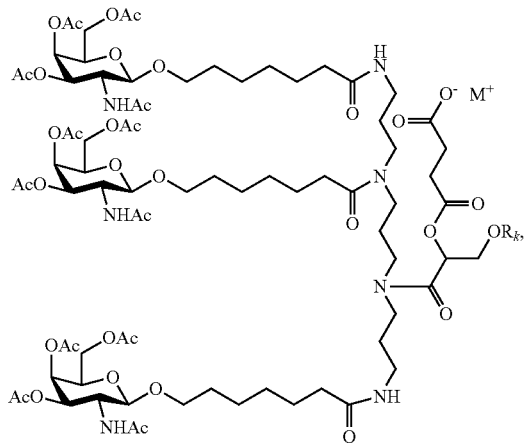
(407)
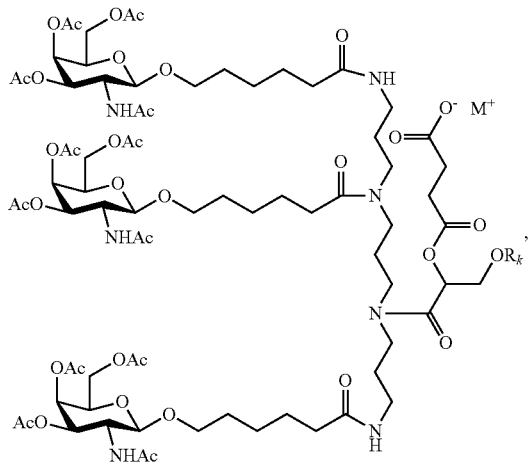
(408)
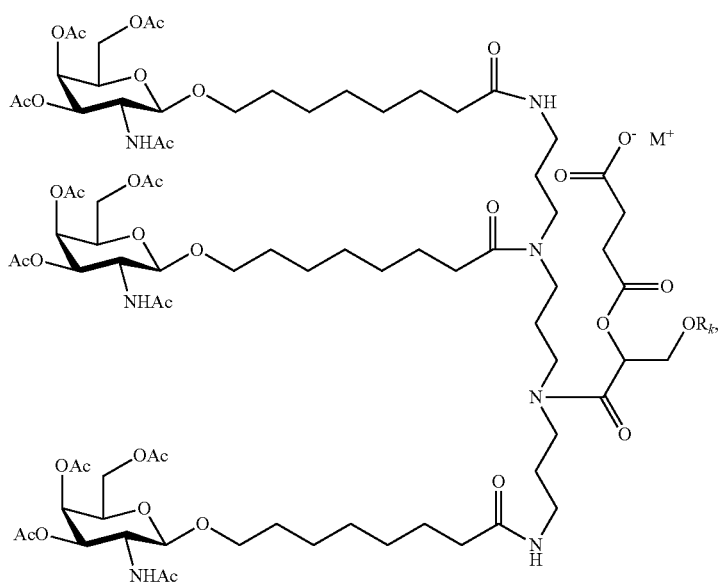
(409)
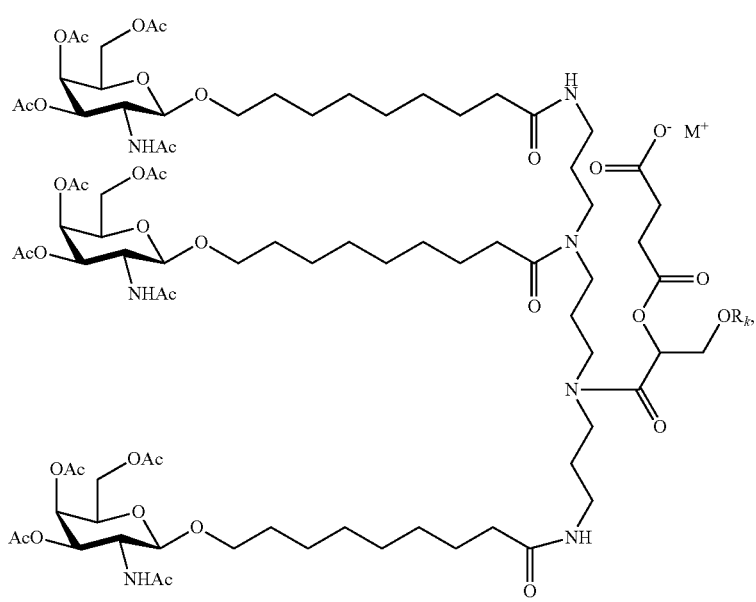
(410)

(411)
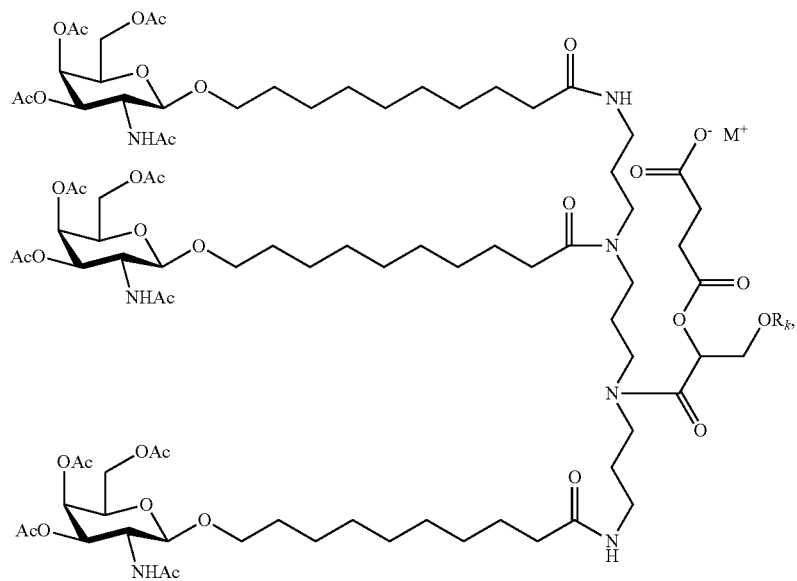
(412)
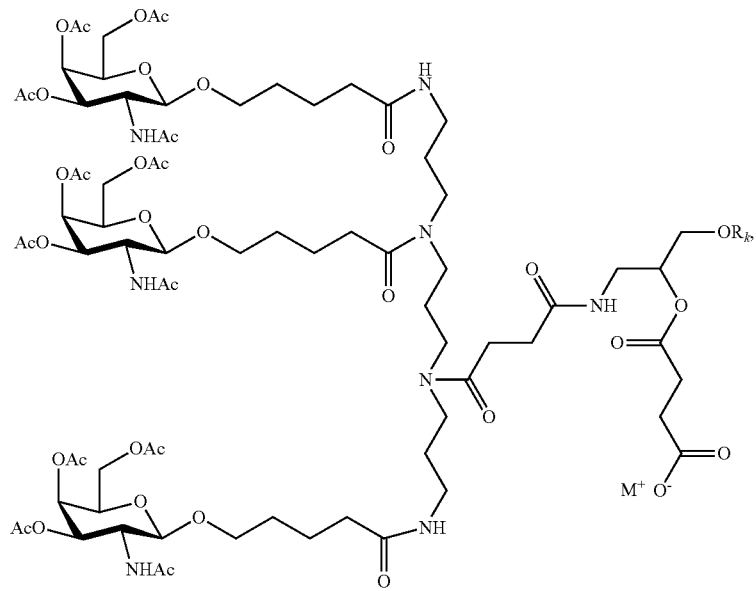

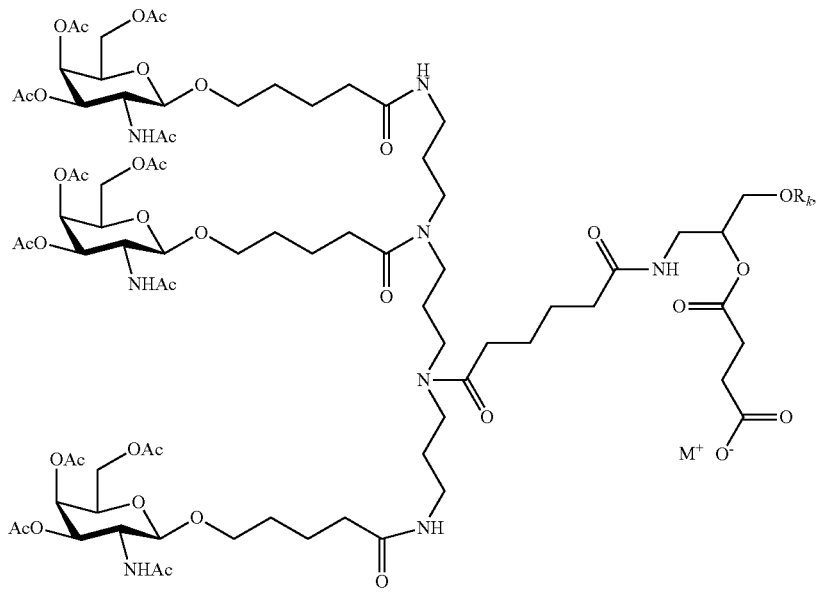
(413)
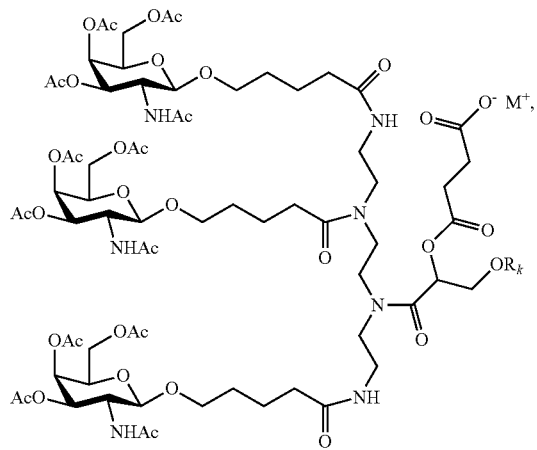
(414)
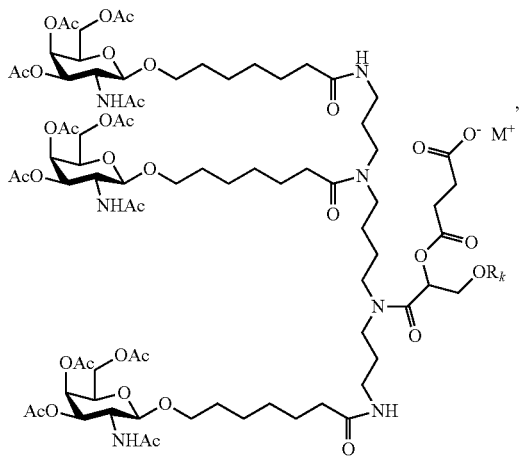
(415)
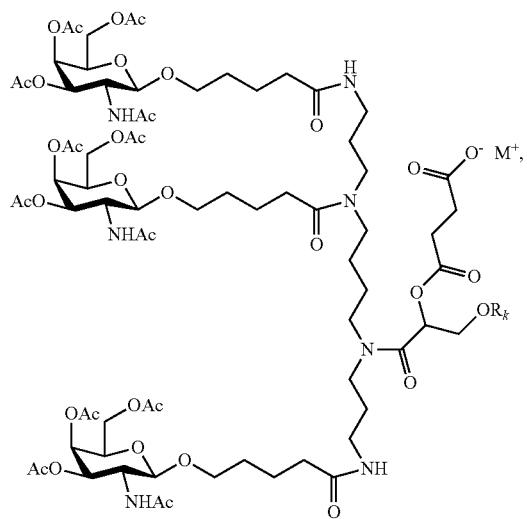
(416)
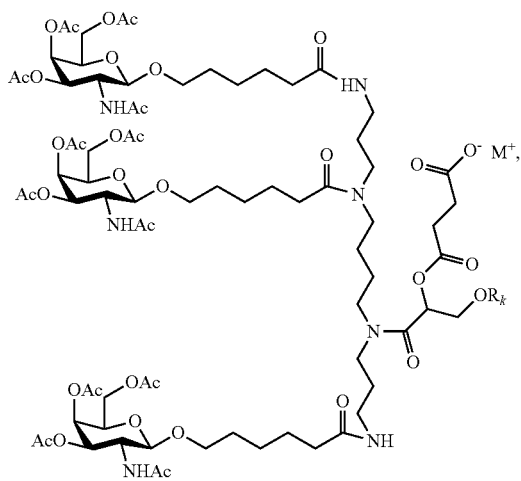
(417)

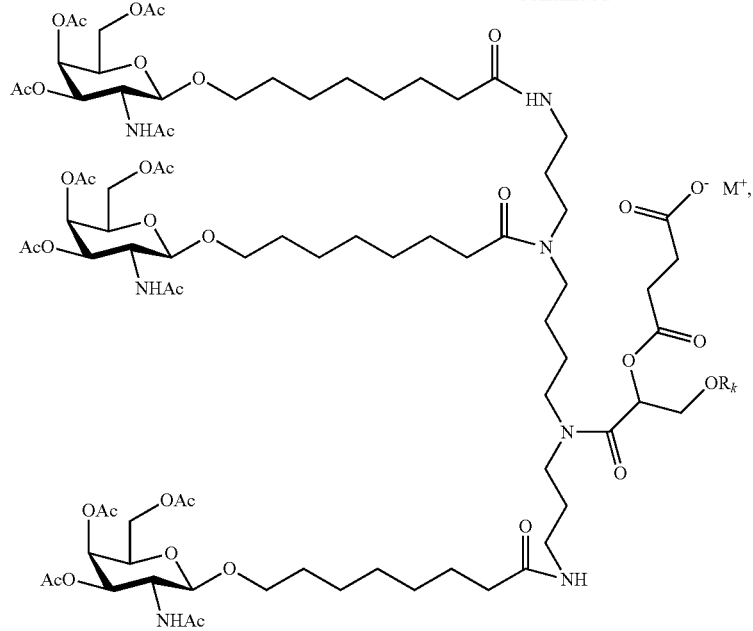
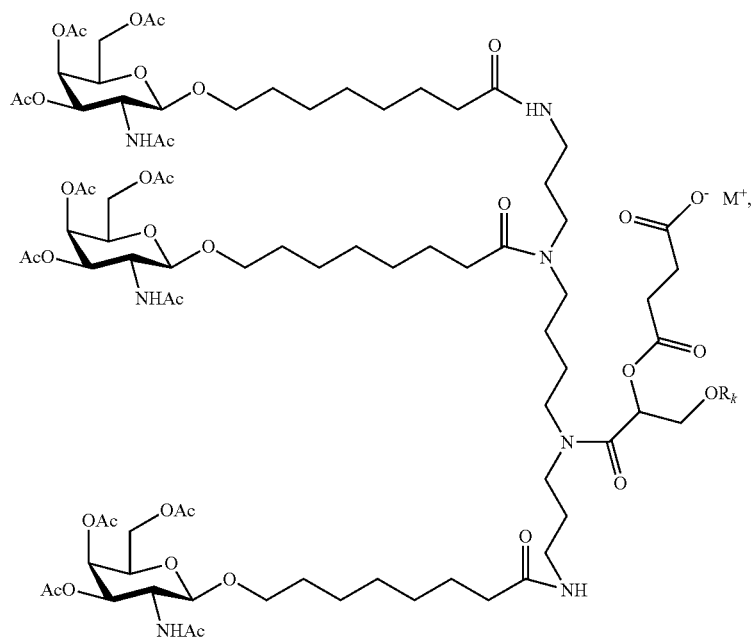
(418)

(419)
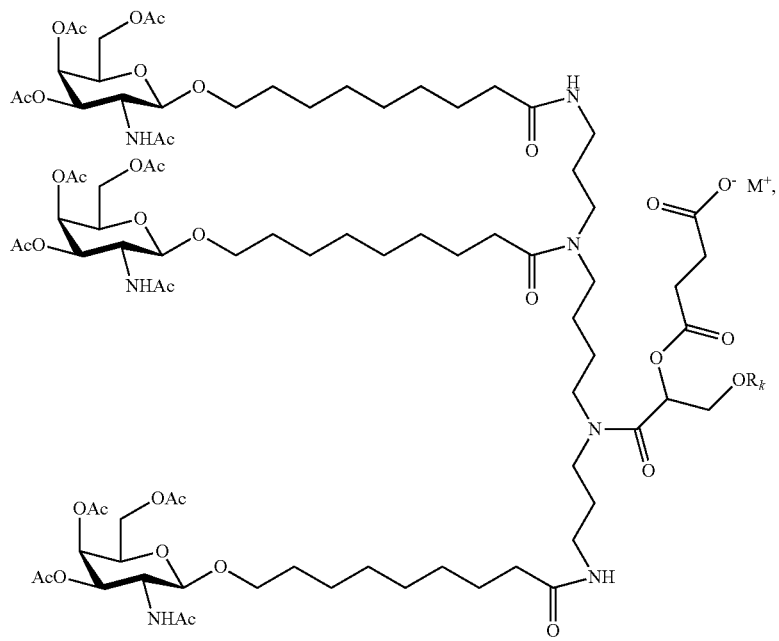
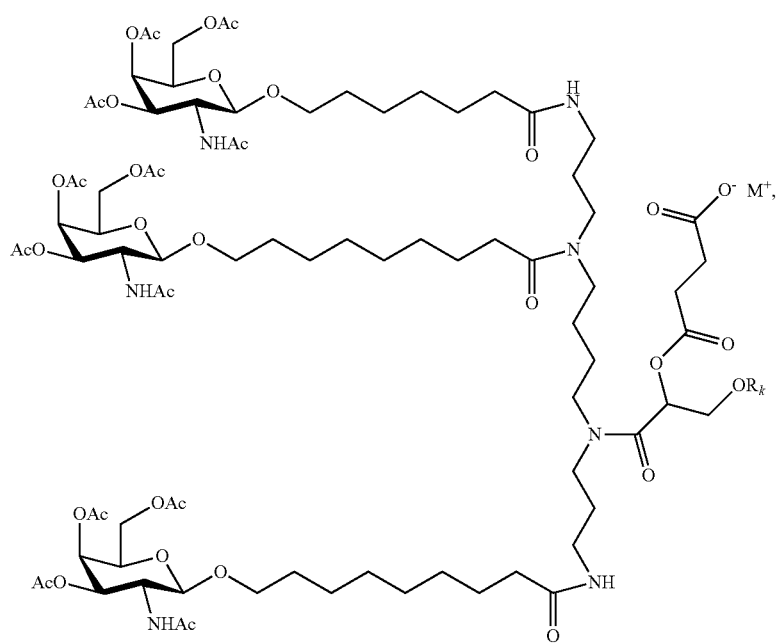

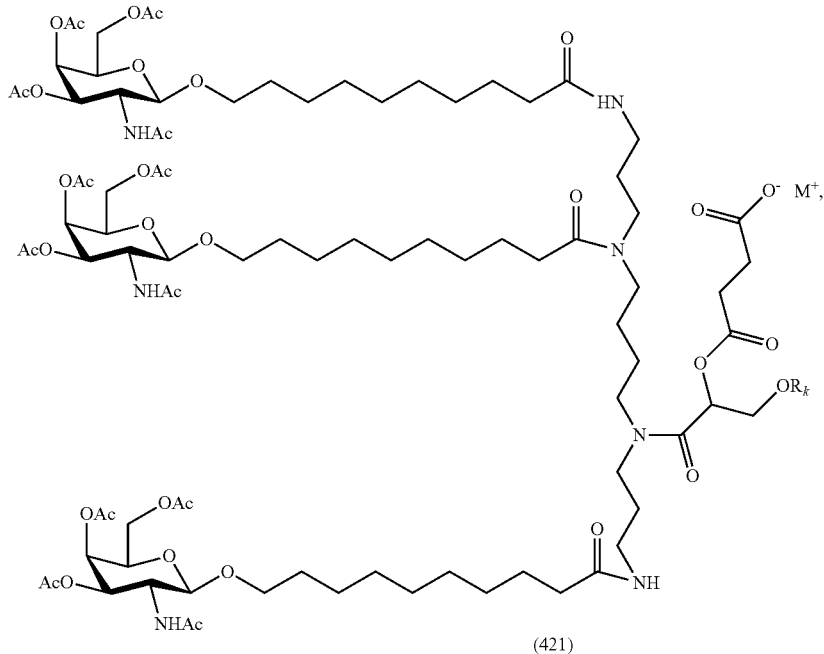
(420)
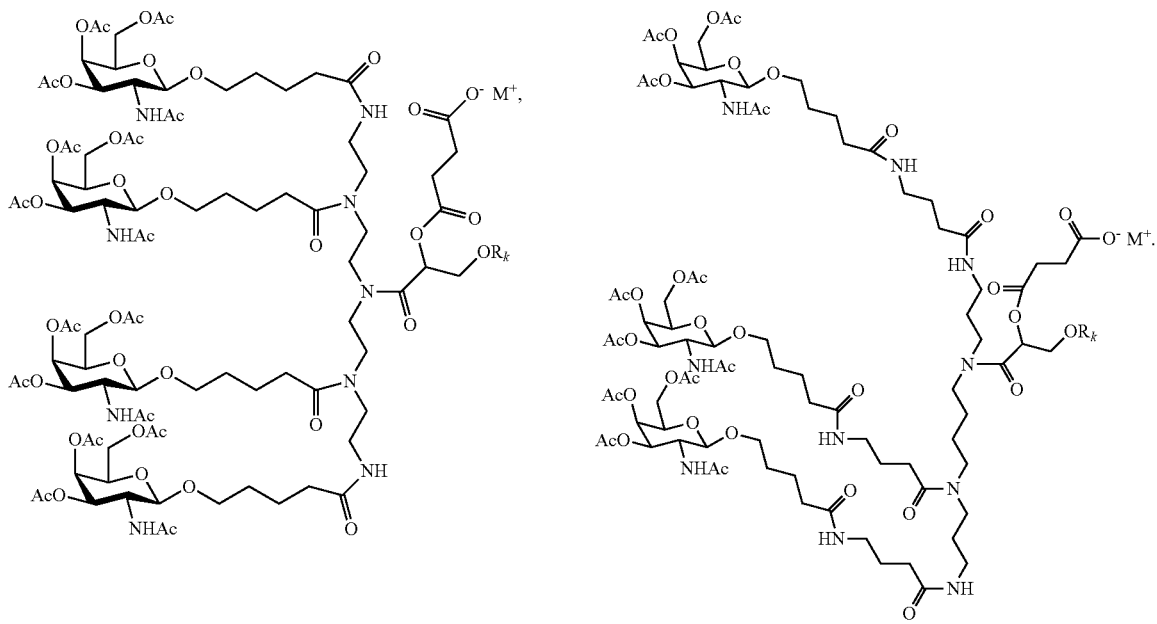
(421)  (422)
In Formulae (403) to (422) above, X is O or NH, $R_k$ is a hydroxy protecting group, and $M^+$ is a metal cation, an ammonium cation, a cation formed from a tertary amine, or a quaternary ammonium cation. In some embodiments, $M^+$ is
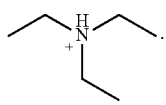
In some embodiments, the conjugating molecule of the present disclosure has a structure represented by Formula (423), (424), (425), (426), (427), (428), (429), (430), (431), (432), (433), (434), (435), (436), (437), (438), (439), (440), (441), or (442):

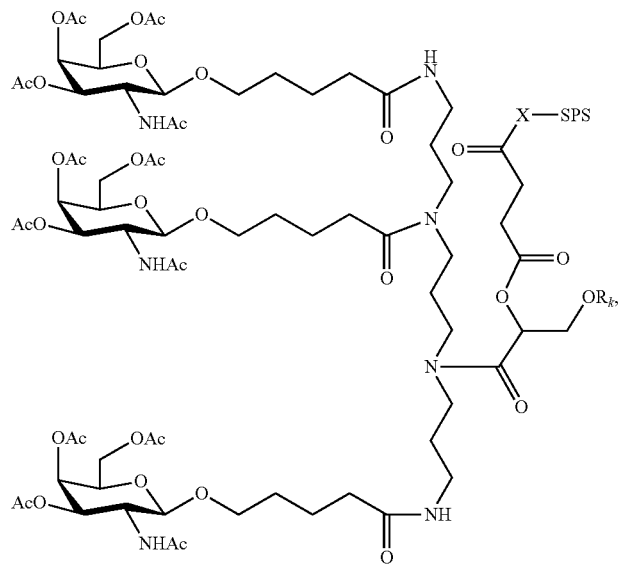
(423)
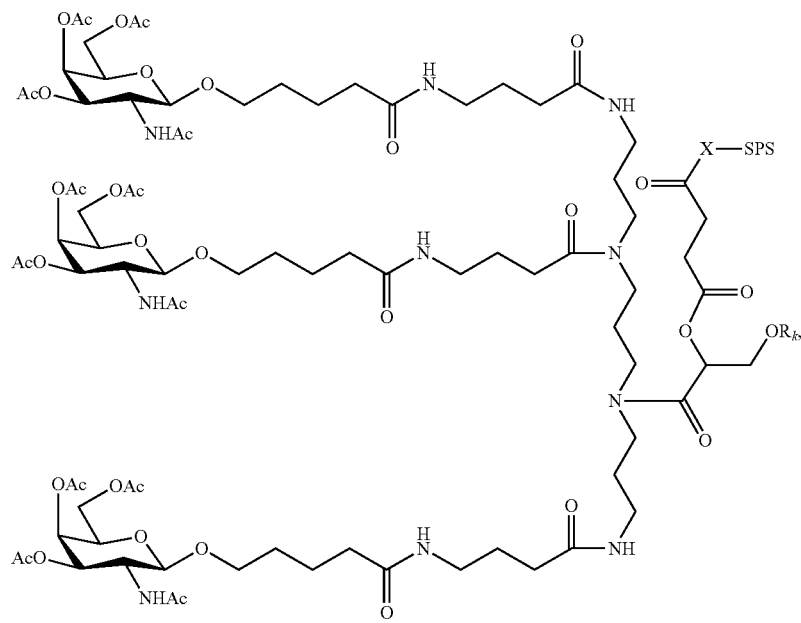
(424)

-continued
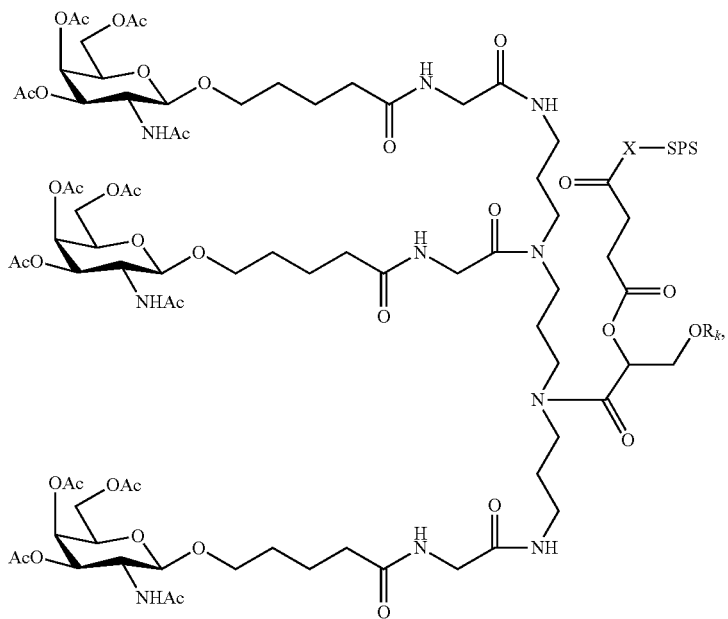
(425)
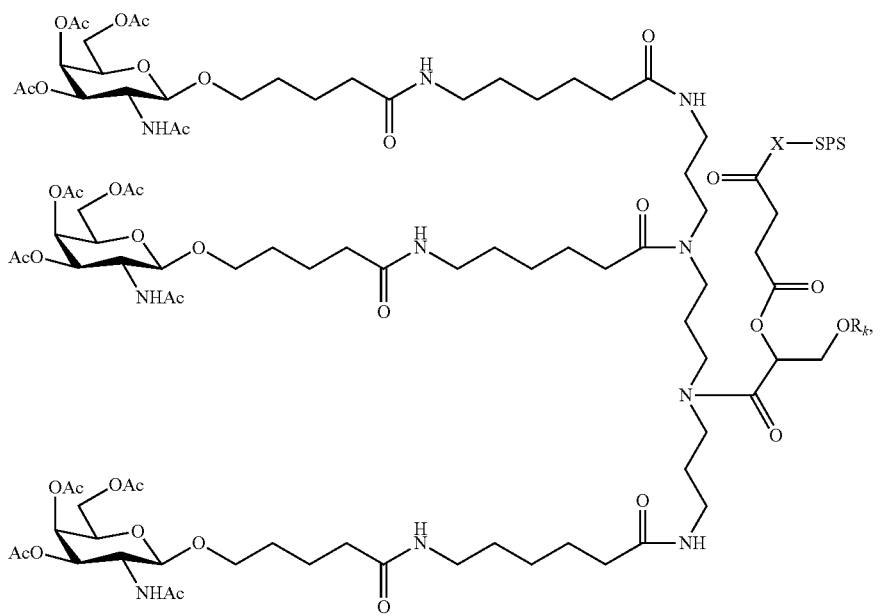
(426)

(427)
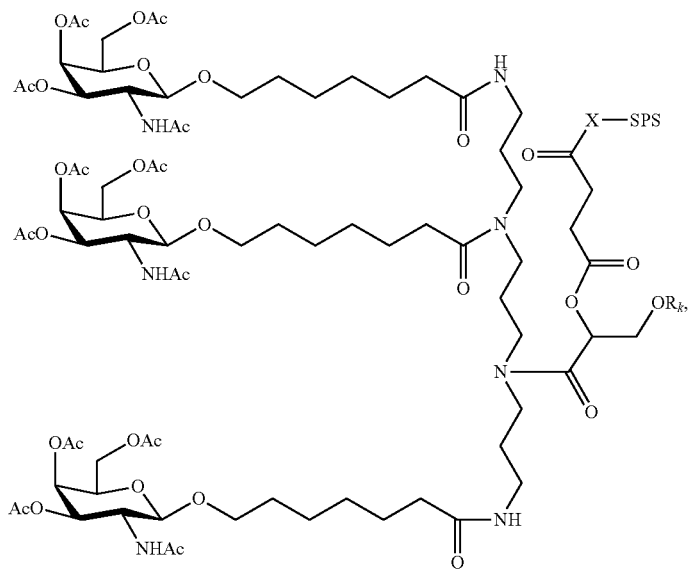
(428)
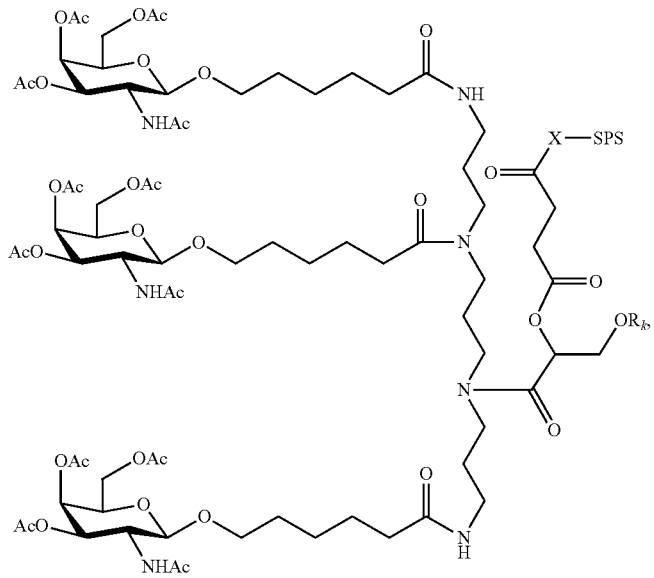

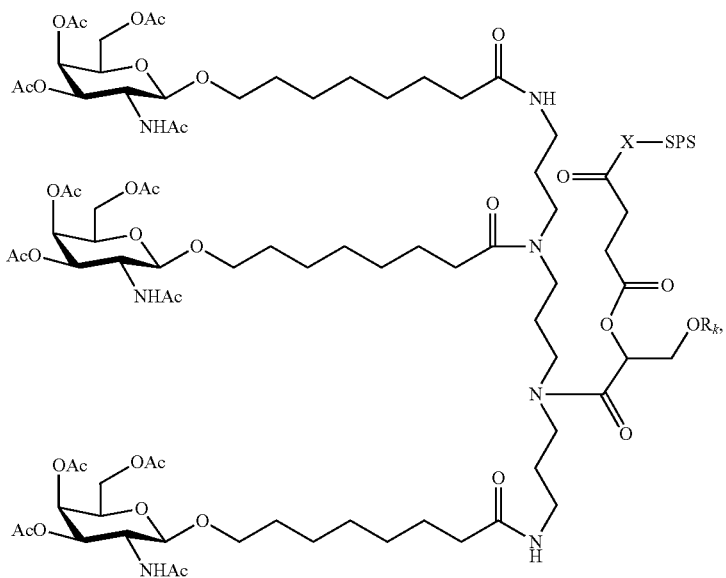
(429)
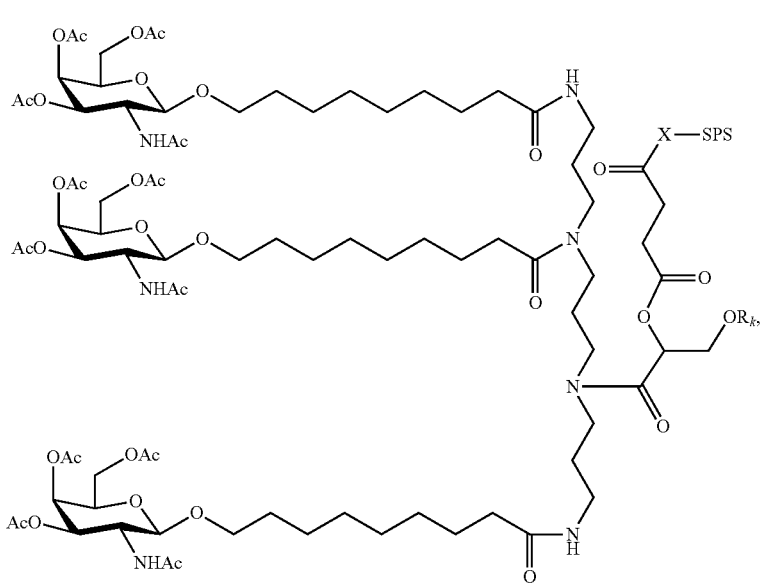
(430)

(431)
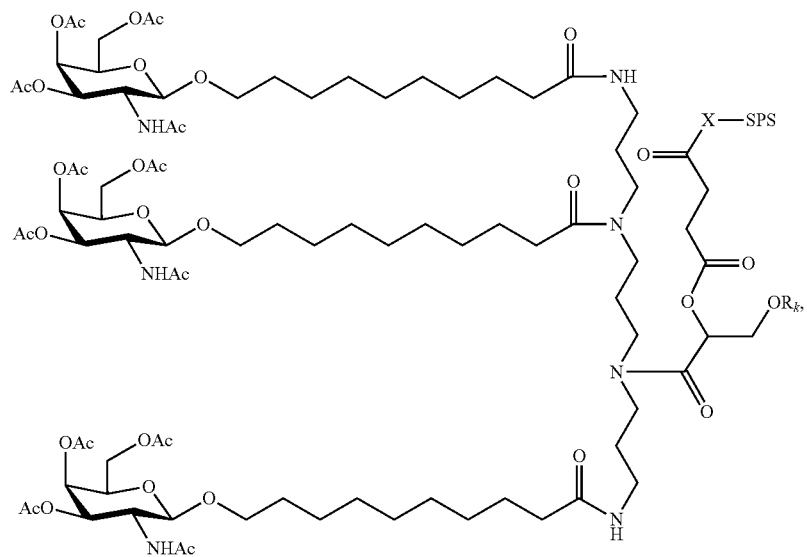
(432)
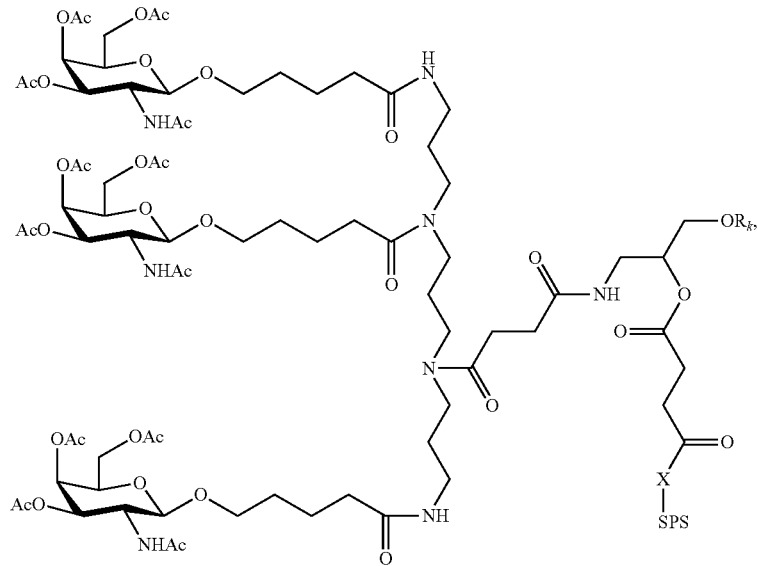

-continued
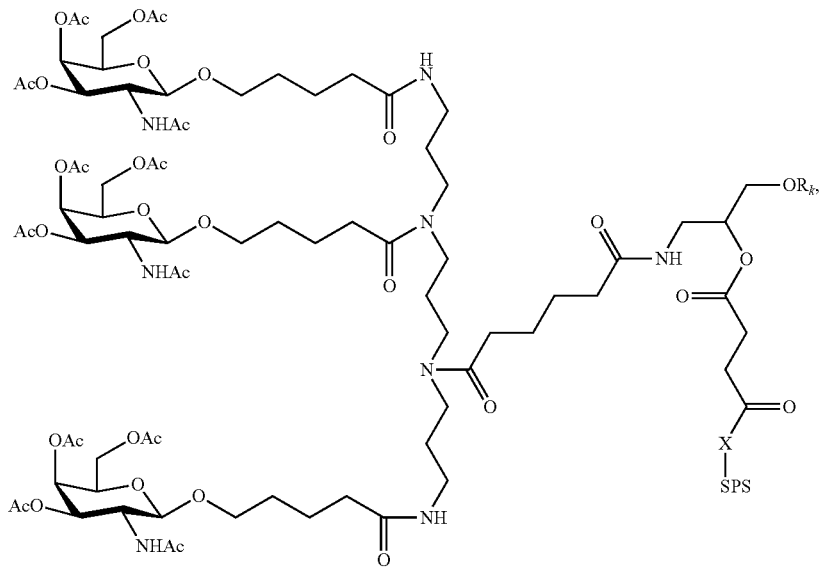
(433)
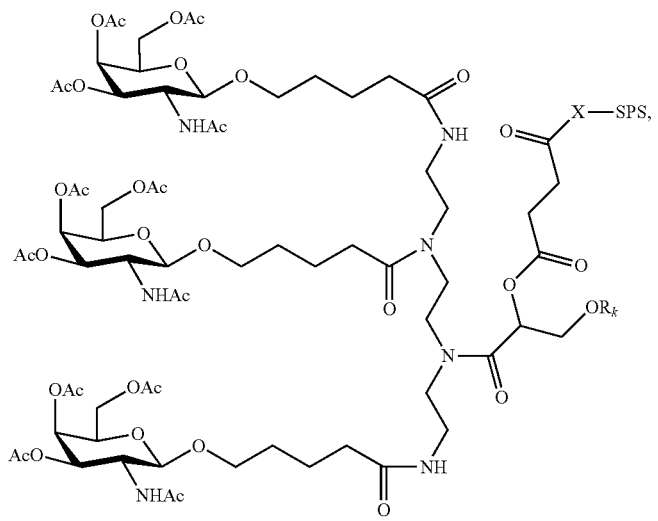
(434)

(435)
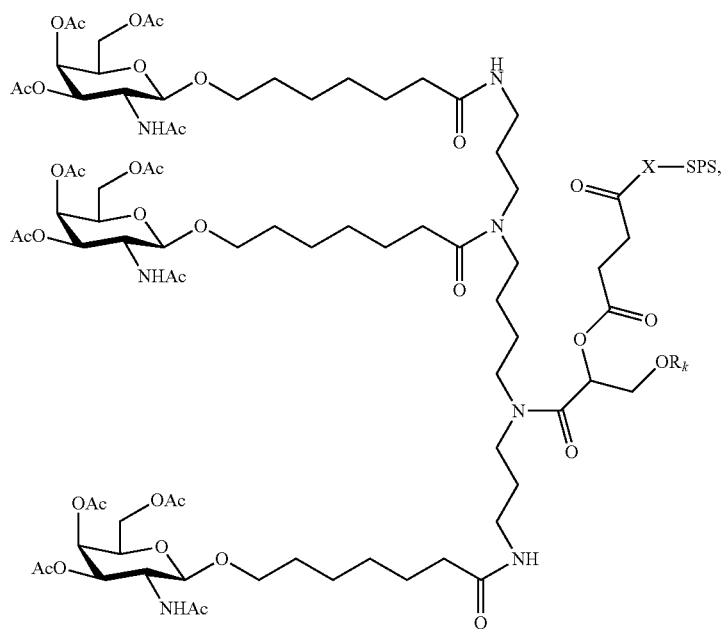
(436)
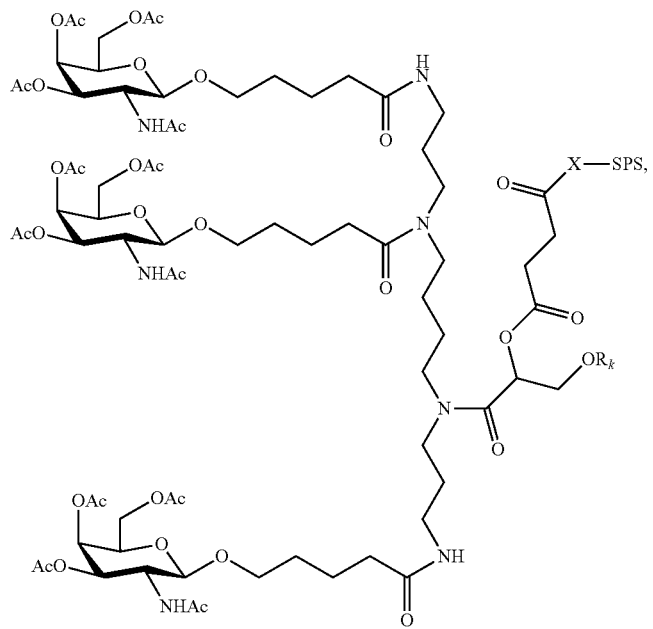

(437)
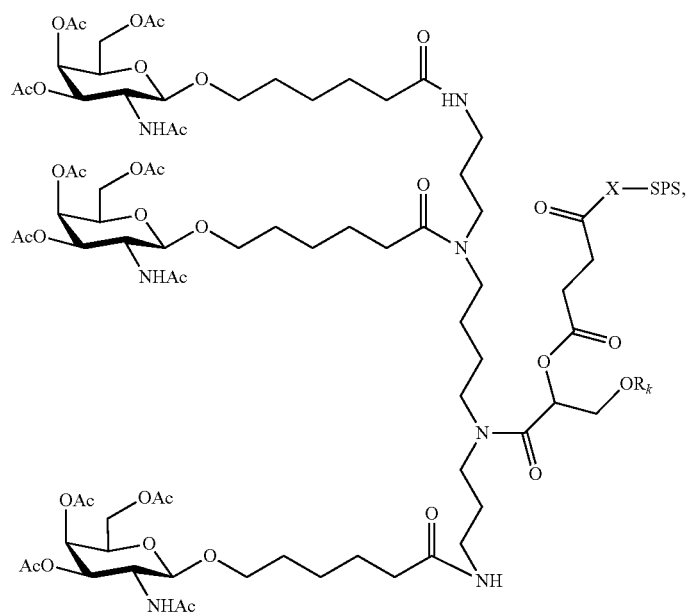
(438)
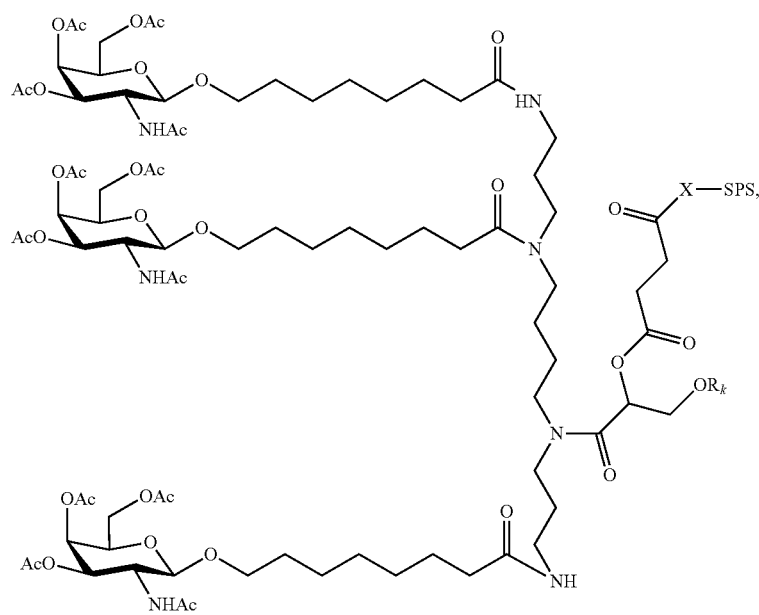

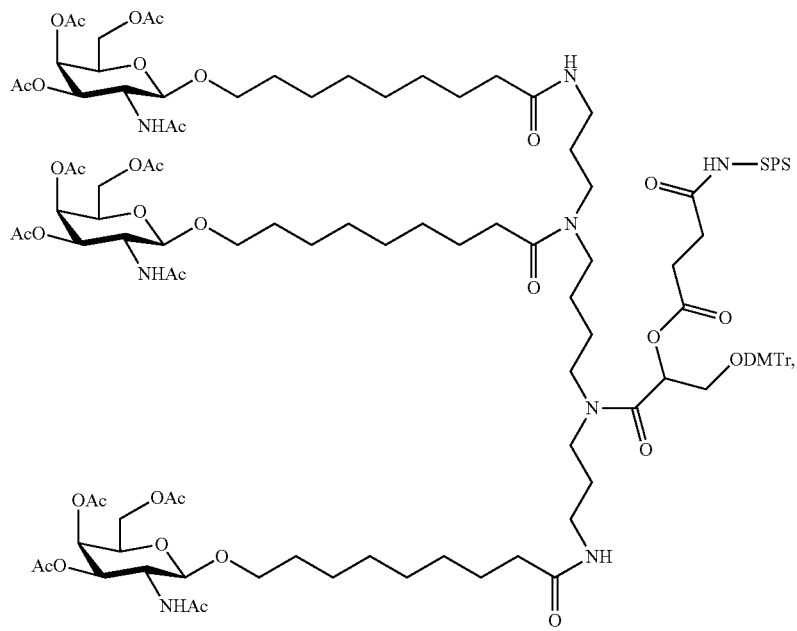
(439)
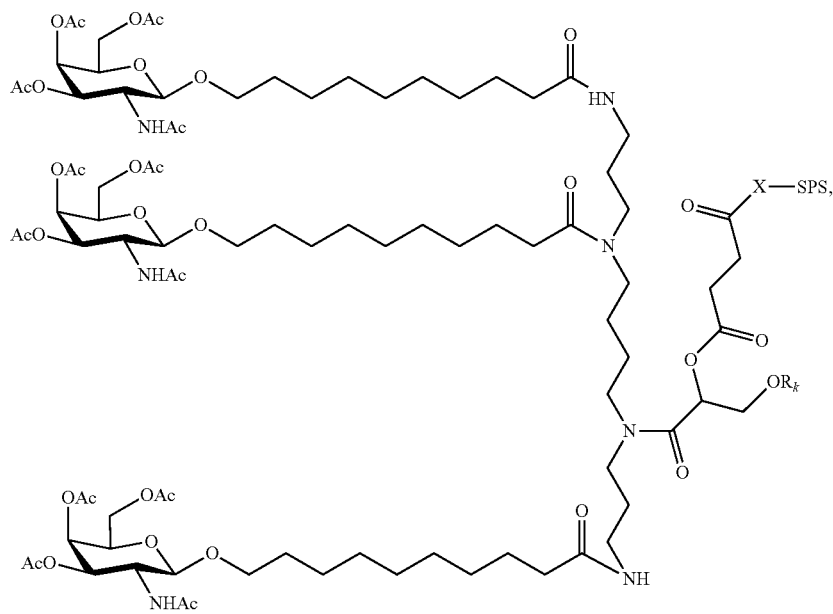
(440)

(441)
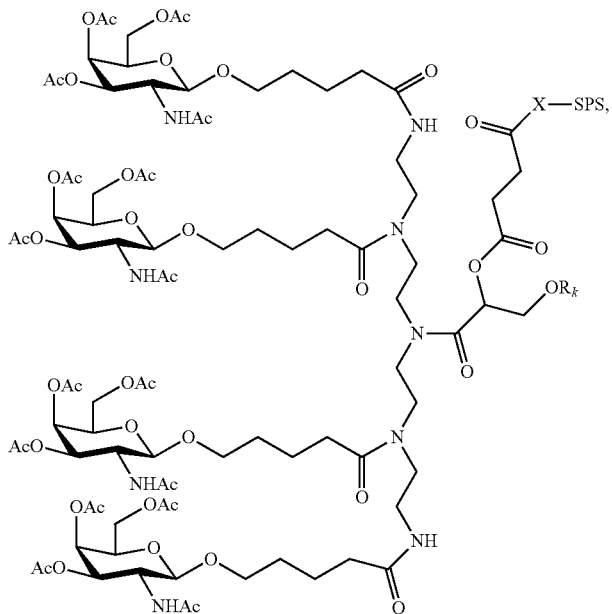
(442)
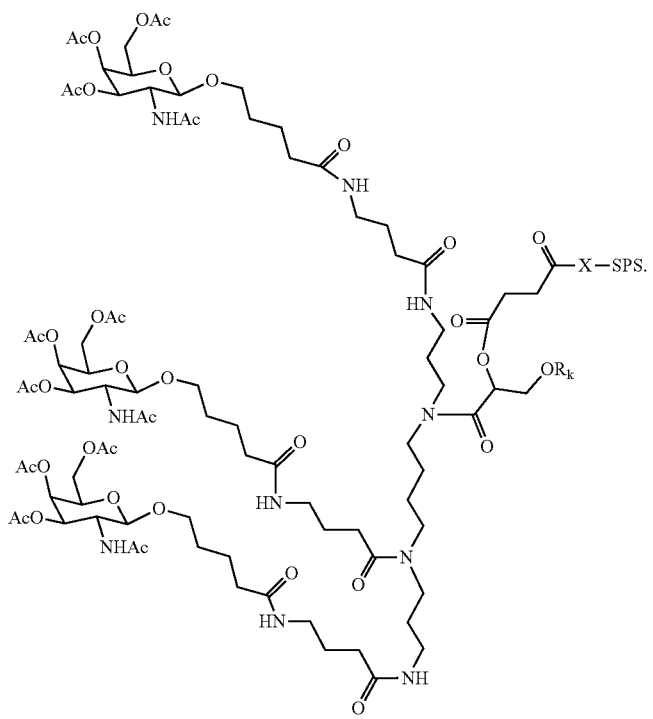
In Formulae (423) to (442) above, X is O or NH, $R_k$ is a hydroxy protecting group, and SPS represents a solid phase support.
In some embodiments, the conjugating molecule of the present disclosure has a structure represented by Formula (503), (504), (505), (506), (507), (508), (509), (510), (511), (512), (513), (514), (515), (516), (517), (518), (519), (520), (521), or (522):

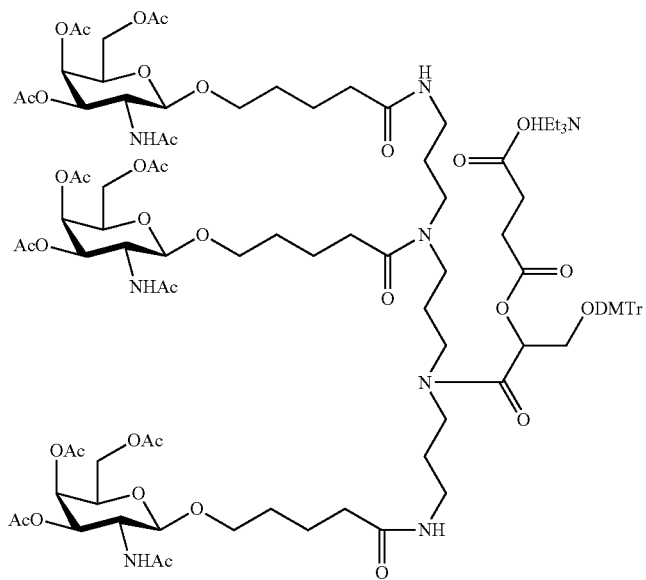
(503)
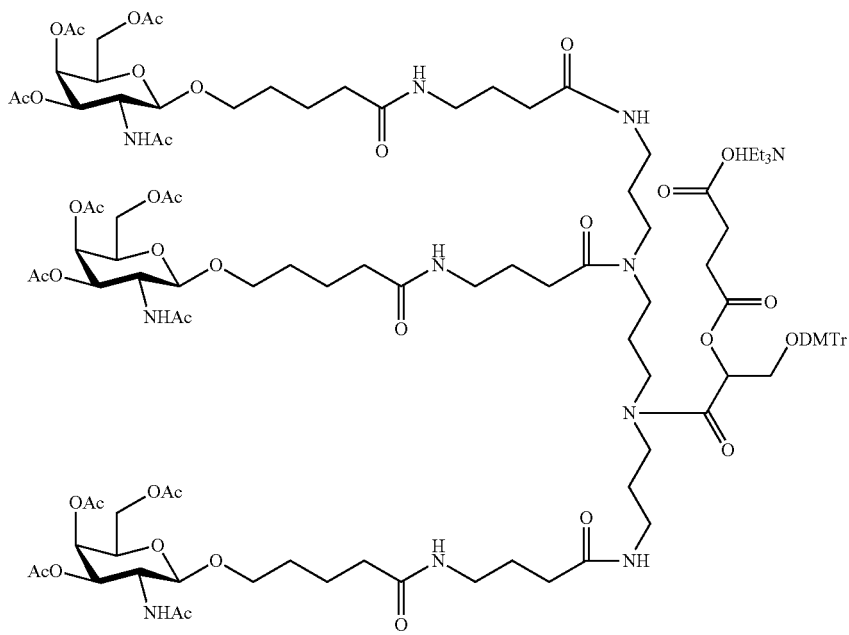
(504)

(505)
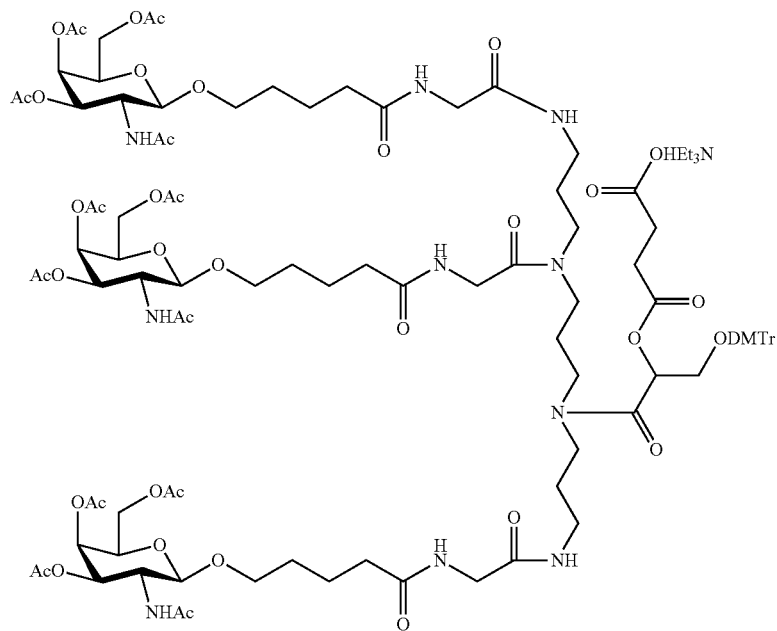
(506)
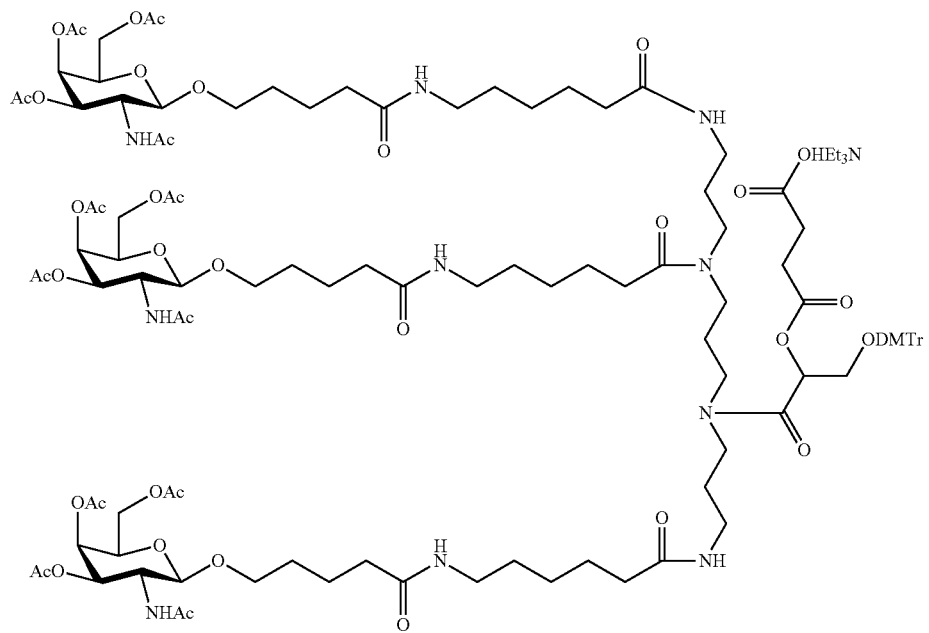

(507)
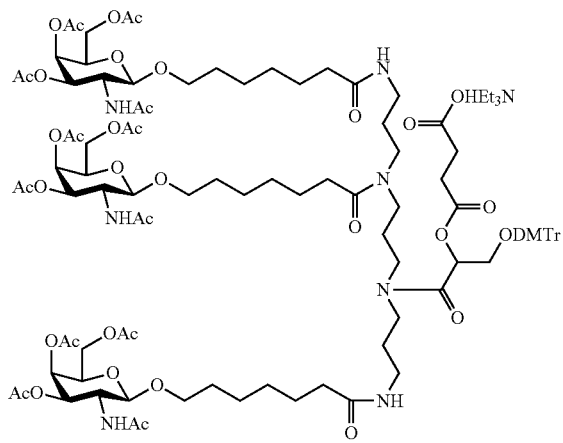
(508)
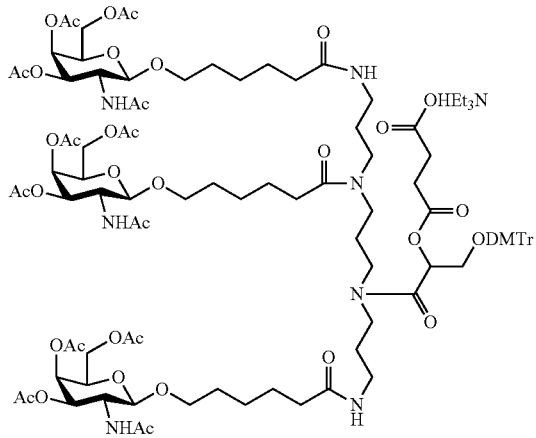
(509)
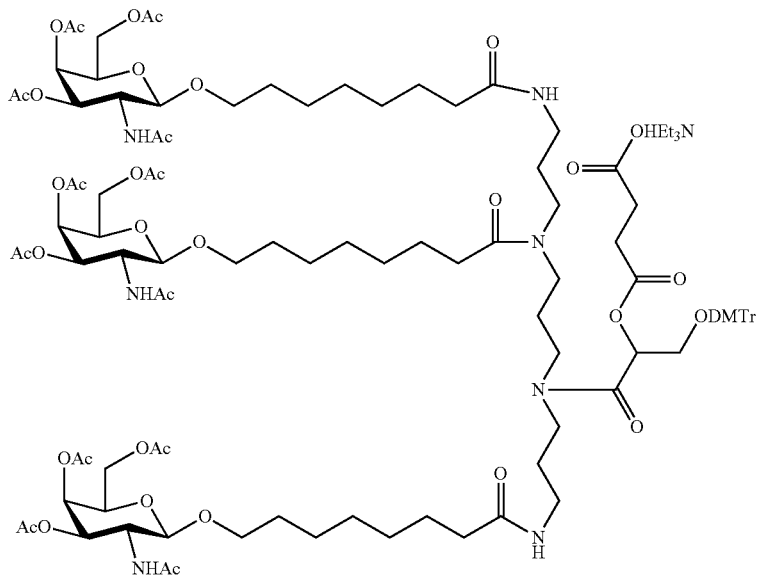
(510)
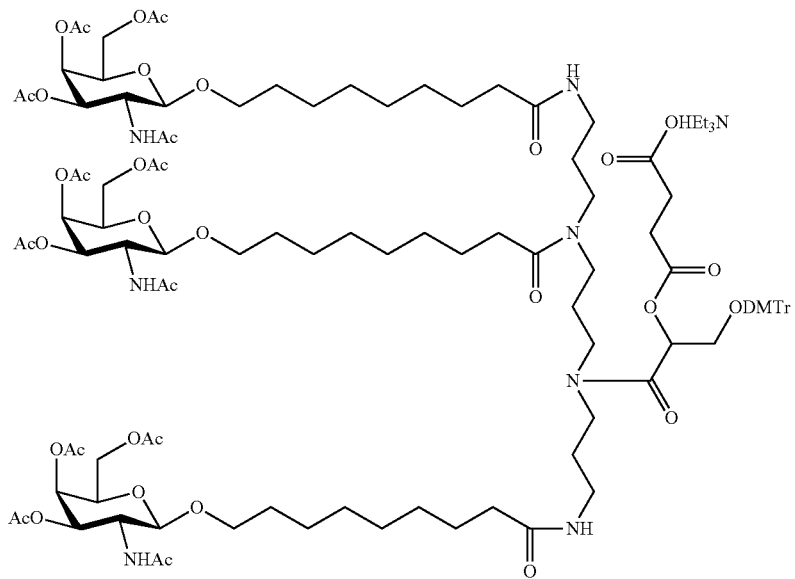

(511)
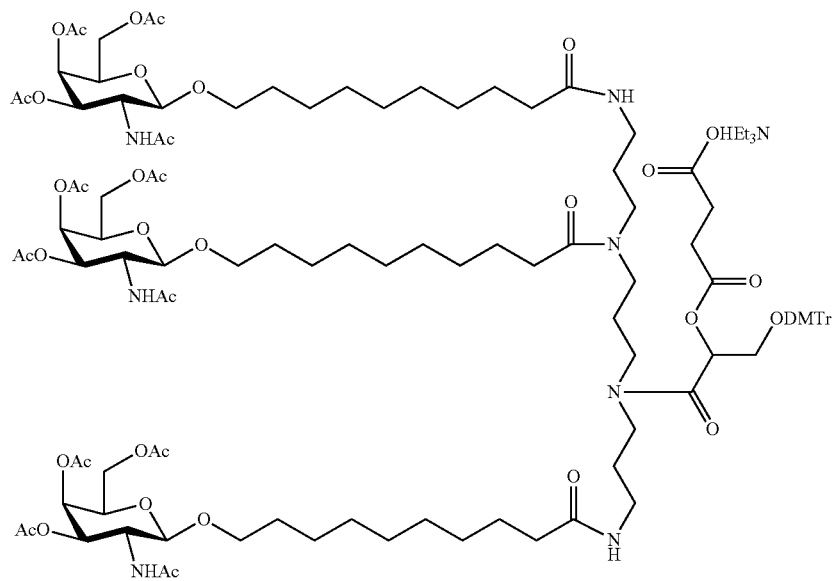
(512)
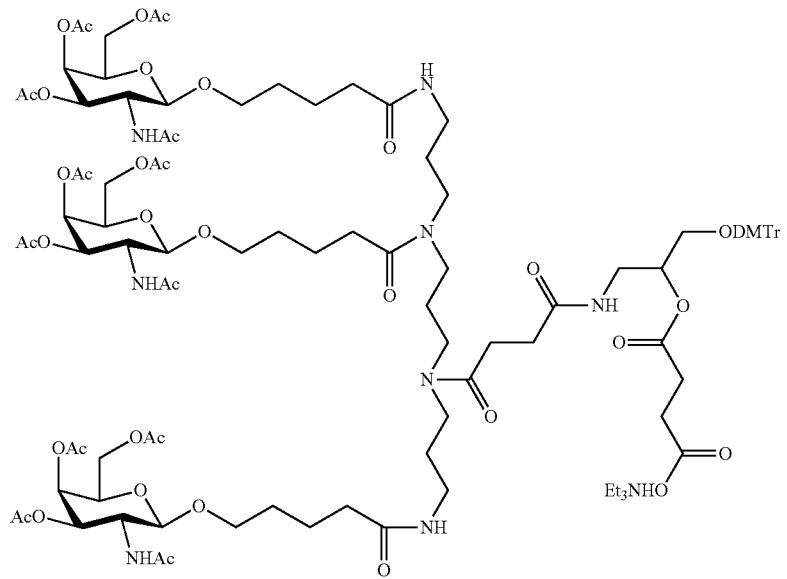

-continued
(513)
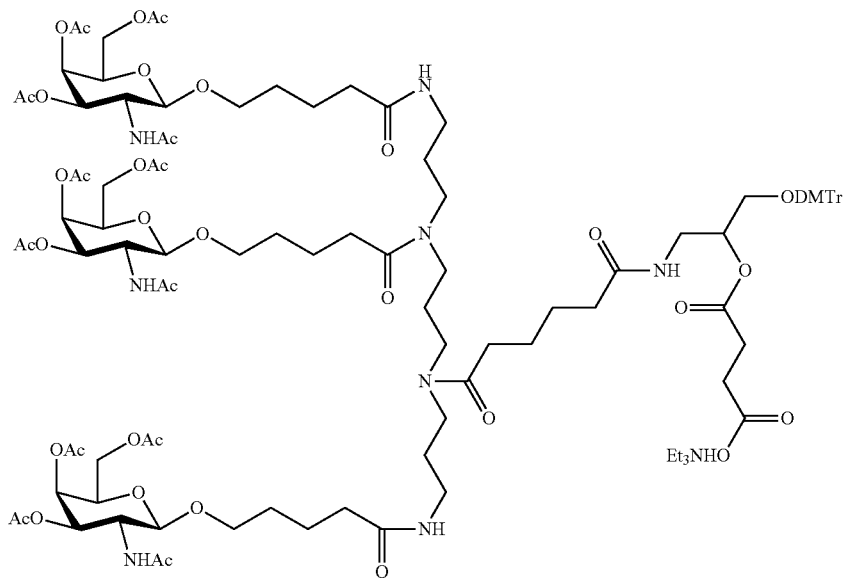
(514)
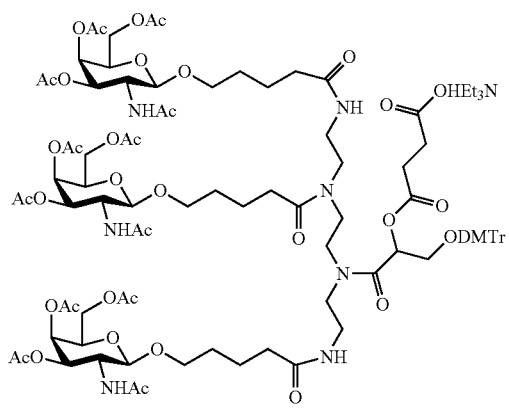
(515)
(516)
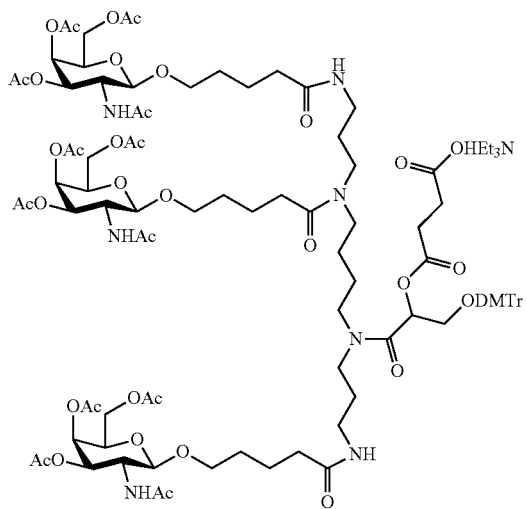
(517)
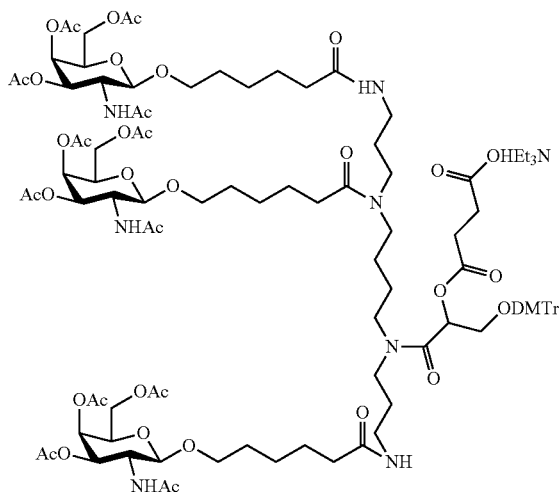

(518)
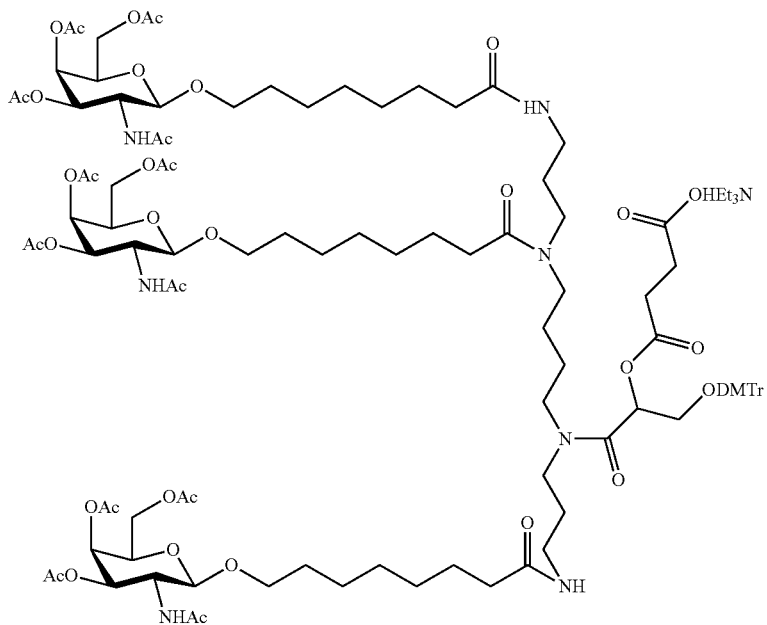
(519)
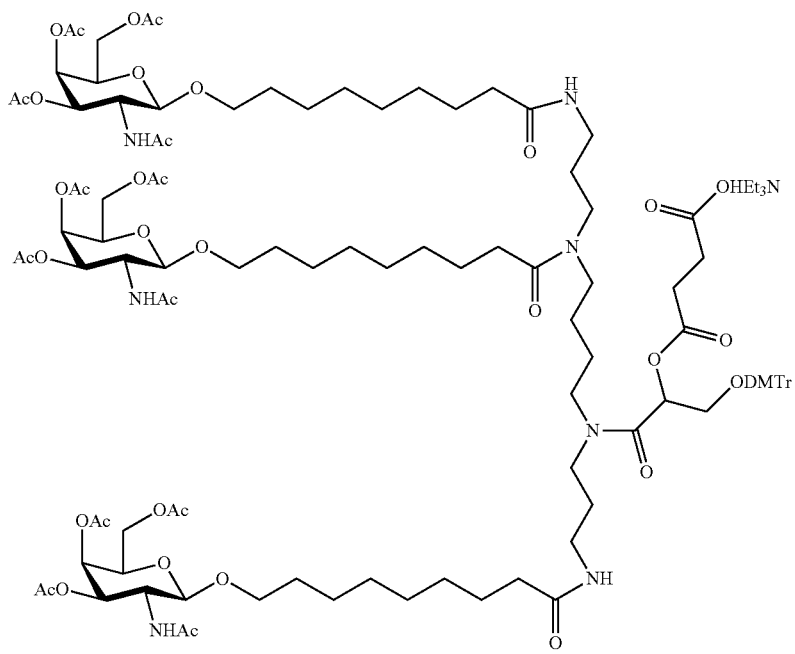

(520)
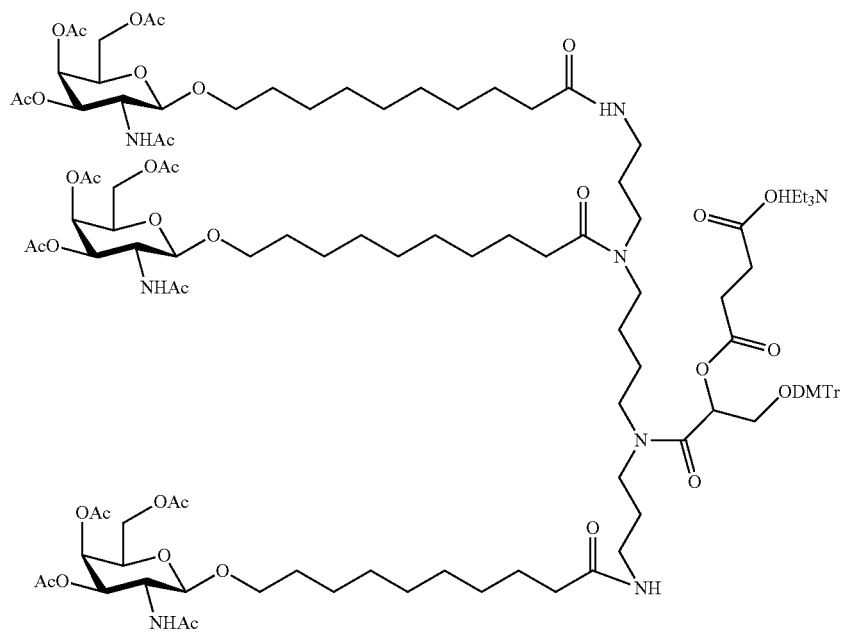
(521)
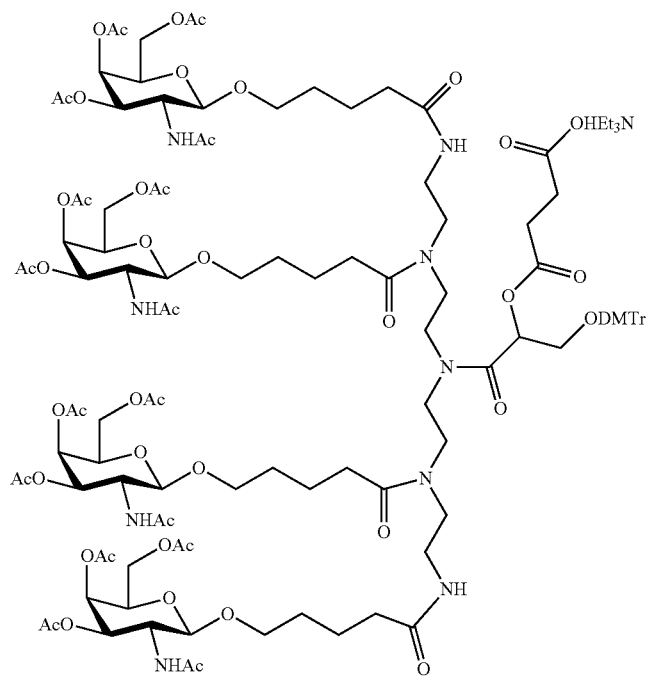

(522)
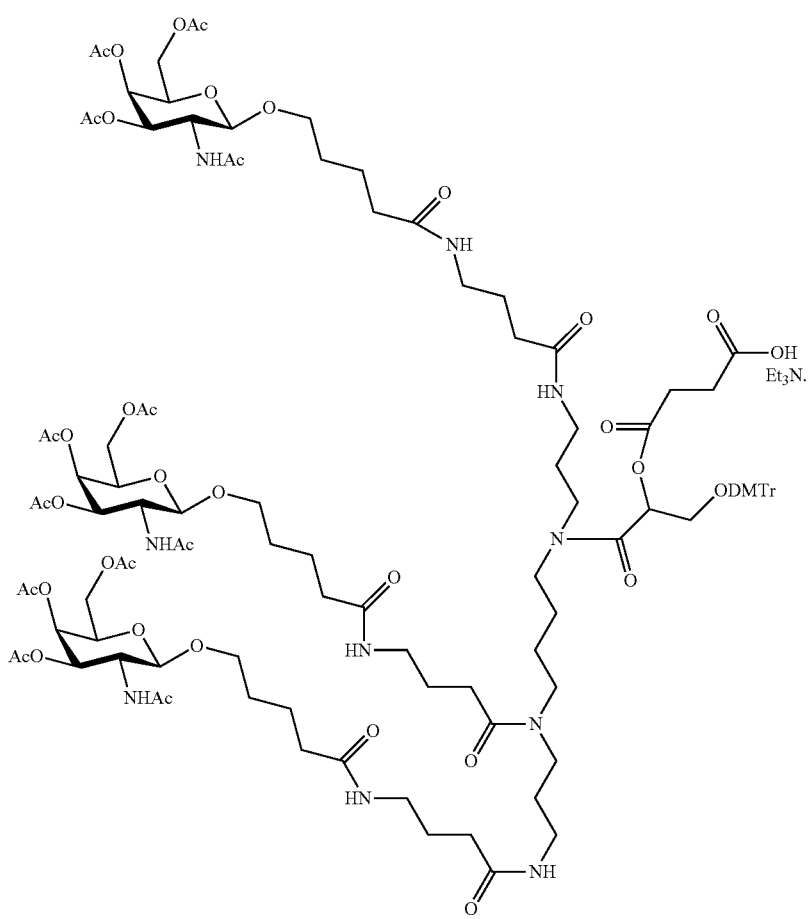
In the above Formulae (503)-(522), DMTr represents 4,4'-dimethoxytrityl. Structure
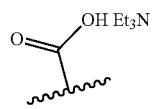
represents the salts formed by corresponding carboxylic acids and triethylamine.
In some embodiments, the conjugating molecule of the present disclosure has a structure represented by Formula (523), (524), (525), (526), (527), (528), (529), (530), (531), (532), (533), (534), (535), (536), (537), (538), (539), (540), (541), or (542):

(523)
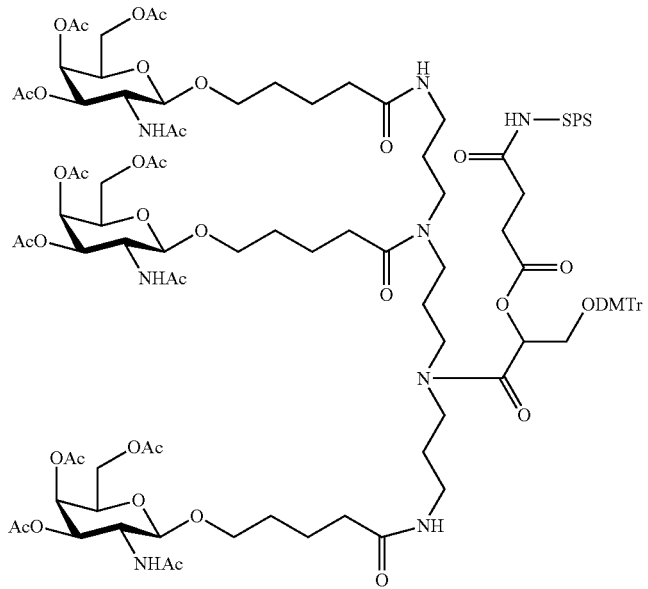
(524)
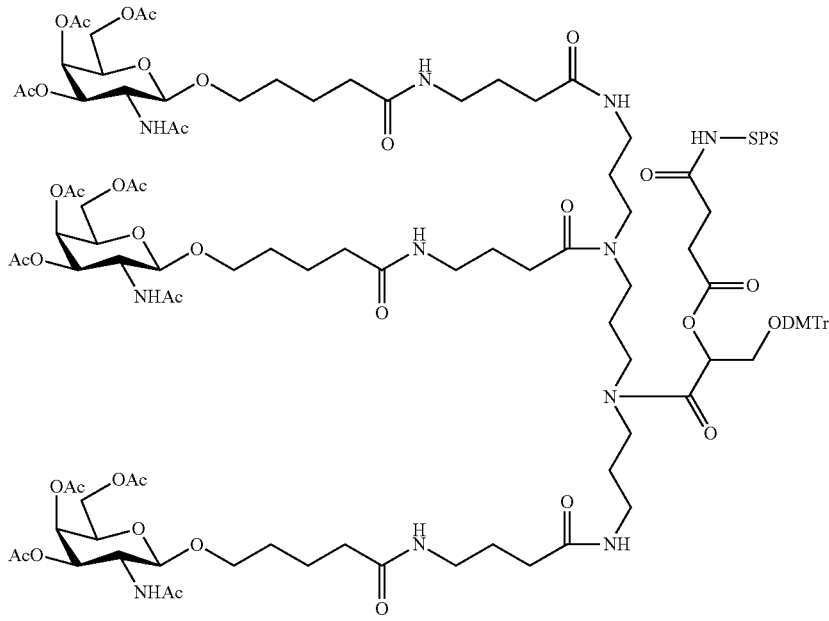

(525)
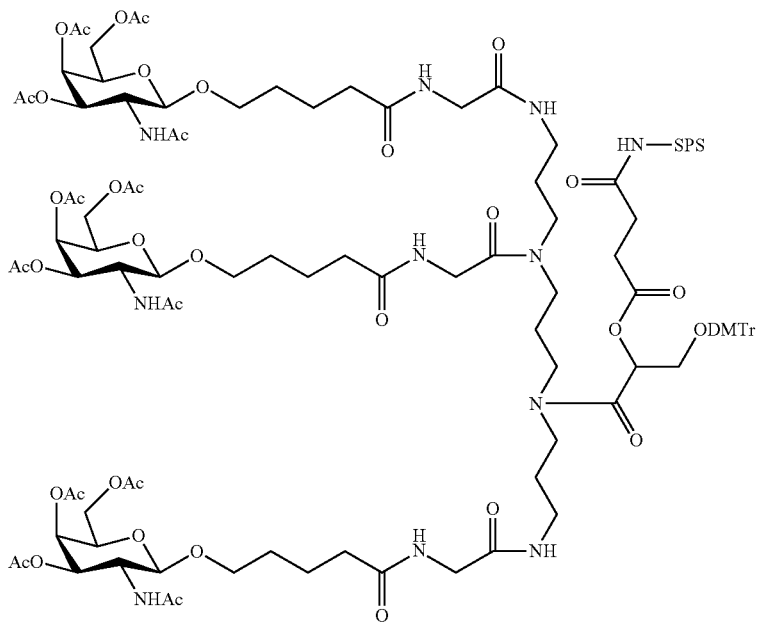
(526)
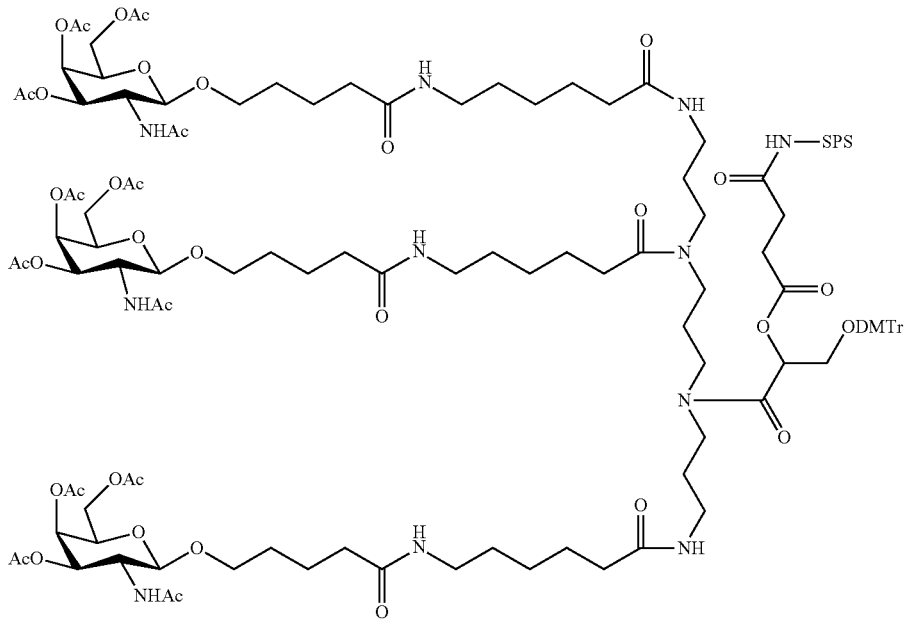

-continued
(527)
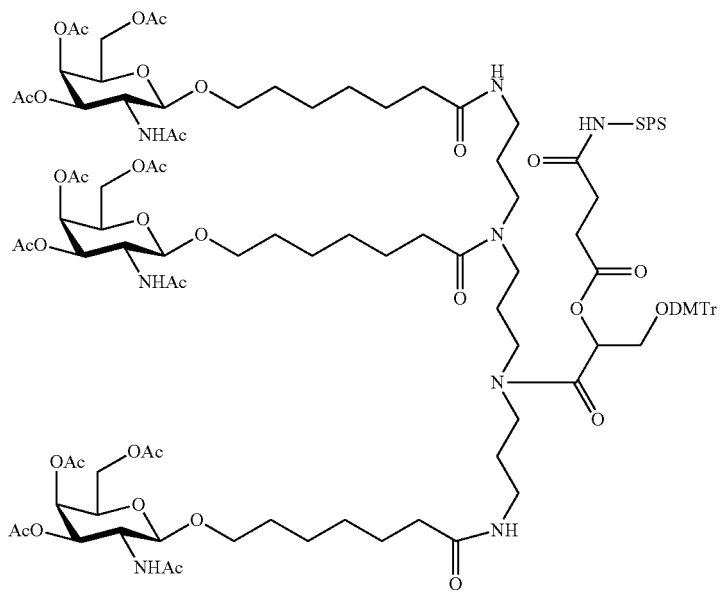
(528)
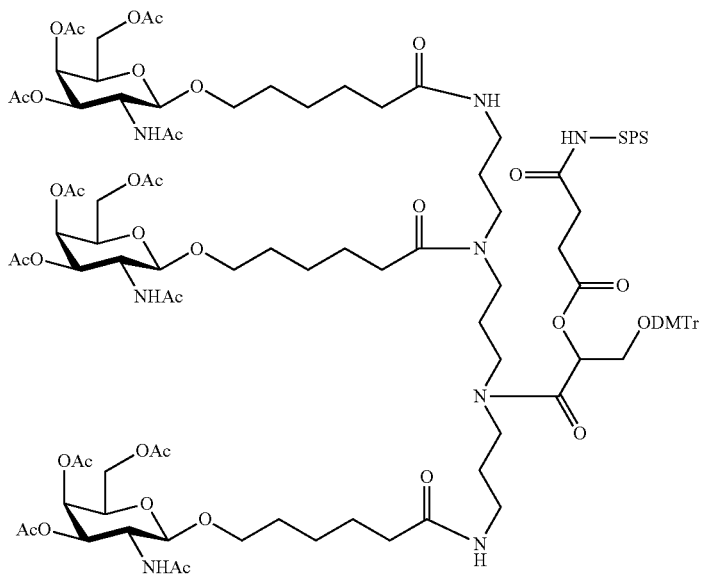

(529)
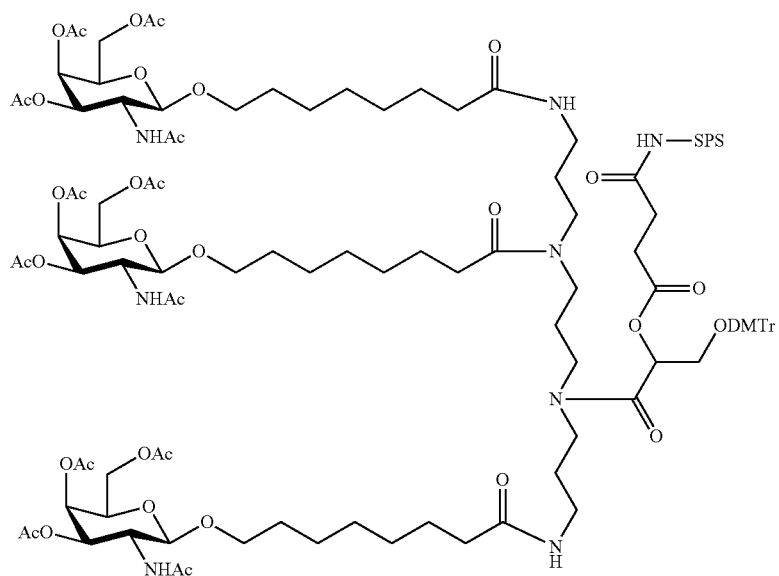
(530)
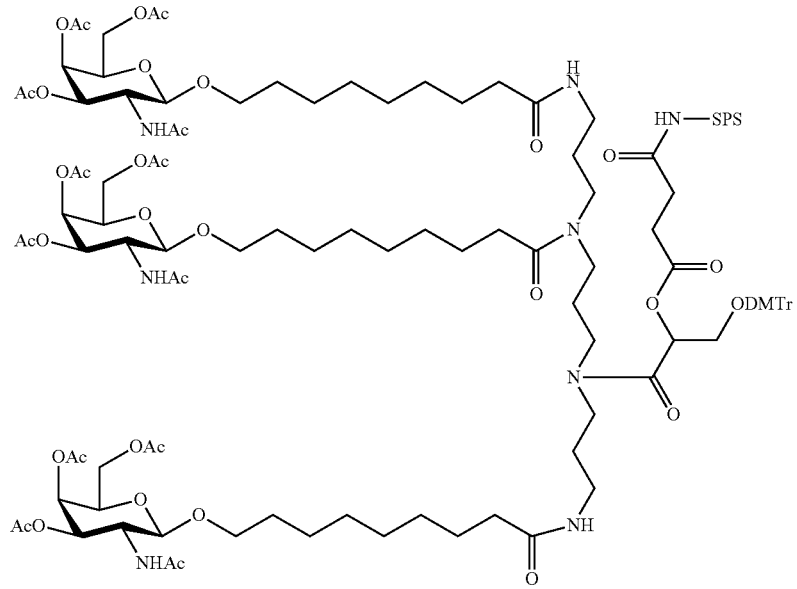

-continued
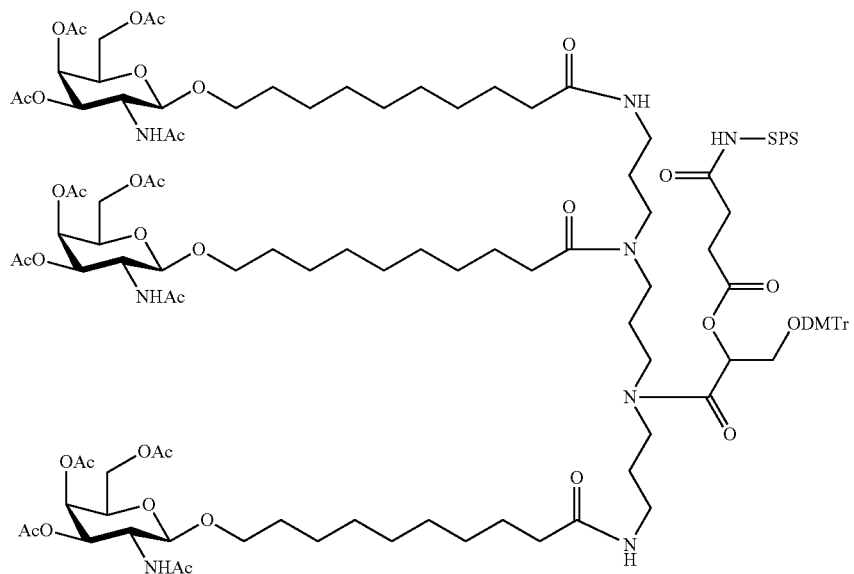
(531)
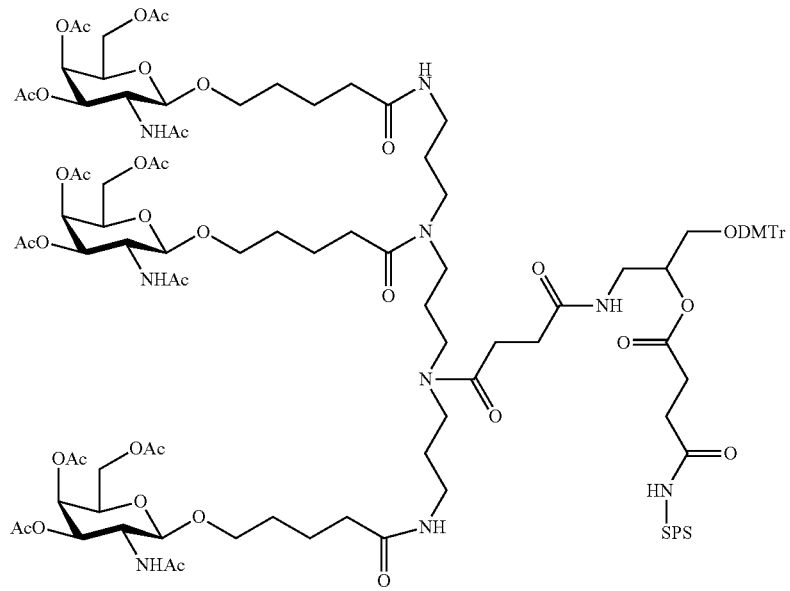
(532)

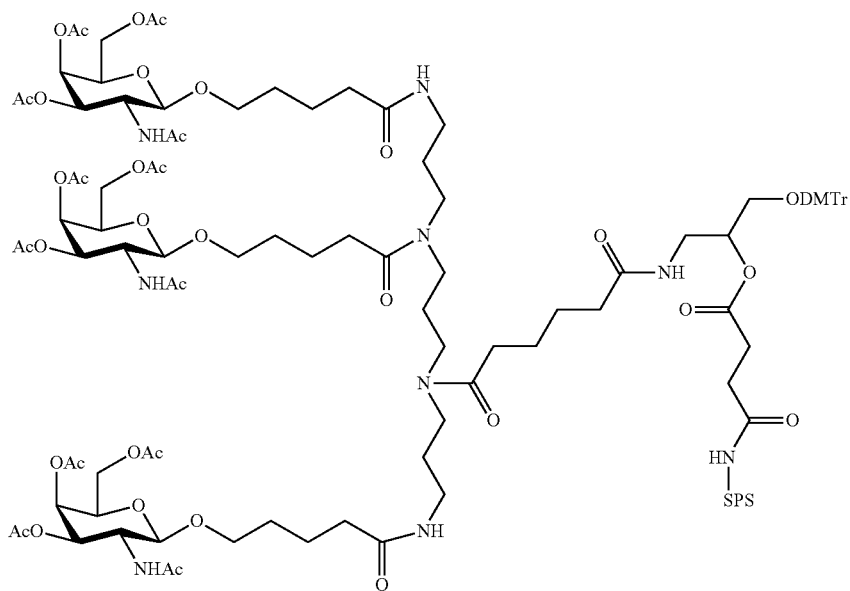
(533)
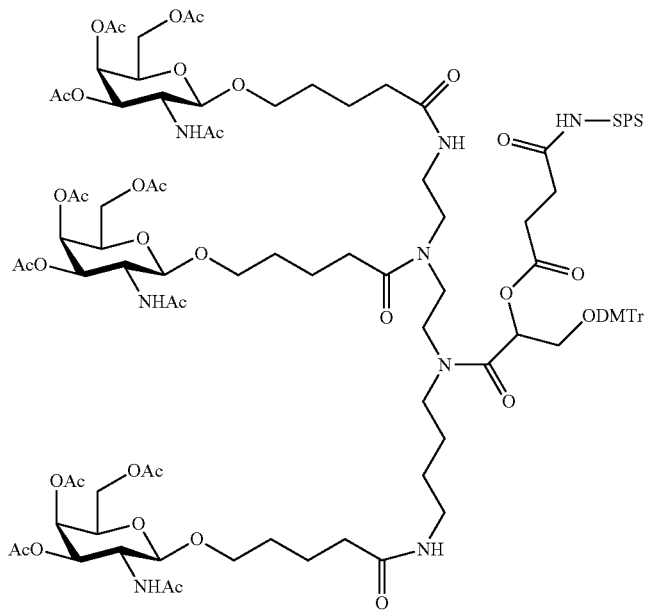
(534)

(535)
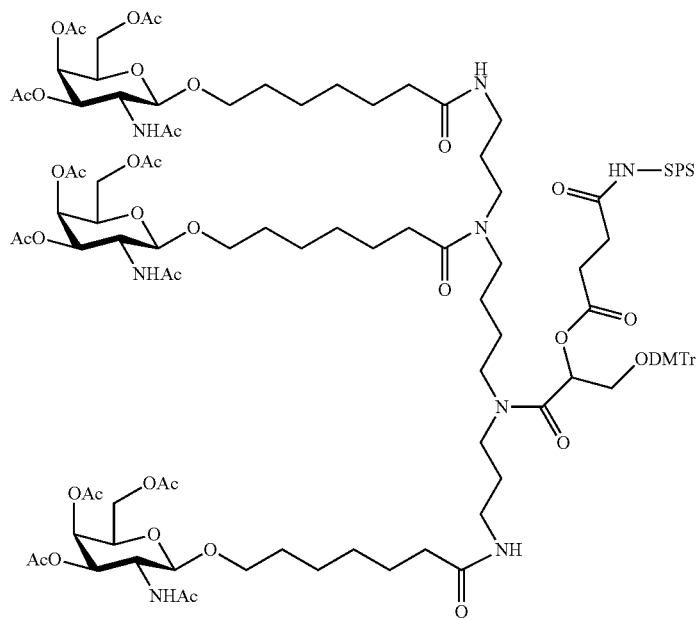
(536)
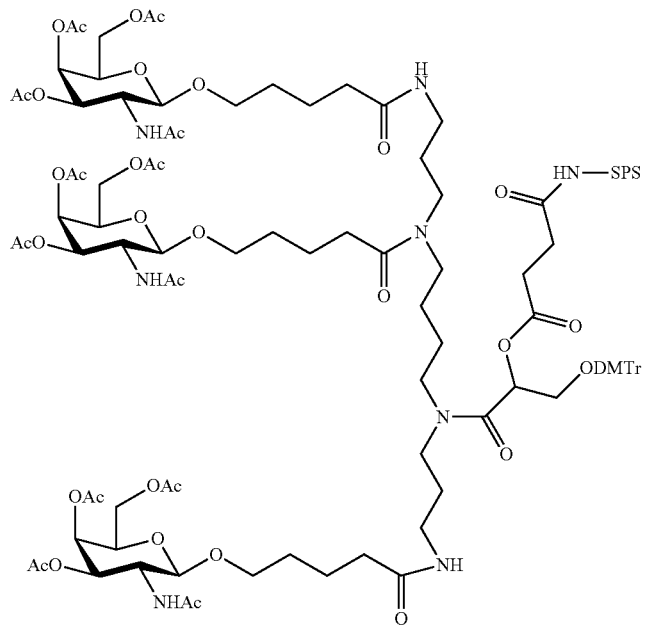

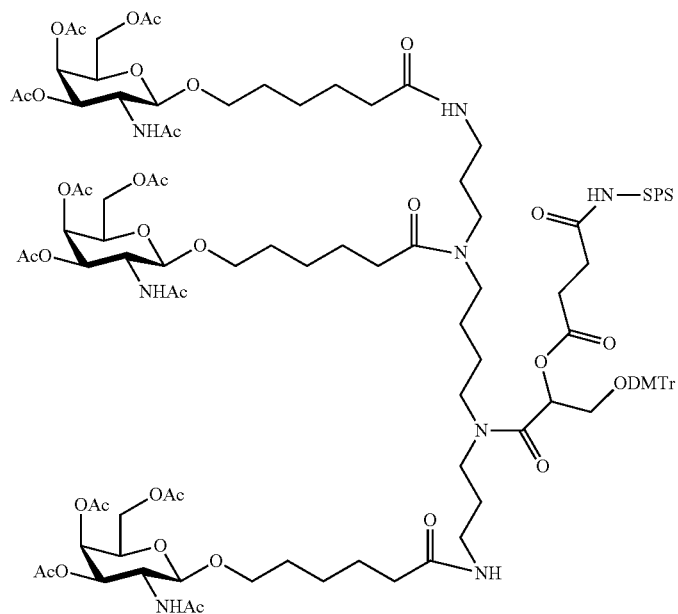
(537)
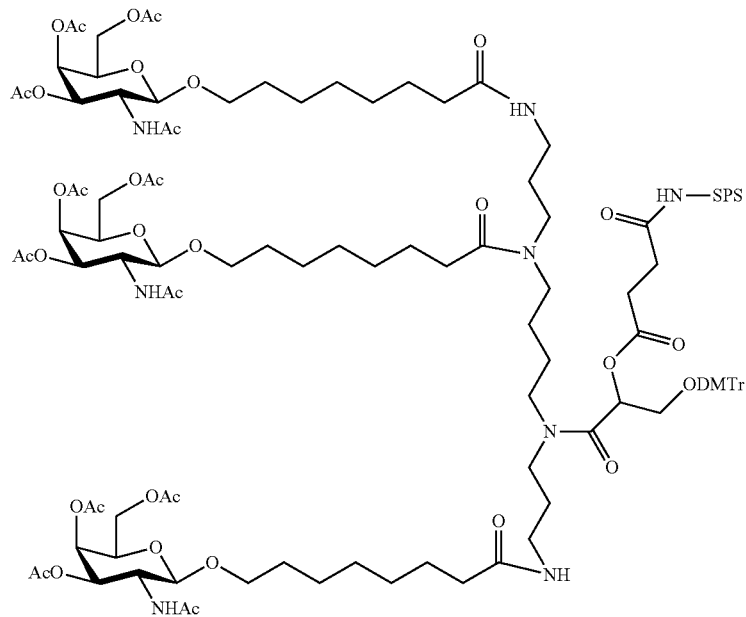
(538)

-continued
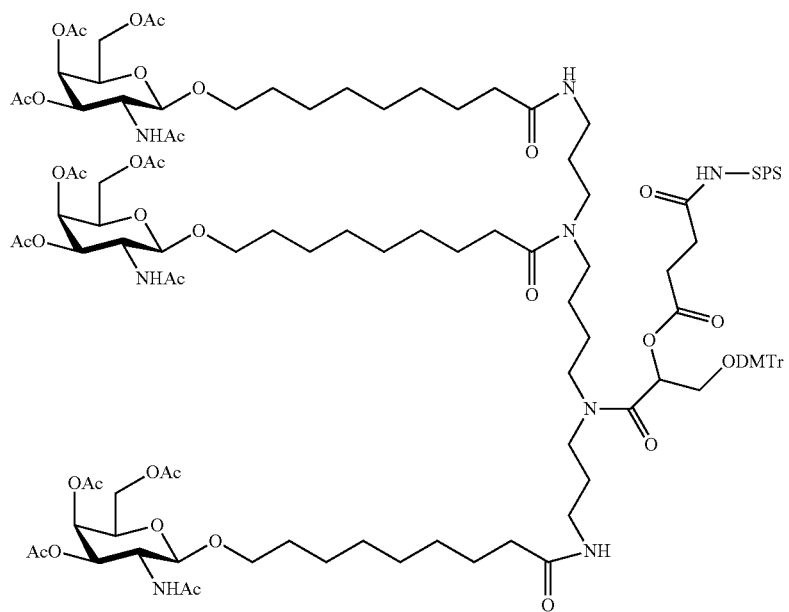
(539)
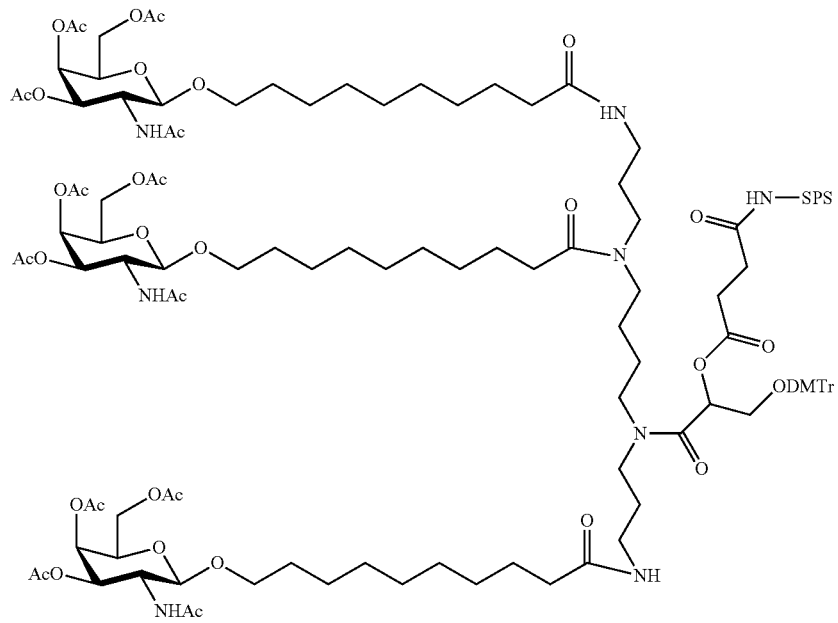
(540)

-continued

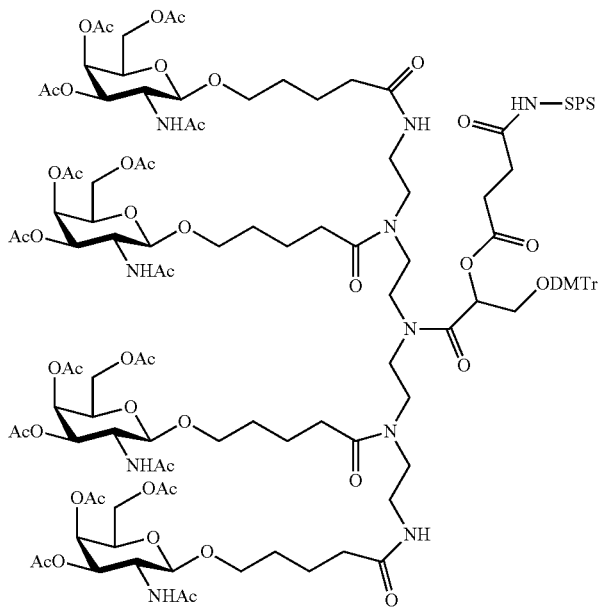

(541)

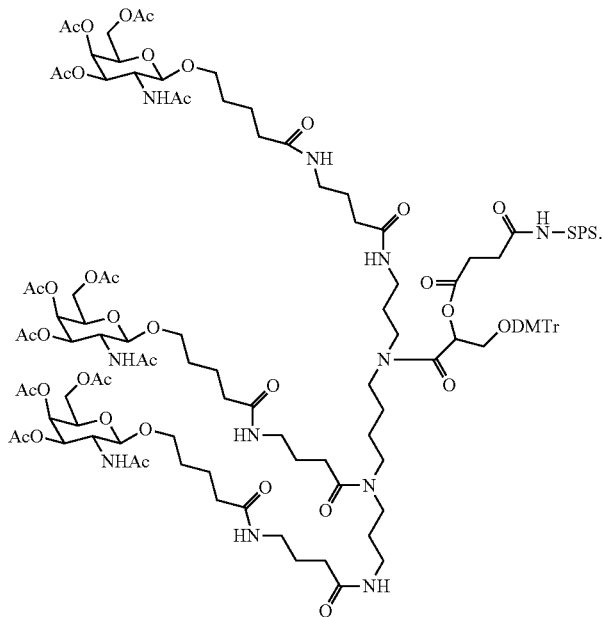

(542)

In Formulae (523) to (542) above, SPS represents a solid phase support, and DMTr refers to a 4,4'-dimethoxytrityl.

Preparation of the Conjugating Molecule of the Present Disclosure

The conjugating molecule of the present disclosure may be prepared via any appropriate synthetic route by those skilled in the art.

In some embodiments of the disclosure, the method for preparing the conjugating molecule represented by Formula (321) comprises contacting a compound represented by Formula (313) with a cyclic anhydride under the esterification reaction condition in the presence of a base and an esterification catalyst in an organic solvent; ion exchanging and isolating the compound represented by Formula (321):

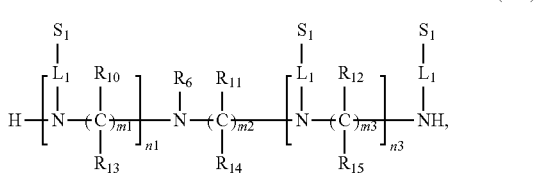

Formula (313)

wherein:

$R_6$ is a group to provide $R_4$ of Formula (321). In some embodiments, for example, $R_6$ has a structure represented by Formula (A61):

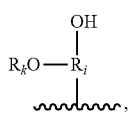
(A61)

the definitions and options of n1, n3, m1, m2, m3, $R_{10}$, $R_{11}$, $R_{12}$, $R_{13}$, $R_{14}$, $R_{15}$, $L_1$, $S_1$ are respectively as described above; $R_i$ is a group capable of linking to the N atom on the nitrogenous backbone, to $R_kO$ and to a free hydroxy group; $R_k$ is a hydroxy protecting group. In this case, a compound represented by Formula (321) is obtained, where $R_4$ comprises a hydroxy protecting group as the first functional group and a group represented by Formula (C1) or (C2) as the second functional group. In some embodiments, $R_6$ is B7 or B8:

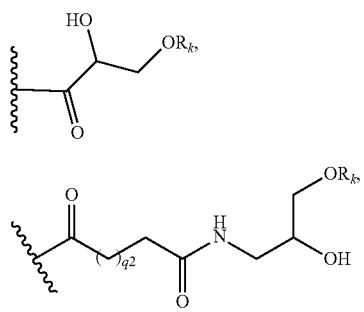

wherein $q_2$ and $R_k$ are respectively as defined above.

The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and In some embodiments, 5-20 L/mol with respect to the compound represented by Formula (313).

In some embodiments, the cyclic anhydride is one of succinic anhydride, glutaric anhydride, adipic anhydride or pimelic anhydride. In some embodiments, the cyclic anhydride is succinic anhydride. The molar ratio of the cyclic anhydride to the compound represented by Formula (313) is 1:1 to 10:1, and in some embodiments is 2:1 to 5:1.

The esterification catalyst may be any catalyst capable of catalyzing the esterification, such as 4-dimethylaminopyridine. The molar ratio of the catalyst to the compound represented by Formula (313) is 1:1 to 10:1, and in some embodiments is 2:1 to 5:1.

In some embodiments, the base may be any inorganic base, organic base or combination thereof. Regarding the solubility as well as the product stability, the base is a tertiary amine. In some embodiments, the tertiary amine is triethylamine or N,N-diisopropylethylamine The molar ratio of the tertiary amine to the compound represented by Formula (313) is 1:1 to 20:1, and in some embodiments is 3:1 to 10:1.

The ion exchanging serves to convert the compound represented by Formula (321) to a desired form of carboxylic acid or salt thereof. For the method for ion exchanging, the conjugating molecule with the M$^+$ cation may be obtained by using suitable ion exchanging solution and ion exchanging condition, which is well known in the art. In some embodiments, a triethylamine phosphate solution is employed in the ion exchanging. In some embodiments, the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment 4-5 L/mol with respect to the compound represented by Formula (313).

The compound represented by Formula (321) may be isolated from the reaction mixture using any suitable methods. In some embodiments, the compound represented by Formula (321) may be isolated by removal of solvent via evaporation followed by chromatography, for example, using the following chromatographic conditions for the isolation: (1) normal phase purification: 200-300 mesh silica gel filler, with gradient elution of 1 wt‰ triethylamine-containing dichloromethane:methanol=100:18-100:20; or (2) reverse phase purification: C18 and C8 reverse phase filler, with gradient elution of methanol:acetonitrile=0.1:1-1:0.1. In some embodiments, the solvent may be removed directly to obtain a crude product of the compound represented by Formula (321), which may be used directly in subsequent reactions.

In some embodiments, the preparation method of the compound represented by Formula (321) further comprises: contacting the product of the above ion exchanging with a solid phase support with amino or hydroxy groups under a condensation reaction condition in the presence of a condensing agent, a condensation catalyst, and a tertiary amine in an organic solvent. In this case, a compound represented by Formula (321) is obtained, wherein $R_4$ comprises a hydroxy protecting group as the first functional group and a group represented by Formula (C1') as the second functional group.

The solid phase support is one of the supports used in siRNA solid phase synthesis, some of which are well known to those skilled in the art. For example, the solid phase support may be selected from one having an active hydroxy or amino functional group. In some embodiments, the solid phase support is an amino or hydroxy resin. In some embodiments, the amino or hydroxy resin has a particle size of 100-400 mesh, and amino or hydroxy surface loading of 0.2-0.5 mmol/g. The ratio of the compound represented by Formula (321) to the solid phase support is 10 μmol compound per gram of solid phase support (μmol/g) to 400 μmol/g. In some embodiments, the ratio of compound of Formula (321) to the solid phase support is 50 μmol/g to 200 μmol/g.

The organic solvent may be any suitable solvent of mixture of solvents known to the skilled ones suitable for the purpose disclosed herein. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tert-butyl ether, the haloalkane solvent is one or more of dichloromethane, trichloromethane and 1,2-dichloroethane. In some embodiments, the organic solvent is acetonitrile. The amount of the organic solvent is 20-200 L/mol, in some embodiments is 50-100 L/mol with respect to the compound represented by Formula (313).

In some embodiments, the condensing agent may be benzotriazol-1-yl-oxytripyrrolidinophosphonium hexafluorophosphate, 3-diethoxyphosphoryl-1,2,3-benzotriazol-4 (3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound represented by Formula (313) is 1:1 to 20:1, and in further embodiments, 1:1 to 5:1.

In some embodiments, the tertiary amine is triethylamine and/or N,N-diisopropylethylamine, and in some embodiments is N,N-diisopropylethylamine. The molar ratio of the tertiary amine to the compound represented by Formula (313) is 1:1 to 20:1, and in some embodiments is 1:1 to 5:1.

In some embodiments, the method for preparing the compound represented by Formula (321) further comprises: contacting the obtained product of condensation reaction with a capping reagent and an acylation catalyst under a capping reaction condition in an organic solvent, and isolating the compound represented by Formula (321). The capping reaction is used to remove any active functional groups that are not reacted, so as to avoid unnecessary by-products in subsequent reactions. The capping reaction condition comprises a reaction temperature of 0-50° C., and in some embodiments of 15-35° C., and a reaction time of 1-10 hours, and in some embodiments, of 3-6 hours. The capping reagent may be the ones used in siRNA solid phase synthesis, which are well known to those skilled in the art. In some embodiments, the capping reagent is composed of capping reagent A (capA) and capping reagent B (capB). The capA is N-methylimidazole, and in some embodiments provided as a solution of N-methylimidazole in a mixture solvent of pyridine/acetonitrile, wherein the volume ratio of pyridine to acetonitrile is 1:10 to 1:1, and in some embodiments is 1:3 to 1:1. In some embodiments, the ratio of the total volume of pyridine and acetonitrile to the volume of N-methylimidazole is 1:1 to 10:1, and in some embodiments is 3:1 to 7:1. In some embodiments, the capping reagent B is acetic anhydride. In some embodiments, the capping reagent B is provided as a solution of acetic anhydride in acetonitrile solvent, wherein the volume ratio of acetic anhydride to acetonitrile is 1:1 to 1:10, and in further embodiments is 1:2 to 1:6.

In some embodiments, the ratio of the volume of the solution of N-methylimidazole in a mixture solvent of pyridine/acetonitrile to the mass of the compound of Formula (313) is 5 ml/g-50 ml/g, and in some embodiments is 15 ml/g-30 ml/g. The ratio of the volume of the solution of acetic anhydride in acetonitrile to the mass of the compound of Formula (313) is 0.5 ml/g-10 ml/g, and in some embodiments is 1 ml/g-5 ml/g.

In some embodiments, the capping reagent is equimolar acetic anhydride and N-methylimidazole. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. In some embodiments, the amount of the organic solvent is 10-50 L/mol, and in some embodiments 5-30 L/mol with respect to the compound represented by Formula (313).

In some embodiments, the acylation catalyst may be selected from any catalyst that may be used for esterification or amidation, such as alkaline heterocyclic compounds. In some embodiments, the acylation catalyst is 4-dimethylaminopyridine. The ratio of the mass of the catalyst to the mass of the compound represented by Formula (313) may be 0.001:1 to 1:1, and in some embodiments is 0.01:1 to 0.1:1.

In some embodiments, the compound represented by Formula (321) may be isolated from the reaction mixture by any suitable methods. In some embodiments, the compound of Formula (321) may be obtained by sufficiently washing with an organic solvent and filtering to remove unreacted reactants, excess capping reagent and other impurities, wherein the organic solvent is selected from acetonitrile, dichloromethane, or methanol. In some embodiments, the organic solvent is acetonitrile.

In some embodiments, the preparation of the conjugating molecule represented by Formula (321) comprises contacting a compound represented by Formula (313) with a phosphorodiamidite under a coupling reaction condition in the presence of a coupling agent in an organic solvent, and isolating the compound represented by Formula (321). In this case, a compound represented by Formula (321) is obtained, where $R_4$ comprises a hydroxy protecting group as the first functional group and a group represented by Formula ($C_3$) as the second functional group.

In some embodiments, the coupling reaction condition comprises a reaction temperature of 0-50° C., such as 15-35° C. The molar ratio of the compound of Formula (322) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, preferably 500-1500 seconds. The phosphorodiamidite may be such as 2-cyanoethyl N,N,N',N'-tetraisopropylphosphorodiamidite, and may be commercially available or prepared according to methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. In some embodiments, the organic solvent is selected from one or more of anhydrous acetonitrile, anhydrous DMF and anhydrous dichloromethane, preferably anhydrous acetonitrile. The amount of the organic solvent may be 3-50 L/mol, such as 5-20 L/mol with respect to the compound represented by Formula (313). Via the coupling reaction, the hydroxy group in the compound (313) reacts with the phosphorodiamidite to form a phosphoramidite group. In some embodiments, the solvent may be removed directly to obtain a crude product of the compound represented by Formula (321), which may be used directly in subsequent reactions.

In some embodiments, the preparation method of the compound represented by Formula (321) further comprises: contacting the isolated product with a solid phase support with hydroxy groups under a coupling reaction condition in the presence of a coupling agent in an organic solvent, followed by capping, oxidation, and isolation to obtain the compound represented by Formula (321), where R comprises a hydroxy protecting group as the first functional group and a group represented by Formula (C3') as the second functional group.

In some embodiments, the solid phase support is a support used in nucleic acid solid phase synthesis, such as a deprotected universal solid phase support, which is commercially available (such as NittoPhase®HL UnyLinker™ 300 Oligonucleotide Synthesis Support, Kinovate Life Sciences, represented by Formula B80):

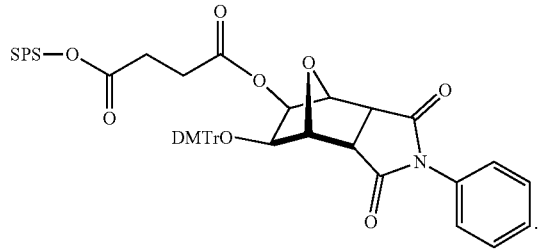

A deprotection reaction is well known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr (4,4'-dimethoxytrityl) on the solid phase support may be 2:1 to 100:1, such as 3:1 to 50:1. Via such deprotection, reactive free hydroxy groups are obtained on the surface of the solid phase support, thus being available for the consequent coupling reaction.

The coupling reaction condition and the coupling agent may be selected as above. Via such coupling, the free hydroxy groups formed in the deprotection react with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds. The capping agent and the amount thereof may be selected as above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the nucleic acid sequence linked to the solid phase support in the coupling step is 1:1 to 100:1, preferably 5:1 to 50:1. In some embodiments, the oxidation reaction is performed in a mixed solvent of tetrahydrofuran:water:pyridine=3:1:1-1:1:3.

In some embodiments, $R_6$ is B7 or B8. In this case, the compound shown in the Formula (313) may be obtained by contacting the compound represented by Formula (314) with a compound represented by Formula (A-1) or (A-2) under an amidation reaction condition in the presence of an condensing agent for amidation reaction and a tertiary amine, in an organic solvent, and followed by isolation:

Formula (314)

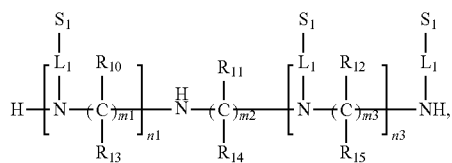

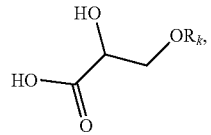

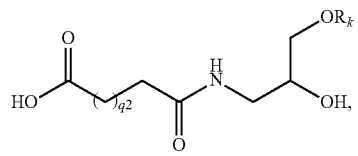

wherein, the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours. In some embodiments, the amidation reaction condition is a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in further embodiments is ethanol. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 3-20 L/mol with respect to the compound represented by Formula (314).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments is 3-(diethoxyphosphoryloxy)-1,2,3-benzotrizin-4(3H)-one. The molar ratio of the condensing agent for amidation reaction to the compound represented by Formula (314) may be 1:1 to 10:1, and in some embodiments is 2.5:1 to 5:1.

In some embodiments, the tertiary amine is triethylamine or N,N-diisopropylethylamine, and in further embodiments is N,N-diisopropylethylamine. The molar ratio of the tertiary amine to the compound represented by Formula (314) may be 3:1 to 20:1, and in some embodiments is 5:1 to 10:1.

In some embodiments, the compounds of Formula (A-1) and (A-2) may be prepared by any suitable means. For example, the compound of Formula (A-1) may be prepared by reacting calcium glycerate with DMTrCl wherein $R_k$ is a DMTr group. Similarly, the compound of Formula (A-2) may be prepared by firstly contacting 3-amino-1,2-propanediol with a cyclic anhydride which may have 4-13 carbon atoms, and in some embodiments 4-8 carbon atoms, followed by reacting with DMTrCl. It will be readily understood by those skilled in the art that the selection of different cyclic anhydride corresponds to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by successively reacting the compound represented by Formula (314) with the cyclic anhydride, 3-amino-1,2-propanediol, and DMTrCl. It will be readily understood by those skilled in the art that these variations would not affect the structure and functions of the compound of Formula (313), and these variations are readily achieved by those skilled in the art on the basis of the above methods.

Similarly, the compound represented by Formula (313) may be isolated from the reaction mixture by any suitable isolation methods. In some embodiments, the compound represented by Formula (313) may be isolated by removal of solvent via evaporation followed by chromatography. For example, the following two sets of chromatographic conditions may be employed for the isolation, (1) normal phase purification: 200-300 mesh silica gel filler, with gradient elution of petroleum ether:ethyl acetate:dichloromethane:N,N-dimethylformamide=1:1:1:0.5-1:1:1:0.6; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (313), which may be directly used in subsequent reactions.

In some embodiments, the compound represented by Formula (314) may be obtained by contacting the compound represented by Formula (315) with haloacetic acid under a deprotection reaction condition in an organic solvent, and followed up by isolation:

Formula (315)

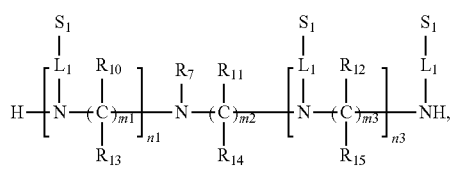

wherein, $R_7$ is selected from the groups represented by Formula (330), (331), (332) or (333), and In some embodiments, $R_7$ has the structure represented by Formula (330):

(330)

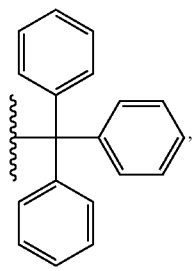

-continued (331)

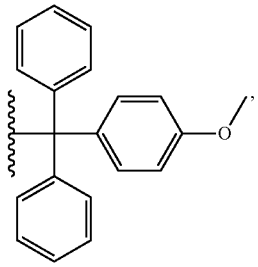

(332)

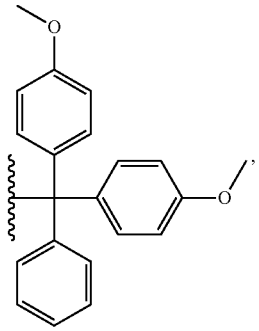

(333)

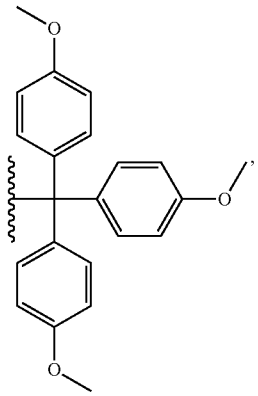

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively as described above.

The haloacetic acid may be selected from one or more of dichloroacetic acid, trichloroacetic acid, monochloroacetic acid and trifluoroacetic acid, and in some embodiments is dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 5-20 L/mol with respect to the compound represented by Formula (315).

The molar ratio of the haloacetic acid to the compound represented by Formula (315) may be 5:1 to 100:1, and in some embodiments is 10:1 to 50:1.

Similarly, the compound represented by Formula (314) may be isolated from the reaction mixture by any suitable isolation methods. In some embodiments, the compound represented by Formula (314) may be isolated by removal of solvent via evaporation followed by chromatography, for example, using the following two sets of chromatographic conditions for the isolation, (1) normal phase purification: 200-300 mesh silica gel filler, with gradient elution of dichloromethane:methanol=100:30-100:40; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (314), which may be directly used in subsequent reactions.

The compound represented by Formula (315) may be obtained by contacting the compound represented by Formula (317) with the compound represented by Formula (316) under a condensation reaction condition in the presence of an condensing agent for amidation reaction and a tertiary amine, in an organic solvent, and followed by isolation:

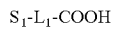   Formula (316)

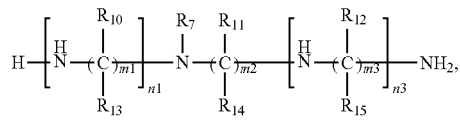   Formula (317)

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively as described above.

Regarding the compound of Formula (316), compounds such as those disclosed in J. Am. Chem. Soc. 2014, 136, 16958-16961 may be employed. Alternatively, compounds of Formula (316) may be prepared by the skilled in the art via various methods. For example, some compounds of Formula (316) may be prepared according to the disclosure in Example 1 of U.S. Pat. No. 8,106,022 B2, the entire content of which is incorporated herein by reference in its entirety.

In some embodiments, the condensation reaction condition comprises a reaction temperature of 0-100° C. and a reaction time of 0.1-24 hours. In some embodiments, the reaction temperature is 10-40° C. and the reaction time is 0.5-16 hours.

The molar ratio of the compound represented by Formula (316) to the compound represented by Formula (317) may be 2:1 to 10:1, and in some embodiments is 2.5:1 to 5:1.

In some embodiments, the organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments is 5-20 L/mol with respect to the compound represented by Formula (317).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in further embodiments may be 4-(4,6-dimethoxytriazin-2-yl)-4-methylmorpholine hydrochloride. The molar ratio of the condensing agent for amidation reaction to the compound represented by Formula (317) may be 2:1 to 10:1, and in some embodiments is 2.5:1 to 5:1.

The tertiary amine may be N-methylmorpholine, triethylamine or N,N-diisopropylethylamine, and in some embodiments is N-methylmorpholine. The molar ratio of the tertiary amine to the compound represented by Formula (317) may be 3:1 to 20:1, and in some embodiments is 5:1 to 10:1.

Similarly, the compound represented by Formula (315) may be isolated from the reaction mixture by any suitable isolation methods. In some embodiments, the compound represented by Formula (315) is isolated by removal of solvent via evaporation followed by chromatography, for example, using the following two sets of chromatographic conditions for the isolation, (1) normal phase purification: 200-300 mesh silica gel filler, with gradient elution of dichloromethane:methanol=100:5-100:7; (2) reverse phase purification: C18 and C8 reverse phase fillers, with gradient elution of methanol:acetonitrile=0.1:1-1:0.1. In some embodiments, the solvent is removed directly to obtain a crude product of the compound represented by Formula (315), which may be used directly in subsequent reactions.

In some embodiments, the compound of Formula (317) is reacted with a sufficient amount of one compound of Formula (316) in one batch to obtain the desired compound of Formula (315) having identical $S_1$-$L_1$ moieties. In some embodiments, the compound of Formula (317) is reacted in batches with different compounds of Formula (316), i.e., the compounds of Formula (316) having different $L_1$ and/or $S_1$, as desired, so as to obtain the compound of Formula (315) having two or more types of $S_1$ and/or $L_1$ therein. For example, 1 eq of the compound of Formula (317) may be firstly contacted with 2 eq of a first compound of Formula (316) to attach a first $S_1$-$L_1$ moieties to the two terminal primary amine groups in the compound of Formula (317), and then contacted with the (n3+n1-1) eq of a second compound of Formula (316) to attach a second $S_1$-$L_1$ moieties to the (n3+n1-1) secondary amine groups (wherein the definition and scope of n3 and n1 are as defined above) in the compound of Formula (317).

In some embodiments, the compound represented by Formula (317) may be obtained by contacting the compound represented by Formula (318) with methylamine aqueous solution under a deprotection reaction condition in the presence of an organic solvent, and follow by isolation:

Formula (318)

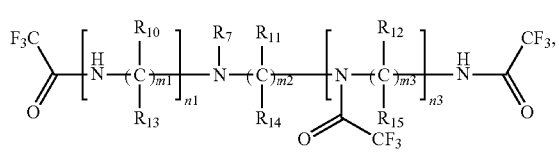

wherein the definitions and options of n1, n3, m1, m2, m3, $R_7$, $R_{10}$, $R_{11}$, $R_{12}$, $R_{13}$, $R_{14}$ and $R_{15}$ are respectively as defined above.

The deprotection reaction condition may comprise a reaction temperature of 0-150° C. and a reaction time of 5-72 hours, and in some embodiments comprises a reaction temperature of 20-80° C. and a reaction time of 10-30 hours.

The organic solvent may be selected from alcohols, in some embodiments is one of methanol, ethanol and isopropanol, and in further embodiments is methanol. The amount of the organic solvent may be 1-20 L/mol, and in some embodiments is 1.5-10 L/mol with respect to the compound represented by Formula (318).

The concentration of the methylamine aqueous solution may be 30%-40% by mass, and the molar ratio of methylamine to the compound represented by Formula (318) may be 10:1 to 500:1, and in some embodiments is 50:1 to 200:1.

Similarly, the compound represented by Formula (317) may be isolated from the reaction mixture using any suitable isolation methods. In some embodiments, the compound represented by Formula (317) may be isolated by removal of solvent via evaporation followed by chromatography, for example, using the following two sets of chromatographic conditions for the isolation, (1) normal phase purification: 200-300 mesh silica gel filler, with gradient elution of dichloromethane:methanol:aqueous ammonia (25 wt %)=1:1:0.05-1:1:0.25; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (317), which may be used directly in subsequent reactions.

The compound represented by Formula (318) may be obtained by contacting the compound represented by Formula (319) with triphenylchloromethane (TrCl), diphenylethylphenylchloromethane, phenyldiethylphenylchloromethane or triethylphenylchloromethane, and in some embodiments with triphenylchloromethane (TrCl) under a substitution reaction condition in the presence of an organic solvent, and followed by isolation:

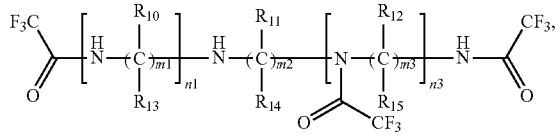

Formula (319)

wherein the definitions and options of n1, n3, m1, m2, m3, $R_{10}$, $R_{11}$, $R_{12}$, $R_{13}$, $R_{14}$ and $R_{15}$ are respectively as defined above.

The substitution reaction condition may comprise a reaction temperature of 0-100° C. and a reaction time of 5-72 hours, and in some embodiments comprises a reaction temperature of 10-40° C. and a reaction time of 10-30 hours.

Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound represented by Formula (319) may be 1:1 to 10:1, and in some embodiments is 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments is 5-20 L/mol with respect to the compound represented by Formula (319).

Similarly, the compound represented by Formula (318) may be isolated from the reaction mixture by any suitable isolation methods. In some embodiments, the compound represented by Formula (318) may be isolated by removal of solvent via evaporation followed by chromatography, for example, using the following two sets of chromatographic conditions for the isolation, (1) normal phase purification: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (318), which may be used directly in subsequent reactions.

In some embodiments, the compound represented by Formula (319) may be obtained by contacting the compound represented by Formula (320) with ethyl trifluoroacetate under a substitution reaction condition in an organic solvent, and followed by isolation:

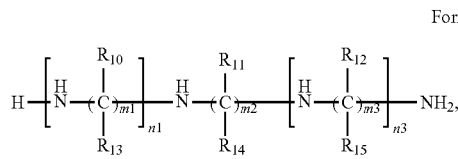

Formula (320)

wherein the definitions and options of n1, n3, m1, m2, m3, $R_{10}$, $R_{11}$, $R_{12}$, $R_{13}$, $R_{14}$ and $R_{15}$ are respectively as defined above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 1-50 L/mol, and in some embodiments is 1-20 L/mol with respect to the compound represented by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound represented by Formula (320) may be commercially purchased, or obtained via methods known to the skilled in the art. For example, in the case that m1=m2=m3=3, n1=1, n3=2, while each of $R_{10}$, $R_{11}$, $R_{12}$, $R_{13}$, $R_{14}$ and $R_{15}$ is H, the compound represented by Formula (320) is available from Alfa Aesar Inc.

The molar ratio of ethyl trifluoroacetate to the compound represented by Formula (320) may be 2:1 to 10:1, and in some embodiments is 3:1 to 5:1.

Similarly, the compound represented by Formula (319) may be isolated from the reaction mixture using any suitable isolation methods. In some embodiments, the compound represented by Formula (319) may be isolated by removal of solvent via evaporation followed by chromatography, for example, using the following two sets of chromatographic conditions for the isolation, (1) normal phase purification: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (319), which may be used directly in subsequent reactions.

Conjugate

In another aspect, provided herein is a conjugate having a structure represented by Formula (1):

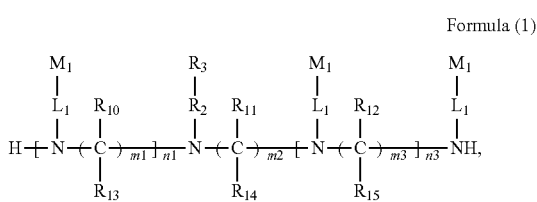

Formula (1)

wherein:

n1 is an integer of 1-3, and n3 is an integer of 0-4;

each of m1, m2, and m3 is independently an integer of 2-10;

each of $R_{10}$, $R_{11}$, $R_{12}$, $R_{13}$, $R_{14}$ and $R_{15}$ is independently selected from H, $C_1$-$C_{10}$ alkyl, $C_1$-$C_{10}$ haloalkyl, and $C_1$-$C_{10}$ alkoxy, and in some embodiments, is independently H, methyl, or ethyl;

$R_3$ is an active drug, in some embodiments comprises a functional oligonucleotide;

$R_2$ is a linear alkylene of 1 to 20 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is independently a linear alkylene of 1 to 70 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl), and in some embodiments, $L_1$ may be selected from the group consisting of A1-A26 or any combinations thereof, wherein the structures and definitions of A1-A26 are shown above;

n1, n3, m1, m2, m3, $R_{10}$, $R_{11}$, $R_{12}$, $R_{13}$, $R_{14}$, $R_{15}$ and $M_1$ are as defined above.

In some embodiments, $R_2$ is a linking group formed by linking $R_4$ group in the compound of Formula (321) to the active drug via reaction. In some embodiments, $R_2$ is a linking group formed by linking $R_4$ group in the compound of Formula (321) to the functional oligonucleotide via reaction. In some embodiments, $R_2$ group has both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments $R_2$ is B5, B6, B5' or B6':

(B5)

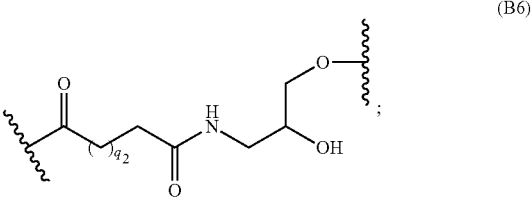

(B6)

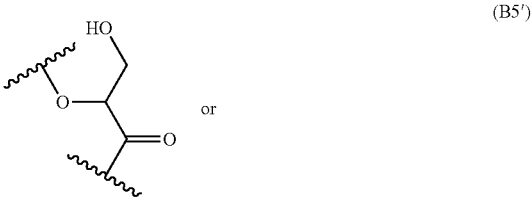

(B5')

or

-continued

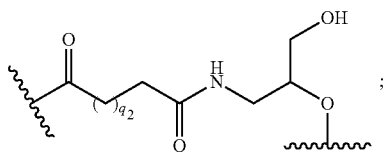
(B6')

wherein, ∿∿∿ represents the site where the groups are covalently linked; the selections and ranges of $q_2$ are as described above.

In some embodiments, $R_3$ is a group having the structure represented by Formula A59:

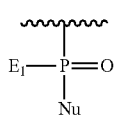
(A59)

wherein $E_1$ is OH, SH or $BH_2$, and in some embodiments is OH or SH; and Nu is a functional oligonucleotide.

In the context of the disclosure, unless otherwise stated, a "conjugating" group or molecule refers to a group or molecule which is capable of forming a covalent linkage to appropriate partner thereof, and both the conjugating group or molecule and its partner have specific functions. Correspondingly, a "conjugate" refers to the compound formed by covalent linkage of such a chemical moiety with its partner. Further, an "oligonucleotide conjugate" represents a compound formed by covalently attached oligonucleotide and one or more conjugating moieties each with specific functions. In some embodiments, the conjugate disclosed herein is an oligonucleotide conjugate. In this context, a "conjugating molecule" may be a specific compound capable of conjugating to an oligonucleotide via reactions, thus finally forming the oligonucleotide conjugating of the disclosure. In some embodiments, the oligonucleotide is an siRNA, hence the oligonucleotide conjugating of the disclosure is an siRNA conjugate.

In some embodiments, the conjugate has a structure represented by Formula (3), (4), (5), (6), (7), (8), (9), (10), (11), (12), (13), (14), (15), (16), (17), (18), (19), (20), (21), or (22):

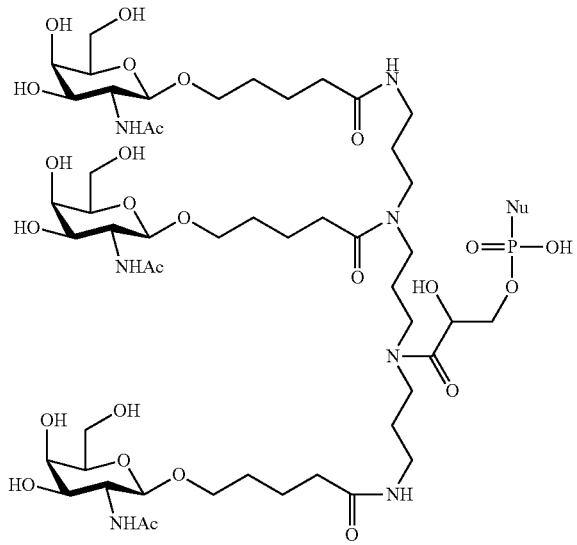

Formula (3)

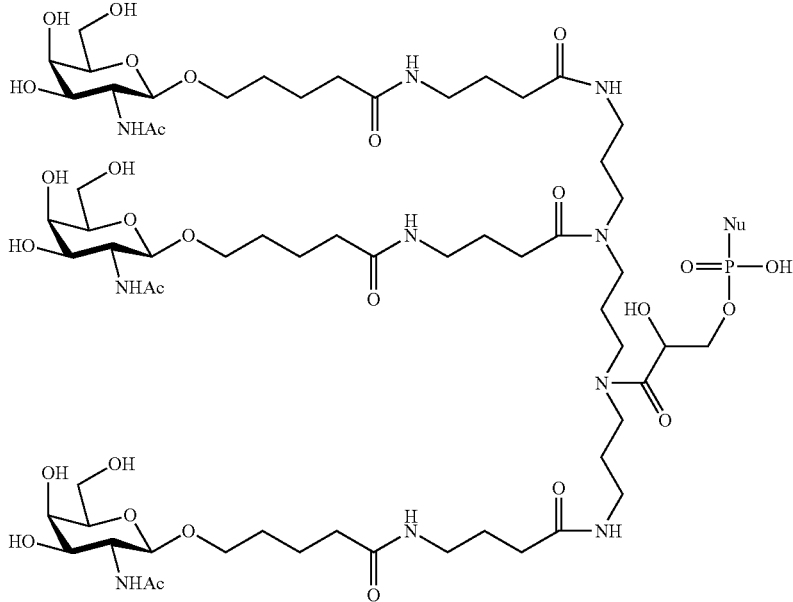

Formula (4)

-continued
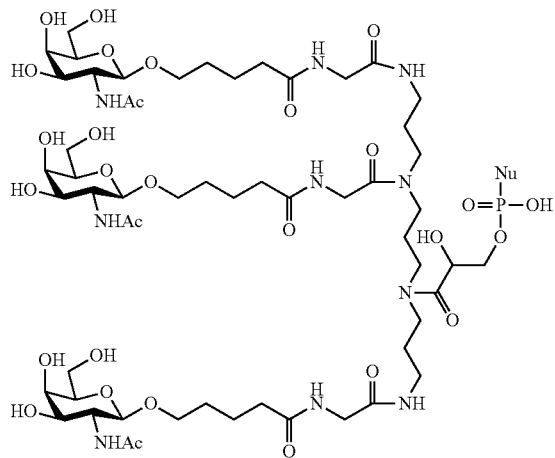
Formula (5)
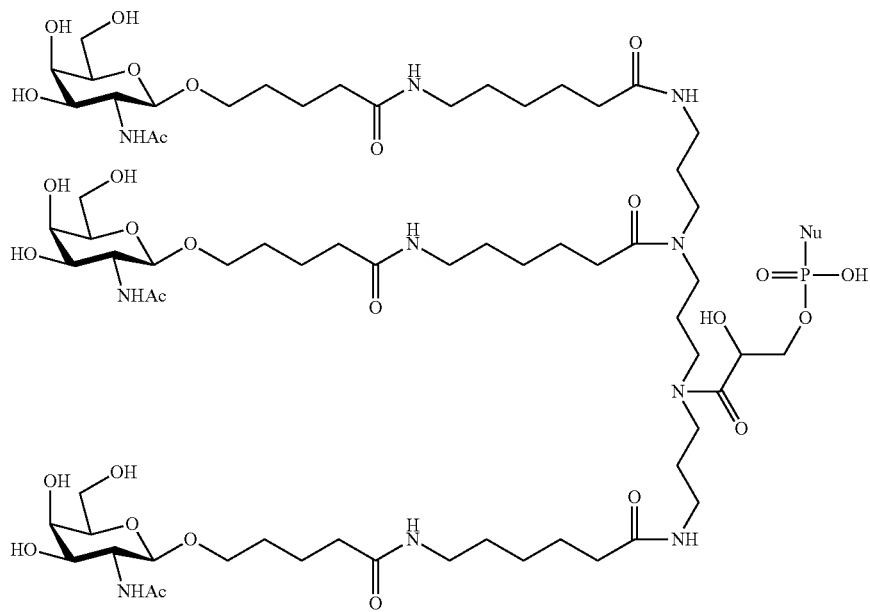
Formula (6)
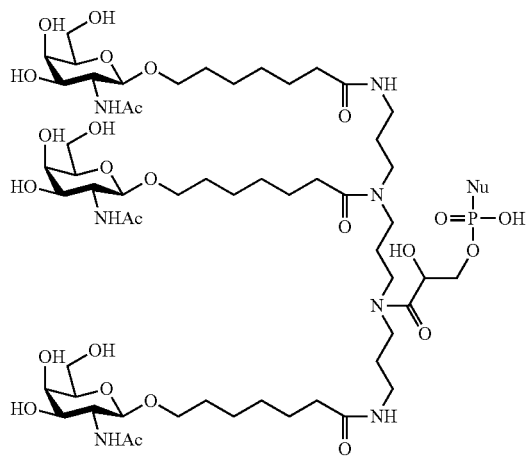
Formula (7)
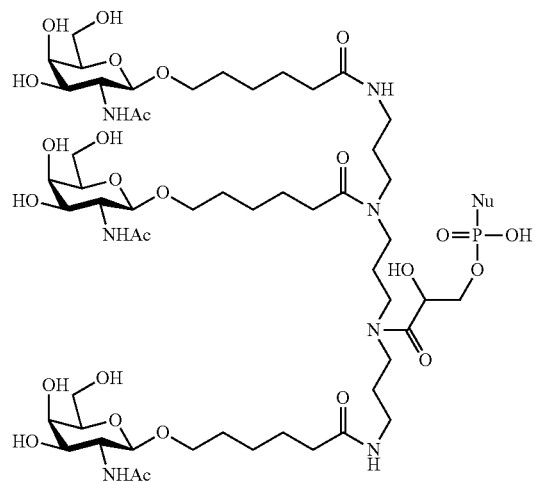
Formula (8)

-continued
Formula (9)
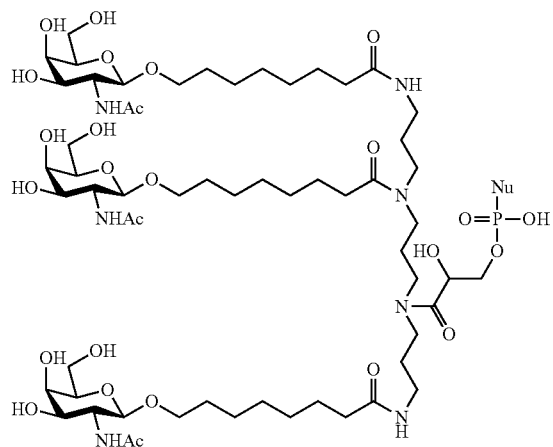
Formula (10)
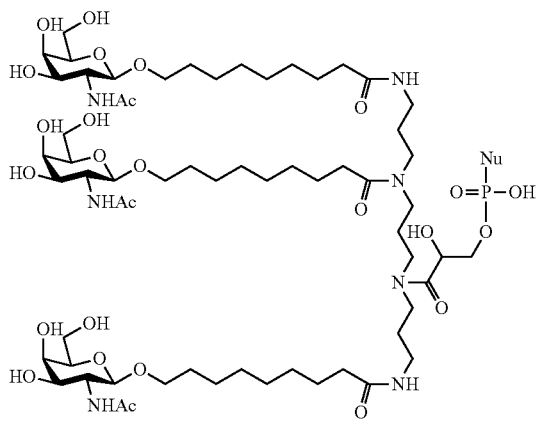
Formula (11)
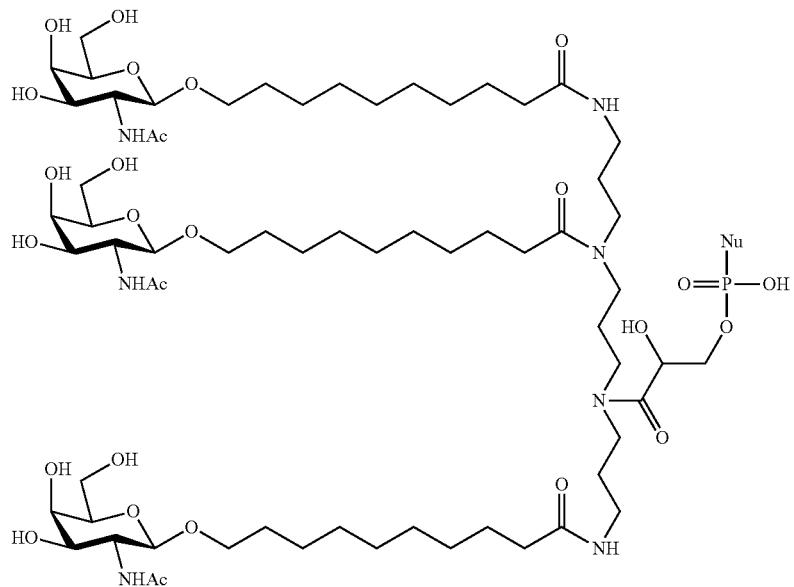
Formula (12)
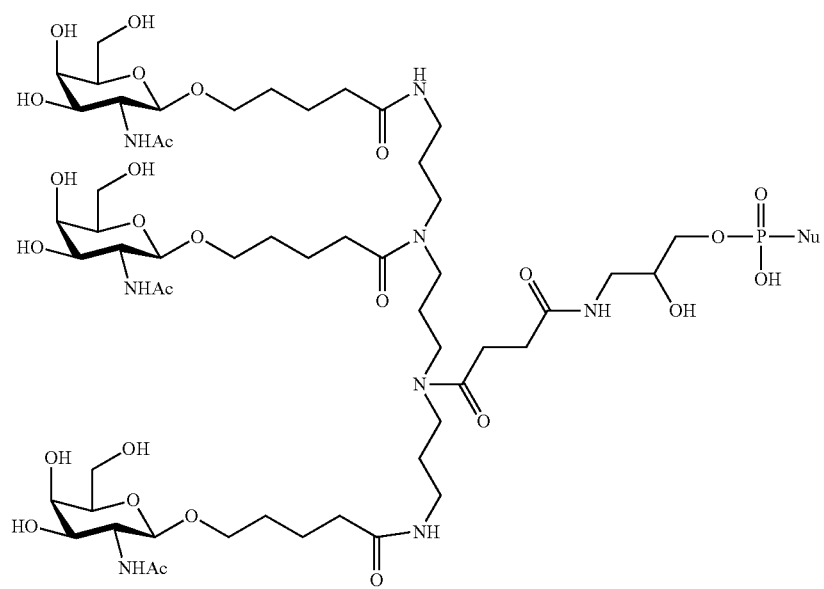

121                                   122
-continued
Formula (13)
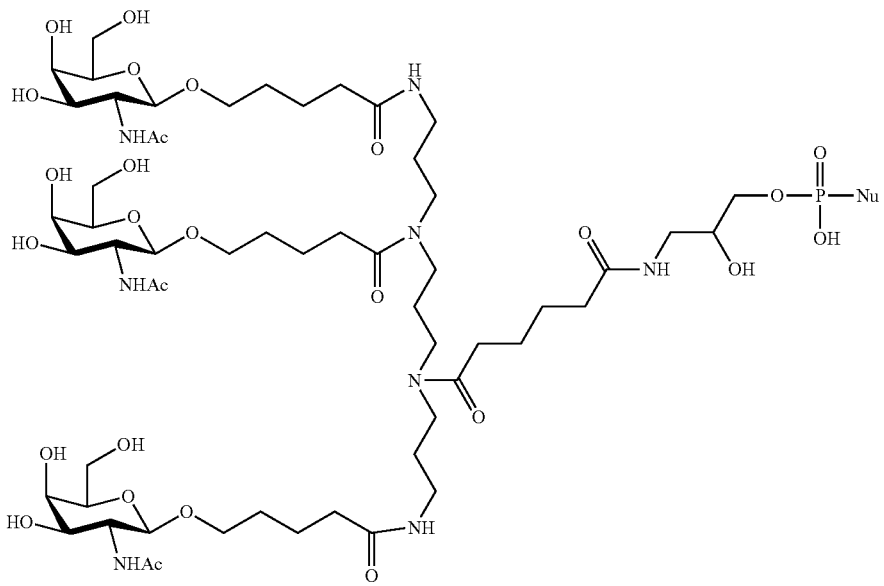
Formula (14)
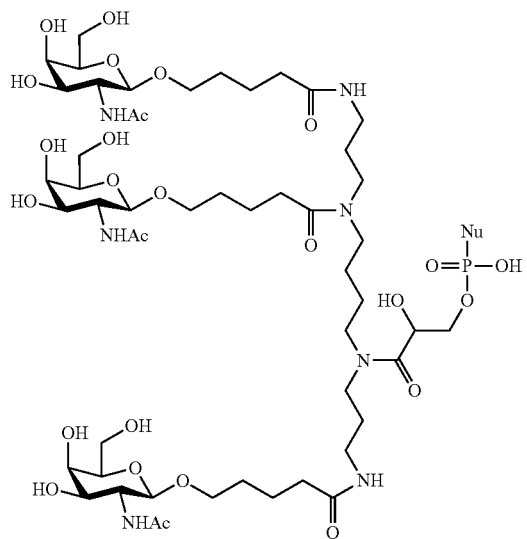
Formula (15)
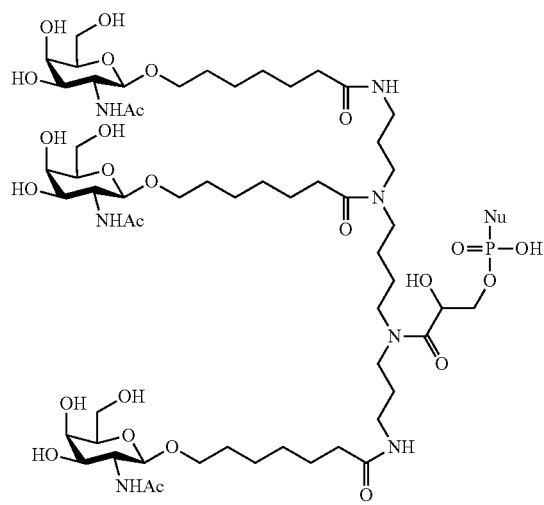
Formula (16)
Formula (17)
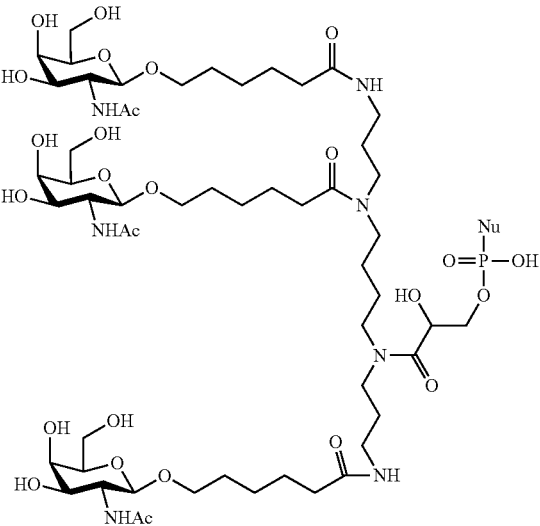

-continued
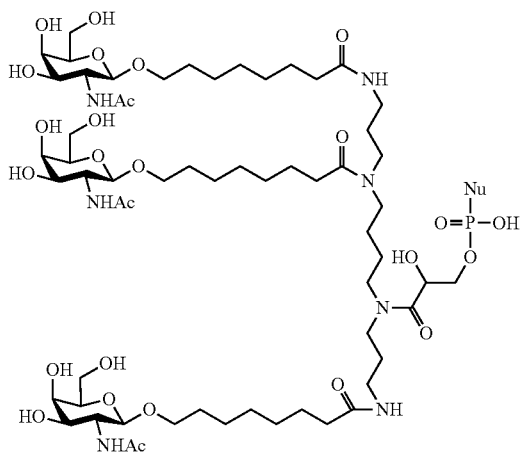
Formula (18)
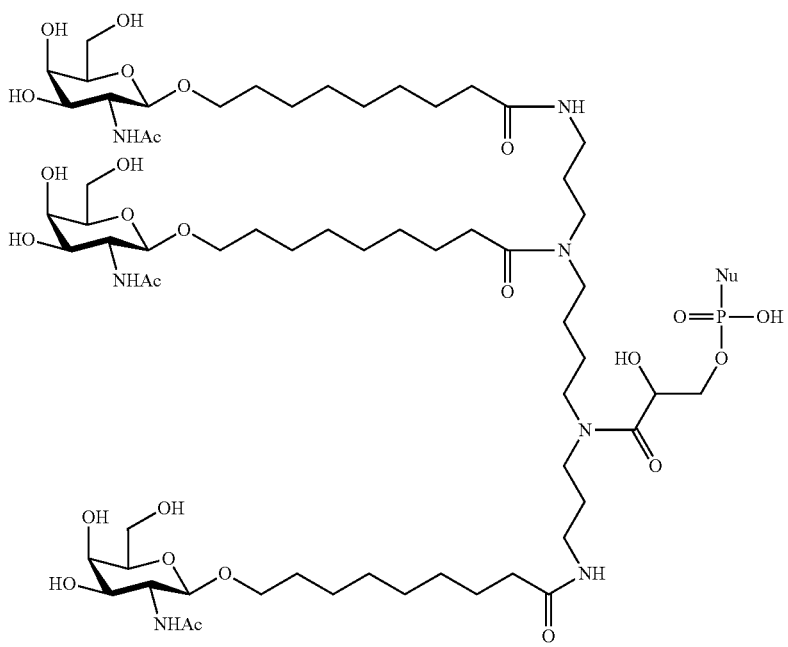
Formula (19)

-continued

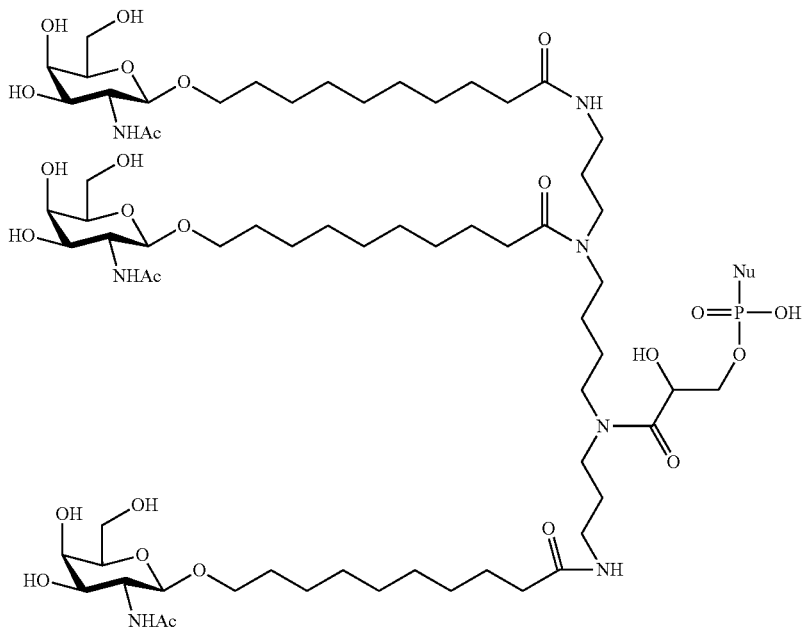

Formula (20)

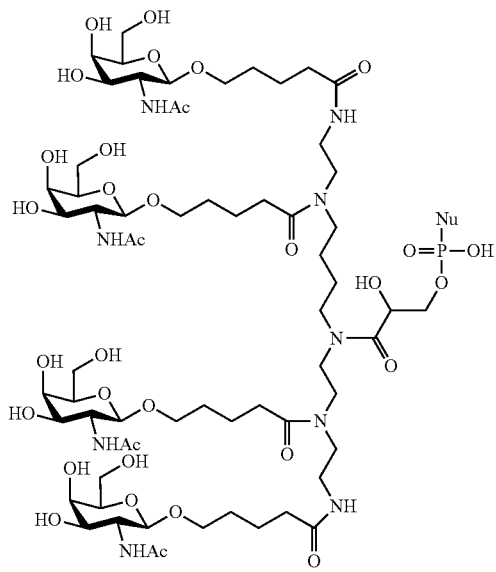

Formula (21)

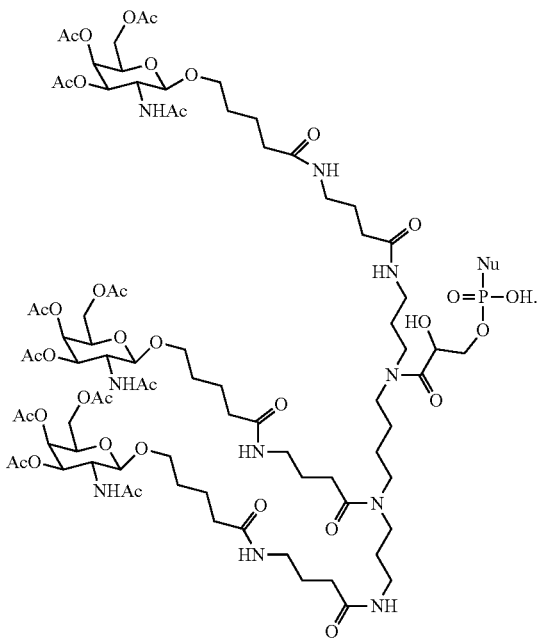

Formula (22)

In some embodiments, the oligonucleotide in the oligonucleotide conjugate of the present disclosure is a functional oligonucleotide. A functional oligonucleotide refers to an oligonucleotide that is capable of up- or down-regulating the expression of a target gene or resulting in alternative splicing of mRNA by producing a stable and specific hybridization to a target sequence, utilizing principles such as RNA activation (RNAa), RNA interference (RNAi), antisense nucleic acid technology, and exon skipping technology. In some embodiments, the functional oligonucleotide may also be a nucleic acid structure that produces a stable and specific binding to a target protein. In addition, it will be readily understood by those skilled in the art that a polynucleotide, such as the mRNA per se or fragments thereof, is also suitable for forming a conjugate by conjugation with the conjugating molecule provided by the present disclosure to achieve targeting delivery such as liver targeting deliver, thereby regulating the expression of protein transcribed by the mRNA. Thus, in the context, the "functional oligonucleotide" can also encompass an mRNA or fragments thereof.

In some embodiments, the functional oligonucleotide is capable of interacting with a target sequence, thereby affecting the normal function of the target sequence molecule, such as causing breakage or translational repression of mRNA or alternative splicing of mRNA resulting from exon skipping, etc. In some embodiments, the functional oligonucleotide is complementary to the bases in the target sequence. In some embodiments, the functional oligonucleotide is complementary to more than 80%, 81%, 82%, 83%, 84%, 85%, 86%, 87%, 88%, 89%, 90%, 91%, 92%, 93%, 94%, 95%, 96%, 97%, 98% or 99% of the bases in the target sequence, or may be fully complementary to the target sequence. In some embodiments, the functional oligonucleotide can have 1, 2, or 3 bases that are not complementary to the target sequence. In some embodiments, the functional oligonucleotide includes deoxyribonucleotides, ribonucleotides, and modified nucleotides. In some embodiments, the functional oligonucleotide is a single strand DNA, RNA or DNA-RNA chimera, or a double stranded DNA, RNA or DNA-RNA hybrid.

As such, in some embodiments, the functional oligonucleotide suitable for the oligonucleotide conjugate of the present disclosure may be one of small interfering RNA (siRNA), microRNA, anti-microRNA (antimiR), microRNA antagonist (antagomir), microRNA mimics, decoy oligonucleotide, immune stimulatory, G-quadruplex, splice altering, single strand RNA (ssRNA), antisense nucleic acid, nucleic acid aptamer, small activating RNA (saRNA), stem-loop RNA, or DNA. WO2015/006740A2 discloses a conjugate with different ligands conjugated to an oligonucleotide, wherein the ligands are linked to the oligonucleotide via linkers. The oligonucleotide is selected from the group consisting of small interfering RNA (siRNA), microRNA, anti microRNA (antimiR), antagomir, microRNA mimics, decoy oligonucleotides (decoy), immune stimulatory, G-quadruplex, splice altering, single stranded RNA (ssRNA), antisense nucleic acid (antisense), aptamer, stem-loop RNA or DNA. These conjugates exhibit good stability in the delivery of oligonucleotides in vivo. In further embodiments, the functional oligonucleotide suitable for the oligonucleotide conjugate of the present disclosure is an oligonucleotides disclosed in WO2009082607A2, WO2009073809A2 or WO2015006740A2, all of which are incorporated herein by reference in their entireties.

The oligonucleotide conjugate of the present disclosure may regulate the aberrant expression of specific genes in certain cells such as hepatocytes by increasing the liver-targeting delivery of the active agent, such as the functional oligonucleotide, and thus improving the interaction of the functional oligonucleotide with the target sequence in the cells. In some embodiments, the specific gene may be an endogenous gene expressed in liver or a pathogen gene reproduced in liver. The gene that is aberrantly expressed in hepatocytes may be a gene such as ApoB, ApoC, ANGPTL3, PCSK9, SCD1, TIMP-1, Col1A1, FVII, STAT3, p53, HBV, and HCV, etc. In some embodiments, the gene that is aberrantly expressed in hepatocytes is an HBV gene, an ANGPTL3 gene, or an APOC3 gene. In the context of the present disclosure, HBV gene refers to a gene having a sequence as shown in Genbank Accession No. NC_003977.1; ANGPTL3 gene refers to a gene having an mRNA sequence as shown in Genbank Accession No. NM_014495.3; and APOC3 gene refers to a gene having an mRNA sequence as shown in Genbank Accession No. NM_000040.1.

In some embodiments, a "target sequence" is a target mRNA. In the context of the present disclosure, a "target mRNA" refers to a mRNA corresponding to a gene that is aberrantly expressed in such as hepatocytes, which may be either a mRNA corresponding to an overexpressed gene or a mRNA corresponding to an under-expressed gene. In some embodiments, a target mRNA is preferably an mRNA corresponding to an overexpressed gene, since most of diseases are derived from the overexpression of mRNA. In some embodiments of the present disclosure, the target mRNA corresponding to the above-mentioned aberrantly expressed gene may be an mRNA corresponding to a gene such as ApoB, ApoC, ANGPTL3, PCSK9, SCD1, TIMP-1, Col1A1, FVII, STAT3, p53, HBV, and HCV, etc. In some embodiments, the target mRNA may be an mRNA transcribed by a corresponding HBV gene, ANGPTL3 gene or APOC3 gene.

The P atom in Formula A59 may be linked to any possible position in the oligonucleotide sequence, for example, to any nucleotide of the oligonucleotide. In some embodiments, the functional oligonucleotide in the oligonucleotide conjugate of the present disclosure is a single strand oligonucleotide (e.g., a single strand RNA or an aptamer). In this case, the P atom in Formula A59 may be linked to a terminal region of the single strand oligonucleotide, which refers to the 4 nucleotides closest to one end of the single strand oligonucleotide. In some embodiments, the P atom in Formula A59 is linked to either end of the single strand oligonucleotide.

In some embodiments, the functional oligonucleotide in the oligonucleotide conjugate of the present disclosure is a double stranded oligonucleotide (e.g., siRNA, microRNA, or DNA) comprising a sense strand and an antisense strand. In some embodiments, the P atom in Formula A59 may be linked to a terminal region of the sense strand or the antisense strand in the double stranded oligonucleotide, which refers to the 4 nucleotides closest to one end of the sense or antisense strand. In some embodiments, the P atom in Formula A59 is linked to either end of the sense or antisense strand. In some embodiments, the P atom in Formula A59 is linked to 3' end of the sense strand. In the case where the P atom in Formula A59 is linked to the above position in the sense strand of the double stranded oligonucleotide, the oligonucleotide conjugate provided by the present disclosure can release a separate antisense strand of the double stranded oligonucleotide during unwinding after entering into cells, thereby blocking the translation of the target mRNA into a protein and inhibiting the expression of a specific gene.

The P atom in Formula A59 may be linked to any possible position of a nucleotide in the oligonucleotide sequence, for example, to position 5', 2' or 3', or to the base of the nucleotide. In some embodiments, the P atom in Formula A59 may be linked to position 2', 3', or 5' of a nucleotide in the oligonucleotide sequence by forming a phosphodiester bond. In some embodiments, the P atom in Formula A59 is linked to an oxygen atom formed after deprotonation of 3'-hydroxy of the nucleotide at 3' end of the sense strand in the double stranded oligonucleotide sequence, or linked to a nucleotide by substituting a hydrogen atom in 2'-hydroxy of a nucleotide of the sense strand or by substituting a hydrogen atom in 5'-hydroxy of the nucleotide at 5' end of the sense strand in the double stranded oligonucleotide sequence.

Without wishing to be limited, the invention is described in further details in the following embodiments and examples with respect to the exemplary embodiments where the functional oligonucleotide in the oligonucleotide conjugate of the disclosure is a small interfering RNA (siRNA). In this case, the oligonucleotide conjugate of the present disclosure is an siRNA conjugate. In the context of the present disclosure, siRNA conjugates in these embodiments are also referred to as siRNA conjugates of the present disclosure just for convenience of description. It does not mean that the oligonucleotide in the oligonucleotide conjugate of the present disclosure can only be siRNA, instead, the oligonucleotide and even the active drug may be additional alternatives as disclosed herein or known to a skilled one. It is envisaged that, based on the detailed illustration on siRNA conjugate, other active drugs or functional oligonucleotides would work similarly when conjugated with the conjugating molecules provided herein.

It is known to those skilled in the art that an siRNA comprises nucleotide groups as building blocks. The nucleotide group, in turn, comprises a phosphate group, a ribose group and a base. Generally, an active siRNA, i.e., a functional siRNA, may have a length of about 12-40 nucleotides, and in some embodiments is about 15-30 nucleotides in length. Each nucleotide in the siRNAs may be independently a modified or unmodified nucleotide. For an increased stability, at least one nucleotide in the siRNA is a modified nucleotide.

The inventors of the present disclosure have found that the siRNAs described in the following embodiments have higher activity and/or stability and thus may be used as siRNAs for the purposes disclosed herein.

In some embodiments, each nucleotide in the siRNA of the siRNA conjugate of the present disclosure (also referred to as the siRNA of the present disclosure hereinafter) is independently a modified or unmodified nucleotide. The siRNA comprises a sense strand and an antisense strand, wherein the sense strand comprises a nucleotide sequence 1, and the antisense strand comprises a nucleotide sequence 2. The nucleotide sequence 1 and the nucleotide sequence 2 both have a length of 10, 11, 12, 13, 14, 15, 16, 17, 18, 19, 20, 21, 22, 23, 24, or 25 nucleotides and are at least partly reverse complementary to form a double-stranded complementary region. The nucleotide sequence 2 is complementary to a first nucleotide sequence segment, which refers to a segment of nucleotide sequence in the target mRNA.

In some embodiments, the siRNA of the present disclosure refers to an siRNA capable of inhibiting at least 50% of the expression of HBV gene, at least 50% of the expression of ANGPTL3 gene, or at least 50% of the expression of APOC3 gene, at a concentration of 3 mg/kg. In some embodiments, the siRNA of the present disclosure refers to an siRNA capable of inhibiting at least 55%, 60%, 65%, 70%, 75%, or 80% of the expression of HBV gene, ANGPTL3 gene, or APOC3 gene, at a concentration of 3 mg/kg.

In some embodiments, the nucleotide sequence 1 has the same length and no more than 3 nucleotides different from the first nucleotide sequence segment; the nucleotide sequence 2 has the same length and no more than 3 nucleotides different from a nucleotide sequence B, which refers to a nucleotide sequence completely reverse complementary to the first nucleotide sequence segment. Without wishing to be bounded by any theory, these special nucleotide differences will not significantly reduce the depressing ability of the siRNA conjugates, and are thus within the scope of the disclosure.

In some embodiments, the nucleotide sequence 1 is basically reverse complementary, Substantially reverse complementary, or completely reverse complementary with the nucleotide sequence 2.

In some embodiments, the nucleotide sequence 1 has no more than 1 nucleotide different from the first nucleotide sequence segment; and/or the nucleotide sequence 2 has no more than 1 nucleotides different from a nucleotide sequence B. In some embodiments, the nucleotide differences between the nucleotide sequence 2 and the nucleotide sequence B includes the difference at the site of the first nucleotide Z' on the nucleotide sequence 2 from 5' end to 3' end. In some embodiments, the last nucleotide Z on the nucleotide sequence 1 from 5' end to 3' end is a nucleotide complementary to Z'.

in some embodiments, the sense strand also comprises a nucleotide sequence 3, and the antisense strand also comprises a nucleotide sequence 4. The nucleotide sequences 3 and 4 have the same length of 1-4 nucleotides. The nucleotide sequence 3 is linked to the 5' end of the nucleotide sequence 1, and the nucleotide sequence 4 is linked to the 3' end of the nucleotide sequence 2. The nucleotide sequence 4 is complementary to a second nucleotide sequence segment, which refers to a nucleotide sequence adjacent to the first nucleotide sequence segment and having the same length as the nucleotide sequence 4 in the target mRNA. In some embodiments, the nucleotide sequence 3 is substantially reverse complementary or completely reverse complementary to the nucleotide sequence 4. Therefore, in some embodiments, the sense strand and the antisense strand may have a length of 19-23 nucleotides.

In some embodiments, the siRNA of the present disclosure also comprises a nucleotide sequence 5, which has a length of 1-3 nucleotides and is linked to 3' end of the antisense strand, thereby constituting a 3' overhang of the antisense strand. In some embodiments, the nucleotide sequence 5 is 1 or 2 nucleotides in length. As such, in some embodiments, the length ratio of the sense strand to the antisense strand in the siRNA of the present disclosure may be 19/20, 19/21, 20/21, 20/22, 21/22, 21/23, 22/23, 22/24, 23/24, or 23/25.

In some embodiments, the nucleotide sequence 5 has 2 nucleotides in length. Moreover, the nucleotide sequence 5 is 2 continuous thymidine deoxynucleotides, or 2 continuous uridine nucleotides in the direction from 5' end to 3' end, or complementary to a third nucleotide sequence segment, which refers to a nucleotide sequence adjacent to the first or second nucleotide sequence segment in the target mRNA, and having the same length as the nucleotide sequence 5. In some embodiments, the length ratio of the sense strand to the antisense strand in the siRNA of the present disclosure is 19/21 or 21/23. Here, the siRNA of the present disclosure exhibits significant silencing activity against mRNA in hepatocytes.

In some embodiments, the nucleotides in the siRNA of the present disclosure are each independently a modified or unmodified nucleotide. In some embodiments, the siRNA of the present disclosure comprises no modified nucleotide. In some embodiments, the siRNA of the present disclosure comprises a modified nucleotide group.

There are currently many means that may be used to modify siRNA in the art, including backbone modification (or internucleotide linkage modification, such as phosphate group modification), ribose group modification, base modification, etc. (see, for example, Watts, J. K., G. F. Deleavey and M. J. Damha, Chemically Modified siRNA: tools and applications. Drug Discov Today, 2008. 13(19-20): p. 842-55, which is incorporated herein by reference in its entirety).

In the context of the disclosure, the term "a modified nucleotide" employed herein comprises a nucleotide where the ribose group is modified, such as those formed by substituting the 2'-hydroxy of the ribose group with other groups, a nucleotide analogue, or a nucleotide with modified base.

In some embodiments of the disclosure, at least one nucleotide in the sense or antisense strand is a modified nucleotide, and/or at least one phosphate is a phosphate group with modified groups. In other words, at least a portion of the phosphate and/or ribose groups in phosphate-ribose backbone of at least one single strand in the sense strand and the antisense strand are phosphate and/or ribose groups with modified groups (or modified phosphate and/or modified ribose). In some embodiments of the disclosure, all nucleotides in the sense strand and/or the antisense strand are modified nucleotides.

In some embodiments, each nucleotide in the sense strand and the antisense strand is independently a fluoro modified nucleotide or a non-fluoro modified nucleotide.

A "fluoro modified nucleotide" refers to a nucleotide formed by substituting the 2'-hydroxy of the ribose group with a fluoro as represented by Formula (207).

A "non-fluoro modified nucleotide" refers to a nucleotide formed by substituting the 2'-hydroxy of the ribose group with a group other than a fluoro, or a nucleotide analogue. In some embodiments, each non-fluoro modified nucleotide is independently a nucleotide formed by substituting the 2'-hydroxy of the ribose group thereof with a non-fluoro group, or a nucleotide analogue.

A nucleotide formed by substituting the 2'-hydroxy of the ribose group with a non-fluoro group is well-known in the art, such as 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides or 2'-deoxy nucleotides.

In some embodiments, the 2'-alkoxy modified nucleotide is a methoxy modified nucleotide represented by Formula (208). In some embodiments, the 2'-substituted alkoxy modified nucleotide is a 2'-O-methoxyethoxy modified nucleotide represented by Formula (209). In some embodiments, the 2'-amino modified nucleotide is represented by Formula (210). In some embodiments, the 2'-deoxy nucleotide (DNA) is represented by Formula (211).

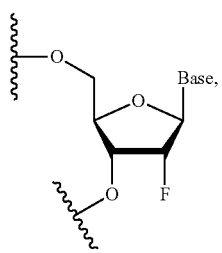

(207)

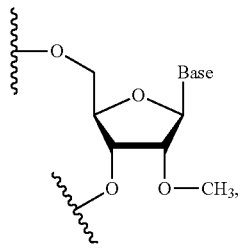

(208)

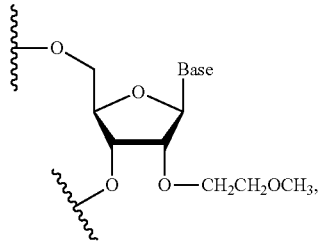

(209)

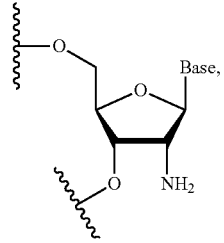

(210)

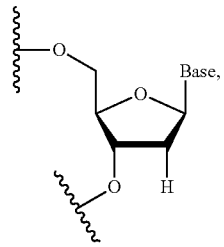

(211)

A "nucleotide analogue" refers to a group that can replace a nucleotide in the nucleic acid, while differs from an adenine ribonucleotide, a guanine ribonucleotide, a cytosine ribonucleotide, a uracil ribonucleotide or thymine deoxyribonucleotide. In some embodiments, the nucleotide analogue may be such as an isonucleotide, a bridged nucleic acid (BNA) nucleotide or a acyclic nucleotide.

A BNA nucleotide is a nucleotide that is constrained or inaccessible. BNA can contain a 5-, 6-membered or even a 7-membered ring bridged structure with a "fixed" C3'-endo sugar puckering. The bridge is typically incorporated at the 2'- and 4'-position of the ribose ring to afford a 2', 4'-BNA nucleotide, such as LNA, ENA and cET BNA which is represented by Formula (212), (213) and (214), respectively.

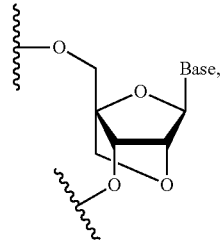

(212)

(213)

(214)

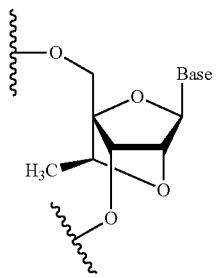

An acyclic nucleotide is a nucleotide in which the ribose ring is opened, such as an unlocked nucleic acid (UNA) nucleotide and a glycerol nucleic acid (GNA) nucleotide, which are respectively represented by Formula (215) and (216).

(215)

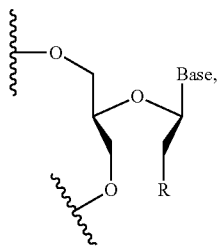

(216)

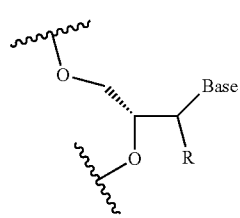

wherein R is H, OH or alkoxy (O-alkyl).

An isonucleotide is a nucleotide in which the position of the base on the ribose ring alters, such as a compound in with the base is moved from 1' to 2' or 3' on the ribose ring represented respectively by Formula (217) or (218).

(217)

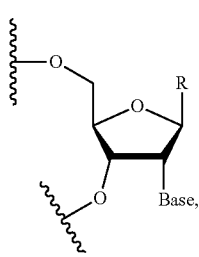

(218)

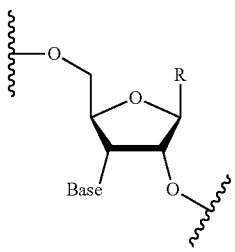

wherein a Base represents a nucleic acid base A, U, G, C or T; R is H, OH, F or a non-fluoro group described above.

In some embodiments, a nucleotide analogue is an isonucleotide, LNA, ENA, cET, UNA or GNA. In some embodiments, each non-fluoro modified nucleotide is a methoxy modified nucleotide, which refers to a nucleotide formed by substituting the 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is substituted with fluoro" and a "nucleotide with 2'-fluororibosyl" have the same meaning, referring to the nucleotide that 2'-hydroxy of the nucleotide is substituted with fluoro to form a structure represented by Formula (207). A "methoxy modified nucleotide", a "2'-methoxy modified nucleotide", a "nucleotide in which 2'-hydroxy of a ribose group is substituted with methoxy" and a "nucleotide with 2'-methoxyribosyl" have the same meaning, referring to the nucleotide that 2'-hydroxy of the ribose group in the nucleotide is substituted with methoxy to form a structure represented by Formula (208).

In some embodiments, the siRNA of the disclosure is a siRNA with the following modifications: in the direction from 5' end to 3' end, the nucleotides at positions 7, 8 and 9 of the nucleotide sequence 1 in the sense strand of the siRNA are fluoro modified nucleotides, and the nucleotides at the rest of positions in the sense strand are methoxy modified nucleotides; and/or the nucleotides at positions 2, 6, 14 and 16 of the nucleotide sequence 2 in the antisense strand are fluoro modified nucleotides, and the nucleotides at the rest of positions in the antisense strand are methoxy modified nucleotides. In some embodiments, the siRNA of the disclosure is a siRNA with the following modifications: in the direction from 5' end to 3' end, the nucleotides at positions 5, 7, 8 and 9 of the nucleotide sequence 1 in the sense strand of the siRNA are fluoro modified nucleotides, and the nucleotides at the rest of positions in the sense strand are methoxy modified nucleotides; and/or the nucleotides at positions 2, 6, 8, 9, 14 and 16 of the nucleotide sequence 2 in the antisense strand are fluoro modified nucleotides, and the nucleotides at the rest of positions in the antisense strand are 2'-methoxy modified nucleotides. In some embodiments, the siRNA of the disclosure is a siRNA with the following modifications: in the direction from 5' end to 3' end, the nucleotides at positions 7, 8 and 9 of the nucleotide sequence 1 in the sense strand of the siRNA are fluoro modified nucleotides, and the nucleotides at the rest of positions in the sense strand are methoxy modified nucleotides; and/or in the direction from 5' end to 3' end, the nucleotides at positions 2, 6, 14 and 16 of the nucleotide sequence 2 in the antisense strand of the siRNA are fluoro modified nucleotides, and the nucleotides at the rest of positions in the antisense strand are methoxy modified nucleotides.

In some embodiments of the siRNA of the present disclosure, the nucleotide has modifications on phosphate groups. In the context of the present disclosure, the modification on a phosphate group is in some embodiments a phosphorothioate modification represented by Formula (201) below, that is, the substitution of a non-bridging oxygen atom in a phosphodiester bond with a sulfur atom so that the phosphodiester bond is changed to a phosphorothioate diester bond. In some embodiments, this modification stabilizes the structure of the siRNA and maintaining high specificity and high affinity for base pairing.

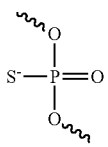

(201)

According to some embodiments of the present disclosure, in the siRNA, a phosphorothioate linkage exists in at least one of the following position: between the first and the second nucleotides from either end of the sense or antisense strand, between the second and the third nucleotides from either end of the sense strand or antisense strand, or any combination thereof. In some embodiments, a phosphorothioate linkage exists at all the above positions except for 5' end of the sense strand. In some embodiments, a phosphorothioate linkage exists at all the above positions except for 3' end of the sense strand. In some embodiments, a phosphorothioate linkage exists in at least one of the following positions:

between the first and second nucleotides from 5' end of the sense strand;

between the second and third nucleotides from 5' end of the sense strand;

between the first and second nucleotides from 3' end of the sense strand;

between the second and third nucleotides from 3' end of the sense strand;

between the first and second nucleotides from 5' end of the antisense strand;

between the second and third nucleotides from 5' end of the antisense strand;

between the first and second nucleotides from 3' end of the antisense strand; and between the second and third nucleotides from 3' end of the antisense strand.

According to some embodiments of the present disclosure, the 5'-terminal nucleotide in the antisense strand sequence of the siRNA molecule is a 5'-phosphate nucleotide or a 5'-phosphate analogue modified nucleotide.

In some embodiments, the 5'-phosphate nucleotide has the following structure represented by Formula (202):

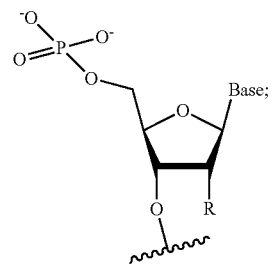

(202)

Common types of the 5'-phosphate analogue modified nucleotides are well known to those skilled in the art, for example, the following 4 nucleotides represented by Formulas (203)-(206) disclosed in Anastasia Khvorova and Jonathan K. Watts, The chemical evolution of oligonucleotide therapies of clinical utility. Nature Biotechnology, 2017, 35(3): 238-48:

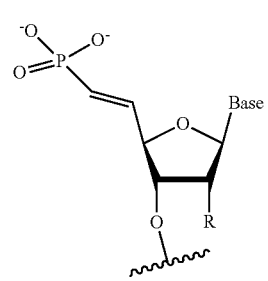

Formula (203)

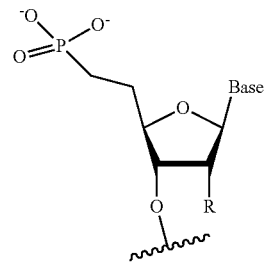

Formula (204)

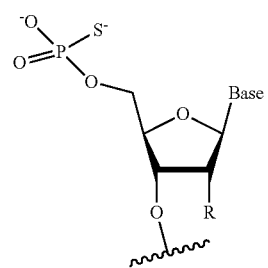

Formula (205)

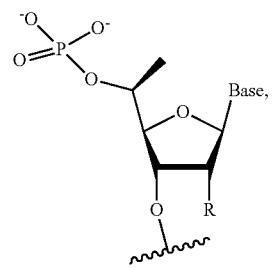

Formula (206)

wherein R represents a group selected from the group consisting of H, OH, F, and methoxy;

"Base" represents a base selected from A, U, C, G, or T.

In some embodiments, the 5'-phosphate nucleotide or the 5'-phosphate analogue modified nucleotide is a nucleotide with a vinyl phosphate (VP) modification represented by Formula (203), a 5'-phosphate nucleotide represented by Formula (202) or a 5'-phosphorothioate modified nucleotide represented by Formula (205).

The inventors of the present disclosure have unexpectedly discovered that the siRNA conjugate of the present disclosure exhibits a significantly improved serum stability while the target mRNA silencing activity is not significantly compromised, leading to an excellent inhibitory effect in vivo on gene expression. It has shown that these siRNA conjugates of the present disclosure have higher delivery efficiency in vivo. According to some embodiments of the present disclosure, the oligonucleotide conjugates of the present disclosure are therefore siRNA conjugates comprising siRNAs such as those shown in Table 1A-Table 1F:

Table 1 siRNA sequences

TABLE 1A

| NO. | | Sequence Direction 5' - 3' | SEQ ID NO |
|---|---|---|---|
| siHBa1 | *S | CCUUGAGGCAUACUUCAAA | 1 |
| | AS | UUUGAAGUAUGCCUCAAGGUU | 2 |
| siHBa2 | S | GACCUUGAGGCAUACUUCAAA | 3 |
| | AS | UUUGAAGUAUGCCUCAAGGUCGG | 4 |
| siHBa1M1 | S | CmCmUmUmGmAmGfGfCfAmUmAmCmUmUmCmAmAmAm | 5 |
| | AS | UmUfUmGmAmAfGmUmAmUmGmCmCmUfCmAfAmGmGmUmUm | 6 |
| siHBa1M2 | S | CmCmUmUmGfAmGfGfCfAmUmAmCmUmUmCmAmAmAm | 7 |
| | AS | UmUfUmGmAmAfGmUfAfUmGmCmCmUfCmAfAmGmGmUmUm | 8 |
| siHBa2M1 | S | GmAmCmCmUmUmGmAmGfGfCfAmUmAmCmUmUmCmAmAmAm | 9 |
| | AS | UmUfUmGmAmAfGmUmAmUmGmCmCmUfCmAfAmGmGmUmCmGmGm | 10 |
| siHBa2M2 | S | GmAmCmCmUmUmGfAmGfGfCfAmUmAmCmUmUmCmAmAmAm | 11 |
| | AS | UmUfUmGmAmAfGmUfAfUmGmCmCmUfCmAfAmGmGmUmCmGmGm | 12 |
| siHBa1M1S | S | CmsCmsUmUmGmAmGfGfCfAmUmAmCmUmUmCmAmAmAm | 13 |
| | AS | UmsUfsUmGmAmAfGmUmAmUmGmCmCmUfCmAfAmGmGmsUmsUm | 14 |
| siHBa1M2S | S | CmsCmsUmUmGfAmGfGfCfAmUmAmCmUmUmCmAmAmAm | 15 |
| | AS | UmsUfsUmGmAmAfGmUfAfUmGmCmCmUfCmAfAmGmGmsUmsUm | 16 |
| siHBa2M1S | S | GmsAmsCmCmUmUmGmAmGfGfCfAmUmAmCmUmUmCmAmAmAm | 17 |
| | AS | UmsUfsUmGmAmAfGmUmAmUmGmCmCmUfCmAfAmGmGmUmCmsGmsGm | 18 |
| siHBa2M2S | S | GmsAmsCmCmUmUmGfAmGfGfCfAmUmAmCmUmUmCmAmAmAm | 19 |
| | AS | UmsUfsUmGmAmAfGmUfAfUmGmCmCmUfCmAfAmGmGmUmCmsGmsGm | 20 |
| siHBa1M1P1 | S | CmCmUmUmGmAmGfGfCfAmUmAmCmUmUmCmAmAmAm | 5 |
| | AS | P1-UmUfUmGmAmAfGmUmAmUmGmCmCmUfCmAfAmGmGmUmUm | 21 |
| siHBa1M2P1 | S | CmCmUmUmGfAmGfGfCfAmUmAmCmUmUmCmAmAmAm | 7 |
| | AS | P1 -UmUfUmGmAmAfGmUfAfUmGmCmCmUfCmAfAmGmGmUmUm | 22 |
| siHBa2M1P1 | S | GmAmCmCmUmUmGmAmGfGfCfAmUmAmCmUmUmCmAmAmAm | 9 |
| | AS | P1 - UmUfUmGmAmAfGmUmAmUmGmCmCmUfCmAfAmGmGmUmCmGmGm | 23 |
| siHBa2M2P1 | S | GmAmCmCmUmUmGfAmGfGfCfAmUmAmCmUmUmCmAmAmAm | 11 |
| | AS | P1 - UmUfUmGmAmAfGmUfAfUmGmCmCmUfCmAfAmGmGmUmCmGmGm | 24 |
| siHBa1M1SP1 | S | CmsCmsUmUmGmAmGfGfCfAmUmAmCmUmUmCmAmAmAm | 13 |
| | AS | P1-UmsUfsUmGmAmAfGmUmAmUmGmCmCmUfCmAfAmGmGmsUmsUm | 25 |
| siHBa1M2SP1 | S | CmsCmsUmUmGfAmGfGfCfAmUmAmCmUmUmCmAmAmAm | 15 |
| | AS | P1 -UmsUfsUmGmAmAfGmUfAfUmGmCmCmUfCmAfAmGmGmsUmsUm | 26 |
| siHBa2M1SP1 | S | GmsAmsCmCmUmUmGmAmGfGfCfAmUmAmCmUmUmCmAmAmAm | 17 |
| | AS | P1 - UmsUfsUmGmAmAfGmUmAmUmGmCmCmUfCmAfAmGmGmUmCmsGmsGm | 27 |
| siHBa2M2SP1 | S | GmsAmsCmCmUmUmGfAmGfGfCfAmUmAmCmUmUmCmAmAmAm | 19 |
| | AS | P1 - UmsUfsUmGmAmAfGmUfAfUmGmCmCmUfCmAfAmGmGmUmCmsGmsGm | 28 |

TABLE 1B

| NO. | | Sequence Direction 5' - 3' | SEQ ID NO |
|---|---|---|---|
| siHBb1 | S | UGCUAUGCCUCAUCUUCUA | 29 |
| | AS | UAGAAGAUGAGGCAUAGCAGC | 30 |
| siHBb2 | S | UGCUAUGCCUCAUCUUCUA | 29 |
| | AS | UAGAAGAUGAGGCAUAGCAUU | 31 |
| siHBb1M1 | S | UmGmCmUmAmUmGfCfCfUmCmAmUmCmUmUmCmUmAm | 32 |
| | AS | UmAfGmAmAmGfAmUmGmAmGmGmCmAfUmAfGmCmAmGmCm | 33 |
| siHBb2M1 | S | UmGmCmUmAmUmGfCfCfUmCmAmUmCmUmUmCmUmAm | 32 |
| | AS | UmAfGmAmAmGfAmUmGmAmGmGmCmAfUmAfGmCmAmUmUm | 34 |
| siHBb1M2 | S | UmGmCmUmAfUmGfCfCfUmCmAmUmCmUmUmCmUmAm | 35 |
| | AS | UmAfGmAmAmGfAmUfGfAmGmGmCmAfUmAfGmCmAmGmCm | 36 |
| siHBb2M2 | S | UmGmCmUmAfUmGfCfCfUmCmAmUmCmUmUmCmUmAm | 35 |
| | AS | UmAfGmAmAmGfAmUfGfAmGmGmCmAfUmAfGmCmAmUmUm | 37 |
| siHBb1M1S | S | UmsGmsCmUmAmUmGfCfCfUmCmAmUmCmUmUmCmUmAm | 38 |
| | AS | UmsAfsGmAmAmGfAmUmGmAmGmGmCmAfUmAfGmCmAmsGmsCm | 39 |
| siHBb2M1S | S | UmsGmsCmUmAmUmGfCfCfUmCmAmUmCmUmUmCmUmAm | 38 |
| | AS | UmsAfsGmAmAmGfAmUmGmAmGmGmCmAfUmAfGmCmAmsUmsUm | 40 |
| siHBb1M2S | S | UmsGmsCmUmAfUmGfCfCfUmCmAmUmCmUmUmCmUmAm | 41 |
| | AS | UmsAfsGmAmAmGfAmUfGfAmGmGmCmAfUmAfGmCmAmsGmsCm | 42 |
| siHBb2M2S | S | UmsGmsCmUmAfUmGfCfCfUmCmAmUmCmUmUmCmUmAm | 41 |
| | AS | UmsAfsGmAmAmGfAmUfGfAmGmGmCmAfUmAfGmCmAmsUmsUm | 43 |
| siHBb1M1P1 | S | UmGmCmUmAmUmGfCfCfUmCmAmUmCmUmUmCmUmAm | 32 |
| | AS | P1-UmAfGmAmAmGfAmUmGmAmGmGmCmAfUmAfGmCmAmGmCm | 44 |
| siHBb2M1P1 | S | UmGmCmUmAmUmGfCfCfUmCmAmUmCmUmUmCmUmAm | 32 |
| | AS | P1-UmAfGmAmAmGfAmUmGmAmGmGmCmAfUmAfGmCmAmUmUm | 45 |
| siHBb1M2P1 | S | UmGmCmUmAfUmGfCfCfUmCmAmUmCmUmUmCmUmAm | 35 |
| | AS | P1-UmAfGmAmAmGfAmUfGfAmGmGmCmAfUmAfGmCmAmGmCm | 46 |
| siHBb2M2P1 | S | UmGmCmUmAfUmGfCfCfUmCmAmUmCmUmUmCmUmAm | 35 |
| | AS | P1-UmAfGmAmAmGfAmUfGfAmGmGmCmAfUmAfGmCmAmUmUm | 47 |
| siHBb1M1SP1 | S | UmsGmsCmUmAmUmGfCfCfUmCmAmUmCmUmUmCmUmAm | 38 |
| | AS | P1-UmsAfsGmAmAmGfAmUmGmAmGmGmCmAfUmAfGmCmAmsGmsCm | 48 |
| siHBb2M1SP1 | S | UmsGmsCmUmAmUmGfCfCfUmCmAmUmCmUmUmCmUmAm | 38 |
| | AS | P1-UmsAfsGmAmAmGfAmUmGmAmGmGmCmAfUmAfGmCmAmsUmsUm | 49 |
| siHBb1M2SP1 | S | UmsGmsCmUmAfUmGfCfCfUmCmAmUmCmUmUmCmUmAm | 41 |
| | AS | P1-UmsAfsGmAmAmGfAmUfGfAmGmGmCmAfUmAfGmCmAmsGmsCm | 50 |
| siHBb2M2SP1 | S | UmsGmsCmUmAfUmGfCfCfUmCmAmUmCmUmUmCmUmAm | 41 |
| | AS | P1-UmsAfsGmAmAmGfAmUfGfAmGmGmCmAfUmAfGmCmAmsUmsUm | 51 |

TABLE 1C

| NO. | | Sequence Direction 5' - 3' | SEQ ID NO |
|---|---|---|---|
| siHBc1 | S | UCUGUGCCUUCUCAUCUGA | 52 |
| | AS | UCAGAUGAGAAGGCACAGACG | 53 |
| siHBc1M1 | S | UmCmUmGmUmGmCfCfUfUmCmUmCmAmUmCmUmGmAm | 54 |
| | AS | UmCfAmGmAmUfGmAmGmAmAmGmGmCfAmCfAmGmAmCmGm | 55 |
| siHBc1M2 | S | UmCmUmGmUfGmCfCfUfUmCmUmCmAmUmCmUmGmAm | 56 |
| | AS | UmCfAmGmAmUfGmAfGfAmAmGmGmCfAmCfAmGmAmCmGm | 57 |
| siHBc1M1S | S | UmsCmsUmGmUmGmCfCfUfUmCmUmCmAmUmCmUmGmAm | 58 |
| | AS | UmsCfsAmGmAmUfGmAmGmAmAmGmGmCfAmCfAmGmAmsCmsGm | 59 |
| siHBc1M2S | S | UmsCmsUmGmUfGmCfCfUfUmCmUmCmAmUmCmUmGmAm | 60 |
| | AS | UmsCfsAmGmAmUfGmAfGfAmAmGmGmCfAmCfAmGmAmsCmsGm | 61 |
| siHBc1M1P1 | S | UmCmUmGmUmGmCfCfUfUmCmUmCmAmUmCmUmGmAm | 54 |
| | AS | P1-UmCfAmGmAmUfGmAmGmAmAmGmGmCfAmCfAmGmAmCmGm | 62 |
| siHBc1M2P1 | S | UmCmUmGmUfGmCfCfUfUmCmUmCmAmUmCmUmGmAm | 56 |
| | AS | P1-UmCfAmGmAmUfGmAfGfAmAmGmGmCfAmCfAmGmAmCmGm | 63 |
| siHBc1M1SP1 | S | UmsCmsUmGmUmGmCfCfUfUmCmUmCmAmUmCmUmGmAm | 58 |
| | AS | P1-UmsCfsAmGmAmUfGmAmGmAmAmGmGmCfAmCfAmGmAmsCmsGm | 64 |
| siHBc1M2SP1 | S | UmsCmsUmGmUfGmCfCfUfUmCmUmCmAmUmCmUmGmAm | 60 |
| | AS | P1-UmsCfsAmGmAmUfGmAfGfAmAmGmGmCfAmCfAmGmAmsCmsGm | 65 |

TABLE 1D

| NO. | | Sequence Direction 5' - 3' | SEQ ID NO |
|---|---|---|---|
| siHBd1 | S | CGUGUGCACUUCGCUUCAA | 66 |
| | AS | UUGAAGCGAAGUGCACACGGU | 67 |
| sHBd1M1 | S | CmGmUmGmUmGmCfAfCfUmCmGmCmUmUmCmAmAm | 68 |
| | AS | UmUfGmAmAmGfCmGmAmAmGmUmGmCfAmCfAmCmGmGmUm | 69 |
| sHBd1M2 | S | CmGmUmGmUfGmCfAfCfUmCmGmCmUmUmCmAmAm | 70 |
| | AS | UmUfGmAmAmGfCmGfAfAmGmUmGmCfAmCfAmCmGmGmUm | 71 |
| siHBd1M1S | S | CmsGmsUmGmUmGmCfAfCfUmCmGmCmUmUmCmAmAm | 72 |
| | AS | UmsUfsGmAmAmGfCmGmAmAmGmUmGmCfAmCfAmCmGmsGmsUm | 73 |
| siHBd1M2S | S | CmsGmsUmGmUfGmCfAfCfUmCmGmCmUmUmCmAmAm | 74 |
| | AS | UmsUfsGmAmAmGfCmGfAfAmGmUmGmCfAmCfAmCmGmsGmsUm | 75 |
| sHBd1M1P1 | S | CmGmUmGmUmGmCfAfCfUmCmGmCmUmUmCmAmAm | 68 |
| | AS | P1-UmUfGmAmAmGfCmGmAmAmGmUmGmCfAmCfAmCmGmGmUm | 76 |
| sHBd1M2P1 | S | CmGmUmGmUfGmCfAfCfUmCmGmCmUmUmCmAmAm | 70 |
| | AS | P1-UmUfGmAmAmGfCmGfAfAmGmUmGmCfAmCfAmCmGmGmUm | 77 |
| sHBd1M1SP1 | S | CmsGmsUmGmUmGmCfAfCfUmCmGmCmUmUmCmAmAm | 72 |
| | AS | P1-UmsUfsGmAmAmGfCmGmAmAmGmUmGmCfAmCfAmCmGmsGmsUm | 78 |
| sHBd1M2SP1 | S | CmsGmsUmGmUfGmCfAfCfUmCmGmCmUmUmCmAmAm | 74 |
| | AS | P1-UmsUfsGmAmAmGfCmGfAfAmGmUmGmCfAmCfAmCmGmsGmsUm | 79 |

TABLE 1E

| NO. | | Sequence Direction 5' - 3' | SEQ ID NO |
|---|---|---|---|
| siAN1 | S | CCAAGAGCACCAAGAACUA | 80 |
| | AS | UAGUUCUUGGUGCUCUUGGCU | 81 |
| siAN2 | S | AGCCAAGAGCACCAAGAACUA | 82 |
| | AS | UAGUUCUUGGUGCUCUUGGCUUG | 83 |
| siAN1M1 | S | CmCmAmAmGfAmGfCfAfCmCmAmAmGmAmAmCmUmAm | 84 |
| | AS | UmAfGmUmUmCfUmUfGfGmUmGmCmUfCmUfUmGmGmCmUm | 85 |
| siAN2M1 | S | AmGmCmCmAmAmGfAmGfCfAfCmCmAmAmGmAmAmCmUmAm | 86 |
| | AS | UmAfGmUmUmCfUmUfGfGmUmGmCmUfCmUfUmGmGmCmUmUmGm | 87 |
| siAN1M2 | S | CmCmAmAmGfAmGfCfAfCmCmAmAmGmAmAmCmUmAm | 84 |
| | AS | UmAfGmUmUmCfUmUmGmGmUmGmCmUfCmUfUmGmGmCmUm | 88 |
| siAN2M2 | S | AmGmCmCmAmAmGfAmGfCfAfCmCmAmAmGmAmAmCmUmAm | 86 |
| | AS | UmAfGmUmUmCfUmUmGmGmUmGmCmUfCmUfUmGmGmCmUmUmGm | 89 |
| siAN1M3 | S | CmCmAmAmGmAmGfCfAfCmCmAmAmGmAmAmCmUmAm | 90 |
| | AS | UmAfGmUmUmCfUmUmGmGmUmGmCmUfCmUfUmGmGmCmUm | 88 |
| siAN2M3 | S | AmGmCmCmAmAmGmGfCfAfCmCmAmAmGmAmAmCmUmAm | 91 |
| | AS | UmAfGmUmUmCfUmUmGmGmUmGmCmUfCmUfUmGmGmCmUmUmGm | 89 |
| siAN1M1S | S | CmsCmsAmAmGfAmGfCfAfCmCmAmAmGmAmAmCmUmAm | 92 |
| | AS | UmsAfsGmUmUmCfUmUfGfGmUmGmCmUfCmUfUmGmGmsCmsUm | 93 |
| siAN2M1S | S | AmsGmsCmCmAmAmGfAmGfCfAfCmCmAmAmGmAmAmCmUmAm | 94 |
| | AS | UmsAfsGmUmUmCfUmUfGfGmUmGmCmUfCmUfUmGmGmCmUmsUmsGm | 95 |
| siAN1M2S | S | CmsCmsAmAmGfAmGfCfAfCmCmAmAmGmAmAmCmUmAm | 92 |
| | AS | UmsAfsGmUmUmCfUmUmGmGmUmGmCmUfCmUfUmGmGmsCmsUm | 96 |
| siAN2M2S | S | AmsGmsCmCmAmAmGfAmGfCfAfCmCmAmAmGmAmAmCmUmAm | 94 |
| | AS | UmsAfsGmUmUmCfUmUmGmGmUmGmCmUfCmUfUmGmGmCmUmsUmsGm | 97 |
| siAN1M3S | S | CmsCmsAmAmGmAmGfCfAfCmCmAmAmGmAmAmCmUmAm | 98 |
| | AS | UmsAfsGmUmUmCfUmUmGmGmUmGmCmUfCmUfUmGmGmsCmsUm | 96 |
| siAN2M3S | S | AmsGmsCmCmAmAmGmGfCfAfCmCmAmAmGmAmAmCmUmAm | 99 |
| | AS | UmsAfsGmUmUmCfUmUmGmGmUmGmCmUfCmUfUmGmGmCmUmsUmsGm | 97 |
| siAN1M1P1 | S | CmCmAmAmGfAmGfCfAfCmCmAmAmGmAmAmCmUmAm | 84 |
| | AS | P1-UmAfGmUmUmCfUmUfGfGmUmGmCmUfCmUfUmGmGmCmUm | 100 |
| siAN2M1P1 | S | AmGmCmCmAmAmGfAmGfCfAfCmCmAmAmGmAmAmCmUmAm | 86 |
| | AS | P1-UmAfGmUmUmCfUmUfGfGmUmGmCmUfCmUfUmGmGmCmUmUmGm | 101 |
| siAN1M2P1 | S | CmCmAmAmGfAmGfCfAfCmCmAmAmGmAmAmCmUmAm | 84 |
| | AS | P1-UmAfGmUmUmCfUmUmGmGmUmGmCmUfCmUfUmGmGmCmUm | 102 |
| siAN2M2P1 | S | AmGmCmCmAmAmGfAmGfCfAfCmCmAmAmGmAmAmCmUmAm | 86 |
| | AS | P1-UmAfGmUmUmCfUmUmGmGmUmGmCmUfCmUfUmGmGmCmUmUmGm | 103 |
| siAN1M3P1 | S | CmCmAmAmGmAmGfCfAfCmCmAmAmGmAmAmCmUmAm | 90 |
| | AS | P1-UmAfGmUmUmCfUmUmGmGmUmGmCmUfCmUfUmGmGmCmUm | 102 |
| siAN2M3P1 | S | AmGmCmCmAmAmGmGfCfAfCmCmAmAmGmAmAmCmUmAm | 91 |
| | AS | P1-UmAfGmUmUmCfUmUmGmGmUmGmCmUfCmUfUmGmGmCmUmUmGm | 103 |
| siAN1M1SP1 | S | CmsCmsAmAmGfAmGfCfAfCmCmAmAmGmAmAmCmUmAm | 92 |
| | AS | P1-UmsAfsGmUmUmCfUmUfGfGmUmGmCmUfCmUfUmGmGmsCmsUm | 104 |
| siAN2M1SP1 | S | AmsGmsCmCmAmAmGfAmGfCfAfCmCmAmAmGmAmAmCmUmAm | 94 |
| | AS | P1-UmsAfsGmUmUmCfUmUfGfGmUmGmCmUfCmUfUmGmGmCmUmsUmsGm | 105 |
| siAN1M2SP1 | S | CmsCmsAmAmGfAmGfCfAfCmCmAmAmGmAmAmCmUmAm | 92 |
| | AS | P1-UmsAfsGmUmUmCfUmUmGmGmUmGmCmUfCmUfUmGmGmsCmsUm | 106 |
| siAN2M2SP1 | S | AmsGmsCmCmAmAmGfAmGfCfAfCmCmAmAmGmAmAmCmUmAm | 94 |
| | AS | P1-UmsAfsGmUmUmCfUmUmGmGmUmGmCmUfCmUfUmGmGmCmUmsUmsGm | 107 |

TABLE 1E-continued

| NO. | | Sequence Direction 5' - 3' | SEQ ID NO |
|---|---|---|---|
| siAN1M3SP1 | S | CmsCmsAmAmGmAmGfCfAfCmCmAmAmGmAmAmCmUmAm | 98 |
| | AS | P1-UmsAfsGmUmUmCfUmUmGmGmUmGmCmUfCmUfUmGmGmsCmsUm | 106 |
| siAN2M3SP1 | S | AmsGmsCmCmAmAmGmAmGfCfAfCmCmAmAmGmAmAmCmUmAm | 99 |
| | AS | P1-UmsAfsGmUmUmCfUmUmGmGmUmGmCmUfCmUfUmGmGmCmUmsUmsGm | 107 |

TABLE 1F

| NO. | | Sequence Direction 5' - 3' | SEQ ID NO |
|---|---|---|---|
| siAP1 | S | CAAUAAAGCUGGACAAGAA | 108 |
| | AS | UUCUUGUCCAGCUUUAUUGGG | 109 |
| siAP2 | S | CCCAAUAAAGCUGGACAAGAA | 110 |
| | AS | UUCUUGUCCAGCUUUAUUGGGAG | 111 |
| siAP1M1 | S | CmAmAmUmAfAmAfGfCfUmGmGmAmCmAmAmGmAmAm | 112 |
| | AS | UmUfCmUmUmGfUmCfCfAmGmCmUmUfUmAfUmUmGmGmGm | 113 |
| siAP2M1 | S | CmCmCmAmAmUmAfAmAfGfCfUmGmGmAmCmAmAmGmAmAm | 114 |
| | AS | UmUfCmUmUmGfUmCfCfAmGmCmUmUfUmAfUmUmGmGmGmAmGm | 115 |
| siAP1M2 | S | CmAmAmUmAmAmAfGfCfUmGmGmAmCmAmAmGmAmAm | 116 |
| | AS | UmUfCmUmUmGfUmCmCmAmGmCmUmUfUmAfUmUmGmGmGm | 117 |
| siAP2M2 | S | CmCmCmAmAmUmAmAmAfGfCfUmGmGmAmCmAmAmGmAmAm | 118 |
| | AS | UmUfCmUmUmGfUmCmCmAmGmCmUmUfUmAfUmUmGmGmGmAmGm | 119 |
| siAP1M1S | S | CmsAmsAmUmAfAmAfGfCfUmGmGmAmCmAmAmGmAmAm | 120 |
| | AS | UmsUfsCmUmUmGfUmCfCfAmGmCmUmUfUmAfUmUmGmsGmsGm | 121 |
| siAP2M1S | S | CmsCmsCmAmAmUmAfAmAfGfCfUmGmGmAmCmAmAmGmAmAm | 122 |
| | AS | UmsUfsCmUmUmGfUmCfCfAmGmCmUmUfUmAfUmUmGmGmGmsAmsGm | 123 |
| siAP1M2S | S | CmsAmsAmUmAmAmAfGfCfUmGmGmAmCmAmAmGmAmAm | 124 |
| | AS | UmsUfsCmUmUmGfUmCmCmAmGmCmUmUfUmAfUmUmGmsGmsGm | 125 |
| siAP2M2S | S | CmsCmsCmAmAmUmAmAmAfGfCfUmGmGmAmCmAmAmGmAmAm | 126 |
| | AS | UmsUfsCmUmUmGfUmCmCmAmGmCmUmUfUmAfUmUmGmGmGmsAmsGm | 127 |
| siAP1M1P1 | S | CmAmAmUmAfAmAfGfCfUmGmGmAmCmAmAmGmAmAm | 112 |
| | AS | P1-UmUfCmUmUmGfUmCfCfAmGmCmUmUfUmAfUmUmGmGmGm | 128 |
| siAP2M1P1 | S | CmCmCmAmAmUmAfAmAfGfCfUmGmGmAmCmAmAmGmAmAm | 114 |
| | AS | P1-UmUfCmUmUmGfUmCfCfAmGmCmUmUfUmAfUmUmGmGmGmAmGm | 129 |
| siAP1M2P1 | S | CmAmAmUmAmAmAfGfCfUmGmGmAmCmAmAmGmAmAm | 116 |
| | AS | P1-UmUfCmUmUmGfUmCmCmAmGmCmUmUfUmAfUmUmGmGmGm | 130 |
| siAP2M2P1 | S | CmCmCmAmAmUmAmAmAfGfCfUmGmGmAmCmAmAmGmAmAm | 118 |
| | AS | P1-UmUfCmUmUmGfUmCmCmAmGmCmUmUfUmAfUmUmGmGmGmAmGm | 131 |
| siAP1M1SP1 | S | CmsAmsAmUmAfAmAfGfCfUmGmGmAmCmAmAmGmAmAm | 120 |
| | AS | P1-UmsUfsCmUmUmGfUmCfCfAmGmCmUmUfUmAfUmUmGmsGmsGm | 132 |
| siAP2M1SP1 | S | CmsCmsCmAmAmUmAfAmAfGfCfUmGmGmAmCmAmAmGmAmAm | 122 |
| | AS | P1-UmsUfsCmUmUmGfUmCfCfAmGmCmUmUfUmAfUmUmGmGmGmsAmsGm | 133 |
| siAP1M2SP1 | S | CmsAmsAmUmAmAmAfGfCfUmGmGmAmCmAmAmGmAmAm | 124 |
| | AS | P1-UmsUfsCmUmUmGfUmCmCmAmGmCmUmUfUmAfUmUmGmsGmsGm | 134 |
| siAP2M2SP1 | S | CmsCmsCmAmAmUmAmAmAfGfCfUmGmGmAmCmAmAmGmAmAm | 126 |
| | AS | P1-UmsUfsCmUmUmGfUmCmCmAmGmCmUmUfUmAfUmUmGmGmGmsAmsGm | 135 |

*S: Sense Strand; AS: Antisense Srand

In the above tables, capital letters C, G, U, and A indicate the base compositions of the nucleotides; lowercase letter m indicates that the nucleotide adjacent to the left side of the letter m is a 2'-methoxy modified nucleotide; lowercase letter f indicates that the nucleotide adjacent to the left side of the letter f is a 2'-fluoro modified nucleotide; lowercase letter s indicates the phosphorothioate linkage between the two nucleotides adjacent to both sides of the letter s; P1 indicates that the nucleotide adjacent to the right side of P1 is a 5'-phosphate nucleotide or a 5'-phosphate analogue modified nucleotide, and in some embodiments is a vinyl phosphate modified nucleotide (represented as VP in the examples below), a phosphate nucleotide (represented as P in the examples below) or a phosphorothioate modified nucleotide (represented as Ps in the examples below).

It is well known to those skilled in the art that a modified nucleotide group may be introduced into the siRNA of the present disclosure by a nucleoside monomer with a corresponding modification. Methods for preparing a nucleoside monomer having a corresponding modification and for introducing a modified nucleotide group into siRNA are also well known to those skilled in the art. Modified nucleoside monomers are either commercially available or may be prepared by known methods.

Preparation of the Oligonucleotide Conjugates

The oligonucleotide conjugates of the present disclosure may be prepared by any appropriate synthetic routes. For example, the oligonucleotide conjugate of the present disclosure may be prepared by a method comprising successively linking nucleoside monomers in 3' to 5' direction according to the nucleotide type and sequence of the oligonucleotide respectively, under a condition of phosphoramidite solid phase synthesis, wherein the linking of each nucleoside monomer includes a four-step reaction of deprotection, coupling, capping, and oxidation or sulfurization. In some embodiments, the method further comprises contacting the compound represented by Formula (321) with a nucleoside monomer or a nucleotide sequence linked to a solid phase support under a coupling reaction condition in the presence of a coupling reagent, thereby linking the compound represented by Formula (321) to the nucleotide sequence through a coupling reaction.

In some embodiments, the method further comprises the step of deprotecting of the protecting groups and cutting down the solid phase support, isolation and purification.

In some embodiments, the oligonucleotide is a double stranded oligonucleotide, and the preparation method comprises the following steps: contacting the compound represented by Formula (321) with the nucleoside monomer at 3' end of the sense or antisense strand under a coupling reaction condition in the presence of a coupling reagent, thereby linking the compound represented by Formula (321) to the first nucleotide in the sequence, successively linking nucleoside monomers from 3' to 5' to synthesize the sense or antisense strand of the double stranded oligonucleotide, wherein, the compound of Formula (321) is a compound in which $R_4$ comprises a protected hydroxy as the first functional group and a group represented by Formula (C1') or (C3') as the second functional group, the compound of Formula (321) is deprotected before linking to the first nucleoside monomer, and the linking of each nucleoside monomer comprising a four-step reaction of deprotection, coupling, capping, and oxidation or sulfurization, thus obtaining a sense or antisense strand linked with the conjugating molecule; successively linking nucleoside monomers from 3' to 5' to synthesize the other strand of the double stranded oligonucleotide, wherein the linking of each nucleoside monomer includes a four-step reaction of deprotection, coupling, capping, and oxidation or sulfurization; removing the protecting groups and cutting down the solid phase support; obtaining the sense strand and the antisense strand via isolation and purification; and annealing.

In some embodiments, the oligonucleotide is a double stranded oligonucleotide, and the preparation method comprises the following steps: successively linking nucleoside monomers from 3' to 5' to synthesize the sense strand and the antisense strand of the double stranded oligonucleotide, the linking of each nucleoside monomer including a four-step reaction of deprotection, coupling, capping, and oxidation or sulfurization, thus obtaining the sense strand linked to the solid phase support and the antisense strand linked to the solid phase support; contacting the compound represented by Formula (321) with the sense strand linked to the solid phase support or the antisense strand linked to the solid phase support under a coupling reaction condition in the presence of a coupling reagent, thereby linking the compound represented by Formula (321) to the sense or antisense strand, wherein, the compound of Formula (321) is a compound in which $R_4$ comprises a phosphoramidite group as the first functional group; removing the protecting groups and cutting down the solid phase support, obtaining the sense strand and the antisense strand of the oligonucleotide via isolation and purification, and annealing, wherein the sense or antisense strand of the oligonucleotide is linked to the conjugating molecule.

In some embodiments, the P atom in formula A59 is linked to the 3' end of the sense strand in the siRNA, and the preparation method of the siRNA conjugate of the present disclosure comprises:

(1) removing the protecting group $R_k$ in the compound of Formula (321) linked to the solid phase support described above (hereinafter also referred to as L-conjugating molecule linked to the solid phase support); contacting the L-conjugating molecule linked to the solid phase support with a nucleoside monomer to obtain a nucleoside monomer linked to a solid phase support via the L-conjugating molecule, under a coupling reaction condition in the presence of a coupling agent;

(2) synthesizing a sense strand of the siRNA from 3' to 5' by a phosphoramidite solid phase synthesis method starting from the nucleoside monomer linked to a solid phase support via the L-conjugating molecule;

(3) synthesizing an antisense strand of the siRNA by a phosphoramidite solid phase synthesis method; and (4) isolating the sense strand and the antisense strand of the siRNA and annealing the same to obtain the siRNA conjugate of the present disclosure.

Wherein, in step (1), the method for removing the protecting group $R_k$ in the solid phase support-linking L-conjugating molecule comprises contacting the compound of Formula (321) with a deprotection agent under a deprotection condition. The deprotection condition comprises a temperature of 0-50° C., and in some embodiments of 15-35° C., and a reaction time of 30-300 seconds, and in some embodiments of 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the compound represented by Formula (322) may be 10:1 to 1000:1, and in some embodiments is 50:1 to 500:1.

The coupling reaction condition and the coupling agent may be any conditions and agents appropriate for the above coupling reaction. In some embodiments, the same condition and agent as the coupling reaction in the solid phase synthesis method employed are used.

In some embodiments, the coupling reaction condition comprises a reaction temperature of 0-50° C., and in some embodiments 15-35° C. The molar ratio of the compound of Formula (321) to the nucleoside monomer may be 1:1 to 1:50, and in some embodiments is 1:2 to 1:5. The molar ratio of the compound of Formula (322) to the coupling agent may be 1:1 to 1:50, and in some embodiments is 1:3 to 1:10. The reaction time may be 200-3000 seconds, and in some embodiments is 500-1500 seconds. The coupling agent may be selected from one or more of 1H-tetrazole, 5-ethylthio-1H-tetrazole and 5-benzylthio-1H-tetrazole, and in some embodiments is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments is anhydrous acetonitrile. The amount of the organic solvent may be 3-50 L/mol, and in some embodiments is 5-20 L/mol with respect to the compound represented by Formula (321).

In step (2), a sense strand S of the siRNA conjugate is synthesized in 3' to 5' direction by the phosphoramidite solid phase synthesis method starting from the nucleoside monomer linked to a solid phase support via an L-conjugating molecule prepared in the above steps. In this case, the L-conjugating molecule is linked to the 3' terminal of the resulting sense strand.

Other conditions for solid phase synthesis described in steps (2) and (3) comprise the deprotection condition for the nucleoside monomer, type and amount of the deprotection agent, the coupling reaction condition, type and amount of the coupling agent, the capping reaction condition, type and amount of the capping agent, the oxidation reaction condition, type and amount of the oxidation agent, the sulfuration reaction condition, and type and amount of the sulfuration agent, various agents, amounts, and conditions conventionally used in the art are employed herein.

In some embodiments, for example, the solid phase synthesis described in steps (2) and (3) can use the following conditions:

The deprotection condition for the nucleoside monomer comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group of 4,4'-dimethoxytrityl on the solid phase support may be 2:1 to 100:1, and in some embodiments is 3:1 to 50:1.

The coupling reaction condition comprises a temperature of 0-50° C., and in some embodiments, 15-35° C. The molar ratio of the nucleic acid sequence linked to the solid phase support to the nucleoside monomer may be 1:1 to 1:50, and in some embodiments is 1:5 to 1:15. The molar ratio of the nucleic acid sequence linked to the solid phase support to the coupling agent may be 1:1 to 1:100, and in some embodiments is 1:50 to 1:80. The reaction time and the coupling agent are selected as above.

The capping reaction condition comprises a temperature of 0-50° C., and in some embodiments, 15-35° C., and a reaction time of 5-500 seconds, and in some embodiments, 10-100 seconds. The capping agent is selected as above. The molar ratio of the total amount of the capping agent to the nucleic acid sequence linked to the solid phase support may be 1:100 to 100:1, and in some embodiments is 1:10 to 10:1. In the case where equimolar acetic anhydride and N-methylimidazole are used as a capping agent, the molar ratio of acetic anhydride, N-methylimidazole, and the nucleic acid sequence linked to the solid phase support may be 1:1:10-10:10:1, and in some embodiments is 1:1:2-2:2:1.

The oxidation reaction condition comprises a temperature of 0-50° C., and in some embodiments 15-35° C., and a reaction time of 1-100 seconds, and in some embodiments, 5-50 seconds. In some embodiments, the oxidation agent is iodine (and in further embodiments provided as iodine water). The molar ratio of the oxidation agent to the nucleic acid sequence linked to the solid phase support in the coupling step may be 1:1 to 100:1, and in some embodiments is 5:1 to 50:1. In some embodiments, the oxidation reaction is performed in a mixed solvent of tetrahydrofuran:water:pyridine=3:1:1-1:1:3. The sulfuration reaction condition comprises a temperature of 0-50° C., and in some embodiments, 15-35° C., and a reaction time of 50-2000 seconds, and in some embodiments, 100-1000 seconds. In some embodiments, the sulfuration agent is xanthane hydride. The molar ratio of the sulfuration agent to the nucleic acid sequence linked to the solid phase support in the coupling step may be 10:1 to 1000:1, and in some embodiments is 10:1 to 500:1. In some embodiments, the sulfuration reaction is performed in a mixed solvent of acetonitrile:pyridine=1:3-3:1.

According to the method provided herein, the method further comprises isolating the sense strand and the antisense strand of the siRNA after linking all nucleoside monomers and before the annealing. Methods for isolation are well known to those skilled in the art and generally comprise removing the synthesized nucleotide sequence from the solid phase support, deprotecting the bases, phosphate groups and ligands, and purifying and desalting.

The synthesized nucleotide sequence may be cleaved from the solid phase support, and protecting groups on bases, phosphate groups and ligands removed, according to conventional cleavage and deprotection methods in the synthesis of siRNA. For example, the resulting nucleotide sequence linked to the solid phase support is contacted with concentrated aqueous ammonia; during deprotection, the protecting group YCOO$^-$ in groups A46-A54 is converted to a hydroxyl group, thus the $S_1$ groups are converted to corresponding $M_1$ groups, providing the conjugate represented by Formula (1). In this case, the concentrated aqueous ammonia may be aqueous ammonia of a concentration of 25-30% by weight. The amount of the concentrated aqueous ammonia may be 0.2 ml/μmol-0.8 ml/μmol with respect to the target siRNA sequence.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resulting target siRNA sequence has a free 2'-hydroxy in the corresponding nucleoside. The amount of pure triethylamine trihydrofluoride with respect to the target siRNA sequence may be 0.4 ml/αmol-1.0 ml/μmol. As such, the siRNA conjugate of the present disclosure may be obtained.

Methods for purification and desalting are well known to those skilled in the art. For example, nucleic acid purification may be performed using a preparative ion chromatography purification column with a gradient elution of NaBr or NaCl; after collection and combination of the product, a reversed phase chromatography purification column may be used for desalting.

During synthesis, the purity and molecular weight of the nucleic acid sequence may be determined at any time, in order to control the synthesis quality more conveniently. Such methods are well known to those skilled in the art. For example, the purity of the nucleic acid may be determined by ion exchange chromatography, and the molecular weight may be determined by liquid chromatography-mass spectrometry (LC-MS).

Methods for annealing are also well known to those skilled in the art. For example, the synthesized sense strand (S strand) and antisense strand (AS strand) may be simply mixed in water for injection in an equimolar ratio, heated to 70-95° C., and then cooled at room temperature to form a double stranded structure via hydrogen bond. Hence, the siRNA conjugates of the disclosure may be thus obtained.

After obtaining the conjugate of the present disclosure, in some embodiments, the siRNA conjugate thus synthesized can also be characterized by using instruments such as LC-MS by means such as molecular weight detection, to confirm that the synthesized siRNA conjugate is the designed target siRNA conjugate and the synthesized siRNA sequence is the desired siRNA sequence, for example, is one of the sequences listed in Table 1 above.

Use of the Conjugate of the Present Disclosure

As disclosed herein, the conjugate is useful to deliver to a cell a certain active agent for treating or preventing a disease or condition where such deliver may be desirable. Without wishing to be bound by any theory, it is believed that the spatial arrangement of the conjugating molecule is especially efficient in targeting a cell surface receptor, and thus bring loaded active agent into contact with the cell. In some embodiments, such a conjugate is an oligonucleotide conjugate targeting hepatocyte.

In some embodiments, the oligonucleotide conjugate of the present disclosure has excellent liver-targeting specificity, and therefore can efficiently deliver the conjugated functional oligonucleotide into liver, thereby effectively regulating expression of specific genes in hepatocytes. Thus, the oligonucleotide conjugate of the present disclosure has a wide application prospect.

In some embodiments of the present disclosure, provided herein is use of the oligonucleotide conjugate of the present disclosure in the preparation of a medicine for treating and/or preventing pathological conditions or diseases caused by the expression of specific genes in hepatocytes. The specific gene may be an endogenous gene expressed in liver or a pathogen gene reproduced in liver. In some embodiments, the specific genes are such as ApoB, ApoC, ANGPTL3, PCSK9, SCD1, TIMP-1, Col1A1, FVII, STAT3, p53, HBV or HCV. In some embodiments, the specific gene is an HBV gene, an ANGPTL3 gene, or an APOC3 gene. Correspondingly, the diseases are selected from chronic liver disease, hepatitis, hepatic fibrosis, liver proliferative diseases and dyslipidemia. In some embodiments, the dyslipidemia is hypercholesterolemia, hypertriglyceridemia, or atherosclerosis.

In some embodiments of the present disclosure, provided herein is a method for treating pathological conditions or diseases caused by the expression of specific genes in hepatocytes, comprising administering the oligonucleotide conjugate of the present disclosure to a subject in need thereof. In some embodiments, the specific genes are such as ApoB, ApoC, ANGPTL3, PCSK9, SCD1, TIMP-1, Col1A1, FVII, STAT3, p53, HBV or HCV. In some embodiments, the specific gene is selected from a HBV gene, an ANGPTL3 gene, and an APO C3 gene. Correspondingly, the diseases are selected from chronic liver disease, hepatitis, hepatic fibrosis, liver proliferative diseases and dyslipidemia. In some embodiments, the dyslipidemia is hypercholesterolemia, hypertriglyceridemia, or atherosclerosis. In some embodiments, the conjugate provided by the disclosure may also be used to treat other liver diseases, including diseases characterized by undesired cell proliferation, blood diseases, metabolic diseases, and diseases characterized by inflammation. Proliferative diseases of liver may be benign or malignant diseases such as cancer, hepatocellular carcinoma (HCC), hepatic metastasis or hepatoblastoma. Liver hematology or inflammatory diseases may be diseases that involve blood coagulation factors, complement-mediated inflammation, or fibrosis. Metabolic diseases of liver include dyslipidemia and irregular glucose regulation. In some embodiments, the method comprises administering one or more oligonucleotides having a high degree of homology to the gene sequences involved in the liver diseases.

In some embodiments of the present disclosure, provided herein is a method for inhibiting the expression of specific genes in hepatocytes, comprising contacting the siRNA conjugate of the present disclosure with the hepatocytes.

The purpose of preventing and/or treating pathological conditions or diseases caused by the expression of specific genes in hepatocytes may be achieved through the mechanism of gene expression regulation by administering the oligonucleotide conjugate of the present disclosure to a subject in need thereof. Therefore, the oligonucleotide conjugate of the present disclosure may be used for preventing and/or treating the pathological conditions or diseases disclosed herein, or for preparing a medicine for preventing and/or treating the pathological conditions or diseases disclosed herein.

As used herein, the term "administration" and its grammatical equivalents refer to the delivery of the conjugate such as the oligonucleotide conjugate into a subject's body by a method or a route that at least partly locating the conjugate at a desired site to produce a desired effect.

Suitable routes of administration for the methods of the present disclosure include but are not limited to topical administration and systemic administration. In general, topical administration results in the delivery of more oligonucleotide conjugates to a particular site compared to the systemic circulation of the subject; whereas systemic administration results in the delivery of the oligonucleotide conjugate to systemic circulation of the patient. In some embodiments, a mode of administration capable of delivering drugs to liver is employed, taking in consideration that the present disclosure aims to provide a means for preventing and/or treating pathological conditions or diseases caused by the expression of specific genes in hepatocytes.

Administration to the patient may be performed by any suitable routes known in the art, including but not limited to oral and parenteral route, such as intravenous administration, intramuscular administration, subcutaneous administration, transdermal administration, intratracheal administration (aerosol), pulmonary administration, nasal administration, rectal administration and topical administration (including buccal administration and sublingual administration). The frequency of administration may be once or more times daily, weekly, biweekly, monthly, or yearly.

The dose of the oligonucleotide conjugate of the present disclosure may be a conventional dose in the art, which may be determined according to various parameters, especially age, weight, and gender of the patient. Toxicity and efficacy may be measured in cell cultures or experimental animals by standard pharmaceutical procedures, for example, by determining LD50 (the lethal dose that causes 50% population death) and ED50 (the dose that can cause 50% of the maximum response intensity in a graded response, and that causes 50% of the experimental subjects to have a positive response in a qualitative response). The dose range for human may be derived based on data obtained from cell culture assays and animal studies.

When administering the conjugate of the present disclosure, for example, to C57BL/6J or C3H/HeNCrlVr mice, male or female, 6-12 weeks old, 18-25 g body weight, for delivering an oligonucleotide conjugate formed by a functional oligonucleotide and the conjugating molecules disclosed herein, the amount of the oligonucleotide to be delivered by the conjugate may be 0.001-100 mg/kg body weight, and in some embodiments is 0.01-50 mg/kg body weight, and in further embodiments is 0.05-20 mg/kg body weight, and in still further embodiments is 0.1-15 mg/kg body weight, and in still yet further embodiments is 0.1-10 mg/kg body weight, as calculated by amount of the oligonucleotide in the oligonucleotide conjugate. When administering the oligonucleotide conjugate of the present disclosure, the above amounts are preferred.

In addition, the purpose of inhibiting the expression of specific genes in hepatocytes may also be achieved through the mechanism of gene expression regulation by introducing the oligonucleotide conjugate of the present disclosure into hepatocytes with aberrant expression of specific genes. In some embodiments, the hepatocytes are hepatitis cells, and in some embodiments are HepG2.2.15 cells. In some embodiments, the hepatocytes may be selected from hepatoma cell lines such as Hep3B, HepG2 or Huh7, and isolated liver primary cells, and in some embodiments are Huh7 hepatoma cells.

In the case where the expression of specific genes in hepatocytes is inhibited by using the method provided by the disclosure, the amount of the functional oligonucleotide in the provided oligonucleotide conjugate is readily determined by those skilled in the art according to the desired effects. For example, in some embodiments where the oligonucleotide conjugate is a siRNA conjugate, the amount of siRNA in the provided siRNA conjugate is an amount sufficient to reduce the expression of the target gene and resulting in an extracellular concentration of 1 pM to 1 μM, or 0.01 nM to 100 nM, or 0.05 nM to 50 nM or 0.05 nM to about 5 nM. The amount required to achieve this local concentration will vary with various factors, including the delivery method, the delivery site, the number of cell layers between the delivery site and the target cells or tissue, the delivery route (topical or systemic), etc. The concentration at the delivery site may be significantly higher than that on the surface of the target cells or tissue.

Beneficial Effects

In some embodiments, the conjugates provided by the present disclosure have higher delivery efficiency of oligonucleotide in vivo, lower toxicity, better stability and/or higher activity. In some embodiments, the conjugates disclosed herein exhibit an inhibition rate of target gene expression of at least 20%, 30%, 40%, 50%, 60%, 70%, 80%, 90%, or 95%. In some embodiments, the conjugates disclosed herein exhibit an inhibition rate of HBV gene expression of at least 20%, 30%, 40%, 50%, 60%, 70%, 80%, 90%, or 95%. In some embodiments, the conjugates disclosed herein exhibit an inhibition rate of HBV gene expression in liver of at least 20%, 30%, 40%, 50%, 60%, 70%, 80%, 90%, or 95%. In some embodiments, the conjugates disclosed herein exhibit an inhibition rate of HBV gene expression in liver in animal models of at least 20%, 30%, 40%, 50%, 60%, 70%, 80%, 90%, or 95%. In some embodiments, the conjugates disclosed herein exhibit an inhibition rate of HBV gene expression in human subjects of at least 20%, 30%, 40%, 50%, 60%, 70%, 80%, 90%, or 95%. In some embodiments, the conjugates disclosed herein exhibit an inhibition rate of HBV surface antigen expression of at least 20%, 30%, 40%, 50%, 60%, 70%, 80%, 90%, or 95%. In some embodiments, the conjugates disclosed herein exhibit an inhibition rate of ANGPTL3 gene expression of at least 20%, 30%, 40%, 50%, 60%, 70%, 80%, 90%, or 95%. In some embodiments, the conjugates disclosed herein exhibit an inhibition rate of ANGPTL3 gene expression in liver of at least 20%, 30%, 40%, 50%, 60%, 70%, 80%, 90%, or 95%. In some embodiments, the conjugates disclosed herein exhibit an inhibition rate of ANGPTL3 gene expression in liver in animal models of at least 20%, 30%, 40%, 50%, 60%, 70%, 80%, 90%, or 95%. In some embodiments, the conjugates disclosed herein exhibit an inhibition rate of ANGPTL3 gene expression in human subjects of at least 20%, 30%, 40%, 50%, 60%, 70%, 80%, 90%, or 95%. In some embodiments, the conjugates disclosed herein exhibit an inhibition rate of ApoC3 gene expression of at least 20%, 30%, 40%, 50%, 60%, 70%, 80%, 90%, or 95%. In some embodiments, the conjugates disclosed herein exhibit an inhibition rate of ApoC3 gene expression in liver of at least 20%, 30%, 40%, 50%, 60%, 70%, 80%, 90%, or 95%. In some embodiments, the conjugates disclosed herein exhibit an inhibition rate of ApoC3 gene expression in liver in animal models of at least 20%, 30%, 40%, 50%, 60%, 70%, 80%, 90%, or 95%. In some embodiments, the conjugates disclosed herein exhibit an inhibition rate of ApoC3 gene expression in human subjects of at least 20%, 30%, 40%, 50%, 60%, 70%, 80%, 90%, or 95%. In some embodiments, the conjugates disclosed herein exhibit no significant off-target effect. An off-target effect may be for example inhibition on a gene expression which is not the target gene. It is considered insignificant if the binding/inhibition of off-target gene expression is at a level of lower than 50%, 40%, 30%, 20%, or 10% of the on-target effect.

According to some embodiments of the present disclosure, the conjugates provided by the disclosure effectively deliver the siRNA to liver, and exhibit an excellent property of inhibiting HBV gene expression, for example, an inhibition rate of 87.4%-92.2% of HBV gene expression in the liver of HBV model mice at a dose of 1 mg/kg, along with a low off-target effect. In some embodiments, the conjugates of the present disclosure effectively reduce the expression of HBV surface antigen in HBV model mice and achieve an inhibition ratio of 96.9% for HBV surface antigen expression and an inhibition ratio of 95.4% for HBV DNA at a dose of 3 mg/kg. In some embodiments, the conjugates provided by the disclosure exhibit an excellent inhibitory effect on HBV expression at low doses over a period of up to 140 days.

According to one embodiment of the present disclosure, the conjugates provided by the present disclosure effectively deliver the siRNA to liver, and exhibit an excellent property of inhibiting HBV gene expression, for example, an inhibition rate of at least 69.3%, or 78.1%-89.1% of HBV gene expression in the liver of HBV model mice at a dose of 1 mg/kg, along with a low off-target effect. In some embodiments, the conjugates of the present disclosure effectively reduce the expression of HBV surface antigen in HBV model mice and achieve an inhibition ratio of 98.4% for HBV surface antigen expression and an inhibition ratio of 95.8% for HBV DNA at a dose of 3 mg/kg. In some embodiments, the specific conjugates provided by the present disclosure exhibit an excellent inhibitory effect on HBV expression at low doses over a period of up to 84 days, compared to reference conjugates.

According to one embodiment of the present disclosure, the conjugates provided by the present disclosure effectively deliver the siRNA to liver, and exhibit an excellent property of inhibiting HBV gene expression, for example, an inhibition rate of at least 48.5%, or 76.8%-80.0% of HBV gene expression in the liver of HBV model mice at a dose of 1 mg/kg, along with a low off-target effect. In some embodiments, the conjugates of the present disclosure also effectively reduce the expression of HBV surface antigen in HBV model mice and achieve an inhibition ratio of 84.6% for HBV surface antigen expression and an inhibition ratio of 85.6% for HBV DNA even at a dose of 3 mg/kg. In some embodiments, the conjugates provided by the present disclosure exhibit a higher inhibitory effect on HBV expression at low doses over a period of 21 days, compared to reference conjugates.

According to one embodiment of the present disclosure, the conjugates provided by the present disclosure effectively deliver the siRNA to liver, and exhibit an excellent property of inhibiting HBV gene expression, for example, an inhibition rate of at least 60.1%, or In some embodiments, 80.7%-84.5% of gene expression of HBV X gene region in the liver of HBV model mice at a dose of 1 mg/kg, along with a low off-target effect. In some embodiments, the conjugates of the present disclosure also effectively reduce the expression of HBV surface antigen in HBV model mice and achieve an inhibition ratio of 94.8% for HBV surface antigen expression and an inhibition ratio of 95.8% for HBV DNA even at a dose of 3 mg/kg. In some embodiments, the conjugates provided by the disclosure exhibit an excellent inhibitory effect on HBV expression at low doses over a period of up to 56 days, compared to reference conjugates.

According to one embodiment of the present disclosure, the conjugates provided by the present disclosure can effectively deliver the siRNA to liver, and exhibit an excellent property of inhibiting ANGPTL3 gene expression, for example, an inhibition rate of at least 57.3% of ANGPTL3 gene expression in the liver of high-fat model mice at a dose of 1 mg/kg and up to 90.4% at a dose of 3 mg/kg. In some embodiments, the conjugates provided by the present disclosure exhibit excellent ANGPTL3 expression inhibition and hypolipidemic effects at low doses and low frequency of administration over a period of up to 49 days, compared to reference conjugates.

According to one embodiment of the present disclosure, the conjugates provided by the present disclosure effectively deliver the siRNA to liver, and exhibit excellent property of inhibiting ApoC3 gene expression, for example, an inhibition rate of at least 75% of ApoC3 gene expression in the liver of high-fat model mice at a dose of 3 mg/kg. In some embodiments, the conjugates provided by the present disclosure exhibit an excellent inhibitory effect on blood lipid at low doses and low frequency of administration over a period of up to 65 days, compared to reference conjugates.

In some embodiments, the conjugates described in the disclosure exhibit low toxicity in animal models, which indicates good safety. For example, in some embodiments, there is no obvious toxic response observed even when the conjugate of the present disclosure is administered to C57BL/6J mice at a concentration up to 100-fold of the effective concentration (3 mg/kg for the effective concentration).

The above instances illustrate the conjugates provided herein are effective to target cell surface receptors and deliver the loaded active agents to the cells expressing the receptors. It is envisaged that the conjugating molecules may be adapted for additional cell surface receptors and additional active agents to target the active agents to the cells expressing these receptors.

Kit

In another aspect, provided herein is a kit comprising the conjugates as described above.

In some embodiments, the kits provided herein comprise conjugates in one container. In some embodiments, the kits provided herein comprise a container comprising pharmaceutically acceptable excipients. In some embodiments, the kits provided herein further comprise pharmaceutically acceptable excipients, such as stabilizers or preservatives. In some embodiments, the kits provided herein comprise at least one additional therapeutic agent. In some embodiments, the kits comprise at least one additional therapeutic agent in a container different than the one comprising the conjugates provided herein. In some embodiments, the kits comprise an instruction for mixing the conjugates with pharmaceutically acceptable excipients or other ingredients (if present).

In the kit of the present disclosure, the conjugates and/or the pharmaceutically acceptable excipients may be provided in any form, e.g., in a liquid form, a dry form, or a lyophilized form. In some embodiments, the conjugates and/or the pharmaceutically acceptable excipients are substantially pure and/or sterile. In some embodiments, sterile water may be provided in the kits of the present disclosure.

EXAMPLES

Hereinafter, the present disclosure will be described in detail by way of examples. Unless otherwise specified, reagents and culture media used in following examples are all commercially available, and operations used such as nucleic acid electrophoresis and real-time PCR are all performed according to methods described in Molecular Cloning (Cold Spring Harbor Laboratory Press (1989)).

HEK293A cells were provided by Nucleic acid technology laboratory, Institute of Molecular Medicine, Peking University and cultured with DMEM complete media (Hyclone company) containing 20% fetal bovine serum (FBS, Hyclone company), 0.2 v % cyanomycin biresistant (Penicillin-Streptomycin, Gibco, Invitrogen company) at 37° C. in an incubator containing 5% CO2/95% air.

Huh7 cells were purchased from the Stem Cell Bank of Chinese Academy of Science and cultured with DMEM complete media (Hyclone company) containing 10% fetal bovine serum (FBS, Hyclone company), 1% nonessential amino acid (NEAA, Corning company) at 37° C. in an incubator containing 5% CO2/95% air.

Unless otherwise specified, Lipofectamine™2000 (Invitrogen company) was used as a transfection reagent when cells were transfected with siRNA conjugates synthesized in Preparation Examples 12-15 below. Detailed operation was performed with reference to the instruction provided by manufacturer.

Unless otherwise specified, ratios of reagents provided below are all calculated by volume ratio (v/v).

Unless otherwise specified, the animal models used are as follows:

C57BL/6J mice: purchased from Beijing Vital River Laboratory Animal Technology Co., Ltd.;

SD rats: provided by Beijing Vital River Laboratory Animal Technology Co., Ltd.;

HBV transgenic mice C57B/6N-Tg (1.28 HBV)/Vst (genotype A), purchased from Beijing Vitalstar Biotechnology Co., Ltd. Mice with COI>$10^4$ (referred as 1.28 copy mice for short below) are selected before experiments;

HBV transgenic mice C57BL/6J-Tg (Alb1HBV) 44Bri/J: purchased from Department of Laboratory Animal Science, Peking University Health Science Center. Mice with S/COV>10 are selected before experiments;

HBV transgenic mice: named M-TgHBV, purchased from Department of Animal, Shanghai Public Health Center. The preparation methods of transgenic mice were described as Ren J. et al., in J. Medical Virology. 2006, 78:551-560;

AAV-HBV transgenic mice: prepared according to the literature method (Xiaoyan Dong et al., Chin J Biotech 2010, May 25; 26(5): 679-686) by using rAAV8-1.3HBV, D type (ayw) virus (purchased from Beijing FivePlus Molecular Medicine Institute Co. Ltd., $1×10^{12}$ viral genome (v.g.)/mL, Lot number 2016123011). The rAAV8-1.3HBV was diluted to $5×10^{11}$ v.g./mL with sterile PBS. 200 μL of the diluted rAAV8-1.3HBV was injected into each mouse, i.e., $1×10^{11}$ v.g. per mouse. The blood (about 100 μL) was taken from orbits of all mice at day 28 after injection of the virus to collect serum for detection of HBsAg and HBV DNA;

Low concentration AAV-HBV transgenic mice: Using the almost same modeling method as above, the difference was that the virus was diluted to $1×10^{11}$ v.g./mL with sterile PBS before the experiment. 100 μL virus was injected into each mouse, i.e., $1×10^{10}$ v.g. per mouse;

BALB/c mice: 6-8 week old, purchased from Beijing Vital River Laboratory Animal Technology Co., Ltd.;

ob/ob mice: 6-8 week old, purchased from Changzhou Cavens Laboratory Animal Co., Ltd.;

Human APOC3 transgenic mice: B6; CBA-Tg(APOC3) 3707Bres/J, purchased from Jackson Lab;

Metabolic syndrome monkey: All male, provided by Non-human primate research center, Institute of Molecular Medicine, Peking University;

Preparation Example 1 Preparation of L-9 Conjugating Molecule (Conjugating Molecule 1)

In this preparation example, Conjugating Molecule 1 (also referred to as L-9 Conjugating Molecule hereinafter) was synthesized according to following method.

(1-1) Synthesis of GAL-5 (a Molecule at End Segment of the L-9 Conjugating Molecule)

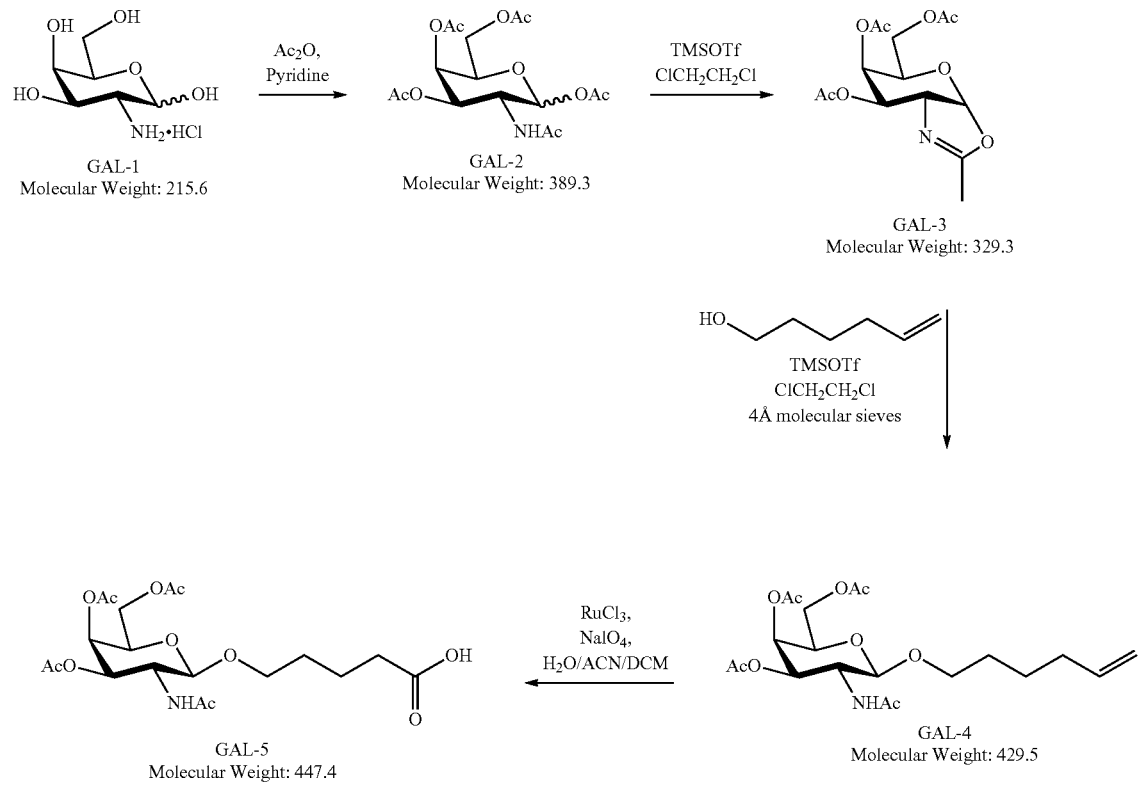

(1-1a) Synthesis of GAL-2

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added under an ice water bath to react for 1.5 hours under stirring at room temperature. The resulting reaction solution was poured into 10 L of ice water and suction filtration under reduced pressure. The residue was washed with 2 L of ice water, and then added with a mixed acetonitrile/toluene solvent (v/v of acetonitrile:toluene=1:1) until completely dissolved. The solvent was evaporated to give 130.0 g of product GAL-2 as a white solid.

(1-1b) Synthesis of GAL-3

GAL-2 (35.1 g, 90.0 mmol) obtained in step (1-1a) was dissolved in 213 ml of anhydrous 1,2-dichloroethane, to which 24.0 g of TMSOTf (CAS No.: 27607-77-8, purchased from Macklin Inc., 108.0 mmol) was added under an ice water bath and nitrogen atmosphere to react overnight at room temperature.

400 ml dichloromethane was added to the reaction solution for dilution, filtered with diatomite, and then 1 L saturated aqueous sodium bicarbonate solution was added to the resulting reaction solution and stirred evenly. An organic phase was isolated. The aqueous phase remained was extracted twice, each with 300 ml of dichloroethane, and all organic phases were combined and washed with 300 ml of saturated aqueous sodium bicarbonate solution and 300 ml of saturated brine, respectively. The organic phase resulted from washing was isolated and dried with anhydrous sodium sulfate. The solvent was evaporated under reduced pressure to give 26.9 g of product GAL-3 as a light yellow viscous syrup.

(1-1c) Synthesis of GAL-4

GAL-3 (26.9 g, 81.7 mmol) obtained in step (1-1b) was dissolved in 136 ml of anhydrous 1,2-dichloroethane, added with 30 g of 4 Å molecular sieve as a dry powder followed by 9.0 g of 5-hexen-1-ol (CAS No.: 821-41-0, purchased from Adamas-beta Inc., 89.9 mmol), and stirred for 30 minutes at room temperature. 9.08 ml of TMSOTf (40.9 mmol) was added under an ice bath and the protection of nitrogen to react overnight under stirring at room temperature. The 4 Å molecular sieve powder was removed by filtration. 300 ml dichloroethane was added to the filtrate for dilution, filtered with diatomite, and then 500 ml of saturated aqueous sodium bicarbonate solution was added to the resulting reaction solution and stirred for 10 minutes for washing. An organic phase was isolated. The aqueous phase remained was extracted once with 300 ml of dichloroethane. All organic phases were combined and washed with 300 ml of saturated aqueous sodium bicarbonate solution and 300 ml of saturated brine respectively. The organic phase resulted from the washing was isolated and dried with anhydrous sodium sulfate. The solvent was evaporated under reduced pressure to give 41.3 g of product GAL-4 as a yellow syrup, which was directly used in the next oxidation reaction without purification.

(1-1d) Synthesis of GAL-5

GAL-4 (14.9 g, 34.7 mmol) obtained according to the method described in step (1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred under an ice bath for 10 minutes. Ruthenium trichloride (CAS No.: 14898-67-0, available from Energy Chemical, 238 mg, 1.145 mmol) was added to react overnight at room temperature. The resulting reaction solution was diluted by adding 300 ml of water, stirred, and adjusted to a pH of about 7.5 by adding saturated sodium bicarbonate. The organic phase isolated was discarded. The aqueous phase remained was extracted three times, each with 200 ml of dichloromethane, and the organic phase resulted from the extraction was discarded. The aqueous phase resulted from the extraction was adjusted to a pH of about 3 with citric acid solids and extracted three times, each with 200 ml of dichloromethane, and the organic phases were combined and dried with anhydrous sodium sulfate. The solvent is evaporated under reduced pressure to give 6.85 g of product GAL-5 as a white foamy solid.

The L-9 Conjugating Molecule was synthesized by using the compound GAL-5 obtained according to the above method via following process routes:

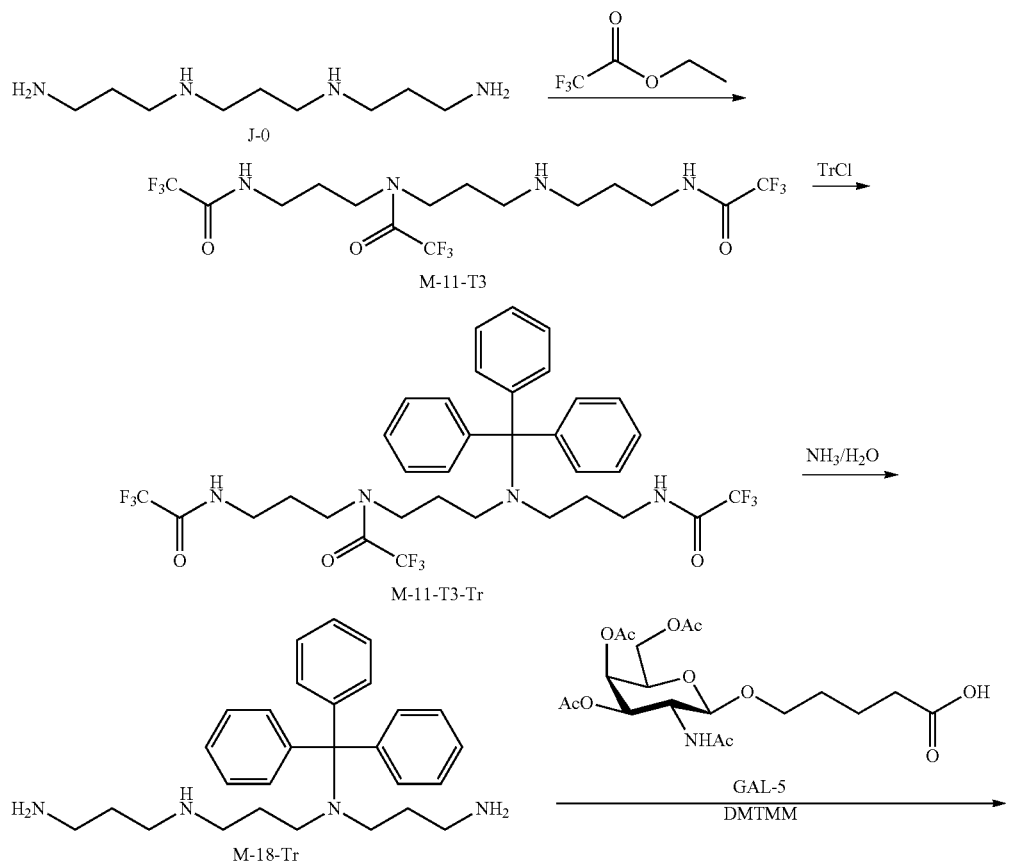

-continued
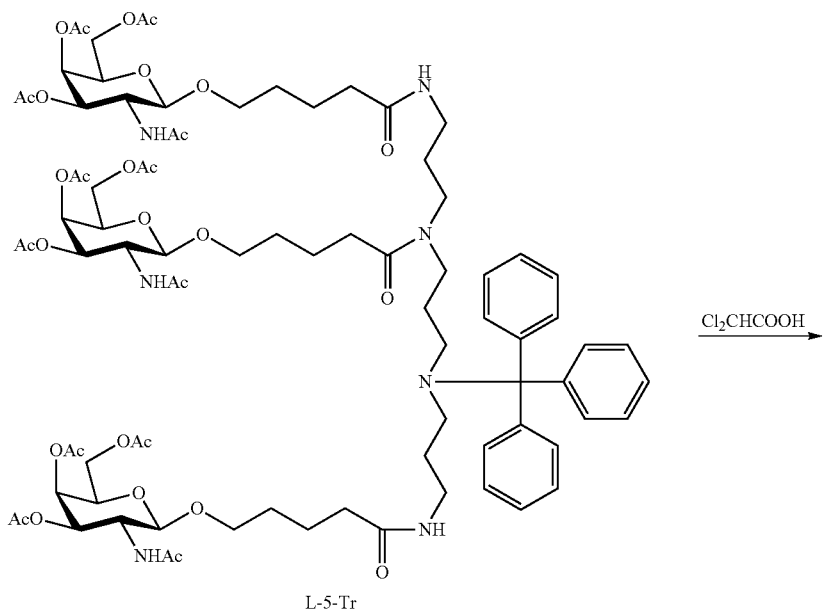
L-5-Tr
$\xrightarrow{\text{Cl}_2\text{CHCOOH}}$
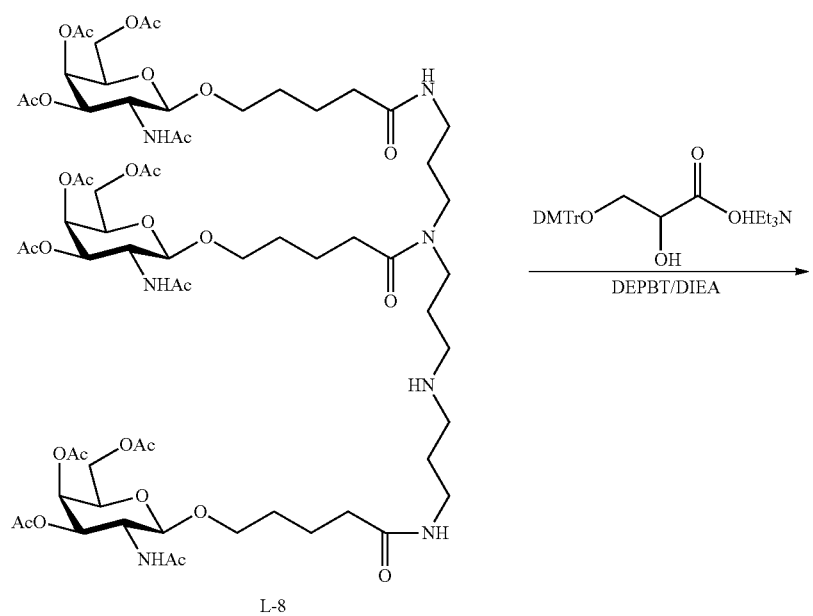
L-8
$\xrightarrow[\text{DEPBT/DIEA}]{\text{DMTrO}\diagup\diagdown\text{OHEt}_3\text{N}, \text{OH}}$

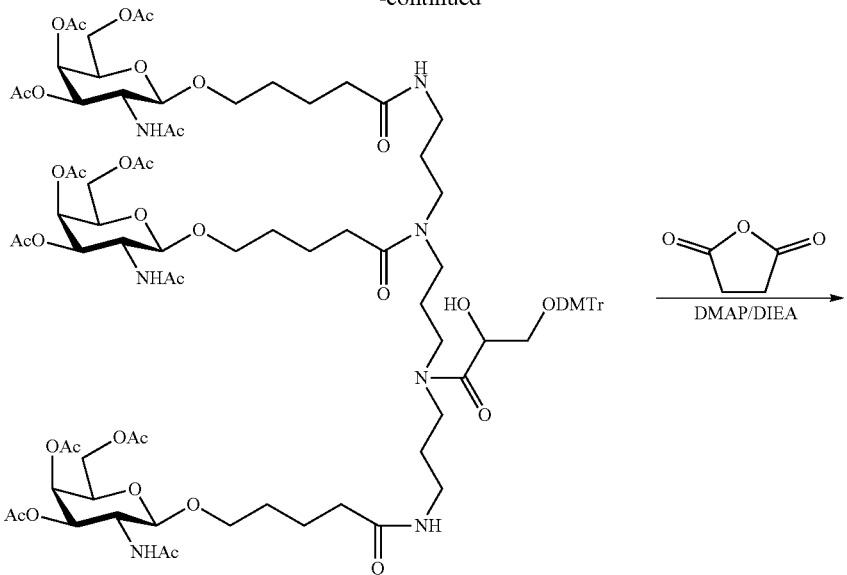

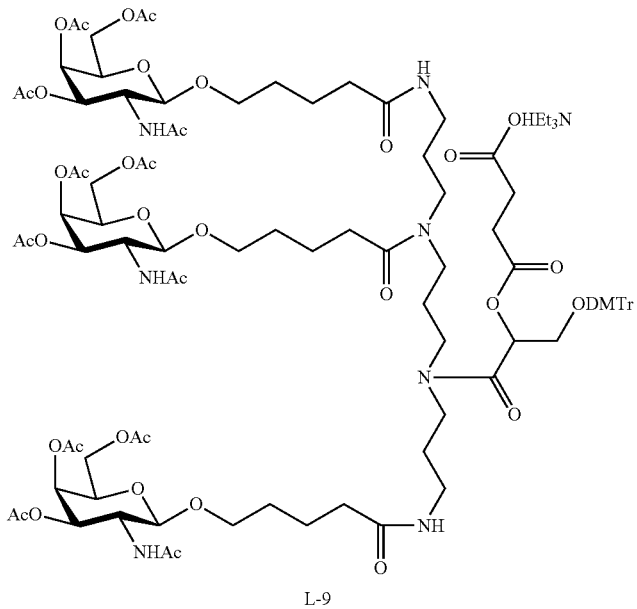

L-9

(1-2) Synthesis of M-11-T3:

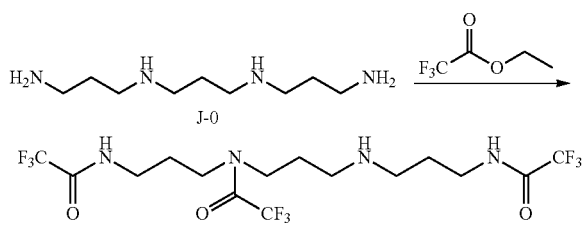

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react for 22 hours at room temperature. The solvent was evaporated under reduced pressure, and the residue was foam-dried with a vacuum oil pump for 18 hours to give 5.342 g of crude solid product M-11-T3, which was directly used in subsequent reaction without further purification. MS m/z: C15H22F9N4O3, [M+H]+, calcd: 477.35, measured: 477.65.

(1-3) Synthesis of M-11-T3-Tr:

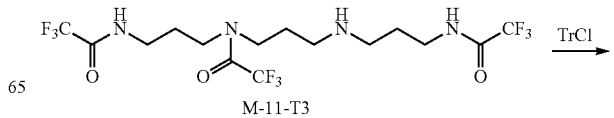

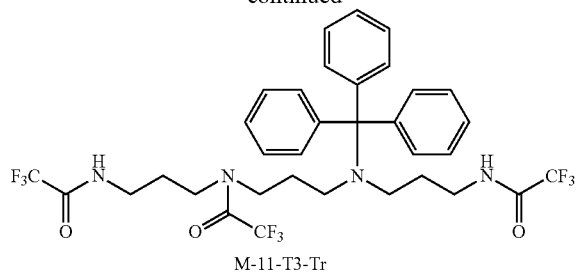

M-11-T3-Tr

The crude product M-11-T3 (5.342 g, 10 mmol) was dissolved in 50 ml of dichloromethane. The resulting reaction solution was added with TrCl (3.345 g, 12 mmol) and triethylamine (1.518 g, 15 mmol) to react for 20 hours under stirring at room temperature. The reaction solution was washed twice, each with 20 ml of saturated sodium bicarbonate and once with 20 ml of saturated brine. An organic phase was dried with anhydrous sodium sulfate and filtered. The solvent was evaporated under reduced pressure, and the residue was foam-dried with a vacuum oil pump overnight to give 7.763 g of crude solid product M-11-T3-Tr. MS m/z: C34H36F9N4O3, [M+Na]+, calcd: 741.25, measured: 741.53. The crude solid product M-11-T3-Tr was then used in the next step for synthesis of M-18-Tr without purification.

(1-4) Synthesis of M-18-Tr:

The crude product M-11-T3-Tr (7.763 g, 10 mmol) obtained in step (1-3) was dissolved in 100 ml of methanol, and added with 100 ml of aqueous methylamine solution (40 mass %) to react for 23 hours under stirring at 50° C. Insoluble particles were removed by filtration. The solvent was evaporated under reduced pressure, and to the residue was added 200 ml of mixed solvent of DCM:methanol in a volume ratio of 1:1, washed with 50 ml of saturated sodium bicarbonate. The aqueous phase obtained was extracted three times, each with 50 ml of dichloromethane. All organic phases were combined, dried with anhydrous sodium sulfate and filtered. The solvent was evaporated under reduced pressure, and the residue was foam-dried with a vacuum oil pump overnight, and purified by using a normal phase silica gel column, 200-300 mesh. The column was packed with petroleum ether, added with 1 wt % triethylamine for neutralizing the acidity of silica gel, and gradient eluted with dichloromethane:methanol:aqueous ammonia (25 wt %)=1:1:0.05-1:1:0.25. The eluate was collected, the solvent was evaporated under reduced pressure, and the residue was foam-dried with a vacuum oil pump to give 2.887 g of pure product M-18-Tr. 1H NMR (400 MHz, DMSO) δ 7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: C28H39N4, [M+H]+, calcd: 431.65, measured: 432.61.

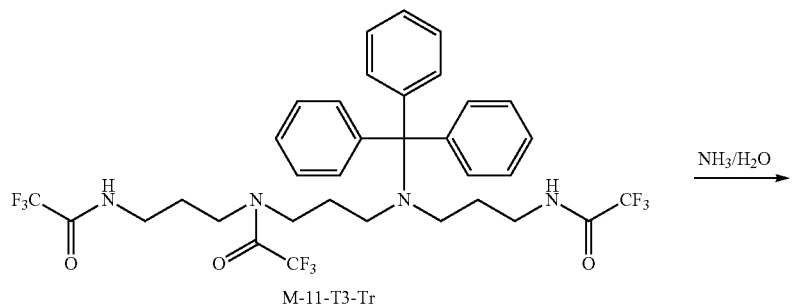

M-11-T3-Tr $\xrightarrow{NH_3/H_2O}$

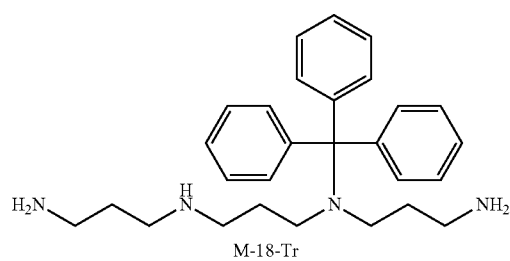

M-18-Tr (1-5) Synthesis of L-5-Tr:

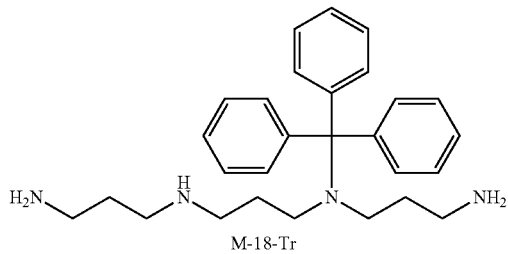 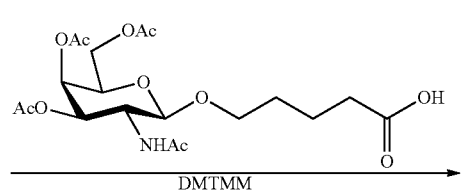

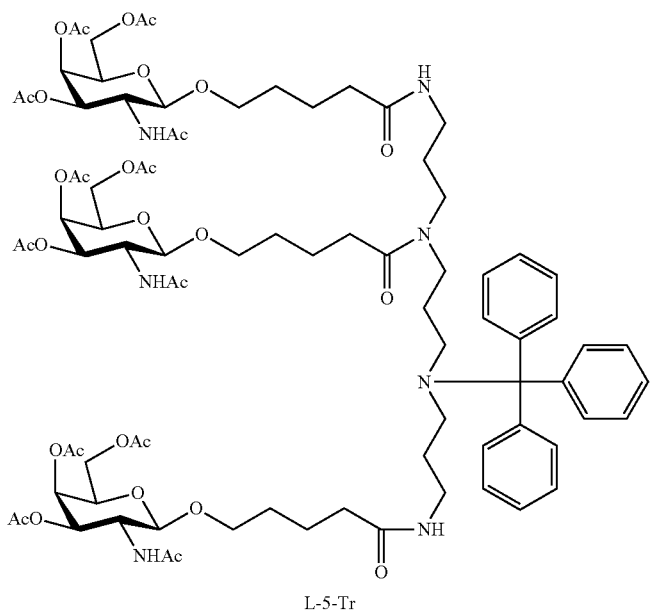

M-18-Tr (2.02 g, 4.69 mmol) obtained in step (1-4) and GAL-5 (6.93 g, 15.48 mmol) obtained in step (1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane, washed with 100 ml of a saturated sodium bicarbonate solution and 100 ml of saturated brine, dried with anhydrous sodium sulfate, and filtered. Then the solvent was evaporated under reduced pressure to give a crude product. The crude product was purified by using a normal phase silica gel column, 200-300 mesh. The column was packed with petroleum ether, added with 1 wt % triethylamine for neutralizing the acidity of silica gel, and gradient eluted with dichloromethane:methanol=100:5-100:7. The eluate was collected, and the solvent was evaporated to dry under reduced pressure to give 7.49 g of pure product L-5-Tr. 1H NMR (400 MHz, DMSO) δ 7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: C85H119N7O30, [M+H]+, calcd: 1718.81, measured: 1718.03.

(1-6) Synthesis of L-8:

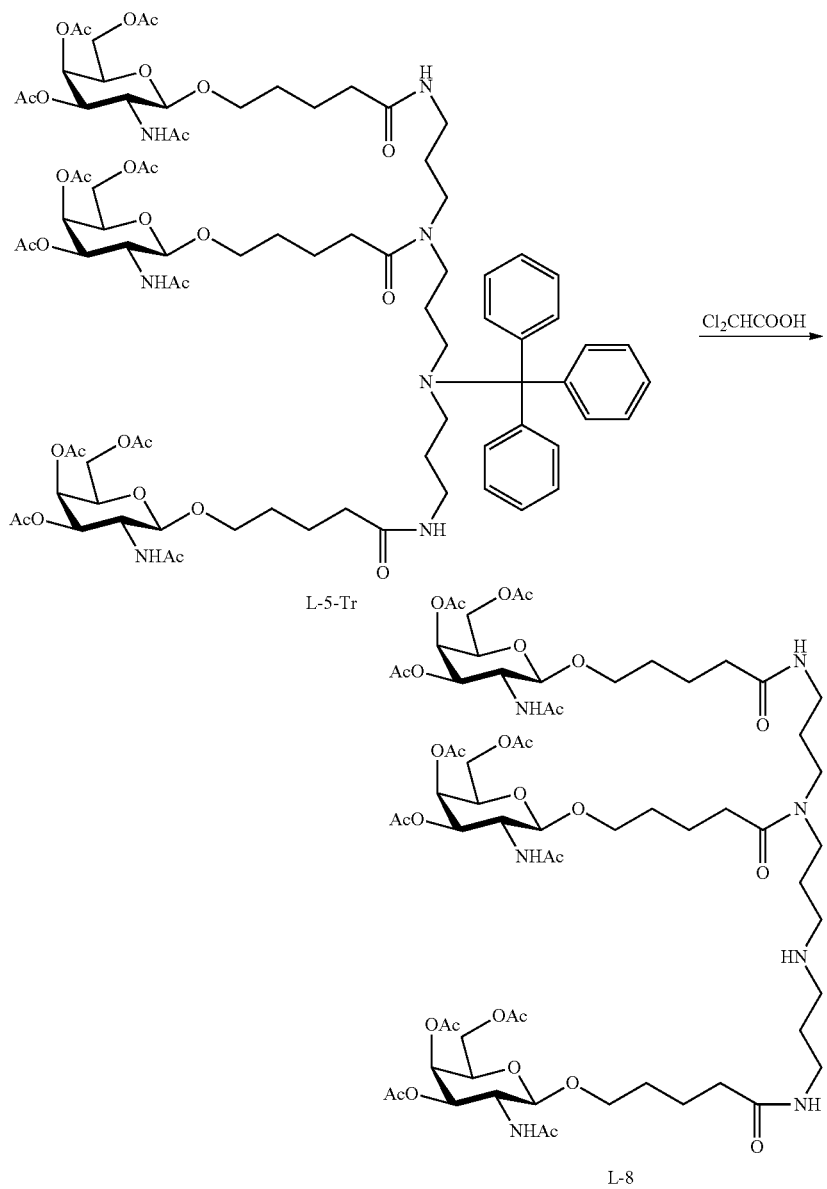

L-5-Tr (5.94 g, 3.456 mmol) obtained in step (1-5) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtrated. Then the solvent was evaporated under reduced pressure to give a crude product. The crude product was purified by using a normal phase silica gel column, 200-300 mesh, adding with 10 wt % triethylamine for neutralizing the acidity of silica gel. The column was equilibrated with 1 wt‰ triethylamine and gradient eluted with dichloromethane:methanol=100:30-100:40. The eluate was collected, and the solvent was evaporated under reduced pressure to give 4.26 g of pure product L-8. 1H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: C85H119N7O30, [M+H]+, calcd: 1477.59, measured: 1477.23.

(1-7a) Synthesis of A-1

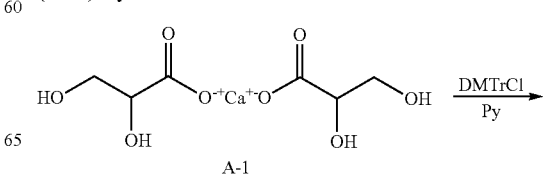

-continued

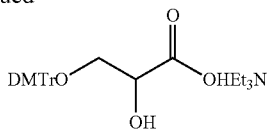

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react for 22 hours at 45° C. The resulting reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase isolated was extracted twice, each with 200 ml of dichloromethane. All organic phases were combined, dried with anhydrous sodium sulfate, and filtered. The solvent was evaporated under reduced pressure, and the residue was purified by using a normal phase silica gel column, 200-300 mesh, gradient eluted with petroleum ether:ethyl acetate:dichloromethane:methanol=1:1:1:0.35-1:1:1:0.55. The eluate was collected, and the solvent was evaporated under reduced pressure. The residue was redissolved in 500 ml of dichloromethane, and washed once with 200 ml of 0.5 M triethylamine phosphate. The aqueous phase isolated was extracted twice, each with 200 ml of dichloromethane. All organic phases were combined, dried with anhydrous sodium sulfate, and filtered. The solvent was evaporated under reduced pressure, and the residue was subject to a reduced pressure with a vacuum oil pump to dryness overnight to give 20.7 g of product A-1 as a white solid. 1H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: C24H23O6, [M−H]−, calcd: 407.15, measured: 406.92.

(1-7b) Synthesis of L-7:

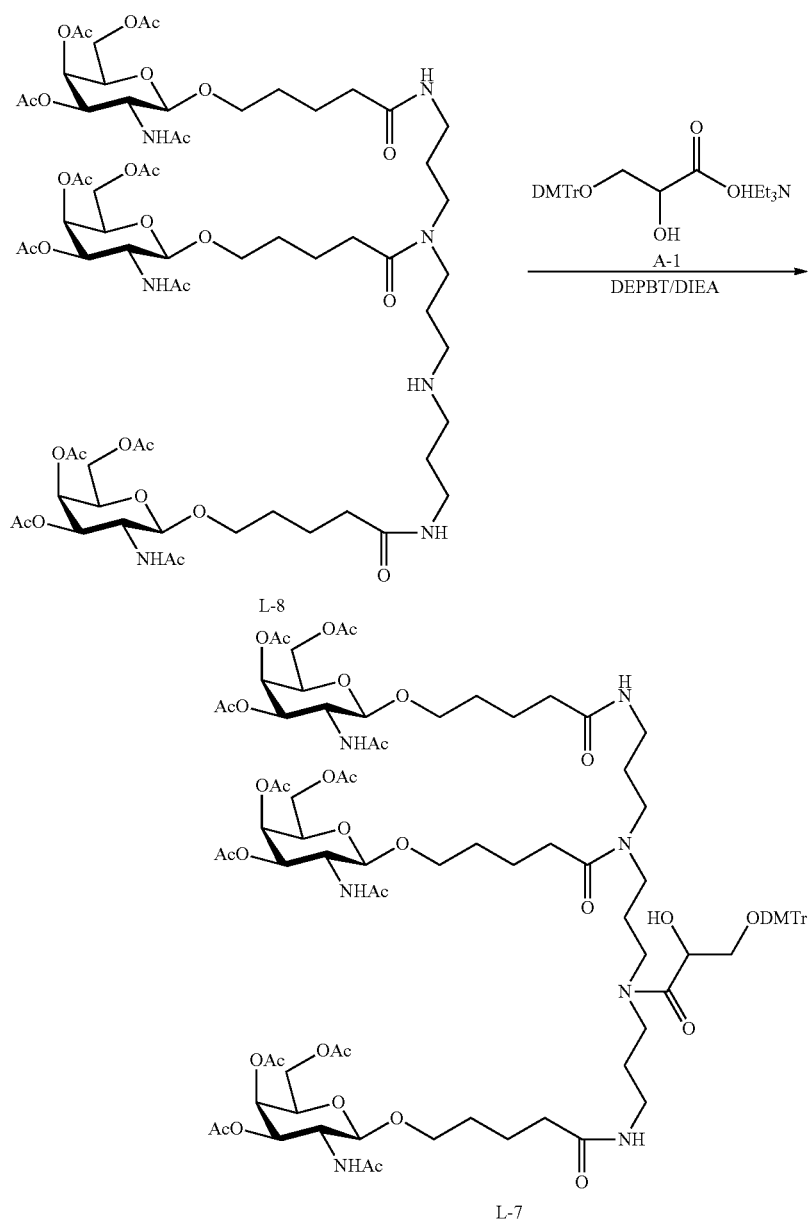

L-8 (2.262 g, 1.532 mmol) obtained in step (1-6) and A-1 (2.342 g, 4.596 mmol) obtained in step (1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react for 2 hours under stirring at 25° C., washed with 10 ml of saturated sodium bicarbonate. The aqueous phase isolated was extracted three times, each with 10 ml of dichloromethane. All organic phases were combined and washed with 10 ml of saturated brine, and the aqueous phase isolated was extracted twice, each with 10 ml of dichloromethane, and the obtained organic phases were combined, dried with anhydrous sodium sulfate and filtrated. The solvent was evaporated under reduced pressure, and the residue was foam-dried overnight with a vacuum oil pump to give 4.900 g of crude product. The crude product was subjected to a column purification by using a normal phase silica gel, 200-300 mesh, 120 g, with 20 ml triethylamine for neutralizing the acidity of silica gel. The column was equilibrated with petroleum ether containing 1 wt % triethylamine and gradient eluted with petroleum ether:ethyl acetate:dichloromethane:N,N-dimethylformamide=1:1:1:0.5-1:1:1:0.6.

The eluate was collected, and the solvent was evaporated under reduced pressure to give 2.336 g of pure product L-7. 1H NMR (400 MHz, DMSO) δ 7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: C90H128N7O35, [M-DMTr]+, calcd: 1564.65, measured: 1564.88.

(1-8) Synthesis of L-9:

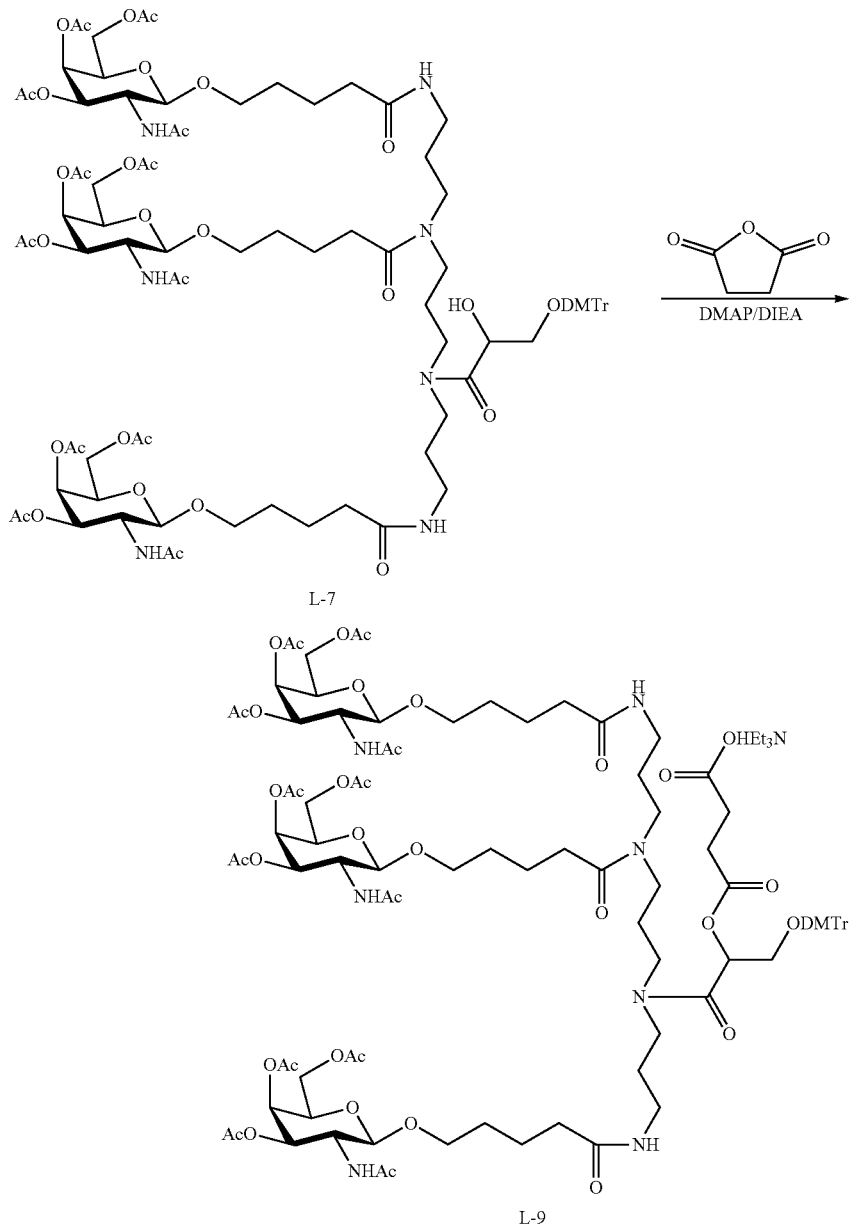

L-7 (2.300 g, 1.26 mmol) obtained in step (1-7b), succinic anhydride (0.378 g, 3.78 mmol) and 4-dimethylaminopyridine (DMAP, 0.462 g, 3.78 mmol) were mixed and dissolved in 13 ml of dichloromethane, further added with DIPEA (0.814 g, 6.30 mmol), and stirred for 24 hours at 25° C. The resulting reaction solution was washed with 5 ml of 0.5 M triethylamine phosphate. The aqueous phase isolated was extracted three times, each with 5 ml of dichloromethane. All organic phases were combined, and the solvent was evaporated under reduced pressure to give 2.774 g of crude product. The crude product was subjected to a column purification by using a normal phase silica gel, 200-300 mesh, 60 g, with 1 wt % triethylamine for neutralizing the acidity of silica gel. The column was equilibrated with dichloromethane and gradient eluted with 1 wt‰ triethylamine-containing dichloromethane:methanol=100:18-100:20. The eluate was collected, and the solvent was evaporated under reduced pressure to give 1.874 g of pure product of L-9 Conjugating Molecule (Conjugating Molecule 1). 1H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: C94H132N7O38, [M-DMTr]+, calcd: 1664.72, measured: 1655.03. The structure of the resulting L-9 Conjugating Molecule is represented by Formula (503).

Preparation Example 2 Preparation of P-9 Conjugating Molecule (Conjugating Molecule 2)

In this preparation example, Conjugating Molecule 2 (also referred to as P-9 Conjugating Molecule hereinafter) was synthesized according to following method:

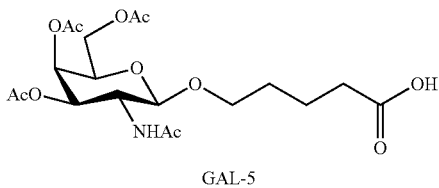

GAL-5

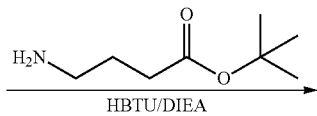

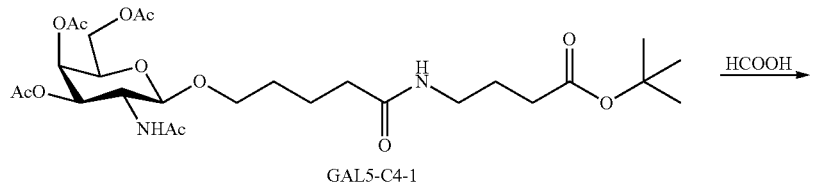

GAL5-C4-1

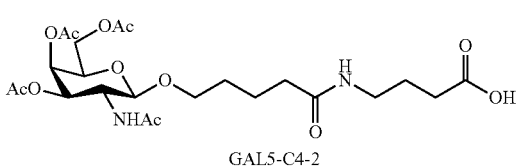

GAL5-C4-2

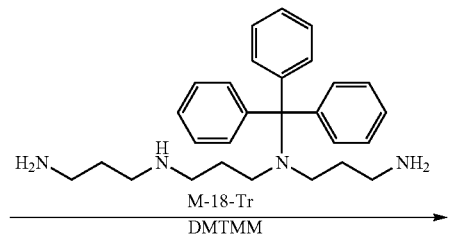

M-18-Tr
DMTMM

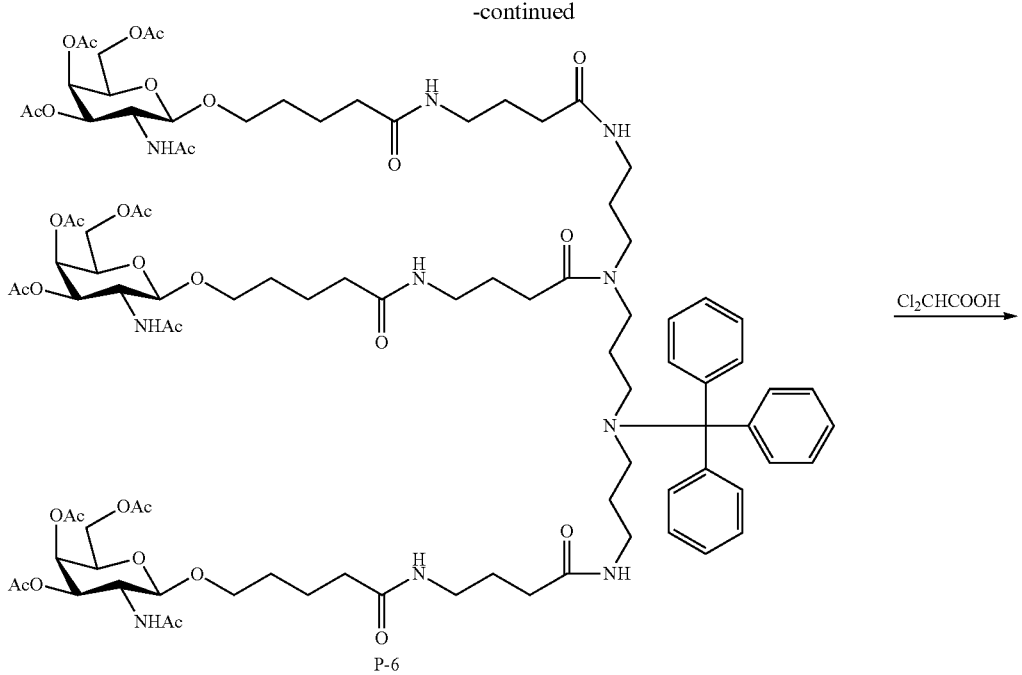
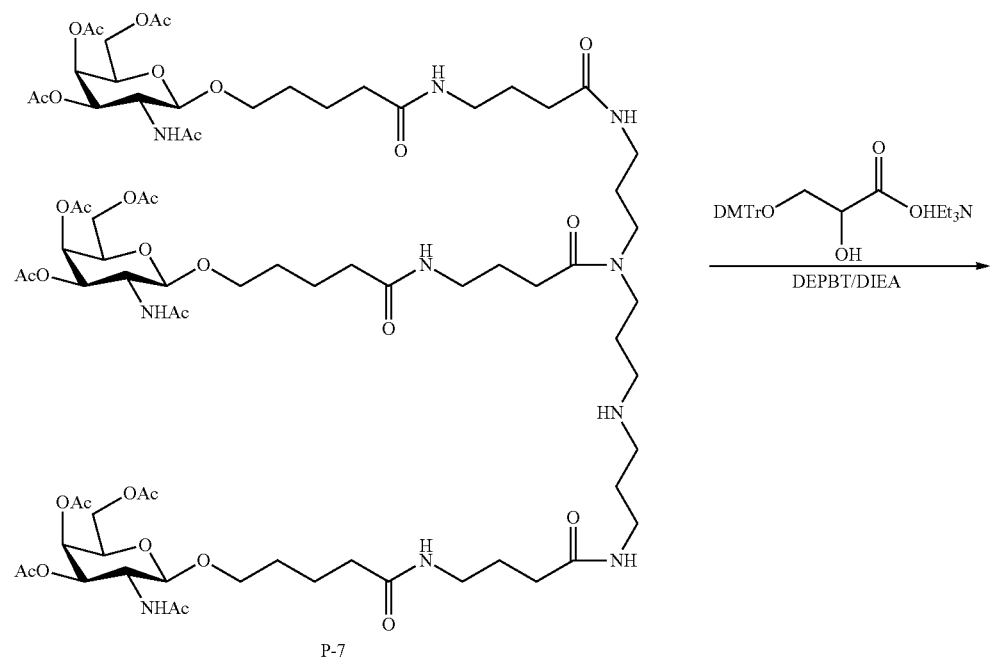

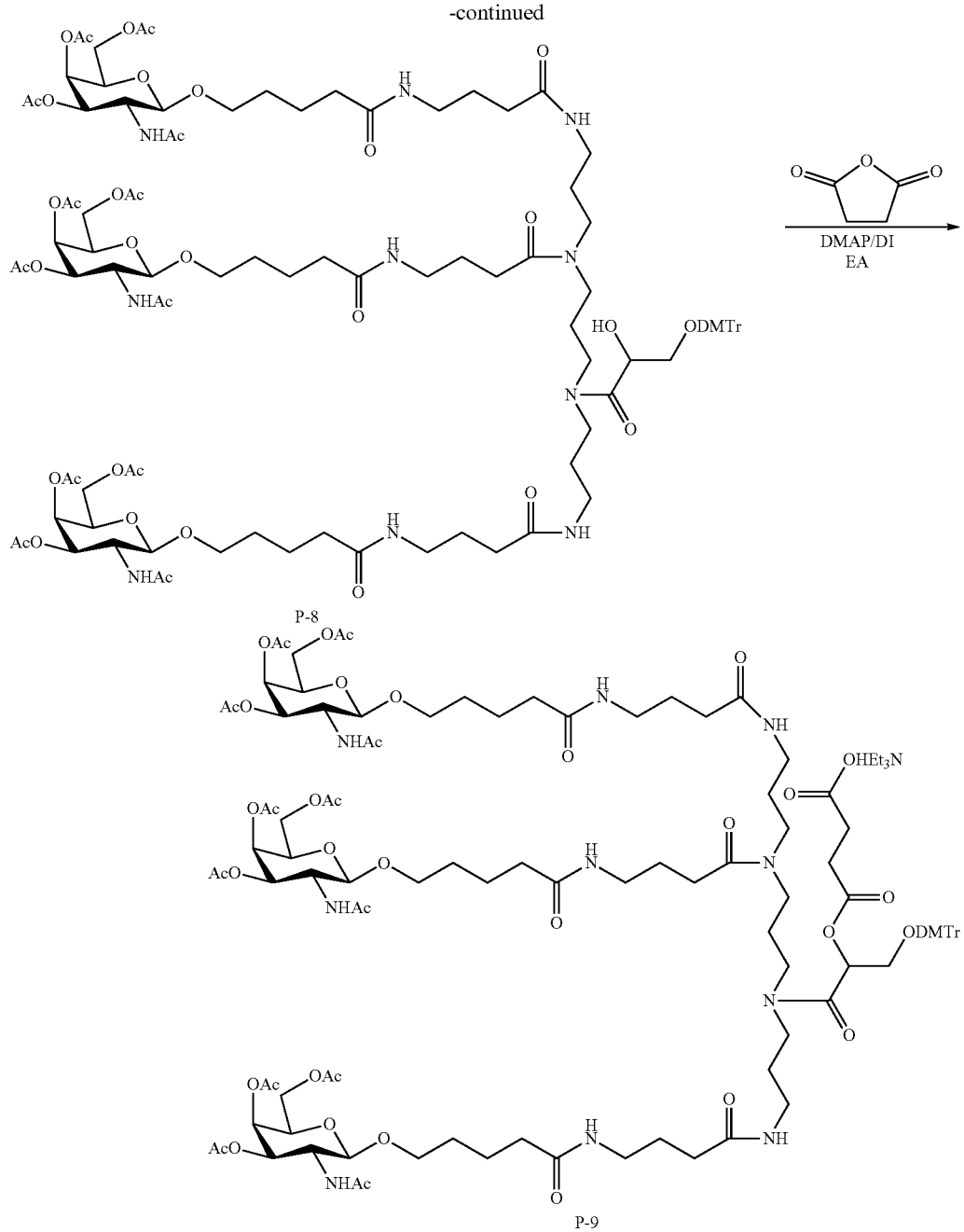

(2-1) Synthesis of GAL5-C4-1

GAL-5 (13.43 g, 30.0 mmol) obtained according to the method described in (1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added into 40 ml of N,N-dimethylformamide, dissolved uniformly and then stirred at room temperature to react for 5 hours. 300 ml of saturated aqueous sodium bicarbonate solution was added into the resulting reaction solution. The aqueous phase isolated was extracted three times, each with 200 ml of ethyl acetate. All organic phases were combined and washed once with 200 ml of saturated brine. The organic phases resulted from washing was isolated and dried with anhydrous sodium sulfate. The solvent was evaporated under reduced pressure to dryness to give 30.3 g of crude product GAL5-C4-1 as oil, which was directly used in the next reaction.

(2-2) Synthesis of GAL5-C4-2

The crude product GAL5-C4-1 (30.3 g, 30 mmol) obtained in step (2-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The eluate was collected and concentrated to remove the solvents to give a total of 14.84 g of target product GAL5-C4-2.

(2-3) Synthesis of P-6:

M-18-Tr (2.02 g, 4.69 mmol) obtained according to the method described in step (1-4) and GAL5-C4-2 (8.24 g, 15.48 mmol) obtained in step (2-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The resulting organic phase was washed with 100 ml of saturated sodium bicarbonate solution and 100 ml of saturated brine, respectively. All organic phases were combined, dried with anhydrous sodium sulfate, and filtrated. The solvent was evaporated under reduced pressure to give a crude product, which was purified by using a normal phase silica gel column, 200-300 mesh. The column was packed with petroleum ether, added with 1 wt % triethylamine for neutralizing the acidity of silica gel, and gradient eluted with dichloromethane:methanol=100:5-100:7. The eluate was collected, and the solvent was evaporated under reduced pressure to give a total of 8.27 g of pure product P-6.

(2-4) Synthesis of P-7:

P-6 (6.82 g, 3.456 mmol) obtained in (2-3) above was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtrated. Then the solvent was evaporated under reduced pressure to give a crude product. The crude product was purified by using a normal phase silica gel column, 200-300 mesh, with 10 wt % triethylamine for neutralizing the acidity of silica gel. The column was equilibrated with 1 wt‰ triethylamine and gradient eluted with dichloromethane:methanol=100:30-100:40. The eluate was collected, and the solvent was evaporated under reduced pressure to give a total of 4.82 g of P-7. MS m/z: C78H127N10O33, [M+H]+, calcd: 1732.91, measured: 1735.73.

(2-5) Synthesis of P-8:

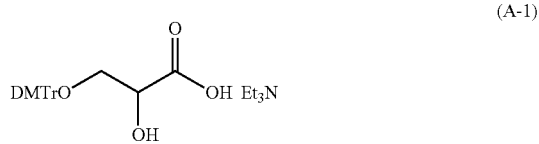

(A-1)

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotriazol 4(3H)-one (DEPBT) (1.375 g, 4.596 mmol) followed by diisopropylethylamine (1.188 g, 9.191 mmol) to react for 2 hours under stirring at 25° C., washed with 10 ml of saturated sodium bicarbonate. The aqueous phase isolated was extracted three times, each with 10 ml of dichloromethane. All organic phases were combined and washed with 10 ml of saturated brine. The aqueous phase isolated was extracted twice, each with 10 ml of dichloromethane, and the obtained organic phases were combined, dried with anhydrous sodium sulfate and filtrated. The solvent was evaporated under reduced pressure, and the residue was foam-dried overnight with a vacuum oil pump to give a crude product. The crude product was subjected to a column purification by using normal phase silica gel, 200-300 mesh, 120 g, with 20 ml triethylamine for neutralizing the acidity of silica gel. The column was equilibrated with petroleum ether containing 1 wt % triethylamine and gradient eluted with petroleum ether:ethyl acetate:dichloromethane:N,N-dimethylformamide=1:1:1:0.5-1:1:1:0.6. The eluate was collected, and the solvent was evaporated under reduced pressure to give a total of 2.793 g of pure product P-8.

(2-6) Synthesis of P-9:

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIPEA, 149 mg, 1.155 mmol) to react for 21 hours under stirring at 25° C. 50 ml dichloromethane was added to the resulting reaction solution for dilution, and then washed with 100 ml of 0.5 M triethylamine phosphate. The aqueous phase isolated was extracted three times, each with 10 ml of dichloromethane. All organic phases were combined, and the solvent was evaporated under reduced pressure to give a crude product. The crude product was subjected to a column purification by using a normal phase silica gel, 200-300 mesh, 80 g, with 1 wt % triethylamine for neutralizing the acidity of silica gel. The column was equilibrated with dichloromethane and gradient eluted with dichloromethane containing 1 wt‰ triethylamine:methanol=100:18-100:20. The eluate was collected, and the solvent was evaporated under reduced pressure to give a total of 200 mg of pure product, P-9 Conjugating Molecule (Conjugating Molecule 2). MS m/z: C106H153N10O41, [M-DMTr]+, calcd: 1921.05, measured: 1920.97. The structure of the resulting P-9 Conjugating Molecule is represented by Formula (504).

Preparation Example 3 Preparation of R-4 Conjugating Molecule (Conjugating Molecule 3)

In this preparation example, Conjugating Molecule 3 (also referred to as R-4 Conjugating Molecule hereinafter) was synthesized according to following method:

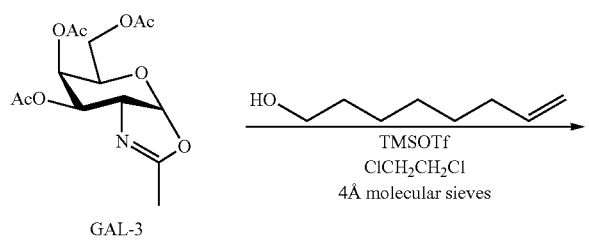

-continued
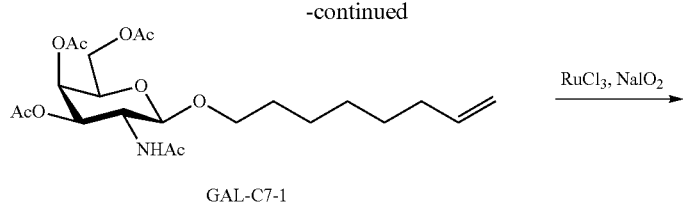
GAL-C7-1
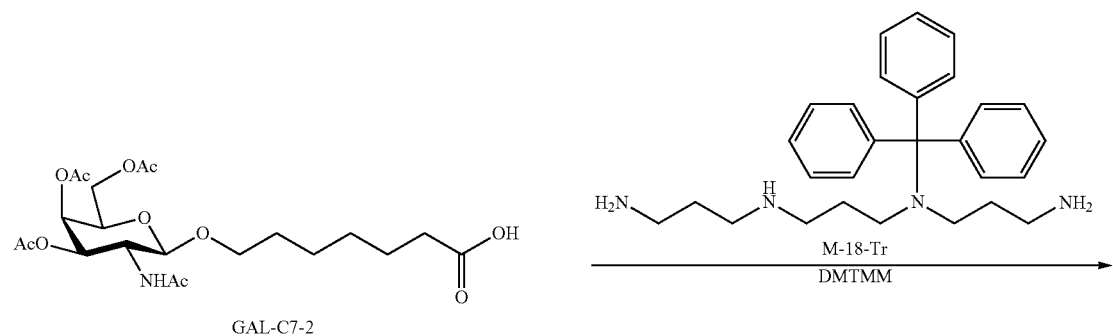
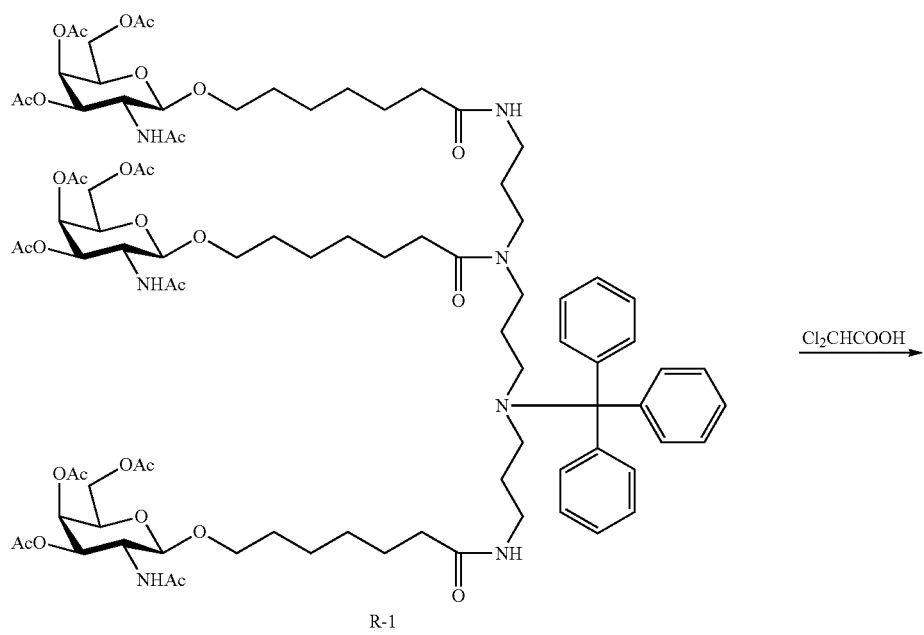

-continued
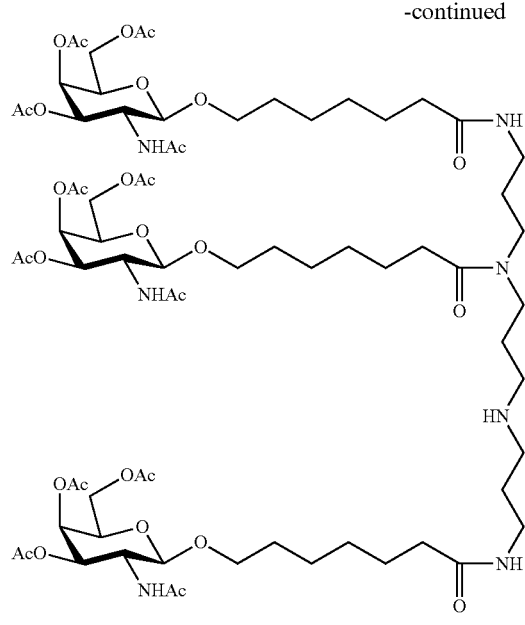
R-2
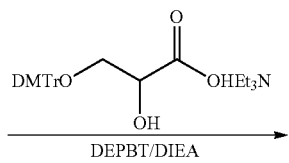
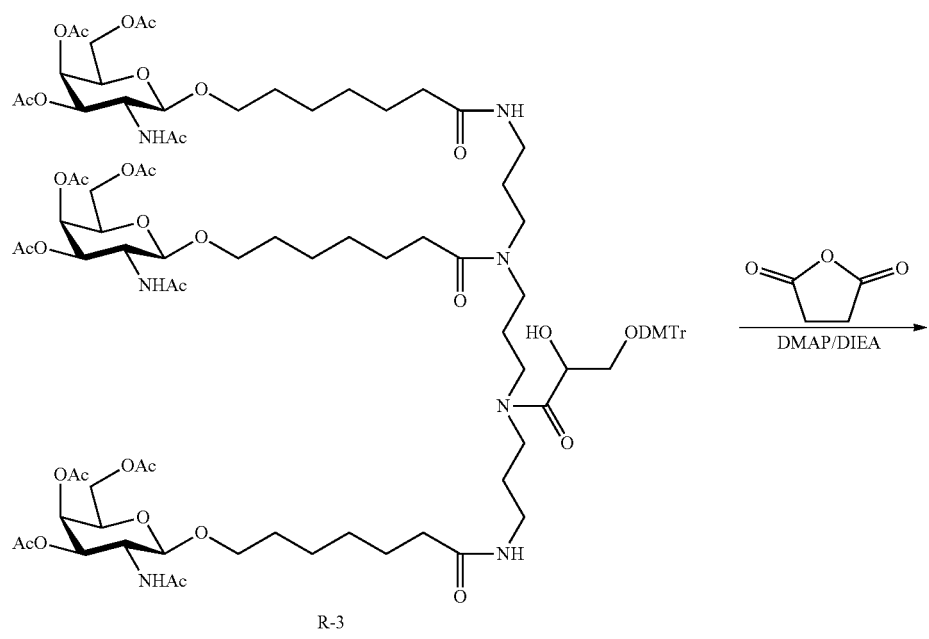
R-3

-continued

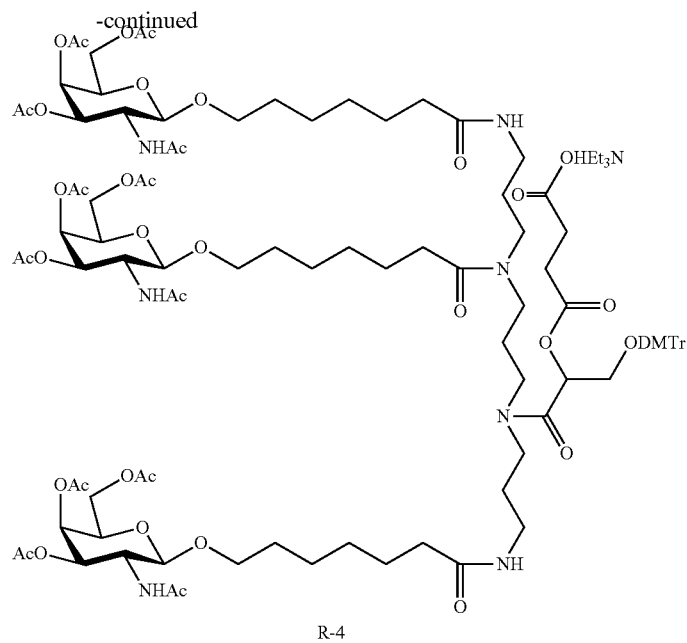

R-4

(3-1) Synthesis of GAL-C7-1

GAL-3 (26.4 g, 80.2 mmol) obtained according to the method described in step (1-1b) was dissolved in 134 ml of anhydrous 1,2-dichloroethane, and added with 60 g of 4 Å molecular sieve as a powder followed by 7-octen-1-ol (11.3 g, 88.2 mmol) to react for 10 minutes under stirring at room temperature. Trimethylsilyl trifluoromethanesulphonate (TMSOTf, 8.9 g, 40.1 mmol) was added under an ice bath and the protection of nitrogen to react for 24 hours under stirring at room temperature. The 4 Å molecular sieve powder was removed by filtration. 500 ml of saturated aqueous sodium bicarbonate solution was added to the filtrate for washing. An organic phase was isolated. An aqueous phase remained was extracted once with 100 ml of dichloromethane. All organic phases were combined and washed once with 250 ml of saturated brine. The organic phase resulted from washing was dried with anhydrous sodium sulfate. The solvent was evaporated under reduced pressure to dryness to give 33.3 g of product GAL-C7-1 as yellow syrup, which was directly used in the next oxidation reaction without purification.

(3-2) Synthesis of GAL-C7-2

GAL-C7-1 (33.3 g, 72.8 mmol) obtained in step (3-1) was dissolved in a mixed solvent of 160 ml of dichloromethane and 160 ml of acetonitrile, added with 216 ml of water and sodium periodate solid (62.3 g, 291.2 mmol) respectively, stirred under an ice water bath for 10 minutes, and added with a catalyst ruthenium trichloride (498 mg, 2.4 mmol). The reaction was naturally warmed to room temperature and stirred for 23 hours. The resulting reaction solution was diluted by adding 200 ml of water, stirred, and adjusted to pH 7.5 by adding saturated sodium bicarbonate. The organic phase isolated was discarded. The aqueous phase remained was extracted three times, each with dichloromethane. The organic phases resulted from the extraction were discarded. The aqueous phase resulted from the extraction was adjusted to a pH of about 3 with citric acid solid, extracted three times, each with 200 ml of dichloromethane, and the obtained organic phases were combined, dried with anhydrous sodium sulfate. The solvent was evaporated under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: C21H32NO11, [M+H]+, calcd: 476.50, measured: 475.94.

(3-3) Synthesis of R-1:

M-18-Tr (2.02 g, 4.69 mmol) obtained according to the method described in step (1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The resulting organic phase was washed with 100 ml of saturated sodium bicarbonate solution and 100 ml of saturated brine, respectively. All organic phases were combined, dried with anhydrous sodium sulfate, and filtrated. The solvent was evaporated under reduced pressure to give a crude product, which was purified by using a normal phase silica gel column, 200-300 mesh. The column was packed with petroleum ether, added with 1 wt % triethylamine for neutralizing the acidity of silica gel, and gradient eluted with dichloromethane:methanol=100:5-100:7. The eluate was collected and the solvent was evaporated under reduced pressure to give 7.82 g of pure product R-1.

(3-4) Synthesis of R-2:

R-1 (6.23 g, 3.456 mmol) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjust to pH 7-8 with saturated sodium bicarbonate solution. The aqueous phase isolated was extracted six times, each with 30 ml of dichloromethane. All organic phases were combined, dried with anhydrous sodium sulfate, and filtrated. Then the solvent was evaporated under reduced pressure to give a crude product. The crude product was purified by using a normal phase silica gel column, 200-300 mesh, with 10 wt % triethylamine for neutralizing the acidity of silica gel. The column was equilibrated with 1 wt‰ triethylamine and gradient eluted with dichloromethane:methanol=100:30-100:40. The solvent of the eluate was evaporated under reduced pressure to give 4.49 g of pure product R-2.

(3-5) Synthesis of R-3:

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react for 2 hours under stirring at 25° C., washed with 10 ml of saturated sodium bicarbonate. The aqueous phase isolated was extracted three times, each with 10 ml of dichloromethane. All organic phases were combined and washed with 10 ml of saturated brine. The aqueous phase isolated was extracted twice, each with 10 ml of dichloromethane, and the obtained organic phases were combined, dried with anhydrous sodium sulfate and filtrated. The solvent was evaporated under reduced pressure, and the residue was foam-dried overnight with a vacuum oil pump to give a crude product. The crude product was subjected to a column purification by using normal phase silica gel, 200-300 mesh, 120 g, with 20 ml triethylamine for neutralizing the acidity of silica gel. The column was equilibrated with petroleum ether containing 1 wt % triethylamine and gradient eluted with petroleum ether:ethyl acetate:dichloromethane:N,N-dimethylformamide=1:1:1:0.5-1:1:1:0.6. The solvent was evaporated under reduced pressure to give 2.642 g of pure product R-3.

(3-6) Synthesis of R-4:

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIPEA, 100 mg, 0.8148 mmol) to react for 18 hours under stirring at 25° C. The resulting reaction solution was washed with 5 ml of 0.5 M triethylamine phosphate. An aqueous phase was extracted three times, each with 5 ml of dichloromethane. All organic phases were combined, and the solvent was evaporated under reduced pressure to give a crude product. The crude product was subjected to a column purification by using normal phase silica gel, 200-300 mesh, 30 g, with 1 wt % triethylamine for neutralizing the acidity of silica gel. The column was equilibrated with dichloromethane and gradient eluted with dichloromethane containing 1 wt‰ triethylamine:methanol=100:18-100:20. The eluate was collected, and the solvent was evaporated under reduced pressure to give 505 mg of pure product of R-4 Conjugating Molecule (Conjugating Molecule 3). The structure of the resulting R-4 Conjugating Molecule is represented by Formula (507).

Preparation Example 4 Preparation of LA-4 Conjugating Molecule (Conjugating Molecule 4)

It is expected that Conjugating Molecule 4 (also referred to as LA-4 Conjugating Molecule hereinafter) can be synthesized according to following process route. The structure of the resulting LA-4 Conjugating Molecule is represented by Formula (512).

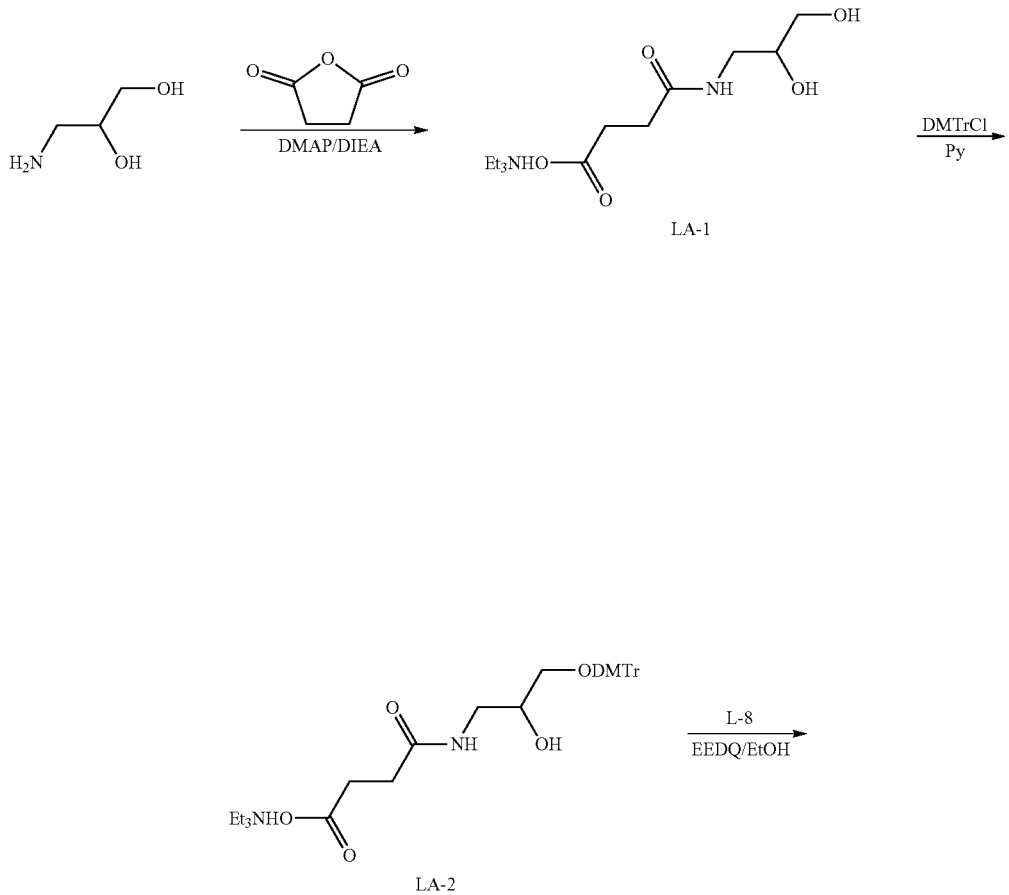

-continued
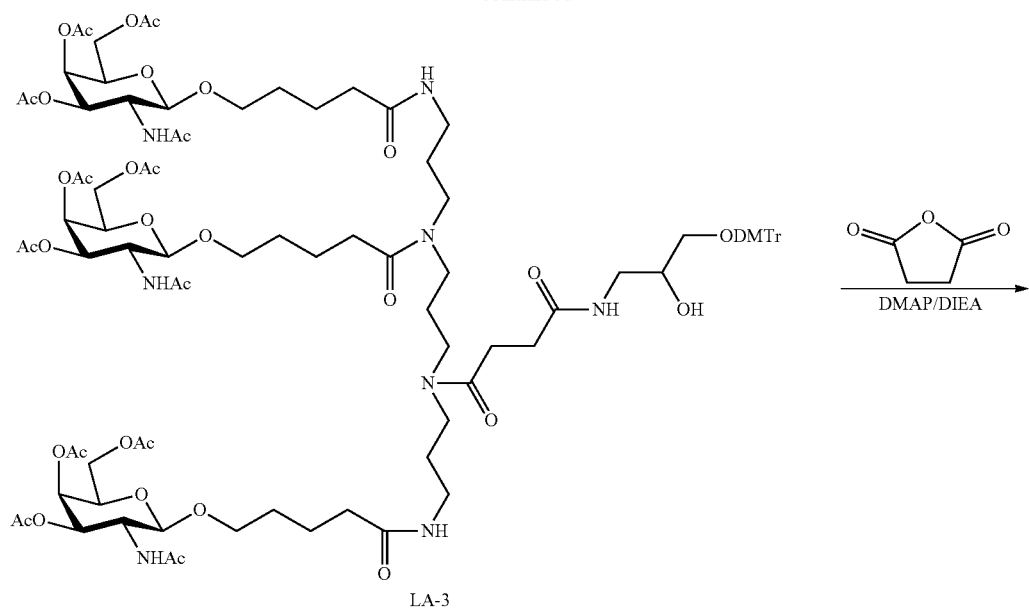
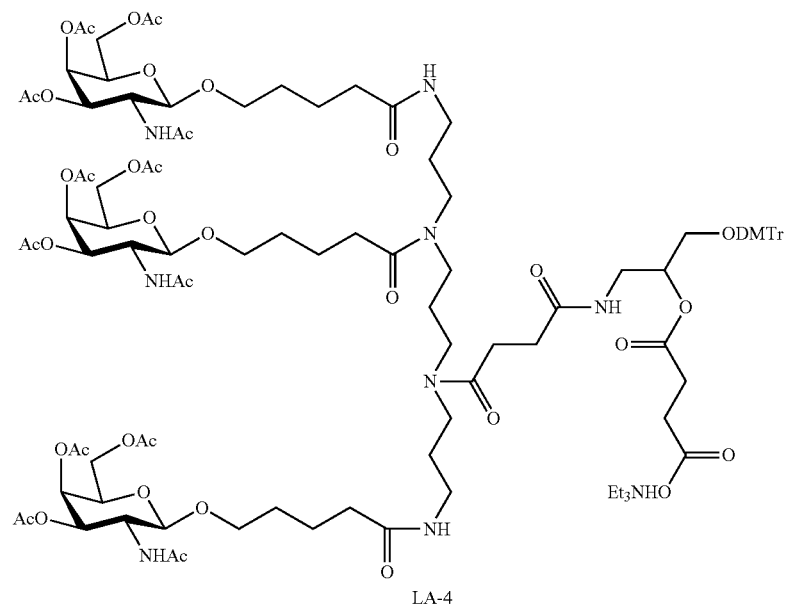

Preparation Example 5 Preparation of LB-4 Conjugating Molecule (Conjugating Molecule 5)
In this preparation example, Conjugating Molecule 5 (also referred to as LB-4 Conjugating Molecule hereinafter) was synthesized according to following method:
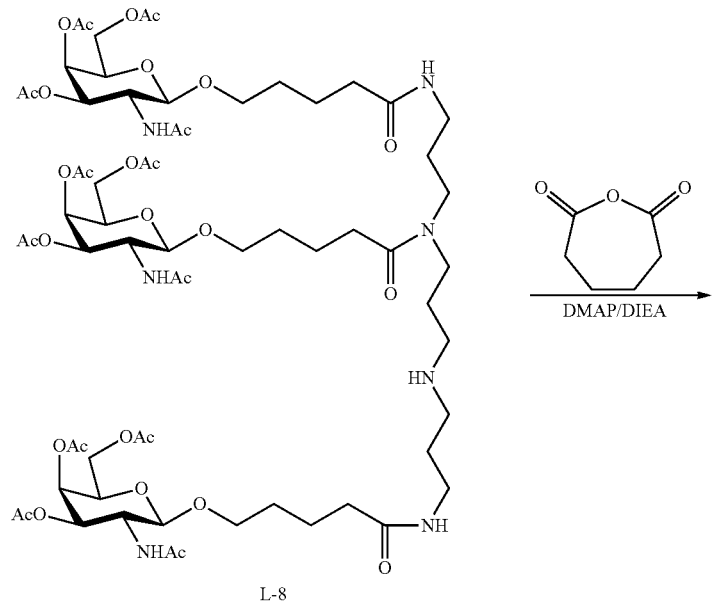
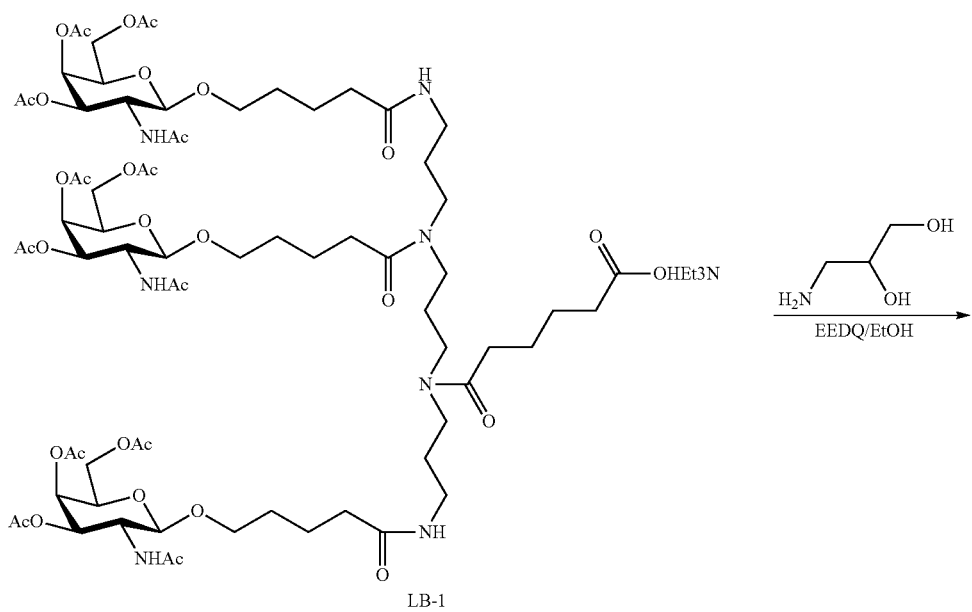

-continued
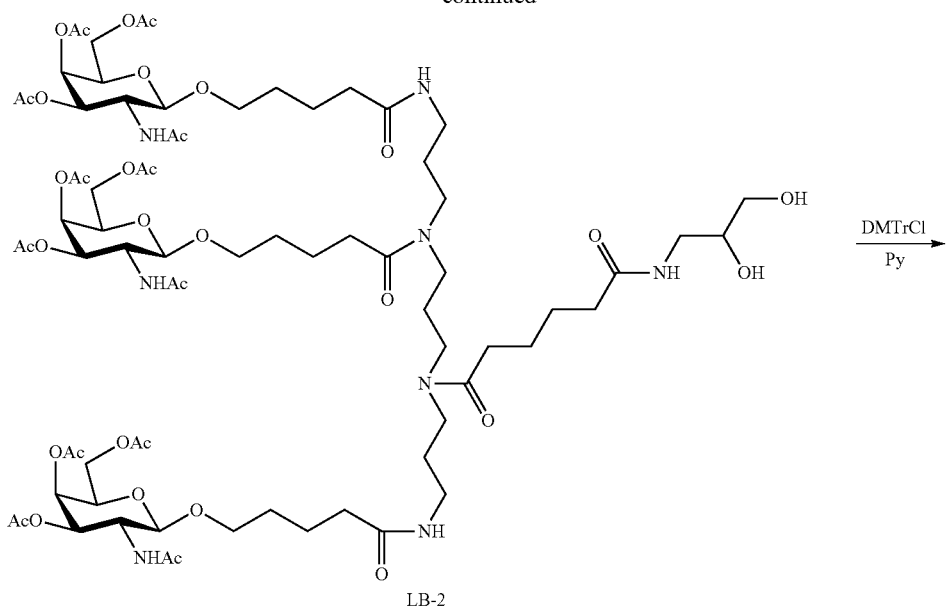
LB-2
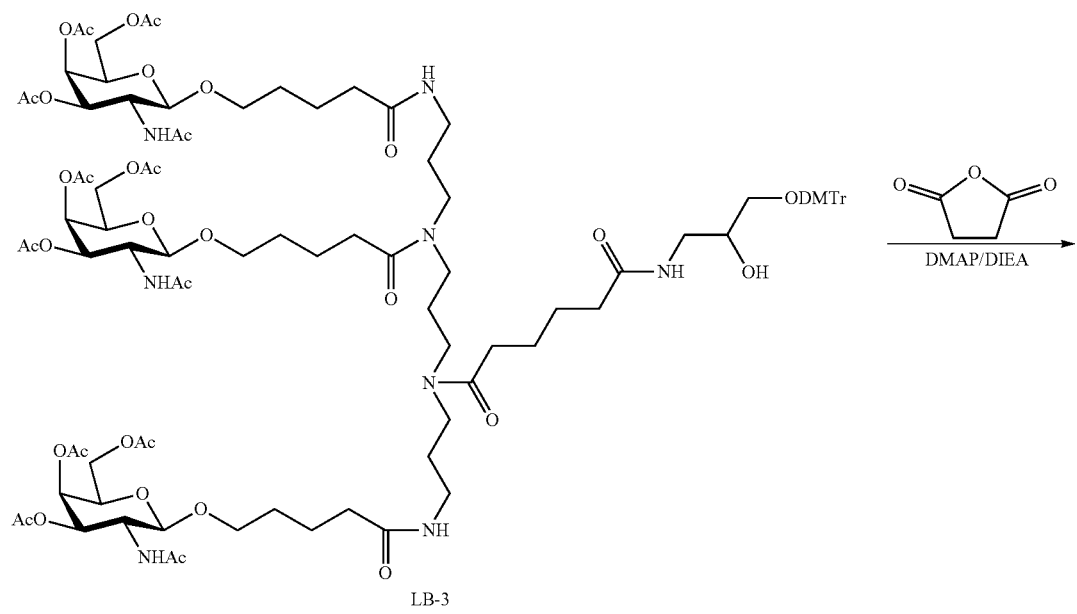
LB-3

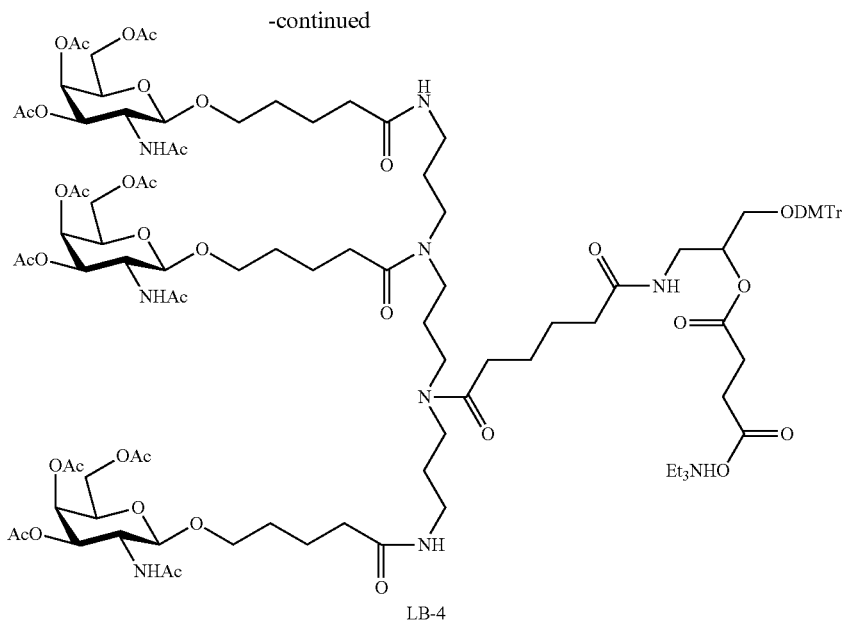

LB-4

(5-1) Synthesis of LB-1:

L-8 (5.0 g, 3.386 mmol) obtained according to the method described in step (1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIPEA, 2.2 g, 16.931 mmol) to react for 4 hours under stirring at 25° C. 70 ml dichloromethane was added to the resulting reaction solution for dilution, and then washed with 0.5 M triethylamine phosphate. The aqueous phase isolated was extracted for four times, each with 10 ml of dichloromethane. All organic phases were combined, and the solvent was evaporated under reduced pressure to give a crude product. The crude product was subjected to a column purification by using normal phase silica gel, 200-300 mesh, 120 g, with 1 wt % triethylamine for neutralizing the acidity of silica gel. The column was equilibrated with dichloromethane and gradient eluted with petroleum ether:ethyl acetate:dichloromethane:methanol=1:1:1:0.2-1:1:1:1. The solvent was evaporated under reduced pressure to give 4.267 g of pure product LB-1.

(5-2) Synthesis of LB-2:

LB-1 (4.697 g, 2.753 mmol, combination of 2 batches) obtained according to the method described in step (5-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixture of 30 ml of acetonitrile and 3 ml of methanol to react overnight under stirring at room temperature. The reaction was transferred to an oil bath at 60° C. and stirring for 18 hours. The solvent was evaporated to dryness, and the residue was purified by column chromatography (200-300 mesh normal phase silica gel, with a gradient elution of dichloromethane:methanol=1:0.07-1:0.5). The eluate was collected and concentrated to remove the solvents to give 3.27 g of target product LB-2.

(5-3) Synthesis of LB-3:

LB-2 (2.27 g, 1.353 mmol) was dissolved in 14 ml of anhydrous pyridine, and added with 4,4'-dimethoxytrityl chloride (688 mg, 2.03 mmol) to react overnight under stirring at room temperature. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2). The eluate was collected and concentrated to remove the solvents to give 1.647 g of target product LB-3.

(5-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIPEA (270 mg, 2.075 mmol), and stirred at 25° C. to react overnight. The resulting reaction liquid was washed with 0.5 M triethylamine phosphate for three times. The aqueous phase isolated was extracted three times, each with 2 ml of dichloromethane. All organic phases were combined, and the solvent was evaporated under reduced pressure to give a crude product. The crude product was subjected to a column purification by using normal phase silica gel, 200-300 mesh, with 5 wt % triethylamine for neutralizing the acidity of silica gel. The column was equilibrated with petroleum ether and gradient eluted with 1 wt‰ triethylamine-containing dichloromethane:methanol=100:5-100:20. The solvent was evaporated under reduced pressure to give 787 mg of pure product, LB-4 Conjugating Molecule (Conjugating Molecule 5). The structure of the resulting LB-4 Conjugating Molecule is represented by Formula (513).

Preparation Example 6 Synthesis of V-7 Conjugating Molecule (Conjugating Molecule 6)

It is expected that Conjugating Molecule 6 (also referred to as V-7 Conjugating Molecule hereinafter) can be synthesized according to following process route. The structure of the resulting V-7 Conjugating Molecule is represented by Formula (514). Conjugating Molecule

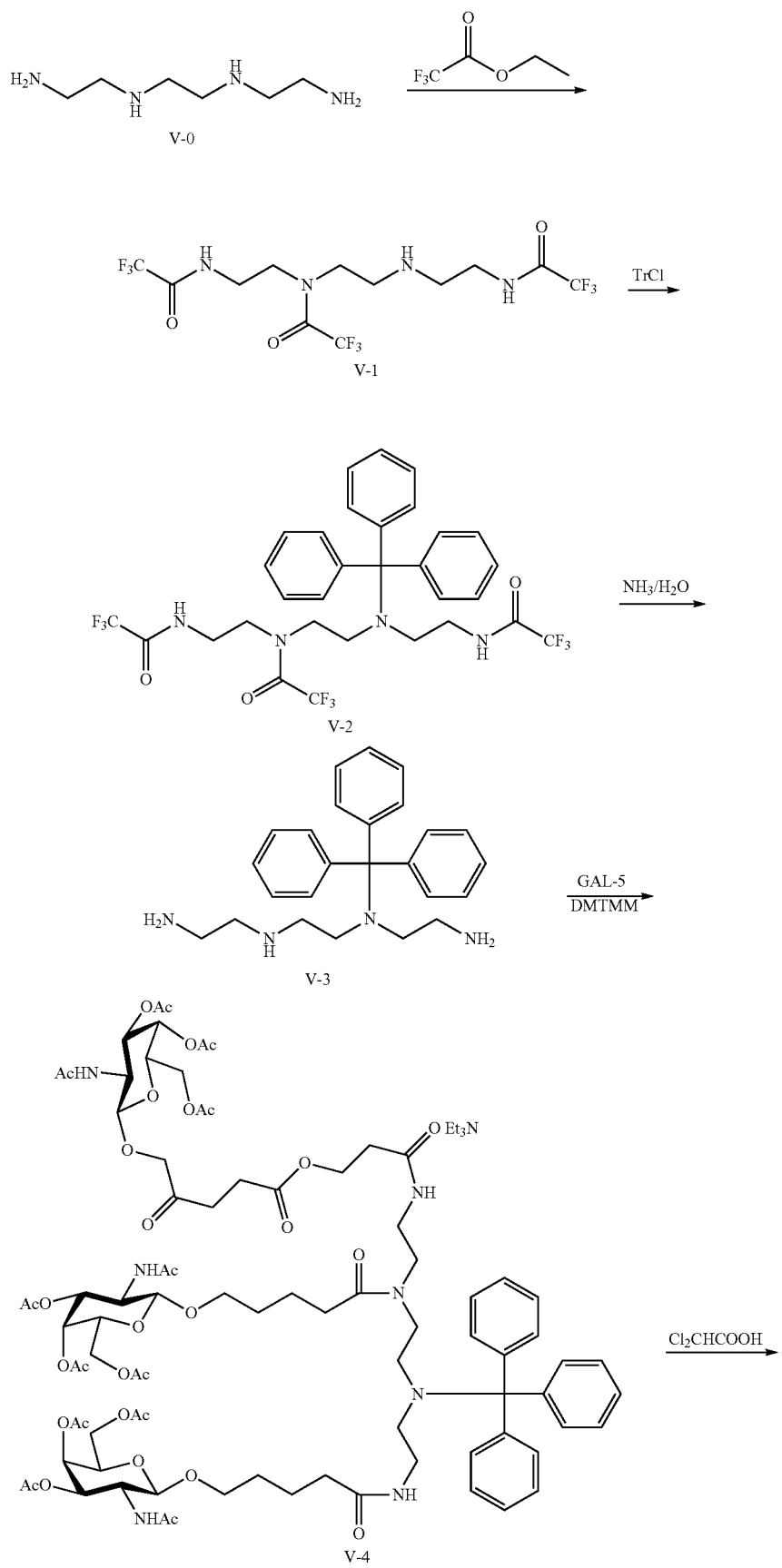

-continued
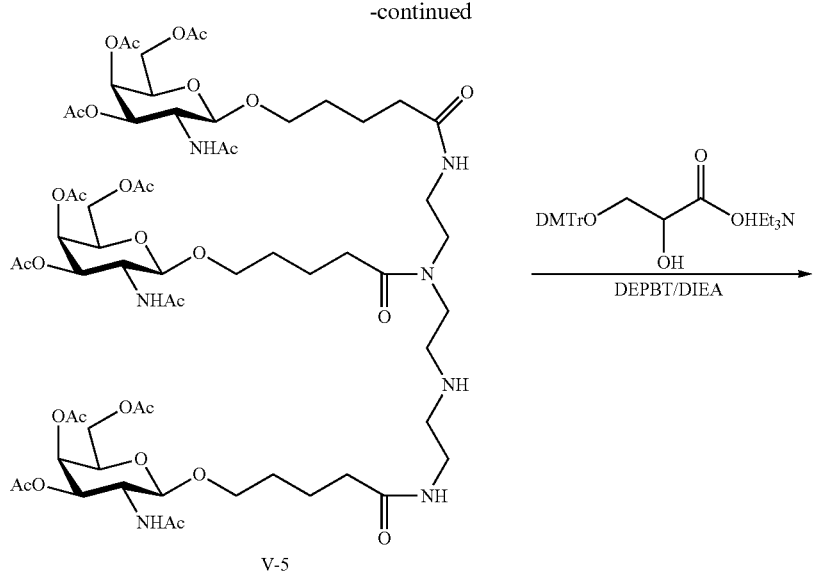
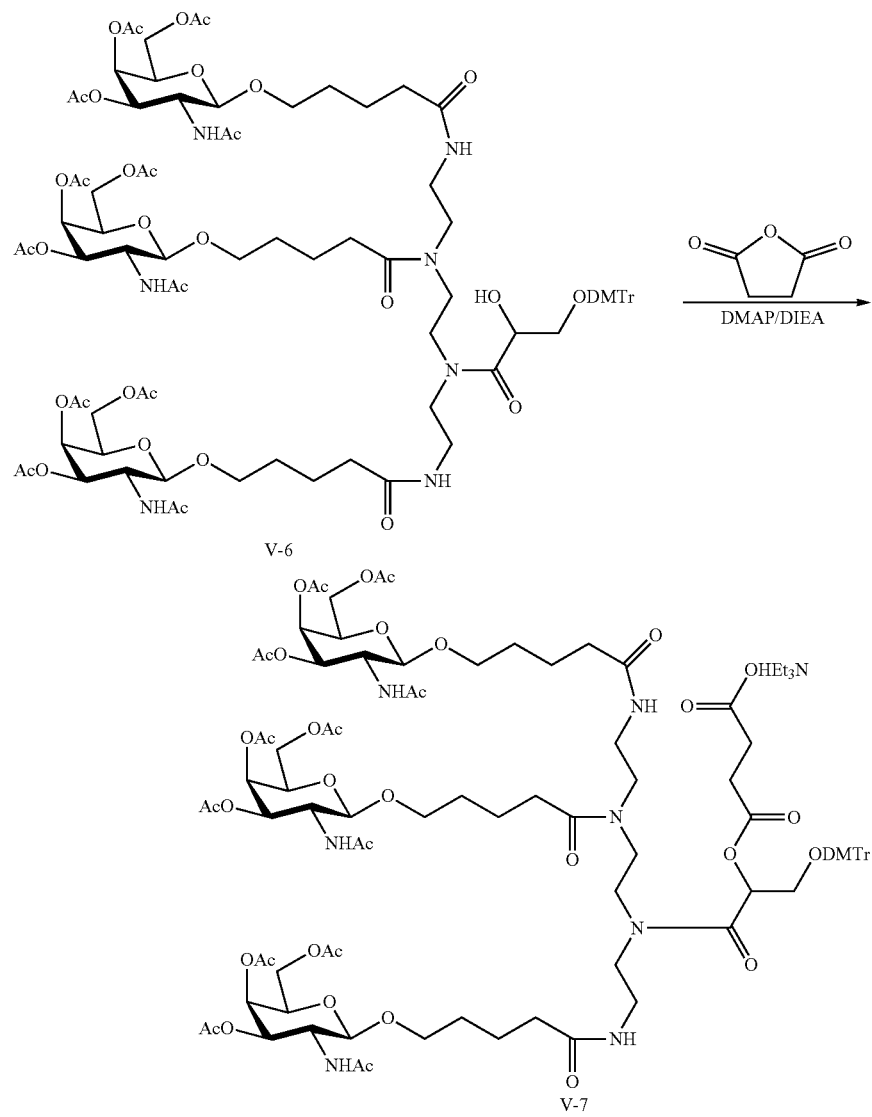

Conjugating Molecule
Preparation Example 7 Preparation of W-7 Conjugating Molecule (Conjugating Molecule 7)
In this preparation example, Conjugating Molecule 7 (also referred to as W-7 Conjugating Molecule hereinafter) was synthesized according to following method.
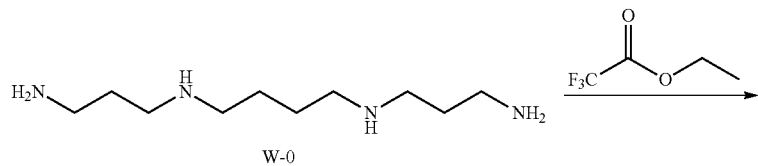
W-0
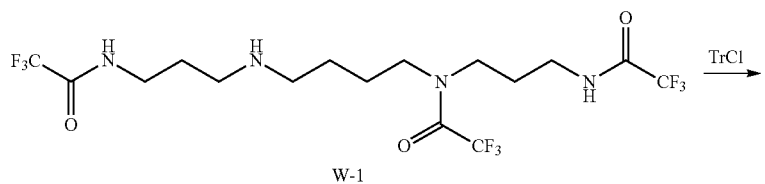
W-1
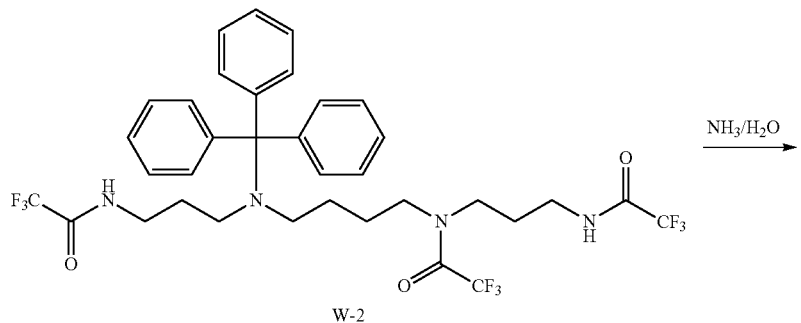
W-2
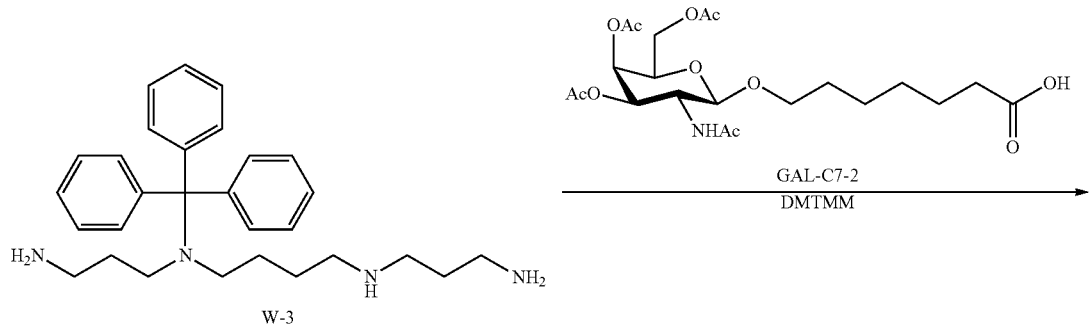
W-3

-continued
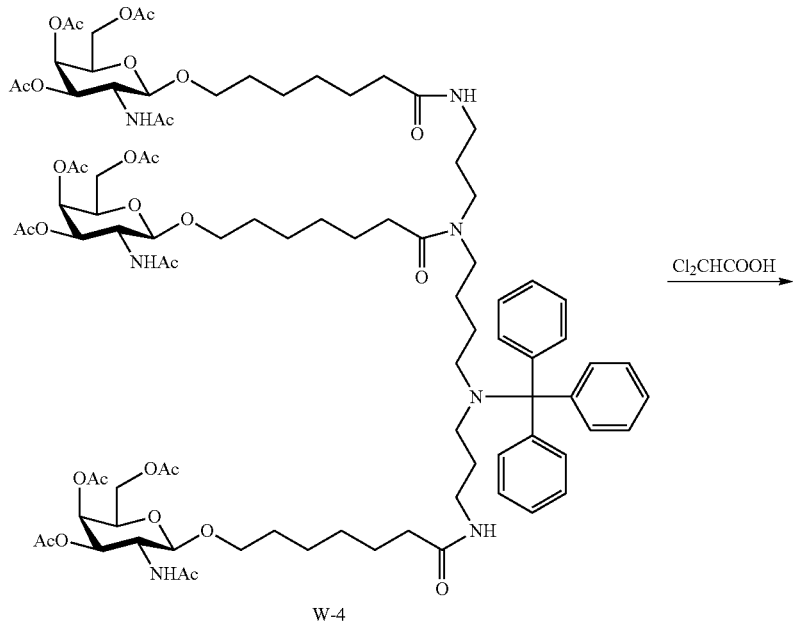
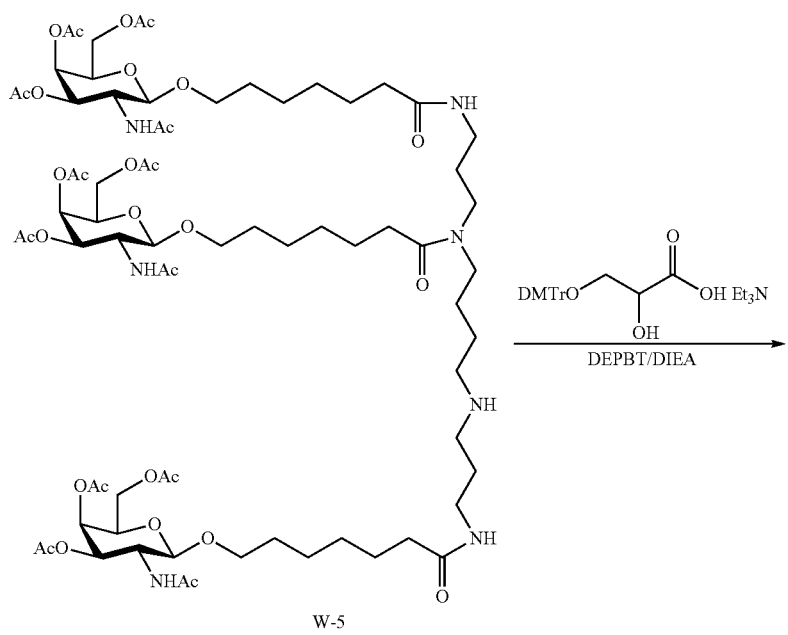

-continued

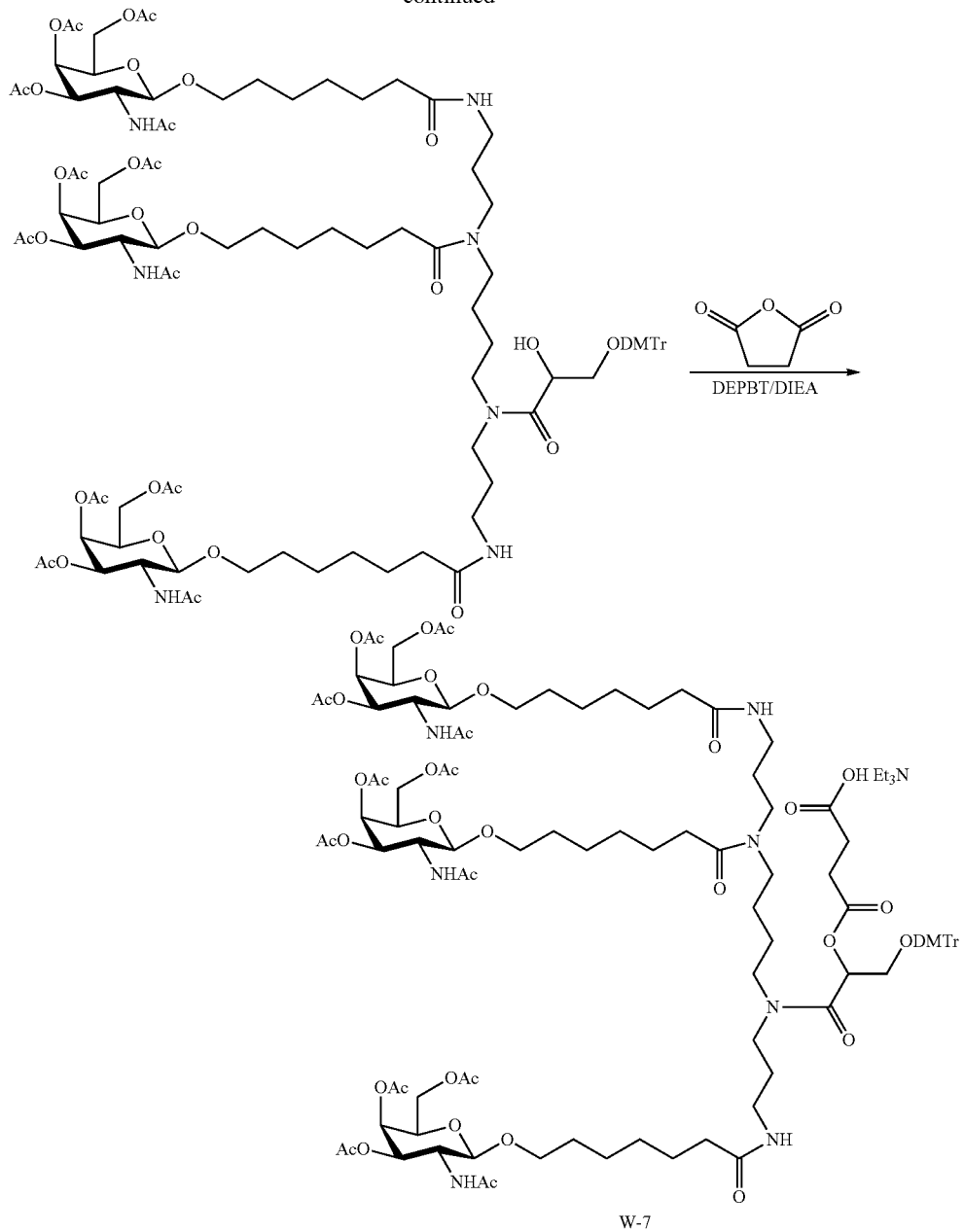

W-7

(7-1) Synthesis of W-1:

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react for 22 hours at room temperature. The solvent was evaporated under reduced pressure, and the residue was foam-dried with a vacuum oil pump for 18 hours to give 5.835 g of crude solid product W-1.

(7-2) Synthesis of W-2:

The crude product W-1 (5.835 g, 10 mmol) was dissolved in 50 ml of dichloromethane. TrCl (3.345 g, 12 mmol) and triethylamine (1.518 g, 15 mmol) were added to react for 20 hours under stirring at room temperature. The resulting reaction liquid was washed twice with 20 ml of saturated sodium bicarbonate and once with 20 ml of saturated brine. All organic phases were combined, dried with anhydrous sodium sulfate and filtered. The organic solvent was evaporated under reduced pressure, and the residue was foam-dried with a vacuum oil pump overnight to give 8.012 g of crude solid product W-2. The crude solid product W-2 was used in the next deprotection reaction without treatment.

(7-3) Synthesis of W-3:

The crude product W-2 (8.012 g, 10 mmol) was dissolved in 100 ml of methanol, and added with 100 ml of aqueous methylamine solution (40 wt %) to react for 23 hours under stirring at 50° C. Insoluble particles were removed from the reaction mixture by filtration. The solvent was evaporated under reduced pressure. The residue was added with 200 ml of mixed solvent of DCM:methanol in a volume ratio of 1:1, and the resulting organic phase was washed with 50 ml of saturated sodium bicarbonate. The aqueous phase isolated was extracted three times, each with 50 ml of dichloromethane. All organic phases were combined, dried with anhydrous sodium sulfate and filtered. The solvent was evaporated under reduced pressure, and the residue was foam-dried with a vacuum oil pump overnight, and purified by using a normal phase silica gel column, 200-300 mesh. The column was packed with petroleum ether, added with 1 wt % triethylamine for neutralizing the acidity of silica gel, and gradient eluted with dichloromethane:methanol:aqueous ammonia (25 wt %)=1:1:0.05-1:1:0.25. The eluate was collected. The solvent was evaporated under reduced pressure, and the residue was foam-dried with a vacuum oil pump to give 3.062 g of pure product W-3.

(7-4) Synthesis of W-4:

W-3 (675 mg, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react for 2.5 hours under stirring at room temperature. The resulting reaction liquid was diluted with 100 ml of dichloromethane. The organic phase obtained was washed with 80 ml of saturated sodium bicarbonate solution and 80 ml of saturated brine, respectively. All organic phases were combined, dried with anhydrous sodium sulfate, and filtrated. The solvent was evaporated under reduced pressure to give a crude product, which was purified by using a normal phase silica gel column, 200-300 mesh. The column was packed with petroleum ether, added with 1 wt % triethylamine for neutralizing the acidity of silica gel, and gradient eluted with dichloromethane:methanol=100:5-100:7. The eluate was collected, and the solvent was evaporated under reduced pressure to give 1.610 g of pure product W-4.

(7-5) Synthesis of W-5:

W-4 (1.61 g, 0.886 mmol) was dissolved in 125 ml of dichloromethane, and added with dichloroacetic acid (3.5 ml, 42.43 mmol) to react for 1 hour at room temperature. The resulting reaction liquid was neutralized by adding 150 ml of pyridine. The solvent was evaporated under reduced pressure to give a crude product. The crude product was purified by using a normal phase silica gel column, 200-300 mesh, with 10 wt % triethylamine for neutralizing the acidity of silica gel. The column was equilibrated with 1 wt‰ triethylamine and gradient eluted with dichloromethane:methanol=100:30-100:40. The eluate was collected, and the solvent was evaporated under reduced pressure to give 1.26 g of pure product W-5.

(7-6) Synthesis of W-6:

W-5 (1.25 g, 0.793 mmol) and A-1 (1.21 g, 2.38 mmol) obtained according to the method described in step (1-7a) were mixed and dissolved in 12 ml of dichloromethane, and added with 3-(diethoxyphosphoryloxy)-1,2,3-benzotrizin-4 (3H)-one (DEPBT, 0.712 g, 2.38 mmol) followed by diisopropylethylamine (0.615 g, 4.76 mmol) to react for 3 hours under stirring at 25° C., washed with 80 ml of saturated sodium bicarbonate. The aqueous phase isolated was extracted three times, each with 10 ml of dichloromethane. All organic phases were combined and washed with 10 ml of saturated brine. The obtained organic phases were combined, dried with anhydrous sodium sulfate, filtrated. The solvent was evaporated under reduced pressure, and the residue was foam-dried overnight with a vacuum oil pump to give a crude product. The crude product was subjected to a column purification by using normal phase silica gel, 200-300 mesh, 185 g, with 20 ml triethylamine for neutralizing the acidity of silica gel. The column was equilibrated with petroleum ether containing 1 wt % triethylamine and gradient eluted with petroleum ether:ethyl acetate:dichloromethane:N,N-dimethylformamide=1:1:1:0.1-1:1:1:0.7.

The eluate was collected, and the solvent was evaporated under reduced pressure to give 1.57 g of pure product W-6.

(7-7) Synthesis of W-7:

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react for 24 hours under stirring at 25° C. The resulting reaction liquid was washed with 5 ml of 0.5 M triethylamine phosphate. The aqueous phase isolated was extracted three times, each with 5 ml of dichloromethane. All organic phases were combined, and the solvent was evaporated under reduced pressure to give a crude product. The crude product was subjected to a column purification by using normal phase silica gel, 200-300 mesh, 30 g, with 1 wt % triethylamine for neutralizing the acidity of silica gel. The column was equilibrated with dichloromethane and gradient eluted with 1 wt‰ triethylamine-containing dichloromethane:methanol=100:18-100:20. The eluate was collected, and the solvent was evaporated under reduced pressure to give 1.033 g of pure product, W-7 Conjugating Molecule (Conjugating Molecule 7). MS m/z: C101H146N7O38, [M-DMTr]+, calcd: 1763.92, measured: 1763.21. The structure of the resulting W-7 Conjugating Molecule is represented by Formula (515).

Preparation Example 8 Preparation of X-7 Conjugating Molecule (Conjugating Molecule 8)

It is expected that Conjugating Molecule 8 (also referred to as X-7 Conjugating Molecule hereinafter) can be synthesized according to following process route. The structure of the resulting X-7 Conjugating Molecule is represented by Formula (521). Conjugating Molecule

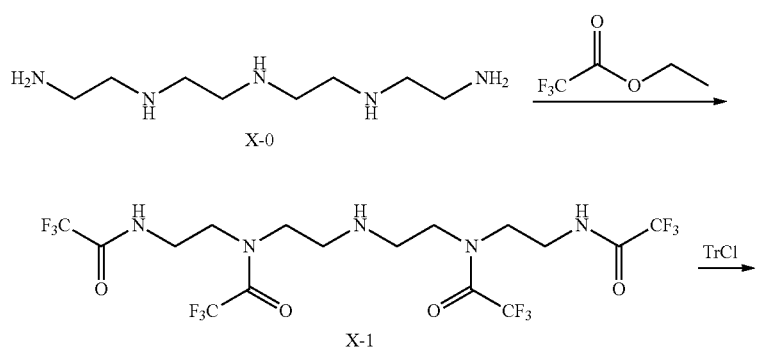

-continued
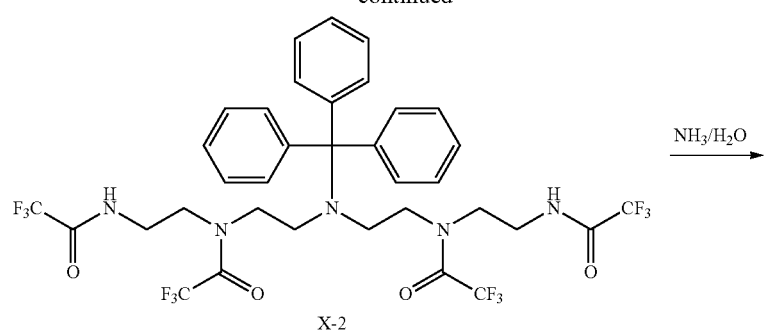
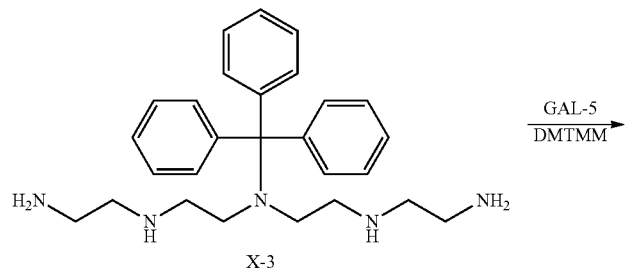
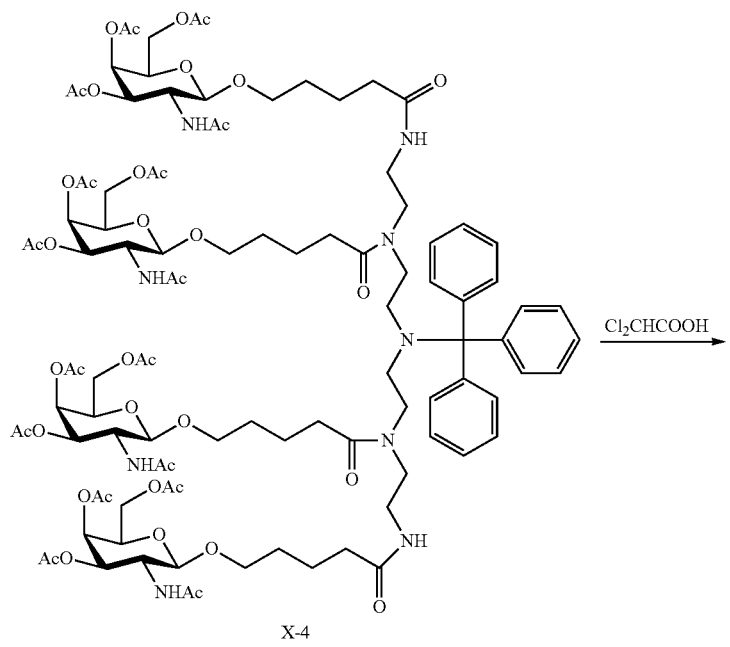

-continued
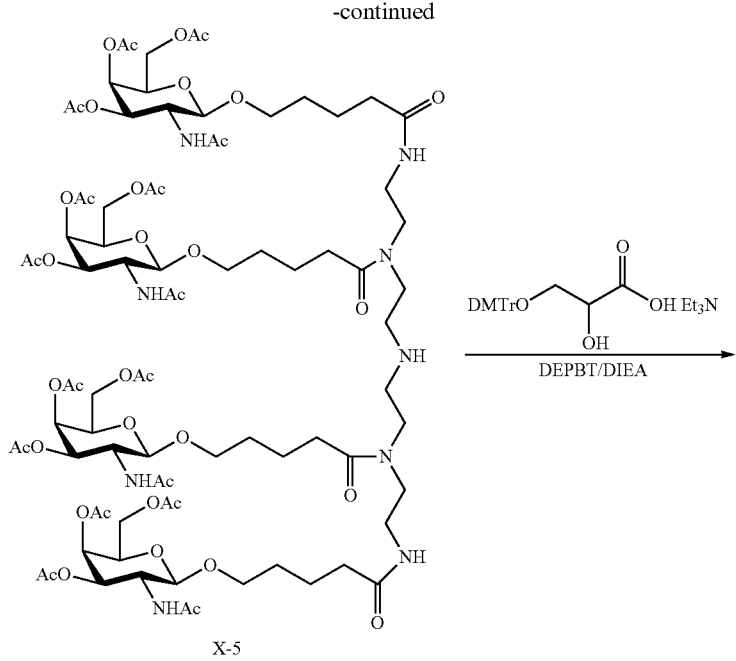
X-5
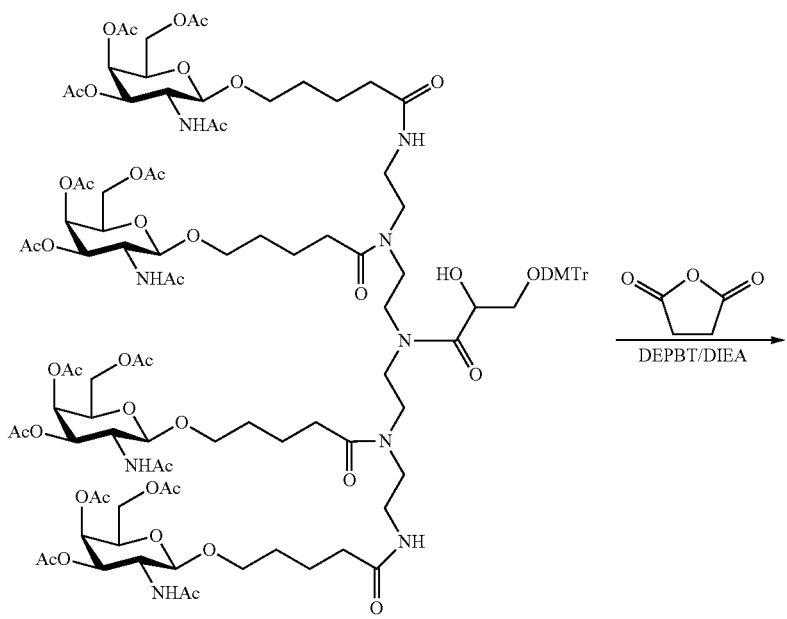
X-6

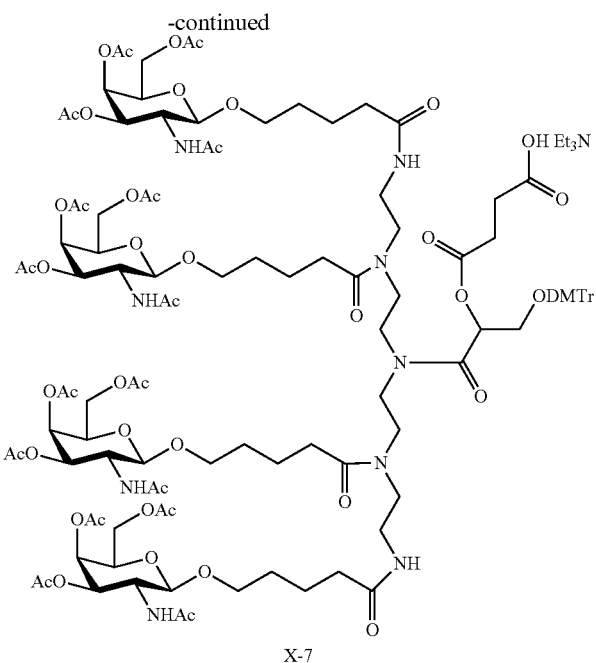
X-7
Conjugating Molecule
Preparation Example 9 Preparation of K-3 Conjugating Molecule (Comparative Conjugating Molecule 1)
In this preparation example, K-3 Conjugating Molecule (also referred to as comparative Conjugating Molecule 1 Conjugating Molecule hereinafter) was synthesized according to following method:
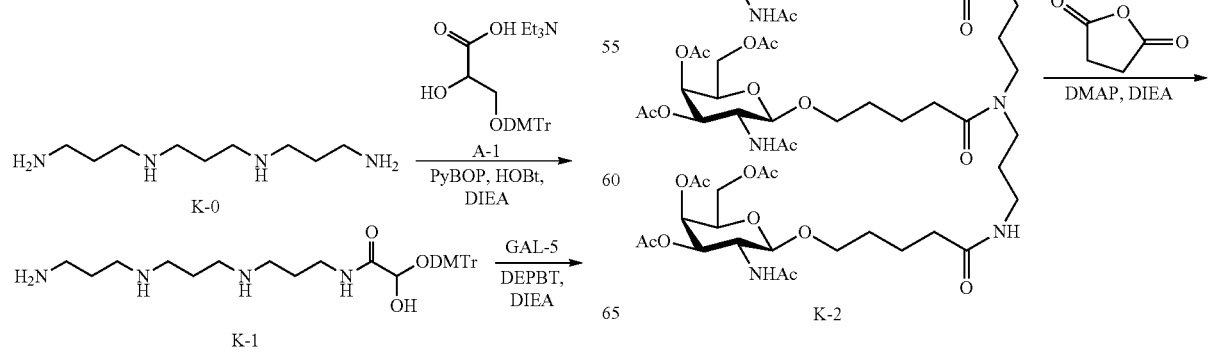

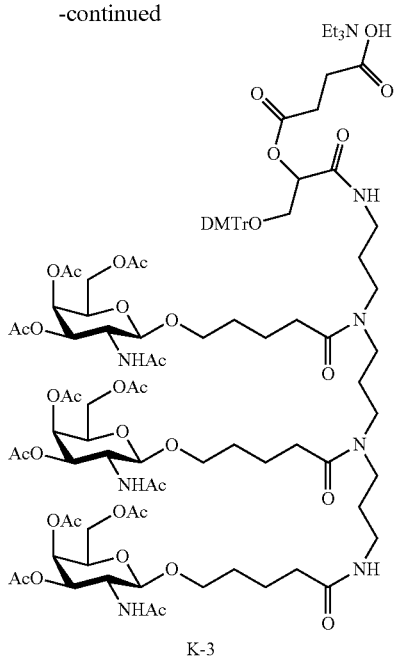

K-3

(9-1) Synthesis of K-1:

A-1 (3.0 g, 6.0 mmol) obtained according to the method described in step (1-7a), PyBOP (6.2 g, 12.0 mmol), HOBt (1.6 g, 2.0 mmol) and diisopropylethylamine (DIPEA, 3.9 g, 30.0 mmol) were added to 60 ml of dichloromethane to react for 10 minutes under stirring at room temperature. Then the above solution was added into K-0 (5.6 g, 30.0 mmol) to react at room temperature for 1 hour and 50 minutes. The reaction liquid was poured into 30 ml of saturated sodium bicarbonate solution. The aqueous phase isolated was extracted three times, each with 30 ml of dichloromethane. All organic phases were combined, washed with saturated sodium chloride solution, dried with anhydrous sodium sulfate, then filtrated and concentrated, and purified by using a normal phase silica gel column, 200-300 mesh, with a gradient elution of dichloromethane:methanol:aqueous ammonia (25 wt %)=10:2:0.1-4:4:1. The eluate was collected, concentrated to remove the solvents, and foam-dried with a vacuum oil pump to give 2.2 g of product K-1 as a white solid. 1H NMR (400 MHz, DMSO-d6) δ 8.02 (s, 1H), 7.43 (d, J=7.8 Hz, 2H), 7.34-7.17 (m, 7H), 6.87 (d, J=8.6 Hz, 4H), 4.05 (d, J=5.2 Hz, 1H), 3.74 (s, 6H), 3.20-3.01 (m, 5H), 2.60-2.38 (m, 12H), 1.60-1.39 (m, 8H), 1.24 (s, 1H). MS m/z: C33H47N4O5, [M+H]+, calcd: 579.35, measured: 579.26.

(9-2) Synthesis of K-2:

GAL-5 (483 mg, 1.08 mmol) obtained according to the method described in step (1-1), 3-(diethoxyphosphoryloxy)-1,2,3-benzotrizin-4(3H)-one (359 mg, 1.2 mmol) and diisopropylethylamine (DIPEA, 310 mg, 2.4 mmol) were added into 3 ml of dichloromethane, and stirred at room temperature for 30 minutes. Then K-1 (174 mg, 0.3 mmol) was added to react at room temperature for 16 hours. The reaction liquid was poured into 10 ml of saturated sodium bicarbonate solution. The aqueous phase isolated was extracted three times, each with 10 ml dichloromethane. All organic phases were combined, washed with 10 ml of saturated sodium chloride solution, dried with anhydrous sodium sulfate, then filtrated and concentrated, and purified by using a normal phase silica gel column, 200-300 mesh, with a gradient elution of dichloromethane:methanol=20:1. The eluate was collected, concentrated to remove the solvents, and foam-dried with a vacuum oil pump to give 205 mg of product K-2 as a yellow solid.

(9-3) Synthesis of K-3:

K-2 (205 mg, 0.11 mmol), succinic anhydride (22 mg, 0.22 mmol), 4-dimethylaminopyridine (DMAP, 27 mg, 0.22 mmol) and diisopropylethylamine (DIPEA, 71 mg, 0.55 mmol) were added into 1.1 ml of dichloromethane to react overnight under stirring at room temperature. The reaction liquid was washed three times, each with 0.5 ml of 0.5 M triethylamine phosphate solution, and the aqueous phase resulted from each washing was reverse extracted once with 0.5 ml of dichloromethane. All organic phases were combined, dried with anhydrous sodium sulfate, and concentrated to remove the solvent, and foam-dried with a vacuum oil pump to give 218 mg of product as a light yellow solid, K-3 conjugate molecule (Comparative Conjugating Molecule 1).

Preparation Example 10—This Preparation Example is Used to Illustrate the Synthesis of (GalNAc)3 Conjugating Molecule (Comparative Conjugating Molecule 2)

In this preparation example, compound 47 was synthesized according to the preparation method described in Example 1-4 of WO2014025805A1. The structure of compound 47 is shown in the following formula, which is herein referred to as (GalNAc)3 Conjugating Molecule (Comparative Conjugating Molecule 2):

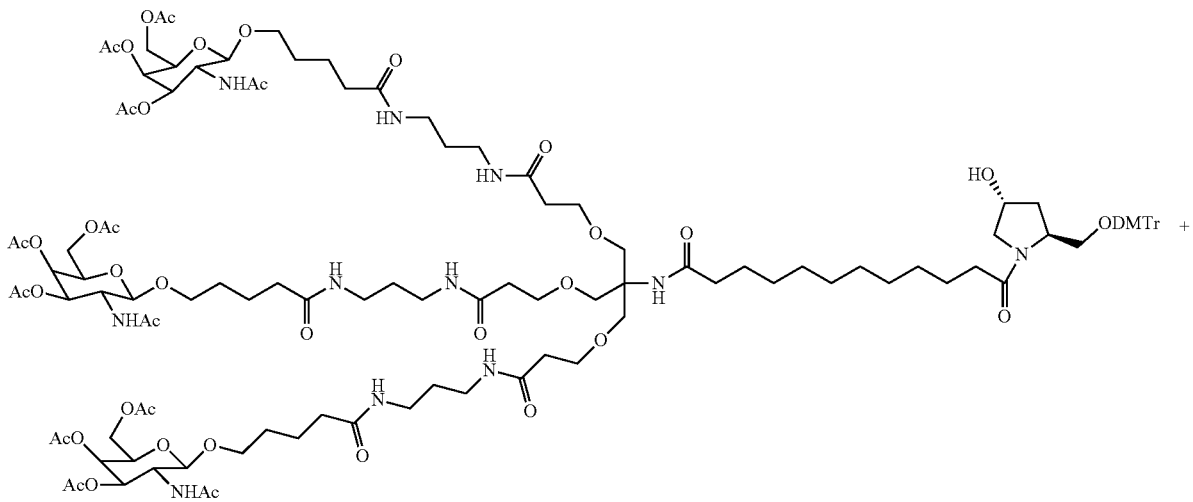

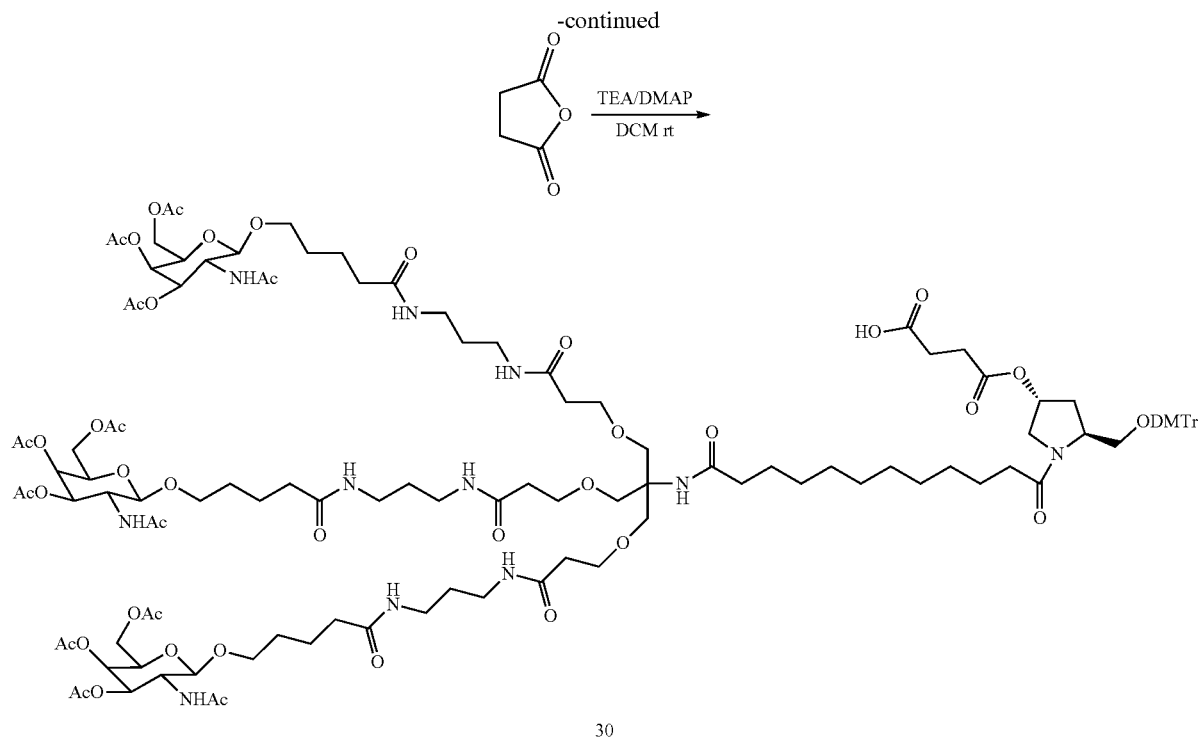

Preparation Example 11—this Preparation Example is Used to Illustrate the Preparation of FIN-2 Conjugating Molecule (Comparative Conjugating Molecule 3)

In this preparation example, FIN-2 Conjugating Molecule (Comparative Conjugating Molecule 3) was synthesized with reference to the preparation method described in Rajeev et al., ChemBioChem 2015, 16, 903-908 according to the following process route:

(11-1) Synthesis of compound PRO-10

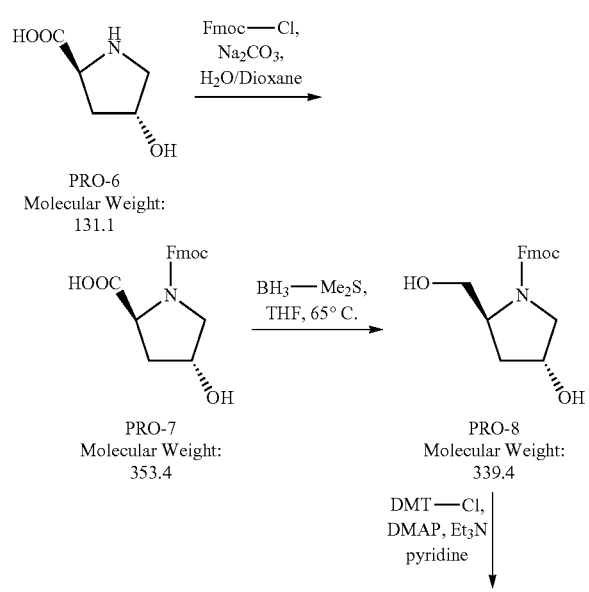

(11-1-1) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane and added with 34 ml of 10% (w/w) aqueous Na2CO3 solution. 6.954 g of Fmoc-Cl (9-fluorenylmethyl chloroformate, CAS No.: 28920-43-6, purchased from Energy Chemical, 26.8 mmol) was dissolved in 56.5 ml of 1,4-dioxane, added into the above reaction mixture under an ice bath, and naturally warmed to room temperature for reacting overnight. The reaction liquid was poured into 150 ml of ice water, and extracted three times, each with 100 ml of methyl t-butyl ether, the resulting organic phases were discarded. The aqueous phase remained was adjusted to pH≤5 with concentrated hydrochloric acid, extracted twice with 100 ml of ethyl acetate, and the obtained organic phases were combined and dried with anhydrous sodium sulfate. The solvent was evaporated under reduced pressure to give 7.83 g of product PRO-7 as a white foamy solid. 1H NMR (400 MHz, DMSO-d6) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calcd for C20H19NO5 [M−H]- 352.1190, measured: 352.1033.

(11-1-2) Synthesis of PRO-8

7.83 g of PRO-7 (22.2 mmol) was dissolved in 80 ml of THF, heated to 65° C. under an oil bath, added with 36.6 ml of 2 mol/L solution of BH3-Me2S in THF (CAS No. 13292-87-0, purchased from J&K Scientific Ltd., 73.2 mmol) under reflux, and refluxed continually to react for 3 hours. The reaction liquid was poured out, and the remaining solid therein was dissolved in methanol. To the resulting reaction liquid methanol was added under stirring until no gas evolved, stirred continually for 30 minutes. The solvent was evaporated under reduced pressure, and then the residue was purified three times, each with petroleum ether to give 7.1 g of product PRO-8 as a white solid. 1H NMR (400 MHz, DMSO-d6) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z calcd for C20H21NO4 [M+Na]+ 362.1368, measured: 362.1012.

(11-1-3) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react for 5 hours under stirring at room temperature. The solvent was removed by evaporation under reduced pressure. The resulting crude product was dissolved in ethyl acetate and filtered to remove salt impurities. The solvent was evaporated under reduced pressure, and then the residue was purified by using a silica gel column. For purification, the crude product dissolved in DCM was loaded onto the silica gel column pretreated with pyridine to alkalify the column. DMTr-Cl was eluted with DCM containing 1% (v/v) pyridine, and then the product was eluted with ethyl acetate. The eluate was collected, and the solvent was evaporated under reduced pressure to give 8.2 g of product PRO-9 as a white solid. HRMS (ESI) m/z calcd for C41H39NO6 [M+Na]+ 664.2675, measured: 664.2348; C18 RP-HPLC (Lot Number: JJS160324-1); purity: 94.20%.

(11-1-4) Synthesis of PRO-10

8.2 g of PRO-9 (12.8 mmol) was dissolved in 64 ml of DMF and added with 40 ml of piperidine (384 mmol) to react for 30 minutes under stirring at room temperature. The reaction liquid was poured into 300 ml of ice water and extracted three times, each with 150 ml of ethyl acetate. The resulting organic phases were combined, washed with 200 ml of saturated brine, and the organic phases resulted from washing was dried with anhydrous sodium sulfate. The solvent was evaporated under reduced pressure, and then the residue was purified by using a silica gel column. For purification, the crude product dissolved in DCM was loaded onto the silica gel column pretreated with pyridine to alkalify the column. Fmoc was eluted with DCM containing 1% (v/v) pyridine, and then the product was eluted with ethyl acetate. The eluate was collected, and the solvent was evaporated under reduced pressure to give 4.65 g of product PRO-10 as a white solid. 1H NMR (400 MHz, DMSO-d6) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); HRMS (ESI) m/z calcd for C26H29NO4 [M+Na]+ 442.1994, measured: 442.1999; C18 RP-HPLC (Lot Number: JJS160329-1), purity: 97.07%.

(11-2) Synthesis of FIN-1

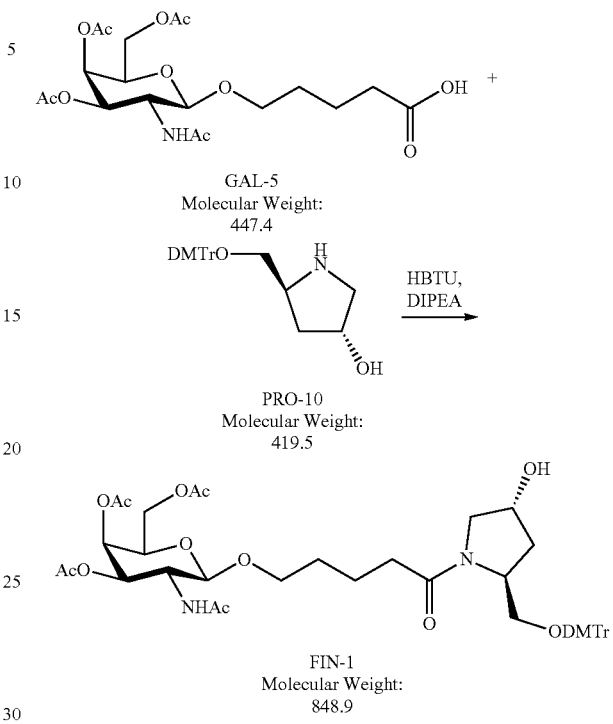

GAL-5 (4.5 g, 10 mmol) obtained according to the method described in (1-1) was dissolved in 40 ml of DMF, sequentially added with 3.9 g of DIPEA (N,N-diisopropylethylamine, CAS No.: 7087-68-5, purchased from Aladdin Inc., 30 mmol) and 3.8 g of HBTU (benzotriazol-N,N,N', N'-tetramethyluronium hexafluorophosphate, CAS No.: 94790-37-2, purchased from Aladdin Inc., 11 mmol), and stirred at room temperature for 10 minutes to obtain a reaction liquid. PRO-10 (4.2 g, 10 mmol) obtained in step (12-4) was dissolved in 40 ml of DMF, then added into the above reaction liquid. The resulting reaction liquid was dried by addition of anhydrous sodium sulfate and stirred at room temperature for 2 hours. The reaction liquid was poured into 120 ml of ice water and extracted three times, each with 60 ml of ethyl acetate. The resulting organic phases were combined, washed with 20 ml of water and 20 ml of saturated brine, respectively. The organic phase obtained from washing was isolated, dried with anhydrous sodium sulfate. The solvent was evaporated under reduced pressure, and then the residue was purified by using a silica gel column. For purification, a sample was loaded onto the silica gel column pretreated with pyridine to alkalify the column, and was eluted with dichloromethane (DCM) solution containing 1% (v/v) triethylamine and 1% (v/v) methanol. The eluate was collected, and the solvent was evaporated under reduced pressure to give 6.5 g of product FIN-1 as a light yellow foamy solid. 1H NMR (400 MHz, DMSO-d6) δ 7.83 (d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(11-3) Synthesis of FIN-2

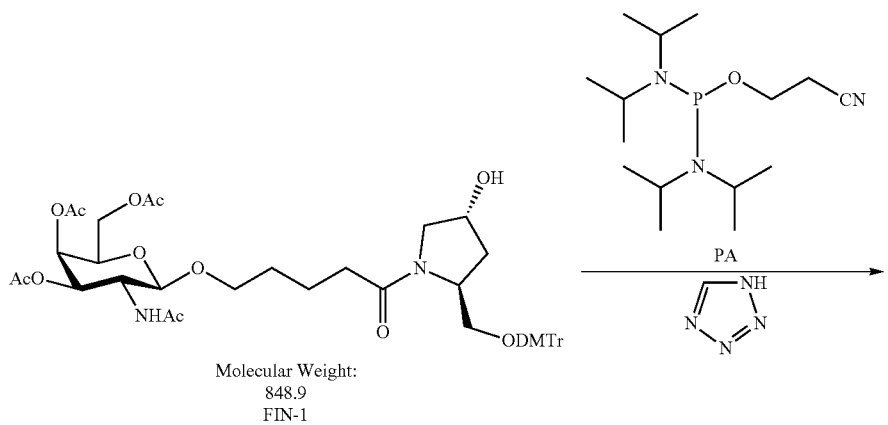

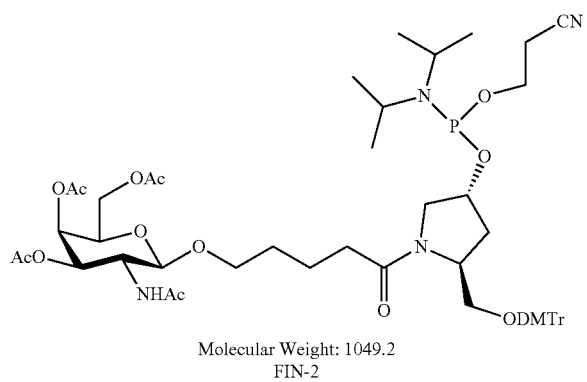

Molecular Weight: 1049.2
FIN-2

FIN-1 (3.0 g, 3.53 mmol) obtained in step (11-2) was dissolved in 10 ml of DMF, added with 2.13 g of PA (2-cyanoethyl N,N,N',N'-tetraisopropylphosphorodiamidite, Adamas Inc., product No. 11356B, 7.06 mmol) and 346 mg tetrazole (CAS No.: 288-94-8, purchased from Aladdin Inc., 4.94 mmol) under nitrogen atmosphere, and stirred to reaction at room temperature. 10 ml of DMF was supplemented and continually stirred to react for 1 hour. The solvent was removed by evaporation under reduced pressure, and then the residue was purification by silica gel column chromatography. For purification, the crude product dissolved in DCM was loaded onto the silica gel column pretreated with pyridine to alkalify the column, and eluted with ethyl acetate. The eluate was collected, and the solvent was evaporated under reduced pressure to give 4.5 g of crude product as a colorless syrup. The crude product was completely dissolved in 50% (v/v) aqueous acetonitrile solution and purified by using a medium pressure column (C-18, 330 g, 300 Å) pretreated with a solution of 1% (v/v) pyridine in acetonitrile to alkalify the column. A product was collected by gradient elution and the solvent was evaporated under reduced pressure to give 2.2 g of product as a white powder, FIN-2 Conjugating Molecule (Comparative Conjugating Molecule 3). 31P NMR (162 MHz, CDCl3) δ 148.04, 147.94, 147.62, 147.19, purity of 31P NMR: 92%; purity of C18 RP-HPLC: 90.54%.

Preparation Example 12—this Preparation Example is Used to Illustrate the Preparation of Z-4 Conjugating Molecule (Conjugating Molecule 153)

In this preparation example, Conjugating Molecule 153 (also referred to as Z-4 Conjugating Molecule hereinafter) was synthesized according to following method.

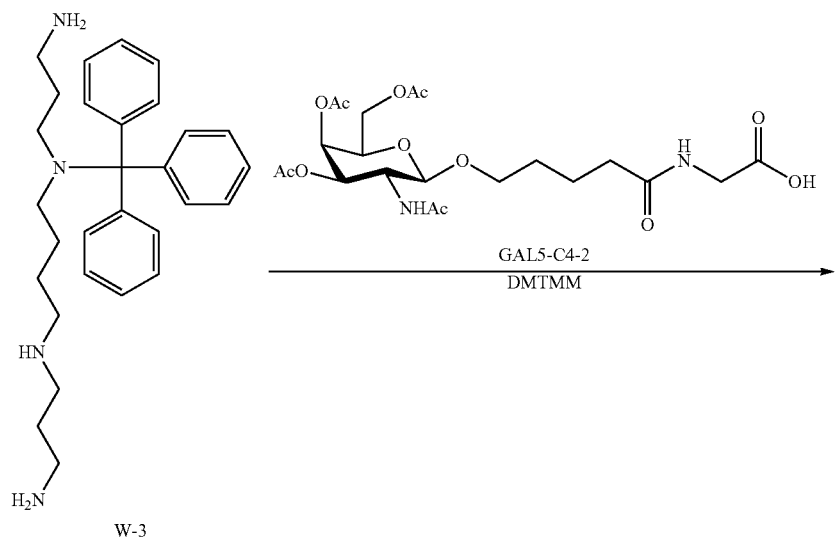
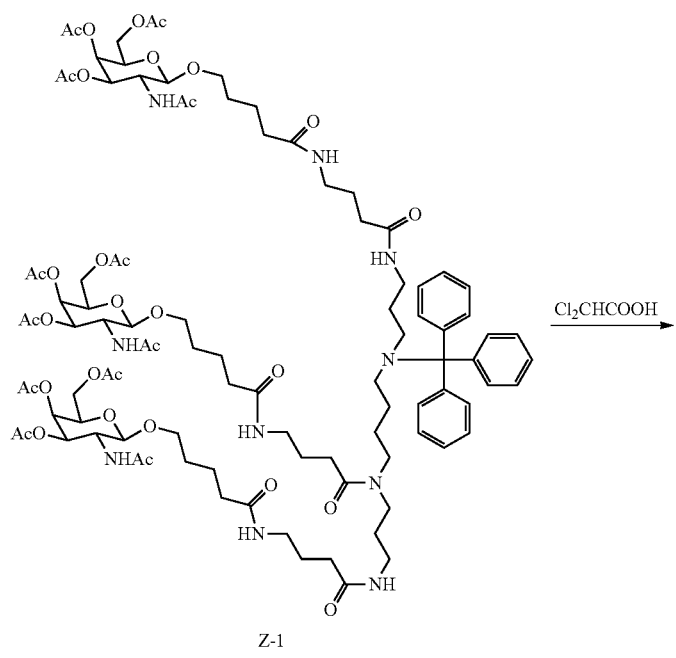

-continued
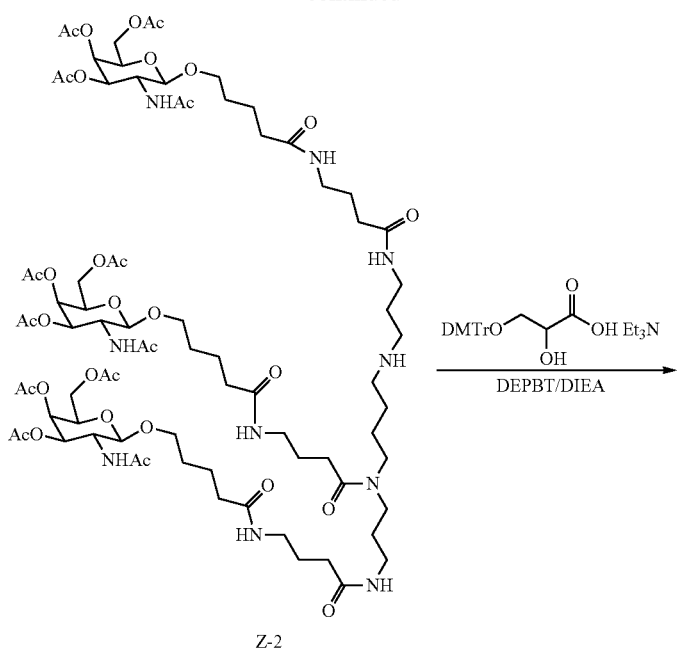
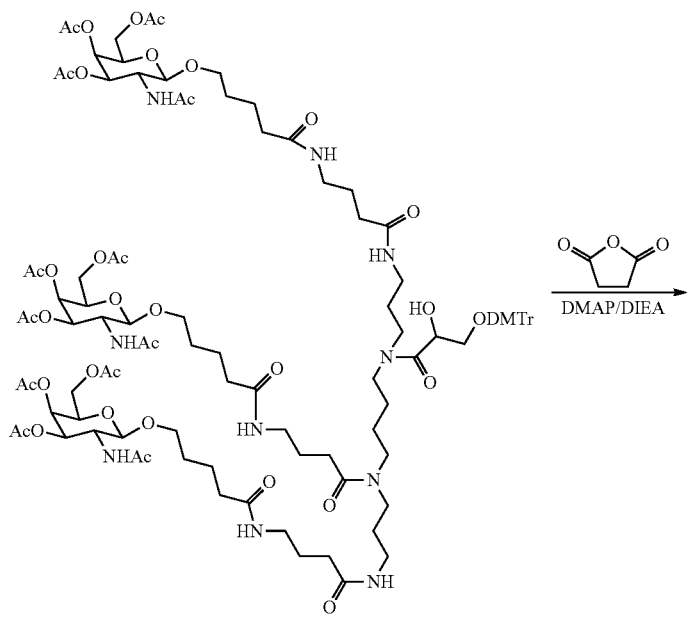

-continued

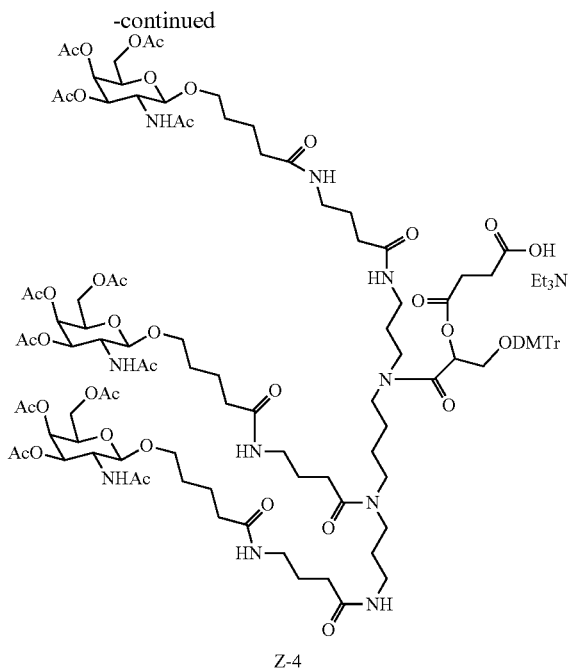

Z-4

(12-1) synthesis of Z-1:

W-3 (1.50 g, 3.37 mmol) obtained according to the method described in step (7-3) and GAL5-C4-2 (7.18 g, 13.48 mmol) obtained according to the method described in step (2-2) were mixed and dissolved in 34 ml of dichloromethane, added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react for 4.5 hours under stirring at room temperature. The resulting liquid solution was diluted with 100 ml of dichloromethane, washed with 80 ml of saturated sodium bicarbonate solution and 80 ml of saturated brine, respectively. All organic phases were combined, dried with anhydrous sodium sulfate, and filtrated. The solvent was evaporated under reduced pressure to give a crude product, which was purified by using a normal phase silica gel column, 200-300 mesh. The column was packed with petroleum ether, added with 1 wt % triethylamine for neutralizing the acidity of silica gel, and gradient eluted with dichloromethane:methanol=30:1-15:1. The eluate was collected and evaporated under reduced pressure to give 3.97 g of pure product Z-1. MS m/z: C98H143N10O33, [M+H]+, calcd: 1987.98, measured: 1987.90.

(12-2) Synthesis of Z-2:

Z-1 (3.97 g, 2.00 mmol) obtained according to the method described in (12-1) was dissolved in 250 ml of dichloromethane, and added with dichloroacetic acid (10.941 g, 84.85 mmol) to react for 1 hour at room temperature. Pyridine was added to neutralize the resulting reaction solution to neutral. The solvent was evaporated under reduced pressure to give a crude product. The column was loaded with 200 g 200-300 mesh normal phase silica gel, and with 10 wt % pyridine for neutralizing the acidity of silica gel. The column was equilibrated with 1 wt‰ pyridine and gradient eluted with dichloromethane:methanol=10:1-2:1. The eluate was collected, and the solvent was evaporated under reduced pressure to give 3.49 g of pure product Z-2. MS m/z: C79H129N10O33, [M+H]+, calcd: 1746.94, measured: 1746.90.

(12-3) Synthesis of Z-3:

Z-2 (3.49 g, 2.0 mmol) and A-1 (3.06 g, 6.0 mmol) obtained according to the method described in step (1-7a) were mixed and dissolved in 30 ml of dichloromethane, and added with 3-(diethoxyphosphoryloxy)-1,2,3-benzotrizin-4(3H)-one (DEPBT, 1.80 g, 6.0 mmol) followed by diisopropylethylamine (1.55 g, 12.0 mmol) to react for 3 hours under stirring at 25° C. 100 ml dichloromethane was added to the resulting reaction solution for dilution. The organic phase was washed twice with 30 ml of saturated sodium bicarbonate. The aqueous phase was extracted with 10 ml of dichloromethane. All organic phases were combined and washed with 50 ml of saturated brine. And the obtained organic phases were combined and dried with anhydrous sodium sulfate, and filtrated. The solvent was evaporated under reduced pressure, and the residue was foam-dried overnight with a vacuum oil pump to give a crude product. The crude product was subjected to a column purification by using normal phase silica gel, 200-300 mesh, 200 g, with 20 ml triethylamine for neutralizing the acidity of silica gel. The column was equilibrated with petroleum ether containing 1 wt % triethylamine and gradient eluted with dichloromethane:methanol=25:1-15:1. The eluate was collected, and the solvent was evaporated under reduced pressure to give 2.2 g of pure product Z-3. MS m/z: C103H151N10O38, [M+H]+, calcd: 2136.02, measured: 2136.20.

(12-4) Synthesis of Z-4:

Z-3 (2.10 g, 0.983 mmol) was dissolved in 14.8 ml of dichloromethane containing DIEA (635 mg, 4.915 mmol), 4-dimethylaminopyridin (DMAP, 240 mg, 1.966 mmol) was added to the resulting solution and stirred to clarity. Succinic anhydride (197 mg, 1.966 mmol) was added to react for 18 hours under stirring at 25° C. 50 ml dichloromethane was added to the resulting reaction solution for dilution, and washed with 80 ml of 0.5 M triethylamine phosphate. The aqueous phase was extracted twice with 50 ml of dichloromethane. All organic phases were combined, and the solvent was evaporated under reduced pressure to give a crude product. The crude product was subjected to a column purification by using normal phase silica gel, 200-300 mesh, 188 g, with 1 wt % triethylamine for neutralizing the acidity of silica gel. The column was equilibrated with dichloromethane and gradient eluted with dichloromethane containing 1 wt‰ triethylamine:methanol=10:1-3:1. The eluate was collected, and the solvent was evaporated under reduced pressure to give 1.95 g of pure product, Z-4 Conjugating Molecule (Conjugating Molecule 12). MS m/z: C107H155N10O41, [M+H]+, calcd: 1935.07, measured: 1935.29. The structure of the resulting Z-4 Conjugating Molecule is represented by Formula (422).

Preparation Example 13 Preparation of L10-siHBa1 Conjugate (Conjugate 9)

In this preparation example, L10-siHBa1 conjugate (also referred to as conjugate 9 hereinafter) was prepared from the L-9 Conjugating Molecule (Conjugating Molecule 1) according to the following method.

(13-1) Synthesis of Compound L-10:

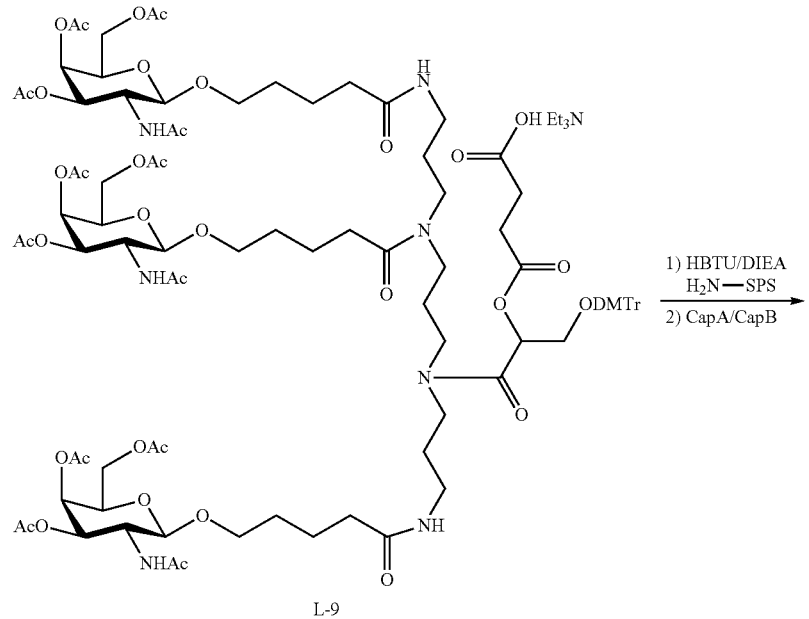

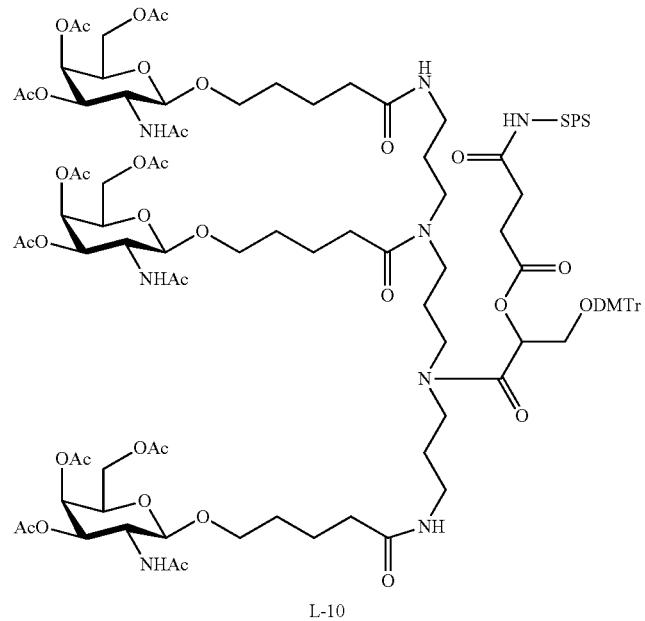

In this step, a compound L-10 was prepared by linking the L-9 Conjugating Molecule to a solid phase support.

The L-9 Conjugating Molecule (0.233 g, 0.1126 mmol) obtained in step (1-8), 0-benzotriazol-tetramethyluronium hexafluorophosphate (HBTU, 0.064 g, 0.1689 mmol) and diisopropylethylamine (DIPEA, 0.029 g, 0.2252 mmol) were mixed and dissolved in 19 ml of acetonitrile, and stirred at room temperature for 5 minutes. Aminomethyl resin (0.901 g, 100-200 mesh, amino loading: 400 μmol/g, purchased from Tianjin Nankai HECHENG S&T Co., Ltd.) was added into the reaction liquid. A reaction was performed on a shaker at 25° C. and 220 rpm/min for 15 hours, followed by filtration. The residue was rinsed twice, each with 30 ml of DCM, three times, each with 30 ml of acetonitrile, and once with 30 ml of ethyl ether, and dried for 2 hours with a vacuum oil pump. Then a capping reaction was performed according to the charge ratio shown in Table 2.

TABLE 2

The charge ratio of capping reaction

| Starting Materials | Amount | Level | Lot No. | Manufacturer |
|---|---|---|---|---|
| Cap1 | 20 ml | — | — | — |
| Cap2 | 2.3 ml | — | — | — |
| DMAP | 0.01 g | analytical pure | 11422139 | Aladdin |
| acetonitrile | 2.3 ml | spectroscopic pure | 015161001 | CINC (Shanghai) Co., Ltd |

In the above table, Cap 1 and Cap 2 are solutions of capping reagents. Cap 1 is a solution of 20% by volume of N-methylimidazole in a mixture of pyridine/acetonitrile, wherein the volume ratio of pyridine to acetonitrile is 3:5. Cap 2 is a solution of 20% by volume of acetic anhydride in acetonitrile.

Cap1, Cap2, 4-dimethylaminopyridine (DMAP) and acetonitrile were added into the above reaction mixture. A reaction was performed on a shaker at 25° C. and 200 rpm/min for 5 hours. The reaction liquid was filtrated. The residue was rinsed three times, each with 30 ml of acetonitrile, the solvent was evaporated to dryness, and the mixture was dried overnight under a reduced pressure with a vacuum oil pump to give 1.100 g of compound L-10 (i.e., L-9 Conjugating Molecule linked to a solid phase support), with a loading of 90.8 μmol/g. The structure of compound L-10 can be represented by Formula (523).

(13-2) Synthesis of a Sense Strand of the L10-siHB1 Conjugate

In this step, siRNA of the siRNA conjugate is a sequence numbered as siHBa1: siHBa1

```
                                            (SEQ ID NO: 1)
sense strand:      5'- CCUUGAGGCAUACUUCAAA-3', (SEQ ID NO: 2)
antisense strand:  5'- UUUGAAGUAUGCCUCAAGGUU -3'.
```

Nucleoside monomers were linked one by one in 3' to 5' direction according to the sequence above by the phosphoramidite solid phase synthesis method starting from the compound L-10 prepared in the above step. The linking of each nucleoside monomer included a four-step reaction of deprotection, coupling, capping, and oxidation. The synthesis condition was given as follows.

The nucleoside monomers were provided in a 0.1 M acetonitrile solution. The conditions were the same for each deprotection reaction, i.e., a temperature of 25° C., a reaction time of 70 seconds, a solution of dichloroacetic acid in dichloromethane (3% v/v) as a deprotection reagent, and a molar ratio of dichloroacetic acid to the protecting group on the solid phase support of 4,4'-dimethoxytrityl of 5:1.

The conditions were the same for each coupling reaction, including a temperature of 25° C., a molar ratio of the nucleic acid sequence linked onto the solid phase support to nucleoside monomers of 1:10, a molar ratio of the nucleic acid sequence linked onto the solid phase support to a coupling reagent of 1:65, a reaction time of 600 seconds, and 0.5 M acetonitrile solution of 5-ethylthio-1H-tetrazole as a coupling reagent.

The conditions were the same for each capping reaction, including a temperature of 25° C. and a reaction time of 15 seconds. A capping reagent was a mixed solution of Cap 1 and Cap 2 in a molar ratio of 1:1; and a molar ratio of the capping reagent to the nucleic acid sequence linked onto the solid phase support was acetic anhydride:N-methylimidazole:the nucleic acid sequence linked onto the solid phase support=1:1:1.

The conditions were the same for each oxidation reaction, including a temperature of 25° C., a reaction time of 15 seconds, and 0.05 M iodine water as an oxidation reagent; and a molar ratio of iodine to the nucleic acid sequence linked onto the solid phase support in the coupling step was 30:1. The reaction was carried out in a mixed solvent of tetrahydrofuran:water:pyridine=3:1:1.

The conditions for cleavage and deprotection were as follows. The synthesized nucleotide sequence linked to the support was added into 25 wt % aqueous ammonia to react for 16 hours at 55° C., and the aqueous ammonia is in an amount of 0.5 ml/μmol with respect to the nucleotide sequence. The liquid was removed, and the residue was concentrated in vacuum to dryness. After treatment with aqueous ammonia, the product was dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose. Purification and desalination: purification of the nucleic acid was achieved by using a preparative ion chromatography column (Source 15Q) with a gradient elution of NaCl. Specifically, eluent A: 20 mM sodium phosphate (pH 8.1), solvent:water/acetonitrile=9:1 (v/v); eluent B: 1.5 M sodium chloride, 20 mM sodium phosphate (pH 8.1), solvent:water/acetonitrile=9:1 (v/v); elution gradient:the ratio of eluent A:eluent B=100:0-50:50. The eluate was collected, combined and desalted by using a reversed phase chromatography column. The specific condition included that a Sephadex column was used for desalination, with Sephadex-G25 as the filler and deionized water for eluting.

Detection: the purity detected by ion exchange chromatography (IEX-HPLC) was 92.4%; and the molecular weight was analyzed by Liquid Chromatography-Mass Spectrometry (LC-MS), with a calculated value of 7253.96 and a measured value of 7253.12.

Thus, in this step, the L-9 Conjugating Molecule was linked to the 3' terminal of the resulting sense strand, resulting in a sense strand S of siRNA in which the L-9 Conjugating Molecule was conjugated to the 3' terminal of siRNA.

(13-3) Synthesis of an Antisense Strand

In this step, an antisense strand AS of the L10-siHB1 conjugate was synthesized by using a universal solid phase support (UnyLinker™ loaded NittoPhase®HL Solid Supports, Kinovate Life Sciences Inc.). The antisense strand AS of siRNA was obtained by the same conditions as that in the synthesis of the sense strand, including conditions of deprotection, coupling, capping, and oxidation reaction in the solid phase synthesis method, conditions of deprotection and cleavage, and isolation conditions.

Detection: the purity detected by IEX-HPLC was 93.2%; and the molecular weight was analyzed by LC-MS, with a calculated value of 6675.04 and a measured value of 6674.50.

(13-4) Synthesis of the L10-siHBa1 Conjugate

The S strand and AS strand were dissolved in water for injection to get a solution of 40 mg/mL, respectively. They are mixed in an equimolar ratio, heated for 15 min at 50° C., and then cooled to room temperature to form a double stranded structure via hydrogen bonds.

After completion of the synthesis above, the conjugate was diluted to a concentration of 0.2 mg/mL by using ultra-pure water (homemade by Milli-Q ultra-pure water instrument, with resistivity of 18.2M Ω*cm (25° C.)). The molecular weight was measured by LC-MS (purchased from Waters Corp., model: LCT Premier). As a result, the calculated values of the molecular weight for S and AS are 7253.96 and 6675.04 respectively, and the measured values thereof are 7253.24 and 6674.61 respectively. It is confirmed that the synthesized conjugate is the target designed double stranded nucleic acid sequence with the L9 Conjugating Molecule, since the measured values are in conformity with the calculated values. The structure of the L10-siHBa1 conjugate (Conjugate 9) is represented by Formula (3).

Preparation Example 14 Preparation of Conjugates 16-18, 24-26, 42-43, 62, 78, 105, 109, 111, 115, 144, and 154-171

The given conjugates were prepared by using the same method as in Preparation Example 13, except that: 1) the conjugated siRNAs have sequences shown in Tables 3A-3G corresponding to conjugates 16-18, 24-26, 42-43, 62, 78, 105, 109, 111, 115, 144, 157-163, and 167-171; 2) when a phosphorothioate linkage exists between two nucleotides in the target sequence, the following sulfuration reaction step was used to replace the oxidation reaction step during linking of the later of the two nucleotides; the conditions were the same for each sulfuration reaction, including a temperature of 25° C., a reaction time of 300 seconds, and xanthane hydride as a sulfurization reagent; a molar ratio of the sulfurization reagent to the nucleic acid sequence linked onto the solid phase support in the coupling step was 120:1; the reaction was carried out in a mixed solvent of acetonitrile:pyridine=1:1; and 3) when 2'-positions of all nucleotides in the target sequence are modified hydroxyl groups, the step of removing the 2'-TBDMS protection on ribose was not included in the conditions for cleavage and deprotection. Therefore, the conjugates 16-18, 24-26, 42-43, 62, 78, 105, 109, 111, 115, 144, 157-163 of the present disclosure were prepared.

In addition, conjugates 154-156 and 164-166 were prepared by using the same method as in Preparation Example 13, except that: the following Conjugating Molecule were used to replace L-9 Conjugating Molecule, respectively: Conjugate 164 was prepared from P-9 Conjugating Molecule (Conjugating Molecule 2) which obtained in Preparation Example 2; Conjugate 155, 156 and 165 were prepared from W-7 Conjugating Molecule (Conjugating Molecule 7) which obtained in Preparation Example 7; Conjugate 154 and 166 were prepared from Z-4 (Conjugating Molecule 12) which obtained in Preparation Example 12, and the conjugated siRNAs have sequences shown in Tables 3A-3G corresponding to conjugates 154-156 and 164-166, respectively, and the conjugates were numbered separately according to Tables 3A-3G. Their structures were represented by Formula (3), Formula (4), Formula (15) and Formula (22), respectively. The molecular weights of the conjugates were measured by LC-MS as follows:

Conjugate 142: Calculated values S: 7649.55, AS: 6991.46, Measured values: S: 7649.1, AS: 6991;

Conjugate 170: Calculated values S: 7649.55, AS: 6995.47, Measured values: S: 7648.8, AS: 6994.8;

Conjugate 171: Calculated values S: 7649.55, AS: 7011.53, Measured values: S: 7648.8, AS: 7010.9;

Conjugate 115: Calculated values S: 7584.5, AS: 7007.46, Measured values: S: 7584, AS: 7006.2;

Conjugate 109: Calculated values S: 7584.5, AS: 6931.47, Measured values: S: 7584, AS: 6930.9;

Conjugate 106: Calculated values S: 7572.47, AS: 6907.41, Measured values: S: 7571.8, AS: 6906.9;

Conjugate 113: Calculated values S: 7584.5, AS: 7011.47, Measured values: S: 7584, AS: 7011.3;

Conjugate 17: Calculated values S: 7504.34, AS: 6961.52, Measured values: S: 7503.4, AS: 6960.9;

Conjugate 25: Calculated values S: 7504.34, AS: 7037.51, Measured values: S: 7503.6, AS: 7036.9;

Conjugate 18: Calculated values S: 8218.83, AS: 7703.05, Measured values: S: 8218, AS: 7702.5;

Conjugate 16: Calculated values S: 7516.37, AS: 6985.58, Measured values: S: 7516.5, AS: 6984.9;

Conjugate 159: Calculated values S: 7504.34, AS: 7057.58, Measured values: S: 7503.6, AS: 7057;

Conjugate 160: Calculated values S: 7504.34, AS: 7041.52, Measured values: S: 7503.6, AS: 7040.8;

Conjugate 161: Calculated values S: 7516.37, AS: 7065.58, Measured values: S: 7516.6, AS: 7064.5;

Conjugate 162: Calculated values S: 7504.34, AS: 7139.68, Measured values: S: 7515.6, AS: 7138.9;

Conjugate 163: Calculated values S: 7516.37, AS: 7081.64, Measured values: S: 7515.6, AS: 7080.9;

Conjugate 62: Calculated values S: 7485.3, AS: 7161.7, Measured values: S: 7484.4, AS: 7160.9;

Conjugate 78: Calculated values S: 7423.22, AS: 7207.78, Measured values: S: 7422.6, AS: 7207.2;

Conjugate 42: Calculated values S: 7407.22, AS: 7208.77, Measured values: S: 7406.4, AS: 7208.1;

Conjugate 43: Calculated values S: 7407.22, AS: 7170.72, Measured values: S: 7406.5, AS: 7170.1, and the measured values are in conformity with the calculated values.

TABLE 3A siRNA conjugates
Table 3A

| Conjugate | NO. | | Sequence Direction 5' - 3' | SEQ ID NO |
|---|---|---|---|---|
| Conjugate 10 | L10-siHBa1 | S* | CCUUGAGGCAUACUUCAAA | 1 |
| | | AS | UUUGAAGUAUGCCUCAAGGUU | 2 |
| Conjugate 11 | L10-siHBa2 | S | GACCUUGAGGCAUACUUCAAA | 3 |
| | | AS | UUUGAAGUAUGCCUCAAGGUCGG | 4 |
| Conjugate 12 | L10-siHBa1M1 | S | CmCmUmGmAmGfGfCfAmUmAmCmUmUmCmAmAmAm | 5 |
| | | AS | UmUfUmGmAmAfGmUmAmUmGmCmCmUfCmAfAmGmGmUmUm | 6 |
| Conjugate 13 | L10-siHBa1M2 | S | CmCmUmGfAmGfGfCfAmUmAmCmUmUmCmAmAmAm | 7 |
| | | AS | UmUfUmGmAmAfGmUfAfUmGmCmCmUfCmAfAmGmGmUmUm | 8 |
| Conjugate 14 | L10-siHBa2M1 | S | GmAmCmCmUmUmGmAmGfGfCfAmUmAmCmUmUmCmAmAmAm | 9 |
| | | AS | UmUfUmGmAmAfGmUmAmUmGmCmCmUfCmAfAmGmGmUmCmGmGm | 10 |
| Conjugate 15 | L10-siHBa2M2 | S | GmAmCmCmUmGfAmGfGfCfAmUmAmCmUmUmCmAmAmAm | 11 |
| | | AS | UmUfUmGmAmAfGmUfAfUmGmCmCmUfCmAfAmGmGmUmCmGmGm | 12 |
| Conjugate 16 | L10-siHBa1M1S | S | CmsCmsUmUmGmAmGfGfCfAmUmAmCmUmUmCmAmAmAm | 13 |
| | | AS | UmsUfsUmGmAmAfGmUmAmUmGmCmCmUfCmAfAmGmGmsUmsUm | 14 |
| Conjugate 17 | L10-siHBa1M2S | S | CmsCmsUmUmGfAmGfGfCfAmUmAmCmUmUmCmAmAmAm | 15 |
| | | AS | UmsUfsUmGmAmAfGmUfAfUmGmCmCmUfCmAfAmGmGmsUmsUm | 16 |
| Conjugate 18 | L10-siHBa2M1S | S | GmsAmsCmCmUmUmGmAmGfGfCfAmUmAmCmUmUmCmAmAmAm | 17 |
| | | AS | UmsUfsUmGmAmAfGmUmAmUmGmCmCmUfCmAfAmGmGmUmCmsGmsGm | 18 |
| Conjugate 19 | L10-siHBa2M2S | S | GmsAmsCmCmUmUmGfAmGfGfCfAmUmAmCmUmUmCmAmAmAm | 19 |
| | | AS | UmsUfsUmGmAmAfGmUfAfUmGmCmCmUfCmAfAmGmGmUmCmsGmsGm | 20 |
| Conjugate 20 | L10-siHBa1M1P | S | CmCmUmGmAmGfGfCfAmUmAmCmUmUmCmAmAmAm | 5 |
| | | AS | VP-UmUfUmGmAmAfGmUmAmUmGmCmCmUfCmAfAmGmGmUmUm | 136 |
| Conjugate 21 | L10-siHBa1M2P | S | CmCmUmGfAmGfGfCfAmUmAmCmUmUmCmAmAmAm | 7 |
| | | AS | VP-UmUfUmGmAmAfGmUfAfUmGmCmCmUfCmAfAmGmGmUmUm | 137 |
| Conjugate 22 | L10-siHBa2M1P | S | GmAmCmCmUmUmGmAmGfGfCfAmUmAmCmUmUmCmAmAmAm | 9 |
| | | AS | VP-UmUfUmGmAmAfGmUmAmUmGmCmCmUfCmAfAmGmGmUmCmGmGm | 138 |
| Conjugate 23 | L10-siHBa2M2P | S | GmAmCmCmUmGfAmGfGfCfAmUmAmCmUmUmCmAmAmAm | 11 |
| | | AS | VP-UmUfUmGmAmAfGmUfAfUmGmCmCmUfCmAfAmGmGmUmCmGmGm | 139 |

TABLE 3A-continued

| | siRNA conjugates Table 3A | | | |
|---|---|---|---|---|
| Conjugate | NO. | | Sequence Direction 5' - 3' | SEQ ID NO |
| Conjugate 24 | L10-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |
| Conjugate 25 | L10-siHBa1M2SP | S | CmsCmsUmUmGfAmGfGfCfAmUmAmCmUmUmCmAmAmAm | 15 |
| | | AS | VP-UmsUfsUmGmAmAfGmUfAfUmGmCmCmUfCmAfAmGmGmsUmsUm | 141 |
| Conjugate 26 | L10-siHBa2M1SP | S | GmsAmsCmCmUmUmGmAmGfGfCfAmUmAmCmUmUmCmAmAmAm | 17 |
| | | AS | VP-UmsUfsUmGmAmAfGmUmAmUmGmCmCmUfCmAfAmGmGmUmCmsGmsGm | 142 |
| Conjugate 27 | L10-siHBa2M2SP | S | GmsAmsCmCmUmUmGfAmGfGfCfAmUmAmCmUmUmCmAmAmAm | 19 |
| | | AS | VP-UmsUfsUmGmAmAfGmUfAfUmGmCmCmUfCmAfAmGmGmUmCmsGmsGm | 143 |
| Conjugate 28 | L10-siHBa1M5SP | S | CmsCmsUmUmGfAmGfGfCfAmUmAmCmUmUmCmAmAmAm | 15 |
| | | AS | VP-UmsUfsUmGmAmAfGmUmAmUmGmCmCmUfCmAfAmGmGmsUmsUm | 140 |
| Conjugate 29 | L10-siHBa1M3SP | S | CmsCmsUmUmGmAmGfGmCfAmUfAmCmUmUmCmAmAmAm | 144 |
| | | AS | VP-UmsUfsUmGmAmAfGmUmAmUmGmCmCmUfCmAfAmGmGmsUmsUm | 140 |
| Conjugate 30 | L10-siHBa1M4SP | S | CmsCmsUmUmGmAmGfGfCfAmUmAmCmUmUmCmAmAmAm | 13 |
| | | AS | VP-UmsUfsUmGmAmAfGmUfAmUmGmCmCmUfCmAfAmGmGmsUmsUm | 145 |
| Conjugate 31 | P10-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |
| Conjugate 32 | R5-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |
| Conjugate 33 | LA5-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |
| Conjugate 34 | LBS-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |
| Conjugate 35 | V8-siHBa1M1SP | S | CmsCmsUmUmGmAmGfGfCfAmUmAmCmUmUmCmAmAmAm | 13 |
| | | AS | VP-UmsUfsUmGmAmAfGmUmAmUmGmCmCmUfCmAfAmGmGmsUmsUm | 140 |

TABLE 3A-continued

| | | | siRNA conjugates Table 3A | |
|---|---|---|---|---|
| Conjugate | NO. | | Sequence Direction 5' - 3' | SEQ ID NO |
| Conjugate 36 | W8-siHBa1M1SP | S | CmsCmsUmUmGmAmGfGfCfAmUmAmCmUmUmCmA mAmAm | 13 |
| | | AS | VP-UmsUfsUmGmAmAfGmUmAmUmGmCmCmUfCmAfAm GmGmsUmsUm | 140 |
| Conjugate 37 | X8-siHBa1M1SP | S | CmsCmsUmUmGmAmGfGfCfAmUmAmCmUmUmCmA mAmAm | 13 |
| | | AS | VP-UmsUfsUmGmAmAfGmUmAmUmGmCmCmUfCmAfAm GmGmsUmsUm | 140 |
| Conjugate 154 | Z5-siHBa1M2SP | S | CmsCmsUmUmGfAmGfGfCfAmUmAmCmUmUmCmA AmAm | 15 |
| | | AS | VP-UmsUfsUmGmAmAfGmUfAfUmGmCmCmUfCmAfAmG mGmsUmsUm | 141 |
| Conjugate 155 | W8-siHBa1M2SP | S | CmsCmsUmUmGfAmGfGfCfAmUmAmCmUmUmCmA AmAm | 15 |
| | | AS | VP-UmsUfsUmGmAmAfGmUfAfUmGmCmCmUfCmAfAmG mGmsUmsUm | 141 |
| Comparative Conjugate 4 | K4-siHBa1M1SP | S | CmsCmsUmUmGmAmGfGfCfAmUmAmCmUmUmCmA mAmAm | 13 |
| | | AS | VP-UmsUfsUmGmAmAfGmUmAmUmGmCmCmUfCmAfAm GmGmsUmsUm | 140 |
| Comparative Conjugate 5 | (GalNAc)3 - siHBa1M1SP | S | CmsCmsUmUmGmAmGfGfCfAmUmAmCmUmUmCmA mAmAm | 13 |
| | | AS | VP-UmsUfsUmGmAmAfGmUmAmUmGmCmCmUfCmAfAm GmGmsUmsUm | 140 |
| Comparative Conjugate 6 | FIN-siHBa1M1SP | S | CmsCmsUmUmGmAmGfGfCfAmUmAmCmUmUmCmA mAmAm | 13 |
| | | AS | VP-UmsUfsUmGmAmAfGmUmAmUmGmCmCmUfCmAfAm GmGmsUmsUm | 140 |

TABLE 3B

| Conjugate | NO. | | Sequence Direction 5' - 3' | SEQ ID NO |
|---|---|---|---|---|
| Conjugate 38 | L10-siHBb1M1S | S | UmsGmsCmUmAmUmGfCfCfUmCmAmUmCmUmUm CmUmAm | 38 |
| | | AS | UmsAfsGmAmAmGfAmUmGmAmGmGmCmAfUmAf GmCmAmsGmsCm | 39 |
| Conjugate 39 | L10-siHBb2M1S | S | UmsGmsCmUmAmUmGfCfCfUmCmAmUmCmUmUm CmUmAm | 38 |
| | | | | 40 |
| | | AS | UmsAfsGmAmAmGfAmUmGmAmGmGmCmAfUmAf GmCmAmsUmsUm | |
| Conjugate 40 | L10-siHBb1M2 | S | UmGmCmUmAfUmGfCfCfUmCmAmUmCmUmUmCm UmAm | 35 |
| | | AS | UmAfGmAmAmGfAmUfGfAmGmGmCmAfUmAfGmC mAmGmCm | 36 |
| Conjugate 41 | L10-siHBb2M2 | S | UmGmCmUmAfUmGfCfCfUmCmAmUmCmUmUmCm UmAm | 35 |
| | | AS | UmAfGmAmAmGfAmUfGfAmGmGmCmAfUmAfGmC mAmUmUm | 37 |

TABLE 3B-continued

| Conjugate | NO. | | Sequence Direction 5' - 3' | SEQ ID NO |
|---|---|---|---|---|
| Conjugate 42 | L10-siHBb1M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsGmsCm | 146 |
| Conjugate 43 | L 10-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 44 | L10-siHBb1M2SP | S | UmsGmsCmUmAfUmGfCfCfUmCmAmUmCmUmUmCmUmAm | 41 |
| | | AS | VP-UmsAfsGmAmAmGfAmUfGfAmGmGmCmAfUmAfGmCmAmsGmsCm | 148 |
| Conjugate 45 | L10-siHBb2M2SP | S | UmsGmsCmUmAfUmGfCfCfUmCmAmUmCmUmUmCmUmAm | 41 |
| | | AS | VP-UmsAfsGmAmAmGfAmUfGfAmGmGmCmAfUmAfGmCmAmsUmsUm | 149 |
| Conjugate 46 | L10-siHBb1M5SP | S | UmGmCmUmAfUmGfCfCfUmCmAmUmCmUmUmCmUmAm | 41 |
| | | AS | VP-UmsAfsGmAmAmGfAmUmGmAmGmGmCmAfUmAfGmCmAmsGmsCm | 146 |
| Conjugate 47 | L10-siHBb1M3SP | S | UmsGmsCmUmAfUmGfCmCfUmCmAmUmCmUmUmCmUmAm | 150 |
| | | AS | VP-UmsAfsGmAmAmGfAmUmGmAmGmGmCmAfUmAfGmCmAmsGmsCm | 146 |
| Conjugate 48 | L10-siHBb1M4SP | S | UmsGmsCmUmAmUmGfCfCfUmCmAmUmCmUmUmCmUmAm | 38 |
| | | AS | VP-UmsAfsGmAmAmGfAmUfGmAmGmGmCmAfUmAfGmCmAmsGmsCm | 151 |
| Conjugate 49 | L10-siHBb4M1SP | S | GmsCmsUmGmCmUmAmUmGfCfCfUmCmAmUmCmUmUmCmUmAm | 152 |
| | | AS | VP-UmsAfsGmAmAmGfAmUmGmAmGmGmCmAfUmAfGmCmAmGmCmsGmsCm | 153 |
| Conjugate 50 | L10-siHBb1 | S | UGCUAUGCCUCAUCUUCUA | 29 |
| | | AS | UAGAAGAUGAGGCAUAGCAGC | 30 |
| Conjugate 51 | L10-siHBb2 | S | UGCUAUGCCUCAUCUUCUA | 29 |
| | | AS | UAGAAGAUGAGGCAUAGCAUU | 31 |
| Conjugate 52 | P10-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 53 | R5-sHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 54 | LA5-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |

TABLE 3B-continued

| Conjugate | NO. | | Sequence Direction 5' - 3' | SEQ ID NO |
|---|---|---|---|---|
| Conjugate 55 | LB5-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 56 | V8-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 57 | W8-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Conjugate 58 | X8-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Comparative Conjugate 7 | K4-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Comparative Conjugatee 8 | GalNAc-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |
| Comparative Conjugate 9 | FIN-siHBb2M1SP | S | UmsGmsCmUmAmUmGfCfCfUmCmAmUmCmUmUmCmUmAm | 38 |
| | | AS | VP-UmsAfsGmAmAmGfAmUmGmAmGmGmCmAfUmAfGmCmAmsUmsUm | 147 |

TABLE 3C

| Conjugate | NO. | | Sequence Direction 5' - 3' | SEQ ID NO |
|---|---|---|---|---|
| Conjugatee 59 | L10-siHBc1 | S | UCUGUGCCUUCUCAUCUGA | 52 |
| | | AS | UCAGAUGAGAAGGCACAGACG | 53 |
| Conjugate 60 | L10-siHBc1M1 | S | UmCmUmGmUmGmCfCfUfUmCmUmCmAmUmCmUmGmAm | 54 |
| | | AS | UmCfAmGmAmUfGmAmGmAmAmGmGmCfAmCfAmGmAmCmGm | 55 |
| Conjugate 61 | L10-siHBc1M2 | S | UmCmUmGmUfGmCfCfUfUmCmUmCmAmUmCmUmGmAm | 56 |
| | | AS | UmCfAmGmAmUfGmAfGfAmAmGmGmCfAmCfAmGmAmCmGm | 57 |
| Conjugate 62 | L10-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |

TABLE 3C-continued

| Conjugate | NO. | | Sequence Direction 5' - 3' | SEQ ID NO |
|---|---|---|---|---|
| Conjugate 63 | L10-siHBc1M2SP | S | UmsCmsUmGmUfGmCfCfUfUmCmUmCmAmUmCmUmGmAm | 60 |
| | | AS | VP-UmsCfsAmGmAmUfGmAfGfAmAmGmGmCfAmCfAmGmAmsCmsGm | 155 |
| Conjugate 64 | L10-siHBc1M3SP | S | UmsCmsUmGmUfGmCfCmUfUmCmUmCmAmUmCmUmGmAm | 156 |
| | | AS | VP-UmsCfsAmGmAmUfGmAmGmAmAmGmGmCfAmCfAmGmAmsCmsGm | 154 |
| Conjugate 65 | L10-siHBc1M4SP | S | UmsCmsUmGmUmGmCfCfUfUmCmUmCmAmUmCmUmGmAm | 58 |
| | | AS | VP-UmsCfsAmGmAmUfGmAfGmAmAmGmGmCfAmCfAmGmAmsCmsGm | 157 |
| Conjugate 66 | L10-siHBc1M5SP | S | UmsCmsUmGmUfGmCfCfUfUmCmUmCmAmUmCmUmGmAm | 60 |
| | | AS | VP-UmsCfsAmGmAmUfGmAmGmAmAmGmGmCfAmCfAmGmAmsCmsGm | 154 |
| Conjugate 67 | L10-siHBc2M1SP | S | CmsGmsUmCmUmGmUmGmCfCfUfUmCmUmCmAmUmCmUmGmAm | 158 |
| | | AS | VP-UmsCfsAmGmAmUfGmAfGfAmAmGmGmCfAmCfAmGmAmsCmsGmGmGm | 159 |
| Conjugate 68 | P10-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Conjugate 69 | R5-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Conjugate 70 | LA5-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Conjugate 71 | LB5-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Conjugate 72 | V8-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Conjugate 73 | W8-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |

TABLE 3C-continued

| Conjugate | NO. | | Sequence Direction 5' - 3' | SEQ ID NO |
|---|---|---|---|---|
| Conjugate 74 | X8-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |
| Comparative Conjugate 10 | K4-siHBc1M1SP | S | UmsCmsUmGmUmGmCfCfUfUmCmUmCmAmUmCmUmGmAm | 58 |
| | | AS | VP-UmsCfsAmGmAmUfGmAmGmAmAmGmGmCfAmCfAmGmAmsCmsGm | 154 |

TABLE 3D

| Conjugate | NO. | | Sequence Direction 5' - 3' | SEQ ID NO |
|---|---|---|---|---|
| Conjugate 75 | L10-siHBd1 | S | CGUGUGCACUUCGCUUCAA | 66 |
| | | AS | UUGAAGCGAAGUGCACACGGU | 67 |
| Conjugate 76 | L10-siHBd1M1 | S | CmGmUmGmUmGmCfAfCfUmUmCmGmCmUmUmCmAmAm | 68 |
| | | AS | UmUfGmAmAmGfCmGmAmAmGmUmGmCfAmCfAmCmGmGmUm | 69 |
| Conjugate 77 | L10-siHBd1M2 | S | CmGmUmGmUfGmCfAfCfUmUmCmGmCmUmUmCmAmAm | 70 |
| | | AS | UmUfGmAmAmGfCmGfAfAmGmUmGmCfAmCfAmCmGmGmUm | 71 |
| Conjugate 78 | L10-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 79 | L10-siHBd1M2SP | S | CmsGmsUmGmUfGmCfAfCfUmUmCmGmCmUmUmCmAmAm | 74 |
| | | AS | VP-UmsUfsGmAmAmGfCmGfAfAmGmUmGmCfAmCfAmCmGmsGmsUm | 161 |
| Conjugate 80 | L10-siHBd1M3SP | S | CmsGmsUmGmUfGmCfAfCfUmUmCmGmCmUmUmCmAmAm | 162 |
| | | AS | VP-UmsUfsGmAmAmGfCmGmAmAmGmUmGmCfAmCfAmCmGmsGmsUm | 160 |
| Conjugate 81 | L10-siHBd1M4SP | S | CmsGmsUmGmUmGmCfAfCfUmUmCmGmCmUmUmCmAmAm | 72 |
| | | AS | VP-UmsCfsAmGmAmUfGmAfGmAmAmGmGmCfAmCfAmGmAmsCmsGm | 163 |
| Conjugate 82 | L10-siHBd1M5SP | S | CmsGmsUmGmUfGmCfAfCfUmUmCmGmCmUmUmCmAmAm | 74 |
| | | AS | VP-UmsUfsGmAmAmGfCmGmAmAmGmUmGmCfAmCfAmCmGmsGmsUm | 160 |

TABLE 3D-continued

| Conjugate | NO. | | Sequence Direction 5' - 3' | SEQ ID NO |
|---|---|---|---|---|
| Conjugate 83 | L10-siHBd2M1SP | S | AmsCmsCmGmUmGmUmGmCfAfCfUmUmCmGmCmUmUmCmAmAm | 164 |
| | | AS | VP-UmsUfsGmAmAmGfCmGmAmAmGmUmGmCfAmCfAmCmGmUmsCmsCm | 165 |
| Conjugate 84 | P10-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 85 | R5-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 86 | LA5-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 87 | LB5-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 88 | V8-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 89 | W8-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Conjugate 90 | X8-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |
| Comparative Conjugate 11 | K4-siHBd1M1SP | S | CmsGmsUmGmUmGmCfAfCfUmUmCmGmCmUmUmCmAmAm | 72 |
| | | AS | VP-UmsUfsGmAmAmGfCmGmAmAmGmUmGmCfAmCfAmCmGmsGmsUm | 160 |

TABLE 3E

| Conjugate | NO. | | Sequence Direction 5' - 3' | SEQ ID NO |
|---|---|---|---|---|
| Conjugate 91 | L10-siAN1 | S | CCAAGAGCACCAAGAACUA | 80 |
| | | AS | UAGUUCUUGGUGCUCUUGGCU | 81 |

TABLE 3E-continued

| Conjugate | NO. | | Sequence Direction 5' - 3' | SEQ ID NO |
|---|---|---|---|---|
| Conjugate 92 | L10-siAN2 | S | AGCCAAGAGCACCAAGAACUA | 82 |
| | | AS | UAGUUCUUGGUGCUCUUGGCUUG | 83 |
| Conjugate 93 | L10-siAN1M1 | S | CmCmAmAmGfAmGfCfAfCmCmAmAmGmAmAmCmUmAm | 84 |
| | | AS | UmAfGmUmUmCfUmUfGfGmUmGmCmUfCmUfUmGmGmCmUm | 85 |
| Conjugatee 94 | L10-siAN2M1 | S | AmGmCmCmAmAmGfAmGfCfAfCmCmAmAmGmAmAmCmUmAm | 86 |
| | | AS | UmAfGmUmUmCfUmUfGfGmUmGmCmUfCmUfUmGmGmCmUmUmGm | 87 |
| Conjugatee 95 | L10-siAN1M2 | S | CmCmAmAmGfAmGfCfAfCmCmAmAmGmAmAmCmUmAm | 84 |
| | | AS | UmAfGmUmUmCfUmUmGmGmUmGmCmUfCmUfUmGmGmCmUm | 88 |
| Conjugate 96 | L10-siAN2M2 | S | AmGmCmCmAmAmGfAmGfCfAfCmCmAmAmGmAmAmAmCmUmAm | 86 |
| | | AS | UmAfGmUmUmCfUmUmGmGmUmGmCmUfCmUfUmGmGmCmUmUmGm | 89 |
| Conjugate 97 | L10-siAN1M3 | S | CmCmAmAmGmAmGfCfAfCmCmAmAmGmAmAmCmUmAm | 90 |
| | | AS | UmAfGmUmUmCfUmUmGmGmUmGmCmUfCmUfUmGmGmCmUm | 88 |
| Conjugate 98 | L10-siAN2M3 | S | AmGmCmCmAmAmGmAmGfCfAfCmCmAmAmGmAmAmCmUmAm | 91 |
| | | AS | UmAfGmUmUmCfUmUmGmGmUmGmCmUfCmUfUmGmGmCmUmUmGm | 89 |
| Conjugate 99 | L10-siAN1M1P | S | CmCmAmAmGfAmGfCfAfCmCmAmAmGmAmAmCmUmAm | 84 |
| | | AS | VP-UmAfGmUmUmCfUmUfGfGmUmGmCmUfCmUfUmGmGmCmUm | 166 |
| Conjugate 100 | L10-siAN2M1P | S | AmGmCmCmAmAmGfAmGfCfAfCmCmAmAmGmAmAmCmUmAm | 86 |
| | | AS | VP-UmAfGmUmUmCfUmUfGfGmUmGmCmUfCmUfUmGmGmCmUmUmGm | 167 |
| Conjugate 101 | L10-siAN1M2P | S | CmCmAmAmGfAmGfCfAfCmCmAmAmGmAmAmCmUmAm | 84 |
| | | AS | VP-UmAfGmUmUmCfUmUmGmGmUmGmCmUfCmUfUmGmGmCmUm | 168 |
| Conjugate 102 | L10-siAN2M2P | S | AmGmCmCmAmAmGfAmGfCfAfCmCmAmAmGmAmAmCmUmAm | 86 |
| | | AS | VP-UmAfGmUmUmCfUmUmGmGmUmGmCmUfCmUfUmGmGmCmUmUmGm | 169 |
| Conjugate 103 | L10-siAN1M3P | S | CmCmAmAmGmAmGfCfAfCmCmAmAmGmAmAmCmUmAm | 90 |
| | | AS | VP-UmAfGmUmUmCfUmUmGmGmUmGmCmUfCmUfUmGmGmCmUm | 168 |

TABLE 3E-continued

| Conjugate | NO. | | Sequence Direction 5' - 3' | SEQ ID NO |
|---|---|---|---|---|
| Conjugate 104 | L10-siAN2M3P | S | AmGmCmCmAmAmGmAmGfCfAfCmCmAmAmGmAmAmCmUmAm | 91 |
| | | AS | VP-UmAfGmUmUmCfUmUmGmGmUmGmCmUfCmUfUmGmGmCmUmUmGm | 169 |
| Conjugate 105 | L10-siAN1M1S | S | CmsCmsAmAmGfAmGfCfAfCmCmAmAmGmAmAmCmUmAm | 92 |
| | | AS | UmsAfsGmUmUmCfUmUfGfGmUmGmCmUfCmUfUmGmGmsCmsUm | 93 |
| Conjugate 106 | L10-siAN2M1S | S | AmsGmsCmCmAmAmGfAmGfCfAfCmCmAmAmGmAmAmCmUmAm | 94 |
| | | AS | UmsAfsGmUmUmCfUmUfGfGmUmGmCmUfCmUfUmGmGmCmUmsUmsGm | 95 |
| Conjugate 107 | L10-siAN1M2S | S | CmsCmsAmAmGfAmGfCfAfCmCmAmAmGmAmAmCmUmAm | 92 |
| | | AS | UmsAfsGmUmUmCfUmUmGmGmUmGmCmUfCmUfUmGmGmsCmsUm | 96 |
| Conjugate 108 | L10-siAN2M2S | S | AmsGmsCmCmAmAmGfAmGfCfAfCmCmAmAmGmAmAmCmUmAm | 94 |
| | | AS | UmsAfsGmUmUmCfUmUmGmGmUmGmCmUfCmUfUmGmGmCmUmsUmsGm | 97 |
| Conjugate 109 | L10-siAN1M3S | S | CmsCmsAmAmGmAmGfCfAfCmCmAmAmGmAmAmCmUmAm | 98 |
| | | AS | UmsAfsGmUmUmCfUmUmGmGmUmGmCmUfCmUfUmGmGmsCmsUm | 96 |
| Conjugate 110 | L10-siAN2M3S | S | AmsGmsCmCmAmAmGmAmGfCfAfCmCmAmAmGmAmAmCmUmAm | 99 |
| | | AS | UmsAfsGmUmUmCfUmUmGmGmUmGmCmUfCmUfUmGmGmCmUmsUmsGm | 97 |
| Conjugate 111 | L10-siAN1M1SP | S | CmsCmsAmAmGfAmGfCfAfCmCmAmAmGmAmAmCmUmAm | 92 |
| | | AS | VP-UmsAfsGmUmUmCfUmUfGfGmUmGmCmUfCmUfUmGmGmsCmsUm | 170 |
| Conjugate 112 | L10-siAN2M1SP | S | AmsGmsCmCmAmAmGfAmGfCfAfCmCmAmAmGmAmAmCmUmAm | 94 |
| | | AS | VP-UmsAfsGmUmUmCfUmUfGfGmUmGmCmUfCmUfUmGmGmCmUmsUmsGm | 171 |
| Conjugate 113 | L10-siAN1M2SP | S | CmsCmsAmAmGfAmGfCfAfCmCmAmAmGmAmAmCmUmAm | 92 |
| | | AS | VP-UmsAfsGmUmUmCfUmUmGmGmUmGmCmUfCmUfUmGmGmsCmsUm | 172 |
| Conjugate 114 | L10-siAN2M2SP | S | AmsGmsCmCmAmAmGfAmGfCfAfCmCmAmAmGmAmAmCmUmAm | 94 |
| | | AS | VP-UmsAfsGmUmUmCfUmUmGmGmUmGmCmUfCmUfUmGmGmCmUmsUmsGm | 173 |

TABLE 3E-continued

| Conjugate | NO. | | Sequence Direction 5' - 3' | SEQ ID NO |
|---|---|---|---|---|
| Conjugate 115 | L10-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |
| Conjugate 116 | L10-siAN2M3SP | S | AmsGmsCmCmAmAmGmAmGfCfAfCmCmAmAmGm AmAmCmUmAm | 99 |
| | | AS | VP-UmsAfsGmUmUmCfUmUmGmUmGmCmUfCmUf UmGmGmCmUmsUmsGm | 173 |
| Conjugate 117 | L10-siAN1M4S | S | CmsCmsAmAmGmAmGfCfAfCmCmAmAmGmAmAm CmUmAm | 98 |
| | | AS | UmsAfsGmUmUmCfUmUfGmUmGmCmUfCmUfU mGmGmsCmsUm | 174 |
| Conjugate 118 | L10-siAN1M4SP | S | CmsCmsAmAmGmAmGfCfAfCmCmAmAmGmAmAm CmUmAm | 98 |
| | | AS | VP-UmsAfsGmUmUmCfUmUfGmUmGmCmUfCmUfU mGmGmsCmsUm | 175 |
| Conjugate 119 | L10-siAN1M5S | S | CmsCmsAmAmGfAmGfCmAfCmCmAmAmGmAmAm CmUmAm | 176 |
| | | AS | UmsAfsGmUmUmCfUmUmGmUmGmCmUfCmUf UmGmGmsCmsUm | 177 |
| Conjugate 120 | L10-siAN1M5SP | S | CmsCmsAmAmGfAmGfCmAfCmCmAmAmGmAmAm CmUmAm | 176 |
| | | AS | VP-UmsAfsGmUmUmCfUmUmGmUmGmCmUfCmUf UmGmGmsCmsUm | 178 |
| Conjugate 121 | P10-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |
| Conjugate 122 | R5-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |
| Conjugate 123 | LA5-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |
| Conjugate 124 | LB5-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |
| Conjugate 125 | V8-siAN1M3SP | S | CmsCmsAmAmGmAmGfCfAfCmCmAmAmGmAmAm CmUmAm | 98 |
| | | AS | VP-UmsAfsGmUmUmCfUmUmGmUmGmCmUfCmUf UmGmGmsCmsUm | 172 |

TABLE 3E-continued

| Conjugate | NO. | | Sequence Direction 5' - 3' | SEQ ID NO |
|---|---|---|---|---|
| Conjugate 126 | W8-siAN1M3SP | S | CmsCmsAmAmGmAmGfCfAfCmCmAmAmGmAmAm CmUmAm | 98 |
| | | AS | VP-UmsAfsGmUmUmCfUmUmGmGmUmGmCmUfCmUf UmGmGmsCmsUm | 172 |
| Conjugate 127 | X8-siAN1M3SP | S | CmsCmsAmAmGmAmGfCfAfCmCmAmAmGmAmAm CmUmAm | 98 |
| | | AS | VP-UmsAfsGmUmUmCfUmUmGmGmUmGmCmUfCmUf UmGmGmsCmsUm | 172 |
| Conjugate 156 | W8-siAN1M3SPs | S | CmsCmsAmAmGmAmGfCfAfCmCmAmAmGmAmAm CmUmAm | 98 |
| | | AS | Ps-UmsAfsGmUmUmCfUmUmGmGmUmGmCmUfCmUf UmGmGmsCmsUm | 203 |
| Conjugate 157 | L10-siAN1M3SPs | S | CmsCmsAmAmGmAmGfCfAfCmCmAmAmGmAmAm CmUmAm | 98 |
| | | AS | Ps-UmsAfsGmUmUmCfUmUmGmGmUmGmCmUfCmUf UmGmGmsCmsUm | 203 |
| Comparative Conjugate 12 | K4-siAN1M3SP | S | CmsCmsAmAmGmAmGfCfAfCmCmAmAmGmAmAm CmUmAm | 98 |
| | | AS | VP-UmsAfsGmUmUmCfUmUmGmGmUmGmCmUfCmUf UmGmGmsCmsUm | 172 |

TABLE 3F

| Conjugate | NO. | | Sequence Direction 5' - 3' | SEQ ID NO |
|---|---|---|---|---|
| Conjugate 128 | L10-siAP1 | S | CAAUAAAGCUGGACAAGAA | 108 |
| | | AS | UUCUUGUCCAGCUUUAUUGGG | 109 |
| Conjugate 129 | L10-siAP2 | S | CCCAAUAAAGCUGGACAAGAA | 110 |
| | | AS | UUCUUGUCCAGCUUUAUUGGGAG | 111 |
| Conjugate 130 | L10-siAP1M1 | S | CmAmAmUmAfAmAfGfCfUmGmGmAmCmAmAmG mAmAm | 112 |
| | | AS | UmUfCmUmUmGfUmCfCfAmGmCmUmUmUfAmUfUmU mGmGmGm | 113 |
| Conjugate 131 | L10-siAP2M1 | S | CmCmCmAmAmUmAfAmAfGfCfUmGmGmAmCmAm AmGmAmAm | 114 |
| | | AS | UmUfCmUmUmGfUmCfCfAmGmCmUmUmUfAmUfUmU mGmGmGmAmGm | 115 |
| Conjugate 132 | L10-siAP1M2 | S | CmAmAmUmAmAmAfGfCfUmGmGmAmCmAmAmG mAmAm | 116 |
| | | AS | UmUfCmUmUmGfUmCmCmAmGmCmUmUmUfAmUfUm UmGmGmGm | 117 |
| Conjugate 133 | L10-siAP2M2 | S | CmCmCmAmAmUmAmAmAfGfCfUmGmGmAmCmA mAmGmAmAm | 118 |
| | | AS | UmUfCmUmUmGfUmCmCmAmGmCmUmUmUfAmUfUm UmGmGmGmAmGm | 119 |

TABLE 3F-continued

| Conjugate | NO. | | Sequence Direction 5' - 3' | SEQ ID NO |
|---|---|---|---|---|
| Conjugate 134 | L10-siAP1M1P | S | CmAmAmUmAfAmAfGfCfUmGmGmAmCmAmAmGmAmAm | 112 |
| | | AS | VP-UmUfCmUmUmGfUmCfCfAmGmCmUmUfUmAfUmUmGmGm | 179 |
| Conjugate 135 | L10-siAP2M1P | S | CmCmCmAmAmUmAfAmAfGfCfUmGmGmAmCmAmAmGmAmAm | 114 |
| | | AS | VP-UmUfCmUmUmGfUmCfCfAmGmCmUmUfUmAfUmUmGmGmGmAmGm | 180 |
| Conjugate 136 | L10-siAP1M2P | S | CmAmAmUmAmAmAfGfCfUmGmGmAmCmAmAmGmAmAm | 116 |
| | | AS | VP-UmUfCmUmUmGfUmCmCmAmGmCmUmUfUmAfUmUmGmGmGm | 181 |
| Conjugate 137 | L10-siAP2M2P | S | CmCmCmAmAmUmAmAmAfGfCfUmGmGmAmCmAmAmGmAmAm | 118 |
| | | AS | VP-UmUfCmUmUmGfUmCmCmAmGmCmUmUfUmAfUmUmGmGmGmAmGm | 182 |
| Conjugate 138 | L10-siAP1M1S | S | CmsAmsAmUmAfAmAfGfCfUmGmGmAmCmAmAmGmAmAm | 120 |
| | | AS | UmsUfsCmUmUmGfUmCfCfAmGmCmUmUfUmAfUmUmGmsGmsGm | 121 |
| Conjugate 139 | L10-siAP2M1S | S | CmsCmsCmAmAmUmAfAmAfGfCfUmGmGmAmCmAmAmGmAmAm | 122 |
| | | AS | UmsUfsCmUmUmGfUmCfCfAmGmCmUmUfUmAfUmUmGmGmGmsAmsGm | 123 |
| Conjugate 140 | L10-siAP1M2S | S | CmsAmsAmUmAmAmAfGfCfUmGmGmAmCmAmAmGmAmAm | 124 |
| | | AS | UmsUfsCmUmUmGfUmCmCmAmGmCmUmUfUmAfUmUmGmsGmsGm | 125 |
| Conjugate 141 | L10-siAP2M2S | S | CmsCmsCmAmAmUmAmAmAfGfCfUmGmGmAmCmAmAmGmAmAm | 126 |
| | | AS | UmsUfsCmUmUmGfUmCmCmAmGmCmUmUfUmAfUmUmGmGmGmsAmsGm | 127 |
| Conjugate 142 | L10-siAP1M1SP | S | CmsAmsAmUmAfAmAfGfCfUmGmGmAmCmAmAmGmAmAm | 120 |
| | | AS | VP-UmsUfsCmUmUmGfUmCfCfAmGmCmUmUfUmAfUmUmGmsGmsGm | 183 |
| Conjugate 143 | L10-siAP2M1SP | S | CmsCmsCmAmAmUmAfAmAfGfCfUmGmGmAmCmAmAmGmAmAm | 122 |
| | | AS | VP-UmsUfsCmUmUmGfUmCfCfAmGmCmUmUfUmAfUmUmGmGmGmsAmsGm | 184 |
| Conjugate 144 | L10-siAP1M2SP | S | CmsAmsAmUmAmAmAfGfCfUmGmGmAmCmAmAmGmAmAm | 124 |
| | | AS | VP-UmsUfsCmUmUmGfUmCmCmAmGmCmUmUfUmAfUmUmGmsGmsGm | 185 |

TABLE 3F-continued

| Conjugate | NO. | | Sequence Direction 5' - 3' | SEQ ID NO |
|---|---|---|---|---|
| Conjugate 145 | L10-siAP2M2SP | S | CmsCmsCmAmAmUmAmAmAfGfCfUmGmGmAmCm AmAmGmAmAm | 126 |
| | | AS | VP-UmsUfsCmUmUmGfUmCmCmAmGmCmUmUfUmAfU mUmGmGmsAmsGm | 186 |
| Conjugate 146 | P10-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 147 | R5-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 148 | LA5-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 149 | LB5-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 150 | V8-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 151 | W8-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Conjugate 152 | X8-siAP1M2SP | S | CmsAmsAmUmAmAmAfGfCfUmGmGmAmCmAmAm GmAmAm | 124 |
| | | AS | VP-UmsUfsCmUmUmGfUmCmCmAmGmCmUmUfUmAfU mUmGmsGmsGm | 185 |
| Comparative Conjugate 13 | K4-siAP1M3SP | S | CmsAmsAmUmAmAmAfGfCfUmGmGmAmCmAmAm GmAmAm | 124 |
| | | AS | VP UmsUfsCmUmUmGfUmCmCmAmGmCmUmUfUmAfU mUmGmsGmsGm | 185 |

TABLE 3G

| Conjugate | NO. | | Sequence Direction 5' - 3' | SEQ ID NO |
|---|---|---|---|---|
| Conjugate 158 | L10-simTTR | S | AfsAmsCfAmGfUmGfUmUfCfUfUmGfCmUfCmUfA mUfAmAf | 204 |
| | | AS | UmsUfsAmUfAmGfAmGfCmAfAmGmAmAfCmAfC mUfGmUfUmsUmsUm | 205 |

TABLE 3G-continued

| Conjugate | NO. | | Sequence Direction 5' - 3' | SEQ ID NO |
|---|---|---|---|---|
| Conjugate 159 | L10-siHBa1M2Sps | S | CmsCmsUmUmGfAmGfGfCfAmUmAmCmUmUmCmAmAmAm | 206 |
| | | AS | ps-UmsUfsUmGmAmAfGmUfAfUmGmCmCmUfCmAfAmGmGmsUmsUm | 207 |
| Conjugate 160 | L10-siHBa1M2Sp | S | CmsCmsUmUmGfAmGfGfCfAmUmAmCmUmUmCmAmAmAm | 208 |
| | | AS | p-UmsUfsUmGmAmAfGmUfAfUmGmCmCmUfCmAfAmGmGmsUmsUm | 209 |
| Conjugate 161 | L10-siHBa1M1Sp | S | CmsCmsUmUmGmAmGfGfCfAmUmAmCmUmUmCmAmAmAm | 210 |
| | | AS | p-UmsUfsUmGmAmAfGmUmAmUmGmCmCmUfCmAfAmGmGmsUmsUm | 211 |
| Conjugate 162 | L10-siHBa1M1SpsT | S | CmsCmsUmUmGmAmGfGfCfAmUmAmCmUmUmCmAmAmAm | 212 |
| | | AS | ps-TmoesUfsUmGmAmAfGmUmAmUmGmCmCmUfCmAfAmGmGmsUmsUm | 213 |
| Conjugate 163 | L10-siHBa1M1Sps | S | CmsCmsUmUmGmAmGfGfCfAmUmAmCmUmUmCmAmAmAm | 214 |
| | | AS | ps-UmsUfsUmGmAmAfGmUmAmUmGmCmCmUfCmAfAmGmGmsUmsUm | 215 |
| Conjugate 164 | P10-siHBa1M2SP | S | CmsCmsUmUmGfAmGfGfCfAmUmAmCmUmUmCmAmAmAm | 216 |
| | | AS | VP-UmsUfsUmGmAmAfGmUfAfUmGmCmCmUfCmAfAmGmGmsUmsUm | 217 |
| Conjugate 165 | W8-siHBa1M2SP | S | CmsCmsUmUmGfAmGfGfCfAmUmAmCmUmUmCmAmAmAm | 218 |
| | | AS | VP-UmsUfsUmGmAmAfGmUfAfUmGmCmCmUfCmAfAmGmGmsUmsUm | 219 |
| Conjugate 166 | Z5-siHBa1M2SP | S | CmsCmsUmUmGfAmGfGfCfAmUmAmCmUmUmCmAmAmAm | 220 |
| | | AS | VP-UmsUfsUmGmAmAfGmUfAfUmGmCmCmUfCmAfAmGmGmsUmsUm | 221 |
| Conjugate 167 | L10-siP1M1Sp | S | GmsAmsAmAmGmUmAfUfGfUmCmAmAmCmGmAmAmUmAm | 222 |
| | | AS | p-UmsAfsUmUmCmGfUmUmGmAmCmAmUmAfCmUfUmUmCmsUmsUm | 223 |
| Conjugate 168 | L10-siP1M1SP | S | GmsAmsAmAmGmUmAfUfGfUmCmAmAmCmGmAmAmUmAm | 224 |
| | | AS | VP-UmsAfsUmUmCmGfUmUmGmAmCmAmUmAfCmUfUmUmCmsUmsUm | 225 |
| Conjugate 169 | L10-siAN2M1Sp | S | AmsGmsCmAmAmGmAmGfCfAfCmCmAmAmGmAmAmCmUmAm | 226 |
| | | AS | p-UmsAfsGmUmUmCfUmUmGmGmUmGmCmUfCmUfUmGmCmUmsUmsGm | 227 |

TABLE 3G-continued

| Conjugate | NO. | | Sequence Direction 5' - 3' | SEQ ID NO |
|---|---|---|---|---|
| Conjugate 170 | L10-siAP1M1Sp | S | CmsAmsAmUmAmAmAfGfCfUmGmGmAmCmAmAmGmAmAm | 228 |
| | | AS | p-UmsUfsCmUmUmGfUmCmCmAmGmCmUmUfUmAfUmUmGmsGmsGm | 229 |
| Conjugate 171 | L10-siAP1M1Sps | S | CmsAmsAmUmAmAmAfGfCfUmGmGmAmCmAmAmGmAmAm | 230 |
| | | AS | ps-UmsUfsCmUmUmGfUmCmCmAmGmCmUmUfUmAfUmUmGmsGmsGm | 231 |
| Comparative conjugate 14 | K4-simTTR | S | CmsAmsAmUmAmAmAfGfCfUmGmGmAmCmAmAmGmAmAm | 232 |
| | | AS | VP-UmsUfsCmUmUmGfUmCmCmAmGmCmUmUfUmAfUmUmGmsGmsGm | 233 |
| Comparative conjugate 15 | AD-66810 | S | CmsAmsAmUmAmAmAfGfCfUmGmGmAmCmAmAmGmAmAm | 234 |
| | | AS | VP-UmsUfsCmUmUmGfUmCmCmAmGmCmUmUfUmAfUmUmGmsGmsGm | 235 |
| Comparative conjugate 16 | AD-65695 | S | AmsCmsAmUmAmUmUfUmGfAfUfCmAmGmUmCmUmUmUmUm | 195 |
| | | AS | AmsAfsAmAmAmGfAmCmUmGmAmUmCmAfAmAfUmAmUmGmUmsUmsGm | 196 |
| Comparative conjugate 17 | AD-69535 | S | GmsCmsUmUmAmAmAmGfGmGfAmCmAmGmUmAmUmCmAm | 197 |
| | | AS | UmsGfsAmAmUmAmCmUmGmUmCmCfCmUfUmUmUmAmAmGmCmsAmsAm | 198 |
| Comparative siRNA 18 | X2M2 | S | CmCmUmUmGAGGCmAUmACmUmUmCmAAAdTsdT | 236 |
| | | AS | UfUmUfGAAGUfAUGCCUfCAAGGdTsdT | 237 |

*S: sense strand; AS: antisense strand

Note: capital letters C, G, U, and A indicate the base composition of nucleotides; dT indicate a deoxythymine nucleotide; a lowercase letter m indicates that the nucleotide adjacent to the left side of the letter m is a 2'-methoxy modified nucleotide; a lowercase letter f indicates that the nucleotide adjacent to the left side of the letter f is a 2'-fluoro modified nucleotide; a lowercase letter s indicates the phosphorothioate linkage between the two nucleotides adjacent to both sides of the letter s; VP indicates that the nucleotide adjacent to the right side of the letters VP is a vinyl phosphate modified nucleotide; P indicates that the nucleotide adjacent to the right side of the letter P is a phosphate nucleotide; Ps indicates that the nucleotide adjacent to the right side of the letters Ps is a phosphorothioate modified nucleotide; Tmoe indicates thymine nucleotide modified with 2'-methoxyethoxyl.

A vinyl phosphate and 2'-methoxy modified uridine monomer (VP-Um) was synthesized according to the following method:

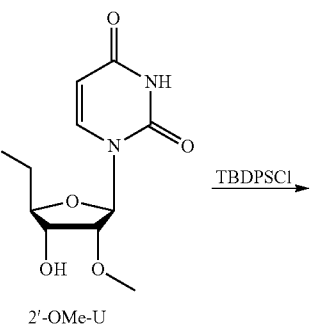

2'-OMe-U

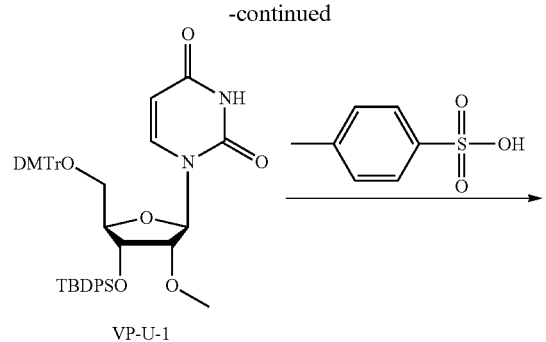
VP-U-1
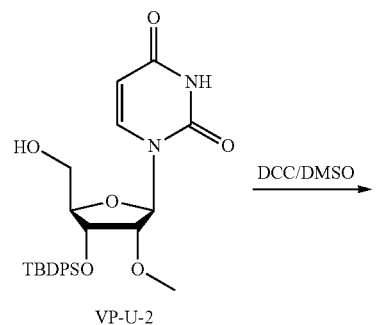
VP-U-2
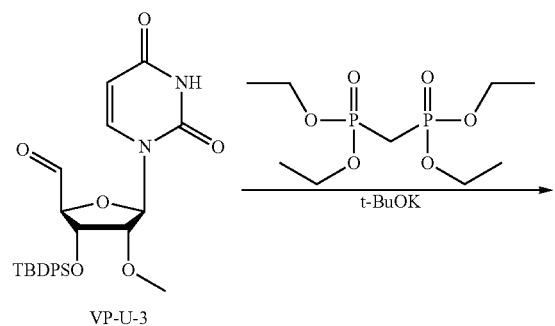
VP-U-3
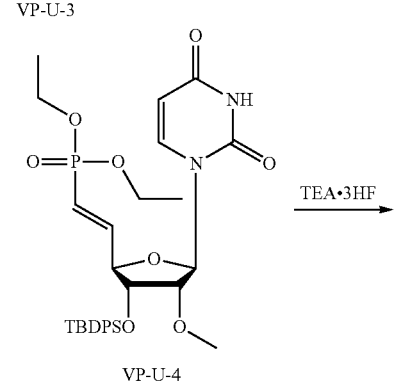
VP-U-4
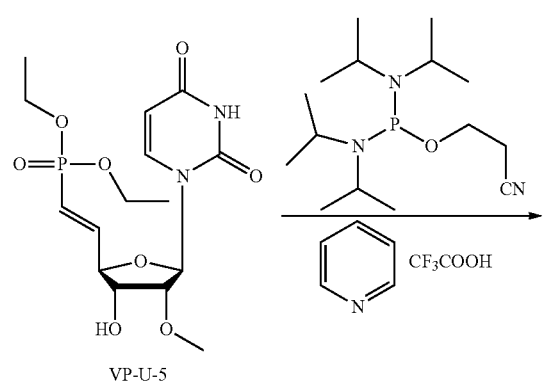
VP-U-5
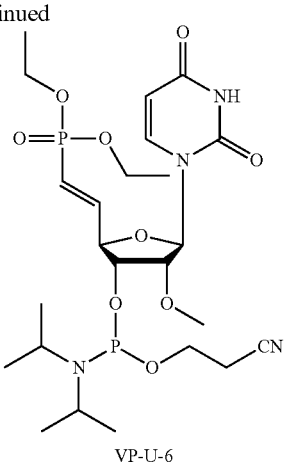
VP-U-6
(14-1) Synthesis of VP-U-2
A VP-U-2 molecule was synthesized according to the following method:
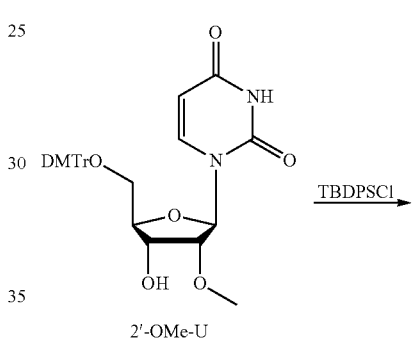
2'-OMe-U
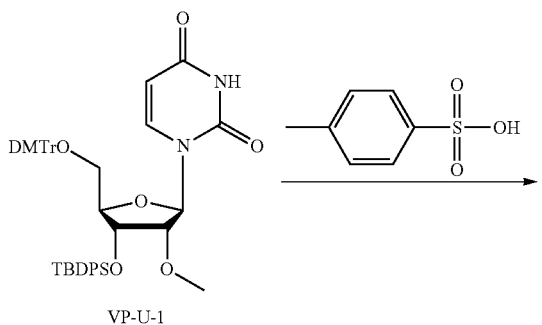
VP-U-1
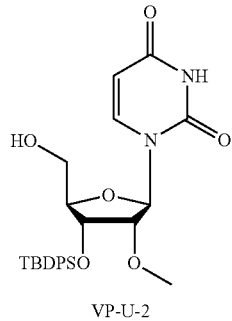
VP-U-2
A 2'-methoxy modified uracil nucleoside (2'-OMe-U, 51.30 g, 91.6 mmol), tert-butyl diphenylchlorosilane (TBDPSCl, 50.35 g, 183.2 mmol), and imidazole (12.47 g, 183.2 mmol) were mixed and dissolved in 450 ml of N,N-dimethylformamide (DMF) to react for 20 hours under stirring at room temperature. DMF was removed by evaporation, and the residue was dissolved with 600 ml of dichloromethane and washed with 300 ml of saturated sodium bicarbonate. The aqueous phase isolated was extracted three times, each with 300 ml of dichloromethane. All organic phases were combined, washed with 5% oxalic acid until an aqueous phase of pH <5 was obtained. The solvent was evaporated to dryness to give a crude product VP-U-1, which was directly used in the subsequent synthesis of VP-U-2.

The crude product VP-U-1 was dissolved in 100 ml of dichloromethane, and then stirred for 10 minutes under an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase obtained was washed by addition of saturated sodium bicarbonate solution to pH=8. Aqueous phases were combined and extracted twice with 200 ml of dichloromethane. All organic phases were combined and washed once with 200 ml of saturated brine. The solvent was evaporated, and the residue was purified by using a normal phase silica gel column, 200-300 mesh. The column was packed with petroleum ether and gradient eluted with petroleum ether: ethyl acetate:dichloromethane:methanol=1:1:1:0.05-1:1:1:0.25. The eluate was collected, the solvent was evaporated under reduced pressure, and the residue was foam-dried with a vacuum oil pump to give a total of 40.00 g of pure product VP-U-2. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: C26H33N2O6Si, [M+H]+, calcd: 497.21, Measured: 497.45.

(14-2) Synthesis of VP-U-4:

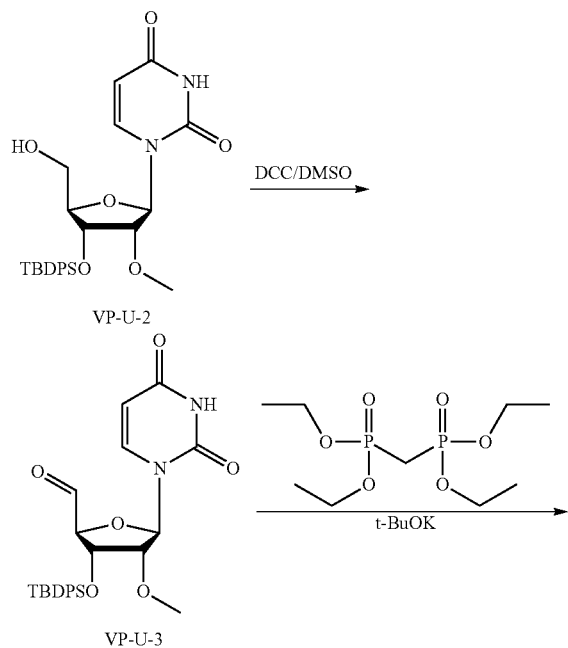

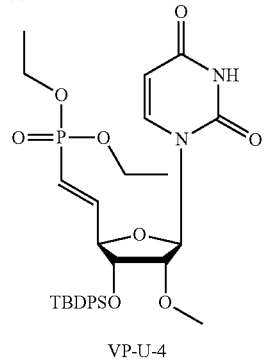

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react for 20 hours under stirring at room temperature to obtain a reaction liquid. Separately, tetraethyl methylenediphosphate (21.44 g, 74.4 mmol) was dissolved in 120 ml of THF, cooled under an ice bath, added with t-BuOK (11.36 g, 101.2 mmol) at a temperature of the ice bath to react for 10 min, warmed to room temperature to react for 0.5 h and added into the above reaction liquid over about 1 h. The reaction was carried out for 1 h at a temperature of the ice bath and then warmed to room temperature to react for 18 h. The reaction was quenched by addition of water. The aqueous phase isolated was extracted three times, each with 200 ml of dichloromethane. All organic phases were combined and washed once with 200 ml of saturated brine. The solvent was evaporated to dryness, and the residue was purified by using a normal phase silica gel column, 200-300 mesh. The column was packed with petroleum ether and gradient eluted with petroleum ether:ethyl acetate=1:1-1:4. The eluate was collected, the solvent was evaporated under reduced pressure, and the residue was foam-dried with a vacuum oil pump to give a total of 14.00 g of pure product VP-U-4. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: C31H42N2O8PSi, [M+H]+, calcd: 629.24, measured: 629.51.

(14-3) Synthesis of VP-U-5:

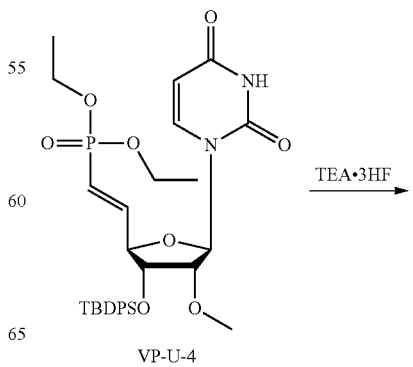

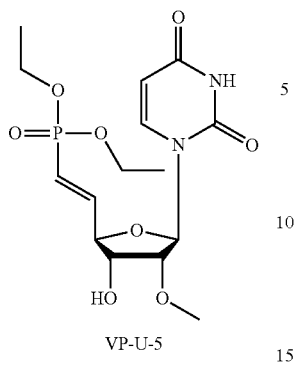

VP-U-5

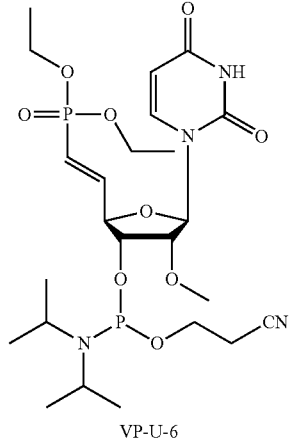

VP-U-6

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. A crude product was obtained by direct evaporation of the solvent to dryness followed by dissolution in dichloromethane and evaporation to dryness twice with 50 ml of dichloromethane. The crude product was purified by using a normal phase silica gel column, 200-300 mesh. The column was packed with petroleum ether and gradient eluted with petroleum ether:ethyl acetate:dichloromethane:methanol=1:1:1:0.05-1:1:1:0.25. The eluate was collected, the solvent was evaporated under reduced pressure, and the residue was foam-dried with a vacuum oil pump to give a total of 6.70 g of pure product VP-U-5. 1H NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: C15H24N2O8P, [M+H]+, calcd: 391.13, measured: 391.38.

(14-4) Synthesis of VP-U-6:

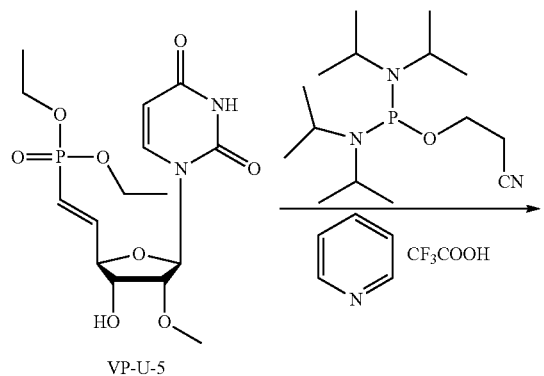

VP-U-5

VP-U-5 (391 mg, 1.0 mmol), pyridine trifluoroacetate (0.232 g, 1.2 mmol), N-methylimidazole (0.099 g, 1.2 mmol), and 2-cyanoethyl N,N,N',N'-tetraisopropylphosphorodiamidite (0.452 g, 1.5 mmol) were added into 10 ml of anhydrous dichloromethane under argon atmosphere to react for 5 hours under stirring at room temperature. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP-U-6. 31P NMR (161 MHz, DMSO-d6) δ 150.34, 150.29, 17.07, 15.50. MS m/z: C24H41N4O9P2, [M+H]+, calcd: 591.23, measured: 591.55. It indicates that VP-U-6 is the target product VP-Um, which involves in the synthesis of RNA strands as a nucleoside monomer.

A 5'-phosphate ester modification is linked to 5' terminal using the following method:

As a starting material, a phosphorylated structural monomer with the following structure of Formula CPR-I (purchased by Suzhou GenePharma Inc. as Cat #13-2601-XX) is employed:

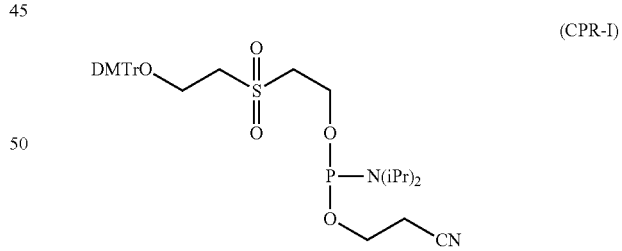

(CPR-I)

After all nucleosides of the antisense strand is linked, the monomer of Formula (CPR-I) is linked to the 5' terminal of the antisense strand by a four-step reaction of deprotection, coupling, capping, and oxidation according to the method of solid phase phosphoramidite synthesis of nucleic acid, following by cutting down and deprotection according to the following condition, thus obtaining the antisense strand:

The synthesized nucleotide sequence linked to the support was added into 25 wt % aqueous ammonia to react for 16 hours at 55° C., and the aqueous ammonia is in an amount of 0.5 ml/μmol with respect to the nucleotide sequence. The liquid was removed, and the residue was concentrated in vacuum to dryness. After treatment with aqueous ammonia, the product was dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose. Purification and desalination: purification of the nucleic acid was achieved by using a preparative ion chromatography column (Source 15Q) with a gradient elution of NaCl. Specifically, eluent A: 20 mM sodium phosphate (pH 8.1), solvent:water/acetonitrile=9:1 (v/v); eluent B: 1.5 M sodium chloride, 20 mM sodium phosphate (pH 8.1), solvent:water/acetonitrile=9:1 (v/v); elution gradient: the ratio of eluent A:eluent B=100:0-50:50. The eluate was collected, combined and desalted by using a reversed phase chromatography column. The specific condition included that a Sephadex column was used for desalination, with Sephadex-G25 as the filler and deionized water for eluting.

In the case where the target product has a 5'-phosphorothioate modification, the same procedure as above is employed, except that the above oxidation reaction conditions is replaced with a sulfuration reaction condition in the linking, thereby carrying out the sulfuration reaction.

For the sense strand and antisense strand synthesized above, the purity was determined by ion exchange chromatography (IEX-HPLC), and the molecular weight was analyzed by LC-MS, and it was confirmed that the synthesized nucleic acid sequence corresponds to the respective siRNAs of the examples and comparative examples in Table 5.

Preparation Example 15 Preparation of the Rest of the Conjugates in Tables 3A-3G Otherwise, it is expected that the rest of the conjugates in tables 3A-3G can be prepared by employing the same method as in Preparation Example 13, except that: 1) As to Conjugates 31-37, 52-58, 68-74, 84-90, 121-127 and 146-152, Comparative conjugates 4-5, 7-8 and 10-13, the L-9 Conjugating Molecule is replaced with the Conjugating Molecules 2-8 or 12 and Comparative Conjugating Molecules 1-2 obtained from Examples 2-10 or 12 (e.g., when the L-9 Conjugating Molecule is replaced with the P-9 Conjugating Molecule (Conjugating Molecule 2) it is anticipated that the conjugates 31, 52, 68, 84, 121 and 146 which are numbered with a P10 conjugate can be obtained. When the L-9 Conjugating Molecule is replaced with the R-4 Conjugating Molecule (Conjugating Molecule 3), it is anticipated that the conjugates 32, 53, 69, 85, 122 and 147 which are numbered with a R5 conjugate can be obtained, and so forth; 2) the conjugated siRNAs have sequences shown in Tables 3A-3G corresponding to conjugates 10-15, 19-23, 27-41, 44-61, 63-77, 79-104, 106-108, 110, 112-114, 116-141 and 143-152, and comparative conjugates 4-5, 7-8 and 10-17; 3) when a phosphorothioate linkage exists between two nucleotides in the target sequence, the sulfuration reaction step described in Preparation Example 13 was used to replace the oxidation reaction step during linking of the later of the two nucleotides; and 4) when 2'-positions of all nucleotides in the target sequence are modified hydroxyl groups, the step of removal of the 2'-TBDMS protection on ribose was not included in the conditions for cleavage and deprotection. Therefore, it is anticipated that conjugates 10-15, 19-23, 27-41, 44-61, 63-77, 79-104, 106-108, 110, 112-114, 116-141 and 143-152, and comparative conjugates 4-5, 7-8 and 10-17 can be obtained, and the conjugates were numbered separately according to Tables 3A-3G. The disclosure conjugates are represented by Formulas (3), (4), (7), (12), (13), (14), (15), (21), and (22) respectively, and the comparative conjugates are represented by Formulas (901) and (902) respectively:

Formula (901)

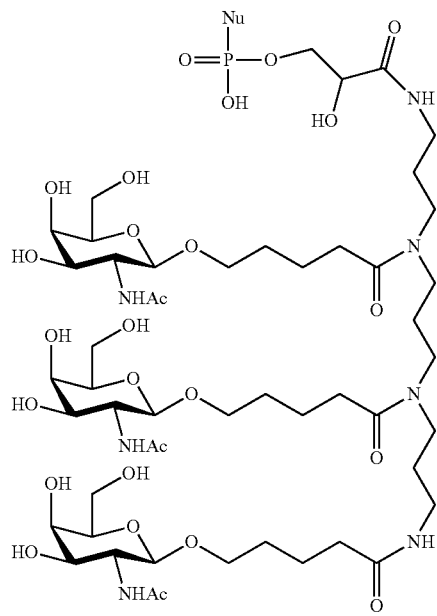

Formula (902)

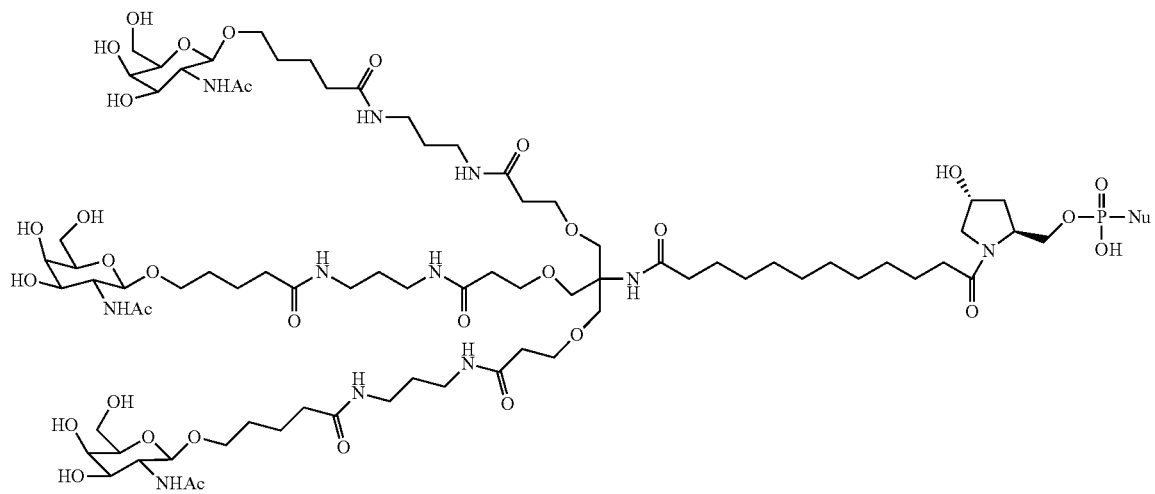

wherein, Nu is siRNA in comparative conjugates 4-5, 7-8 and 10-13.

Preparation Example 16 Synthesis of Comparative Conjugates 6 and 9

The comparative conjugates 6 and 9 were synthesized by using FIN-2 obtained in the above step (11-3). The conditions for RNA solid phase synthesis and deprotection are the same as solid phase synthesis of nucleic acid described in the aforementioned step (11-2). The only difference is that FIN_FIN_FIN was firstly conjugated to the 3' terminal of the sense strand of RNA through three reaction cycles of FIN-2, followed by solid phase synthesis by using a universal solid phase support (UnyLinker™ loaded NittoPhase®HL Solid Supports).

The connection of FIN_FIN_FIN conjugating group was proceeded according to the method described in Rajeev et al., Chem Bio Chem 2015, 16, 903-908. Specifically, the hydroxy protecting group was firstly removed from the above-mentioned universal solid phase support, and the solid phase support was subsequently brought into contact and coupled with the FIN-2 conjugating molecule under the coupling condition and a coupling agent, and a FIN conjugating molecule connected to the solid phase support was obtained after the capping and oxidation reaction. Moreover, the hydroxy protecting group DMTr was removed from the FIN conjugating molecule connected to the solid phase support, and the solid phase support was further brought into contact and coupled with another FIN-2 conjugating molecule, followed by capping and oxidation reaction. After a still further cycle of Deprotection-Coupling-Capping-Oxidation, a third FIN-2 conjugating molecule was connected, and a conjugating group (FIN_FIN_FIN) connected to the solid phase support was thus obtained. Thereafter, started with the conjugating group connected to the solid phase support, nucleotide monomers were consequently connected, and an RNA sense strand with the conjugating group (FIN_FIN_FIN) conjugated to 3' end was finally obtained.

In the reactions above, the conditions, solvents and agents of the deprotection, coupling, capping, and oxidation are in accordance with the RNA solid phase synthesis described in the step (11-2).

Subsequently, cleavage and deprotection, purification and desalting, detection, and annealing were performed by the same method as in Preparation Example 12 to finally obtain comparative conjugates 6 and 9 (sometimes also simply referred to as FIN conjugates hereinafter). The molecular weight was measured by LC-MS (purchased from Waters Corp., model: LCT Premier). It is confirmed that the synthesized FIN-siHBa1M1SP conjugate is the target designed compound, since the measured values is in conformity with the theoretical values. Its structure is as represented by Formula (903):

Formula (903)

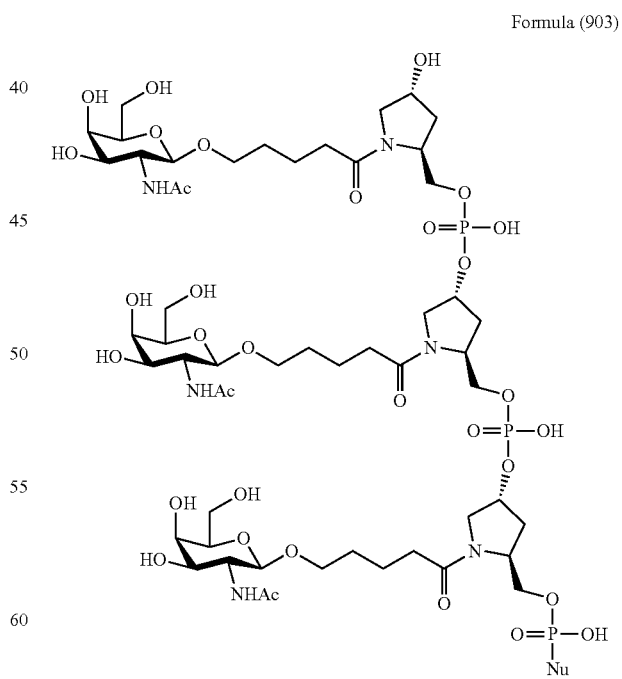

wherein, Nu is siRNA in the comparative conjugates 6 or 9.

After the preparation of the conjugates above, they were lyophilized to solid powder via standard process and stored until used. When required, they can be resolved with such as water for injection or normal saline to a solution at a desired concentration.

Experimental Example 1—this Experiment Illustrates the Toxicity of the siRNA Conjugates of the Present Disclosure In C57BL/6J mice, Conjugate 24 was subcutaneously administrated to each mouse, respectively, with a single dose of 100 mg/kg or 200 mg/kg (by siRNA, in the form of 0.9 wt % NaCl aq., 10 mL/kg was administrated each at the concentration of 10 mg/mL or 20 mg/mL). During a period of administration for continuous observation, no animal death occurred, no clinical symptoms associated with adverse drug responses were observed, and no abnormalities were found in clinical pathology test or gross anatomy, both of which being proceeded at 24 h after the administration. Thus, the above results indicate a relatively low toxicity of the conjugates of the present disclosure at animal level.

Experimental Example 2 this Experiment Illustrates the Stability of the Conjugates of the Disclosure Experimental Example 2-1 Stability in the Lysosome Lysate In Vitro Conjugates 24, 25, 42, 43, 62, 78, and Comparative Sequence 1 (each provided in the form of 0.9 wt % NaCl aqueous solution at 20 µM with regard to siRNA, 12 µl for each group, respectively) were individually mixed well with 27.2 µL of sodium citrate aqueous solution (pH 5.0), 4.08 µL of deionized water and 2.72 µL of Rat Tritosomes (purchased from Xenotech Inc., Cat. R0610LT, No. 1610069, at a final concentration of 0.2 mU/µL), and incubated at a constant temperature of 37° C. 5 µL samples were taken at each time point of 0 h, 5 min, 15 min, 30 min, 1 h, 2 h, 4 h, and 8 h respectively, each added to 15 µL of 9 M urea aqueous solution for denaturation, and 4 µL of loading buffer (purchased from Solarbio Inc., Cat. 20160830) was added, then immediately cryopreserved in a −80° C. freezer to quench the reaction. 0h represents the moment when the samples are mixed well with the lysosome lysate and immediately taken out. As for samples untreated with the lysosome lysate, 1.5 µL for each of the conjugates above at equal moles (20 µM) was mixed well with 7.5 µL of sodium citrate aqueous solution (pH 5.0) and 1 µL of deionized water, each added to 15 µL of 9 M urea aqueous solution for denaturation, and 4 µL of loading buffer (purchased from Solarbio Inc., Cat. 20160830) was added, then immediately cryopreserved in a −80° C. freezer to quench the reaction. The control samples for each conjugated is mark as Con in the electrophoretofram. 16 wt % of non-denatured polyacrylamide gel was prepared. Each cryopreserved sample was all mixed with 4 µL of loading buffer (purchased from Solarbio Inc., aquarious solution of 20 mM EDTA, 36 wt % glycerol, and 0.06 wt % bromophenol blue) and then 20 µL of the mixture was loaded into the gel to perform electrophoresis for 10 minutes under 20 mA and then 30 minutes under 40 mA. After finishing the electrophoresis, the gel was stained with Gelred dye (BioTium, Cat. 13G1203) for 10 minutes followed by imaging. The results are shown in FIG. 1A. The comparative sequence 1 is as follows: Sense: 5'-CC-UUGAGGCAUACUUCAAA-3' (SEQ ID NO: 250); antisense strand: 5'-UUUGAAGUAUGCCUCAAGGUU-3' (SEQ ID NO: 251).

Figure 1B:
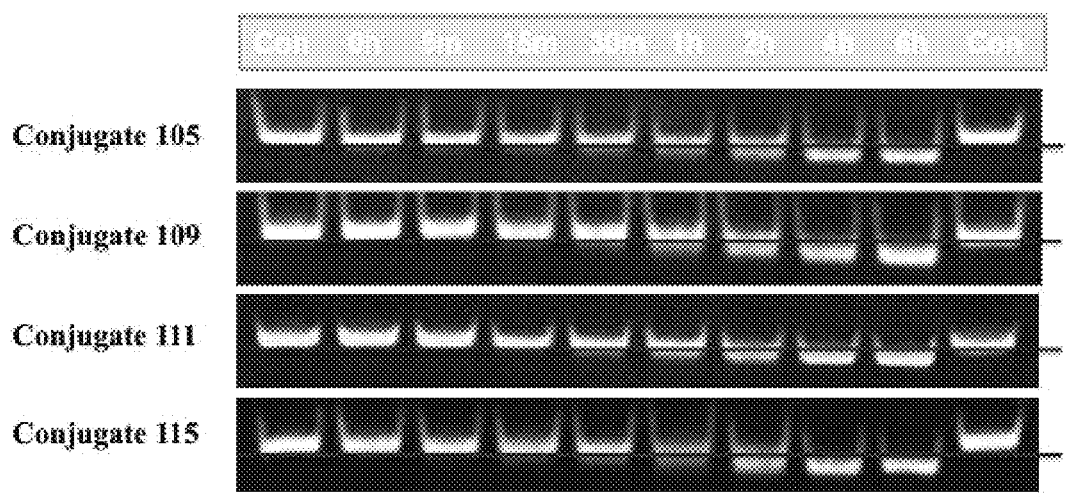

According to the same method, the stability of Conjugates 105, 109, 111 and 115 in 6 hours is measured, the result of which is shown in FIG. 1B.

FIGS. 1A and 1B show the semiquantitative result of the stability test of the siRNA conjugates in the Tritosome in vitro. It is demonstrated that the conjugates of the disclosure can remain undegraded in a long time in Tritosome, showing good stability.

Experimental Example 2-2 Stability in the Human Plasma In Vitro

Figure 2A:
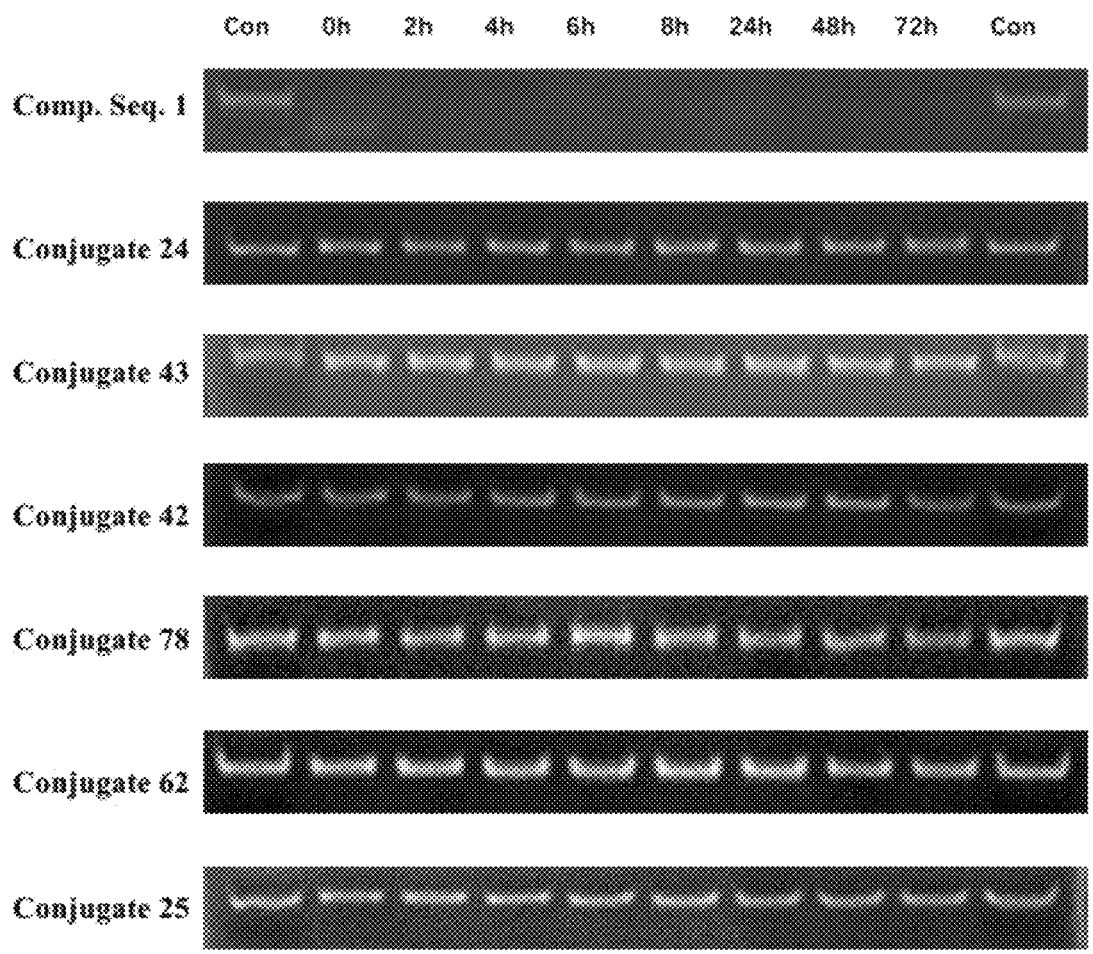
FIGS. 2A and 2B show the semiquantitative result of the stability test of the tested siRNA conjugates in the human plasma in vitro.

Conjugates 24, 25, 42, 43, 62, 78, and Comparative Sequence 1 (each provided in the form of 0.9 wt % NaCl aqueous solution at 20 µM with regard to siRNA, 12 µl for each group) were individually mixed well with 108 µL of 90% human plasma (diluted in PBS) and incubated at a constant temperature of 37° C. 10 µL samples were taken at each time point of 0 h, 2 h, 4 h, 6 h, 8 h, 24 h, 48 h and 72 h respectively, and immediately frozen in liquid nitrogen and cryopreserved in a −80° C. freezer for use. Meanwhile, each of the conjugates above at equal moles (2 µM, 2 µL) was mixed well with 8 µL of 1×PBS, thus obtaining 10 µL of samples untreated with human plasma (marked as Con). 20 wt % of non-denatured polyacrylamide gel was prepared. Each cryopreserved sample was all mixed with 4 µL of loading buffer (aquarious solution of 20 mM EDTA, 36 wt % glycerol, and 0.06 wt % bromophenol blue) and then loaded into the gel to perform electrophoresis for 60 minutes under 80 mA constant current. After finishing the electrophoresis, the gel was stained with 1× Sybr Gold dye (Invitrogen, Cat. 11494) for 15 minutes followed by imaging. The results are shown in FIG. 2A. The comparative sequence 1 is as follows: Sense: 5'-CCUUGAGGCAUACUUCAAA-3' (SEQ ID NO: 250); antisense strand: 5'-UUUGA-AGUAUGCCUCAAGGUU-3' (SEQ ID NO: 251).

Figure 2B:
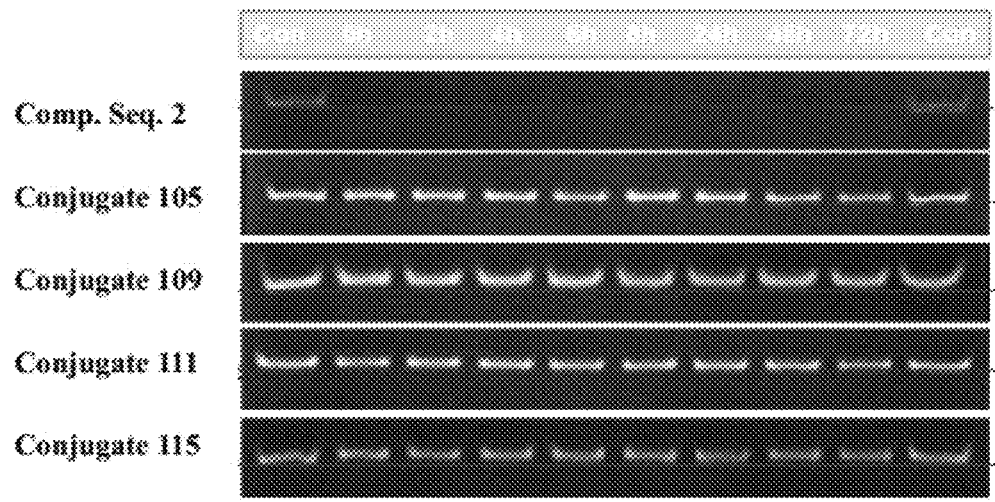

According to the same method, the stability of Conjugates 105, 109, 111 and 115 in 72 hours is measured, the result of which is shown in FIG. 2B.

FIGS. 2A and 2B show the semiquantitative result of the stability test of the tested siRNA conjugates in the human plasma in vitro. It is demonstrated that in human plasma, the conjugates of the disclosure remain undegraded in up to 72 hours, showing good stability in human plasma.

Experimental Example 2-3 Stability in the Monkey Plasma In Vitro

Conjugates 24, 25, 42, 43, 62, 78, and Comparative Sequence 2 (each provided in the form of 0.9 wt % NaCl aqueous solution at 20 µM respectively with regard to siRNA, 12 µl for each group, wherein Comparative Sequence 2 is an siRNA with a sense strand having a sequence represented by SEQ ID NO: 80 and an antisense strand having a sequence represented by SEQ ID NO: 81, while without being conjugated to any conjugating molecule) were individually mixed well with 108 µL of 90% cynomolgus monkey plasma (Monkey plasma, purchased form HONGQUAN Bio, Cat. HQ70082, diluted in PBS) and incubated at a constant temperature of 37° C. 10 µL samples were taken at each time point of 0 h, 2 h, 4 h, 6 h, 8 h, 24 h, 48 h and 72 h respectively, and immediately frozen in liquid nitrogen and cryopreserved in a −80° C. freezer. After sampling at each time point, each sample was diluted 5-fold with 1×PBS (pH 7.4) and then taken in a volume of 10 µL for use. Meanwhile, each of the conjugates above at equal moles (2 µM, 2 µL) was mixed well with 8 µL of 1×PBS, thus obtaining 10 μL of samples untreated with monkey plasma (marked as Con). 20 wt % of non-denatured polyacrylamide gel was prepared. Each diluted sample was all mixed with 4 μL of loading buffer (aquarious solution of 20 mM EDTA, 36 wt % glycerol, and 0.06 wt % bromophenol blue) and then loaded into the gel to perform electrophoresis for 60 minutes under 80 mA constant current. After finishing the electrophoresis, the gel was stained with 1× Sybr Gold dye (Invitrogen, Cat. 11494) for 15 minutes followed by imaging. The results are shown in FIG. 3A.

Figure 3A:
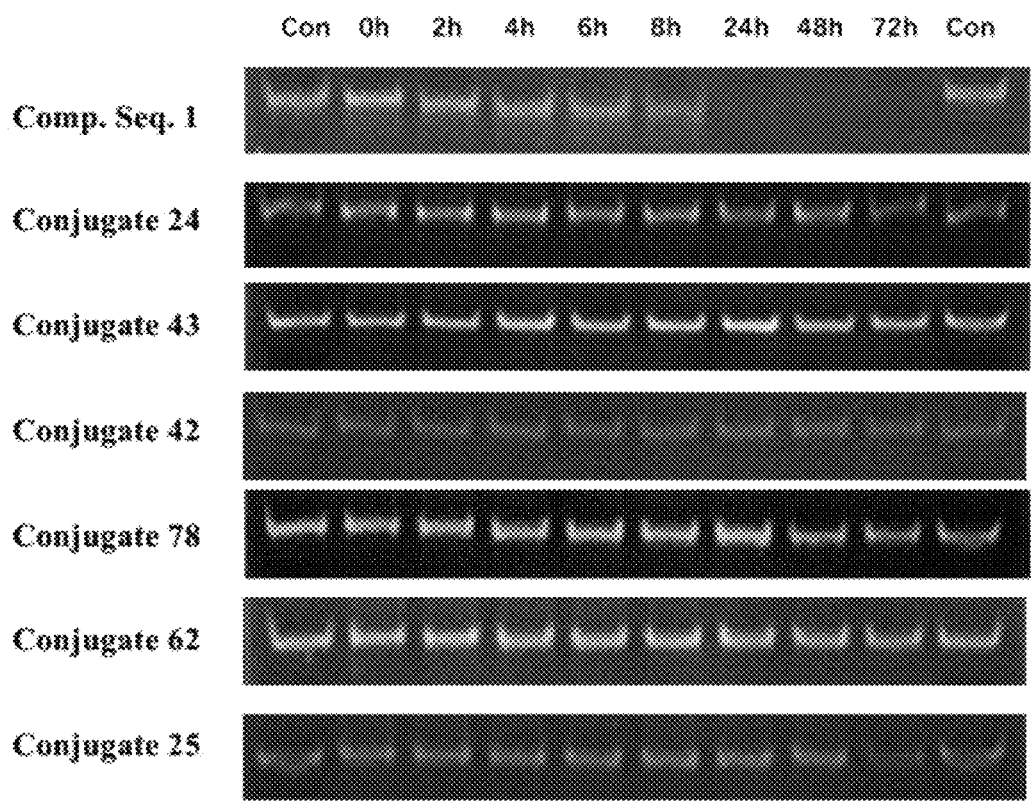
FIGS. 3A and 3B show the semiquantitative result of the stability test of the tested siRNA conjugates in the monkey plasma in vitro.
Figure 3B:
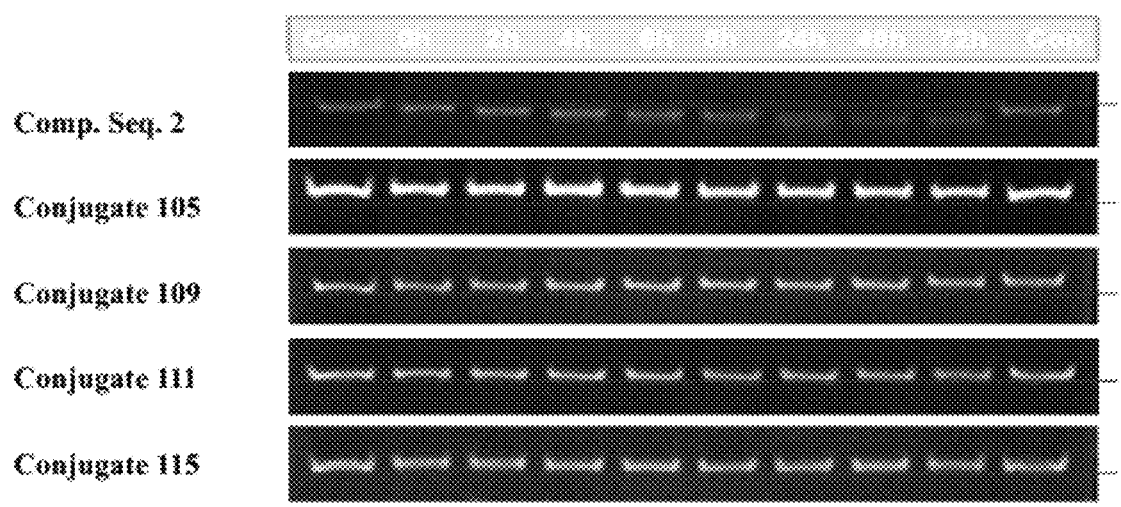

The stability of Conjugates 105, 109, 111 and 115 in 72 hours is measured according to the same method, the result of which is shown in FIG. 3B.

FIGS. 3A and 3B show the semiquantitative result of the stability test of the tested siRNA conjugates in the monkey plasma in vitro. It is demonstrated that in cynomolgus monkey plasma, the conjugates of the disclosure remain undegraded in up to 72 hours, showing good stability in monkey plasma.

Experimental Example 3 this Experiment Illustrates the Pharmacokinetics of Conjugates 24 and 25 in Rats In Vivo In this experimental example, Conjugates 24 and 25 were administered to rats in each experimental group (10 rats in each group, half female and half male) by subcutaneous injection, respectively, with a single dose of 10 mg/kg and 50 mg/kg. Subsequently, the drug concentration in plasma, liver and kidney tissue of rats were measured at each time point.

Firstly, SD rats were randomly divided into groups according to the body weight and gender thereof by using the PRISTIMA 7.2.0 data system, followed by respectively administration of the conjugates according to the designed dosage. The drug dosages for all animals were calculated according to the body weight. A single dose was administered subcutaneously, with the dosage of 10 mg/kg and 50 mg/kg respectively in the form of 1 mg/ml and 5 mg/ml of 0.9% NaCl aqueous solution and the volume of 10 ml/kg. Rat whole blood was collected from the jugular vein before administration and at 5 minutes (30 seconds), 30 minutes (±1 minute), 1 hour (+2 minutes), 2 hours (2 minutes), 6 hours (5 minutes), 24 hours (10 minutes), 48 hours (+20 minutes), 72 hours (20 minutes), 120 hours (30 minutes), and 168 hours (+30 minutes) after administration. Then the whole blood samples were centrifugated at 2-8° C. under 1800×g for 10 minutes to separate plasma. About 70 μL volume of a plasma sample was placed in one tube, and the remaining of the same sample was placed in another, both of which were cryopreserved at −70° C. to −86° C. for inspection. Liver and kidney tissues of rats were collected at about 24, 48, 72, 120, and 168 hours after administration by the method comprising anesthetizing the rats with pentobarbital sodium according to the weight thereof (60 mg/kg by intraperitoneal injection), euthanizing the rats by blood collection from abdominal aorta, and performing gross anatomy. The liver and kidney of each rat were sampled and stored in 1 mL cryotube at below −68° C. until measurement and analysis.

The concentrations of the conjugates of Conjugates 24 and 25 in plasma, liver and kidney tissues of rats were measured quantitatively by High Performance Liquid Chromatography with Fluorescence Detection (HPLC-FLD) according to following steps:

(1) grinding the tissue until a tissue mass of no more than 80 mg was obtained, then adding Tissue and Cell Lysis Solution (supplier: Epicentre, Cat. MTC096H) to prepare a tissue homogenate of 66.7 mg/mL;

(2) subjecting the tissue homogenate to a sonication (150 W, 30 s) to disrupt cells;

(3) for each group of tissue samples, adding 75 μL of tissue samples to a 96-well PCR plate, adding 5 μL of proteinase K (supplier: Invitrogen, Cat. 25530-015) and 10 μL of mixed aqueous solution of 10 wt % acetonitrile and 0.01 wt % Tween 20; for each group of plasma samples, adding 20 μL of plasma to a 96-well PCR plate, adding 45 μL of Tissue and Cell Lysis Solution, 5 μL of proteinase K, and 20 μL of mixed liquid of 10 wt % acetonitrile and 0.01 wt % Tween 20;

(4) closing the plates and placing them in a PCR instrument (supplier: Applied Biosystems, model: GeneAmp® PCR system 9700) and incubating at 65° C. for 45 minutes;

(5) after finishing incubation, adding 10 μl of 3 M KCl aqueous solution (supplier: Sigma-aldrich, Cat. 60135-250 ML), shaking well, and centrifuging at 3200 rcf at 4° C. for 15 minutes;

(6) for each group of tissue samples, adding 80 μL of supernatant into 120 μL of hybridization mixture (formula: 0.5 mL of 6 μM PNA probe (supplier: TAHE-PNA), 1 mL of 200 mM Trizma/pH=8, 5 mL of 8 M urea aqueous solution, 3.5 mL of H2O, 2 mL of acetonitrile); for each group of plasma samples, adding 40 μL of supernatant into 160 μL of hybridization mixture (formula: 0.5 mL of 6 μM PNA probe, 1 mL of 200 mM Trizma/pH=8, 5 mL of 8 M urea aqueous solution, 7.5 mL of H2O, 2 mL of acetonitrile);

(7) closing the plates and placing them in a PCR instrument, incubating at 95° C. for 15 minutes, then immediately placing on ice for 5 minutes;

(8) transferring the samples to new 96-well plates with conical bottom, shaking well, and centrifuging at 3200 rcf for 1 minute;

(9) injecting the samples for measurement and quantitatively analyzing by using HPLC-FLD (liquid-phase system supplier: Thermo Fisher, chromatography model: ultimate 3000).

Figure 4:
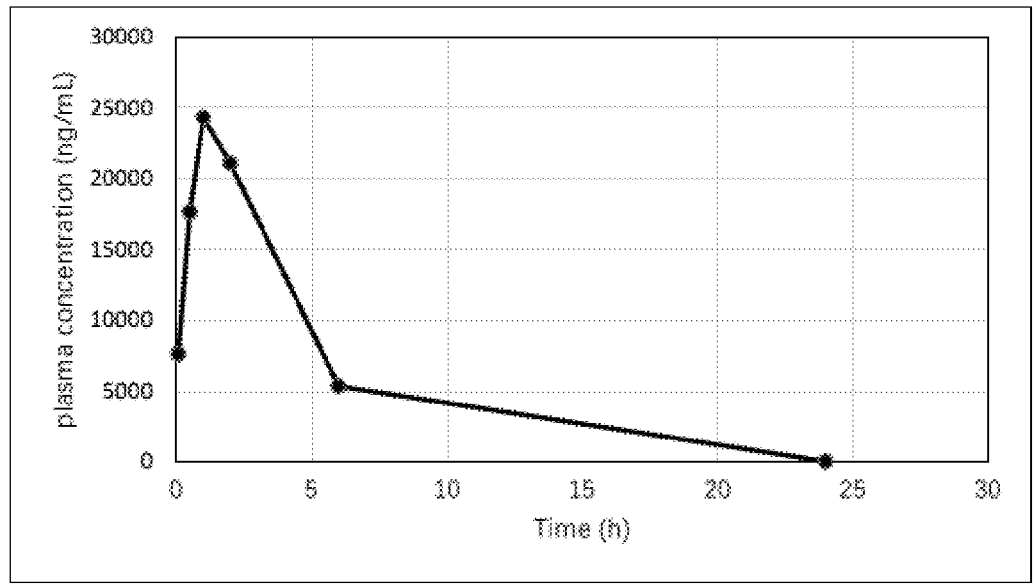
FIGS. 4-11 are metabolic profiles over time showing PK/TK plasma or tissue concentration for: Conjugate 24 in rat plasma at a dosage of 10 mg/kg (FIG. 4); Conjugate 24 in rat liver and kidney at a dosage of 10 mg/kg (FIG. 5); Conjugate 24 in rat plasma at a dosage of 50 mg/kg (FIG. 6); Conjugate 24 in rat liver and kidney at a dosage of 50 mg/kg (FIG. 7); Conjugate 25 in rat plasma at a dosage of 10 mg/kg (FIG. 8); Conjugate 25 in rat liver and kidney at a dosage of 10 mg/kg (FIG. 9); Conjugate 25 in rat plasma at a dosage of 50 mg/kg (FIG. 10); Conjugate 25 in rat liver and kidney at a dosage of 50 mg/kg (FIG. 11).

The analysis results can be found in FIGS. 4-11. FIGS. 4-7 show metabolic profiles over time of PK/TK plasma concentrations in rat plasma and PK/TK tissue concentrations in rat liver and kidney for Conjugate 24, respectively; FIGS. 8-11 show metabolic profiles over time of PK/TK plasma concentrations in rat plasma and PK/TK tissue concentrations in rat liver and kidney for Conjugate 25, respectively. Specifically, FIG. 4 is a metabolic profile over time showing PK/TK plasma concentration for Conjugate 24 in rat plasma at a dosage of 10 mg/kg.

Figure 5:
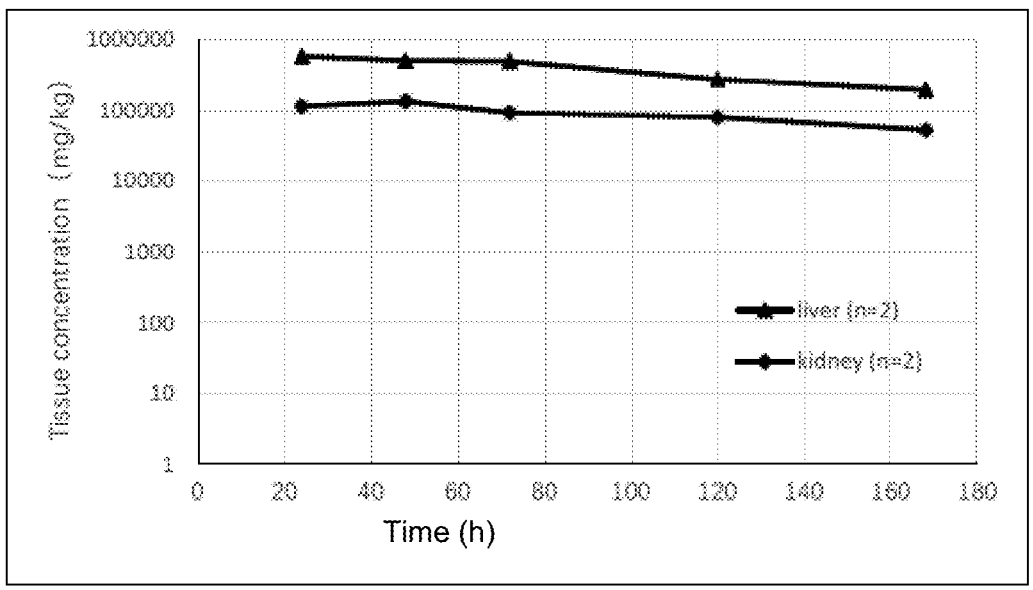

FIG. 5 is a metabolic profile over time showing PK/TK tissue concentrations for Conjugate 24 in rat liver and kidney at a dosage of 10 mg/kg.

Figure 6:
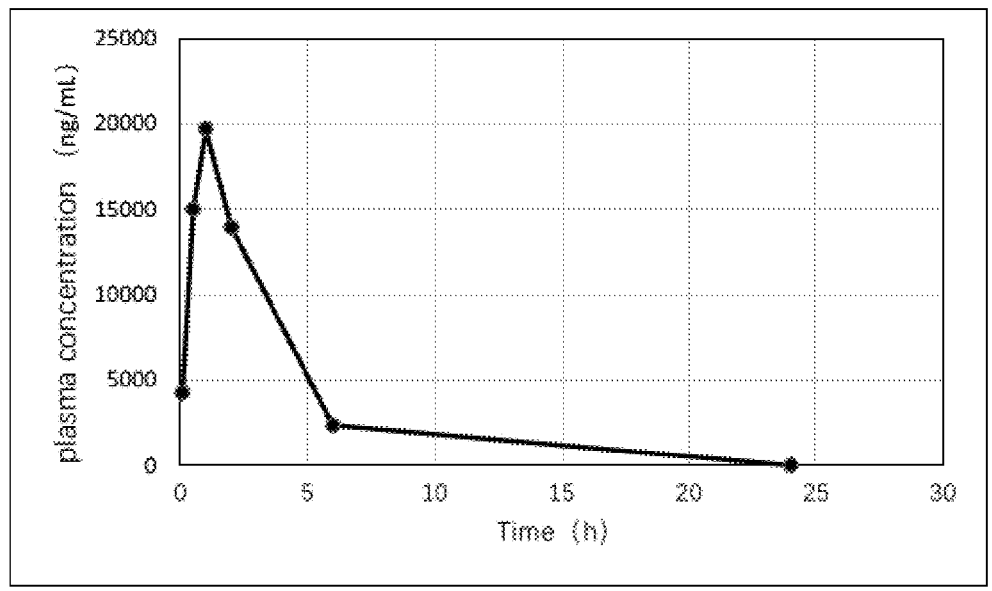

FIG. 6 is a metabolic profile over time showing PK/TK plasma concentration for Conjugate 24 in rat plasma at a dosage of 50 mg/kg.

Figure 7:
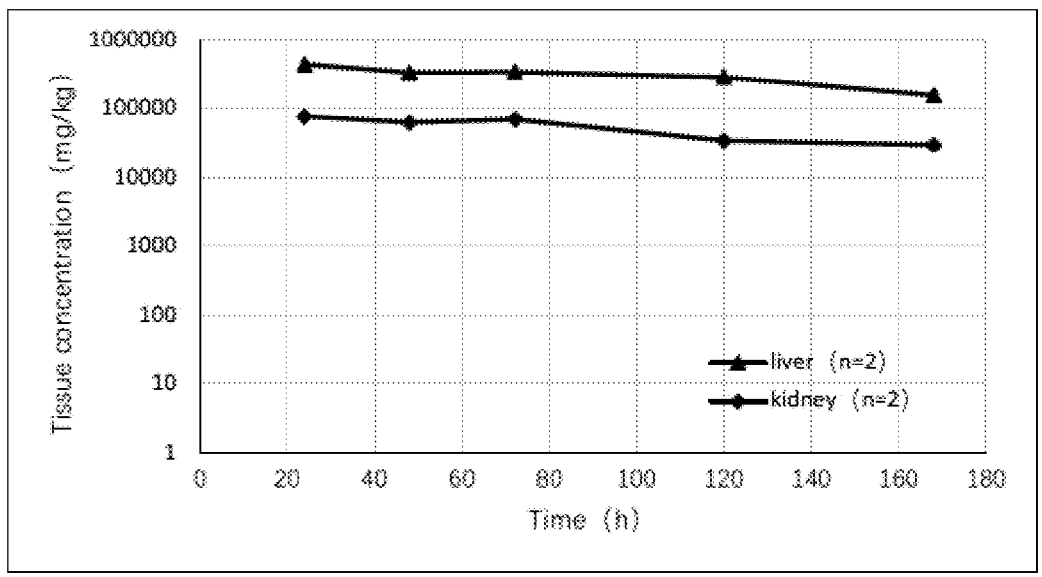

FIG. 7 is a metabolic profile over time showing PK/TK tissue concentrations for Conjugate 24 in rat liver and kidney at a dosage of 50 mg/kg.

Figure 8:
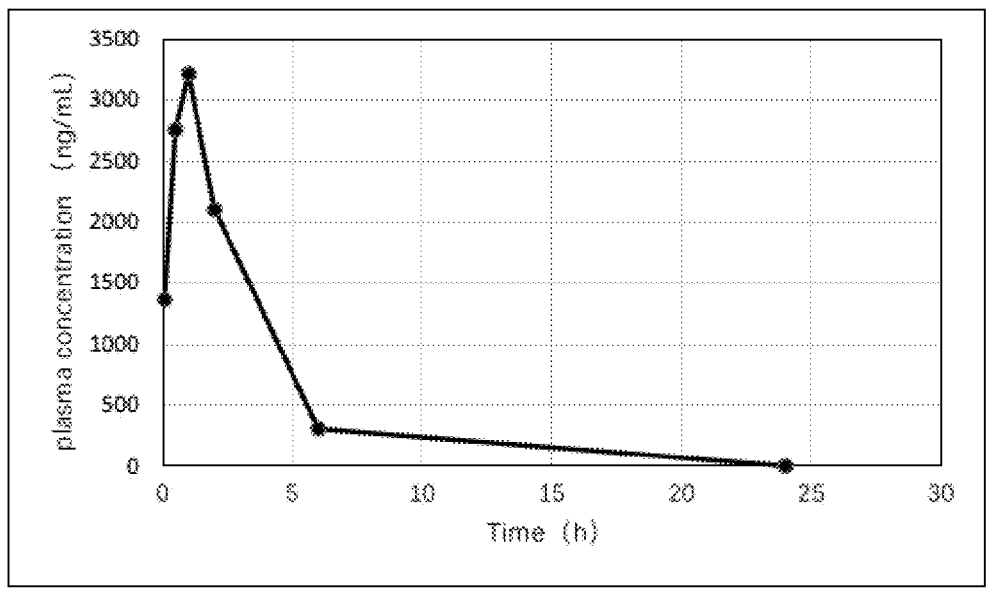

FIG. 8 is a metabolic profile over time showing PK/TK plasma concentration for Conjugate 25 in rat plasma at a dosage of 10 mg/kg.

Figure 9:
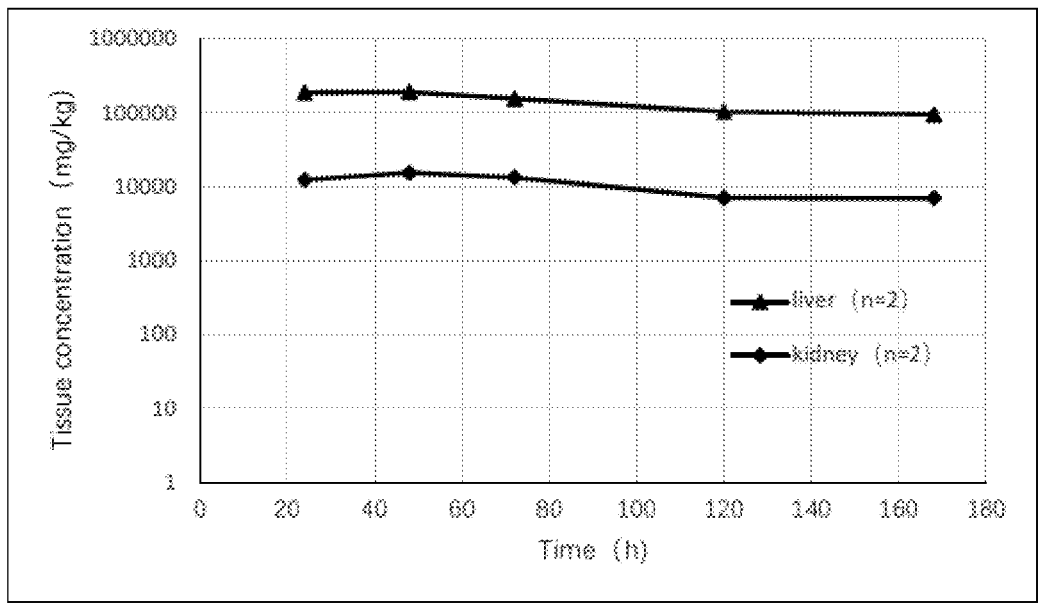

FIG. 9 is a metabolic profile over time showing PK/TK tissue concentrations for Conjugate 25 in rat liver and kidney at a dosage of 10 mg/kg.

Figure 10:
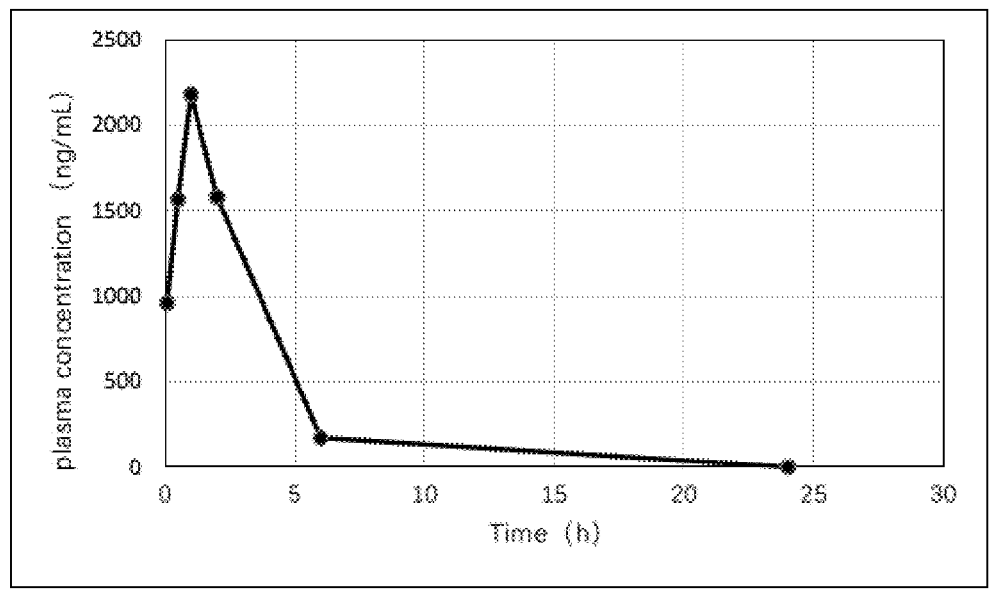

FIG. 10 is a metabolic profile over time showing PK/TK plasma concentration for Conjugate 25 in rat plasma at a dosage of 50 mg/kg.

Figure 11:
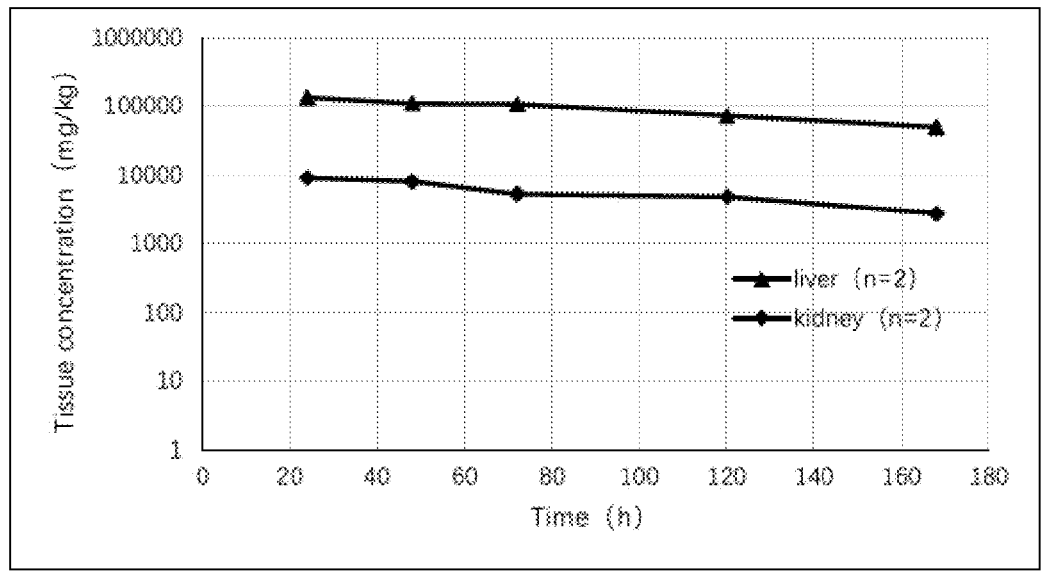
Figure 12A:
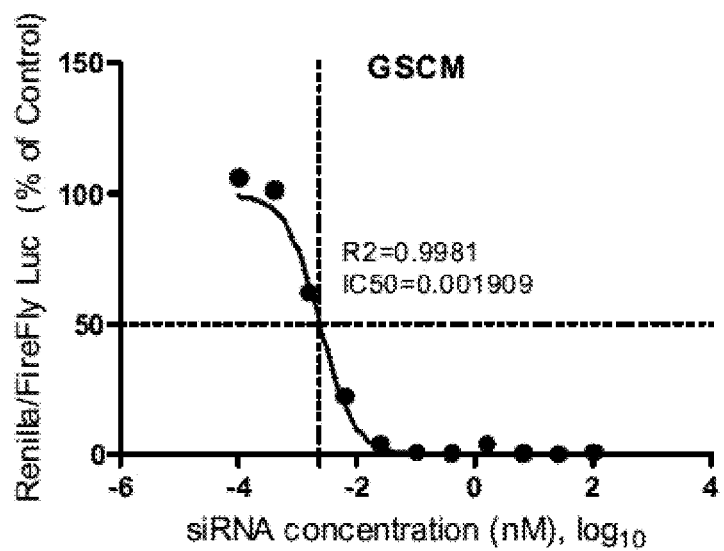
FIGS. 12A, 12B, 12C, and 12D show the determination of $IC_{50}$ value of Conjugate 24 in inhibiting expression of GSCM compared with GSSM, PSCM and PSSM, respectively.
Figure 12B:
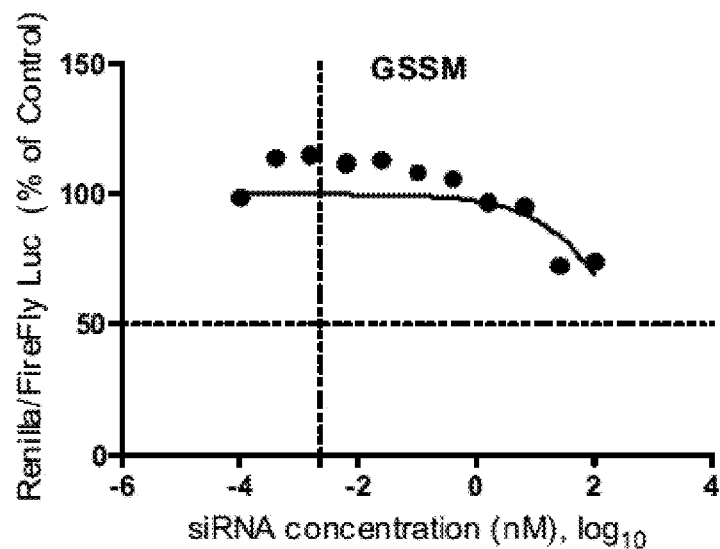
Figure 12C:
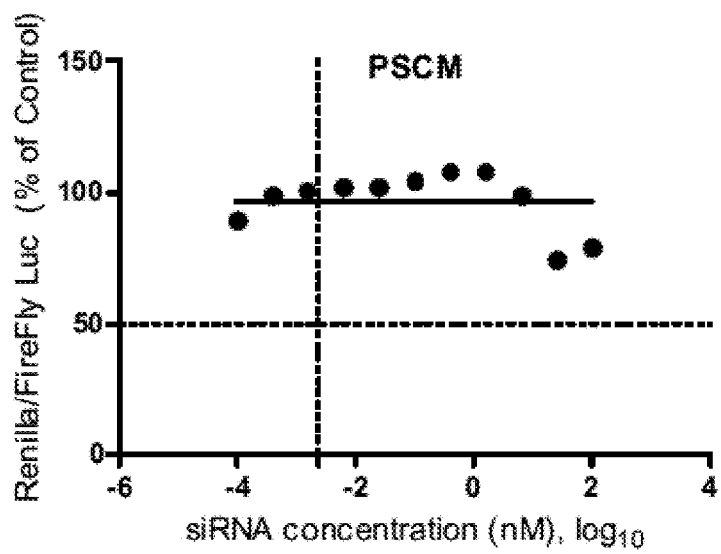
Figure 12D:
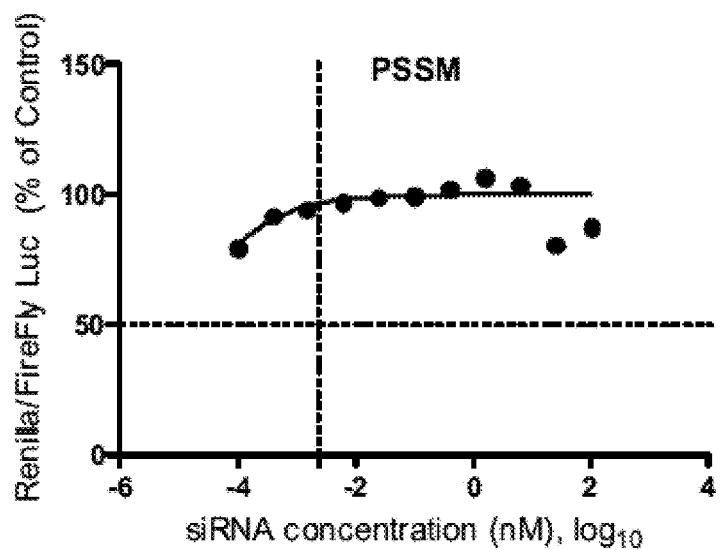

FIG. 11 is a metabolic profile over time showing PK/TK tissue concentrations for Conjugate 25 in rat liver and kidney at a dosage of 50 mg/kg.

As can be seen from the results of FIGS. 4-11, the concentrations for Conjugates 24 and 25 in rat plasma were rapidly decreased below the detection limit within several hours, while the concentrations at a relatively stable level were maintained over at least 168 hours in rat liver tissue, either at a low dosage (10 mg/kg) or at a relatively high dosage (50 mg/kg). This shows that the siRNA conjugate obtained by conjugating the L-9 conjugating molecule can be specifically and significantly enriched in liver and remain stable, showing a high degree of targeting.

Experimental Example 4 this Experiment Demonstrates the Inhibition Effect on Target mRNA Caused by Conjugates Formed of Different Conjugated Molecules in C57BL/6J Mice Firstly, C57BL/6J mice (all females) were randomly divided into groups. The experiment groups were numbered with Conjugate 158 (5 mice), Comparative Conjugate 14 (5 mice), and the PBS control group (8 mice), respectively. All animals were dosed according to body weight, and were subcutaneously administered at different single doses of 1 mg/kg or 0.1 mg/kg. The dosing volume was 5 ml/kg. For different doses, the conjugates were dissolved in a 0.9% aqueous solution of sodium chloride at the concentration of 0.2 mg/mL and 0.02 mg/mL. The animals were sacrificed 72 h after the administration, and the liver was collected; the liver tissue was homogenized with a tissue homogenizer, and total RNA was extracted by RNAVzol (VIGOROUS, lot: 161G) according to the standard procedure of total RNA extraction.

The expression level of TTR mRNA in liver tissue was detected by real-time fluorescent-based quantitative PCR. Specifically, the total RNA extracted was reverse-transcribed into cDNA using the Reverse Transcription System (Promega, Lot #0000223677, REF: A3500) according to the instructions. The quantitative fluorescence PCR instrument (ABI step One) was subsequently used to detect the inhibition efficiency of siRNA on mTTR mRNA expression in liver tissue. In this detection method, the GAPDH gene was used as an internal reference gene, and mTTR and GAPDH expressions were detected using primers for TTR and primers for GAPDH, respectively.

The sequences of the detection primers are shown in table 4.

TABLE 4

The sequences of detection primers

| gene | Upstream primer | Downstream primer |
| --- | --- | --- |
| mTTR | 5'-CCGTCTGTGCCTTCTCA TCT-3' (SEQ ID NO: 187) | 5'-TAATCTCCTCCCCCAAC TCC-3' (SEQ ID NO: 188) |
| GAPDH | 5'-AGAAGGCTGGGGCTCAT TTG-3' (SEQ ID NO: 189) | 5'-AGGGGCCATCCACAGTC TTC-3' (SEQ ID NO: 190) |

In this real-time PCR method, the expression of mTTR mRNA is expressed by the percentage of the remaining amount of TTR gene expression, and is calculated as follows:

Remaining amount of TTR gene expression=(copy number of TTR gene in test group/copy number of GAPDH in test group)/(copy number of TTR gene in control group/copy number GAPDH in control group)×100%

The mRNA inhibition rate of the conjugate is then calculated according to the following formula:

mRNA inhibition ratio=(1−remaining amount of TTR gene expression)×100%,

Wherein, the control group was mice which PBS was administered in the experiment, and each test group was a group of mice administered with different siRNA conjugates. The results are shown in Table 5.

TABLE 5

Inhibition effect of mTTR mRNA in mice

| | | mRNA inhibition ratio (%) | |
| --- | --- | --- | --- |
| siRNA conjugate | Sample serial number | 1 mg/kg | 0.1 mg/kg |
| Conjugate158 | L10-simTTR | 94 | 51 |
| Comp. Conjugate 14 | K4--simTTR | 74 | 18 |

The result demonstrates that, although with the same siRNA sequences and modifications, the target mRNA inhibition ratio of the Conjugate 158 was significantly higher than that of the Comparative Conjugate 14.

In the following experimental example 5 to experimental example 11, the properties and effects of the siRNA conjugates in tables 3A to 3F were experimentally verified according to the siRNA target position and sequence correlation.

Experimental Example 5—an Experiment for Verifying Effects of the siRNA Conjugates in Table 3A Experimental Example 5-1—an Experiment for Verifying Off-Target Effects of Conjugate 26

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008. 36(7), 2136-2151, plasmids for detection were constructed and co-transfected with the siRNA conjugates to be detected into HEK293A cells; and the expression level of the dual luciferase reporter gene were measured using a dual luciferase reporter detection kit. Specific steps are as follows:

Construction of Plasmids for Detection

Four recombinant plasmids were constructed using psi-CHECK™-2 (Promega™) plasmid, in which GSCM was expressed as the on-target plasmid; and PSCM, GSSM, and PSSM were expressed as the off-target plasmids:

(1) GSCM, containing a target sequence, the target sequence is fully complementarily pared with all 21 nucleotide sequences of the antisense strand in the conjugate to be detected.

(2) PSCM, containing a target sequence, the target sequence is fully complementarily pared with all 21 nucleotide sequences of the sense strand in the conjugate to be detected.

(3) GSSM, containing a target sequence, the target sequence is fully complementarily pared with the nucleotide sequence at positions 1-8 from the 5' end of antisense strand in the conjugate to be detected. The nucleotide sequence at positions 9-21 from the 5' end of antisense strand in the conjugate to be detected is complementary mismatched with its corresponding target sequence. The mismatch rule is: the nucleotide G, C, A or U in any position between 9 and 21 from the 5' end of antisense strand in the conjugate to be detected is respectively mismatched with the nucleotides T, A, C or G, in the corresponding position of the target sequence.

(4) PSSM, containing a target sequence, the target sequence is fully complementarily pared with the nucleotide sequence at positions 1-8 from the 5' end of sense strand in the conjugate to be detected. The nucleotide sequence at positions 9-21 from the 5' end of sense strand in the conjugate to be detected is complementary mismatched with its corresponding target sequence. The mismatch rule is: the nucleotide G, C, A or U in any position between 9 and 21 from the 5' end of sense strand in the conjugate to be detected is respectively mismatched with the nucleotides T, A, C or G, in the corresponding position of the target sequence.

The target sequence was inserted into the Xho I/Not I site of the psiCHECK™-2 plasmid.

Transfection

In a 96-well plate, siRNA and each of the above plasmids were co-transfected according to the instructions of Lipofectamine™ 2000 (Invitrogen), each plasmid with 11 groups of corresponding siRNA at certain concentrations, respectively. Specifically, 10 ng of plasmid was transfected per well; and the final concentration of siRNA co-transfected per well was from 100 nM to 0.0001 nM (4-fold serial dilutions), 3 replicate wells per group, using 0.2 μL of Lipofectamine™ 2000 per well.

Detection 24 hours post co-transfection, the HEK293A cells were lysed by using a dual luciferase reporter gene assay kit (Promega, cat. E2940) according to the instruction manual to detect the expression level of the dual luciferase reporter gene. For each test group of certain concentration, those untreated with the conjugate are used as control (con). The Renilla luciferase protein level (Ren) was normalized to the firefly luciferase protein level (Fir). The dose-response curves were plotted by the activity results measured at different siRNA concentrations, and the curves were modeled using Function log(inhibitor) vs. response-Variable slope of Graphpad 5.0 software with the formula below:

$$Y = \text{Bot} + \frac{\text{Top} - \text{Bot}}{1 + 10^{(LogIC50-X) \times HillSlope}}$$

wherein
Y is the expression level of remaining mRNA,
X is the logarithm of the concentration of transfected siRNA,
Bot is the Y value at the bottom of the asymptote,
Top is the Y value at the top of the asymptote,
LogIC$_{50}$ is the X value at which Y is median value between the bottom and the top of the asymptote, and HillSlope is the slope of the curve.

The IC$_{50}$ of the conjugate to be detected corresponding to GSCM was determined via calculation based on the dose-effect curve, and then was compared with PSCM, GSSM or PSSM.

For Conjugate 24, the results are shown in FIGS. 12A-12D, and the IC$_{50}$ value of Conjugate 24 corresponding to GSCM was calculated as 0.0019 nM; compared with PSCM, GSSM or PSSM, Conjugate 24 showed no significant inhibitory effect at each siRNA concentration, indicating that the siRNA conjugate of the present disclosure possesses relatively high activity in vitro and low off-target effects.

Experimental Example 5-2—this Experiment Illustrates the Inhibitory Efficiency of the siRNA Conjugates in Table 3A in Expression of HBV mRNA In Vivo In this experimental example, the inhibitory efficiencies of Conjugates 16 and 24 in the expression of HBV mRNA in HBV transgenic mice C57BL/6J-Tg (Alb1HBV) 44Bri/J were investigated.

At first, C57BL/6J-Tg (Alb1HBV) 44Bri/J mice were randomly divided into groups based on HBsAg content in serum (all female, 4 mice in each group) and respectively numbered as Conjugate 16 and Conjugate 24, and a normal saline (NS) group was added as a control group. The drug dosages for all animals were calculated according to the body weight. A single dose was administered subcutaneously, with the dosage of 1 mg/kg, respectively in a conjugate concentration of 0.2 mg/ml and 0.02 mg/ml in 0.9 wt % NaCl aqueous solution and the dosage volume of 5 ml/kg. Animals were sacrificed at day 14 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction thereof, and then the inhibitory efficiency of siRNAs in the expression of HBV mRNA in liver tissue was measured by using the fluorescent qPCR kit (Beijing Cowin Biosicences Co., Ltd). In this fluorescent qPCR method, β-actin gene was used as an internal control gene, the HBV and 3-actin were detected by using primers for HBV and β-actin, respectively.

Sequences of primers for detection are shown in Table 5A.

TABLE 5A

Sequences of primers for detection

| Genes | Upstream Primers | Downstream Primers |
|---|---|---|
| HBV | 5'-CCGTCTGTGCCTTCTCA TCT-3' (SEQ ID NO: 187) | 5'-TAATCTCCTCCCCCAA CTCC-3' (SEQ ID NO: 188) |
| β-actin | 5'-AGCTTCTTTGCAGCTCC TTCGTTG-3' (SEQ ID NO: 191) | 5'-TTCTGACCCATTCCCA CCATCACA-3' (SEQ ID NO: 192) |

In this fluorescent qPCR method, the expression of HBV mRNA was expressed as the remaining expression of HBV gene and calculated by the following equation: The remaining expression of HBV gene=(the copy number of HBV gene in the test group/the copy number of β-actin gene in the test group)/(the copy number of HBV gene in the control group/the copy number of β-actin gene in the control group)×100%, which is marked as HBV X/β-actin mRNA expression.

Figure 13:
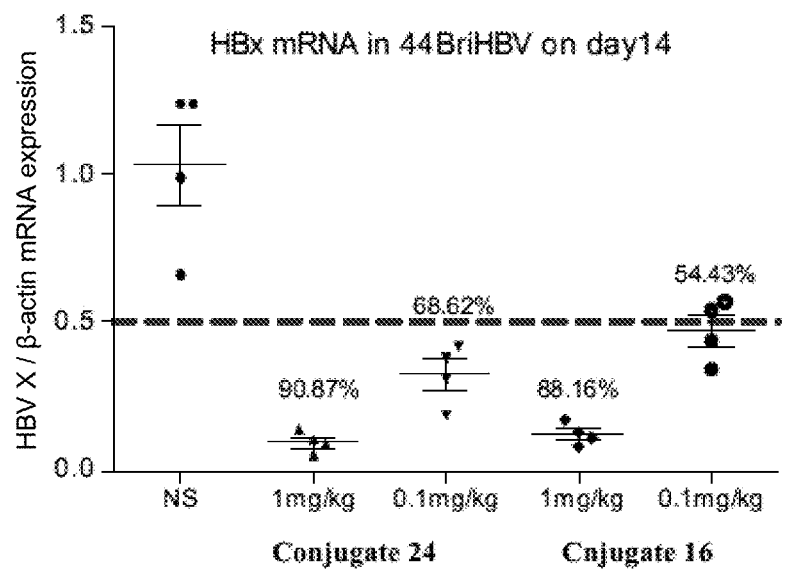
FIGS. 13-15 show inhibition of HBV mRNA by the conjugates disclosed herein in vivo.

Then, the inhibition ratio against mRNA of the conjugate was calculated according to the following equation:

The inhibition ratio against mRNA=(1−the remaining expression of HBV gene)×100%, wherein, the control group was a group of control mice administrated with NS in this experiment and each test group was a group of mice administrated with different siRNA conjugates, respectively. The results are shown in FIG. 13.

Figure 14:
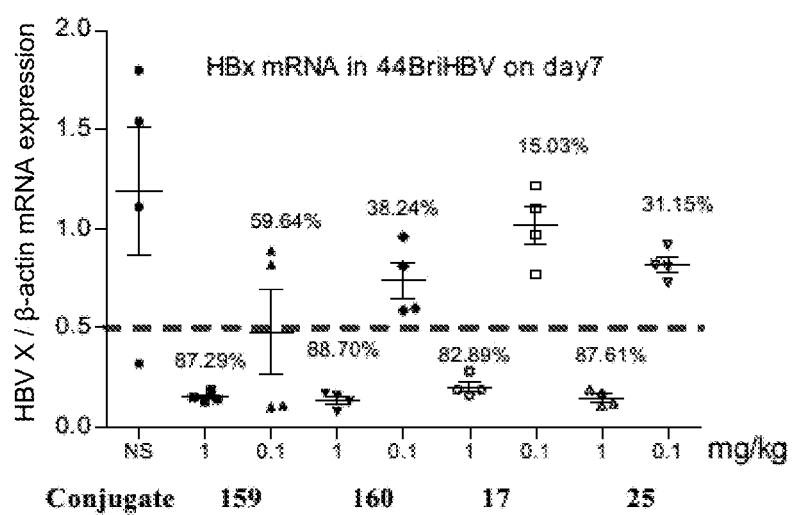
Figure 15:
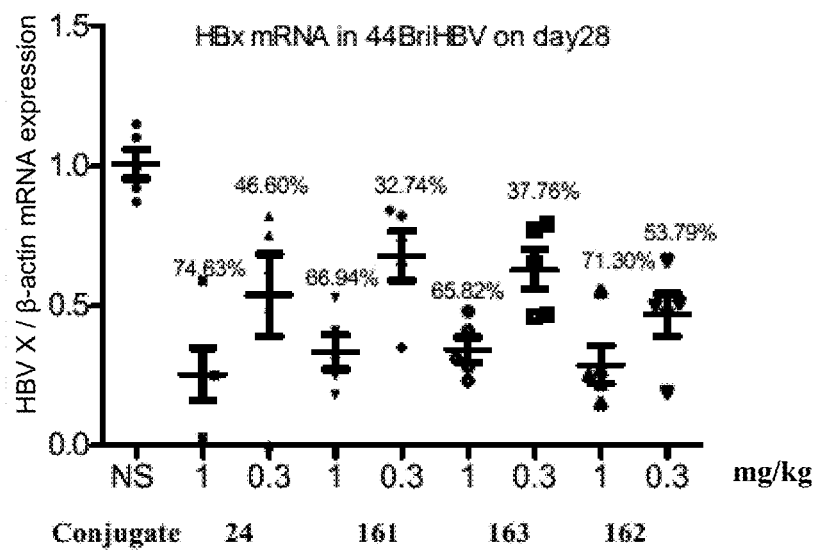

In other experiments, two tests were further proceeded according to the protocol below: Method same to the above was employed, except in that the siRNA conjugated administrated for testing is replaced with Conjugate 17, 25, 159 and 160, and the data is collected in day 7; and Method same to the above was employed, except in that the siRNA conjugated administrated for testing is replaced with Conjugate 24, 161, 162 and 163, and the data is collected in day 28, and each conjugate is administrated in the dosages of 1 mg/kg and 0.3 mg/kg (wherein the dosage volume remain the same, while the concentration of the conjugate solution respectively adjusted). The results thereof are respectively shown in FIGS. 14 and 15.

As can be seen from the above results, in several experiments with different testing time points, all conjugates above of the present disclosure show high inhibitory activity in the expression of HBV mRNA in mice in vivo.

Experimental Example 5-3—this Experiment Illustrates the Inhibitory Efficiency of the siRNA Conjugates with Different Conjugating Molecules in Table 3A in the Expression of HBsAg and HBV DNA in HBV Transgenic Mice Serum According to the method of Experimental Example 4, in 44Bri HBV mice, Sequences for detection of Table 5A were used as primers to measure the inhibitory efficiency of Conjugates 25, 164, 165 and 166 to the target mRNA. The results thereof are respectively shown in Table 6A.

TABLE 6A

Inhibitory efficiency of siRNA conjugates to the target mRNA

| siRNA conjugate | NO. | mRNA Inhibitory efficiency (%) | |
|---|---|---|---|
| | | 1 mg/kg | 0.1 mg/kg |
| Conjugate 25 | L10-siHBa1M2SP | 91 | 40 |
| Conjugate 164 | P10-siHBa1M2SP | 92 | 65 |
| Conjugate 165 | W8-siHBa1M2SP | 96 | 74 |
| Conjugate 166 | Z5-siHBa1M2SP | 96 | 78 |

As can be seen from Table 6A, siRNA conjugates formed by various conjugating molecules of the present disclosure show excellent inhibitory efficiency to the target mRNA in mice in vivo.

Experimental Example 5-4—This experiment illustrates a time-dependent test of the inhibitory efficiency of the siRNA conjugates in Table 3A to HBsAg and HBV DNA in HBV transgenic mice serum.

An AAV-HBV mouse model was employed. After successful establishment of the animal models, these mice were randomly divided into groups based on HBsAg content in serum (5 mice in each group). Conjugates 24, 25 and Comparative Conjugate 15 were respectively administered to each group, and NS was used as a blank control. The drug dosages for all animals were calculated according to the body weight. A single dose was administered subcutaneously, with the dosage of 3 mg/kg, and is provided at 0.6 mg/ml in 0.9 wt % NaCl aqueous solution and the volume of 5 ml/kg. The blood was taken from mouse orbital venous plexus before administration and at days 7, 14, 21, 28, 56, 84, 112, 140, 154, 168 and 182 after administration, and HBsAg level in serum was measured for each time point. During the experiment, a test to a subject is ended once the HBsAg content in serum is close to or over the original value in the test result thereof.

The blood taken from the orbit was about 100 µl each time, and the serum was no less than 20 µl after centrifugation. The expression level of HBsAg in serum was measured by using HBsAg CLIA kit (Autobio, CL0310). The expression level of HBV DNA was measured by extraction of the DNA from the serum with reference to the instruction of QIAamp 96 DNA Blood Kit followed by qPCR.

The normalized HBsAg expression=(the content of HBsAg after administration/the content of HBsAg before administration)×100%.

The inhibition ratio against HBsAg=(1−the content of HBsAg after administration/the content of HBsAg before administration)×100%, wherein the content of HBsAg was expressed in equivalents(UI) of HBsAg per milliliter(ml) of serum.

The normalized HBV DNA expression=(the content of HBV DNA after administration/the content of HBV DNA before administration)×100%.

The inhibition ratio against HBV DNA=(1−the content of HBV DNA after administration/the content of HBV DNA before administration)×100%, wherein the content of HBV DNA was expressed in copies of HBV DNA per milliliter (ml) of serum.

Figure 16:
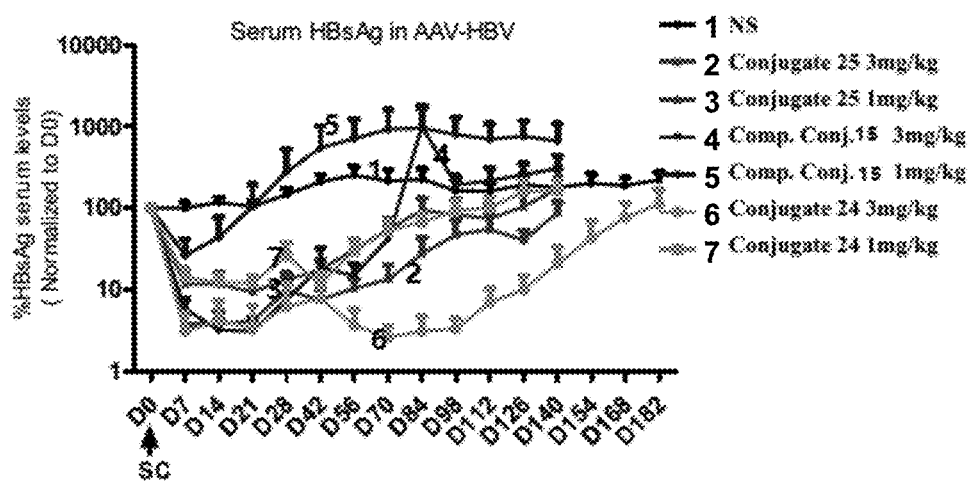
FIG. 16 shows a time-dependent inhibition of HBsAg expression in HBV transgenic mice serum by conjugates disclosed herein.
Figure 17:
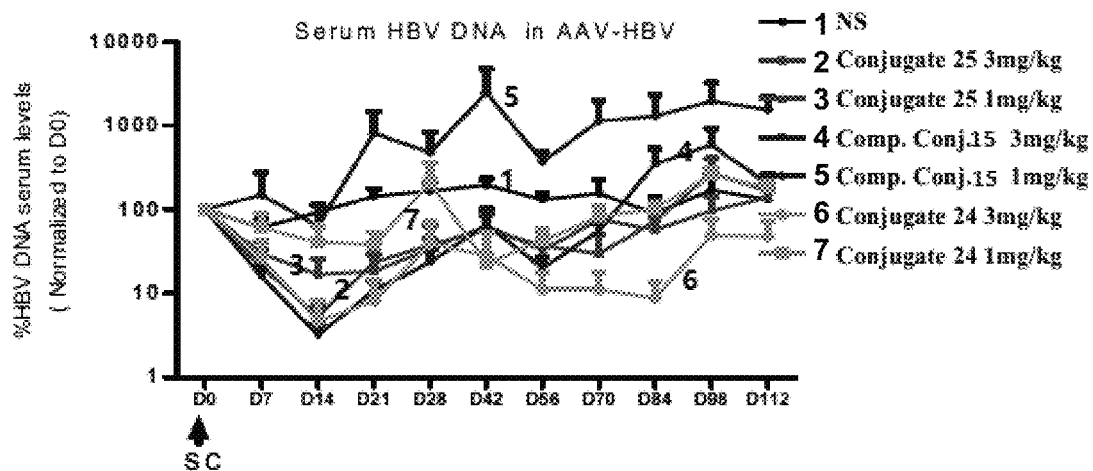
FIG. 17 shows a time-dependent inhibition of HBV DNA expression in HBV transgenic mice serum by conjugates disclosed herein.

The results are shown in FIGS. 16 and 17. As can be seen from the results of FIG. 16, the NS negative control group shows no inhibitory effect at different time points after administration; in contrast, both Conjugates 24 and 25 show excellent inhibitory effect against HBsAg at different time points after administration. In particular, Conjugate 24 at the dose of 3 mg/kg consistently shows high inhibition ratio against HBsAg in serum over a period of up to 140 days, indicating that it can stably and efficiently inhibit the expression of HBV gene over a longer period.

As can be seen from the results of FIG. 17, the siRNA conjugate of each example also shows efficient inhibition against the expression of HBV DNA and maintains a relatively high inhibition ratio over a period of up to 84 days.

In contrast, although Comparative Conjugates 15 achieve approximate mRNA inhibitory effects as in each example in the first 28 days, the inhibitory effects markedly reduced thereafter, thus the duration of the inhibitory effects thereof shown in FIG. 16 and FIG. 17 are significantly shorter than that of Conjugates 24 and 25 at same dose level.

Figure 18:
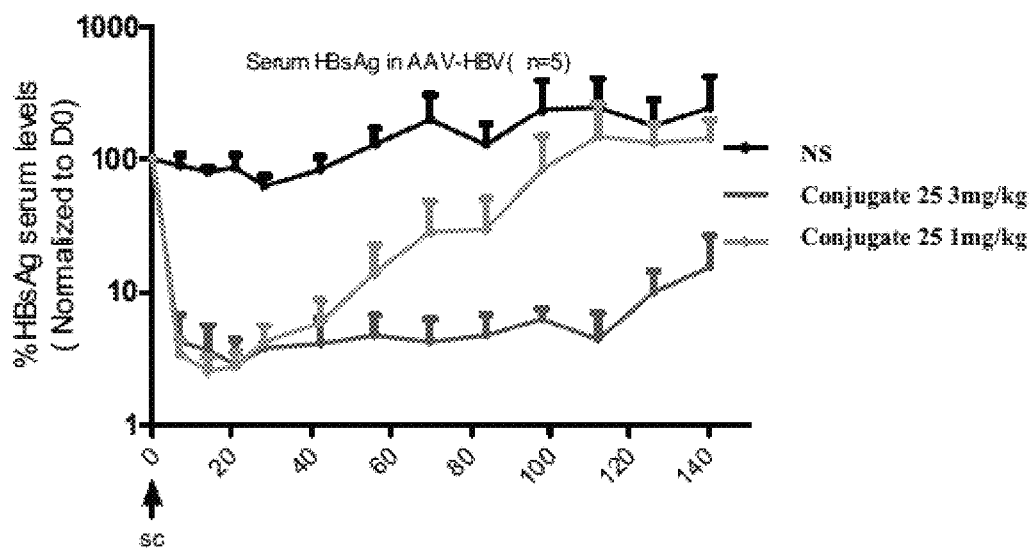
FIG. 18 shows a time-dependent inhibition of HBsAg expression in HBV transgenic mice serum by Conjugate 25 disclosed herein.
Figure 19:
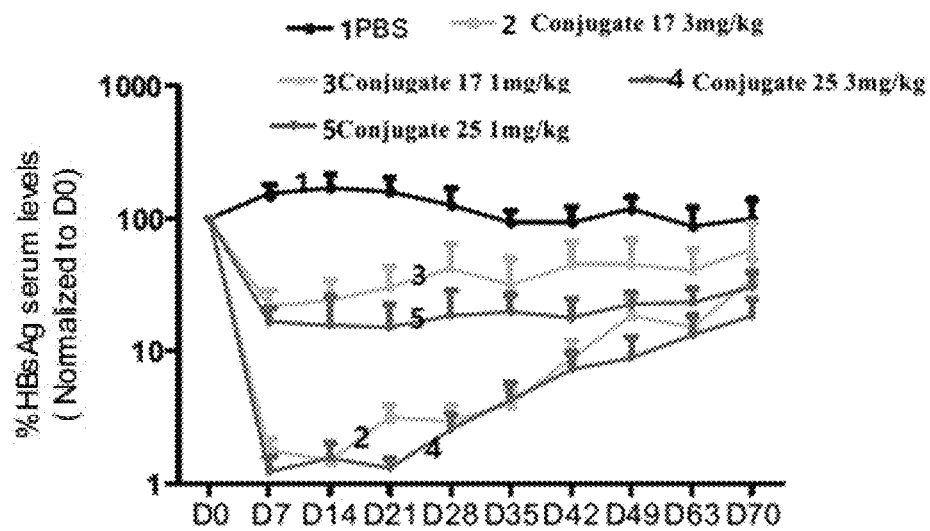
FIG. 19 shows a time-dependent inhibition of HBsAg expression in M-Tg models by conjugates disclosed herein.
Figure 20:
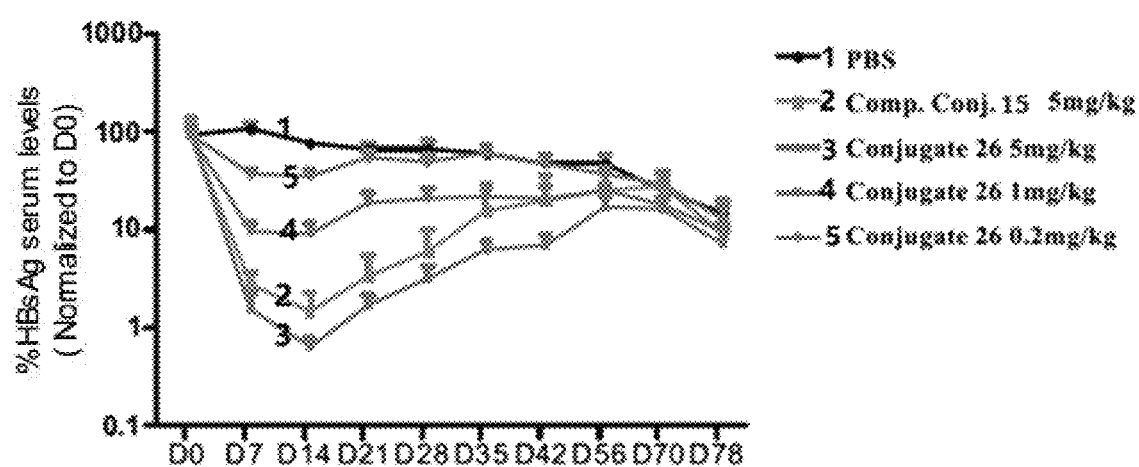
FIG. 20 shows a time-dependent inhibition of HBsAg expression in M-Tg models by conjugates disclosed herein.
Figure 21:
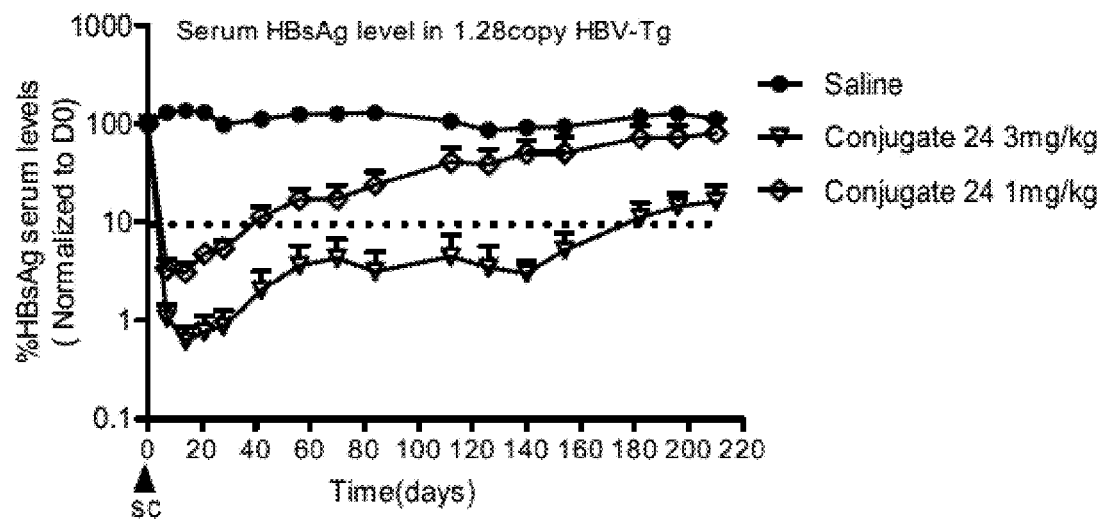
FIG. 21 shows a time-dependent inhibition of HBsAg expression in 1.28 copy HBV-Tg models by conjugates disclosed herein.

According to the same methods as above, four more tests were further proceeded, wherein serum HBsAg is measured, except in that:

In AAV-HBV low concentration mouse models, 3 mg/kg and 1 mg/kg of Conjugate 25 were dosed respectively, NS was used as a control, the test continues until day 140, and the results are shown in FIG. 18;

In M-Tg models, 3 mg/kg and 1 mg/kg of Conjugates 17 and 25 were dosed respectively, PBS was dosed as control, the test continues until day 70, and the results are shown in FIG. 19;

In M-Tg models, 5 mg/kg, 1 mg/kg and 0.2 mg/kg of Conjugate 26 and 5 mg/kg of Comparative Conjugate 15 were dosed respectively, PBS was dosed as control, the test continues until day 78, and the results are shown in FIG. 20; In 1.28 copy models, 3 mg/kg and 1 mg/kg of Conjugate 24 were dosed respectively, the test continues until day 210, and the results are shown in FIG. 21.

For various dosages above, each conjugate was administrated in the same dose volume, while concentration of the conjugate solution individually adjusted, so as to be dosed accordingly.

From the results of FIGS. 18-21, it can be seen that the siRNA conjugates of the disclosure show prolonged and efficient inhibitory efficiency to serum HBsAg in various animal models, and regular dose dependency was revealed.

Experimental Example 6—an Experiment for Verifying Effects of the siRNA Conjugates in Table 3B-3D Experimental Example 6-1—Off-Target Effect Tests for Conjugates 43, 62 and 78

Figure 22:
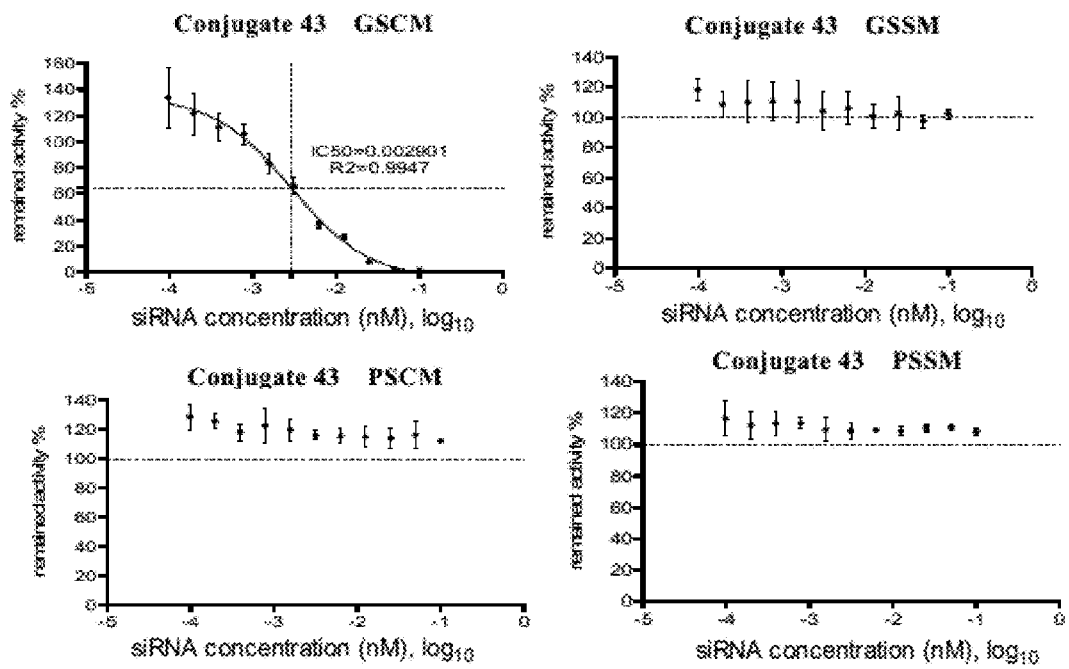
FIGS. 22-24 show the inhibition on target mRNA vs. off-target mRNA of the conjugates disclosed herein.
Figure 23:
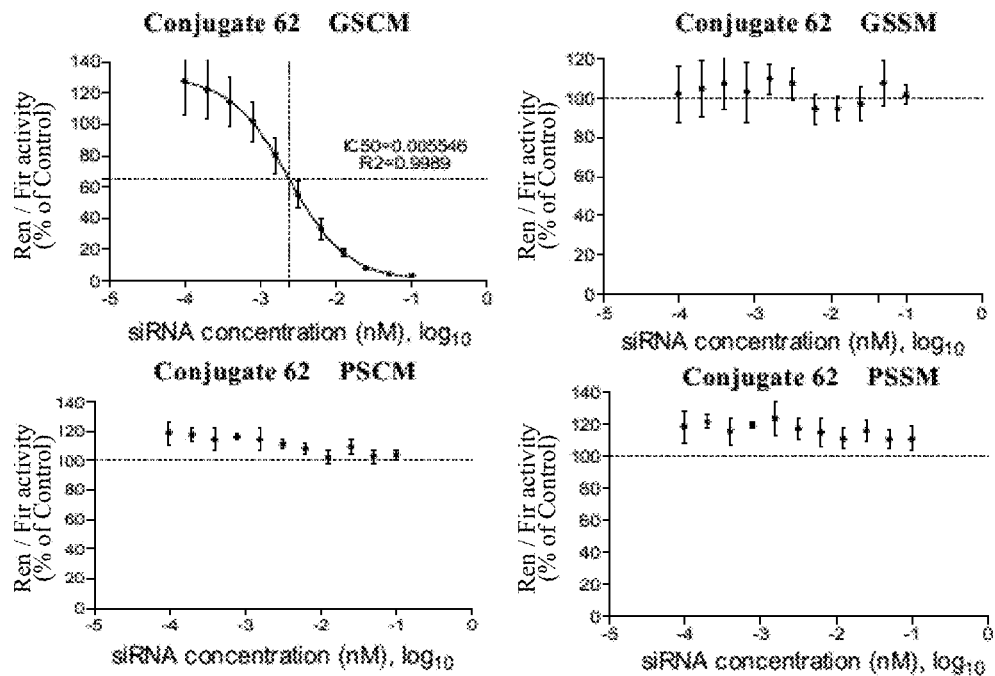
Figure 24:
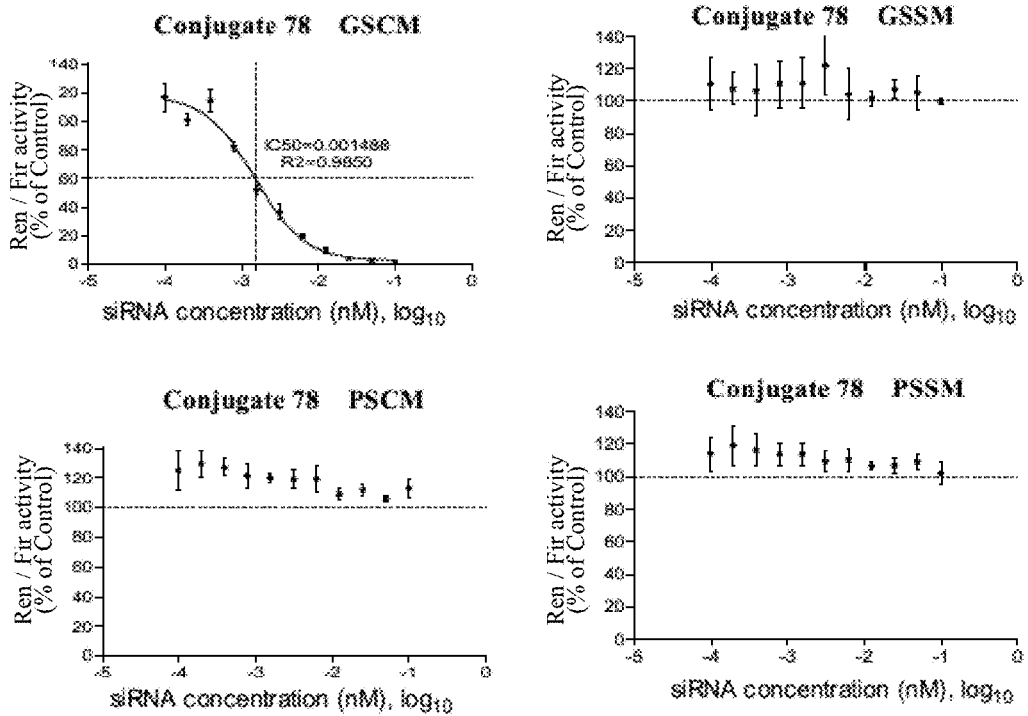

According to methods described in Experimental Example 5-1, Off-target effect of Conjugates 43, 62 and 78 was individually tested, except in that: for each conjugate, a target sequence fully complementarily paired with the anti-sense strand sequence of the siRNA in the corresponding conjugate is employed to construct the on-target plasmid GSCM, while target sequences fully the same with the anti-sense strand sequence, complementarily paired with positions 1-8 of the antisense strand sequence or the same with positions 1-8 of the antisense strand sequence of the siRNA in the corresponding conjugate were respectively employed to construct the off-target plasmids GSSM, PSCM and PSSM. The results are shown in FIGS. 22-24, respectively. From the results of FIGS. 22-24, it can be seen that all the conjugates above not only have excellent inhibitory effect to the target mRNA, but also show low off-target effects.

Experimental Conjugate 6-2—this Experiment Illustrates the Inhibitory Efficiency of the Conjugates of the Present Disclosure in Expression of HBV mRNA in Mice In Vivo In this experimental example, the inhibitory efficiencies of Conjugates 25, 42, 43, 62 and 78 in the expression of HBV mRNA in HBV transgenic mice C57BL/6J-Tg (Alb1HBV) 44Bri/J were investigated.

At first, C57BL/6J-Tg (Alb1HBV) 44Bri/J mice were randomly divided into groups based on HBsAg content in serum (all female, 4 mice in each group) and numbered individually, and an NS group was added as a control group. The drug dosages for all animals were calculated according to the body weight. A single dose of Conjugate 24 or 42 was administered subcutaneously, each with the dosage of 1 mg/kg or 0.1 ml/kg, respectively as 0.2 mg/ml and 0.02 mg/ml conjugate in 0.9 wt % NaCl aqueous solution and the dosage volume of 5 ml/kg. Animals were sacrificed at day 7 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction thereof, and then the inhibitory efficiency of siRNAs in the expression of HBV mRNA in liver tissue was measured by using the fluorescent qPCR kit (Beijing Cowin Biosicences Co., Ltd). In this fluorescent qPCR method, β-actin gene was used as an internal control gene, the HBV and 3-actin were detected by using primers for HBV and β-actin, respectively.

Sequences of primers for detection are shown in Table 5A.

Figure 25:
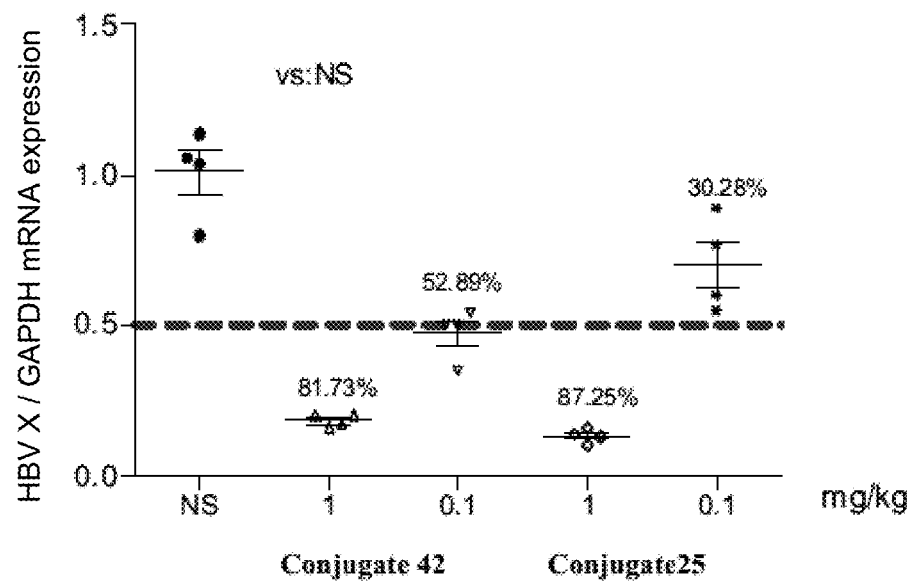
FIGS. 25-27 show inhibition of HBV mRNA by the conjugates disclosed herein in vivo.

In this fluorescent qPCR method, the calculation of the expression of HBV mRNA as well as the inhibition ratio against mRNA for the conjugates are in accordance with Experimental Example 5-2.

wherein, the control group was a group of control mice administrated with NS in this experiment and each test group was a group of mice administrated with different siRNA conjugates, respectively. The results are shown in FIG. 25.

Figure 26:
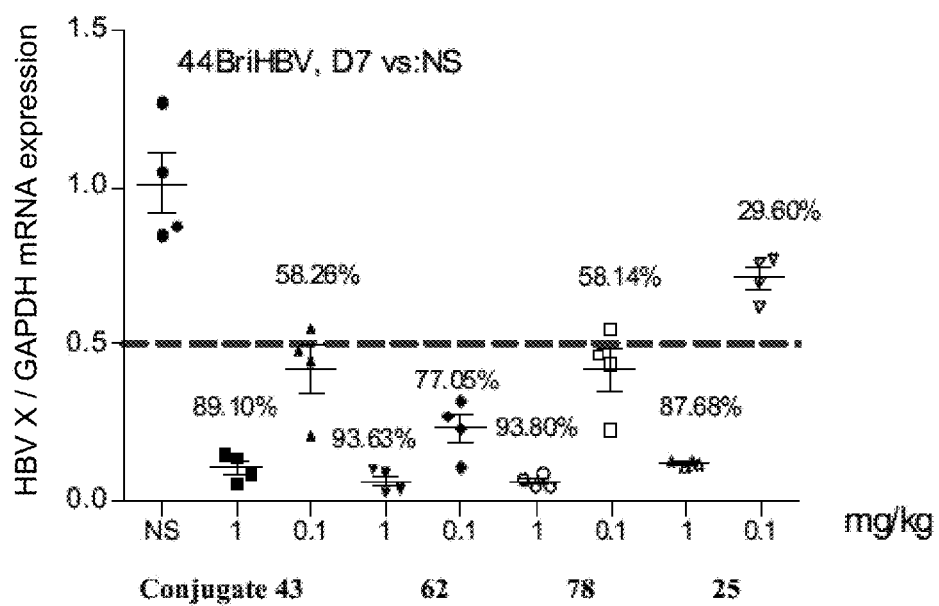

In other experiments, two tests were further proceeded according to the protocol below:

Method same to the above was employed, except in that the siRNA conjugated administrated for testing is replaced with Conjugate 43, 62, 78 and 25, and the data is collected in day 7, the results are shown in FIG. 26; and Method same to the above was employed, except in that the siRNA conjugated administrated for testing is replaced with Conjugate 42, 43 and 25, and each of Conjugate 42 and 25 is administrated in the dosages of 1 mg/kg and 0.1 mg/kg (wherein the dosage volume remain the same, while the concentration of the conjugate solution respectively adjusted). Moreover, the sequences of primers for detection are replaced with sequences shown in Table 5B. The results are shown in FIG. 27.

TABLE 5B

| | Sequences of primers for detection | |
|---|---|---|
| Genes | Upstream Primers | Downstream Primers |
| HBV | 5'-CCGTCTGTGCCTTCTCA TCT-3' (SEQ ID NO: 187) | 5'-TAATCTCCTCCCCCAA CTCC-3' (SEQ ID NO: 188) |
| β-actin | 5'-AGCTTCTTTGCAGCTCC TTCGTTG-3' (SEQ ID NO: 191) | 5'-TTCTGACCCATTCCCA CCATCACA-3' (SEQ ID NO: 192) |

Figure 27:
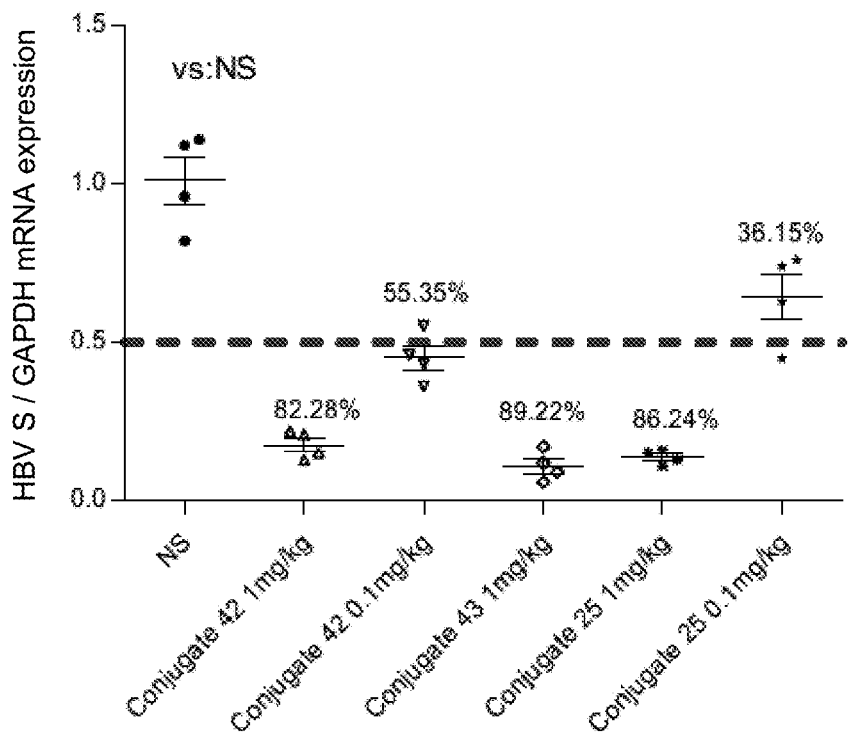

As can be seen from FIGS. 26 and 27, all conjugates above of the present disclosure show high inhibitory activity in the expression of HBV mRNA in mice in vivo. Moreover, inhibitory effects thereof to different kinds of HBV mRNA remain basically the same.

Experimental Example 6-3—this Experiment Illustrates a Time-Dependent Test of the Inhibitory Efficiency of the siRNA Conjugates in Table 3B in the Expression of HBsAg and HBV DNA in HBV Transgenic Mice Serum An AAV-HBV low concentration mouse model was employed. After successful establishment of the animal models, these mice were randomly divided into groups based on HBsAg content in serum (5 mice in each group). Conjugate 43 were respectively administered to each group, and PBS was used as a blank control. The drug dosages for all animals were calculated according to the body weight. A single dose was administered subcutaneously, with the dosage of 3 mg/kg or 1 mg/kg, with respect to 0.6 mg/ml or 0.2 mg/ml of conjugate in 0.9 wt % NaCl aqueous solution and the volume of 5 ml/kg. The blood was taken from mouse orbital venous plexus before administration and at days 7, 14, 21, 28, 56, 84, 112, 126 and 140 after administration, and HBsAg level in serum was measured for each time point.

The blood taken from the orbit was about 100 µl each time, and the serum was no less than 20 µl after centrifugation. The content of HBsAg in serum was measured by using HBsAg CLIA kit (Autobio, CL0310).

The normalized HBsAg expression=(the content of HBsAg after administration/the content of HBsAg before administration)×100%.

> The inhibition ratio against HBsAg=(1−the content of HBsAg after administration/the content of HBsAg before administration)×100%, wherein the content of HBsAg was expressed in equivalents(UI) of HBsAg per milliliter(ml) of serum.

Figure 28:
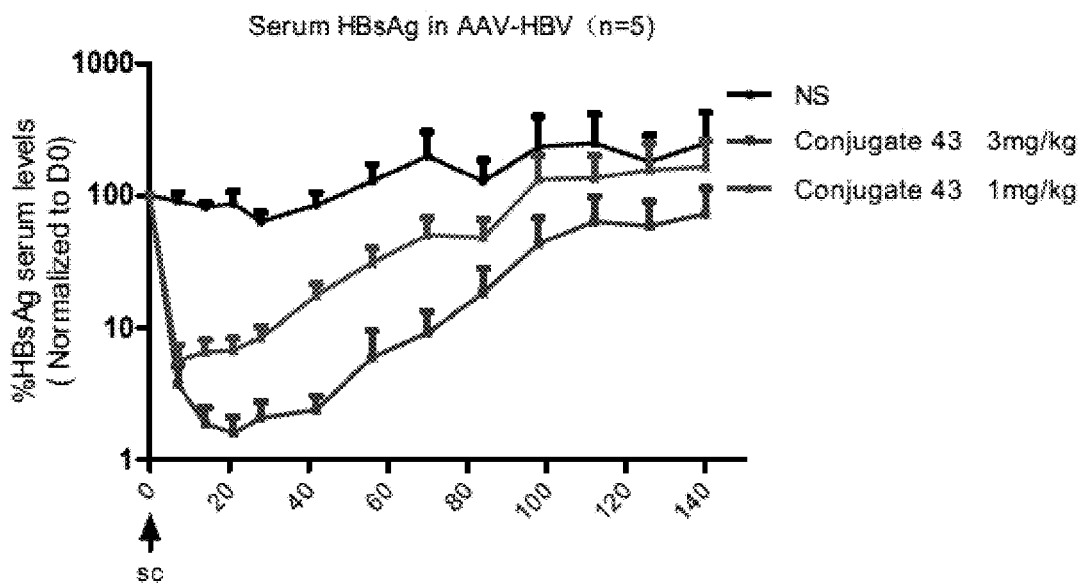
FIG. 28 shows a time-dependent inhibition of HBsAg expression in HBV transgenic mice serum by conjugates disclosed herein.

The results are shown in FIG. 28. As can be seen from the results of FIG. 28, the NS negative control group shows no inhibitory effect at different time points after administration; in contrast, Conjugate 43 shows excellent inhibitory effect against HBsAg at different time points after administration, and consistently shows high inhibition ratio against HBsAg in serum over a period of up to 100 days, indicating that it can stably and efficiently inhibit the expression of HBV gene over a longer period.

In further experiments, according to the methods described above, in M-tg model mice, 3 mg/kg and 1 mg/kg of Conjugates 24, 62 and 78 were dosed respectively, with respect to 0.6 mg/ml or 0.2 mg/ml of conjugate in 0.9 wt % NaCl aqueous solution and the volume of 5 ml/kg. The test continues until day 85, and the results are shown in FIGS. 29 and 30.

Figure 29:
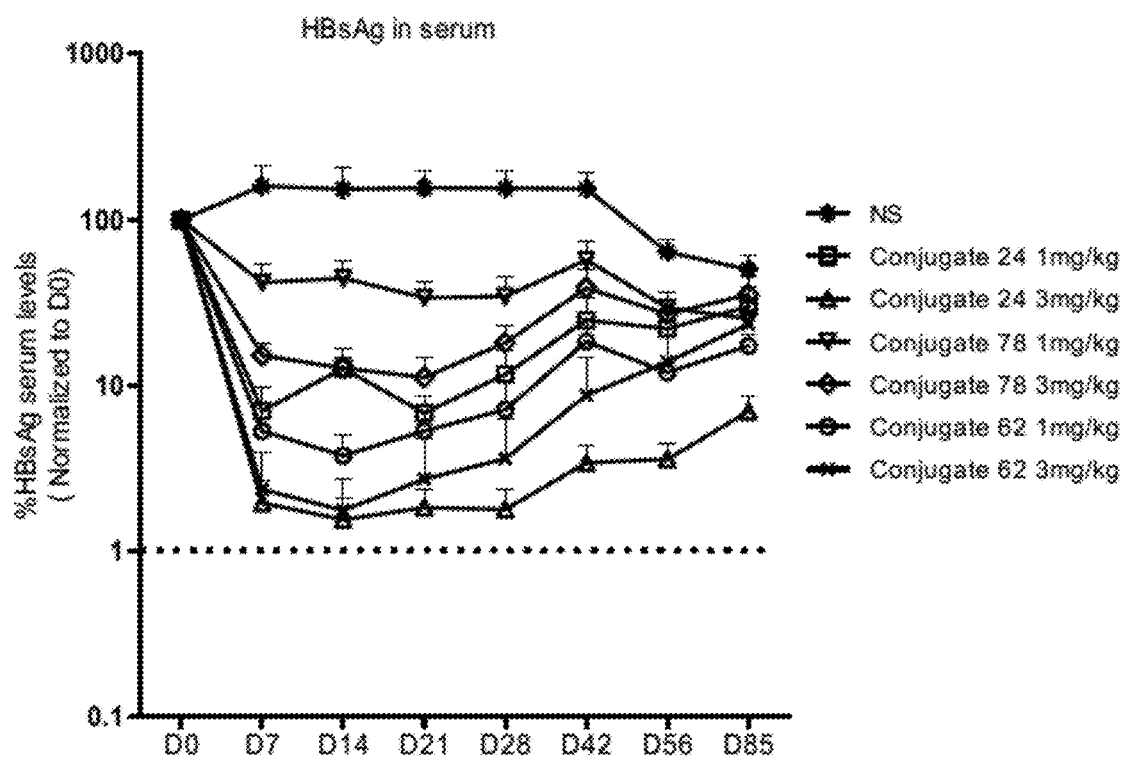
FIG. 29 shows a time-dependent inhibition of HBsAg expression in HBV transgenic mice serum by conjugates disclosed herein.
Figure 30:
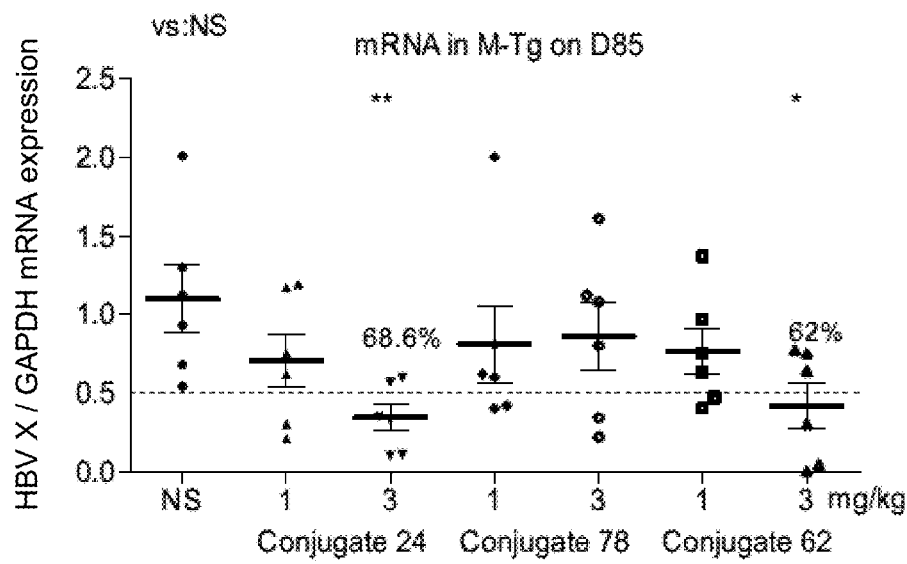
FIG. 30 shows inhibition of HBV mRNA at D85 by the conjugates disclosed herein in vivo.

From the results of FIG. 29, it can be seen that Conjugates 24, 62 and 78 all show prolonged and efficient inhibitory efficiency to serum HBsAg in up to 85 days. From the results of FIG. 30, at day 85 after administration, Conjugates 24 and 78 at the dosage of 3 mg/kg still shows 68.6% and 62% of inhibitory of HBV mRNA, respectively.

In further experiments, according to the methods described above, in 1.28 copy model mice, 3 mg/kg and 1 mg/kg of Conjugate 43 were dosed respectively, with respect to 0.6 mg/ml or 0.2 mg/ml of conjugate in 0.9 wt % NaCl aqueous solution and the volume of 5 ml/kg. The test continues until day 85. The inhibitory effects to HBsAg and HBV DNA are measured according to Experimental Example 5-4, and the results are shown in FIGS. 31 and 32.

Figure 31:
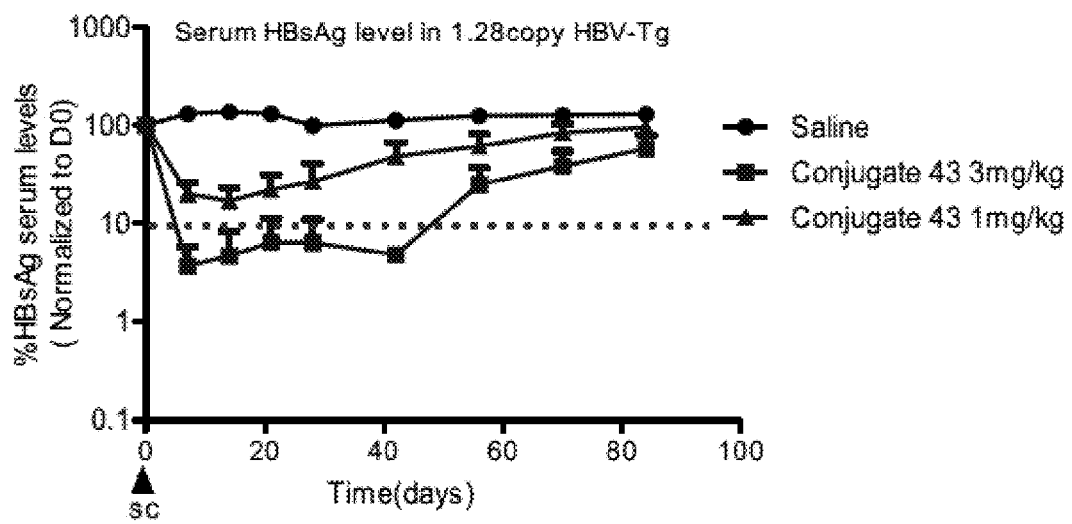
FIG. 31 shows a time-dependent inhibition of HBsAg expression in HBV transgenic mice serum by Conjugate 43.
Figure 32:
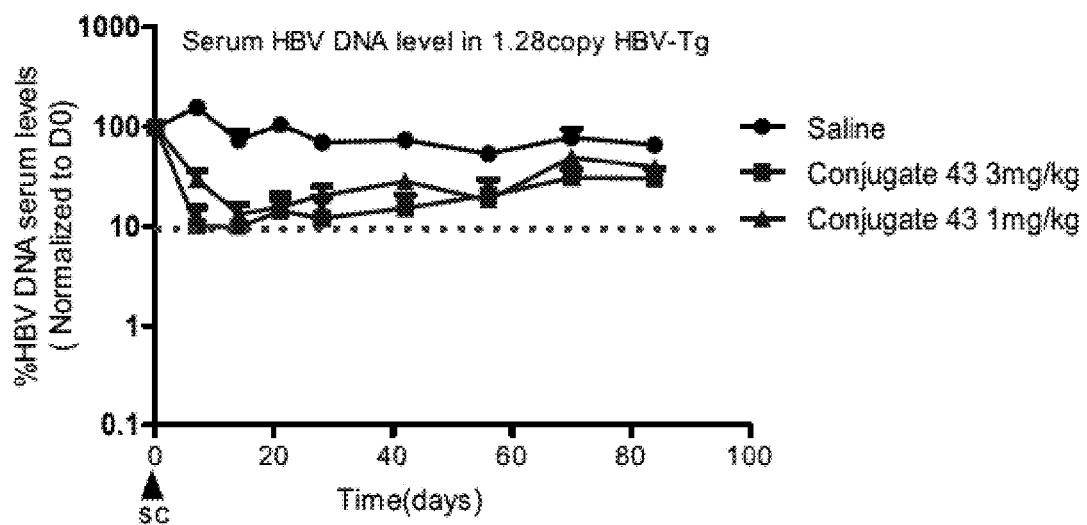
FIG. 32 shows a time-dependent inhibition of HBV DNA expression in HBV transgenic mice serum by Conjugate 43.

From the results of FIGS. 31 and 32, it can be seen that in 1.28 copy model mice, Conjugate 43 continuously showed efficient inhibitory to expression of HBV as well as HBV DNA in up to 85 days.

Experimental Example 7—an Experiment for Verifying Effects of Conjugates 167 and 168

Experimental Example 7-1—this Experiment Illustrates that the siRNA Conjugate of the Present Disclosure not Only have Relatively High In Vitro Activity, but Also Show Low Off-Target Effect In this experimental example, Conjugate 168 was investigated in in vitro psiCHECK system for the on-target activity and off-target effect. Specifically speaking, Conjugate 168 was tested for the activity of targeting completely matching target sequence (in which the nuecleotide sequence is completely complementary or the same with the nucleotide sequence of the whole length of the antisense strand of Conjugate 168) or targeting seed region matching target sequence (in which the nuecleotide sequence is complementary or the same with the neucleotide sequence of position 1-8 of the antisense strand of Conjugate 168).

According to methods described in Experimental Example 5-1, Conjugate 168 was tested, except in that, a target sequence fully complementarily paired with the antisense strand sequence of the siRNA in Conjugate 168 is employed to construct the on-target plasmid GSCM, while target sequences fully the same with the anti-sense strand sequence, complementarily paired with positions 1-8 of the antisense strand sequence or the same with positions 1-8 of the antisense strand sequence of the siRNA in Conjugate 168 were respectively employed to construct the off-target plasmids GSSM, PSCM and PSSM. From the test results, it can be seen that all the conjugates above not only have excellent inhibitory effect to the target mRNA (with $IC_{50}$=0.0513 nM), but also show low off-target effects.

Experimental Example 7-2—this Experiment Illustrates the Stability of the siRNA Conjugates Lysosome Lysate In Vitro Conjugates 167, and Comparative Sequence 1 obtained in Preparative Example 1 (each provided in the form of 0.9 wt % NaCl aqueous solution at 20 µM with regard to siRNA, 6 µl for each group, respectively, and Comparative Sequence 1 was marked as NC) were individually mixed well with 27.2 µL of sodium citrate aqueous solution (pH 5.0), 4.08 µL of deionized water and 2.72 µL of Rat Tritosomes (purchased from Xenotech Inc., Cat. R0610LT, at a final concentration of 0.2 mU/µL), and incubated at a constant temperature of 37° C. 5 µL samples were taken at each time point of 0 h, 1 h, 2 h, 6 h, and 24 h respectively, each added to 15 µL of 9 M urea aqueous solution for denaturation, and immediately cryopreserved in a −80° C. freezer for use, wherein 0 h represents the time point when the siRNA conjugate is mixed well with the lysosome lysate and instantly taken out for testing. Meantime, as for Conjugate 167 and Comparative Sequence 1, equal molar ratio of siRNA (20 µM, 1.5 µL) were individually mixed well with 7.5 µL of sodium citrate aqueous solution (pH 5.0) and 1 µL of deionized water, then added to 30 µL of 9 M urea aqueous solution for denaturation, and consequently mixed well with 8 µL of 6× loading buffer (aquarious solution of 20 mM EDTA, 36 wt % glycerol, and 0.06 wt % bromophenol blue), and immediately cryopreserved in a −80° C. freezer to quench the reaction, thus preparing samples for testing which are not treated with the lysosome lysate (marked as M in the electrophoretogram). 16 wt % of non-denatured polyacrylamide gel was prepared. 20 µL of each sample for testing was separately loaded into the gel to perform electrophoresis for 60 minutes under 80 mA constant current. After finishing the electrophoresis, the gel was stained with 1× Sybr Gole dye (Invitrogen, Cat. 11494) for 15 minutes followed by imaging. The results are shown in FIG. 33.

The stability in rat-origined lysosome lysate of Conjugate 167 and Comparative Sequence 1 (marked as NC in FIG. 34) is measured according to the same method, except in that the human-origined lysosome lysate were replaced with rat-origined lysosome lysate (Rat Liver Tritosomes purchased from Xenotech Inc., Cat. R0610.LT, at a final concentration of 0.2 mU/µL). The result of which is shown in FIG. 34.

Figure 33:
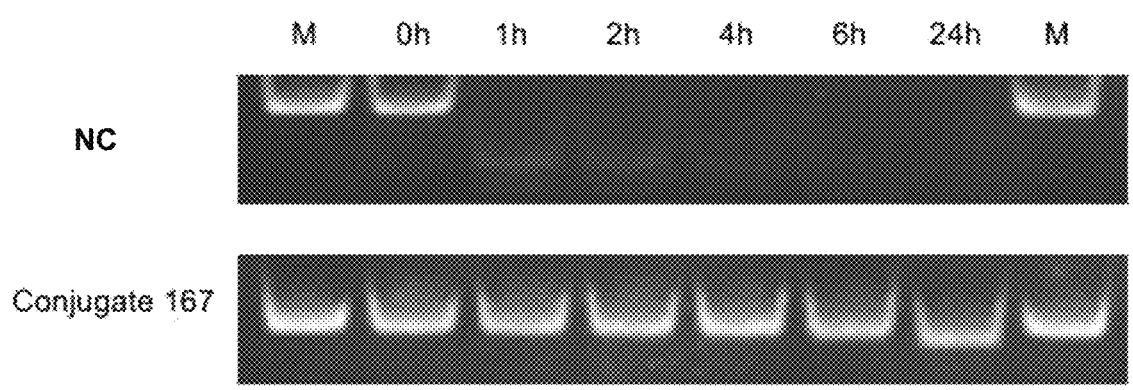
FIGS. 33 and 34 show stability of Conjugate 167 in human- and rat-originated lysosome lysate.
Figure 34:
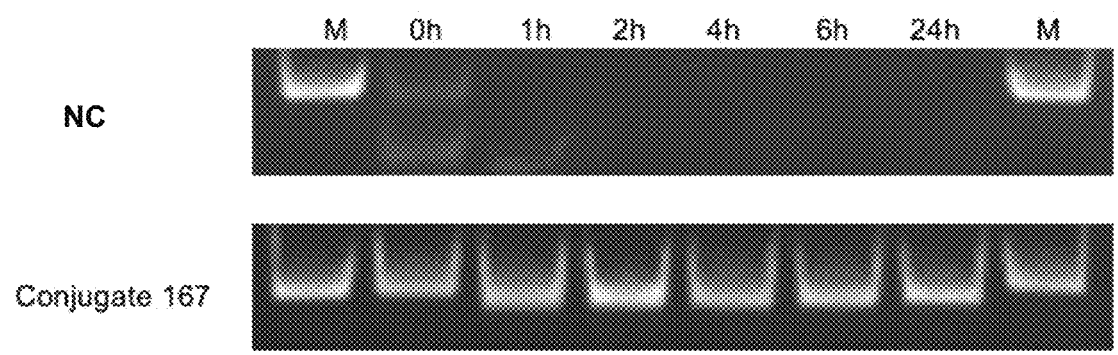

FIGS. 33 and 34 indicated that the conjugates of the disclosure can remain undegraded in at least 24 hours both in human- and rat-origined lysosome lysate, showing good stability.

Experimental Conjugate 7-3—this Experiment Illustrates the Inhibitory Efficiency of the Conjugates of the Present Disclosure in Expression of HBV mRNA in Mice In Vivo In this experimental example, the inhibitory efficiencies of Conjugates 167 and 168 in the expression of HBV mRNA in HBV transgenic mice C57BL/6J-Tg (Alb1HBV) 44Bri/J were investigated.

At first, C57BL/6J-Tg (Alb1HBV) 44Bri/J mice were randomly divided into groups based on HBsAg content in serum (all female, 5 mice in each group) and PBS group and Conjugates 167 and 168 were individually administrated. Wherein, 5 mg/kg of 1×PBS was administered subcutaneously to each animal for the PBS group. As for Conjugate 167 or 168, a single dose of the conjugate was administered subcutaneously, each with the dosage of 1 mg/kg as 0.2 mg/ml conjugate in 0.9 wt % NaCl aqueous solution and the dosage volume of 5 ml/kg. Animals were sacrificed at day 28 after administration. The liver was collected and kept with RNA later (Sigma Aldrich), and the liver tissue was homogenized with a tissue homogenizer. Then the total RNA was extracted and obtained by using Trizol according to the standard procedure for total RNA extraction.

The expression level of HBV mRNA in liver tissue was measured by real-time fluorescent qPCR. Specifically, the extracted total RNA was reverse transcribed into cDNA by using ImProm-II™ reverse transcription kit (Promega) according to the instruction thereof, and then the inhibitory efficiency of siRNAs in the expression of HBV mRNA in liver tissue was measured by using the fluorescent qPCR kit (Beijing Cowin Biosicences Co., Ltd). In this fluorescent qPCR method, β-actin gene was used as an internal control gene, the HBV and β-actin were detected by using primers for HBV and β-actin, respectively.

Sequences of primers for detection are shown in Table 5G.

TABLE 5G

Sequences of primers for detection

| Genes | Upstream Primers | Downstream Primers |
|---|---|---|
| HBV | 5'-GTCTTTTGGGTTTTGCT GCC-3' (SEQ ID NO: 238) | 5'-GCAACGGGGTAAAGGT TCAG-3' (SEQ ID NO: 239) |
| β-actin | 5'-GGTCGGAGTCAACGGAT TT-3' (SEQ ID NO: 240) | 5'-CCAGCATCGCCCCACT TGA-3' (SEQ ID NO: 241) |

In this fluorescent qPCR method, the calculation of the expression of HBV mRNA as well as the inhibition ratio against mRNA for the conjugates are in accordance with Experimental Example 5-2. The results are shown in Table 6G.

In other experiments, method same to the above was employed, except in that the siRNA conjugated administrated for testing is replaced with Conjugate 167 and 168, and the dosage of administration alters, the results are shown in Table 6G.

TABLE 6G

Inhibition of HBV Mma expression by siRNA conjugates in mouse liver

| Conjugate | Dose (mg/kg) | Inhibitory to Liver HBV mRNA (%) |
|---|---|---|
| — | NA | 0 |
| Conjugate 167 | 1 | 77.41 |
| Conjugate 168 | 1 | 88.27 |
| Conjugate 168 | 0.3 | 57.95 |

As can be seen from the results above, all conjugates above of the present disclosure show high inhibitory activity in the expression of HBV mRNA in mice in vivo, illustrating good in vivo delivery efficiency of the siRNA conjugates of the present disclosure.

Experimental Example 7-4—this Experiment Illustrates a Time-Dependent Test of the Inhibitory Efficiency of the siRNA Conjugates in Table 3B in the Expression of HBsAg and HBV DNA in HBV Transgenic Mice Serum In 1.28 copy models, these mice were randomly divided into groups (6 mice for each group, half female and half male). Normal saline and different dosages of Conjugate 168 were respectively administered to each group, and for NS groups, 5 ml/kg of normal saline was administered subcutaneously. For the conjugate groups, the drug dosages for all animals were calculated according to the body weight. A single dose was administered subcutaneously, with the dosage of 3 mg/kg or 1 mg/kg, with respect to 0.6 mg/ml or 0.2 mg/ml of conjugate in 0.9 wt % NaCl aqueous solution and the volume of 5 ml/kg. The blood was taken from mouse orbital venous plexus before administration and at days 7, 13, 21, 28, 42, 56, 70, 84, 98, 112, 126, 140 and 154 after administration, and HBsAg, HBeAg as well as HBV DNA level in serum was measured for each time point.

The blood taken from the orbit was about 100 μl each time, and the serum was no less than 20 μl after centrifugation. The content of HBsAg in serum was measured by using HBsAg CLIA kit (Autobio, CL0310). The content of HBeAg in serum was measured by using HBeAg CLIA kit (Autobio, CL0310). The expression level of HBV DNA was measured by extraction of the DNA from the serum with reference to the instruction of QIAamp 96 DNA Blood Kit followed by qPCR.

The normalized HBsAg expression=(the content of HBsAg after administration/the content of HBsAg before administration)×100%.

The inhibition ratio against HBsAg=(1−the content of HBsAg after administration/the content of HBsAg before administration)×100%, wherein the content of HBsAg was expressed in equivalents (UI) of HBsAg per milliliter (ml) of serum.

The normalized HBeAg expression=(the content of HBeAg after administration/the content of HBeAg before administration)×100%.

The inhibition ratio against HBeAg=(1−the content of HBeAg after administration/the content of HBeAg before administration)×100%, wherein the content of HBeAg was expressed in equivalents (UI) of HBeAg per milliliter (ml) of serum.

The normalized HBV DNA expression=(the content of HBV DNA after administration/the content of HBsAg before administration)×100%.

The inhibition ratio against HBV DNA=(1−the content of HBV DNA after administration/the content of HBV DNA before administration)×100%, wherein the content of HBV DNA was expressed in copies of HBV DNA per milliliter (ml) of serum.

Figure 35:
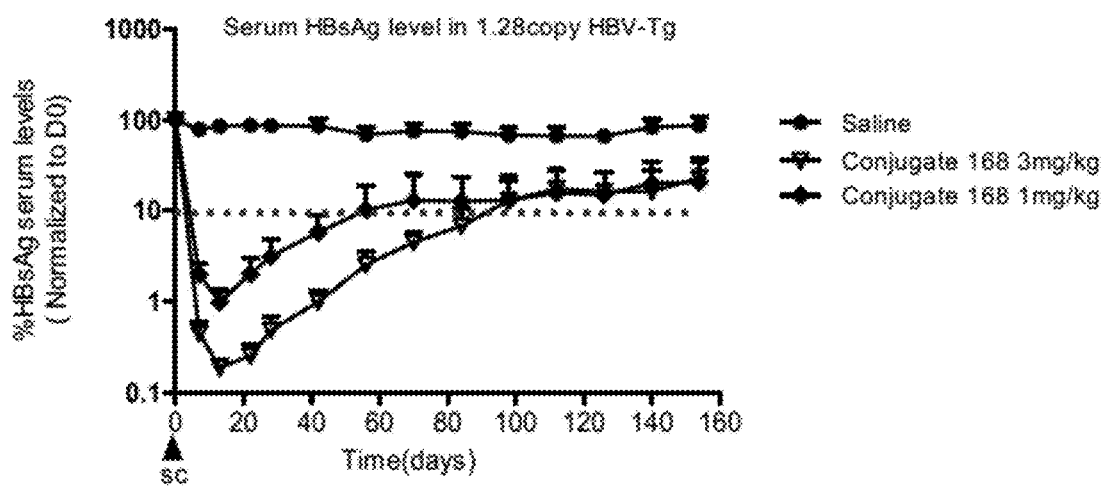
FIG. 35 shows a time-dependent inhibition of HBsAg expression in 1.28 copy HBV-Tg models by Conjugate 168.
Figure 36:
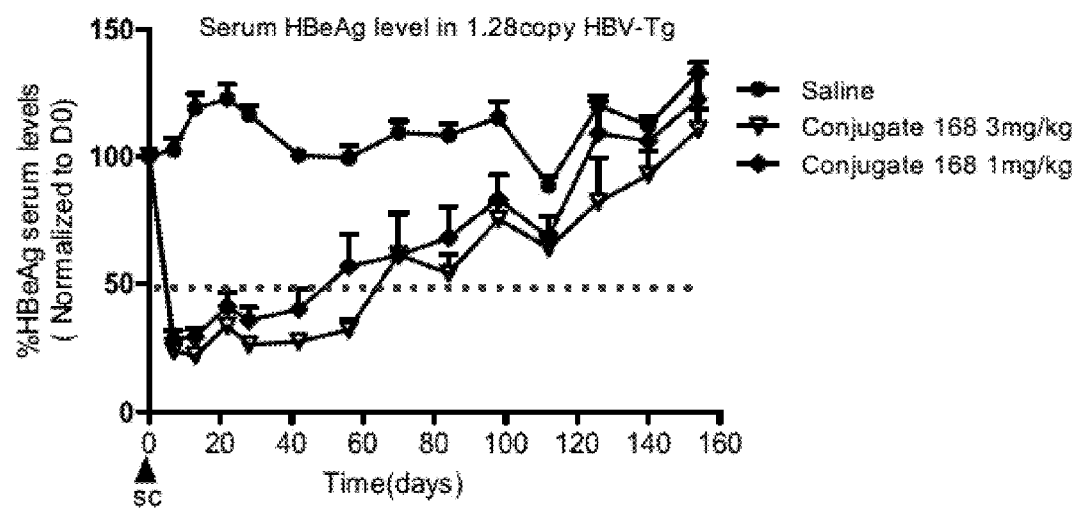
FIG. 36 shows a time-dependent inhibition of HBeAg expression in 1.28 copy HBV-Tg models by Conjugate 168.
Figure 37:
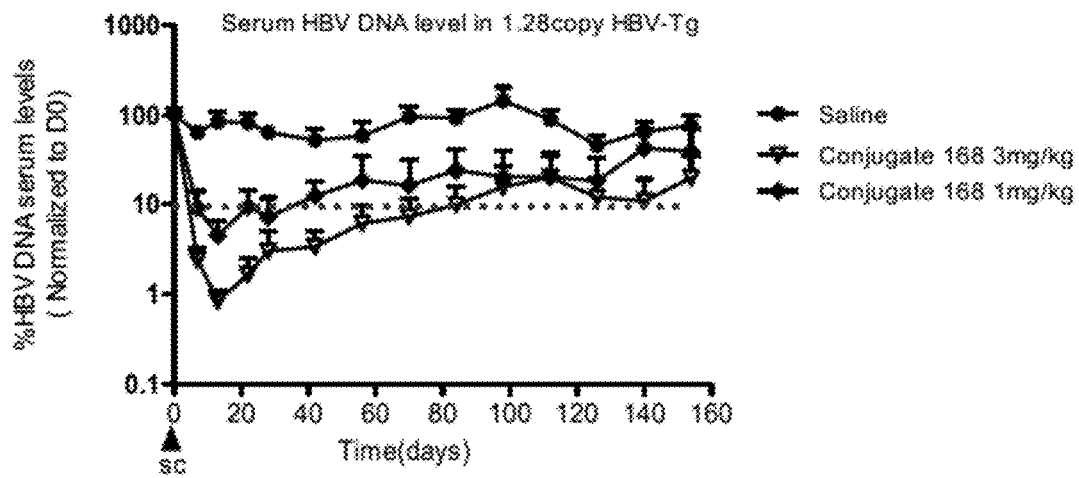
FIG. 37 shows a time-dependent inhibition of HBV DNA expression in 1.28 copy HBV-Tg models by Conjugate 168.

The results are shown in FIGS. 35-37. As can be seen from the results of FIG. 35, the NS negative control group shows no inhibitory effect at different time points after administration; in contrast, Both of Conjugate 168 showed excellent inhibitory effect against HBsAg at different time points after administration, particularly the 3 mg/kg group consistently shows an inhibition ratio over 90% against HBsAg in serum over a period of up to 100 days, indicating that it can stably and efficiently inhibit the expression of HBV gene over a longer period.

As can be seen from the results of FIG. 36, the siRNA conjugates can also nhibit HBeAg expression. Wherein, both 3 mg/kg groups consistently show an inhibition ratio over 50% against HBeAg in serum over a period of up to 70 days.

From the results of FIG. 37, it can be seen that the conjugates also show efficient inhibitory efficiency to the expression of HBV DNA and show a relatively high inhibition ratio against HBV DNA over a period of up to 154 days.

Experimental Example 8—an Experiment for Verifying Effects of the siRNA Conjugates in Table 3E

Experimental Example 8-1—this Experiment Illustrates the Inhibitory Efficiency of the siRNA Conjugates in Table 3E in Expression of ANGPTL3 mRNA In Vivo In this experimental example, the inhibition ratios of Conjugates 105, 109, 111 and 115 in the expression level of ANGPTL3 in liver tissue of normal BALB/c mice were investigated.

Normal BALB/c mice (6-8 week old, purchased from Beijing Vital River Laboratory Animal Technology Co., Ltd.) were randomly divided into groups (5 mice in each group). Conjugates 105, 109, 111, 115 and PBS were individually administrated to the mice in each group. The drug dosages for all animals were calculated according to the body weight. A single dose was administered subcutaneously, with the dosage of 3 mg/kg and 0.3 mg/kg (by the amount of siRNA) as 0.3 mg/ml and 0.03 mg/ml of 0.9 wt % NaCl aqueous solution and the dose volume of 10 ml/kg for the siRNA conjugates. Mice were sacrificed in batches respectively at day 14 and day 28 after administration. The liver was collected and kept with RNA later (Sigma Aldrich), and the liver tissue was homogenized with a tissue homogenizer. Then the total RNA was extracted and obtained by using Trizol (Thermo Fisher) according to the standard procedure for total RNA extraction.

The expression level of ANGPTL3 mRNA in liver tissue was measured by real-time fluorescent qPCR. Specifically, the extracted total RNA was reverse transcribed into cDNA using ImProm-II™ reverse transcription kit (Promega) according to the instruction thereof, and then the inhibitory efficiency of siRNAs in the expression of ANGPTL3 mRNA in liver tissue was measured by using the fluorescent qPCR kit (Beijing Cowin Biosicences Co., Ltd). In this fluorescent qPCR method, GAPDH gene was used as an internal control gene, and ANGPTL3 and GAPDH were detected by using primers for ANGPTL3 and GAPDH, respectively.

Sequences of primers for detection are shown in Table 5E.

| Genes | Upstream Primers | Downstream Primers |
|---|---|---|
| Mouse ANGPTL3 | 5'-GAGGAGCAGCTAACCAA CTTAAT-3' (SEQ ID NO: 199) | 5'-TCTGCATGTGCTGTTG ACTTAAT-3' (SEQ ID NO: 200) |
| Mouse GAPDH | 5'-AACTTTGGCATTGTGGA AGGGCTC-3' (SEQ ID NO: 201) | 5'-TGGAAGAGTGGGAGTT GCTGTTGA-3' (SEQ ID NO: 202) |

The expression of ANGPTL3 mRNA was calculated by the equation: the expression of ANGPTL3 mRNA=(the expression of ANGPTL3 mRNA in the test group/the expression of GAPDH mRNA in the test group)/(the expression of ANGPTL3 mRNA in the control group/the expression of GAPDH mRNA in the control group)×100%.

The inhibition ration against ANGPTL3 mRNA by the conjugates was calculated by the equation: the expression of ANGPTL3 mRNA=(1−the expression of ANGPTL3 mRNA in the test group/the expression of GAPDH mRNA in the test group)/(the expression of ANGPTL3 mRNA in the control group/the expression of GAPDH mRNA in the control group)×100%.

The control group was a group of control mice administrated with PBS in this experiment and each test group was a group of mice administrated with different siRNA conjugates, respectively. The results are shown in FIGS. 38A and 38B.

Figure 38A:
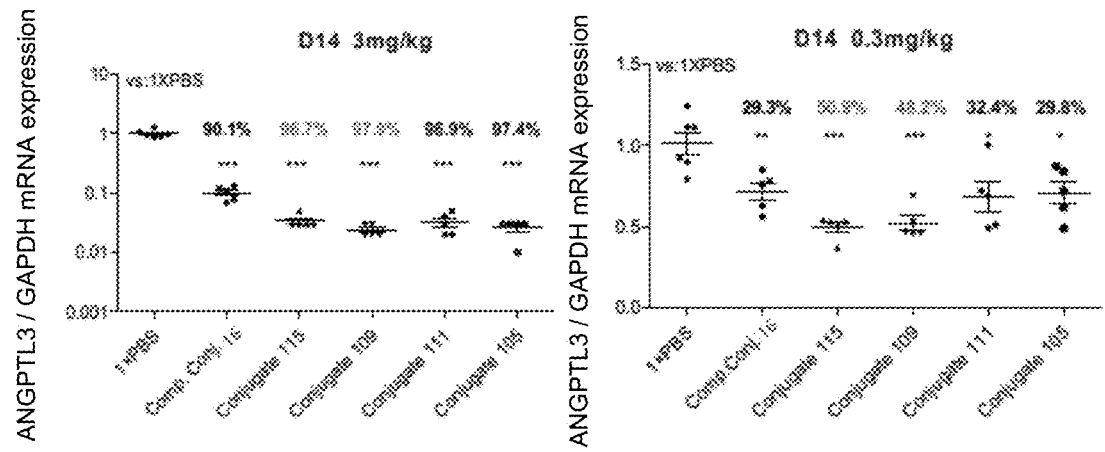
FIGS. 38A and 38B show the inhibition ratio of ANGPTL mRNA expression at D14 and D28.
Figure 38B:
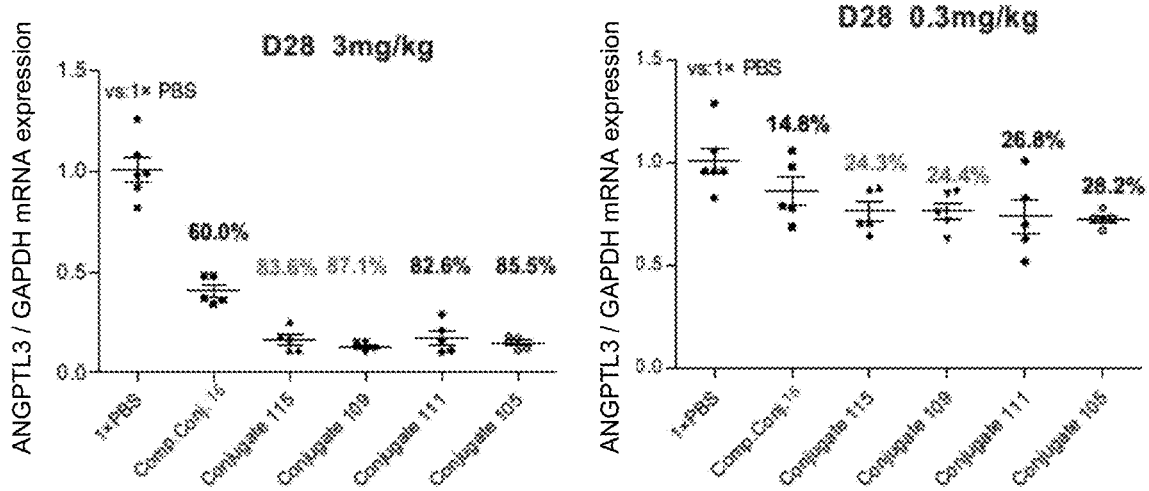

As can be seen from the results of FIGS. 38A and 38B, the siRNA conjugates above all show excellent inhibitory activity against the expression of ANGPTL3 mRNA.

The blood (about 100 μL) was taken from orbits of the experimental subjects above and centrifuged to obtain serum. The contents of total cholesterol (CHO) and triglyceride (TG) in serum were further measured by using a PM1P000/3 full-automatic serum biochemical analyzer (SABA, Italy). The results of blood lipid were normalized and the inhibition ratio against blood lipid levels was calculated by the equation: the inhibition ratio=(1−the blood lipid content in the test group after administration/the blood lipid content in the test group before administration)×100%. The blood lipid refers to total cholesterol or triglyceride. The test results are shown in FIGS. 39A and 39B.

Figure 39A:
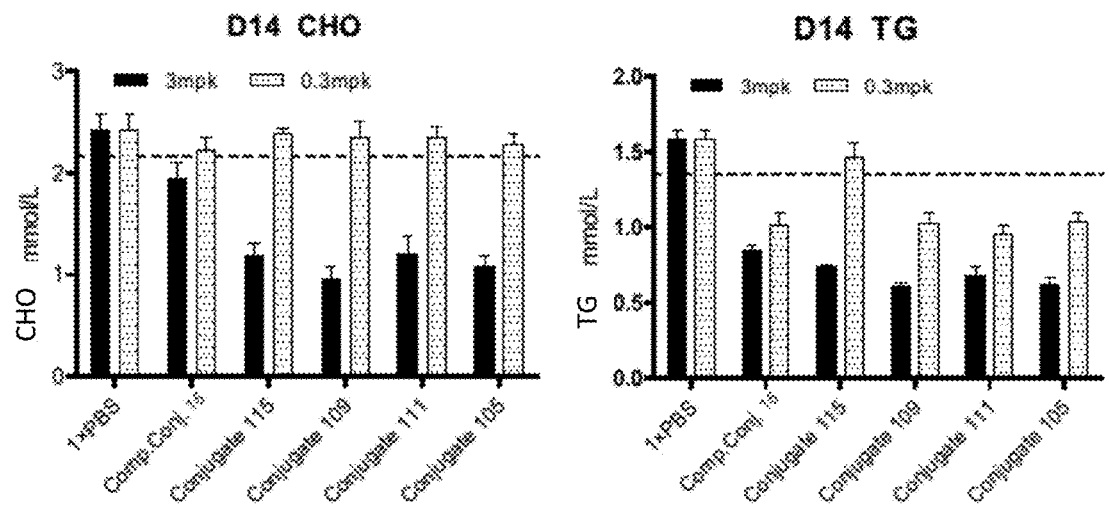
FIGS. 39A and 39B shows the inhibition ratio of blood lipid, represented by total cholesterol (CHO) and triglyceride (TG) in serum, by conjugates disclosed herein.
Figure 39B:
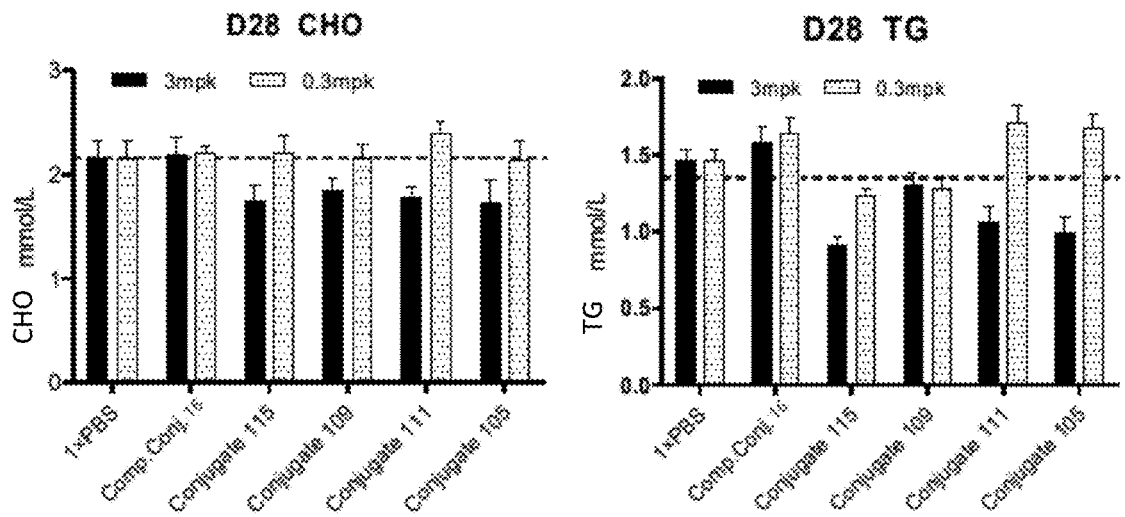

As can be seen from the results of FIGS. 39A and 39B, in the serum of the mice treated with different dosages of Conjugates 105, 109, 111 and 115, both contents of CHO and TG were reduced significantly, and blood lipid level reduction is observed until at least 28 days after administration.

Experimental Conjugate 8-2—this Experiment Illustrates the Effects on Blood Lipid for the siRNA Conjugates of the Present Disclosure Tg(APOC3)3707Bres mice were randomly divided into groups based on TG content >2 mmol/L (5 mice in each group) and to each group, PBS negative control and Conjugate 115 were individually administrated. The drug dosages for all animals were calculated according to the body weight. A single dose of the conjugates was administered subcutaneously, each with the dosage of 3 mg/kg or 1 mg/kg, each as 0.6 mg/ml or 0.2 mg/ml conjugate in 0.9 wt % NaCl aqueous solution and the dosage volume of 5 ml/kg. Blood was taken from orbits of the mice before the administration and 7, 14, 21, 28, 35, 56, 70, 84, 98, 112, 126, 140, 154 and 168 days after the administration, and the contents of CHO and TG in serum were measured.

The blood taken from the orbit was about 0.1 ml each time, and the serum was no less than 20 µl after centrifugation. The contents of total cholesterol (CHO) and triglyceride (TG) in serum by using a PM1P000/3 full-automatic serum biochemical analyzer (SABA, Italy).

The results of blood lipid were normalized: Normalized blood lipid levels=(the blood lipid content in the test group after administration/the blood lipid content in the test group before administration), and the inhibition ratio against blood lipid levels=(1–the blood lipid content in the test group after administration/the blood lipid content in the test group before administration)×100%. The test results are shown in FIGS. 40A and 40B.

Figure 40A:
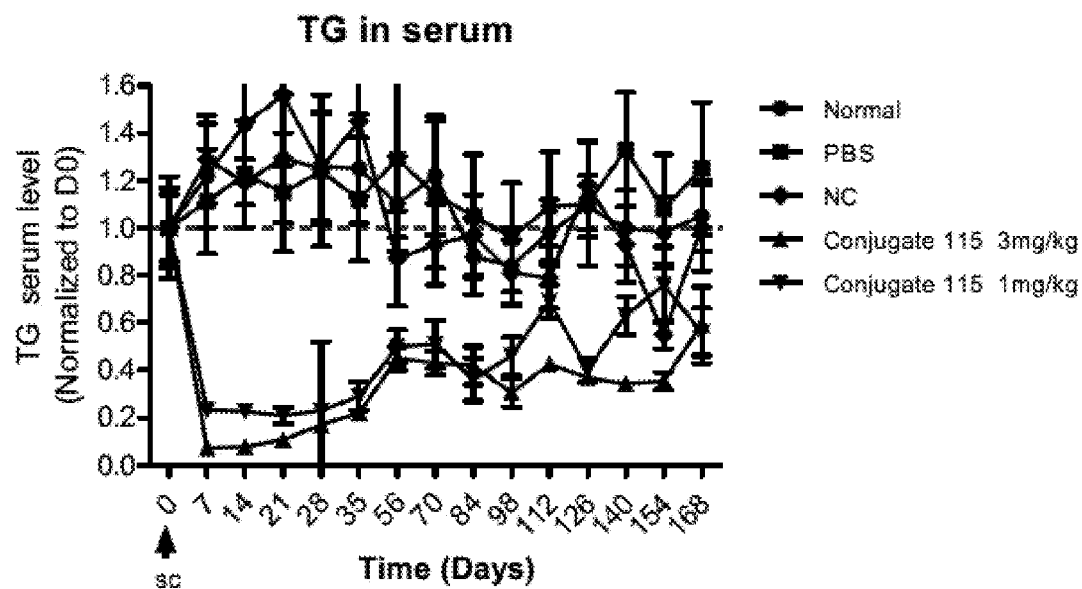
FIGS. 40A and 40B show the time-dependent inhibition ratio of blood lipid, represented by total cholesterol (CHO) and triglyceride (TG) in serum, by Conjugate 115.
Figure 40B:
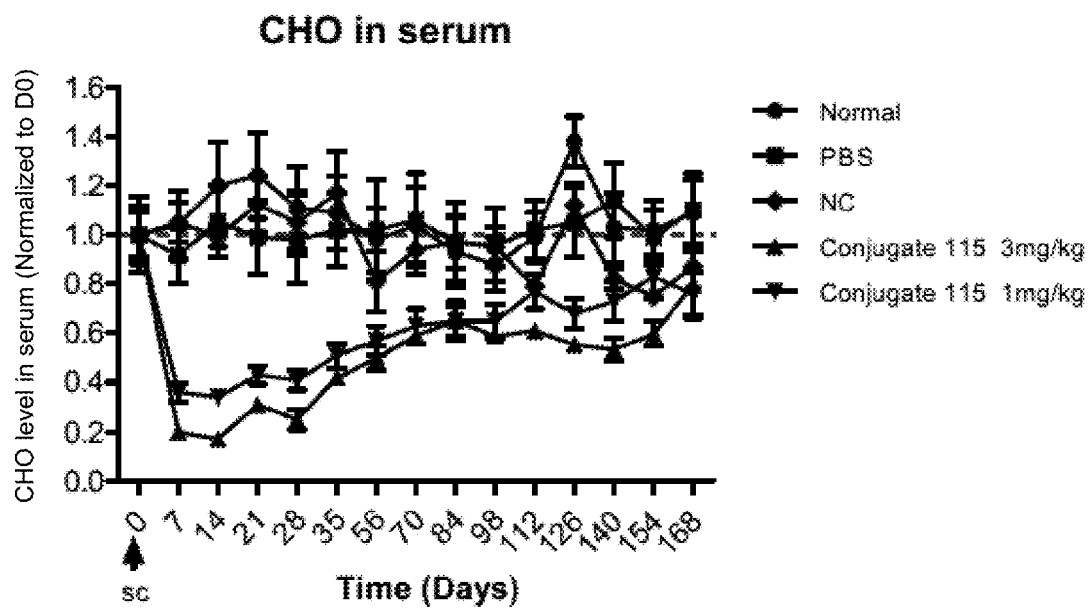

As can be seen from the results of FIGS. 40A and 40B, in various time points after administration, Conjugate 115 show significant effects of TG and CHO reduction during up to 168 days, indicating a long-time stable and effective inhibition against the expression of ANGPTL3 gene expression in mice in vivo.

In other experiments, method same to the above was employed, except in that: ob/ob model mice were employed; Conjugates 111, 115 and Comparative Conjugate 16 were separately administrated, each at the dosage of 3 mg/kg and 1 mg/kg; and the data is collected in days 0, 7, 14, 21, 28, 35 and 41 after administration. The result is shown in FIGS. 41A-41B.

Figure 41A:
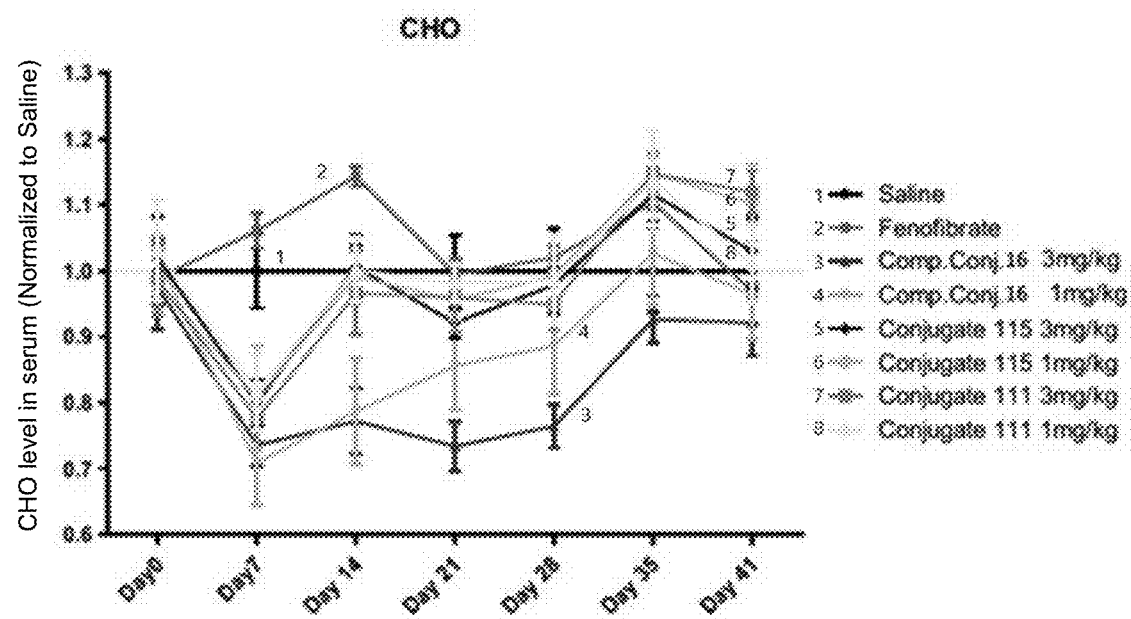
FIGS. 41A and 41B show the time dependent inhibition ratio of blood lipid, represented by total cholesterol (CHO) and triglyceride (TG) in serum, by Conjugates 115 and 111.
Figure 41B:
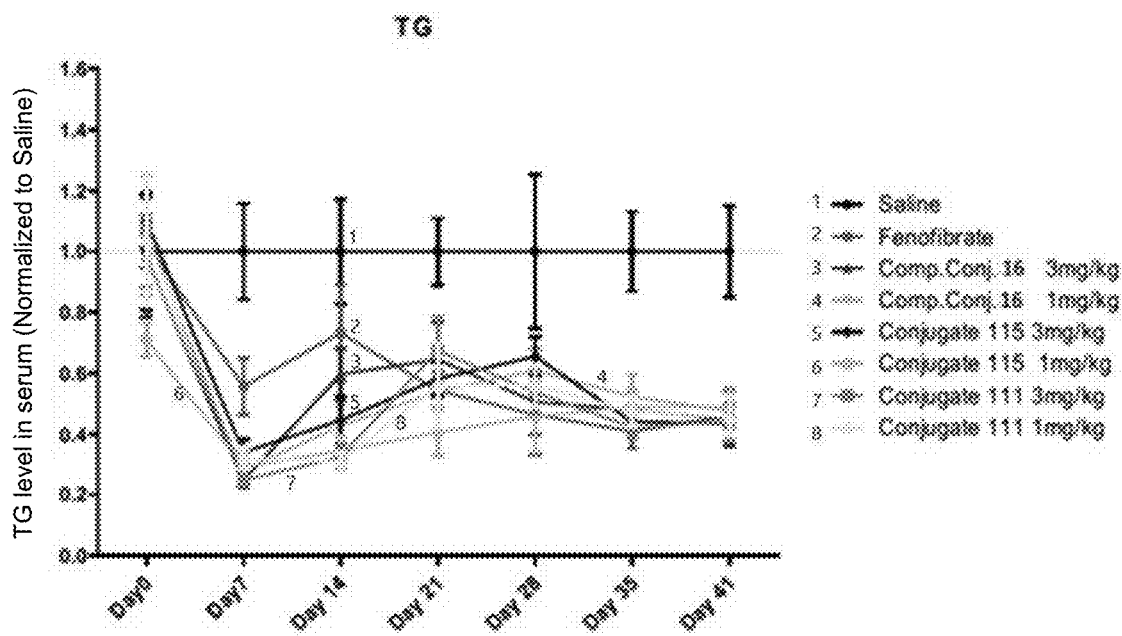
Figure 42A:
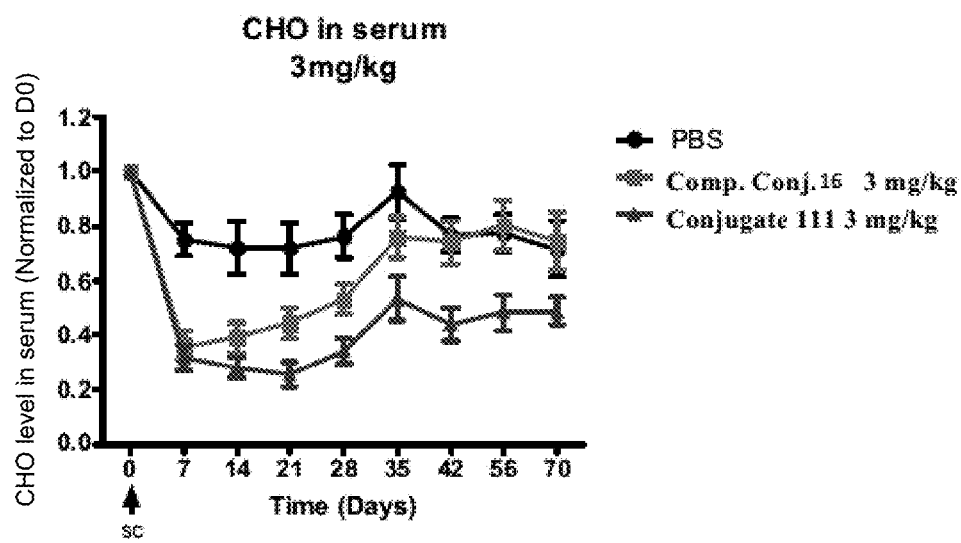
FIGS. 42A, 42B, 42C and 42D show the time-dependent inhibition ratio of blood lipid, represented by total cholesterol (CHO) and triglyceride (TG) in serum, by Conjugate 111 at different dosages.
Figure 42B:
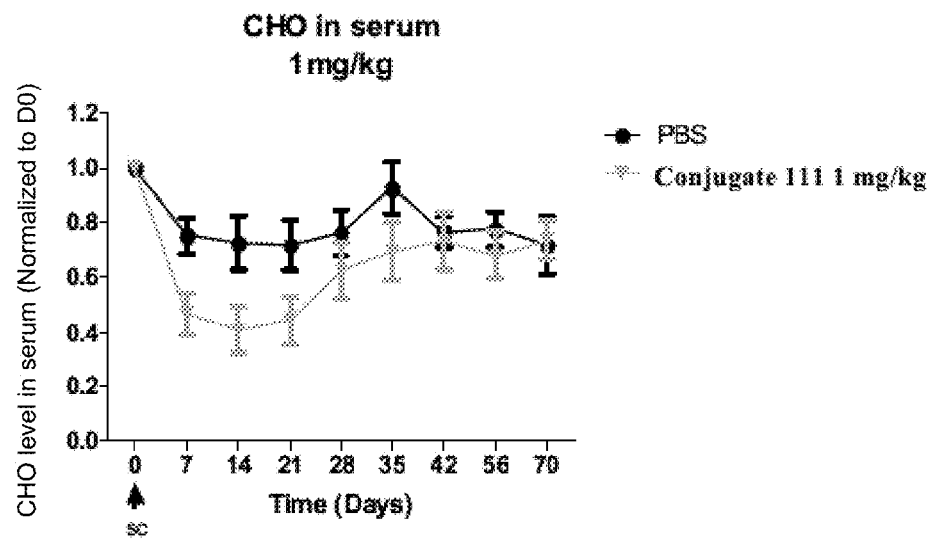
Figure 42C:
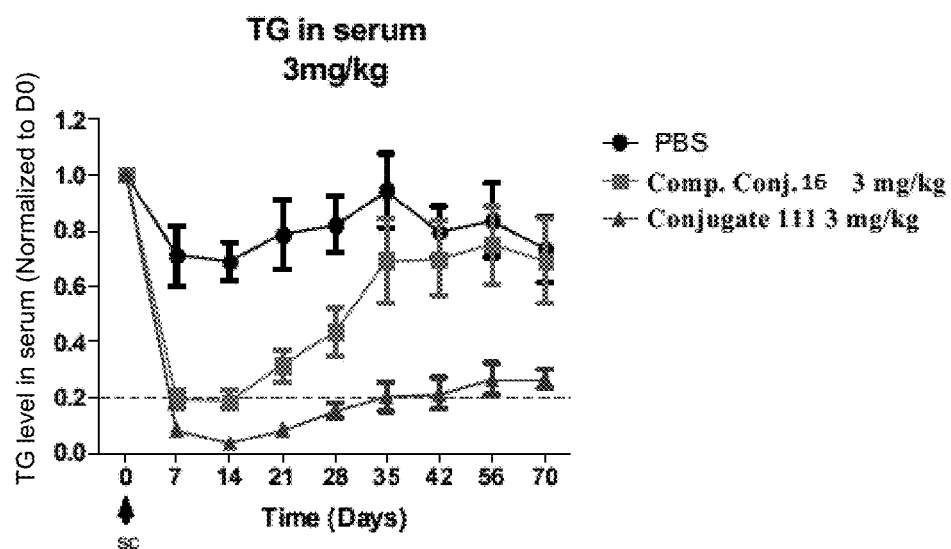
Figure 42D:
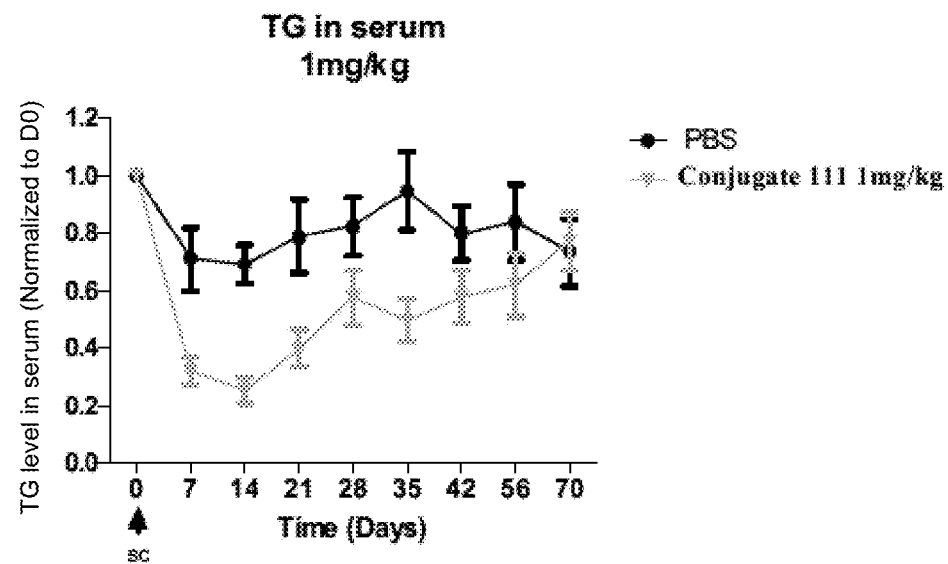

As can be seen from the results of FIGS. 41A-41B, it can be seen that Conjugates 111 and 115 of the present disclosure can continuously reduce the blood lipid level in ob/ob mice in vivo in 41 days, showing excellent inhibitory activity.

In other experiments, method same to the above was employed, except in that: Conjugate 111 and Comparative Conjugate 16 was separately administrated, each at the dosage of 3 mg/kg and 1 mg/kg respectively as 0.6 mg/ml and 0.2 mg/ml of 0.9 wt % NaCl aqueous solution, and the dosage volume is 5 ml/kg; and CHO and TG value were tested in days 0, 7, 14, 21, 28, 35, 42, 56 and 70 after administration. The result is shown in FIGS. 42A-42D.

As can be seen from the results of FIGS. 42A-42D, it can be seen that Conjugate 111 of the present disclosure can continuously reduce the blood lipid in 70 days, which is superior to Comparative Conjugate 16 under the same dosage level.

Experimental Example 8-3—this Experiment Illustrates the Inhibitory Efficiency of the siRNA Conjugates with Different Conjugating Molecules in Table 3A Against the Expression of ANGPTL3 mRNA and Effects on the Blood Lipids in Non-Human Primates As for Monkeys with metabolic syndrome (all male), 12 animals were grouped as 8 for the experimental group dosaging Conjugate 169 and 4 for the control group dosaging Conjugate 25; the base data of the monkeys were tested and observed for 3 weeks, blood was taken weekly, measuring the blood lipid level (TG, CHO, HDL). Later, Conjugate 169 and Conjugate 25 (as a comparative conjugate as the siRNA thereof targets a completely irrelevant mRNA) were administrated. The drug dosages for all animals were calculated according to the body weight. A single dose was administered subcutaneously, with the dosage of 9 mg/kg (by the amount of siRNA) as 100 mg/ml of 0.9 wt % NaCl aqueous solution and the dose volume of no more than 2 ml for each administration site. Blood was taken before and days 7, 14, 21, 28 and 35 after administration, the TG and CHO level in serum was tested at each time point.

The results of blood lipid were normalized and Normalized blood lipid levels=(the blood lipid content in the test group after administration/the blood lipid content in the test group before administration), and the inhibition ratio against blood lipid levels=(1–the blood lipid content in the test group after administration/the blood lipid content in the test group before administration)×100%. Wherein the blood lipid content in the test group before administration is the mean value of the blood lipid during 3 weeks before administration, and is marked as DO in FIGS. 43A and 43B.

In day 0 (the very day of administration) and day 28, a Percutanous transhepatic biopsy was proceeded to measure the mRNA expression level of the ANGPTL3 in the liver tissue. Liver was collected and kept with RNA Later (Sigma Aldrich), and the liver tissue was homogenized with a tissue homogenizer. Then the total RNA was extracted and obtained by using Trizol according to the standard procedure for total RNA extraction.

The expression level of ANGPTL3 mRNA in liver tissue was measured by real-time fluorescent qPCR. Specifically, the extracted total RNA was reverse transcribed into cDNA by using ImProm-II™ reverse transcription kit (Promega) according to the instruction thereof, and then the inhibitory efficiency of siRNAs in the expression of ANGPTL3 mRNA in liver tissue was measured by using the fluorescent qPCR kit (Beijing Cowin Biosicences Co., Ltd). In this fluorescent qPCR method, GAPDH gene was used as an internal control gene, the ANGPTL3 and GAPDH were detected by using primers for ANGPTL3 and GAPDH, respectively.

Sequences of primers for detection are shown in Table 6E.

TABLE 6E

| Sequences of primers for detection | | |
|---|---|---|
| Genes | Upstream Primers (5'-3') | Downstream Primers (5'-3') |
| Monkey ANGPTL3 | CTGGTGGTGGCATGATG AGT (SEQ ID NO: 242) | CTCTTCTCCGCTCTGGCT TAG (SEQ ID NO: 243) |
| Monkey GAPDH | GGGAGCCAAAAGGGTCA TCA (SEQ ID NO: 244) | CGTGGACTGTGGTCATG AGT (SEQ ID NO: 245) |

The calculation for the expression of ANGPTL3 mRNA and the inhibition ration against ANGPTL3 mRNA was in accordance with Experimental Example (8-1). The control group was a group of control monkeys administrated with PBS in this experiment and each test group was a group of monkeys administrated with different siRNA conjugates, respectively. The results are shown in FIGS. 43A-43C.

Figure 43A:
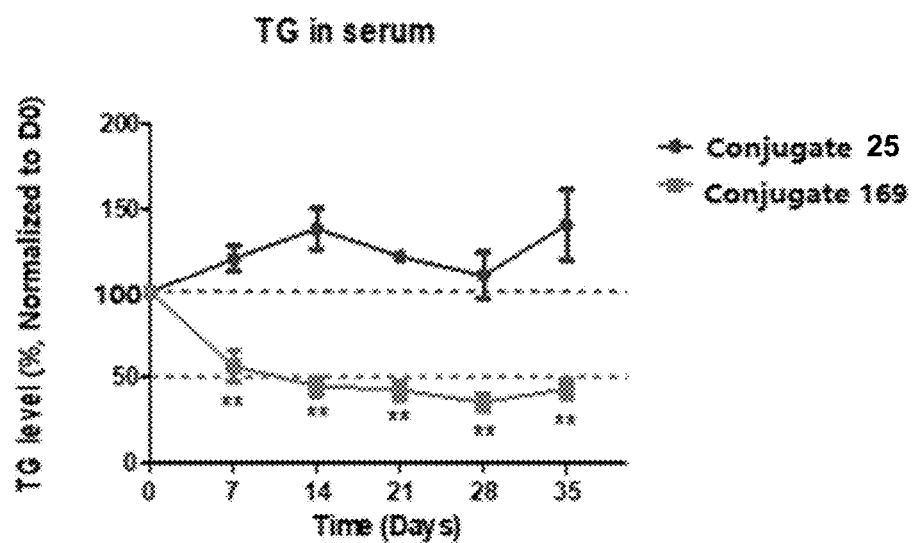
FIGS. 43A and 43B show the time-dependent inhibition ratio of blood lipid, represented by total cholesterol (CHO) and triglyceride (TG) in serum, by Conjugates 25 and 169.
Figure 43B:
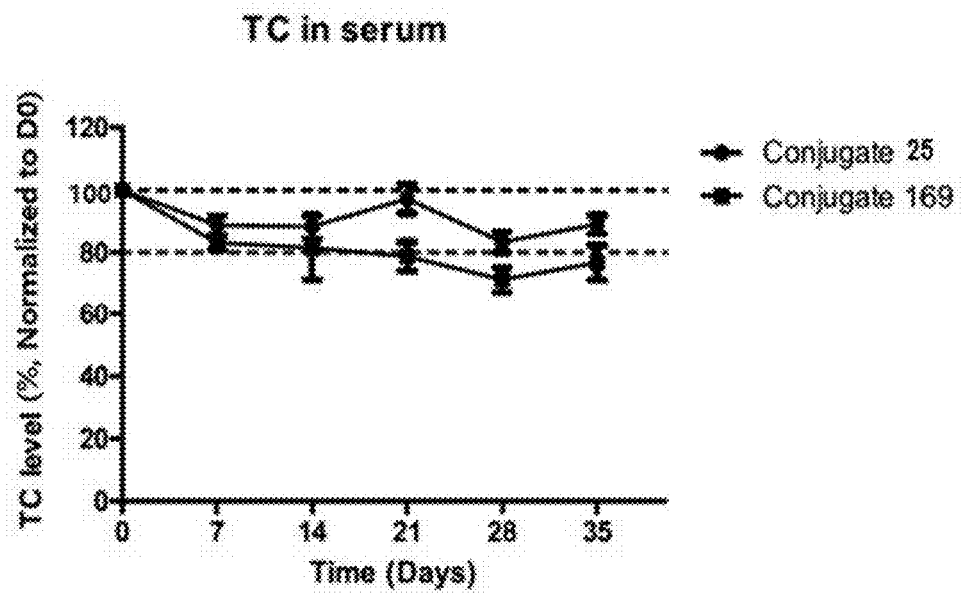
Figure 43C:
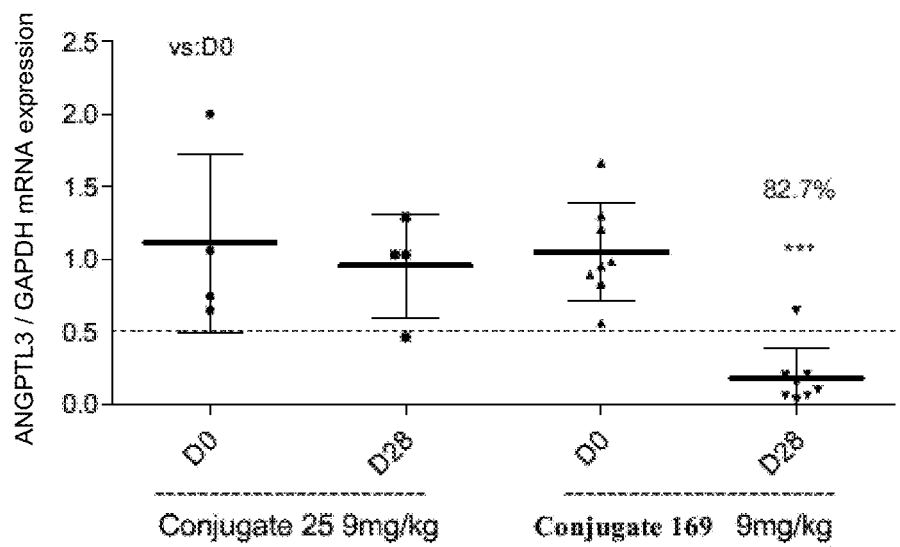
FIG. 43C shows the inhibition ratio of ANGPTL mRNA expression.

As can be seen from the results of FIGS. 43A-43C, Conjugate 169 shows significant TG reduction and inhibitory against the expression of ANGPTL3 gene, reducing 82.7% of ANGPTL3 gene mRNA at day 28 after administration.

Experimental Example 9—an Experiment for Verifying Effects of the siRNA Conjugates in Table 3F

Experimental Example 9-1—this Experiment Illustrates the Inhibitory Efficiency of the siRNA Conjugates in Table 3F Against Expression of APOC3 mRNA In Vivo In this experimental example, the inhibition ratios of Conjugate 144 in the expression level of APOC3 in liver tissue of human APOC3 transgenic mice (B6; CBA-Tg (APOC3)3707Bres/J, purchased from Jackson Lab) in vivo were investigated.

Human APOC3 transgenic mice (6-8 week old, triglyceride >2 mmol/L) were randomly divided into groups (5 mice in each group). Conjugates 144 and Conjugate 25 (as a comparative conjugate as the siRNA thereof targets a completely irrelevant mRNA) were administered to the mice in each group respectively. The drug dosages for all animals were calculated according to the body weight. A single dose was administered subcutaneously, with the dosage of 1 mg/kg

TABLE 7F

Sequences of primers for detection

| Genes | Upstream Primers | Downstream Primers |
|---|---|---|
| Human APOC3 | 5'-GTGACCGATGGCTTC AGTTC-3' (SEQ ID NO: 248) | 5'-ATGGATAGGCAGGTGG ACTT-3' (SEQ ID NO: 249) |
| Mouse β-actin | 5'-AGCTTCTTTGCAGCT CCTTCGTTG-3' (SEQ ID NO: 246) | 5'-TTCTGACCCATTCCCA CCATCACA-3' (SEQ ID NO: 247) |

The expression of APOC3 mRNA was calculated by the equation: the expression of APOC3 mRNA=(the expression of APOC3 mRNA in the test group/the expression of β-actin m RNA in the test group)/(the expression of APOC3 mRNA in the control group/the expression of β-actin mRNA in the control group)×100%.

The inhibition ratio of conjugates against the expression of APOC3 mRNA was calculated by the equation: the inhibition ratio=[1-(the expression of APOC3 mRNA in the test group/the expression of β-actin mRNA in the test group)/(the expression of APOC3 mRNA in the control group/the expression of β-actin mRNA in the control group)×100%. Therein, the control group was a group of control mice administrated with PBS in this experiment and each test group was a group of mice administrated with different siRNA conjugates, respectively. The results are shown in FIG. 44A.

Figure 44A:
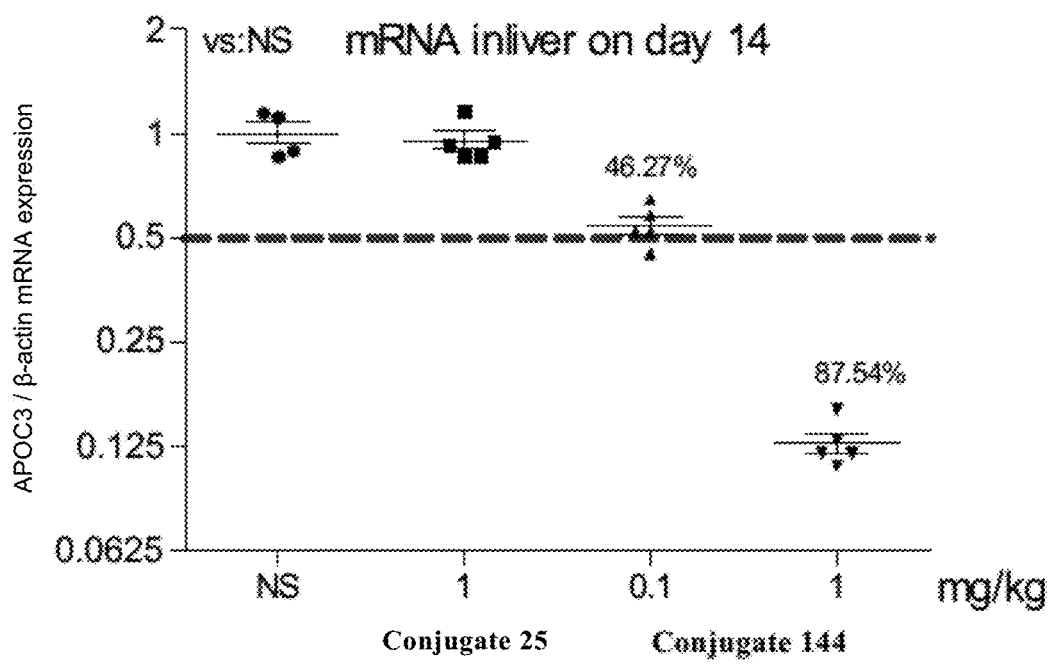
FIG. 44A shows the inhibition ratio of APOC3 expression in liver at D14.

As can be seen from the results of FIG. 44A, Conjugates 144 shows excellent inhibitory activity in the expression of human APOC3 gene in transgene mice in vivo.

Experimental Conjugate 9-2—this Experiment Illustrates the Effect of the siRNA Conjugate of Conjugates 144 on the Blood Lipid Content In Vivo In this experimental example, the effects of the siRNA conjugate of Conjugate 144 on the contents of total cholesterol (CHO) and triglyceride (TG) in serum in human APOC3 transgenic mice (B6; CBA-Tg(APOC3)3707Bres/J, purchased from Jackson Lab) in vivo were investigated.

The human APOC3 transgenic mice (6-8 week old, TG content >2 mmol/L) were randomly divided into groups (7 mice for each group): (1) NS control group; (2) 3 mg/kg group for the conjugate of Conjugate 144; (3) 1 mg/kg group for the conjugate of Conjugate 144. The drug dosages for all animals were calculated according to the body weight. A single dose was administered subcutaneously, respectively as 0.6 mg/ml and 0.2 mg/ml of 0.9 wt % NaCl aqueous solution with the volume of 5 ml/kg for the siRNA conjugate.

The blood (about 100 μL) was taken from orbits before administration (recorded as day 0) and at days 7, 14, 21, 28, 35, 42, 49, 63, 77, 91, 112, 133, 147, 154, 161, 175 and 189 after administration respectively and centrifuged to obtain serum. The contents of total cholesterol (CHO) and triglyceride (TG) in serum were further measured by using a PM1P000/3 full-automatic serum biochemical analyzer (SABA, Italy). The results of blood lipid were normalized and normalized blood lipid levels as well as the inhibition ratio for the blood lipid levels are in accordance with Experimental Example 8-3. The test results are shown in FIGS. 44B and 44C.

Figure 44B:
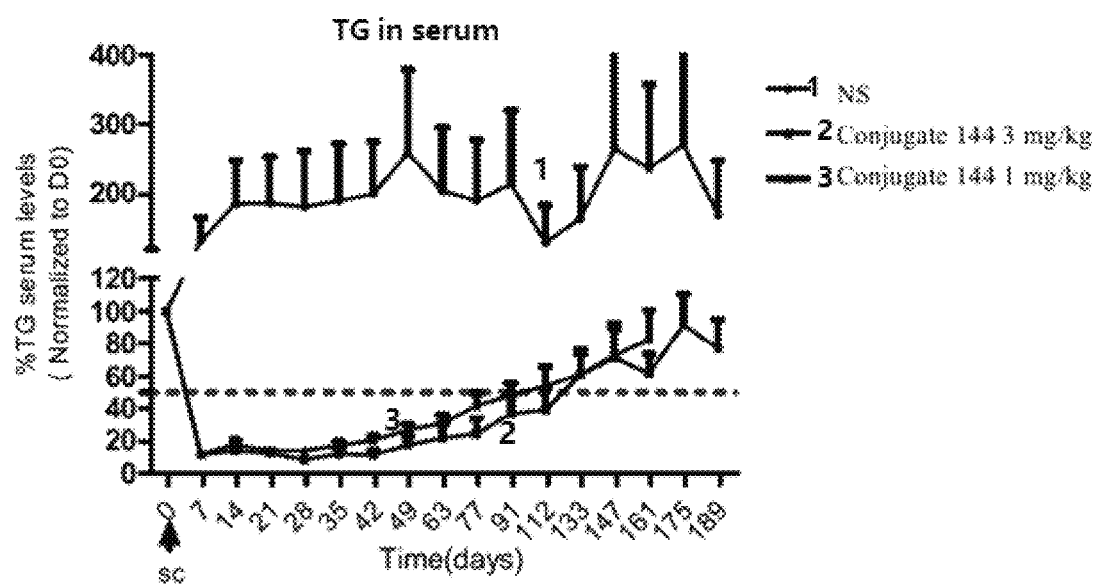
FIGS. 44B and 44C shows the inhibition ratio of blood lipid, represented by total cholesterol (CHO) and triglyceride (TG) in serum, by Conjugate 144 at different dosages.
Figure 44C:
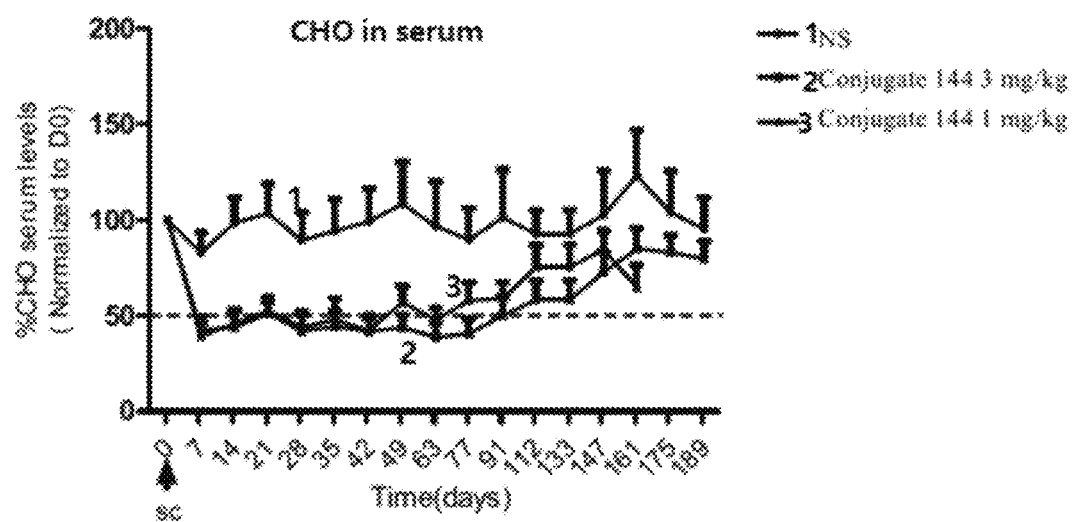

As can be seen from FIGS. 44B and 44C, Conjugate 144 showed a significant down-regulation effect for the contents of TG and CHO lever in mouse serum in up to 189 days, indicating a long-time, stable and efficient inhibitory against the expression of human APOC3 gene.

In other experiments, method same to the above was employed, except in that Conjugate 170 was administrated, each at the dosage of 0.1, 0.3, 1, 3 and 9 mg/kg (with same dosage volume and concentration of the cogjugates in the solution respectively adjusted); and the data is collected until day 112 after administration. The result is shown in FIGS. 45A and 45B.

Figure 45A:
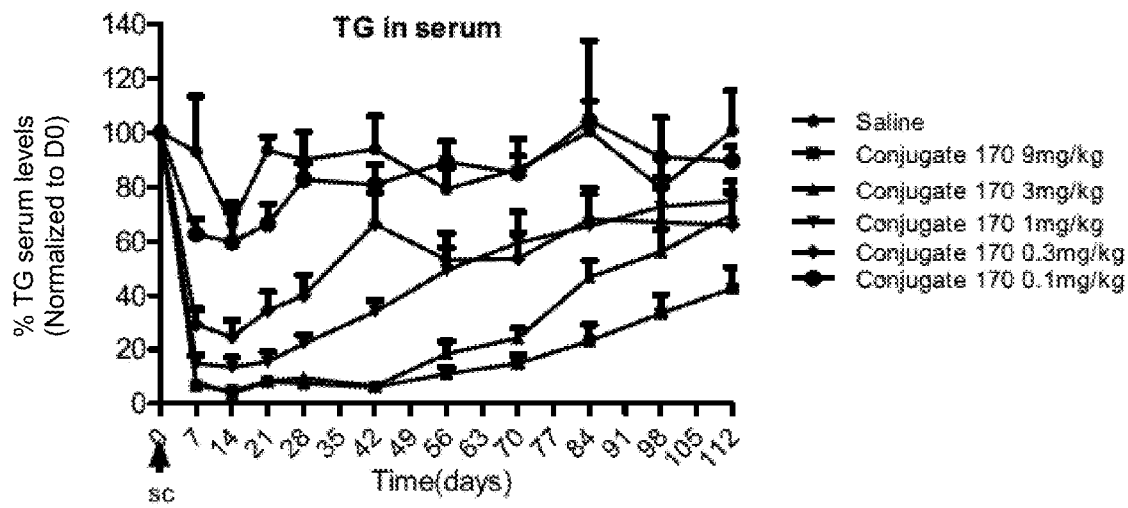
FIGS. 45A and 45B show the inhibition ratio of blood lipid, represented by total cholesterol (CHO) and triglyceride (TG) in serum, by Conjugate 170 at different dosages.
Figure 45B:
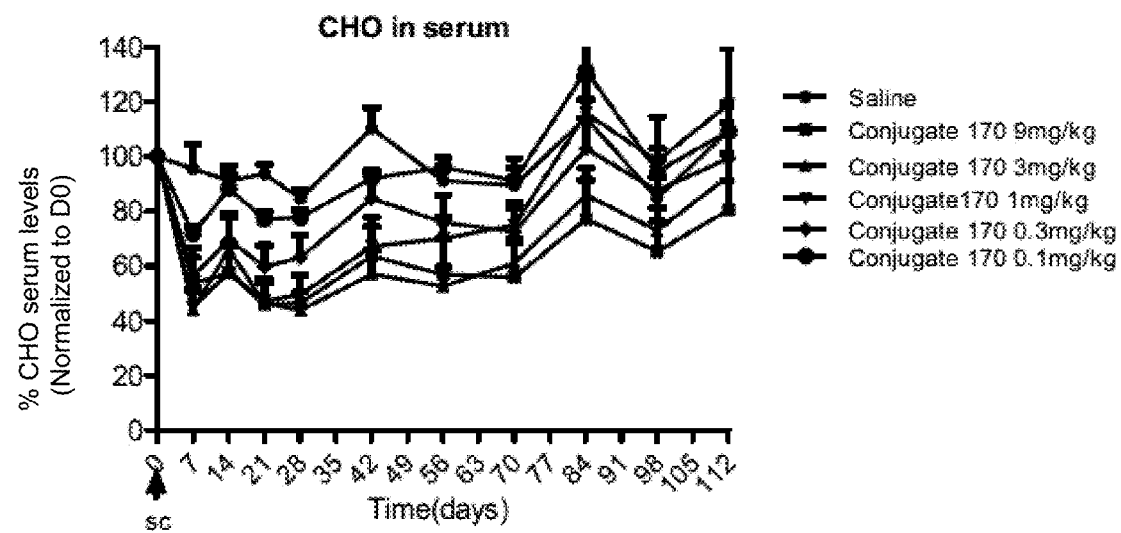
Figure 46A:
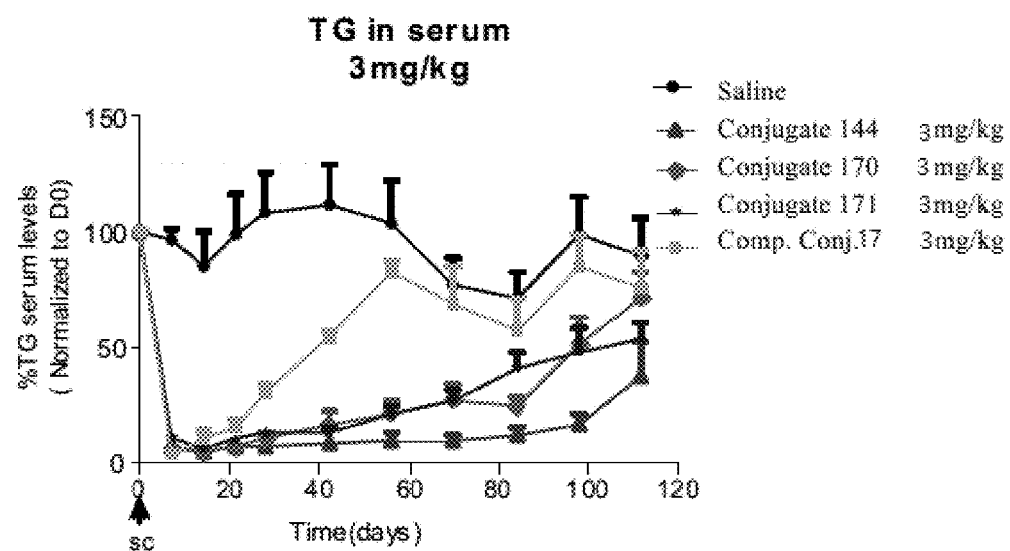
FIGS. 46A, 46B, 46C and 46D show the inhibition ratio of blood lipid, represented by total cholesterol (CHO) and triglyceride (TG) in serum, by conjugates disclosed herein.
Figure 46B:
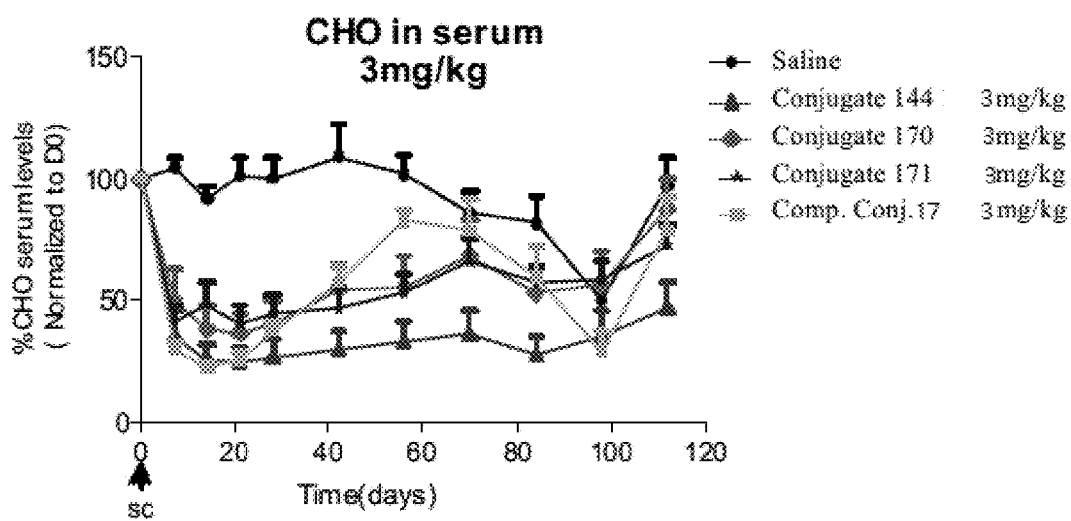
Figure 46C:
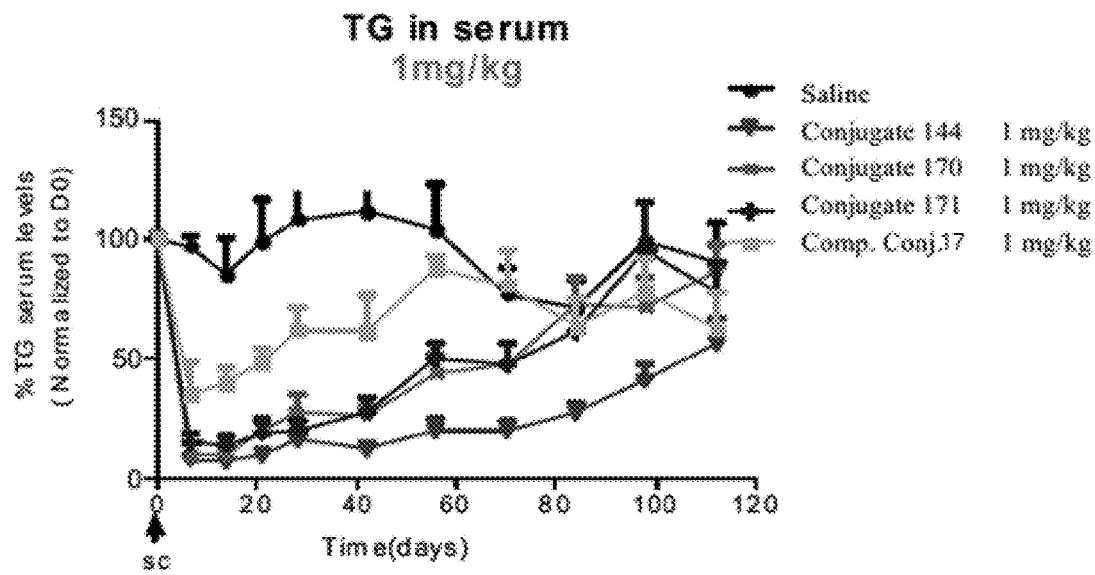
Figure 46D:
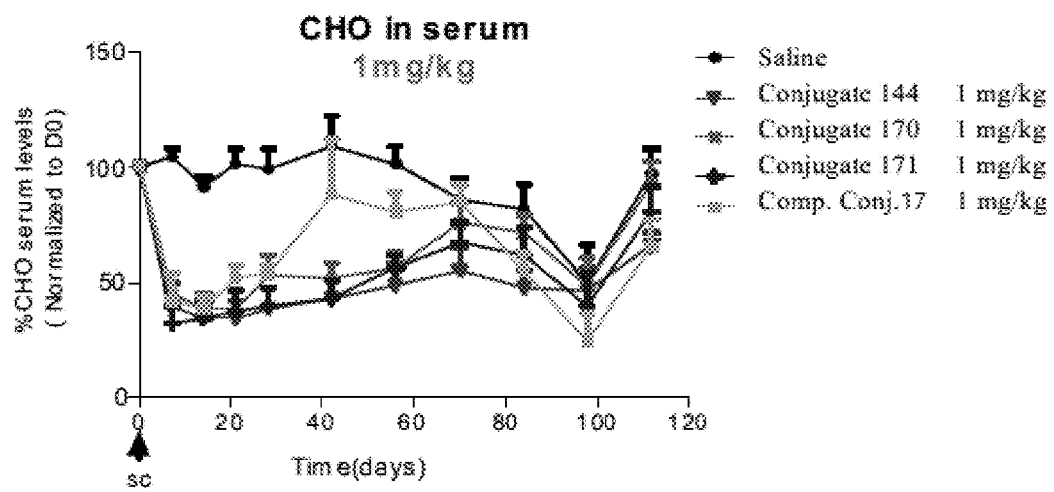

As can be seen from the results of FIGS. 45A and 45B, it can be seen that Conjugates 170 can continuously reduce the blood lipid and ANGPTL3 mRNA level in transgene mice in vivo in up to 112 days, and the reduction shows significant dose dependency.

In other experiments, method same to the above was employed to measure the contents of total cholesterol (CHO) and triglyceride (TG) in serum of the mice, except in that Conjugates 144, 170 and 171 as well as Comparative Conjugate 17 were administrated, each at the dosage of 1 mg/kg and 3 mg/kg (with same dosage volume and concentration of the conjugates in the solution respectively adjusted); and the data is collected until day 112 after administration. The result is shown in FIGS. 46A-46D.

As can be seen from the results of FIGS. 46A-46D, it can be seen that Conjugates 144, 170 and 171 showed continuously reduction on the blood lipid in transgene mice during up to 112 days, and the lasting effect of the reduction is generally superior to Comparative Conjugate 17.

Embodiments of the present disclosure are described in detail above, but the present disclosure is not limited to the specific details of the above-described embodiments. Various simple variations of the technical solution of the present disclosure can be made within the scope of the technical concept of the present disclosure, and these simple variations are within the scope of the present disclosure.

It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

What is claimed is:

1. A compound having a structure represented by Formula (321):

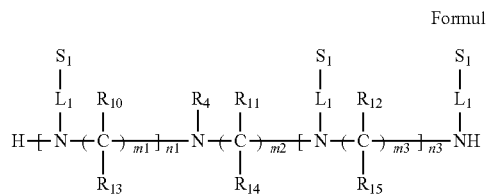

Formula (321)

wherein, n1 is an integer of 1-2, n3 is an integer of 0-1, and n1+n3=2-3;

each of m1, m2, and m3 is independently an integer of 2-10;

each of $R_{10}$, $R_{11}$, $R_{12}$, $R_{13}$, $R_{14}$ and $R_{15}$ is independently selected from H, $C_1$-$C_{10}$ alkyl, $C_1$-$C_{10}$ haloalkyl, and $C_1$-$C_{10}$ alkoxy;

$R_4$ is a moiety capable of binding to an active drug or active agent via a covalent bond;

each $L_1$ is a linear alkylene of 1 to 70 carbon atoms in length, wherein one or more carbon atoms are optionally replaced with any one or more of the group consisting of: C(O), NH, O, S, CH=N, S(O)$_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $S_1$ is independently an $M_1$, wherein any active hydroxyl, if any, is protected with a hydroxyl protecting group;

each $M_1$ is independently selected from a ligand capable of binding to a cell surface receptor; and wherein the receptor is an asialoglycoprotein receptor on human hepatocytes.

2. The compound according to claim 1, wherein each $L_1$ is independently selected from the group consisting of groups A1-A26 and any combinations thereof:

(A1)

(A2)

(A3)

(A4)

(A5)

(A6)

(A7)

(A8)

(A9)

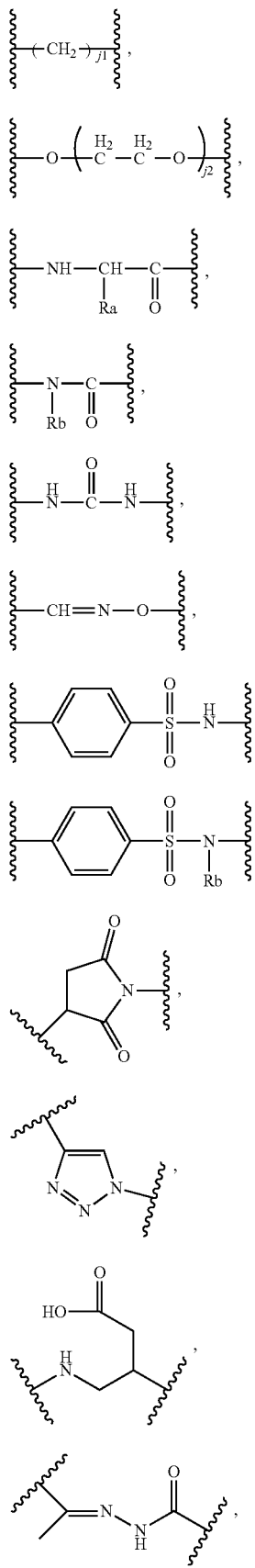
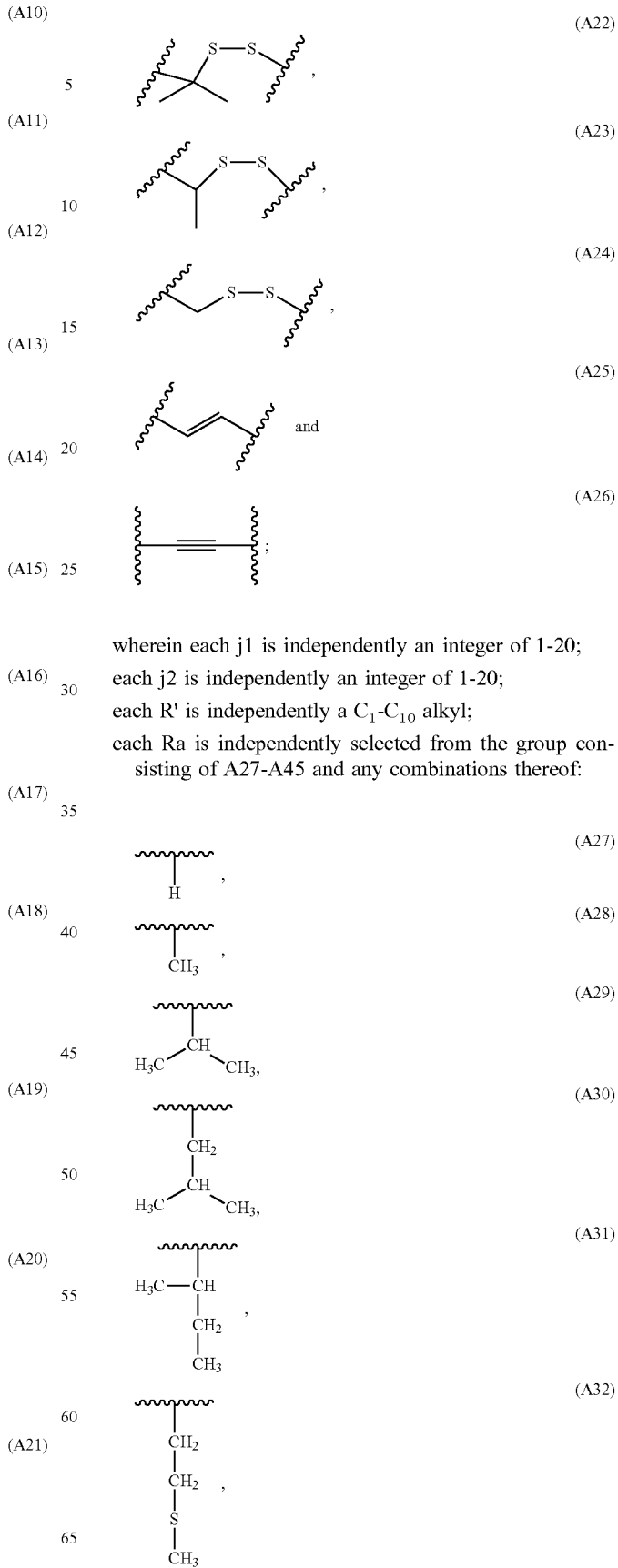
wherein each j1 is independently an integer of 1-20;
each j2 is independently an integer of 1-20;
each R' is independently a $C_1$-$C_{10}$ alkyl;
each Ra is independently selected from the group consisting of A27-A45 and any combinations thereof:

-continued (A33) 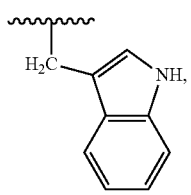

(A34) 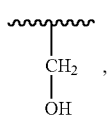

(A35) 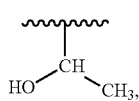

(A36) 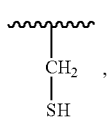

(A37) 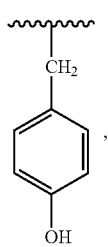

(A38) 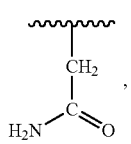

(A39) 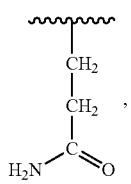

(A40) 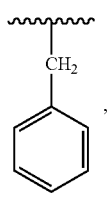

(A41) 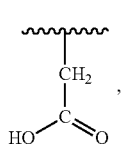

(A42) 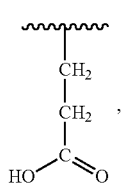

-continued (A43) 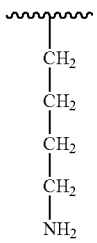

(A44) 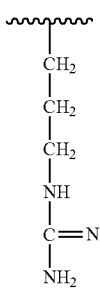

(A45) 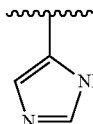

each Rb is independently a $C_1$-$C_{10}$ alkyl; and

∿∿∿ represents a site where a group is attached to the rest of the molecule.

3. The compound according to claim 2, wherein $L_1$ is selected from the group consisting of groups A1, A4, A5, A6, A8, A10, A11, A13, and connection combinations thereof.

4. The compound according to claim 1, wherein the length of $L_1$ is 3 to 25 atoms, wherein the length of $L_1$ refers to the number of chain-forming atoms in $L_1$ within the longest atom chain formed from the atom linked to the N atom on the nitrogenous backbone to the atom linked to $S_1$.

5. The compound according to claim 1, wherein each of m1, m2 and m3 is independently an integer of 2-5, or m1=m2=m3.

6. The compound according to claim 1, wherein each $M_1$ is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

7. The compound according to claim 1, wherein $R_4$ is a group capable of binding to an oligonucleotide via a phosphodiester bond.

8. The compound according to claim 1, wherein $R_4$ comprises a first functional group that can react with a group on an oligonucleotide or a nucleotide to form a phosphate ester bond.

9. The compound according to claim 8, wherein $R_4$ further comprises a second functional group which is capable of forming a covalent bond with a hydroxy group or an amino group, or is a solid phase support attached to the rest of the molecule via a covalent bond formed with a hydroxy group or an amino group.

10. The compound according to claim 8, wherein the first functional group is a phosphoramidite, a hydroxy or a protected hydroxy.

11. The compound according to claim 9, wherein the second functional group is a phosphoramidite group, a carboxyl or a carboxylate.

12. The compound according to claim 8, wherein the compound has a structure represented by Formula (403)-(442):

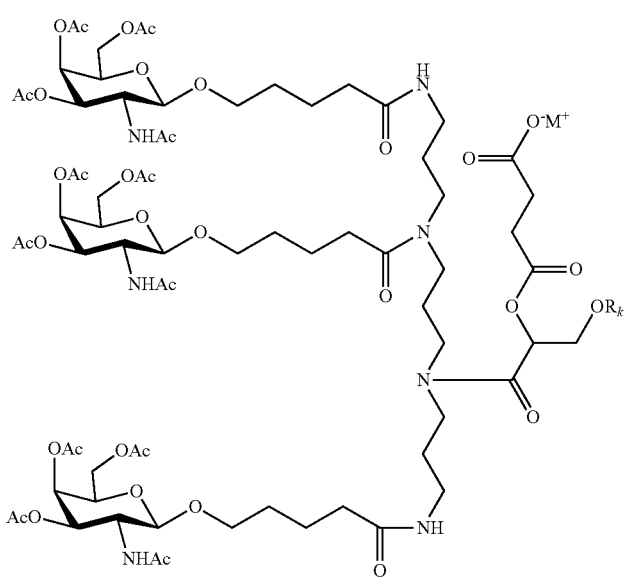

(403)

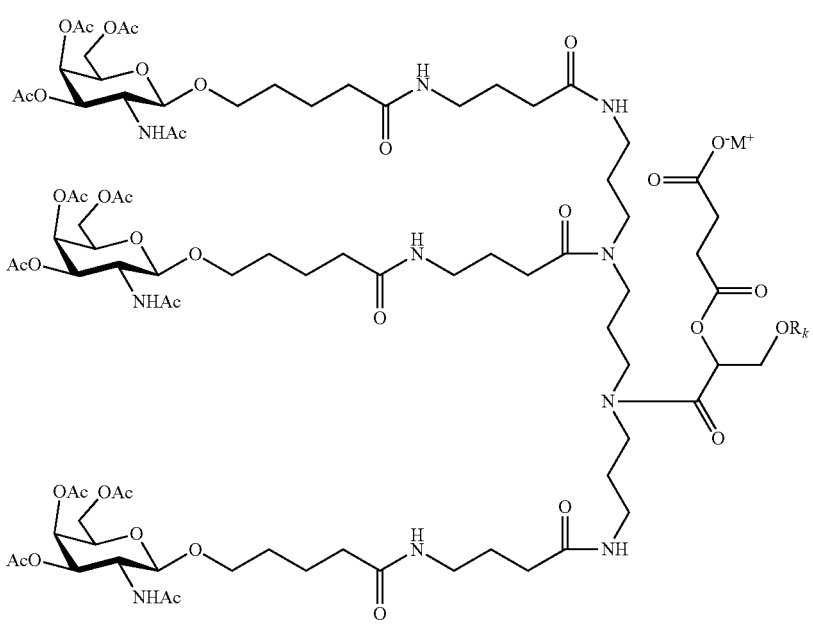

(404)

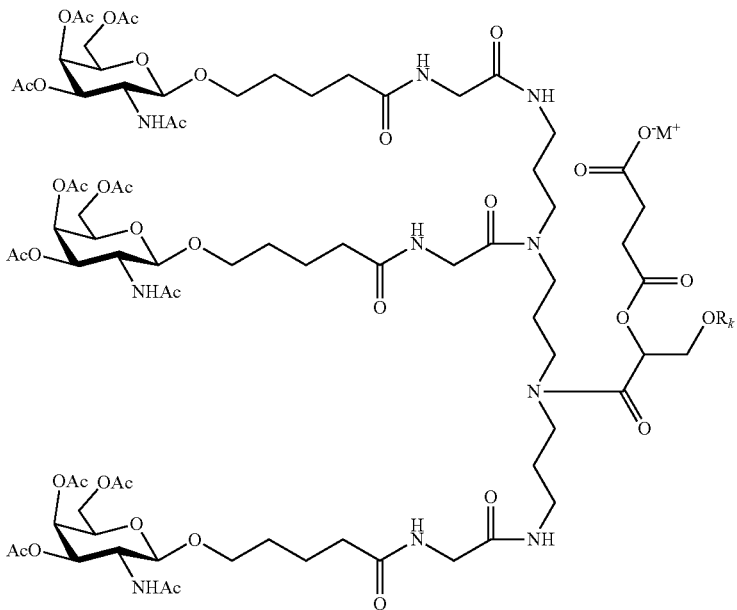
(405)
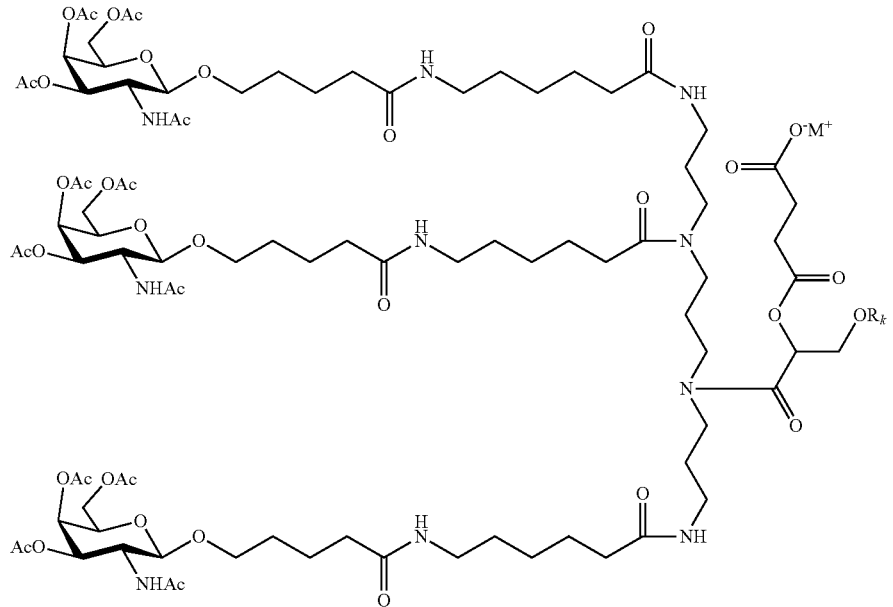
(406)

-continued
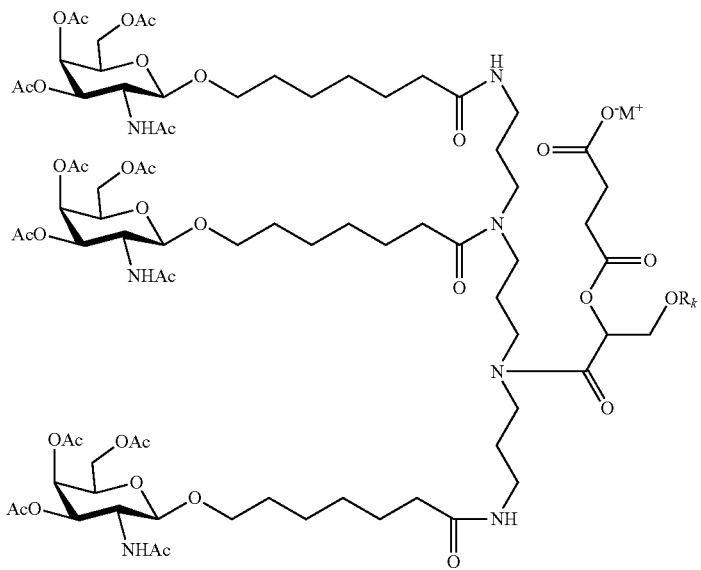
(407)
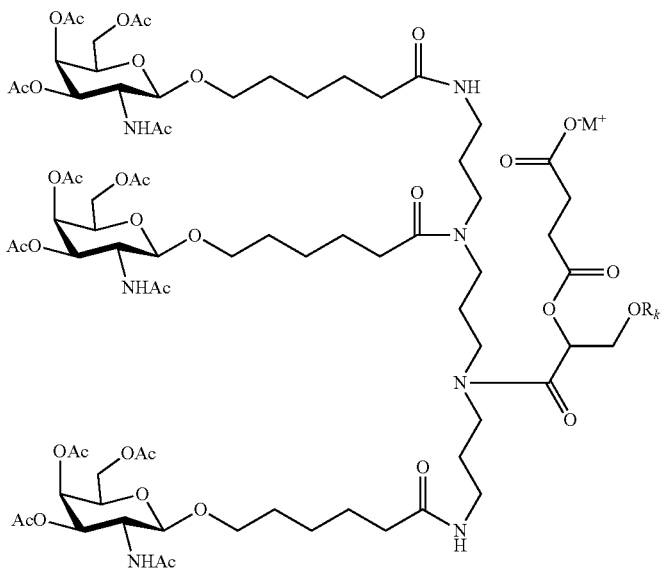
(408)

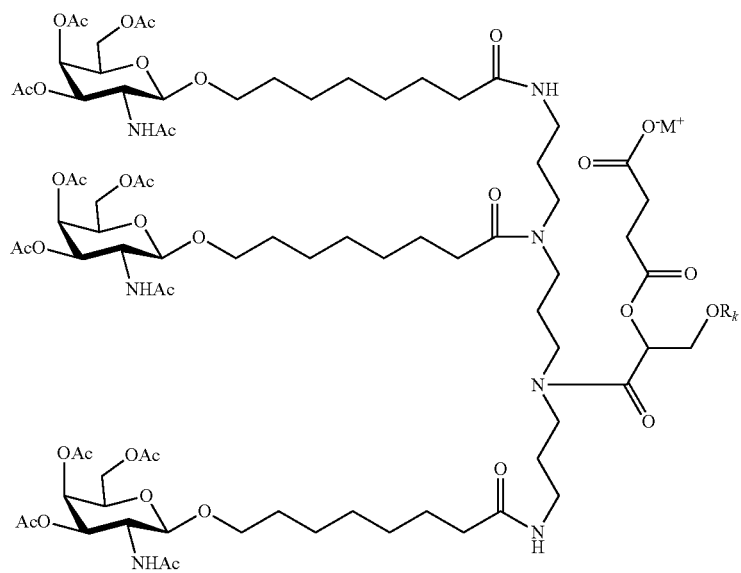
(409)
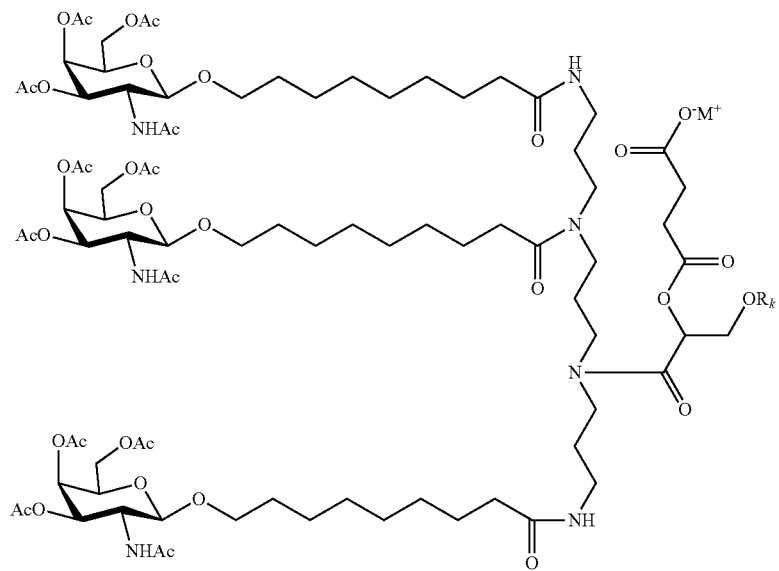
(410)

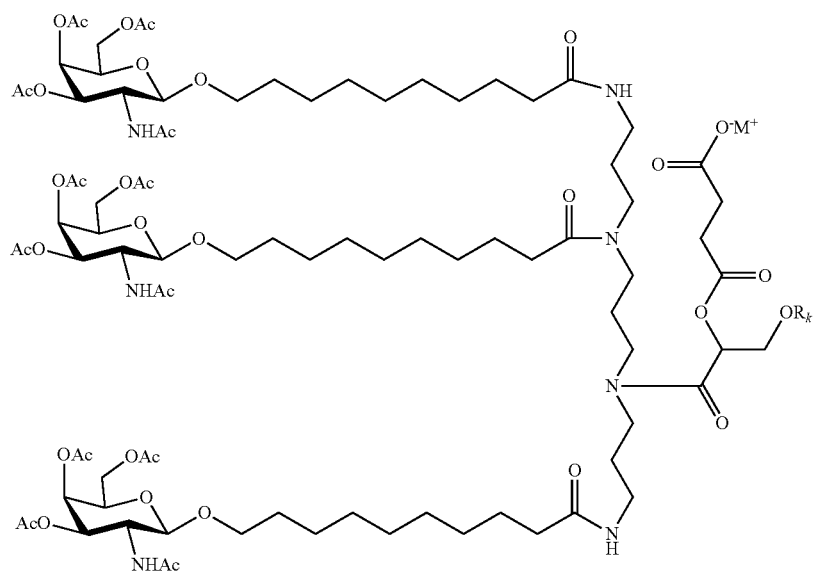
(411)
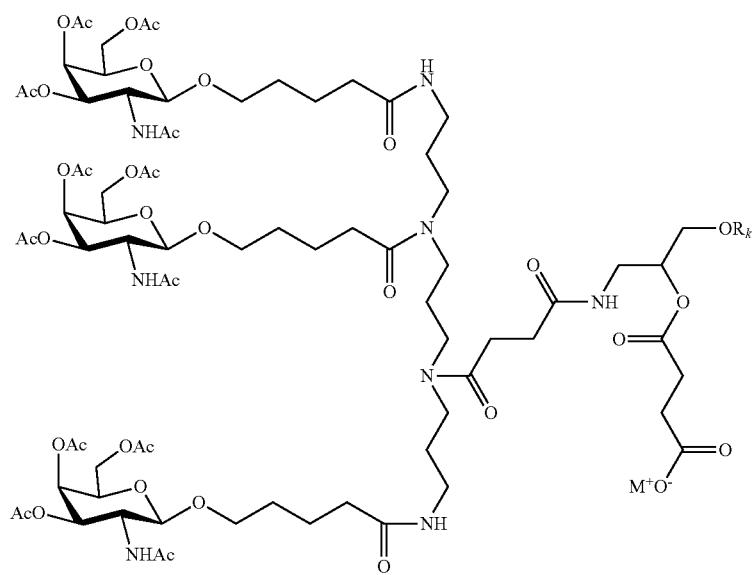
(412)

(413)
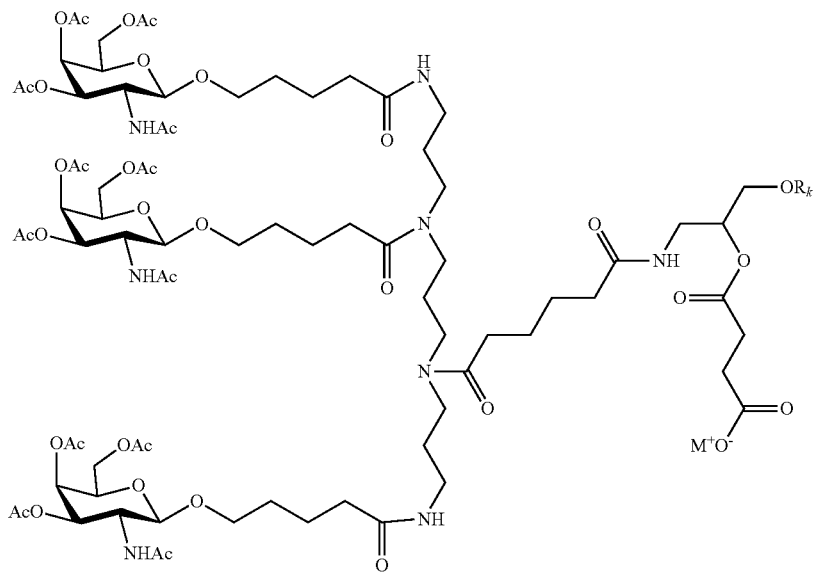
(414)
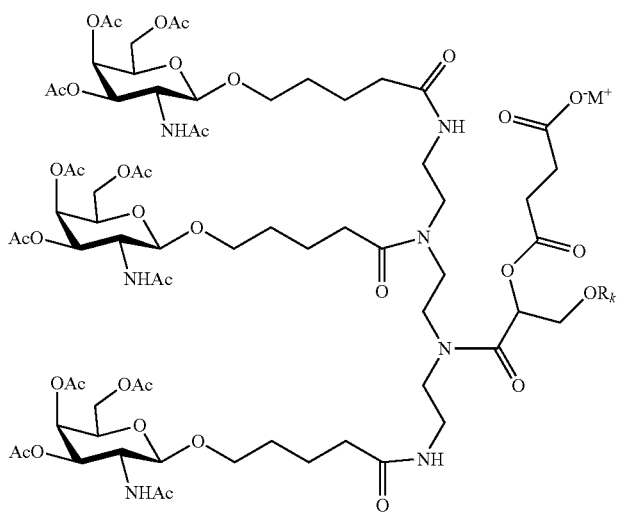

-continued
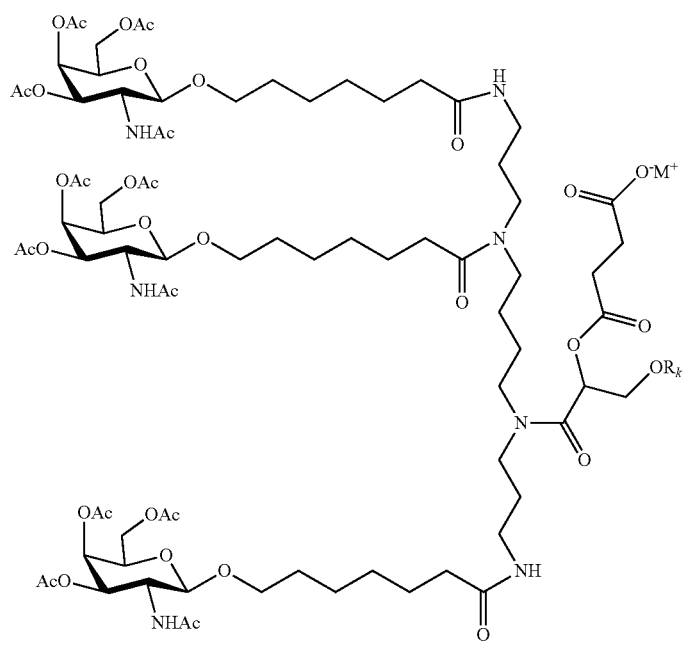
(415)
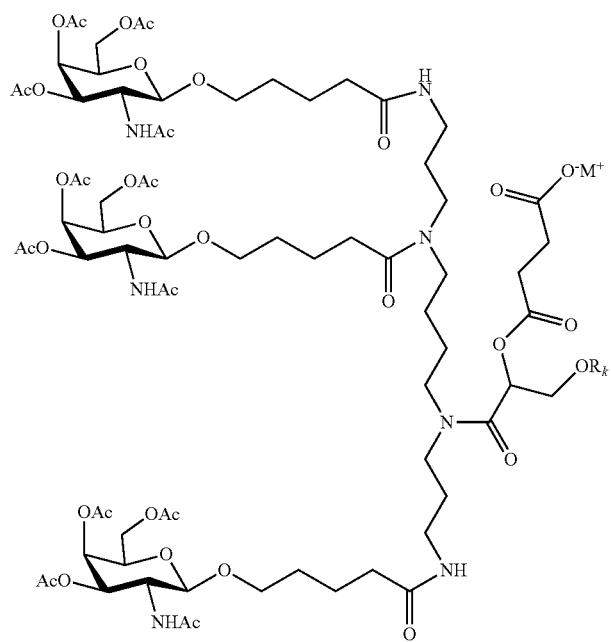
(416)

(417)
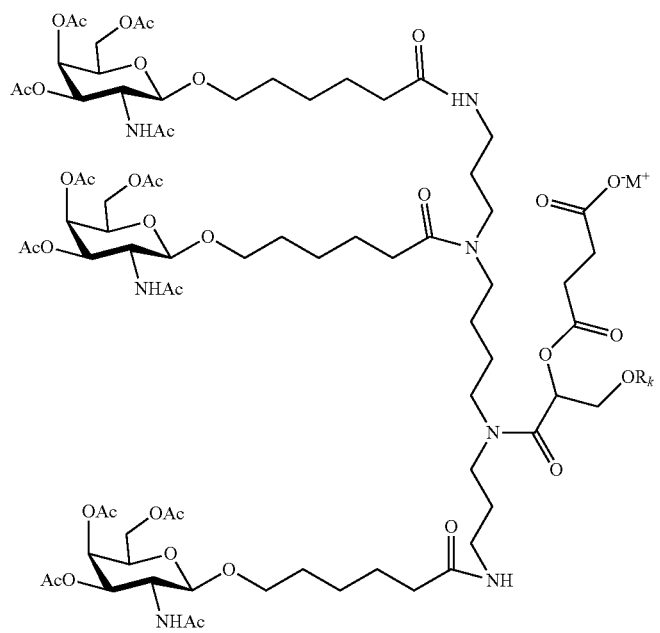
(418)
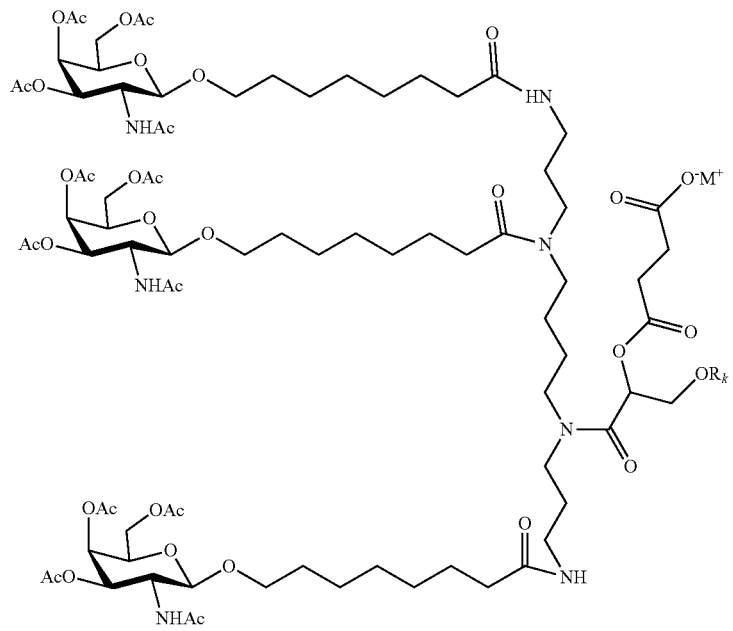

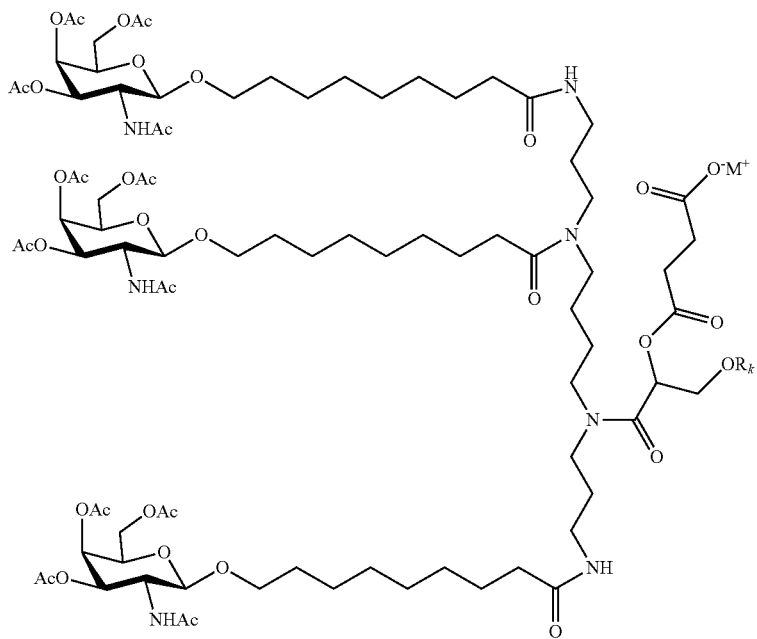
(419)
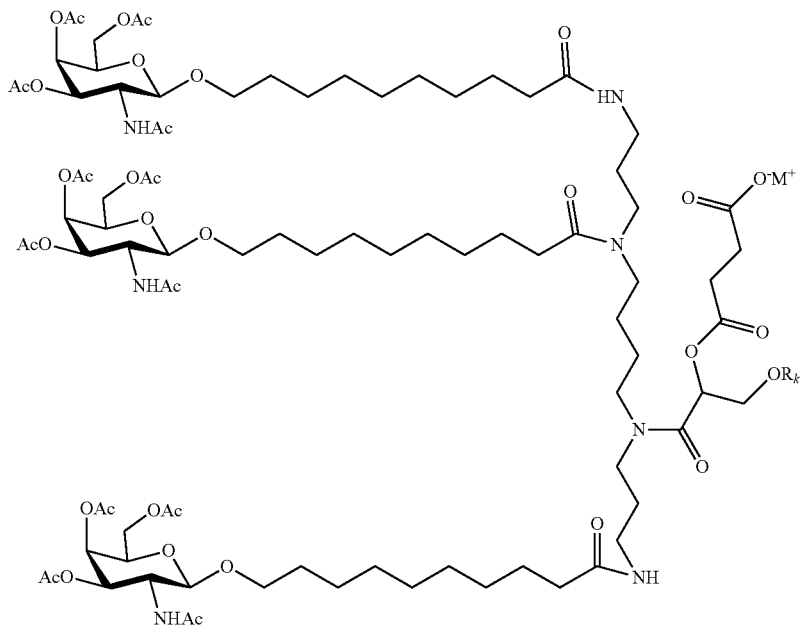
(420)

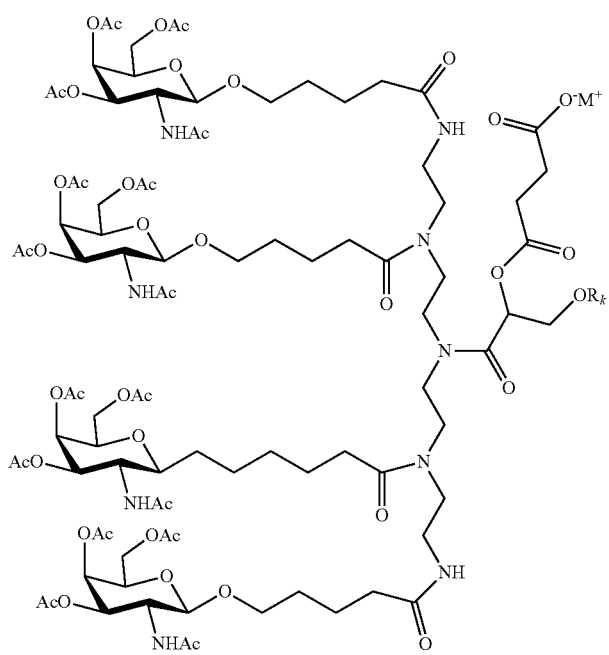
(421)
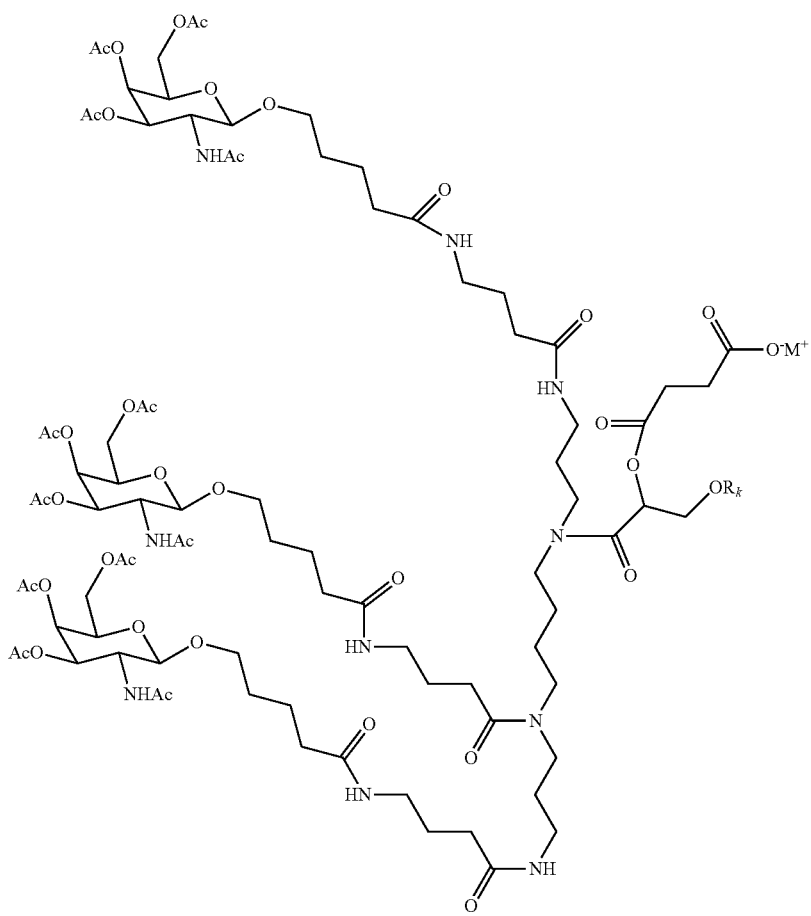
(422)

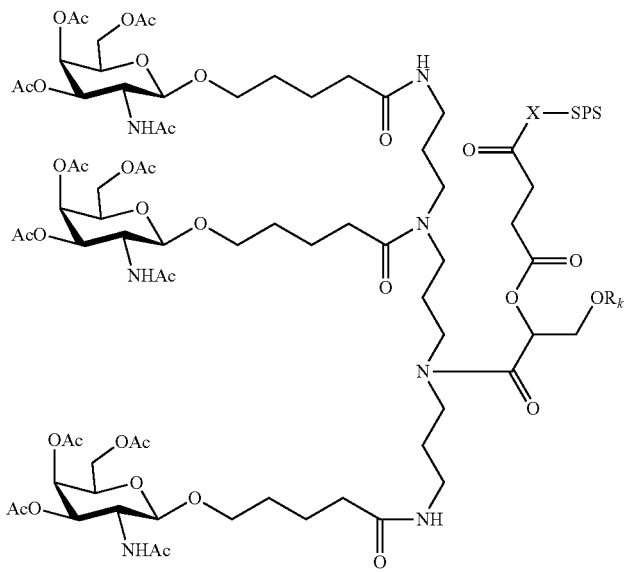
(423)
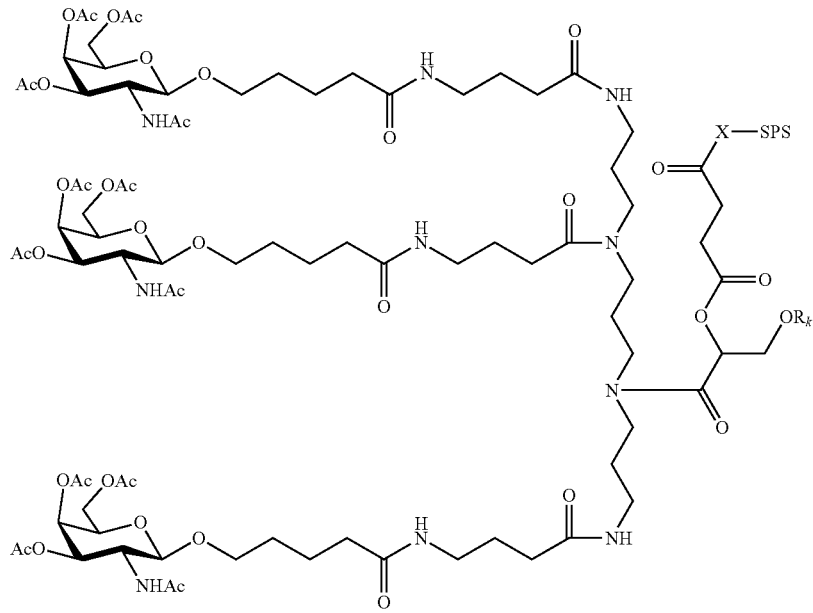
(424)

-continued
(425)
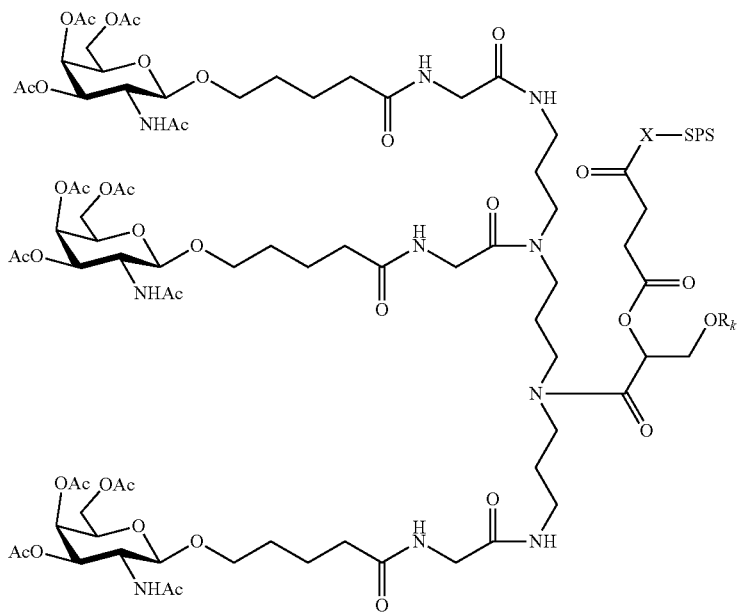
(426)
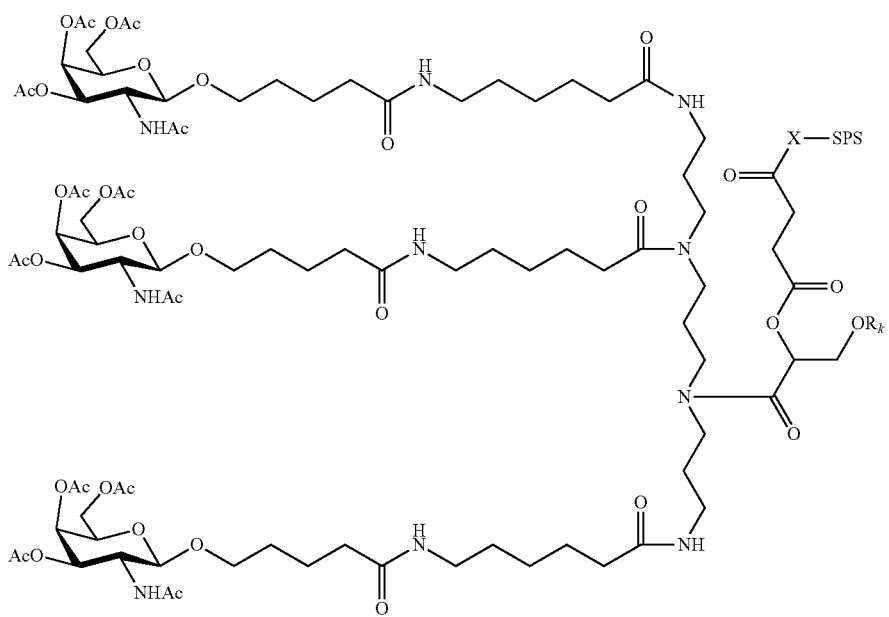

-continued
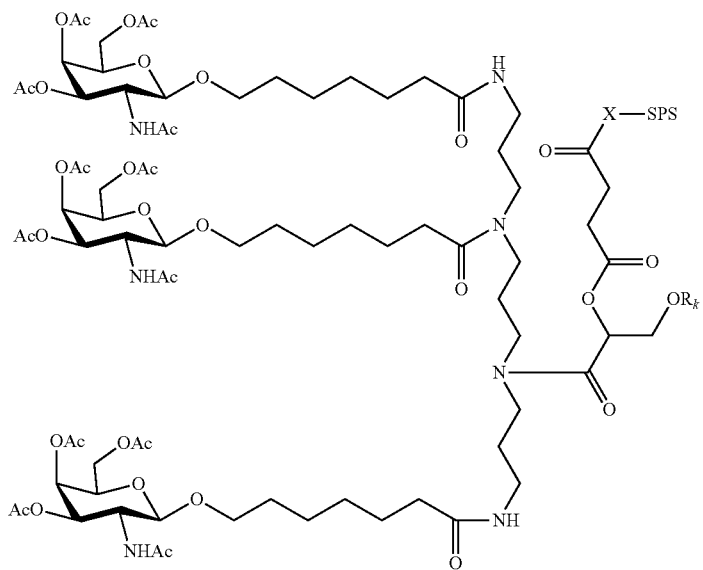
(427)
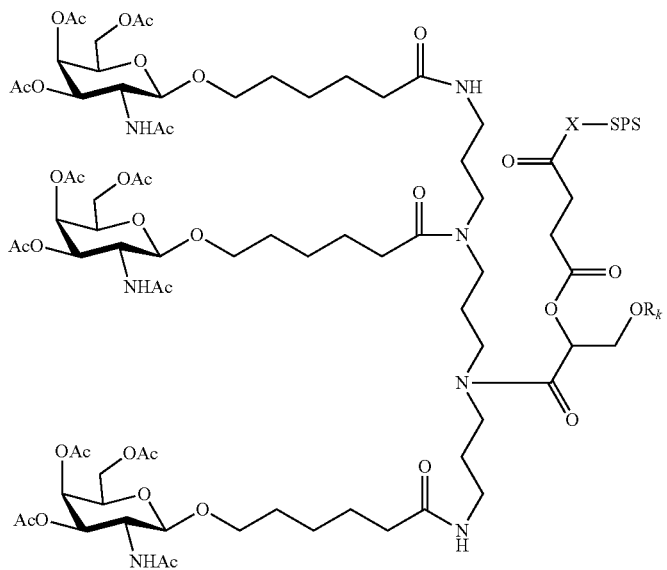
(428)

(429)
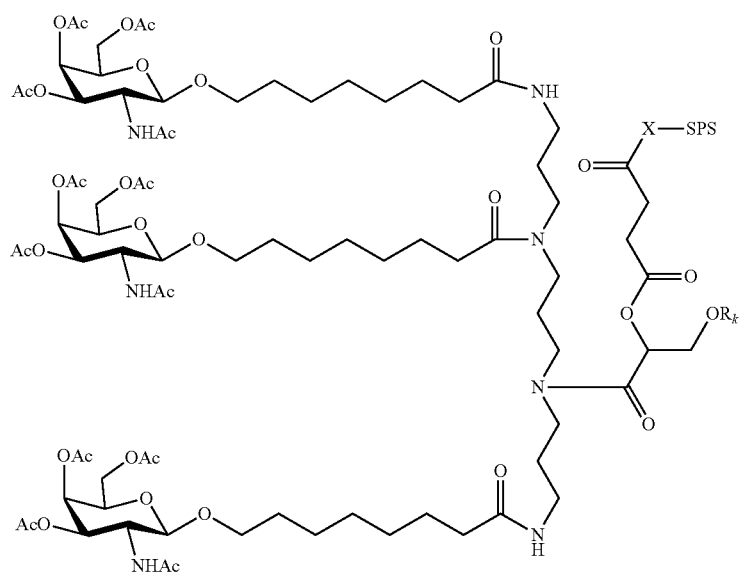
(430)
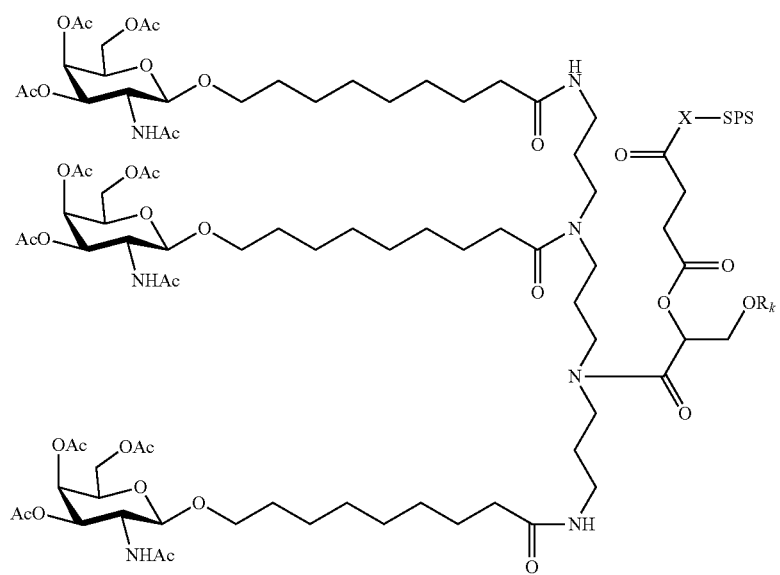

-continued
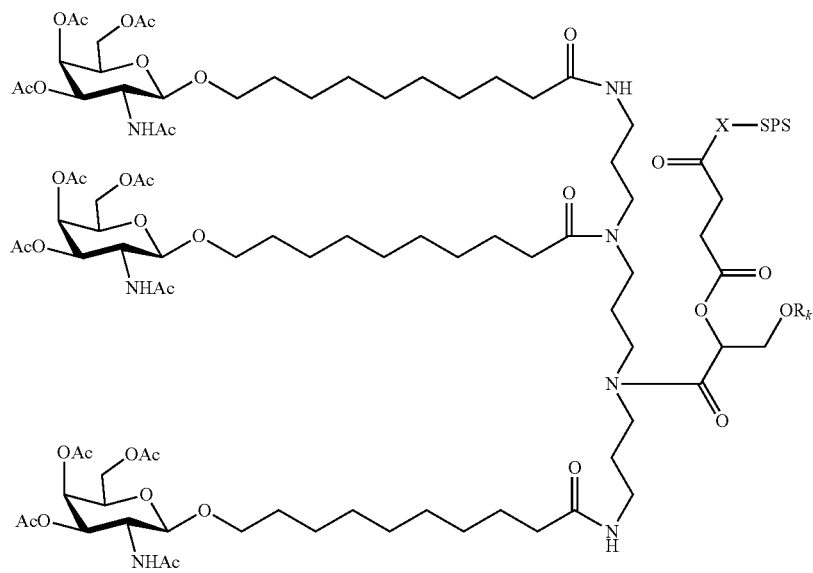
(431)
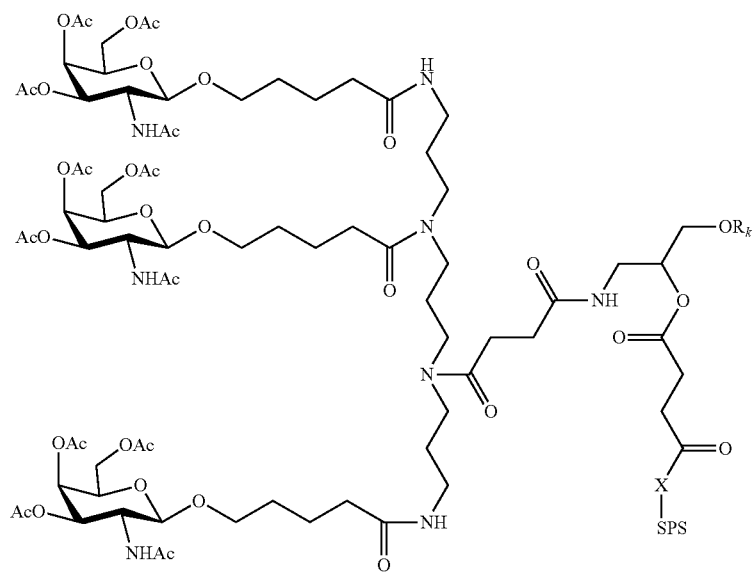
(432)

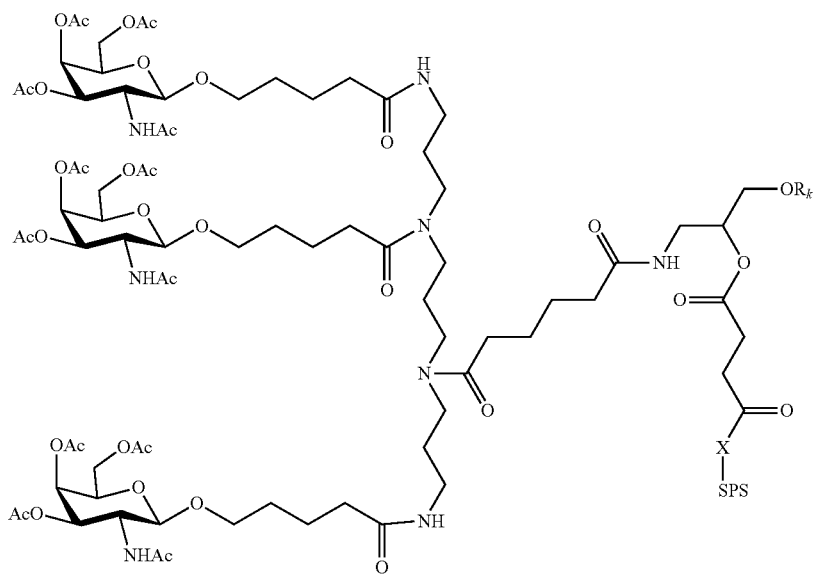
(433)
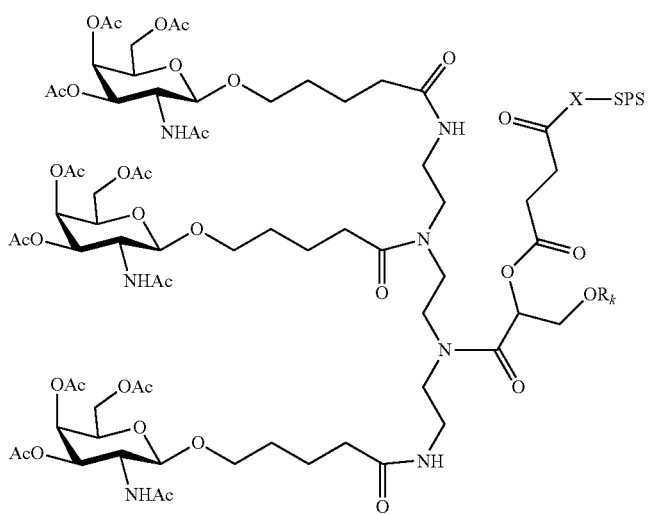
(434)

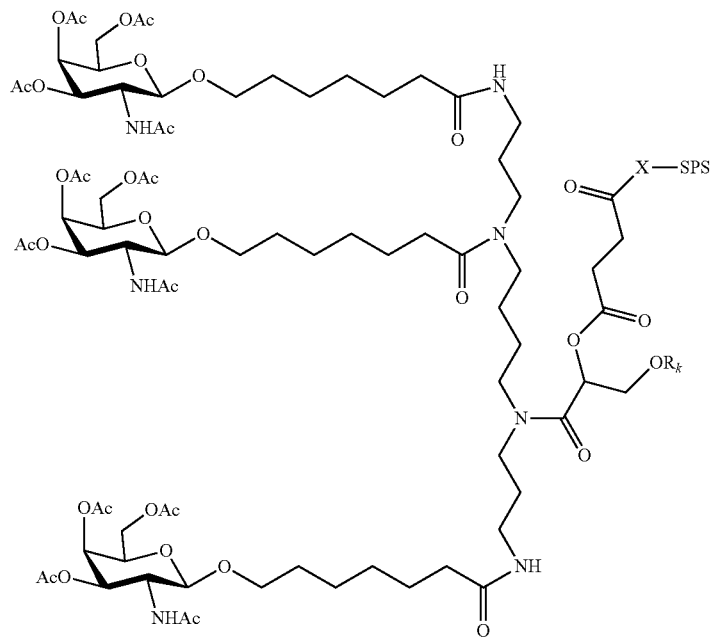
(435)
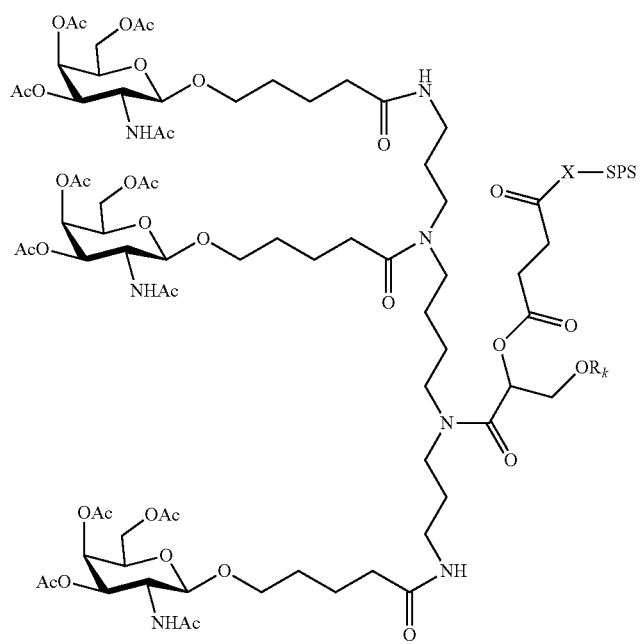
(436)

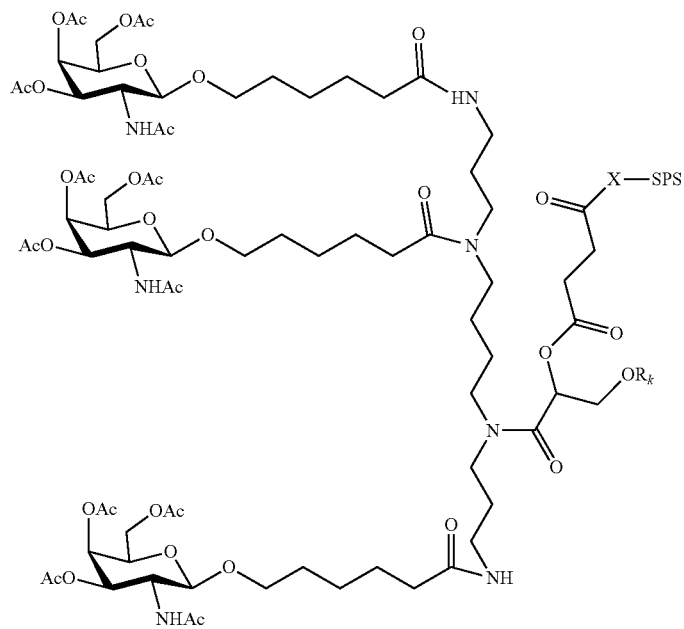
(437)
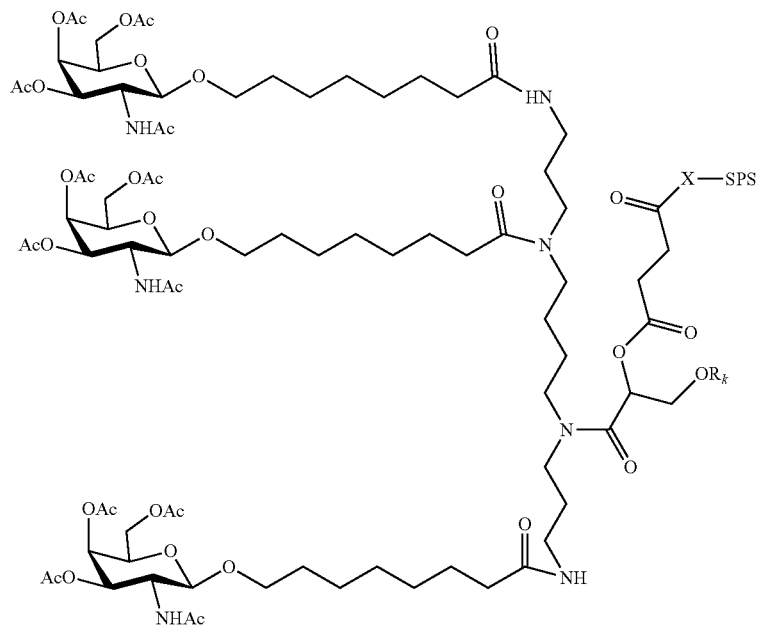
(438)

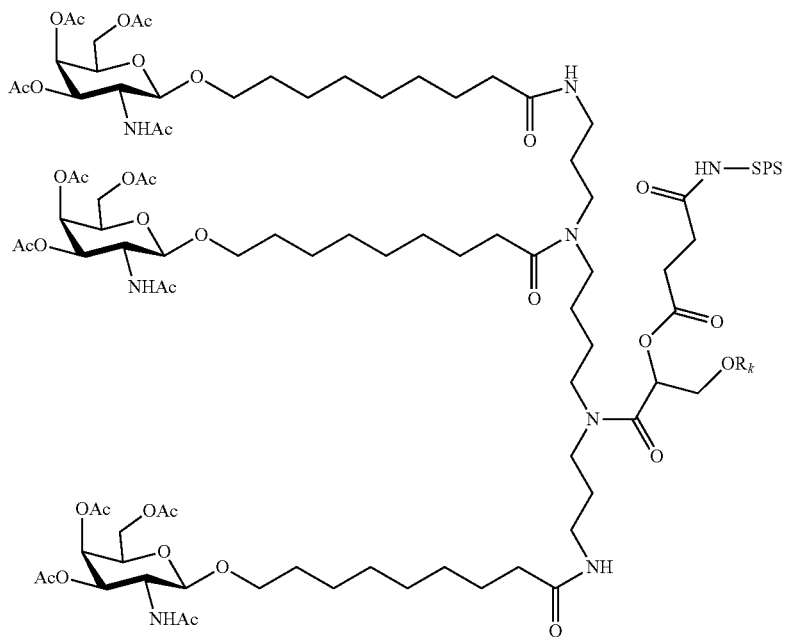
(439)
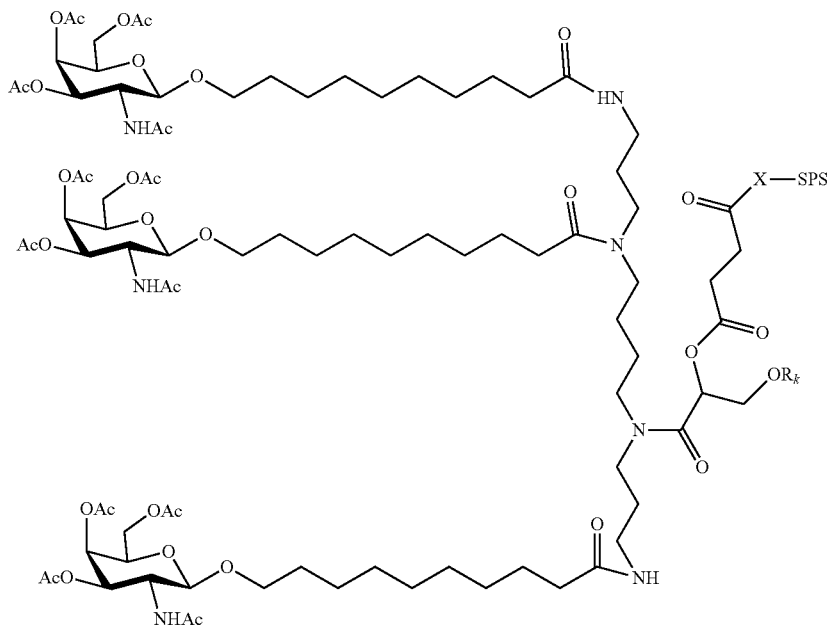
(440)

-continued
(441)
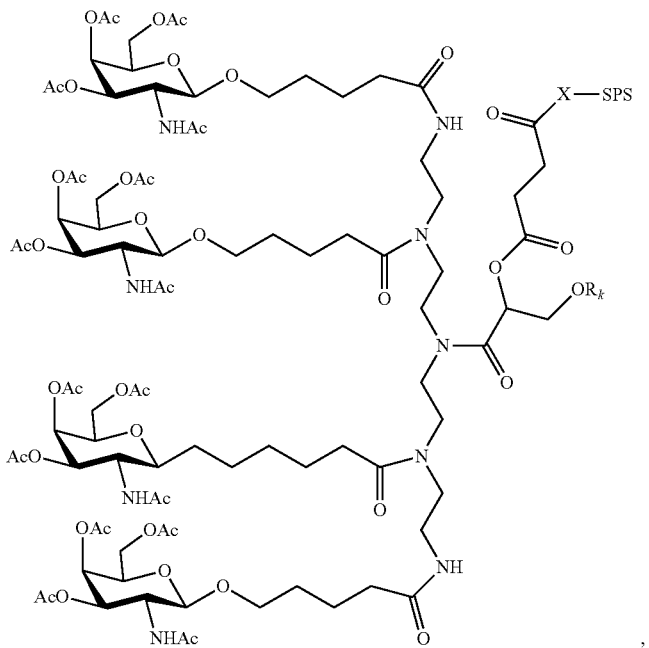
(442)
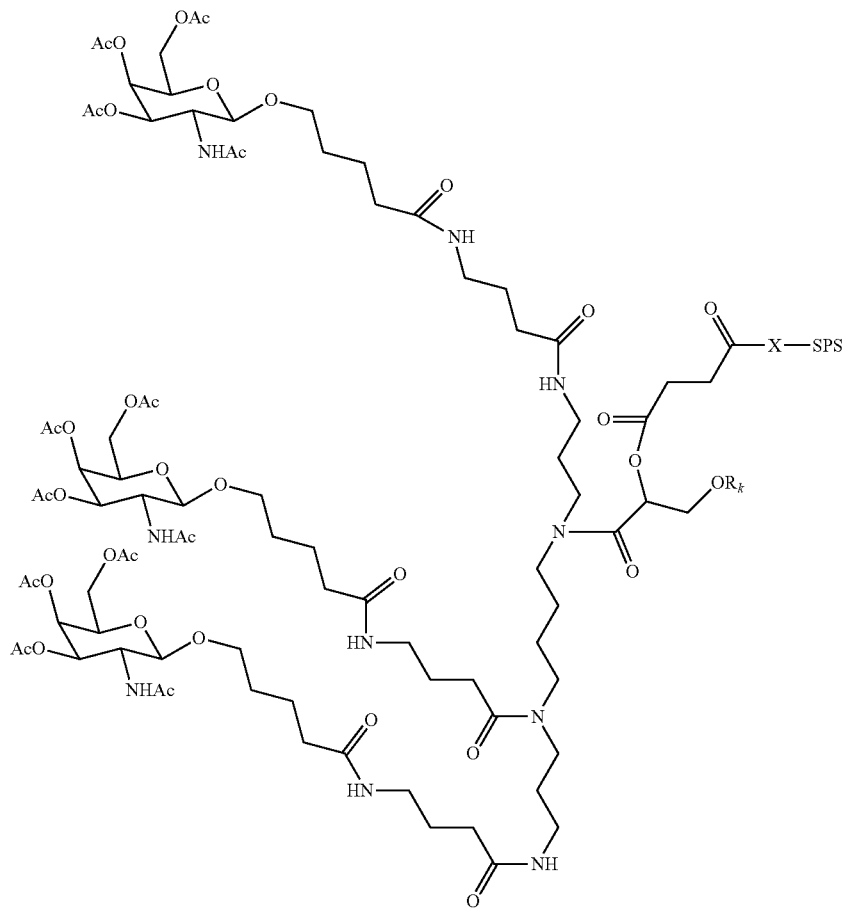

wherein X is O or NH, M+ is a cation, $R_k$ is a hydroxy protecting group, SPS represents a solid phase support.

13. The compound according to claim 12, wherein M+ is an alkali metal cation, an ammonium cation, a cation formed from a tertiary amine, or a quaternary ammonium cation, $R_k$ is trityl, 4-methoxytrityl, 4,4'-dimethoxytrityl, or 4,4',4"-trimethoxytrityl, and SPS represents a resin.

14. A conjugate having a structure represented by Formula (1):

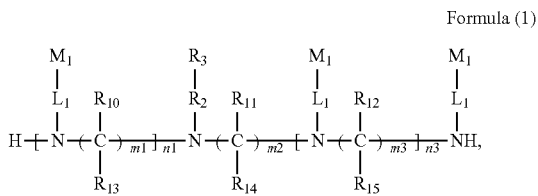

Formula (1)

wherein, n1 is an integer of 1-2, n3 is an integer of 0-1, and n1+n3=2-3;

each of m1, m2, and m3 is independently an integer of 2-10;

each of R10, R11, R12, R13, R14 and R15 is independently selected from H, $C_1$-$C_{10}$ alkyl, $C_1$-$C_{10}$ haloalkyl, and $C_1$-$C_{10}$ alkoxy;

$R_3$ is an active drug;

$R_2$ is a linear alkylene of 1 to 20 carbon atoms in length, wherein one or more carbon atoms are optionally replaced with any one or more of the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is independently a linear alkylene of 1 to 70 carbon atoms in length, wherein one or more carbon atoms are optionally replaced with any one or more of the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), alkyl)($C_1$-$C_{10}$ alkylphenyl), —NH($C_1$-$C_{10}$ alkylphenyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $M_1$ is selected from one of ligands capable of binding to a cell surface receptor; and wherein the receptor is an asialoglycoprotein receptor on human hepatocytes.

15. The conjugate according to claim 14, wherein each $L_1$ is independently selected from the group consisting of groups A1-A26 and any combinations thereof:

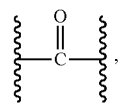 (A1)

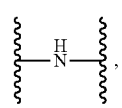 (A2)

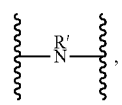 (A3)

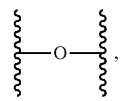 (A4)

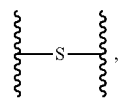 (A5)

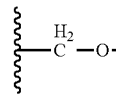 (A6)

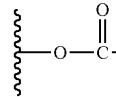 (A7)

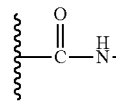 (A8)

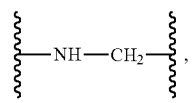 (A9)

-continued
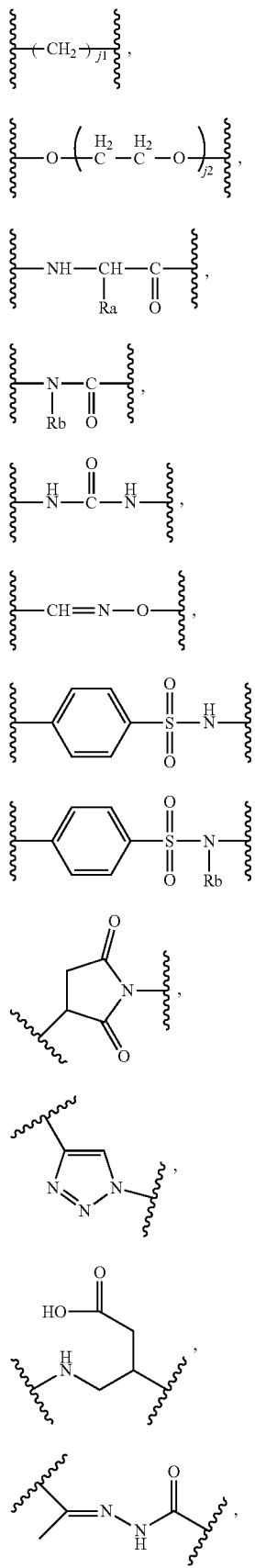
(A10)
(A11)
(A12)
(A13)
(A14)
(A15)
(A16)
(A17)
(A18)
(A19)
(A20)
(A21)
-continued
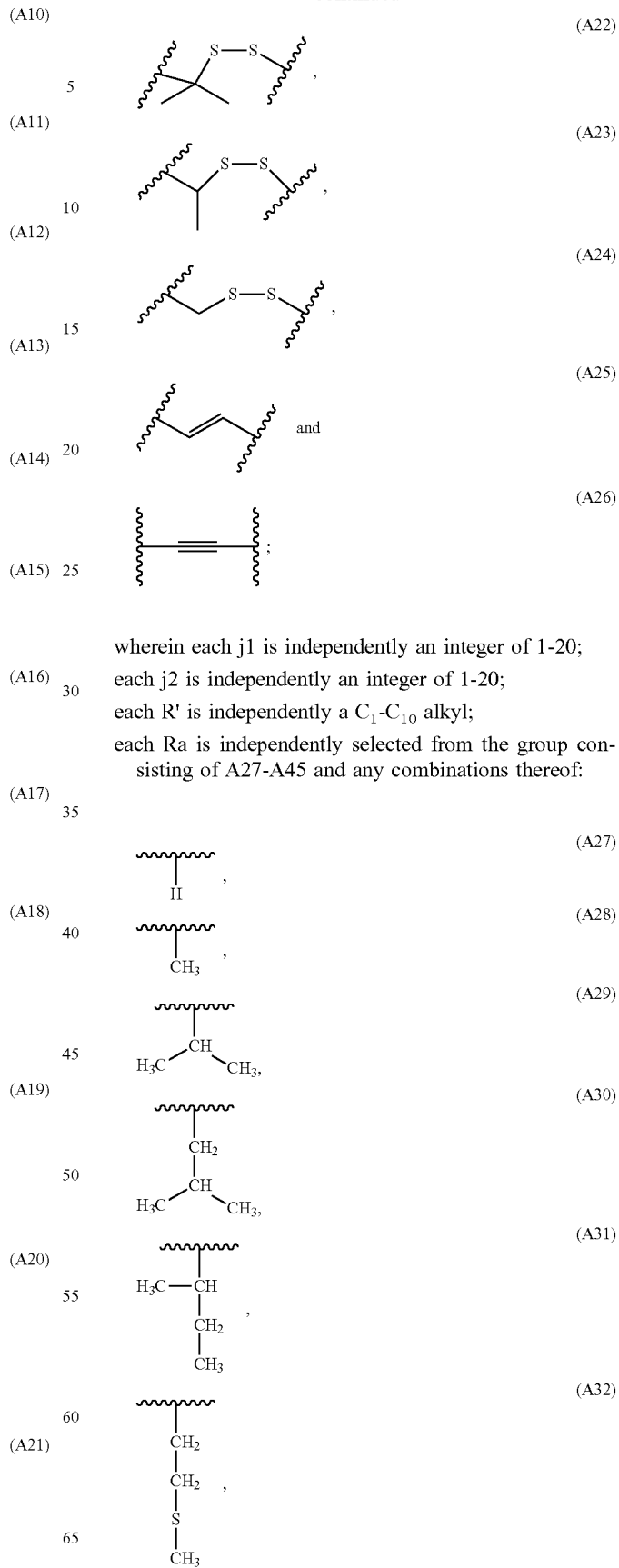
(A22)
(A23)
(A24)
(A25)
(A26)
wherein each j1 is independently an integer of 1-20;
each j2 is independently an integer of 1-20;
each R' is independently a $C_1$-$C_{10}$ alkyl;
each Ra is independently selected from the group consisting of A27-A45 and any combinations thereof:
(A27)
(A28)
(A29)
(A30)
(A31)
(A32)

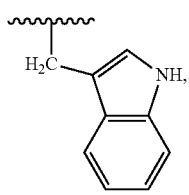 (A33)

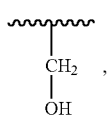 (A34)

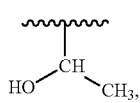 (A35)

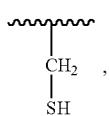 (A36)

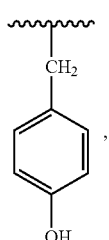 (A37)

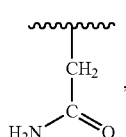 (A38)

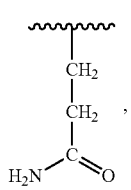 (A39)

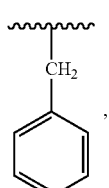 (A40)

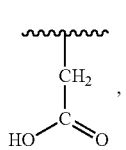 (A41)

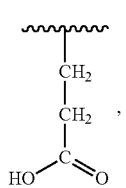 (A42)

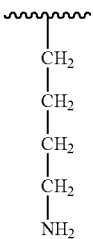 (A43)

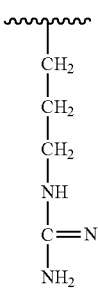 (A44)

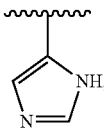 (A45)

each Rb is independently a $C_1$-$C_{10}$ alkyl; and
∿∿∿ represents a site where a group is attached to the rest of the molecule.

16. The conjugate according to claim 15, wherein $L_1$ is selected from the group consisting of groups A1, A4, A5, A6, A8, A10, A11, A13, and connection combinations thereof.

17. The conjugate according to claim 14, wherein the length of $L_1$ is 3 to 25 atoms.

18. The conjugate according to claim 14, wherein each of m1, m2 and m3 is independently an integer of 2-5; or m1=m2=m3.

19. The conjugate according to claim 14, wherein each $M_1$ is independently a monosaccharide, disaccharide, trisaccharide, or polysaccharide.

20. The conjugate according to claim 14, wherein each $M_1$ is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, 3-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

21. The conjugate according to claim 14, wherein $R_3$ is a group having a structure represented by Formula A59:

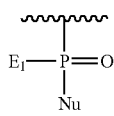

(A59)

wherein $E_1$ is OH, SH or $BH_2$, and Nu is a functional oligonucleotide.

22. The conjugate according to claim 21, wherein $R_2$ forms a phosphoester bond with the P atom in $R_3$.

23. The conjugate according to claim 14, wherein the conjugate has a structure represented by Formula (3), (4), (5), (6), (7), (8), (9), (10), (11), (12), (13), (14), (15), (16), (17), (18), (19), (20), (21), or (22):

Formula (3)

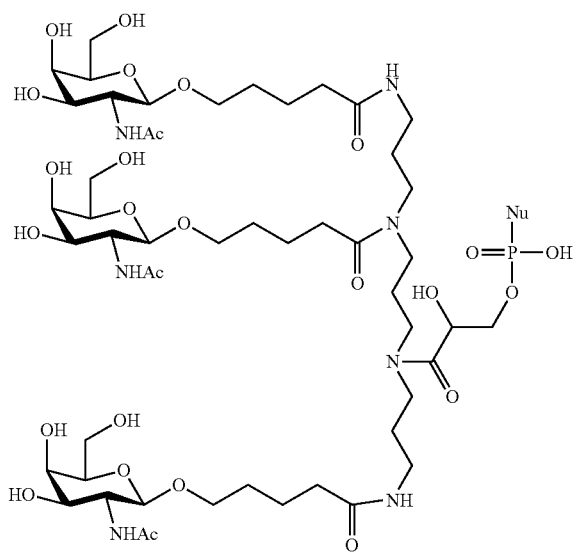

Formula (4)

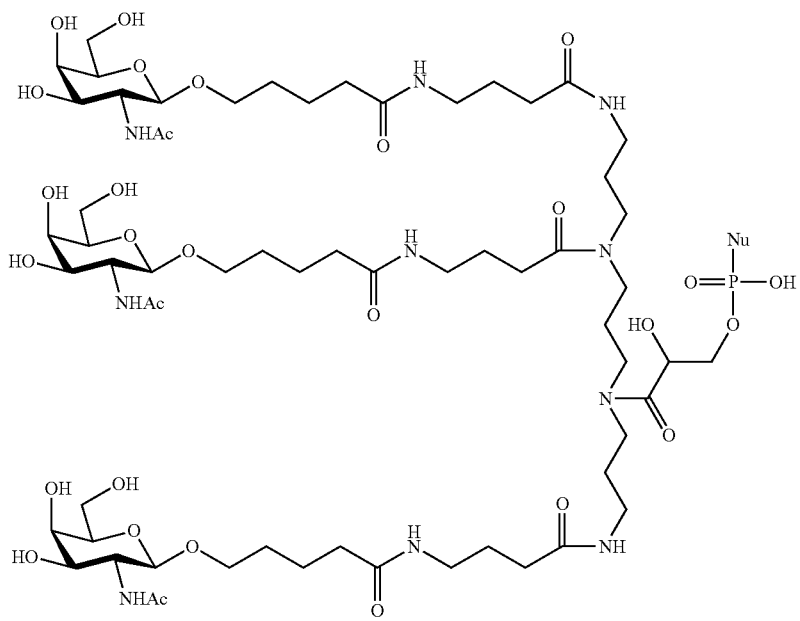

431 432
-continued
Formula (5)
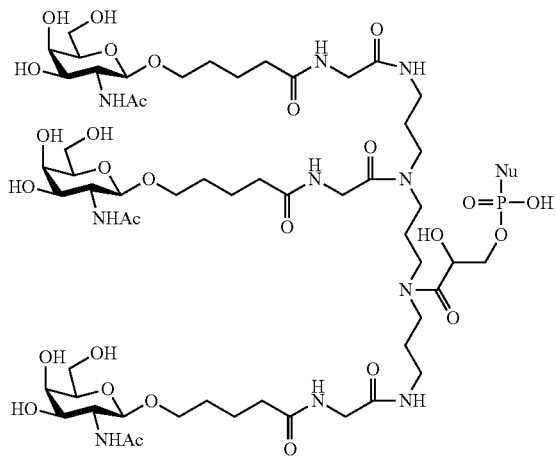
Formula (6)
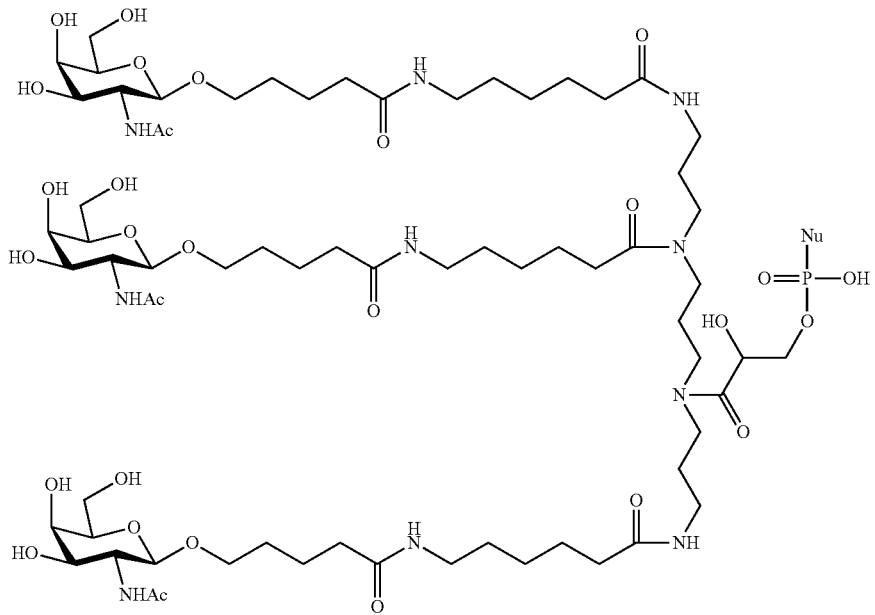
Formula (7)
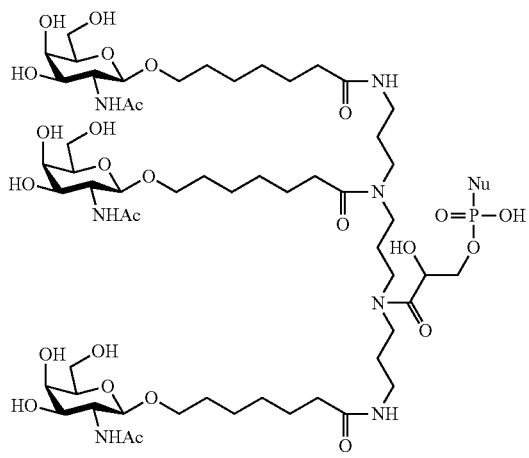
Formula (8)
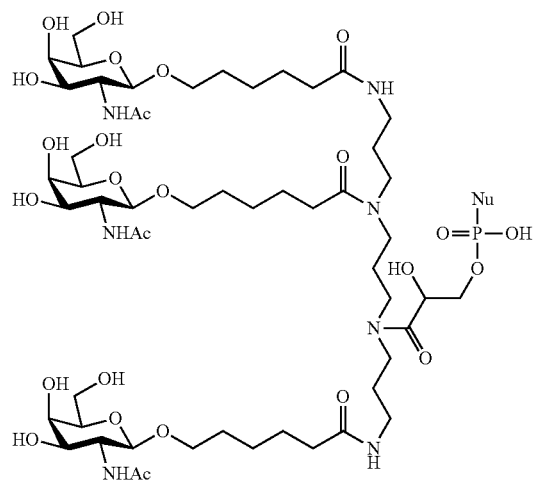

433
Formula (9)
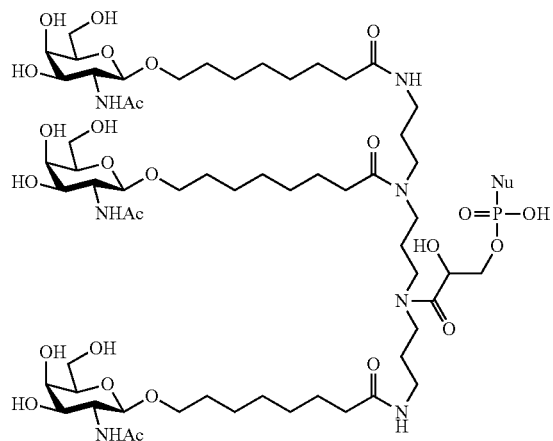
434
Formula (10)
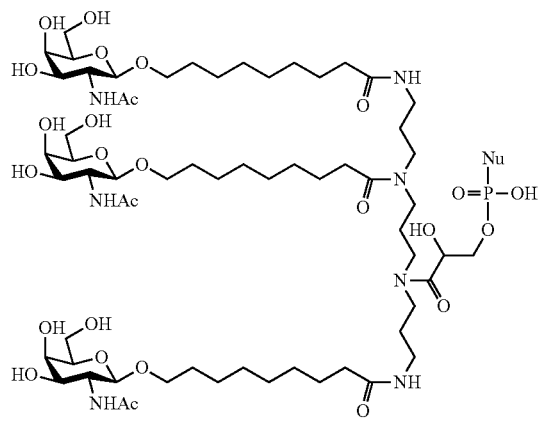
Formula (11)
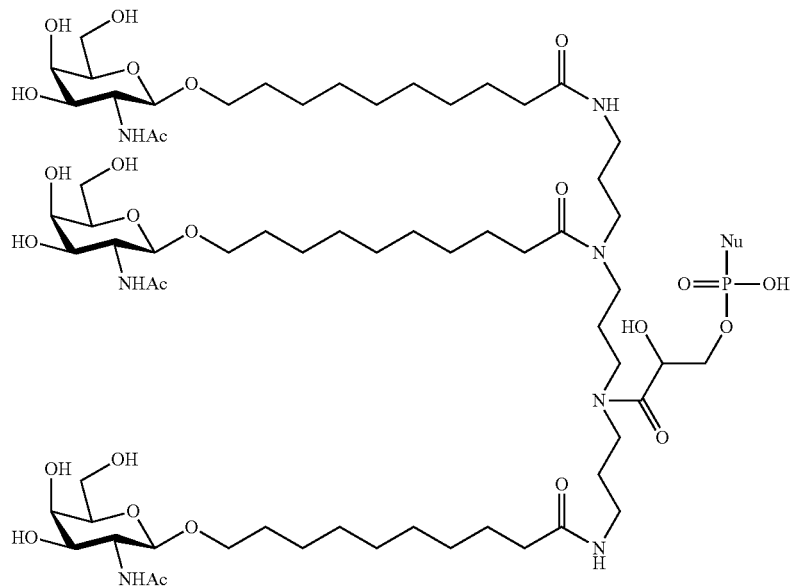
Formula (12)
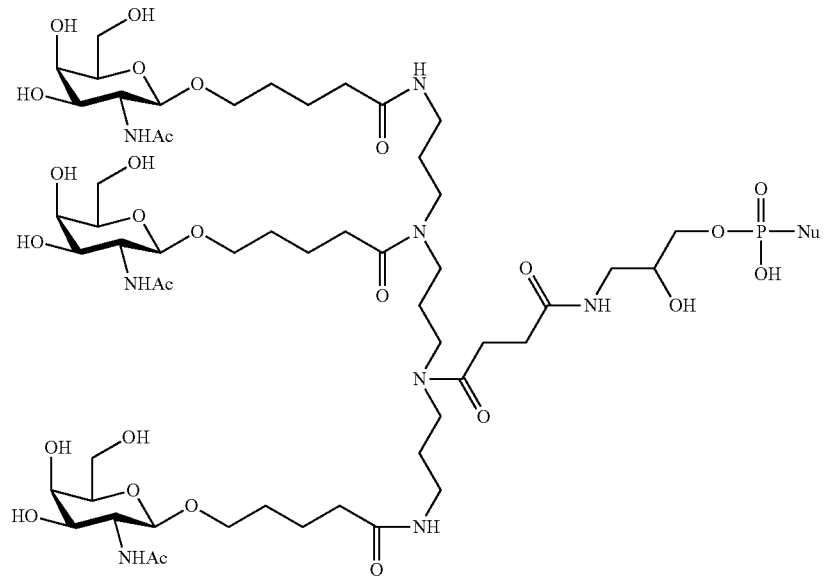

-continued
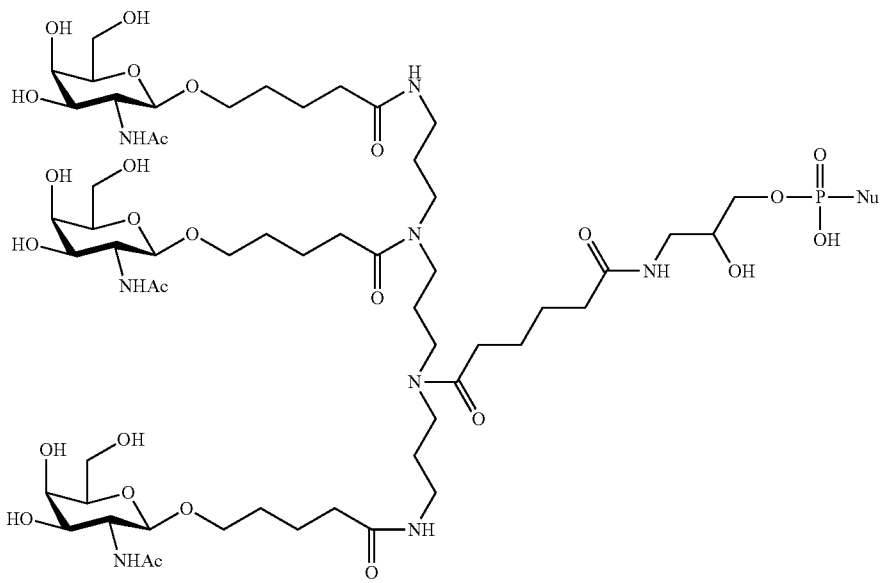
Formula (13)
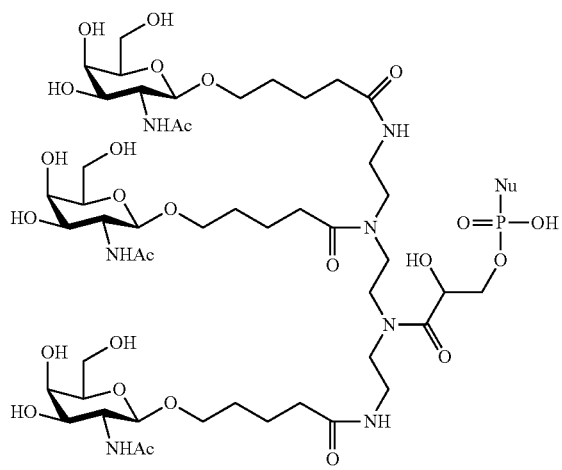
Formula (14)
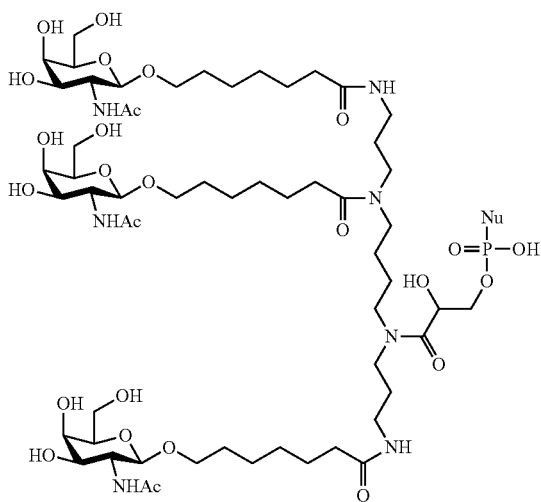
Formula (15)
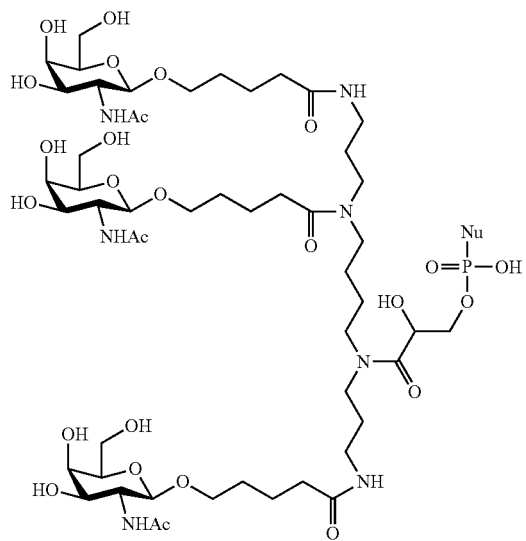
Formula (16)
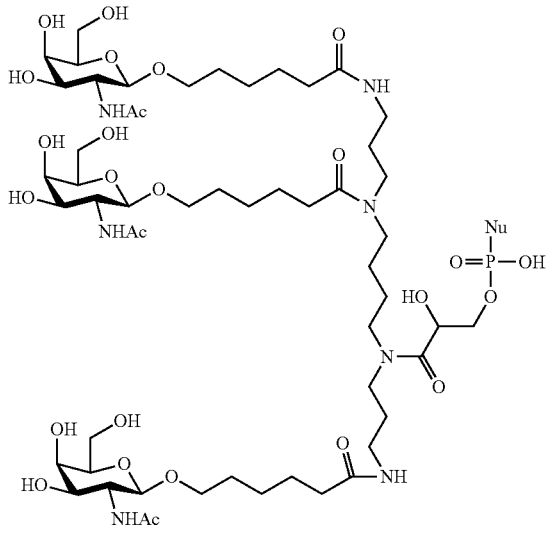
Formula (17)

-continued
Formula (18)
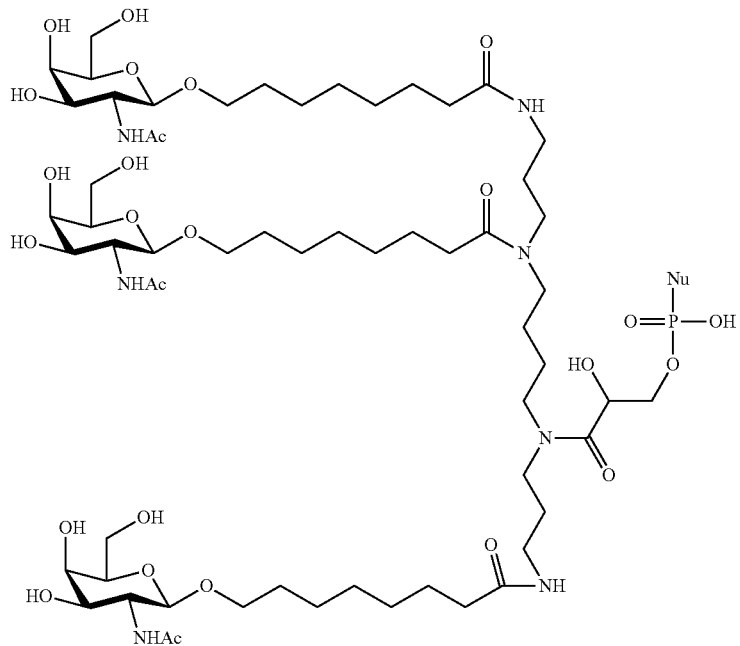
Formula (19)
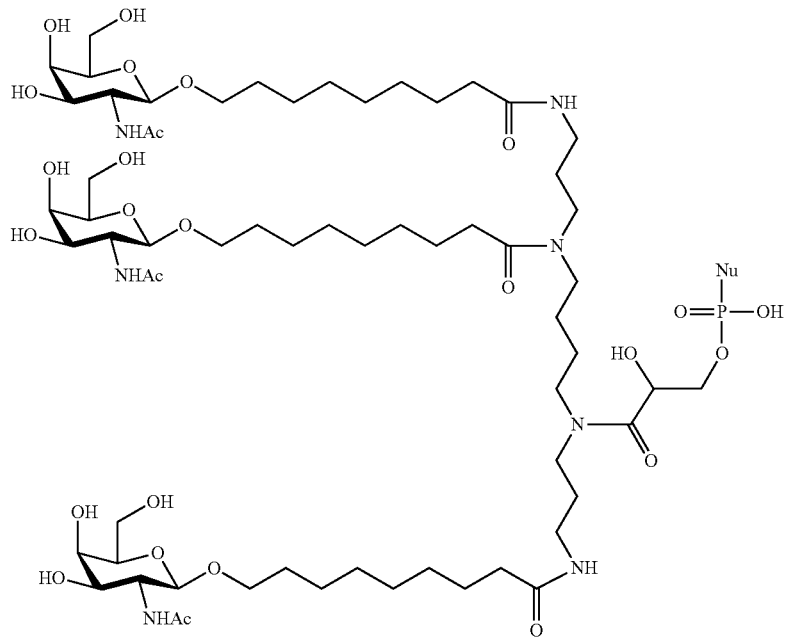

-continued

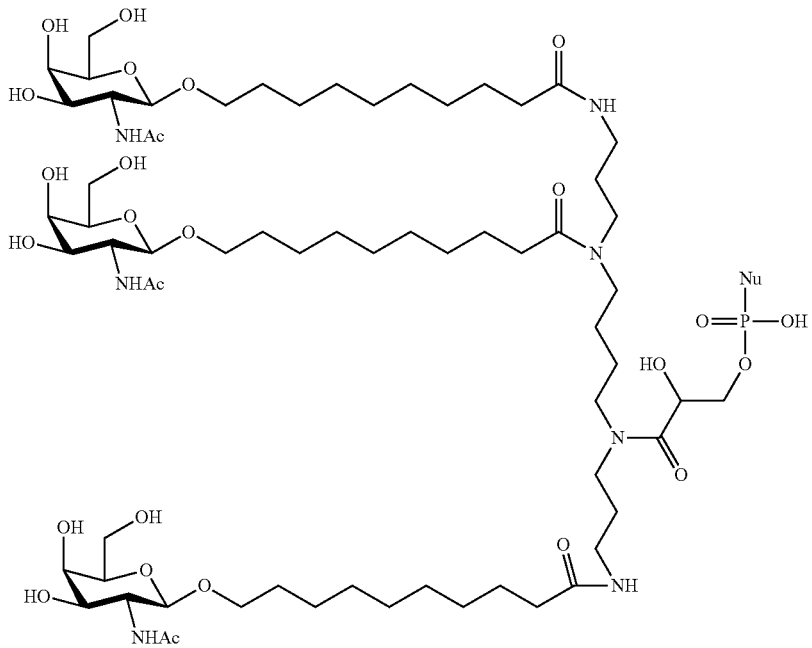

Formula (20)

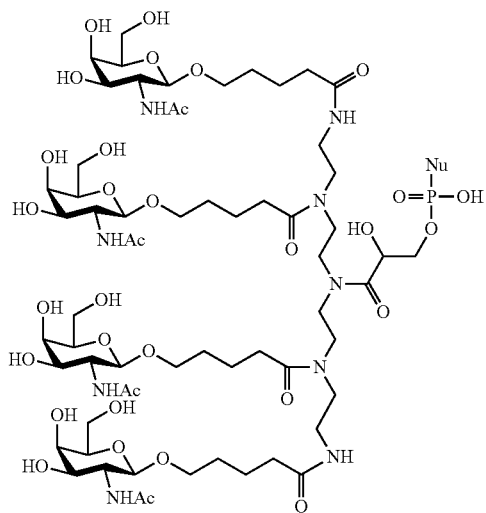

Formula (21)

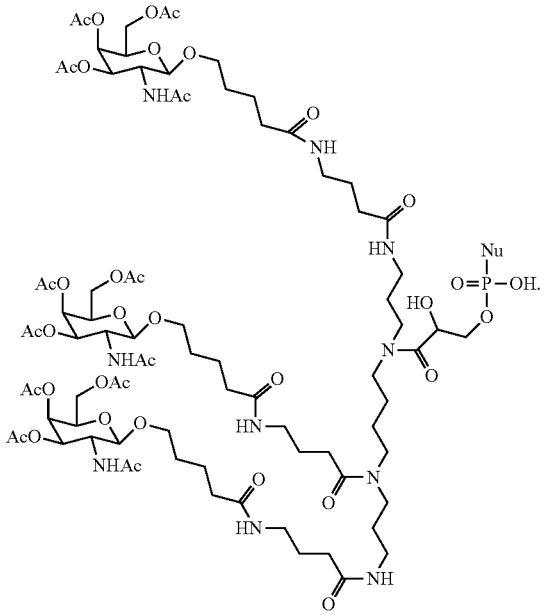

Formula (22)

24. The conjugate according to claim 21, wherein the functional oligonucleotide is selected from the group consisting of small interfering RNA, microRNA, anti-microRNA, microRNA antagonist, microRNA mimics, decoy oligonucleotide, immune stimulatory, G-quadruplex, splice altering, single strand RNA, antisense nucleic acid, nucleic acid aptamer, stem-loop RNA, mRNA fragments, activating RNA, or DNA.

25. The conjugate according to claim 24, wherein
the functional oligonucleotide is a single strand oligonucleotide, and the P atom in formula A59 is linked to 3' terminal of the single strand oligonucleotide; or
the functional oligonucleotide is a double stranded oligonucleotide comprising a sense strand and an antisense strand, and the P atom in formula A59 is linked to 3' terminal region of the sense strand.

26. The conjugate according to claim 25, wherein the double stranded oligonucleotide is an siRNA, and each nucleotide in the siRNA is independently a modified or unmodified nucleotide; the siRNA contains a sense strand and an antisense strand, wherein the sense strand comprises a nucleotide sequence 1, and the antisense strand comprises a nucleotide sequence 2, both of which have a length of 19 nucleotides and are at least partly reverse complementary to form a double-stranded complementary region; the nucleotide sequence 2 is at least partly complementary to a first nucleotide sequence segment which refers to a segment of nucleotide in a target mRNA; and the target mRNA refers to a mRNA of a gene that is aberrantly expressed in hepatocytes.

27. The conjugate according to claim 26, wherein the target mRNA is the mRNA corresponding to ApoB, ApoC, ANGPTL3, PCSK9, SCD1, TIMP-1, Col1A1, FVII, STAT3, p53, HBV or HCV.

28. The conjugate according to claim 26, wherein the nucleotide sequence 1 has the same length with the first nucleotide sequence segment and no more than 3 nucleotides different from the first nucleotide sequence segment; the nucleotide sequence 2 has the same length with a nucleotide sequence B and no more than 3 nucleotides different from the nucleotide sequence B, which refers to a nucleotide sequence completely reverse complementary to the first nucleotide sequence segment.

29. The conjugate according to claim 28, wherein the nucleotide differences between the nucleotide sequence 2 and the nucleotide sequence B includes the difference at the site of the first nucleotide Z' on the nucleotide sequence 2 from 5' end to 3' end.

30. The conjugate according to claim 26, wherein the sense strand further comprises a nucleotide sequence 3, and the antisense strand further comprises a nucleotide sequence 4; the nucleotide sequences 3 and 4 have an identical length of 1-4 nucleotides; the nucleotide sequence 3 is linked to 5' end of the nucleotide sequence 1, and the nucleotide sequence 4 is linked to 3' end of the nucleotide sequence 2; the nucleotide sequence 4 is complementary to a second nucleotide sequence segment; the second nucleotide sequence segment refers to a nucleotide sequence adjacent to the first nucleotide sequence segment in the target mRNA, and having a same length as the nucleotide sequence 4; and the nucleotide sequence 3 is Substantially reverse complementary, or completely reverse complementary to the nucleotide sequence 4.

31. The conjugate according to claim 26, wherein the siRNA further comprises a nucleotide sequence 5, which has a length of 1-3 nucleotides and is linked to 3' end of the antisense strand, thereby constituting a 3' overhang of the antisense strand.

32. The conjugate according to claim 26, wherein each nucleotide in the sense and antisense strand is independently a fluoro modified nucleotide or a non-fluoro modified nucleotide, the fluoro modified nucleotide refers to a nucleotide formed by substituting the 2'-hydroxy of the ribose group thereof with a fluoro group; the non-fluoro modified nucleotide refers to a nucleotide formed by substituting the 2'-hydroxy of the ribose group thereof with a group other than a fluoro, or a nucleotide analogue, the nucleotide analogue refers to a group capable of replacing a nucleotide in a nucleic acid, while having a different structure from any one of adenine ribonucleotide, guanine ribonucleotide, cytosine ribonucleotide, uracil ribonucleotide or thymine deoxyribonucleotide.

33. The conjugate according to claim 32, wherein both of the sense and antisense strand comprises fluoro and non-fluoro modified nucleotides, the fluoro modified nucleotides exist in the nucleotide sequence 1 and the nucleotide sequence 2, no more than 5 fluoro modified nucleotides exist in the nucleotide sequence 1, and in the direction from 5' terminal to 3' terminal, the nucleotides at positions 7, 8 and 9 in the nucleotide sequence 1 are fluoro modified nucleotides; no more than 7 fluoro modified nucleotides exist in the nucleotide sequence 2, and in the direction from 5' terminal to 3' terminal, the nucleotides at positions 2, 6, 14 and 16 in the nucleotide sequence 2 are fluoro modified nucleotides.

34. The conjugate according to claim 32, wherein each non-fluoro modified nucleotide is a methoxy modified nucleotide, wherein a methoxy modified nucleotide refers to a nucleotide formed by substituting the 2'-hydroxy of the ribose group thereof with a methoxy group.

35. The conjugate according to claim 26, wherein in the siRNA, at least one phosphate group is a phosphorothioate group, and a phosphorothioate linkage exists in at least one of following positions:
between the first nucleotide and the second nucleotide from 5' end of the sense strand;
between the second nucleotide and the third nucleotide from 5' end of the sense strand;
between the first nucleotide and the second nucleotide from 3' end of the sense strand;
between the second nucleotide and the third nucleotide from 3' end of the sense strand;
between the first nucleotide and the second nucleotide from 5' end of the antisense strand;
between the second nucleotide and the third nucleotide from 5' end of the antisense strand;
between the first nucleotide and the second nucleotide from 3' end of the antisense strand; and
between the second nucleotide and the third nucleotide from 3' end of the antisense strand.

36. The conjugate according to claim 26, wherein a nucleotide at 5' end of the antisense strand is a 5'-phosphate nucleotide or a 5'-phosphate analogue modified nucleotide.

37. A method for treating in a subject in need thereof a pathological condition or disease caused by expression of a specific gene in hepatocytes, comprising administering to the subject an effective amount of the conjugate according to claim 14.

38. The method according to claim 37, wherein the specific gene is selected from a group consisting of a hepatitis B virus gene, an angiopoietin-like protein 3 gene, and an apolipoprotein C3 gene.

39. The method according to claim 37, wherein the disease is selected from a group consisting of chronic liver disease, hepatitis, hepatic fibrosis, liver proliferative diseases, and dyslipidemia.

40. The method according to claim 39, wherein the dyslipidemia is hypercholesterolemia, hypertriglyceridemia, or atherosclerosis.

41. A method for inhibiting expression of a specific gene in hepatocytes, comprising contacting the conjugate according to claim 14 with the hepatocytes.

42. The method according to claim 41, wherein the specific gene is ApoB, ApoC, ANGPTL3, PCSK9, SCD1, TIMP-1, Col1A1, FVII, STAT3, p53, HBV or HCV.

* * * * *

SEQUENCE LISTING

<160> NUMBER OF SEQ ID NOS: 251

<210> SEQ ID NO 1
<211> LENGTH: 19
<212> TYPE: RNA
<213> ORGANISM: Artificial sequence
<220> FEATURE:
<223> OTHER INFORMATION: sense sequence for siHBa1

<400> SEQUENCE: 1
ccuugaggca uacuucaaa                            19

<210> SEQ ID NO 2
<211> LENGTH: 21
<212> TYPE: RNA
<213> ORGANISM: Artificial sequence
<220> FEATURE:
<223> OTHER INFORMATION: Antisense sequence for siHBa1

<400> SEQUENCE: 2
uuugaaguau gccucaaggu u                         21

<210> SEQ ID NO 3
<211> LENGTH: 21
<212> TYPE: RNA
<213> ORGANISM: Artificial sequence
<220> FEATURE:
<223> OTHER INFORMATION: Sense sequence for siHBa2

<400> SEQUENCE: 3
gaccuugagg cauacuucaa a                         21

<210> SEQ ID NO 4
<211> LENGTH: 23
<212> TYPE: RNA
<213> ORGANISM: Artificial sequence
<220> FEATURE:
<223> OTHER INFORMATION: Antisense sequence for siHBa2

<400> SEQUENCE: 4
uuugaaguau gccucaaggu cgg                       23

<210> SEQ ID NO 5
<211> LENGTH: 19
<212> TYPE: RNA
<213> ORGANISM: Artificial sequence
<220> FEATURE:
<223> OTHER INFORMATION: Sense sequence for siHBa1M1

<400> SEQUENCE: 5
ccuugaggca uacuucaaa                            19

<210> SEQ ID NO 6
<211> LENGTH: 21
<212> TYPE: RNA
<213> ORGANISM: Artificial sequence
<220> FEATURE:
<223> OTHER INFORMATION: Antisense sequence for siHBa1M1

<400> SEQUENCE: 6
uuugaaguau gccucaaggu u                         21

<210> SEQ ID NO 7
<211> LENGTH: 19
<212> TYPE: RNA
<213> ORGANISM: Artificial sequence

```
<220> FEATURE:
<223> OTHER INFORMATION: Sense sequence for siHBa1M2

<400> SEQUENCE: 7
ccuugaggca uacuucaaa                                                    19

<210> SEQ ID NO 8
<211> LENGTH: 21
<212> TYPE: RNA
<213> ORGANISM: Artificial sequence
<220> FEATURE:
<223> OTHER INFORMATION: Antisense sequence for siHBa1M2

<400> SEQUENCE: 8
uuugaaguau gccucaaggu u                                                 21

<210> SEQ ID NO 9
<211> LENGTH: 21
<212> TYPE: RNA
<213> ORGANISM: Artificial sequence
<220> FEATURE:
<223> OTHER INFORMATION: Sense sequence for siHBa2M1

<400> SEQUENCE: 9
gaccuugagg cauacuucaa a                                                 21

<210> SEQ ID NO 10
<211> LENGTH: 23
<212> TYPE: RNA
<213> ORGANISM: Artificial sequence
<220> FEATURE:
<223> OTHER INFORMATION: Antisense sequence for siHBa2M1

<400> SEQUENCE: 10
uuugaaguau gccucaaggu cgg                                               23

<210> SEQ ID NO 11
<211> LENGTH: 21
<212> TYPE: RNA
<213> ORGANISM: Artificial sequence
<220> FEATURE:
<223> OTHER INFORMATION: Sense sequence for siHBa2M2

<400> SEQUENCE: 11
gaccuugagg cauacuucaa a                                                 21

<210> SEQ ID NO 12
<211> LENGTH: 23
<212> TYPE: RNA
<213> ORGANISM: Artificial sequence
<220> FEATURE:
<223> OTHER INFORMATION: Antisense sequence for siHBa2M2

<400> SEQUENCE: 12
uuugaaguau gccucaaggu cgg                                               23

<210> SEQ ID NO 13
<211> LENGTH: 19
<212> TYPE: RNA
<213> ORGANISM: Artificial sequence
<220> FEATURE:
<223> OTHER INFORMATION: Sense sequence for siHBa1M1S

<400> SEQUENCE: 13
ccuugaggca uacuucaaa                                                    19
```

```
<210> SEQ ID NO 14
<211> LENGTH: 21
<212> TYPE: RNA
<213> ORGANISM: Artificial sequence
<220> FEATURE:
<223> OTHER INFORMATION: Antisense sequence for siHBa1M1S

<400> SEQUENCE: 14
uuugaaguau gccucaaggu u                                              21

<210> SEQ ID NO 15
<211> LENGTH: 19
<212> TYPE: RNA
<213> ORGANISM: Artificial sequence
<220> FEATURE:
<223> OTHER INFORMATION: Sense sequence for siHBa1M2S

<400> SEQUENCE: 15
ccuugaggca uacuucaaa                                                 19

<210> SEQ ID NO 16
<211> LENGTH: 21
<212> TYPE: RNA
<213> ORGANISM: Artificial sequence
<220> FEATURE:
<223> OTHER INFORMATION: Antisense sequence for siHBa1M2S

<400> SEQUENCE: 16
uuugaaguau gccucaaggu u                                              21

<210> SEQ ID NO 17
<211> LENGTH: 21
<212> TYPE: RNA
<213> ORGANISM: Artificial sequence
<220> FEATURE:
<223> OTHER INFORMATION: Sense sequence for siHBa2M1S

<400> SEQUENCE: 17
gaccuugagg cauacuucaa a                                              21

<210> SEQ ID NO 18
<211> LENGTH: 23
<212> TYPE: RNA
<213> ORGANISM: Artificial sequence
<220> FEATURE:
<223> OTHER INFORMATION: Antisense sequence for siHBa2M1S

<400> SEQUENCE: 18
uuugaaguau gccucaaggu cgg                                            23

<210> SEQ ID NO 19
<211> LENGTH: 21
<212> TYPE: RNA
<213> ORGANISM: Artificial sequence
<220> FEATURE:
<223> OTHER INFORMATION: Sense sequence for siHBa2M2S

<400> SEQUENCE: 19
gaccuugagg cauacuucaa a                                              21

<210> SEQ ID NO 20
<211> LENGTH: 23
<212> TYPE: RNA
<213> ORGANISM: Artificial sequence
<220> FEATURE:
<223> OTHER INFORMATION: Antisense sequence for siHBa2M2S
```

```
<400> SEQUENCE: 20
uuugaaguau gccucaaggu cgg                                              23

<210> SEQ ID NO 21
<211> LENGTH: 21
<212> TYPE: RNA
<213> ORGANISM: Artificial sequence
<220> FEATURE:
<223> OTHER INFORMATION: Antisense sequence for siHBa1M1P1

<400> SEQUENCE: 21
uuugaaguau gccucaaggu u                                                21

<210> SEQ ID NO 22
<211> LENGTH: 21
<212> TYPE: RNA
<213> ORGANISM: Artificial sequence
<220> FEATURE:
<223> OTHER INFORMATION: Antisense sequence for siHBa1M2P1

<400> SEQUENCE: 22
uuugaaguau gccucaaggu u                                                21

<210> SEQ ID NO 23
<211> LENGTH: 23
<212> TYPE: RNA
<213> ORGANISM: Artificial sequence
<220> FEATURE:
<223> OTHER INFORMATION: Antisense sequence for siHBa2M1P1

<400> SEQUENCE: 23
uuugaaguau gccucaaggu cgg                                              23

<210> SEQ ID NO 24
<211> LENGTH: 23
<212> TYPE: RNA
<213> ORGANISM: Artificial sequence
<220> FEATURE:
<223> OTHER INFORMATION: Antisense sequence for siHBa2M2P1

<400> SEQUENCE: 24
uuugaaguau gccucaaggu cgg                                              23

<210> SEQ ID NO 25
<211> LENGTH: 21
<212> TYPE: RNA
<213> ORGANISM: Artificial sequence
<220> FEATURE:
<223> OTHER INFORMATION: Antisense sequence for siHBa1M1SP1

<400> SEQUENCE: 25
uuugaaguau gccucaaggu u                                                21

<210> SEQ ID NO 26
<211> LENGTH: 21
<212> TYPE: RNA
<213> ORGANISM: Artificial sequence
<220> FEATURE:
<223> OTHER INFORMATION: Antisense sequence for siHBa1M2SP1

<400> SEQUENCE: 26
uuugaaguau gccucaaggu u                                                21

<210> SEQ ID NO 27
```

```
<211> LENGTH: 23
<212> TYPE: RNA
<213> ORGANISM: Artificial sequence
<220> FEATURE:
<223> OTHER INFORMATION: Antisense sequence for siHBa2M1SP1

<400> SEQUENCE: 27
uuugaaguau gccucaaggu cgg                                              23

<210> SEQ ID NO 28
<211> LENGTH: 23
<212> TYPE: RNA
<213> ORGANISM: Artificial sequence
<220> FEATURE:
<223> OTHER INFORMATION: Antisense sequence for siHBa2M2SP1

<400> SEQUENCE: 28
uuugaaguau gccucaaggu cgg                                              23

<210> SEQ ID NO 29
<211> LENGTH: 19
<212> TYPE: RNA
<213> ORGANISM: Artificial sequence
<220> FEATURE:
<223> OTHER INFORMATION: Sense sequence for siHBb1

<400> SEQUENCE: 29
ugcuaugccu caucuucua                                                   19

<210> SEQ ID NO 30
<211> LENGTH: 21
<212> TYPE: RNA
<213> ORGANISM: Artificial sequence
<220> FEATURE:
<223> OTHER INFORMATION: Antisense sequence for siHBb1

<400> SEQUENCE: 30
uagaagauga ggcauagcag c                                                21

<210> SEQ ID NO 31
<211> LENGTH: 21
<212> TYPE: RNA
<213> ORGANISM: Artificial sequence
<220> FEATURE:
<223> OTHER INFORMATION: Antisense sequence for siHBb2

<400> SEQUENCE: 31
uagaagauga ggcauagcau u                                                21

<210> SEQ ID NO 32
<211> LENGTH: 19
<212> TYPE: RNA
<213> ORGANISM: Artificial sequence
<220> FEATURE:
<223> OTHER INFORMATION: Sense sequence for siHBb1M1

<400> SEQUENCE: 32
ugcuaugccu caucuucua                                                   19

<210> SEQ ID NO 33
<211> LENGTH: 21
<212> TYPE: RNA
<213> ORGANISM: Artificial sequence
<220> FEATURE:
<223> OTHER INFORMATION: Antisense sequence for siHBb1M1

<400> SEQUENCE: 33
```
uagaagauga ggcauagcag c                                         21

<210> SEQ ID NO 34
<211> LENGTH: 21
<212> TYPE: RNA
<213> ORGANISM: Artificial sequence
<220> FEATURE:
<223> OTHER INFORMATION: Antisense sequence for siHBb2M1

<400> SEQUENCE: 34
uagaagauga ggcauagcau u                                         21

<210> SEQ ID NO 35
<211> LENGTH: 19
<212> TYPE: RNA
<213> ORGANISM: Artificial sequence
<220> FEATURE:
<223> OTHER INFORMATION: Sense sequence for siHBb1M2

<400> SEQUENCE: 35
ugcuaugccu caucuucua                                            19

<210> SEQ ID NO 36
<211> LENGTH: 21
<212> TYPE: RNA
<213> ORGANISM: Artificial sequence
<220> FEATURE:
<223> OTHER INFORMATION: Antisense sequence for siHBb1M2

<400> SEQUENCE: 36
uagaagauga ggcauagcag c                                         21

<210> SEQ ID NO 37
<211> LENGTH: 21
<212> TYPE: RNA
<213> ORGANISM: Artificial sequence
<220> FEATURE:
<223> OTHER INFORMATION: Antisense sequence for siHBb2M2

<400> SEQUENCE: 37
uagaagauga ggcauagcau u                                         21

<210> SEQ ID NO 38
<211> LENGTH: 19
<212> TYPE: RNA
<213> ORGANISM: Artificial sequence
<220> FEATURE:
<223> OTHER INFORMATION: Sense sequence for siHBb1M1S

<400> SEQUENCE: 38
ugcuaugccu caucuucua                                            19

<210> SEQ ID NO 39
<211> LENGTH: 21
<212> TYPE: RNA
<213> ORGANISM: Artificial sequence
<220> FEATURE:
<223> OTHER INFORMATION: Antisense sequence for siHBb1M1S

<400> SEQUENCE: 39
uagaagauga ggcauagcag c                                         21

<210> SEQ ID NO 40
<211> LENGTH: 21
<212> TYPE: RNA

```
<213> ORGANISM: Artificial sequence
<220> FEATURE:
<223> OTHER INFORMATION: Antisense sequence for siHBb2M1S

<400> SEQUENCE: 40
uagaagauga ggcauagcau u                                              21

<210> SEQ ID NO 41
<211> LENGTH: 19
<212> TYPE: RNA
<213> ORGANISM: Artificial sequence
<220> FEATURE:
<223> OTHER INFORMATION: Sense sequence for siHBb1M2S

<400> SEQUENCE: 41
ugcuaugccu caucuucua                                                 19

<210> SEQ ID NO 42
<211> LENGTH: 21
<212> TYPE: RNA
<213> ORGANISM: Artificial sequence
<220> FEATURE:
<223> OTHER INFORMATION: Antisense sequence for siHBb1M2S

<400> SEQUENCE: 42
uagaagauga ggcauagcag c                                              21

<210> SEQ ID NO 43
<211> LENGTH: 21
<212> TYPE: RNA
<213> ORGANISM: Artificial sequence
<220> FEATURE:
<223> OTHER INFORMATION: Antisense sequence for siHBb2M2S

<400> SEQUENCE: 43
uagaagauga ggcauagcau u                                              21

<210> SEQ ID NO 44
<211> LENGTH: 21
<212> TYPE: RNA
<213> ORGANISM: Artificial sequence
<220> FEATURE:
<223> OTHER INFORMATION: Antisense sequence for siHBb1M1P1

<400> SEQUENCE: 44
uagaagauga ggcauagcag c                                              21

<210> SEQ ID NO 45
<211> LENGTH: 21
<212> TYPE: RNA
<213> ORGANISM: Artificial sequence
<220> FEATURE:
<223> OTHER INFORMATION: Antisense sequence for siHBb2M1P1

<400> SEQUENCE: 45
uagaagauga ggcauagcau u                                              21

<210> SEQ ID NO 46
<211> LENGTH: 21
<212> TYPE: RNA
<213> ORGANISM: Artificial sequence
<220> FEATURE:
<223> OTHER INFORMATION: Antisense sequence for siHBb1M2P1

<400> SEQUENCE: 46
uagaagauga ggcauagcag c                                              21
```

<210> SEQ ID NO 47
<211> LENGTH: 21
<212> TYPE: RNA
<213> ORGANISM: Artificial sequence
<220> FEATURE:
<223> OTHER INFORMATION: Antisense sequence for siHBb2M2P1

<400> SEQUENCE: 47
uagaagauga ggcauagcau u                                              21

<210> SEQ ID NO 48
<211> LENGTH: 21
<212> TYPE: RNA
<213> ORGANISM: Artificial sequence
<220> FEATURE:
<223> OTHER INFORMATION: Antisense sequence for siHBb1M1SP1

<400> SEQUENCE: 48
uagaagauga ggcauagcag c                                              21

<210> SEQ ID NO 49
<211> LENGTH: 21
<212> TYPE: RNA
<213> ORGANISM: Artificial sequence
<220> FEATURE:
<223> OTHER INFORMATION: Antisense sequence for siHBb2M1SP1

<400> SEQUENCE: 49
uagaagauga ggcauagcau u                                              21

<210> SEQ ID NO 50
<211> LENGTH: 21
<212> TYPE: RNA
<213> ORGANISM: Artificial sequence
<220> FEATURE:
<223> OTHER INFORMATION: Antisense sequence for siHBb1M2SP1

<400> SEQUENCE: 50
uagaagauga ggcauagcag c                                              21

<210> SEQ ID NO 51
<211> LENGTH: 21
<212> TYPE: RNA
<213> ORGANISM: Artificial sequence
<220> FEATURE:
<223> OTHER INFORMATION: Antisense sequence for siHBb2M2SP1

<400> SEQUENCE: 51
uagaagauga ggcauagcau u                                              21

<210> SEQ ID NO 52
<211> LENGTH: 19
<212> TYPE: RNA
<213> ORGANISM: Artificial sequence
<220> FEATURE:
<223> OTHER INFORMATION: Sense sequence for siHBc1

<400> SEQUENCE: 52
ucugugccuu cucaucuga                                                 19

<210> SEQ ID NO 53
<211> LENGTH: 21
<212> TYPE: RNA
<213> ORGANISM: Artificial sequence
<220> FEATURE:

<223> OTHER INFORMATION: Antisense sequence for siHBc1

<400> SEQUENCE: 53
ucagaugaga aggcacagac g               21

<210> SEQ ID NO 54
<211> LENGTH: 19
<212> TYPE: RNA
<213> ORGANISM: Artificial sequence
<220> FEATURE:
<223> OTHER INFORMATION: Sense sequence for siHBc1M1

<400> SEQUENCE: 54
ucugugccuu cucaucuga               19

<210> SEQ ID NO 55
<211> LENGTH: 21
<212> TYPE: RNA
<213> ORGANISM: Artificial sequence
<220> FEATURE:
<223> OTHER INFORMATION: Antisense sequence for siHBc1M1

<400> SEQUENCE: 55
ucagaugaga aggcacagac g               21

<210> SEQ ID NO 56
<211> LENGTH: 19
<212> TYPE: RNA
<213> ORGANISM: Artificial sequence
<220> FEATURE:
<223> OTHER INFORMATION: Sense sequence for siHBc1M2

<400> SEQUENCE: 56
ucugugccuu cucaucuga               19

<210> SEQ ID NO 57
<211> LENGTH: 21
<212> TYPE: RNA
<213> ORGANISM: Artificial sequence
<220> FEATURE:
<223> OTHER INFORMATION: Antisense sequence for siHBc1M2

<400> SEQUENCE: 57
ucagaugaga aggcacagac g               21

<210> SEQ ID NO 58
<211> LENGTH: 19
<212> TYPE: RNA
<213> ORGANISM: Artificial sequence
<220> FEATURE:
<223> OTHER INFORMATION: Sense sequence for siHBc1M1S

<400> SEQUENCE: 58
ucugugccuu cucaucuga               19

<210> SEQ ID NO 59
<211> LENGTH: 21
<212> TYPE: RNA
<213> ORGANISM: Artificial sequence
<220> FEATURE:
<223> OTHER INFORMATION: Antisense sequence for siHBc1M1S

<400> SEQUENCE: 59
ucagaugaga aggcacagac g               21

```
<210> SEQ ID NO 60
<211> LENGTH: 19
<212> TYPE: RNA
<213> ORGANISM: Artificial sequence
<220> FEATURE:
<223> OTHER INFORMATION: Sense sequence for siHBc1M2S

<400> SEQUENCE: 60
ucugugccuu cucaucuga                                                    19

<210> SEQ ID NO 61
<211> LENGTH: 21
<212> TYPE: RNA
<213> ORGANISM: Artificial sequence
<220> FEATURE:
<223> OTHER INFORMATION: Antisense sequence for siHBc1M2S

<400> SEQUENCE: 61
ucagaugaga aggcacagac g                                                 21

<210> SEQ ID NO 62
<211> LENGTH: 21
<212> TYPE: RNA
<213> ORGANISM: Artificial sequence
<220> FEATURE:
<223> OTHER INFORMATION: Antisense sequence for siHBc1M1P1

<400> SEQUENCE: 62
ucagaugaga aggcacagac g                                                 21

<210> SEQ ID NO 63
<211> LENGTH: 21
<212> TYPE: RNA
<213> ORGANISM: Artificial sequence
<220> FEATURE:
<223> OTHER INFORMATION: Antisense sequence for siHBc1M2P1

<400> SEQUENCE: 63
ucagaugaga aggcacagac g                                                 21

<210> SEQ ID NO 64
<211> LENGTH: 21
<212> TYPE: RNA
<213> ORGANISM: Artificial sequence
<220> FEATURE:
<223> OTHER INFORMATION: Antisense sequence for siHBc1M1SP1

<400> SEQUENCE: 64
ucagaugaga aggcacagac g                                                 21

<210> SEQ ID NO 65
<211> LENGTH: 21
<212> TYPE: RNA
<213> ORGANISM: Artificial sequence
<220> FEATURE:
<223> OTHER INFORMATION: Antisense sequence for siHBc1M2SP1

<400> SEQUENCE: 65
ucagaugaga aggcacagac g                                                 21

<210> SEQ ID NO 66
<211> LENGTH: 19
<212> TYPE: RNA
<213> ORGANISM: Artificial sequence
<220> FEATURE:
<223> OTHER INFORMATION: Sense sequence for siHBd1
```

```
<400> SEQUENCE: 66
cgugugcacu ucgcuucaa                                             19

<210> SEQ ID NO 67
<211> LENGTH: 21
<212> TYPE: RNA
<213> ORGANISM: Artificial sequence
<220> FEATURE:
<223> OTHER INFORMATION: Antisense sequence for siHBd1

<400> SEQUENCE: 67
uugaagcgaa gugcacacgg u                                          21

<210> SEQ ID NO 68
<211> LENGTH: 19
<212> TYPE: RNA
<213> ORGANISM: Artificial sequence
<220> FEATURE:
<223> OTHER INFORMATION: Sense sequence for siHBd1M1

<400> SEQUENCE: 68
cgugugcacu ucgcuucaa                                             19

<210> SEQ ID NO 69
<211> LENGTH: 21
<212> TYPE: RNA
<213> ORGANISM: Artificial sequence
<220> FEATURE:
<223> OTHER INFORMATION: Antisense sequence for siHBd1M1

<400> SEQUENCE: 69
uugaagcgaa gugcacacgg u                                          21

<210> SEQ ID NO 70
<211> LENGTH: 19
<212> TYPE: RNA
<213> ORGANISM: Artificial sequence
<220> FEATURE:
<223> OTHER INFORMATION: Sense sequence for siHBd1M2

<400> SEQUENCE: 70
cgugugcacu ucgcuucaa                                             19

<210> SEQ ID NO 71
<211> LENGTH: 21
<212> TYPE: RNA
<213> ORGANISM: Artificial sequence
<220> FEATURE:
<223> OTHER INFORMATION: Antisense sequence for siHBd1M2

<400> SEQUENCE: 71
uugaagcgaa gugcacacgg u                                          21

<210> SEQ ID NO 72
<211> LENGTH: 19
<212> TYPE: RNA
<213> ORGANISM: Artificial sequence
<220> FEATURE:
<223> OTHER INFORMATION: Sense sequence for siHBd1M1S

<400> SEQUENCE: 72
cgugugcacu ucgcuucaa                                             19

<210> SEQ ID NO 73
<211> LENGTH: 21
```

```
<212> TYPE: RNA
<213> ORGANISM: Artificial sequence
<220> FEATURE:
<223> OTHER INFORMATION: Antisense sequence for siHBd1M1S

<400> SEQUENCE: 73
uugaagcgaa gugcacacgg u                                              21

<210> SEQ ID NO 74
<211> LENGTH: 19
<212> TYPE: RNA
<213> ORGANISM: Artificial sequence
<220> FEATURE:
<223> OTHER INFORMATION: Sense sequence for siHBd1M2S

<400> SEQUENCE: 74
cgugugcacu ucgcuucaa                                                 19

<210> SEQ ID NO 75
<211> LENGTH: 21
<212> TYPE: RNA
<213> ORGANISM: Artificial sequence
<220> FEATURE:
<223> OTHER INFORMATION: Antisense sequence for siHBd1M2S

<400> SEQUENCE: 75
uugaagcgaa gugcacacgg u                                              21

<210> SEQ ID NO 76
<211> LENGTH: 21
<212> TYPE: RNA
<213> ORGANISM: Artificial sequence
<220> FEATURE:
<223> OTHER INFORMATION: Antisense sequence for siHBd1M1P1

<400> SEQUENCE: 76
uugaagcgaa gugcacacgg u                                              21

<210> SEQ ID NO 77
<211> LENGTH: 21
<212> TYPE: RNA
<213> ORGANISM: Artificial sequence
<220> FEATURE:
<223> OTHER INFORMATION: Antisense sequence for siHBd1M2P1

<400> SEQUENCE: 77
uugaagcgaa gugcacacgg u                                              21

<210> SEQ ID NO 78
<211> LENGTH: 21
<212> TYPE: RNA
<213> ORGANISM: Artificial sequence
<220> FEATURE:
<223> OTHER INFORMATION: Antisense sequence for siHBd1M1SP1

<400> SEQUENCE: 78
uugaagcgaa gugcacacgg u                                              21

<210> SEQ ID NO 79
<211> LENGTH: 21
<212> TYPE: RNA
<213> ORGANISM: Artificial sequence
<220> FEATURE:
<223> OTHER INFORMATION: Antisense sequence for siHBd1M2SP1

<400> SEQUENCE: 79
```

```
uugaagcgaa gugcacacgg u                                      21

<210> SEQ ID NO 80
<211> LENGTH: 19
<212> TYPE: RNA
<213> ORGANISM: Artificial sequence
<220> FEATURE:
<223> OTHER INFORMATION: Sense sequence for siAN1

<400> SEQUENCE: 80
ccaagagcac caagaacua                                         19

<210> SEQ ID NO 81
<211> LENGTH: 21
<212> TYPE: RNA
<213> ORGANISM: Artificial sequence
<220> FEATURE:
<223> OTHER INFORMATION: Antisense sequence for siAN1

<400> SEQUENCE: 81
uaguucuugg ugcucuuggc u                                      21

<210> SEQ ID NO 82
<211> LENGTH: 21
<212> TYPE: RNA
<213> ORGANISM: Artificial sequence
<220> FEATURE:
<223> OTHER INFORMATION: Sense sequence for siAN2

<400> SEQUENCE: 82
agccaagagc accaagaacu a                                      21

<210> SEQ ID NO 83
<211> LENGTH: 23
<212> TYPE: RNA
<213> ORGANISM: Artificial sequence
<220> FEATURE:
<223> OTHER INFORMATION: Antisense sequence for siAN2

<400> SEQUENCE: 83
uaguucuugg ugcucuuggc uug                                    23

<210> SEQ ID NO 84
<211> LENGTH: 19
<212> TYPE: RNA
<213> ORGANISM: Artificial sequence
<220> FEATURE:
<223> OTHER INFORMATION: Sense sequence for siAN1M1

<400> SEQUENCE: 84
ccaagagcac caagaacua                                         19

<210> SEQ ID NO 85
<211> LENGTH: 21
<212> TYPE: RNA
<213> ORGANISM: Artificial sequence
<220> FEATURE:
<223> OTHER INFORMATION: Antisense sequence for siAN1M1

<400> SEQUENCE: 85
uaguucuugg ugcucuuggc u                                      21

<210> SEQ ID NO 86
<211> LENGTH: 21
<212> TYPE: RNA
<213> ORGANISM: Artificial sequence
```

```
<220> FEATURE:
<223> OTHER INFORMATION: Sense sequence for siAN2M1

<400> SEQUENCE: 86
agccaagagc accaagaacu a                                              21

<210> SEQ ID NO 87
<211> LENGTH: 23
<212> TYPE: RNA
<213> ORGANISM: Artificial sequence
<220> FEATURE:
<223> OTHER INFORMATION: Antisense sequence for siAN2M1

<400> SEQUENCE: 87
uaguucuugg ugcucuuggc uug                                            23

<210> SEQ ID NO 88
<211> LENGTH: 21
<212> TYPE: RNA
<213> ORGANISM: Artificial sequence
<220> FEATURE:
<223> OTHER INFORMATION: Antisense sequence for siAN1M2

<400> SEQUENCE: 88
uaguucuugg ugcucuuggc u                                              21

<210> SEQ ID NO 89
<211> LENGTH: 23
<212> TYPE: RNA
<213> ORGANISM: Artificial sequence
<220> FEATURE:
<223> OTHER INFORMATION: Antisense sequence for siAN2M2

<400> SEQUENCE: 89
uaguucuugg ugcucuuggc uug                                            23

<210> SEQ ID NO 90
<211> LENGTH: 19
<212> TYPE: RNA
<213> ORGANISM: Artificial sequence
<220> FEATURE:
<223> OTHER INFORMATION: Sense sequence for siAN1M3

<400> SEQUENCE: 90
ccaagagcac caagaacua                                                 19

<210> SEQ ID NO 91
<211> LENGTH: 21
<212> TYPE: RNA
<213> ORGANISM: Artificial sequence
<220> FEATURE:
<223> OTHER INFORMATION: Sense sequence for siAN2M3

<400> SEQUENCE: 91
agccaagagc accaagaacu a                                              21

<210> SEQ ID NO 92
<211> LENGTH: 19
<212> TYPE: RNA
<213> ORGANISM: Artificial sequence
<220> FEATURE:
<223> OTHER INFORMATION: Sense sequence for siAN1M1S

<400> SEQUENCE: 92
ccaagagcac caagaacua                                                 19
```

```
<210> SEQ ID NO 93
<211> LENGTH: 21
<212> TYPE: RNA
<213> ORGANISM: Artificial sequence
<220> FEATURE:
<223> OTHER INFORMATION: Antisense sequence for siAN1M1S

<400> SEQUENCE: 93
uaguucuugg ugcucuuggc u                                              21

<210> SEQ ID NO 94
<211> LENGTH: 21
<212> TYPE: RNA
<213> ORGANISM: Artificial sequence
<220> FEATURE:
<223> OTHER INFORMATION: Sense sequence for siAN2M1S

<400> SEQUENCE: 94
agccaagagc accaagaacu a                                              21

<210> SEQ ID NO 95
<211> LENGTH: 23
<212> TYPE: RNA
<213> ORGANISM: Artificial sequence
<220> FEATURE:
<223> OTHER INFORMATION: Antisense sequence for siAN2M1S

<400> SEQUENCE: 95
uaguucuugg ugcucuuggc uug                                            23

<210> SEQ ID NO 96
<211> LENGTH: 21
<212> TYPE: RNA
<213> ORGANISM: Artificial sequence
<220> FEATURE:
<223> OTHER INFORMATION: Antisense sequence for siAN1M2S

<400> SEQUENCE: 96
uaguucuugg ugcucuuggc u                                              21

<210> SEQ ID NO 97
<211> LENGTH: 23
<212> TYPE: RNA
<213> ORGANISM: Artificial sequence
<220> FEATURE:
<223> OTHER INFORMATION: Antisense sequence for siAN2M2S

<400> SEQUENCE: 97
uaguucuugg ugcucuuggc uug                                            23

<210> SEQ ID NO 98
<211> LENGTH: 19
<212> TYPE: RNA
<213> ORGANISM: artificial sequence
<220> FEATURE:
<223> OTHER INFORMATION: Sense sequence for siAN1M3S

<400> SEQUENCE: 98
ccaagagcac caagaacua                                                 19

<210> SEQ ID NO 99
<211> LENGTH: 21
<212> TYPE: RNA
<213> ORGANISM: Artificial sequence
<220> FEATURE:
<223> OTHER INFORMATION: Sense sequence for siAN2M3S
```

```
<400> SEQUENCE: 99
agccaagagc accaagaacu a                                              21

<210> SEQ ID NO 100
<211> LENGTH: 21
<212> TYPE: RNA
<213> ORGANISM: Artificial sequence
<220> FEATURE:
<223> OTHER INFORMATION: Antisense sequence for siAN1M1P1

<400> SEQUENCE: 100
uaguucuugg ugcucuuggc u                                              21

<210> SEQ ID NO 101
<211> LENGTH: 23
<212> TYPE: RNA
<213> ORGANISM: Artificial sequence
<220> FEATURE:
<223> OTHER INFORMATION: Antisense sequence for siAN2M1P1

<400> SEQUENCE: 101
uaguucuugg ugcucuuggc uug                                            23

<210> SEQ ID NO 102
<211> LENGTH: 21
<212> TYPE: RNA
<213> ORGANISM: Artificial sequence
<220> FEATURE:
<223> OTHER INFORMATION: Antisense sequence for siAN1M2P1

<400> SEQUENCE: 102
uaguucuugg ugcucuuggc u                                              21

<210> SEQ ID NO 103
<211> LENGTH: 23
<212> TYPE: RNA
<213> ORGANISM: Artificial sequence
<220> FEATURE:
<223> OTHER INFORMATION: Antisense sequence for siAN2M2P1

<400> SEQUENCE: 103
uaguucuugg ugcucuuggc uug                                            23

<210> SEQ ID NO 104
<211> LENGTH: 21
<212> TYPE: RNA
<213> ORGANISM: Artificial sequence
<220> FEATURE:
<223> OTHER INFORMATION: Antisense sequence for siAN1M1SP1

<400> SEQUENCE: 104
uaguucuugg ugcucuuggc u                                              21

<210> SEQ ID NO 105
<211> LENGTH: 23
<212> TYPE: RNA
<213> ORGANISM: Artificial sequence
<220> FEATURE:
<223> OTHER INFORMATION: Antisense sequence for siAN2M1SP1

<400> SEQUENCE: 105
uaguucuugg ugcucuuggc uug                                            23

<210> SEQ ID NO 106
```

```
<211> LENGTH: 21
<212> TYPE: RNA
<213> ORGANISM: Artificial sequence
<220> FEATURE:
<223> OTHER INFORMATION: Antisense sequence for siAN1M3SP1

<400> SEQUENCE: 106
uaguucuugg ugcucuuggc u                                              21

<210> SEQ ID NO 107
<211> LENGTH: 23
<212> TYPE: RNA
<213> ORGANISM: Artificial sequence
<220> FEATURE:
<223> OTHER INFORMATION: Antisense sequence for siAN2M3SP1

<400> SEQUENCE: 107
uaguucuugg ugcucuuggc uug                                            23

<210> SEQ ID NO 108
<211> LENGTH: 19
<212> TYPE: RNA
<213> ORGANISM: Artificial sequence
<220> FEATURE:
<223> OTHER INFORMATION: Sense sequence for siAP1

<400> SEQUENCE: 108
caauaaagcu ggacaagaa                                                 19

<210> SEQ ID NO 109
<211> LENGTH: 21
<212> TYPE: RNA
<213> ORGANISM: Artificial sequence
<220> FEATURE:
<223> OTHER INFORMATION: Antisense sequence for siAP1

<400> SEQUENCE: 109
uucuugucca gcuuuauugg g                                              21

<210> SEQ ID NO 110
<211> LENGTH: 21
<212> TYPE: RNA
<213> ORGANISM: Artificial sequence
<220> FEATURE:
<223> OTHER INFORMATION: Sense sequence for siAP2

<400> SEQUENCE: 110
cccaauaaag cuggacaaga a                                              21

<210> SEQ ID NO 111
<211> LENGTH: 23
<212> TYPE: RNA
<213> ORGANISM: Artificial sequence
<220> FEATURE:
<223> OTHER INFORMATION: Antisense sequence for siAP2

<400> SEQUENCE: 111
uucuugucca gcuuuauugg gag                                            23

<210> SEQ ID NO 112
<211> LENGTH: 19
<212> TYPE: RNA
<213> ORGANISM: Artificial sequence
<220> FEATURE:
<223> OTHER INFORMATION: Sense sequence for siAP1M1

<400> SEQUENCE: 112
```

-continued caauaaagcu ggacaagaa                                                19

<210> SEQ ID NO 113
<211> LENGTH: 21
<212> TYPE: RNA
<213> ORGANISM: artificial sequence
<220> FEATURE:
<223> OTHER INFORMATION: Antisense sequence for siAP1M1

<400> SEQUENCE: 113
uucuugucca gcuuuauugg g                                             21

<210> SEQ ID NO 114
<211> LENGTH: 21
<212> TYPE: RNA
<213> ORGANISM: Artificial sequence
<220> FEATURE:
<223> OTHER INFORMATION: Sense sequence for siAP2M1

<400> SEQUENCE: 114
cccaauaaag cuggacaaga a                                             21

<210> SEQ ID NO 115
<211> LENGTH: 23
<212> TYPE: RNA
<213> ORGANISM: Artificial sequence
<220> FEATURE:
<223> OTHER INFORMATION: Antisense sequence for siAP2M1

<400> SEQUENCE: 115
uucuugucca gcuuuauugg gag                                           23

<210> SEQ ID NO 116
<211> LENGTH: 19
<212> TYPE: RNA
<213> ORGANISM: Artificial sequence
<220> FEATURE:
<223> OTHER INFORMATION: Sense sequence for siAP1M2

<400> SEQUENCE: 116
caauaaagcu ggacaagaa                                                19

<210> SEQ ID NO 117
<211> LENGTH: 21
<212> TYPE: RNA
<213> ORGANISM: Artificial sequence
<220> FEATURE:
<223> OTHER INFORMATION: Antisense sequence for siAP1M2

<400> SEQUENCE: 117
uucuugucca gcuuuauugg g                                             21

<210> SEQ ID NO 118
<211> LENGTH: 21
<212> TYPE: RNA
<213> ORGANISM: Artificial sequence
<220> FEATURE:
<223> OTHER INFORMATION: Sense sequence for siAP2M2

<400> SEQUENCE: 118
cccaauaaag cuggacaaga a                                             21

<210> SEQ ID NO 119
<211> LENGTH: 23
<212> TYPE: RNA

```
<213> ORGANISM: Artificial sequence
<220> FEATURE:
<223> OTHER INFORMATION: Antisense sequence for siAP2M2

<400> SEQUENCE: 119
uucuugucca gcuuuauugg gag                                          23

<210> SEQ ID NO 120
<211> LENGTH: 19
<212> TYPE: RNA
<213> ORGANISM: Artificial sequence
<220> FEATURE:
<223> OTHER INFORMATION: Sense sequence for siAP1M1S

<400> SEQUENCE: 120
caauaaagcu ggacaagaa                                               19

<210> SEQ ID NO 121
<211> LENGTH: 21
<212> TYPE: RNA
<213> ORGANISM: Artificial sequence
<220> FEATURE:
<223> OTHER INFORMATION: Antisense sequence for siAP1M1S

<400> SEQUENCE: 121
uucuugucca gcuuuauugg g                                            21

<210> SEQ ID NO 122
<211> LENGTH: 21
<212> TYPE: RNA
<213> ORGANISM: Artificial sequence
<220> FEATURE:
<223> OTHER INFORMATION: Sense sequence for siAP2M1S

<400> SEQUENCE: 122
cccaauaaag cuggacaaga a                                            21

<210> SEQ ID NO 123
<211> LENGTH: 23
<212> TYPE: RNA
<213> ORGANISM: Artificial sequence
<220> FEATURE:
<223> OTHER INFORMATION: Antisense sequence for siAP2M1S

<400> SEQUENCE: 123
uucuugucca gcuuuauugg gag                                          23

<210> SEQ ID NO 124
<211> LENGTH: 19
<212> TYPE: RNA
<213> ORGANISM: Artificial sequence
<220> FEATURE:
<223> OTHER INFORMATION: Sense sequence for siAP1M2S

<400> SEQUENCE: 124
caauaaagcu ggacaagaa                                               19

<210> SEQ ID NO 125
<211> LENGTH: 21
<212> TYPE: RNA
<213> ORGANISM: Artificial sequence
<220> FEATURE:
<223> OTHER INFORMATION: Antisense sequence for siAP1M2S

<400> SEQUENCE: 125
uucuugucca gcuuuauugg g                                            21
```

<210> SEQ ID NO 126
<211> LENGTH: 21
<212> TYPE: RNA
<213> ORGANISM: artificial sequence
<220> FEATURE:
<223> OTHER INFORMATION: Sense sequence for siAP2M2S

<400> SEQUENCE: 126
cccaauaaag cuggacaaga a                                              21

<210> SEQ ID NO 127
<211> LENGTH: 23
<212> TYPE: RNA
<213> ORGANISM: Artificial sequence
<220> FEATURE:
<223> OTHER INFORMATION: Antisense sequence for siAP2M2S

<400> SEQUENCE: 127
uucuugucca gcuuuauugg gag                                            23

<210> SEQ ID NO 128
<211> LENGTH: 21
<212> TYPE: RNA
<213> ORGANISM: Artificial sequence
<220> FEATURE:
<223> OTHER INFORMATION: Antisense sequence for siAP1M1P1

<400> SEQUENCE: 128
uucuugucca gcuuuauugg g                                              21

<210> SEQ ID NO 129
<211> LENGTH: 23
<212> TYPE: RNA
<213> ORGANISM: Artificial sequence
<220> FEATURE:
<223> OTHER INFORMATION: Antisense sequence for siAP2M1P1

<400> SEQUENCE: 129
uucuugucca gcuuuauugg gag                                            23

<210> SEQ ID NO 130
<211> LENGTH: 21
<212> TYPE: RNA
<213> ORGANISM: Artificial sequence
<220> FEATURE:
<223> OTHER INFORMATION: Antisense sequence for siAP1M2P1

<400> SEQUENCE: 130
uucuugucca gcuuuauugg g                                              21

<210> SEQ ID NO 131
<211> LENGTH: 23
<212> TYPE: RNA
<213> ORGANISM: Artificial sequence
<220> FEATURE:
<223> OTHER INFORMATION: Antisense sequence for siAP2M2P1

<400> SEQUENCE: 131
uucuugucca gcuuuauugg gag                                            23

<210> SEQ ID NO 132
<211> LENGTH: 21
<212> TYPE: RNA
<213> ORGANISM: Artificial sequence
<220> FEATURE:

-continued

<223> OTHER INFORMATION: Antisense sequence for siAP1M1SP1

<400> SEQUENCE: 132
uucuugucca gcuuuauugg g                                              21

<210> SEQ ID NO 133
<211> LENGTH: 23
<212> TYPE: RNA
<213> ORGANISM: Artificial sequence
<220> FEATURE:
<223> OTHER INFORMATION: Antisense sequence for siAP2M1SP1

<400> SEQUENCE: 133
uucuugucca gcuuuauugg gag                                            23

<210> SEQ ID NO 134
<211> LENGTH: 21
<212> TYPE: RNA
<213> ORGANISM: Artificial sequence
<220> FEATURE:
<223> OTHER INFORMATION: Antisense sequence for siAP1M2SP1

<400> SEQUENCE: 134
uucuugucca gcuuuauugg g                                              21

<210> SEQ ID NO 135
<211> LENGTH: 23
<212> TYPE: RNA
<213> ORGANISM: Artificial sequence
<220> FEATURE:
<223> OTHER INFORMATION: Antisense sequence for siAP2M2SP1

<400> SEQUENCE: 135
uucuugucca gcuuuauugg gag                                            23

<210> SEQ ID NO 136
<211> LENGTH: 21
<212> TYPE: RNA
<213> ORGANISM: Artificial sequence
<220> FEATURE:
<223> OTHER INFORMATION: Antisense sequence for L10-siHBa1M1P

<400> SEQUENCE: 136
uuugaaguau gccucaaggu u                                              21

<210> SEQ ID NO 137
<211> LENGTH: 21
<212> TYPE: RNA
<213> ORGANISM: Artificial sequence
<220> FEATURE:
<223> OTHER INFORMATION: Antisense sequence for L10-siHBa1M2P

<400> SEQUENCE: 137
uuugaaguau gccucaaggu u                                              21

<210> SEQ ID NO 138
<211> LENGTH: 23
<212> TYPE: RNA
<213> ORGANISM: Artificial sequence
<220> FEATURE:
<223> OTHER INFORMATION: Antisense sequence for L10-siHBa2M1P

<400> SEQUENCE: 138
uuugaaguau gccucaaggu cgg                                            23

```
<210> SEQ ID NO 139
<211> LENGTH: 23
<212> TYPE: RNA
<213> ORGANISM: Artificial sequence
<220> FEATURE:
<223> OTHER INFORMATION: Antisense sequence for L10-siHBa2M2P

<400> SEQUENCE: 139
uuugaaguau gccucaaggu cgg                                              23

<210> SEQ ID NO 140
<211> LENGTH: 21
<212> TYPE: RNA
<213> ORGANISM: Artificial sequence
<220> FEATURE:
<223> OTHER INFORMATION: Antisense sequence for L10-siHBa1M1SP

<400> SEQUENCE: 140
uuugaaguau gccucaaggu u                                                21

<210> SEQ ID NO 141
<211> LENGTH: 21
<212> TYPE: RNA
<213> ORGANISM: Artificial sequence
<220> FEATURE:
<223> OTHER INFORMATION: Antisense sequence for L10-siHBa1M2SP

<400> SEQUENCE: 141
uuugaaguau gccucaaggu u                                                21

<210> SEQ ID NO 142
<211> LENGTH: 23
<212> TYPE: RNA
<213> ORGANISM: Artificial sequence
<220> FEATURE:
<223> OTHER INFORMATION: Antisense sequence for L10-siHBa2M1SP

<400> SEQUENCE: 142
uuugaaguau gccucaaggu cgg                                              23

<210> SEQ ID NO 143
<211> LENGTH: 23
<212> TYPE: RNA
<213> ORGANISM: Artificial sequence
<220> FEATURE:
<223> OTHER INFORMATION: Antisense sequence for L10-siHBa2M2SP

<400> SEQUENCE: 143
uuugaaguau gccucaaggu cgg                                              23

<210> SEQ ID NO 144
<211> LENGTH: 19
<212> TYPE: RNA
<213> ORGANISM: Artificial sequence
<220> FEATURE:
<223> OTHER INFORMATION: Sense sequence for L10-siHBa1M3SP

<400> SEQUENCE: 144
ccuugaggca uacuucaaa                                                   19

<210> SEQ ID NO 145
<211> LENGTH: 21
<212> TYPE: RNA
<213> ORGANISM: Artificial sequence
<220> FEATURE:
<223> OTHER INFORMATION: Antisense sequence for L10-siHBa1M4SP
```

```
<400> SEQUENCE: 145
uuugaaguau gccucaaggu u                                              21

<210> SEQ ID NO 146
<211> LENGTH: 21
<212> TYPE: RNA
<213> ORGANISM: Artificial sequence
<220> FEATURE:
<223> OTHER INFORMATION: Antisense sequence for L10-siHBb1M1SP

<400> SEQUENCE: 146
uagaagauga ggcauagcag c                                              21

<210> SEQ ID NO 147
<211> LENGTH: 21
<212> TYPE: RNA
<213> ORGANISM: Artificial sequence
<220> FEATURE:
<223> OTHER INFORMATION: Antisense sequence for L10-siHBb2M1SP

<400> SEQUENCE: 147
uagaagauga ggcauagcau u                                              21

<210> SEQ ID NO 148
<211> LENGTH: 21
<212> TYPE: RNA
<213> ORGANISM: Artificial sequence
<220> FEATURE:
<223> OTHER INFORMATION: Antisense sequence for L10-siHBb1M2SP

<400> SEQUENCE: 148
uagaagauga ggcauagcag c                                              21

<210> SEQ ID NO 149
<211> LENGTH: 21
<212> TYPE: RNA
<213> ORGANISM: Artificial sequence
<220> FEATURE:
<223> OTHER INFORMATION: Antisense sequence for L10-siHBb2M2SP

<400> SEQUENCE: 149
uagaagauga ggcauagcau u                                              21

<210> SEQ ID NO 150
<211> LENGTH: 21
<212> TYPE: RNA
<213> ORGANISM: Artificial sequence
<220> FEATURE:
<223> OTHER INFORMATION: Sense sequence for L10-siHBb1M3SP

<400> SEQUENCE: 150
uagaagauga ggcauagcag c                                              21

<210> SEQ ID NO 151
<211> LENGTH: 21
<212> TYPE: RNA
<213> ORGANISM: Artificial sequence
<220> FEATURE:
<223> OTHER INFORMATION: Antisense sequence for L10-siHBb1M4SP

<400> SEQUENCE: 151
uagaagauga ggcauagcag c                                              21

<210> SEQ ID NO 152
<211> LENGTH: 21
```

```
<212> TYPE: RNA
<213> ORGANISM: Artificial sequence
<220> FEATURE:
<223> OTHER INFORMATION: Sense sequence for L10-siHBb4M1SP

<400> SEQUENCE: 152
gcugcuaugc cucaucuucu a                                              21

<210> SEQ ID NO 153
<211> LENGTH: 23
<212> TYPE: RNA
<213> ORGANISM: Artificial sequence
<220> FEATURE:
<223> OTHER INFORMATION: Antisense sequence for L10-siHBb4M1SP

<400> SEQUENCE: 153
uagaagauga ggcauagcag cgc                                            23

<210> SEQ ID NO 154
<211> LENGTH: 21
<212> TYPE: RNA
<213> ORGANISM: Artificial sequence
<220> FEATURE:
<223> OTHER INFORMATION: Antisense sequence for L10-siHBc1M1SP

<400> SEQUENCE: 154
ucagaugaga aggcacagac g                                              21

<210> SEQ ID NO 155
<211> LENGTH: 21
<212> TYPE: RNA
<213> ORGANISM: Artificial sequence
<220> FEATURE:
<223> OTHER INFORMATION: Antisense sequence for L10-siHBc1M2SP

<400> SEQUENCE: 155
ucagaugaga aggcacagac g                                              21

<210> SEQ ID NO 156
<211> LENGTH: 19
<212> TYPE: RNA
<213> ORGANISM: Artificial sequence
<220> FEATURE:
<223> OTHER INFORMATION: Sense sequence for L10-siHBc1M3SP

<400> SEQUENCE: 156
ucugugccuu cucaucuga                                                 19

<210> SEQ ID NO 157
<211> LENGTH: 21
<212> TYPE: RNA
<213> ORGANISM: Artificial sequence
<220> FEATURE:
<223> OTHER INFORMATION: Antisense sequence for L10-siHBc1M4SP

<400> SEQUENCE: 157
ucagaugaga aggcacagac g                                              21

<210> SEQ ID NO 158
<211> LENGTH: 21
<212> TYPE: RNA
<213> ORGANISM: Artificial sequence
<220> FEATURE:
<223> OTHER INFORMATION: Sense sequence for L10-siHBc2M1SP

<400> SEQUENCE: 158
```
cgucugugcc uucucaucug a                                               21

<210> SEQ ID NO 159
<211> LENGTH: 23
<212> TYPE: RNA
<213> ORGANISM: Artificial sequence
<220> FEATURE:
<223> OTHER INFORMATION: Antisense sequence for L10-siHBc2M1SP

<400> SEQUENCE: 159
ucagaugaga aggcacagac ggg                                             23

<210> SEQ ID NO 160
<211> LENGTH: 21
<212> TYPE: RNA
<213> ORGANISM: Artificial sequence
<220> FEATURE:
<223> OTHER INFORMATION: Antisense sequence for L10-siHBd1M1SP

<400> SEQUENCE: 160
uugaagcgaa gugcacacgg u                                               21

<210> SEQ ID NO 161
<211> LENGTH: 21
<212> TYPE: RNA
<213> ORGANISM: Artificial sequence
<220> FEATURE:
<223> OTHER INFORMATION: Antisense sequence for L10-siHBd1M2SP

<400> SEQUENCE: 161
uugaagcgaa gugcacacgg u                                               21

<210> SEQ ID NO 162
<211> LENGTH: 19
<212> TYPE: RNA
<213> ORGANISM: Artificial sequence
<220> FEATURE:
<223> OTHER INFORMATION: Sense sequence for L10-siHBd1M3SP

<400> SEQUENCE: 162
cgugugcacu ucgcuucaa                                                  19

<210> SEQ ID NO 163
<211> LENGTH: 21
<212> TYPE: RNA
<213> ORGANISM: Artificial sequence
<220> FEATURE:
<223> OTHER INFORMATION: Antisense sequence for L10-siHBd1M4SP

<400> SEQUENCE: 163
ucagaugaga aggcacagac g                                               21

<210> SEQ ID NO 164
<211> LENGTH: 21
<212> TYPE: RNA
<213> ORGANISM: Artificial sequence
<220> FEATURE:
<223> OTHER INFORMATION: Sense sequence for L10-siHBd2M1SP

<400> SEQUENCE: 164
accgugugca cuucgcuuca a                                               21

<210> SEQ ID NO 165
<211> LENGTH: 23
<212> TYPE: RNA
<213> ORGANISM: Artificial sequence

```
<220> FEATURE:
<223> OTHER INFORMATION: Antisense sequence for L10-siHBd2M1SP

<400> SEQUENCE: 165
uugaagcgaa gugcacacgg ucc                                              23

<210> SEQ ID NO 166
<211> LENGTH: 21
<212> TYPE: RNA
<213> ORGANISM: Artificial sequence
<220> FEATURE:
<223> OTHER INFORMATION: Antisense sequence for L10-siAN1M1P

<400> SEQUENCE: 166
uaguucuugg ugcucuuggc u                                                21

<210> SEQ ID NO 167
<211> LENGTH: 23
<212> TYPE: RNA
<213> ORGANISM: Artificial sequence
<220> FEATURE:
<223> OTHER INFORMATION: Antisense sequence for L10-siAN2M1P

<400> SEQUENCE: 167
uaguucuugg ugcucuuggc uug                                              23

<210> SEQ ID NO 168
<211> LENGTH: 21
<212> TYPE: RNA
<213> ORGANISM: Artificial sequence
<220> FEATURE:
<223> OTHER INFORMATION: Antisense sequence for L10-siAN1M2P

<400> SEQUENCE: 168
uaguucuugg ugcucuuggc u                                                21

<210> SEQ ID NO 169
<211> LENGTH: 23
<212> TYPE: RNA
<213> ORGANISM: Artificial sequence
<220> FEATURE:
<223> OTHER INFORMATION: Antisense sequence for L10-siAN2M2P

<400> SEQUENCE: 169
uaguucuugg ugcucuuggc uug                                              23

<210> SEQ ID NO 170
<211> LENGTH: 21
<212> TYPE: RNA
<213> ORGANISM: Artificial sequence
<220> FEATURE:
<223> OTHER INFORMATION: Antisense sequence for L10-siAN1M1SP

<400> SEQUENCE: 170
uaguucuugg ugcucuuggc u                                                21

<210> SEQ ID NO 171
<211> LENGTH: 23
<212> TYPE: RNA
<213> ORGANISM: Artificial sequence
<220> FEATURE:
<223> OTHER INFORMATION: Antisense sequence for L10-siAN2M1SP

<400> SEQUENCE: 171
uaguucuugg ugcucuuggc uug                                              23
```

```
<210> SEQ ID NO 172
<211> LENGTH: 21
<212> TYPE: RNA
<213> ORGANISM: Artificial sequence
<220> FEATURE:
<223> OTHER INFORMATION: Antisense sequence for L10-siAN1M2SP

<400> SEQUENCE: 172
uaguucuugg ugcucuuggc u                                              21

<210> SEQ ID NO 173
<211> LENGTH: 23
<212> TYPE: RNA
<213> ORGANISM: Artificial sequence
<220> FEATURE:
<223> OTHER INFORMATION: Antisense sequence for L10-siAN2M2SP

<400> SEQUENCE: 173
uaguucuugg ugcucuuggc uug                                            23

<210> SEQ ID NO 174
<211> LENGTH: 21
<212> TYPE: RNA
<213> ORGANISM: Artificial sequence
<220> FEATURE:
<223> OTHER INFORMATION: Antisense sequence for L10-siAN1M4S

<400> SEQUENCE: 174
uaguucuugg ugcucuuggc u                                              21

<210> SEQ ID NO 175
<211> LENGTH: 21
<212> TYPE: RNA
<213> ORGANISM: artificial sequence
<220> FEATURE:
<223> OTHER INFORMATION: Antisense sequence for L10-siAN1M4SP

<400> SEQUENCE: 175
uaguucuugg ugcucuuggc u                                              21

<210> SEQ ID NO 176
<211> LENGTH: 19
<212> TYPE: RNA
<213> ORGANISM: Artificial sequence
<220> FEATURE:
<223> OTHER INFORMATION: Sense sequence for L10-siAN1M5S

<400> SEQUENCE: 176
ccaagagcac caagaacua                                                 19

<210> SEQ ID NO 177
<211> LENGTH: 21
<212> TYPE: RNA
<213> ORGANISM: Artificial sequence
<220> FEATURE:
<223> OTHER INFORMATION: Antisense sequence for L10-siAN1M5S

<400> SEQUENCE: 177
uaguucuugg ugcucuuggc u                                              21

<210> SEQ ID NO 178
<211> LENGTH: 21
<212> TYPE: RNA
<213> ORGANISM: Artificial sequence
<220> FEATURE:
<223> OTHER INFORMATION: Antisense sequence for L10-siAN1M5SP
```

-continued

<400> SEQUENCE: 178
uaguucuugg ugcucuuggc u                                              21

<210> SEQ ID NO 179
<211> LENGTH: 21
<212> TYPE: RNA
<213> ORGANISM: Artificial sequence
<220> FEATURE:
<223> OTHER INFORMATION: Antisense sequence for L10-siAP1M1P

<400> SEQUENCE: 179
uucuugucca gcuuuauugg g                                              21

<210> SEQ ID NO 180
<211> LENGTH: 23
<212> TYPE: RNA
<213> ORGANISM: Artificial sequence
<220> FEATURE:
<223> OTHER INFORMATION: Antisense sequence for L10-siAP2M1P

<400> SEQUENCE: 180
uucuugucca gcuuuauugg gag                                            23

<210> SEQ ID NO 181
<211> LENGTH: 21
<212> TYPE: RNA
<213> ORGANISM: Artificial sequence
<220> FEATURE:
<223> OTHER INFORMATION: Antisense sequence for L10-siAP1M2P

<400> SEQUENCE: 181
uucuugucca gcuuuauugg g                                              21

<210> SEQ ID NO 182
<211> LENGTH: 23
<212> TYPE: RNA
<213> ORGANISM: Artificial sequence
<220> FEATURE:
<223> OTHER INFORMATION: Antisense sequence for L10-siAP2M2P

<400> SEQUENCE: 182
uucuugucca gcuuuauugg gag                                            23

<210> SEQ ID NO 183
<211> LENGTH: 21
<212> TYPE: RNA
<213> ORGANISM: Artificial sequence
<220> FEATURE:
<223> OTHER INFORMATION: Antisense sequence for L10-siAP1M1SP

<400> SEQUENCE: 183
uucuugucca gcuuuauugg g                                              21

<210> SEQ ID NO 184
<211> LENGTH: 23
<212> TYPE: RNA
<213> ORGANISM: Artificial sequence
<220> FEATURE:
<223> OTHER INFORMATION: Antisense sequence for L10-siAP2M1SP

<400> SEQUENCE: 184
uucuugucca gcuuuauugg gag                                            23

<210> SEQ ID NO 185

```
-continued

<211> LENGTH: 21
<212> TYPE: RNA
<213> ORGANISM: Artificial sequence
<220> FEATURE:
<223> OTHER INFORMATION: Antisense sequence for L10-siAP1M2SP

<400> SEQUENCE: 185
uucuugucca gcuuuauugg g                                              21

<210> SEQ ID NO 186
<211> LENGTH: 23
<212> TYPE: RNA
<213> ORGANISM: Artificial sequence
<220> FEATURE:
<223> OTHER INFORMATION: Antisense sequence for L10-siAP2M2SP

<400> SEQUENCE: 186
uucuugucca gcuuuauugg gag                                            23

<210> SEQ ID NO 187
<211> LENGTH: 20
<212> TYPE: DNA
<213> ORGANISM: Artificial sequence
<220> FEATURE:
<223> OTHER INFORMATION: upstream primer for mTTR

<400> SEQUENCE: 187
ccgtctgtgc cttctcatct                                                20

<210> SEQ ID NO 188
<211> LENGTH: 20
<212> TYPE: DNA
<213> ORGANISM: Artificial sequence
<220> FEATURE:
<223> OTHER INFORMATION: downstream primer for mTTR

<400> SEQUENCE: 188
taatctcctc ccccaactcc                                                20

<210> SEQ ID NO 189
<211> LENGTH: 20
<212> TYPE: DNA
<213> ORGANISM: Artificial sequence
<220> FEATURE:
<223> OTHER INFORMATION: upstream primer for GAPDH

<400> SEQUENCE: 189
agaaggctgg ggctcatttg                                                20

<210> SEQ ID NO 190
<211> LENGTH: 20
<212> TYPE: DNA
<213> ORGANISM: Artificial sequence
<220> FEATURE:
<223> OTHER INFORMATION: downstream primer for GAPDH

<400> SEQUENCE: 190
aggggccatc cacagtcttc                                                20

<210> SEQ ID NO 191
<211> LENGTH: 24
<212> TYPE: DNA
<213> ORGANISM: Artificial sequence
<220> FEATURE:
<223> OTHER INFORMATION: upstream primer for -actin

<400> SEQUENCE: 191
```

```
agcttctttg cagctccttc gttg                                    24
```

<210> SEQ ID NO 192
<211> LENGTH: 24
<212> TYPE: DNA
<213> ORGANISM: Artificial sequence
<220> FEATURE:
<223> OTHER INFORMATION: downstream primer for -actin

<400> SEQUENCE: 192

```
ttctgaccca ttcccaccat caca                                    24
```

<210> SEQ ID NO 193
<211> LENGTH: 21
<212> TYPE: DNA
<213> ORGANISM: Artificial sequence
<220> FEATURE:
<223> OTHER INFORMATION: upstream primer for HBV

<400> SEQUENCE: 193

```
cgtttctcct ggctcagttt a                                       21
```

<210> SEQ ID NO 194
<211> LENGTH: 21
<212> TYPE: DNA
<213> ORGANISM: Artificial sequence
<220> FEATURE:
<223> OTHER INFORMATION: downstream primer for HBV

<400> SEQUENCE: 194

```
cagcggtaaa aagggactca a                                       21
```

<210> SEQ ID NO 195
<211> LENGTH: 21
<212> TYPE: RNA
<213> ORGANISM: Artificial sequence
<220> FEATURE:
<223> OTHER INFORMATION: Sense sequence for AD-65695

<400> SEQUENCE: 195

```
acauauuuga ucagucuuuu u                                       21
```

<210> SEQ ID NO 196
<211> LENGTH: 23
<212> TYPE: RNA
<213> ORGANISM: Artificial sequence
<220> FEATURE:
<223> OTHER INFORMATION: Antisense sequence for AD-65695

<400> SEQUENCE: 196

```
aaaaagacug aucaaauaug uug                                     23
```

<210> SEQ ID NO 197
<211> LENGTH: 21
<212> TYPE: RNA
<213> ORGANISM: Artificial sequence
<220> FEATURE:
<223> OTHER INFORMATION: Sense sequence for AD-69535

<400> SEQUENCE: 197

```
gcuuaaaagg gacaguauuc a                                       21
```

<210> SEQ ID NO 198
<211> LENGTH: 23
<212> TYPE: RNA

```
<213> ORGANISM: Artificial sequence
<220> FEATURE:
<223> OTHER INFORMATION: Antisense sequence for AD-69535

<400> SEQUENCE: 198
ugaauacugu cccuuuuaag caa                                             23

<210> SEQ ID NO 199
<211> LENGTH: 23
<212> TYPE: DNA
<213> ORGANISM: Artificial sequence
<220> FEATURE:
<223> OTHER INFORMATION: upstream primer for mouse ANGPTL3

<400> SEQUENCE: 199
gaggagcagc taaccaactt aat                                             23

<210> SEQ ID NO 200
<211> LENGTH: 23
<212> TYPE: DNA
<213> ORGANISM: Artificial sequence
<220> FEATURE:
<223> OTHER INFORMATION: downstream primer for mouse ANGPTL3

<400> SEQUENCE: 200
tctgcatgtg ctgttgactt aat                                             23

<210> SEQ ID NO 201
<211> LENGTH: 24
<212> TYPE: DNA
<213> ORGANISM: artificial sequence
<220> FEATURE:
<223> OTHER INFORMATION: upstream primer for mouse GAPDH

<400> SEQUENCE: 201
aactttggca ttgtggaagg gctc                                            24

<210> SEQ ID NO 202
<211> LENGTH: 24
<212> TYPE: DNA
<213> ORGANISM: Artificial sequence
<220> FEATURE:
<223> OTHER INFORMATION: downstream primer for mouse GAPDH

<400> SEQUENCE: 202
tggaagagtg ggagttgctg ttga                                            24

<210> SEQ ID NO 203
<211> LENGTH: 21
<212> TYPE: RNA
<213> ORGANISM: Artificial sequence
<220> FEATURE:
<223> OTHER INFORMATION: Antisense sequence for W8-siAN1M3SPs

<400> SEQUENCE: 203
uaguucuugg ugcucuuggc u                                               21

<210> SEQ ID NO 204
<211> LENGTH: 21
<212> TYPE: RNA
<213> ORGANISM: Artificial sequence
<220> FEATURE:
<223> OTHER INFORMATION: Sense sequence for L10-simTTR

<400> SEQUENCE: 204
aacaguguuc uugcucuaua a                                               21
```

```
<210> SEQ ID NO 205
<211> LENGTH: 23
<212> TYPE: RNA
<213> ORGANISM: Artificial sequence
<220> FEATURE:
<223> OTHER INFORMATION: Antisense sequence for L10-simTTR

<400> SEQUENCE: 205
uuauagagca agaacacugu uuu                                              23

<210> SEQ ID NO 206
<211> LENGTH: 19
<212> TYPE: RNA
<213> ORGANISM: Artificial sequence
<220> FEATURE:
<223> OTHER INFORMATION: Sense sequence for L10-siHBa1M2Sps

<400> SEQUENCE: 206
ccuugaggca uacuucaaa                                                   19

<210> SEQ ID NO 207
<211> LENGTH: 21
<212> TYPE: RNA
<213> ORGANISM: Artificial sequence
<220> FEATURE:
<223> OTHER INFORMATION: Antisense sequence for L10-siHBa1M2Sps

<400> SEQUENCE: 207
uuugaaguau gccucaaggu u                                                21

<210> SEQ ID NO 208
<211> LENGTH: 19
<212> TYPE: RNA
<213> ORGANISM: Artificial sequence
<220> FEATURE:
<223> OTHER INFORMATION: Sense sequence for L10- siHBa1M2Sp

<400> SEQUENCE: 208
ccuugaggca uacuucaaa                                                   19

<210> SEQ ID NO 209
<211> LENGTH: 21
<212> TYPE: RNA
<213> ORGANISM: Artificial sequence
<220> FEATURE:
<223> OTHER INFORMATION: Antisense sequence for L10- siHBa1M2Sp

<400> SEQUENCE: 209
uuugaaguau gccucaaggu u                                                21

<210> SEQ ID NO 210
<211> LENGTH: 19
<212> TYPE: RNA
<213> ORGANISM: Artificial sequence
<220> FEATURE:
<223> OTHER INFORMATION: Sense sequence for L10-siHBa1M1Sp

<400> SEQUENCE: 210
ccuugaggca uacuucaaa                                                   19

<210> SEQ ID NO 211
<211> LENGTH: 21
<212> TYPE: RNA
<213> ORGANISM: Artificial sequence
<220> FEATURE:
```

<223> OTHER INFORMATION: Antisense sequence for L10-siHBa1M1Sp

<400> SEQUENCE: 211
uuugaaguau gccucaaggu u                                      21

<210> SEQ ID NO 212
<211> LENGTH: 19
<212> TYPE: RNA
<213> ORGANISM: Artificial sequence
<220> FEATURE:
<223> OTHER INFORMATION: Sense sequence for L10- siHBa1M1SpsT

<400> SEQUENCE: 212
ccuugaggca uacuucaaa                                         19

<210> SEQ ID NO 213
<211> LENGTH: 20
<212> TYPE: RNA
<213> ORGANISM: Artificial sequence
<220> FEATURE:
<223> OTHER INFORMATION: Antisense sequence for L10- siHBa1M1SpsT

<400> SEQUENCE: 213
uugaaguaug ccucaagguu                                        20

<210> SEQ ID NO 214
<211> LENGTH: 19
<212> TYPE: RNA
<213> ORGANISM: Artificial sequence
<220> FEATURE:
<223> OTHER INFORMATION: Sense sequence for L10-siHBa1M1Sps

<400> SEQUENCE: 214
ccuugaggca uacuucaaa                                         19

<210> SEQ ID NO 215
<211> LENGTH: 21
<212> TYPE: RNA
<213> ORGANISM: Artificial sequence
<220> FEATURE:
<223> OTHER INFORMATION: Antisense sequence for L10-siHBa1M1Sps

<400> SEQUENCE: 215
uuugaaguau gccucaaggu u                                      21

<210> SEQ ID NO 216
<211> LENGTH: 19
<212> TYPE: RNA
<213> ORGANISM: Artificial sequence
<220> FEATURE:
<223> OTHER INFORMATION: Sense sequence for P10-siHBa1M2SP

<400> SEQUENCE: 216
ccuugaggca uacuucaaa                                         19

<210> SEQ ID NO 217
<211> LENGTH: 21
<212> TYPE: RNA
<213> ORGANISM: Artificial sequence
<220> FEATURE:
<223> OTHER INFORMATION: Antisense sequence for P10-siHBa1M2SP

<400> SEQUENCE: 217
uuugaaguau gccucaaggu u                                      21

```
<210> SEQ ID NO 218
<211> LENGTH: 19
<212> TYPE: RNA
<213> ORGANISM: Artificial sequence
<220> FEATURE:
<223> OTHER INFORMATION: Sense sequence for W8-siHBa1M2SP

<400> SEQUENCE: 218
ccuugaggca uacuucaaa                                                       19

<210> SEQ ID NO 219
<211> LENGTH: 21
<212> TYPE: RNA
<213> ORGANISM: Artificial sequence
<220> FEATURE:
<223> OTHER INFORMATION: Antisense sequence for W8-siHBa1M2SP

<400> SEQUENCE: 219
uuugaaguau gccucaaggu u                                                    21

<210> SEQ ID NO 220
<211> LENGTH: 19
<212> TYPE: RNA
<213> ORGANISM: Artificial sequence
<220> FEATURE:
<223> OTHER INFORMATION: Sense sequence for Z5-siHBa1M2SP

<400> SEQUENCE: 220
ccuugaggca uacuucaaa                                                       19

<210> SEQ ID NO 221
<211> LENGTH: 21
<212> TYPE: RNA
<213> ORGANISM: Artificial sequence
<220> FEATURE:
<223> OTHER INFORMATION: Antisense sequence for Z5-siHBa1M2SP

<400> SEQUENCE: 221
uuugaaguau gccucaaggu u                                                    21

<210> SEQ ID NO 222
<211> LENGTH: 19
<212> TYPE: RNA
<213> ORGANISM: Artificial sequence
<220> FEATURE:
<223> OTHER INFORMATION: Sense sequence for L10-siP1M1Sp

<400> SEQUENCE: 222
gaaaguaugu caacgaaua                                                       19

<210> SEQ ID NO 223
<211> LENGTH: 21
<212> TYPE: RNA
<213> ORGANISM: Artificial sequence
<220> FEATURE:
<223> OTHER INFORMATION: Antisense sequence for L10-siP1M1Sp

<400> SEQUENCE: 223
uauucguuga cauacuuucu u                                                    21

<210> SEQ ID NO 224
<211> LENGTH: 19
<212> TYPE: RNA
<213> ORGANISM: Artificial sequence
<220> FEATURE:
<223> OTHER INFORMATION: Sense sequence for L10-siP1M1SP
```

<400> SEQUENCE: 224
gaaaguaugu caacgaaua                                              19

<210> SEQ ID NO 225
<211> LENGTH: 21
<212> TYPE: RNA
<213> ORGANISM: Artificial sequence
<220> FEATURE:
<223> OTHER INFORMATION: Antisense sequence for L10-siP1M1SP

<400> SEQUENCE: 225
uauucguuga cauacuuucu u                                           21

<210> SEQ ID NO 226
<211> LENGTH: 21
<212> TYPE: RNA
<213> ORGANISM: Artificial sequence
<220> FEATURE:
<223> OTHER INFORMATION: Sense sequence for L10-siAN2M1Sp

<400> SEQUENCE: 226
agccaagagc accaagaacu a                                           21

<210> SEQ ID NO 227
<211> LENGTH: 23
<212> TYPE: RNA
<213> ORGANISM: Artificial sequence
<220> FEATURE:
<223> OTHER INFORMATION: Antisense sequence for L10-siAN2M1Sp

<400> SEQUENCE: 227
uaguucuugg ugcucuuggc uug                                         23

<210> SEQ ID NO 228
<211> LENGTH: 19
<212> TYPE: RNA
<213> ORGANISM: Artificial sequence
<220> FEATURE:
<223> OTHER INFORMATION: Sense sequence for L10-siAP1M1Sp

<400> SEQUENCE: 228
caauaaagcu ggacaagaa                                              19

<210> SEQ ID NO 229
<211> LENGTH: 21
<212> TYPE: RNA
<213> ORGANISM: Artificial sequence
<220> FEATURE:
<223> OTHER INFORMATION: Antisense sequence for L10-siAP1M1Sp

<400> SEQUENCE: 229
uucuugucca gcuuuauugg g                                           21

<210> SEQ ID NO 230
<211> LENGTH: 19
<212> TYPE: RNA
<213> ORGANISM: Artificial sequence
<220> FEATURE:
<223> OTHER INFORMATION: Sense sequence for L10-siAP1M1Sps

<400> SEQUENCE: 230
caauaaagcu ggacaagaa                                              19

<210> SEQ ID NO 231
<211> LENGTH: 21

```
<212> TYPE: RNA
<213> ORGANISM: Artificial sequence
<220> FEATURE:
<223> OTHER INFORMATION: Antisense sequence for L10-siAP1M1Sps

<400> SEQUENCE: 231
uucuugucca gcuuuauugg g                                        21

<210> SEQ ID NO 232
<211> LENGTH: 19
<212> TYPE: RNA
<213> ORGANISM: Artificial sequence
<220> FEATURE:
<223> OTHER INFORMATION: Sense sequence for K4-simTTR

<400> SEQUENCE: 232
caauaaagcu ggacaagaa                                           19

<210> SEQ ID NO 233
<211> LENGTH: 21
<212> TYPE: RNA
<213> ORGANISM: Artificial sequence
<220> FEATURE:
<223> OTHER INFORMATION: Antisense sequence for K4-simTTR

<400> SEQUENCE: 233
uucuugucca gcuuuauugg g                                        21

<210> SEQ ID NO 234
<211> LENGTH: 19
<212> TYPE: RNA
<213> ORGANISM: Artificial sequence
<220> FEATURE:
<223> OTHER INFORMATION: Sense sequence for AD-66810

<400> SEQUENCE: 234
caauaaagcu ggacaagaa                                           19

<210> SEQ ID NO 235
<211> LENGTH: 21
<212> TYPE: RNA
<213> ORGANISM: Artificial sequence
<220> FEATURE:
<223> OTHER INFORMATION: Antisense sequence for AD-66810

<400> SEQUENCE: 235
uucuugucca gcuuuauugg g                                        21

<210> SEQ ID NO 236
<211> LENGTH: 21
<212> TYPE: DNA
<213> ORGANISM: Artificial sequence
<220> FEATURE:
<223> OTHER INFORMATION: Sense sequence for X2M2

<400> SEQUENCE: 236
ccuugaggca uacuucaaat t                                        21

<210> SEQ ID NO 237
<211> LENGTH: 21
<212> TYPE: DNA
<213> ORGANISM: Artificial sequence
<220> FEATURE:
<223> OTHER INFORMATION: Antisense sequence for X2M2

<400> SEQUENCE: 237
```
uuugaaguau gccucaaggt t          21

<210> SEQ ID NO 238
<211> LENGTH: 20
<212> TYPE: DNA
<213> ORGANISM: Artificial sequence
<220> FEATURE:
<223> OTHER INFORMATION: upstream primer for HBV

<400> SEQUENCE: 238
gtcttttggg ttttgctgcc          20

<210> SEQ ID NO 239
<211> LENGTH: 20
<212> TYPE: DNA
<213> ORGANISM: Artificial sequence
<220> FEATURE:
<223> OTHER INFORMATION: downstream primer for HBV

<400> SEQUENCE: 239
gcaacggggt aaaggttcag          20

<210> SEQ ID NO 240
<211> LENGTH: 19
<212> TYPE: DNA
<213> ORGANISM: Artificial sequence
<220> FEATURE:
<223> OTHER INFORMATION: upstream primer for -actin

<400> SEQUENCE: 240
ggtcggagtc aacggattt          19

<210> SEQ ID NO 241
<211> LENGTH: 19
<212> TYPE: DNA
<213> ORGANISM: Artificial sequence
<220> FEATURE:
<223> OTHER INFORMATION: downstream primer for -actin

<400> SEQUENCE: 241
ccagcatcgc cccacttga          19

<210> SEQ ID NO 242
<211> LENGTH: 20
<212> TYPE: DNA
<213> ORGANISM: Artificial sequence
<220> FEATURE:
<223> OTHER INFORMATION: upstream primer for monkey ANGPTL3

<400> SEQUENCE: 242
ctggtggtgg catgatgagt          20

<210> SEQ ID NO 243
<211> LENGTH: 21
<212> TYPE: DNA
<213> ORGANISM: Artificial sequence
<220> FEATURE:
<223> OTHER INFORMATION: downstream primer for monkey ANGPTL3

<400> SEQUENCE: 243
ctcttctccg ctctggctta g          21

<210> SEQ ID NO 244
<211> LENGTH: 20
<212> TYPE: DNA
<213> ORGANISM: Artificial sequence

```
<220> FEATURE:
<223> OTHER INFORMATION: upstream primer for monkey GAPDH

<400> SEQUENCE: 244
gggagccaaa agggtcatca                                                     20

<210> SEQ ID NO 245
<211> LENGTH: 20
<212> TYPE: DNA
<213> ORGANISM: Artificial sequence
<220> FEATURE:
<223> OTHER INFORMATION: downstream primer for monkey GAPDH

<400> SEQUENCE: 245
cgtggactgt ggtcatgagt                                                     20

<210> SEQ ID NO 246
<211> LENGTH: 24
<212> TYPE: DNA
<213> ORGANISM: Artificial sequence
<220> FEATURE:
<223> OTHER INFORMATION: upstream primer for mouse -actin

<400> SEQUENCE: 246
agcttctttg cagctccttc gttg                                                24

<210> SEQ ID NO 247
<211> LENGTH: 24
<212> TYPE: DNA
<213> ORGANISM: Artificial sequence
<220> FEATURE:
<223> OTHER INFORMATION: downstream primer for mouse -actin

<400> SEQUENCE: 247
ttctgaccca ttcccaccat caca                                                24

<210> SEQ ID NO 248
<211> LENGTH: 20
<212> TYPE: DNA
<213> ORGANISM: Artificial sequence
<220> FEATURE:
<223> OTHER INFORMATION: upstream primer for human APOC3

<400> SEQUENCE: 248
gtgaccgatg gcttcagttc                                                     20

<210> SEQ ID NO 249
<211> LENGTH: 20
<212> TYPE: DNA
<213> ORGANISM: Artificial sequence
<220> FEATURE:
<223> OTHER INFORMATION: downstream primer for human APOC3

<400> SEQUENCE: 249
atggataggc aggtggactt                                                     20

<210> SEQ ID NO 250
<211> LENGTH: 19
<212> TYPE: RNA
<213> ORGANISM: Artificial sequence
<220> FEATURE:
<223> OTHER INFORMATION: Sense sequence for comparative sequence 1

<400> SEQUENCE: 250
ccuugaggca uacuucaaa                                                      19
```

```
<210> SEQ ID NO 251
<211> LENGTH: 21
<212> TYPE: RNA
<213> ORGANISM: Artificial sequence
<220> FEATURE:
<223> OTHER INFORMATION: Antisense sequence for comparative sequence 1

<400> SEQUENCE: 251
uuugaaguau gccucaaggu u                                              21
```